US010202412B2

(12) United States Patent
Sommadossi et al.

(10) Patent No.: US 10,202,412 B2
(45) Date of Patent: Feb. 12, 2019

(54) β-D-2'-DEOXY-2'-SUBSTITUTED-4'-SUBSTITUTED-2-SUBSTITUTED-N⁶-SUBSTITUTED-6-AMINO PURINENUCLEOTIDES FOR THE TREATMENT OF PARAMYXOVIRUS AND ORTHOMYXOVIRUS INFECTIONS

(71) Applicant: Atea Pharmaceuticals, Inc., Boston, MA (US)

(72) Inventors: Jean-Pierre Sommadossi, Boston, MA (US); Adel Moussa, Burlington, MA (US)

(73) Assignee: Atea Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 15/645,701

(22) Filed: Jul. 10, 2017

(65) Prior Publication Data
US 2018/0009836 A1 Jan. 11, 2018

Related U.S. Application Data

(63) Continuation of application No. PCT/US2017/040848, filed on Jul. 6, 2017.

(60) Provisional application No. 62/359,877, filed on Jul. 8, 2016.

(51) Int. Cl.
C07H 19/20 (2006.01)
C07H 19/207 (2006.01)
C07H 19/16 (2006.01)
A61P 31/12 (2006.01)

(52) U.S. Cl.
CPC .............. *C07H 19/20* (2013.01); *A61P 31/12* (2018.01); *C07H 19/16* (2013.01); *C07H 19/207* (2013.01)

(58) Field of Classification Search
None
See application file for complete search history.

(56) References Cited

U.S. PATENT DOCUMENTS

| | | | |
|---|---|---|---|
| 5,420,115 A | 5/1995 | Tisdale et al. |
| 6,348,587 B1 | 2/2002 | Schinazi et al. |
| 6,660,721 B2 | 12/2003 | Devos et al. |
| 6,777,395 B2 | 8/2004 | Bhat et al. |
| 6,784,166 B2 | 8/2004 | Devos et al. |
| 6,812,219 B2 | 11/2004 | LaColla et al. |
| 6,911,424 B2 | 6/2005 | Schinazi et al. |
| 7,138,376 B2 | 11/2006 | Gosselin et al. |
| 7,307,065 B2 | 12/2007 | Schinazi et al. |
| 7,323,453 B2 | 1/2008 | Olsen et al. |
| 7,429,572 B2 | 9/2008 | Clark et al. |
| 7,560,434 B2 | 7/2009 | Babu et al. |
| 7,601,820 B2 | 10/2009 | Wang et al. |
| 7,608,599 B2 | 10/2009 | Klumpp et al. |
| 7,608,600 B2 | 10/2009 | Storer et al. |
| 7,824,851 B2 | 11/2010 | Sommadossi et al. |
| 7,879,815 B2 | 2/2011 | MacCoss et al. |
| 7,951,789 B2 | 5/2011 | Sommadossi et al. |
| 7,964,580 B2 | 6/2011 | Sofia et al. |
| 8,008,264 B2 | 8/2011 | Butler et al. |
| 8,012,941 B2 | 9/2011 | Cho et al. |
| 8,071,568 B2 | 12/2011 | Narjes et al. |
| 8,119,607 B2 | 2/2012 | Francom et al. |
| 8,133,870 B2 | 3/2012 | Babu et al. |
| 8,168,583 B2 | 5/2012 | Schinazi et al. |
| 8,173,621 B2 | 5/2012 | Du et al. |
| 8,318,682 B2 | 11/2012 | Butler et al. |
| 8,324,179 B2 | 12/2012 | Chen et al. |
| 8,334,270 B2 | 12/2012 | Sofia et al. |
| 8,415,308 B2 | 4/2013 | Cho et al. |
| 8,415,309 B2 | 4/2013 | Francom et al. |
| 8,455,451 B2 | 6/2013 | Cho et al. |
| 8,481,712 B2 | 7/2013 | Bhat et al. |
| 8,492,539 B2 | 7/2013 | Chun et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,674,085 B2 | 3/2014 | Sommadossi et al. |
| 8,680,071 B2 | 3/2014 | Surleraux et al. |
| 8,691,788 B2 | 4/2014 | Sommadossi et al. |
| 8,716,262 B2 | 5/2014 | Sofia et al. |
| 8,735,372 B2 | 5/2014 | Du et al. |
| 8,742,101 B2 | 6/2014 | Storer et al. |
| 8,759,510 B2 | 7/2014 | Du et al. |
| 8,765,710 B2 | 7/2014 | Sofia et al. |

(Continued)

FOREIGN PATENT DOCUMENTS

WO WO 1998/016184 4/1998
WO WO 1998/016186 4/1998

(Continued)

OTHER PUBLICATIONS

Clark et al., Bioorganic and Medicinal Chemistry Letters, 2015, 25, pp. 2484-2487.*
Chang, W. et al. "Discovery of PSI-353661, a Novel Purine Nucleotide Prodrug for the Treatment of HCV Infection" ACS Med Chem Lett. 2011, 2, 130.
Clark M.O. et al. Bioorganic and Medicinal Chemistry Letters 2015, 25, 2484-2487.
Murakami, E. et at "Adenosine Deaminase-like Protein 1 (ADAL1): Characterization and Substrate Specificity in the Hydrolysis of N6- or O6-Substituted Purine or 2-Aminopurine Nucleoside Monophosphates" J Med Chem 2011, 54, 5902.

(Continued)

*Primary Examiner* — Traviss C McIntosh, III
(74) *Attorney, Agent, or Firm* — Knowles Intellectual Property Strategies, LLC

(57) ABSTRACT

A compound or a pharmaceutically acceptable salt or composition thereof for the treatment of a host infected with or exposed to a virus of the Paramyxoviridae or Orthomyxoviridae family, or other disorders, in particular respiratory syncytial virus, more fully described herein.

20 Claims, No Drawings

(56) References Cited

U.S. PATENT DOCUMENTS

| | | |
|---|---|---|
| 8,772,474 B2 | 7/2014 | Beigelman et al. |
| 8,815,829 B2 | 8/2014 | Schinazi et al. |
| 8,871,737 B2 | 10/2014 | Smith et al. |
| 8,877,731 B2 | 11/2014 | Beigelman et al. |
| 8,877,733 B2 | 11/2014 | Cho et al. |
| 8,906,880 B2 | 12/2014 | Du et al. |
| 8,951,985 B2 | 2/2015 | Surleraux et al. |
| 8,957,045 B2 | 2/2015 | Sofia et al. |
| 8,957,046 B2 | 2/2015 | Du et al. |
| 9,012,427 B2 | 4/2015 | Blatt et al. |
| 9,045,520 B2 | 6/2015 | Chun et al. |
| 9,061,041 B2 | 6/2015 | Girijavallabhan et al. |
| 9,073,960 B2 | 7/2015 | Beigelman et al. |
| 9,085,573 B2 | 7/2015 | Du et al. |
| 9,090,642 B2 | 7/2015 | Cho et al. |
| 9,109,001 B2 | 8/2015 | Parsy et al. |
| 9,139,604 B2 | 9/2015 | Boojamra et al. |
| 9,156,872 B2 | 10/2015 | Girijavallabhan et al. |
| 9,173,893 B2 | 11/2015 | Cho et al. |
| 9,187,515 B2 | 11/2015 | Mayes et al. |
| 9,211,300 B2 | 12/2015 | Mayes et al. |
| 9,243,025 B2 | 1/2016 | Surleraux et al. |
| 9,249,174 B2 | 2/2016 | Beigelman et al. |
| 9,278,990 B2 | 3/2016 | Smith et al. |
| 9,296,777 B2 | 3/2016 | Sofia et al. |
| 9,346,848 B2 | 5/2016 | Beigelman et al. |
| 9,365,605 B2 | 6/2016 | Beigelman et al. |
| 9,422,322 B2 | 8/2016 | Dyatkina et al. |
| 9,441,007 B2 | 9/2016 | Wang et al. |
| 9,603,863 B2 | 3/2017 | Blatt et al. |
| 9,603,864 B2 | 3/2017 | Blatt et al. |
| 9,815,864 B2 | 11/2017 | Beigelman et al. |
| 9,828,410 B2 | 11/2017 | Sommadossi et al. |
| 9,862,742 B2 | 1/2018 | Beigelman et al. |
| 9,890,188 B2 | 2/2018 | Wang et al. |
| 2004/0063658 A1 | 4/2004 | Roberts et al. |
| 2004/0229839 A1 | 11/2004 | Babu et al. |
| 2004/0259934 A1 | 12/2004 | Olsen et al. |
| 2006/0241064 A1 | 10/2006 | Roberts et al. |
| 2010/0240604 A1 | 9/2010 | Beigelman et al. |
| 2010/0249068 A1 | 9/2010 | Beigelman et al. |
| 2011/0257121 A1 | 10/2011 | Chang et al. |
| 2012/0009147 A1 | 1/2012 | Cho et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2013/0315868 A1 | 5/2013 | Mayes et al. |
| 2013/0210757 A1 | 8/2013 | Huang et al. |
| 2014/0038916 A1 | 2/2014 | Wang et al. |
| 2014/0212382 A1 | 7/2014 | Schinazi et al. |
| 2014/0235566 A1 | 8/2014 | Amblard et al. |
| 2014/0309413 A1 | 10/2014 | Rose et al. |
| 2015/0011497 A1 | 1/2015 | Beigelman et al. |
| 2015/0105341 A1 | 4/2015 | Beigelman et al. |
| 2015/0366887 A1 | 12/2015 | Blatt et al. |
| 2015/0366888 A1 | 12/2015 | Blatt et al. |
| 2016/0002281 A1 | 1/2016 | Mayes et al. |
| 2016/0016986 A1 | 1/2016 | Deshpande et al. |
| 2016/0176910 A1 | 6/2016 | Wang et al. |
| 2016/0257706 A1 | 9/2016 | Sommadossi et al. |
| 2016/0271162 A1 | 9/2016 | Moussa et al. |
| 2017/0004669 A1 | 1/2017 | Carroll et al. |
| 2017/0233428 A1 | 8/2017 | Coats et al. |

FOREIGN PATENT DOCUMENTS

| | | |
|---|---|---|
| WO | WO 2001/90121 A2 | 11/2001 |
| WO | WO 2001/92282 A2 | 12/2001 |
| WO | WO 2002/32920 A2 | 4/2002 |
| WO | WO 2002/057425 A2 | 7/2002 |
| WO | WO 2002/100415 A2 | 12/2002 |
| WO | WO 2003/062256 A1 | 7/2003 |
| WO | WO 2003/073989 A2 | 9/2003 |
| WO | WO 2004/002999 A2 | 1/2004 |
| WO | WO 2004/003000 A2 | 1/2004 |
| WO | WO 2005/009418 A2 | 2/2005 |
| WO | WO 2005/020884 A2 | 3/2005 |
| WO | WO 2005/021568 A2 | 3/2005 |
| WO | WO 2006/000922 A2 | 1/2006 |
| WO | WO 2006/012078 A2 | 2/2006 |
| WO | WO 2006/094347 A1 | 9/2006 |
| WO | WO 2006/121820 A1 | 11/2006 |
| WO | WO 2007/113538 A1 | 10/2007 |
| WO | WO 2008/062206 A2 | 5/2008 |
| WO | WO 2008/095040 A2 | 8/2008 |
| WO | WO 2008/117046 A1 | 10/2008 |
| WO | WO 2008/117047 A1 | 10/2008 |
| WO | WO 2008/121634 A2 | 10/2008 |
| WO | WO 2009/067409 A1 | 5/2009 |
| WO | WO 2009/086192 A1 | 7/2009 |
| WO | WO 2009/129120 A2 | 10/2009 |
| WO | WO 2009/132135 A1 | 10/2009 |
| WO | WO 2009/152095 A2 | 12/2009 |
| WO | WO 2010/002877 A2 | 1/2010 |
| WO | WO 2010/030858 A1 | 3/2010 |
| WO | WO 2010/081082 A2 | 7/2010 |
| WO | WO 2010/091386 A2 | 8/2010 |
| WO | WO 2010/108135 A1 | 9/2010 |
| WO | WO 2010/108140 A1 | 9/2010 |
| WO | WO 2011/035231 A1 | 3/2011 |
| WO | WO 2012/012465 A1 | 1/2012 |
| WO | WO 2012/012776 A1 | 1/2012 |
| WO | WO 2012/037038 A1 | 3/2012 |
| WO | WO 2012/040127 A1 | 3/2012 |
| WO | WO 2012/048013 A2 | 4/2012 |
| WO | WO 2012/092484 A2 | 7/2012 |
| WO | WO 2012/154321 A1 | 11/2012 |
| WO | WO 2012/158811 A2 | 11/2012 |
| WO | WO 2013/009737 A1 | 1/2013 |
| WO | WO 2013/019874 A1 | 2/2013 |
| WO | WO 2013/092481 A1 | 6/2013 |
| WO | WO 2013/096679 A1 | 6/2013 |
| WO | WO 2013/096680 A1 | 6/2013 |
| WO | WO 2013/138236 A1 | 9/2013 |
| WO | WO 2013/142157 A1 | 9/2013 |
| WO | WO 2013/142159 A1 | 9/2013 |
| WO | WO 2013/142525 A1 | 9/2013 |
| WO | WO 2013/177219 A1 | 11/2013 |
| WO | WO 2013/187978 A1 | 12/2013 |
| WO | WO 2014/008236 A1 | 1/2014 |
| WO | WO 2014/047117 A1 | 3/2014 |
| WO | WO 2014/070771 A1 | 5/2014 |
| WO | WO 2014/076490 A1 | 5/2014 |
| WO | WO 2014/079903 A1 | 5/2014 |
| WO | WO 2014/082935 A1 | 6/2014 |
| WO | WO 2014/100498 A1 | 6/2014 |
| WO | WO 2014/100505 A1 | 6/2014 |
| WO | WO 2014/124430 A1 | 8/2014 |
| WO | WO 2014/209979 A1 | 12/2014 |
| WO | WO 2014/209983 A1 | 12/2014 |
| WO | WO 2015/081133 A2 | 6/2015 |
| WO | WO 2015/095305 A1 | 6/2015 |
| WO | WO 2015/158913 A1 | 10/2015 |
| WO | WO 2016/041877 A1 | 3/2016 |
| WO | WO 2016/069975 A1 | 5/2016 |
| WO | WO 2016/100569 A1 | 6/2016 |
| WO | WO 2016/115222 A1 | 7/2016 |
| WO | WO 2016/144918 A1 | 9/2016 |
| WO | WO 2016/145142 A1 | 9/2016 |
| WO | WO 2016/188943 A1 | 12/2016 |
| WO | WO 2018/013937 A1 | 1/2018 |

OTHER PUBLICATIONS

PCT/US2017/40848 International Search Report and Written Opinion, dated Nov. 3, 2017; 14 pages.

Pradere, U. et al. "Synthesis of 5'-Methylene-Phosphonate Furanonucleoside Prodrugs: Application to D-2'-Deoxy-2'-α-fluoro 2'-β-C-methyl Nucleosides" Organic Letters 2012, 14, 4426.

Reddy, P. et al. "2'-Deoxy-2'-α-fluoro-2'-β-C-methyl 3',5'-cyclic phosphate nucleotide prodrug analogs as inhibitors of HCV NS5B polymerase: Discovery of PSI-352938" Bioorganic & Medicinal Chemistry Letters 2010, 20, 7376.

(56) References Cited

OTHER PUBLICATIONS

Tao, S., Zhou, L., Zhang, H., Zhou, S., Amiralaei, S., Shelton, J.R., Coats, S.J., Schinazi, R.F.: Comparison of Three 2'-C-Methyl Guanosine Prodrugs for Hepatitis C including a Novel $^2$-D-2'-C-Me-2,6-Diaminopurine Ribonucleoside Phosphoramidate (RS-1389): Interspecies Hepatocyte and Human Cardiomyocyte Metabolism Profiles. The Liver Meeting 2014. Boston, MA, USA. Nov. 6-11, 2014.

Zhou, L. et al. "β-D-2'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem 2015, 58, 3445.

Freeman et al. 2-amino-9(3-azido-2,3-dideoxy-β-D-erythro-pentofuranosyl)-6-Substituted-9H-Purines: Synthesis and Anti-HIV Activity. Bioorganic and Medicinal Chemistry, 1995; 3(4): 447-448.

\* cited by examiner

β-D-2'-DEOXY-2'-SUBSTITUTED-4'-SUBSTITUTED-2-SUBSTITUTED-N⁶-SUBSTITUTED-6-AMINOPURINENUCLEOTIDES FOR THE TREATMENT OF PARAMYXOVIRUS AND ORTHOMYXOVIRUS INFECTIONS

CROSS-REFERENCE TO RELATED APPLICATIONS

This application is a continuation of International Application No. PCT/US2017/40848 filed on Jul. 6, 2017, and also claims the benefit of priority to provisional U.S. Application No. 62/359,877, filed on Jul. 8, 2016. The entirety of each of these applications are hereby incorporated by reference for all purposes.

FIELD OF THE INVENTION

The present invention is directed to nucleotide compounds and their medical uses to treat a paramyxovirus or an orthomyxovirus.

BACKGROUND OF THE INVENTION

The Paramyxoviridae family is a family of single stranded RNA viruses in the order Mononegavirales. Genera of the Paramyxoviridae family include *Paramyxovirus, Pneumovirus, Morbillivirus, Rubulavirus,* and *Henipavirus*. These viruses can be transmitted person to person via direct or close contact with contaminated respiratory droplets or fomites. The *Henipavirus* genus includes the species *Cedar* virus, *Hendra* virus and *Nipah* virus. The *Metapneumovirus* genus includes the human metapneumovirus. The *Morbillivirus* genus includes the species measles virus. The *Respirovirus* genus includes the Sendai virus and the human parainfluenza viruses 1 and 3. The *Rubulavirus* genus includes the mumps virus and the human parainfluenza viruses 2 and 4. The *Pneumovirus* genus includes respiratory syncytial virus (RSV).

RSV is a nonsegmented negative-strand (NNS) RNA virus that can cause respiratory infections and is associated with bronchiolitis and pneumonia. The virus can be the cause of infections in bone marrow as well as solid organ transplant patients, cystic fibrosis patients and congenital heart disease patients, and is increasingly being recognized as the cause of respiratory tract disease in elderly, non-immunocompromised adults. There are currently two known strains of RSV: the A strain and the B strain.

As with most Paramyxoviridae, RSV is transmitted person to person via direct or close contact with contaminated respiratory droplets or fomites. Symptoms of an RSV infection include coughing, sneezing, runny nose, fever, decreased appetite, and wheezing. RSV is the most common cause of bronchiolitis and pneumonia in children under one year of age in the world. In addition, RSV can be the cause of tracheobronchitis in older children and adults. Worldwide, sixty four million people are infected annually with RSV, resulting in up to 200,000 deaths. In the United States, it is estimated that between 75,000 and 125,000 infants are hospitalized each year with RSV. In addition, among adults over the age of sixty five, an estimated 14,000 deaths and 177,000 hospitalizations are attributed to RSV each year.

Treatment options for people infected with RSV are currently limited. There is no reliable vaccine against RSV despite work spanning over forty years. While antibiotics typically prescribed to treat bacterial infections and over-the-counter medications may relieve some RSV symptoms, they are not effective in treating the virus itself In severe cases, a nebulized bronchodilator, such as albuterol, may be prescribed to relieve symptoms such as wheezing. Respi-Gram® (RSV-IGIV, Medimmune, approved for high risk children younger than 24 months of age), Synagis® (palivizumab, Medimmune, approved for high risk children younger than 24 months of age), and Virzole® (ribavirin by aerosol, ICN pharmaceuticals) have been approved for the treatment of RSV.

Palivizumab, a prophylactically administered humanized anti-RSV fusion protein monoclonal antibody is the most widely used preventive therapy against RSV for premature and high-risk infants. Ribavirin must be administered by small-particle aerosol for 12-18 h per day for 3-7 days. The drug is only marginally effective against RSV and is not indicated in adults. See, Dunn et al., "Inhibition of respiratory syncytial virus in vitro and in vivo by the immunosuppressive agent leflunomide", Antiviral Ther., 16, 309-317, 2011.

The Orthomyxoviridae are a family of RNA viruses that includes six genera: Influenzavirus A, Influenzavirus B, Influenzavirus C, Isavirus, Quaranjavirus, and Thogotovirus. The first three genera contain viruses that cause influenza in vertebrates, including birds (see also avian influenza), humans, and other mammals. Influenzavirus A has been further classified into types based on the viral surface proteins: hemagglutinin (H or HA) and neuraminidase (N). There are approximately 16 H antigens (H1 to H16) and 9 N antigens (N1 to N9). Influenza A includes several subtypes including: H1N1, H1N2, H2N2, H3N1, H3N2, H3N8, H5N1, H5N2, H5N3, H5N8, H5N9, H7N1, H7N2, H7N3, H7N4, H7N7, H9N2, H10N7. Isaviruses infect salmon; thogotoviruses infect vertebrates and invertebrates, such as mosquitoes and sea lice.

Influenza is mainly spread from person to person by droplet infection or droplet nuclei created by sneezing, coughing or talking. The port of entry of the virus is the respiratory tract. Complications from an influenza viral infection include pneumonia, bronchitis, dehydration, and sinus and ear infections. Medications currently approved by the FDA for the treatment of an influenza infection include amantadine, Relenza® (zanamivir, GlaxoSmithKline), Rapivab® (peramivir, BioCryst Pharmaceuticals, Inc.), rimantadine, and Tamiflu® (oseltamivir, Genentech).

The RSV non-structural protein RNA-dependent RNA polymerase is a key enzyme responsible for initiating and catalyzing viral RNA synthesis. As a result, RSV RNA-dependent RNA polymerase is an attractive target for the current drug discovery and development of anti-RSV agents. In general, there are two major subclasses of RNA-dependent RNA polymerase inhibitors: nucleoside analogs, which are anabolized to their active triphosphates—which act as alternative substrates for the polymerase—and non-nucleoside inhibitors (NNIs), which bind to allosteric regions on the protein. Nucleoside or nucleotide inhibitors mimic natural polymerase substrates and act as chain terminators. They inhibit the initiation of RNA transcription and elongation of a nascent RNA chain.

In 1976, Moffatt et al. reported on the synthesis of the nucleoside antibiotic nucleocidin; see structure below:

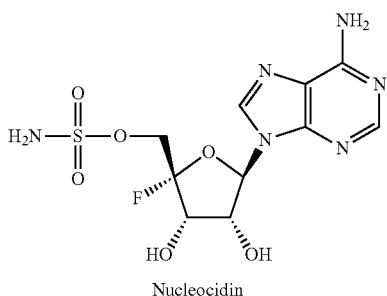 [SMILES: Nc1ncnc2c1ncn2[C@@H]1O[C@](F)(COS(N)(=O)=O)[C@@H](O)[C@H]1O]

Nucleocidin

The structure of nucleocidin was unique in that it was the first natural product to contain either a fluoro carbohydrate or an unsubstituted sulfamoyl group. In addition, it appeared to be the first example of a furanose sugar bearing a functional substituent at the 4'-position, see, "4'-Substituted Nucleosides. 2. Synthesis of the Nucleoside Antibiotic Nucleocidin", Moffatt, J. G. et al., J. Am. Chem. Soc., 98(11)3346-3357, 1976. Moffatt et al. also reported on the synthesis of 4'-fluorouridine derivatives, see, "4'-Substituted Nucleosides. 3. Synthesis of Some 4'-Fluorouridine Derivatives", Owens, G. R., et al., J. Org. Chem., 41(18)3010-3017, 1976.

Patents and patent applications describing nucleosides and nucleotides include WO 1998/016184; WO 1998/016186; WO 2002/100415; WO 2003/073989; U.S. 2004/0229839; US; WO 2005/009418; WO 2005/020884; WO 2005/021568; WO 2006/000922; WO 2006/094347; WO 2007/113538; WO 2008/117047; WO 2008/117046; WO 2008/121634; WO 2009/152095; WO 2009/132135, WO 2012/012776; U.S. 2016/0176910; and U.S. Pat. Nos. 7,964,580; 8,173,621; 8,334,270; 8,580,765; 8,735,372; 8,759,510; 8,906,880; 8,957,046; 9,085,573; 5,420,115; 9,073,960, 9,441,007; 7,429,572; 9,422,322; 7,138,376; 9,187,515; and, 9,211,300.

Additional patent and patent applications include WO 2010/002877; WO 2010/030858; WO 2010/091386; WO 2010/108135; WO 2010/108140; WO 2011/035231; U.S. 2012/0009147; U.S. 2012/0071434; U.S. Pat. No. 8,877,731; WO 2012/012465; WO 2012/037038; U.S. Pat. No. 9,073,960; WO 2013/019874; WO 2013/092481; WO 2013/138236; U.S. 2014/0309413; WO 2014/070771; WO 2014/079903; WO 2014/100505; U.S. 2015/0366888; WO 2016/041877; U.S. 2016/0016986 U.S. Pat. No. 9,296,777; WO 2016/188943; WO 2016/069975; WO 2015/081133; and, U.S. 2016/0257706.

As the treatment options for people infected with viruses of the Paramyxoviridae and Orthomyxoviridae families are limited, there remains a strong medical need to develop anti-Paramyxoviridae and anti-Orthomyxoviridae therapies that are safe, effective and well-tolerated. The need is accentuated by the expectation that drug resistance can arise, as seen in anti-HIV and anti-HCV therapies, and new combination drug therapies may be needed to treat viruses of the Paramyxoviridae and Orthomyxoviridae families. More potent direct-acting antivirals could significantly shorten treatment duration and improve compliance and SVR rates for patients infected with viruses of the Paramyxoviridae and Orthomyxoviridae families.

It is therefore an object of the present invention to provide compounds, pharmaceutical compositions, and methods to treat or prevent infections by viruses of the Paramyxoviridae and Orthomyxoviridae families.

SUMMARY OF THE INVENTION

It has been discovered that the compounds of Formula I, Formula II, Formula III, Formula IV, Formula V, and Formula VI are advantageous against a paramyxovirus or an orthomyxovirus when administered in an effective amount to a host in need thereof. The host can be a human or any other animal that carries the viral infection, for example a dog, horse, cow, or cat.

In one embodiment, a therapeutically effective amount of one or more compounds of Formula I, Formula II, Formula III, Formula IV, Formula V, and Formula VI or a pharmaceutically acceptable salt thereof, can be used to treat a paramyxovirus or an orthomyxovirus infection in a host in need thereof such as a human. In one embodiment, a therapeutically effective amount of one or more compounds of Formula I, Formula II, Formula III, Formula IV, Formula V and Formula VI or a pharmaceutically acceptable salt thereof, can be used to treat an RSV infection in a host in need thereof such as a human.

Thus, in one embodiment, the invention is:

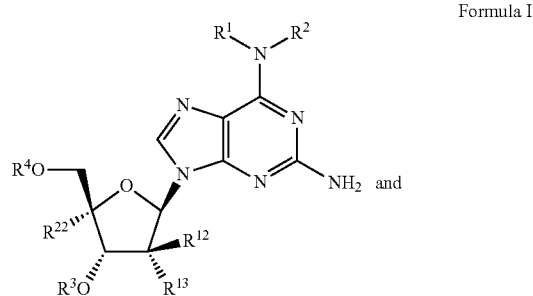

Formula I

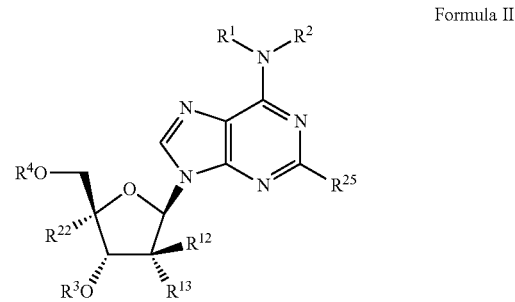

Formula II or a pharmaceutically acceptable composition, salt, or prodrug thereof, wherein:

$R^1$ is $C_1$-$C_5$alkyl (including methyl, ethyl, n-propyl, iso-propyl, n-butyl, iso-butyl, sec-butyl, tert-butyl and pentyl) or —($C_0$-$C_2$alkyl)($C_3$-$C_6$cycloalkyl);

$R^2$ is hydrogen, $C_1$-$C_5$alkyl (including methyl, ethyl, n-propyl, iso-propyl, n-butyl, iso-butyl, sec-butyl, tert-butyl and pentyl), $CHF_2$, $CH_2F$, $CF_3$, —($C_0$-$C_2$alkyl)($C_3$-$C_6$cycloalkyl), —C(O)$R^{3C}$, —($C_0$-$C_2$alkyl)(aryl), —($C_0$-$C_2$alkyl)(heterocycle), —($C_0$-$C_2$alkyl)(heteroaryl); or $R^1$ and $R^2$ together with the nitrogen to which they are bonded can form a heterocycle;

$R^3$ is hydrogen,

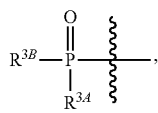

diphosphate, triphosphate, an optionally substituted carbonyl linked amino acid, or —C(O)R$^{3C}$;

$R^{3A}$ can be selected from O$^-$, OH, an —O-optionally substituted aryl, an —O-optionally substituted heteroaryl, or an optionally substituted heterocyclyl;

$R^{3B}$ can be selected from O$^-$, OH, an optionally substituted N-linked amino acid or an optionally substituted N-linked amino acid ester;

$R^{3C}$ is alkyl, alkenyl, alkynyl, —(C$_0$-C$_2$)(cycloalkyl), —(C$_0$-C$_2$)(heterocyclo), —(C$_0$-C$_2$)(aryl), —(C$_0$-C$_2$)(heteroaryl), —O-alkyl, —O-alkenyl, —O-alkynyl, —O-(C$_0$-C$_2$)(cycloalkyl), —O—(C$_0$-C$_2$)(heterocyclo), —O—(C$_0$-C$_2$)(aryl), —O—(C$_0$-C$_2$)(heteroaryl), —S-alkyl, —S-alkenyl, —S-alkynyl, —S—(C$_0$-C$_2$)(cycloalkyl), —S—(C$_0$-C$_2$)(heterocyclo), —S—(C$_0$-C$_2$)(aryl), or —S—(C$_0$-C$_2$)(heteroaryl) each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or $R^3$ and $R^4$ together with the oxygens that they are bonded to can form a 3',5'-cyclic prodrug;

$R^5$ is hydrogen, C$_1$-C$_5$alkyl (including methyl, ethyl, n-propyl, iso-propyl, n-butyl, iso-butyl, sec-butyl, tert-butyl and pentyl), or —(C$_0$-C$_2$alkyl)(C$_3$-C$_6$cycloalkyl);

$R^6$ is C$_1$-C$_5$alkyl (including methyl, ethyl, n-propyl, iso-propyl, n-butyl, iso-butyl, sec-butyl, tert-butyl and pentyl), —(C$_0$-C$_2$alkyl)(C$_3$-C$_6$cycloalkyl), —(C$_{0-6}$alkyl)(aryl), —(C$_{0-6}$alkyl)(heteroaryl), —(C$_{0-6}$alkyl)(heterocycle) or —C(O)R$^{3C}$;

$R^{12}$ is hydrogen, F, Cl, or Br;

$R^{13}$ is hydrogen, OR$^3$, F, Cl, or Br;

$R^{22}$ is CONH$_2$, NH$_2$, NR$^5$R$^6$, CN, optionally substituted C$_{1-6}$ alkyl, optionally substituted C$_{1-6}$ haloalkyl including —CH$_2$F and CH$_2$Cl; optionally substituted C$_{2-6}$ alkenyl, optionally substituted C$_{2-6}$ alkynyl, optionally substituted C$_{3-6}$ cycloalkyl, optionally substituted —O—C$_{1-6}$ alkyl, optionally substituted —O—C$_{3-6}$ alkenyl, or an optionally substituted —O—C$_{3-6}$ alkynyl;

$R^{25}$ is Cl, Br, F, CN, N$_3$, C$_1$-C$_6$ alkyl, C$_2$-C$_6$ alkenyl, C$_2$-C$_6$ alkynyl, —(C$_1$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl), —(C$_0$-C$_2$alkyl)(heteroaryl), —ONHC(=O)OR$^{26}$, —NHOR$^{27}$, —SR$^{28}$, —NH(CH$_2$)$_{1-4}$N(R$^{29}$)$_2$, —NHNHR$^{29}$, —N=NR$^{30}$, —NHC(O)NHNHR$^{30}$, —NHC(S)NHNHR$^{30}$, —C(O)NHNHR$^{30}$, —NR$^{30}$SO$_2$R$^{31}$, —SO$_2$NR$^{30}$R$^{32}$, —C(O)NR$^{30}$R$^{32}$, —CO$_2$R$^{32}$, —SO$_2$R$^{32}$,

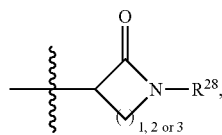

—P(O)H(OR$^{32}$), —P(O)(OR$^{32}$)(OR$^{33}$), —P(O)(OR$^{32}$)(NR$^{32}$R$^{33}$) or —NR$^5$R$^6$; for example including but not limited to the following embodiments, chloro, bromo, fluoro, cyano, azido, methyl, ethyl, n-propyl, iso-propyl, n-butyl, iso-butyl, sec-butyl, tert-butyl and n-pentyl, 1,1-dimethylpropyl, 2,2-dimtheylpropyl, 3-methylbutyl, 1-methylbutyl, 1-ethylpropyl, vinyl, allyl, 1-butynyl, 2-butynyl, acetylenyl, cyclopropyl, cyclobutyl, cyclopentyl, cyclohexyl, —(CH$_2$)-cyclopropyl, —(CH$_2$)-cyclobutyl, —(CH$_2$)-cyclopentyl, —(CH$_2$)-cyclohexyl, aziridine, oxirane, thiirane, azetidine, oxetane, thietane, pyrrolidine, tetrahydrofuran, thiolane, pyrazolidine, piperidine, oxane, thiane, —(CH$_2$)-aziridine, —(CH$_2$)-oxirane, —(CH$_2$)-thiirane, —(CH$_2$)-azetidine, —(CH$_2$)-oxetane, —(CH$_2$)-thietane, —(CH$_2$)-pyrrolidine, —(CH$_2$)-tetrahydrofuran, —(CH$_2$)-thiolane, —(CH$_2$)-pyrazolidine, —(CH$_2$)-piperidine, —(CH$_2$)-oxane, —(CH$_2$)-thiane, phenyl, pyridyl, —ONHC(=O)OCH$_3$, —ONHC(=O)OCH$_2$CH$_3$, —NHOH, NHOCH$_3$, —OCH$_3$, OC$_2$H$_5$, —OPh, OCH$_2$Ph, —SCH$_3$, —SC$_2$H$_5$, —SPh, SCH$_2$Ph, —NH(CH$_2$)$_2$NH$_2$, —NH(CH$_2$)$_2$N(CH$_3$)$_2$, —NHNH$_2$, —NHNHCH$_3$, —N=NH, —N=NCH$_3$, —N=NCH$_2$CH$_3$, —NHC(O)NHNH$_2$, —NHC(S)NHNH$_2$, —C(O)NHNH$_2$, —NHSO$_2$CH$_3$, —NHSO$_2$CH$_2$CH$_3$, —SO$_2$NHCH$_3$, —SO$_2$N(CH$_3$)$_2$, —C(O)NH$_2$, —C(O)NHCH$_3$, —C(O)N(CH$_3$)$_2$, —CO$_2$CH$_3$, —CO$_2$CH$_2$CH$_3$, —CO$_2$Ph, —CO$_2$CH$_2$Ph, —SO$_2$CH$_3$, —SO$_2$CH$_2$CH$_3$, —SO$_2$Ph, —SO$_2$CH$_2$Ph,

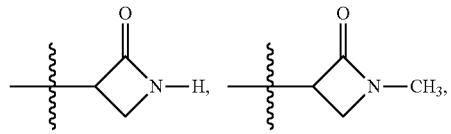

—P(O)H(OH), —P(O)H(OCH$_3$), —P(O)(OH)(OH), —P(O)(OH)(OCH$_3$), —P(O)(OCH$_3$)(OCH$_3$), —P(O)(OH)(NH$_2$), —P(O)(OH)(NHCH$_3$), —P(O)(OH)N(CH$_3$)$_2$, —NHC(O)CH$_3$, —NHC(O)CH$_2$CH$_3$, —NHC(O)CH(CH$_3$)$_2$, —NHC(O)OCH$_3$, —NHC(O)OCH$_2$CH$_3$, —NHC(O)OCH(CH$_3$)$_2$, —NHC(O)OCH$_2$CH$_2$CH$_3$, —NHC(O)OCH$_2$CH$_2$CH$_2$CH$_3$ and NHC(O)OCH$_2$CH$_2$CH$_2$CH$_2$CH$_3$;

$R^{26}$ is C$_1$-C$_5$alkyl, —(C$_0$-C$_2$alkyl)(C$_3$-C$_6$cycloalkyl), —(C$_0$-C$_2$alkyl)(heterocycle)-(C$_{0-2}$alkyl)(aryl) or —(C$_0$-C$_2$alkyl)(heteroaryl) each of which can be optionally substituted;

$R^{27}$ is hydrogen, C$_1$-C$_6$ alkyl, —(C$_1$-C$_2$alkyl)(C$_3$-C$_6$cycloalkyl), —(C$_1$-C$_2$alkyl)(C$_3$-C$_6$heterocycle) —(C$_0$-C$_2$alkyl)(aryl) or —(C$_0$-C$_2$alkyl)(heteroaryl) wherein except for the hydrogen each of which can be optionally substituted;

$R^{28}$ is hydrogen, C$_1$-C$_6$ alkyl, C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) wherein except for the hydrogen each of which can be optionally substituted;

$R^{29}$ is independently selected from hydrogen, C$_1$-C$_6$alkyl, —(C$_0$-C$_2$alkyl)(C$_3$-C$_6$cycloalkyl), —(C$_0$-C$_2$alkyl)(heterocycle), —(C$_0$-C$_2$alkyl)(aryl), or —(C$_0$-C$_2$alkyl)(heteroaryl) wherein except for the hydrogen each of which can be optionally substituted;

$R^{30}$ hydrogen or optionally substituted C$_1$-C$_6$ alkyl;

$R^{31}$ is C$_1$-C$_6$ alkyl, C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) each of which can be optionally substituted;

$R^{32}$ is hydrogen, $C_1$-$C_6$ alkyl, $C_2$-$C_6$ alkenyl, $C_2$-$C_6$ alkynyl, —($C_0$-$C_2$alkyl)($C_3$-$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) wherein except for the hydrogen each of which can be optionally substituted; or $R^{30}$ and $R^{32}$ together with the nitrogen that they are bonded to can form a heterocyclic ring;

$R^{33}$ is hydrogen, $C_1$-$C_6$ alkyl, $C_2$-$C_6$ alkenyl, $C_2$-$C_6$ alkynyl, —($C_0$-$C_2$alkyl)($C_3$$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) wherein except for the hydrogen each of which can be optionally substituted; or $R^{32}$ and $R^{33}$ can be bonded together to form a heterocyclic ring.

In one embodiment, —C(O)$R^{3C}$ can be —C(S)$R^{3C}$.

In an alternative embodiment, the compound of Formula I or II is a pharmaceutically acceptable sulfate salt, such as the $H_2SO_4$.

In particular, it has been discovered that a 5'-stabilized phosphate prodrug or derivative of a β-D-2'-deoxy-2'-substituted-4'-substituted-$N^6$-methyl-2,6-diaminopurine nucleotide, as well as a β-D-2'-deoxy-2'-substituted-4'-substituted-$N^6$-dimethyl-2,6-diaminopurine nucleotide as described below are advantageous against RSV. Example 3 discusses the activity of representative compounds against RSV in dNHBE cells. As shown in Table 3 and Table 4, a number of compounds have $EC_{90}$ values in the nanomolar region. The metabolism of the β-D-2'-deoxy-2'-substituted-4'-substituted-$N^6$-methyl-2,6-diaminopurine nucleoside as a phosphoramidate involves the production of a 5'-monophosphate and the subsequent anabolism of the $N^6$-methyl-2,6-diaminopurine base to generate the β-D-2'-deoxy-2'-substituted-4'-substituted-guanine nucleoside as the 5'-monophosphate. The monophosphate is then further anabolized to the active species: the 5'-triphosphate (Scheme 1 below). Active triphosphate concentration was measured for representative compounds in a hamster lung triphosphate assay (Example 4, Table 7). Compounds were administered to hamsters and after 72 hours, the lung triphosphate concentration was measured. As shown in Table 7, the lung triphosphate concentration after exposure to select compounds of the present invention was greater than 800 ng/g, indicating a superior pharmokinetic profile.

The metabolism of the β-D-2'-deoxy-2'-substituted-4'-substituted-$N^6$-dimethyl-2,6-diaminopurine nucleotide involves both the formation of the β-D-2'-deoxy-2'-substituted-4'-substituted-$N^6$-dimethyl-2,6-diaminopurine nucleoside triphosphate as well as the generation of the corresponding guanine nucleoside triphosphate.

2'-Deoxy-2'-substituted-4'-substituted-$N^6$-substituted-2,6-diaminopurine nucleotides can be further substituted at the $N^2$-position by alkylation or acylation which may enhance the lipophilicity, pharmacokinetics or targeting of the nucleotide to the liver. It has been discovered that 2'-deoxy-2'-substituted-4'-substituted-$N^6$-substituted-2,6-diaminopurine nucleotides further substituted at the 2-position of the diaminopurine can be dealkylated or deacylated by hepatic enzymes to further increase the specificity of the nucleotide derivatives both in vitro and in vivo.

For example, the nucleoside phosphoramidate 2'-deoxy-2'-substituted-4'-substituted-$N^2$-methyl-$N^6$-methyl-2,6-diaminopurine nucleoside phosphoramidate is dealkylated to 2'-deoxy-2'-substituted-4'-substituted-$N^6$-methyl-2,6-diaminopurine nucleoside phosphoramidate when incubated with a human liver S9 fraction in vitro.

Unless otherwise specified, the compounds described herein are provided in the β-D-configuration. In an alternative embodiment, the compounds can be provided in a β-L-configuration. Likewise, any substituent group that exhibits chirality can be provided in racemic, enantiomeric, diastereomeric form or any mixture thereof. Where a phosphoramidate, thiophosphoramidate or other stabilized phosphorus prodrug in which the phosphorus exhibits chirality is used as the $R^4$-stabilized phosphate prodrug, it can be provided as an R or S chiral phosphorus derivative or a mixture thereof, including a racemic mixture. The amino acid of the phosphoramidate or thiophosphoramidate can be in the D- or L-configuration, or a mixture thereof, including a racemic mixture. The amino acid of the phosphoramidate or thiophosphoramidate can also be a dehydroamino acid. All of the combinations of these stereo configurations are included in the invention described herein.

Compounds, methods, and compositions are provided for the treatment of a host infected with a Paramyxoviridae and Orthomyxoviridae virus via administration of an effective amount of the compound of Formula I-VI or its pharmaceutically acceptable salt.

The compounds and compositions can also be used to treat related conditions such as anti-RSV antibody positive and antigen positive conditions. The compound or formulations that include the compounds can also be used prophylactically to prevent or restrict the progression of clinical illness in individuals who are anti-RSV antibody or antigen positive or who have been exposed to respiratory syncytial virus.

Accordingly, the present invention includes a compound of Formula I, or a pharmaceutically acceptable composition, salt, or prodrug thereof, as described below.

Formula I

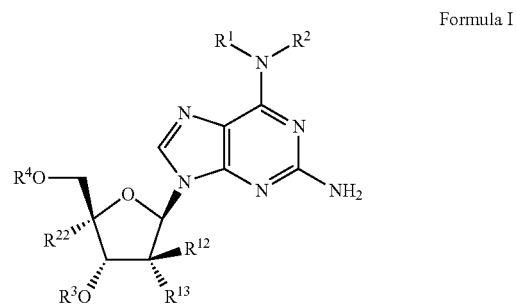

In one specific embodiment, the parent nucleoside, i.e., the nucleoside wherein $R^4$ is hydrogen and the 5'-position thus has a hydroxyl group, is not substantially deaminated by adenosine deaminase under conditions that mimic the in vivo environment (e.g., ambient temperature and aqueous physiological pH), for a period of 7 minutes, 10 minutes, 30 minutes, 60 minutes or 120 minutes. Unless otherwise stated, the time period is 30 minutes. In this embodiment, the term "not substantially deaminated" means that the parent compound is not converted to the corresponding guanine derivative, or 6-oxo derivative, in an amount sufficient to provide a therapeutic effect in vivo. It has been discovered that compounds of the present invention are anabolized to a 5-monophosphate and then subsequently anabolized at the 6-position to generate active guanine triphosphate compounds (Scheme 1) and that this property is advantageous for treating Paramyxoviridae and Orthomyxoviridae infections in a host in combination with substitutions in the 4'-position.

In another embodiment, compounds of Formula Ia are disclosed:

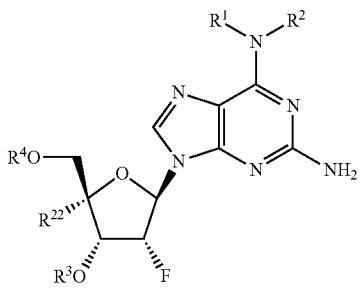

Formula Ia or a pharmaceutically acceptable composition, salt, or prodrug thereof,
wherein:
$R^1$, $R^2$, $R^3$, $R^4$ and $R^{22}$ are as defined above.
In one embodiment of Formula Ia, $R^3$ is hydrogen.
In one embodiment of Formula Ia, $R^1$ is methyl and $R^2$ is hydrogen.
In one embodiment of Formula Ia, both $R^1$ and $R^2$ are methyl.
In one embodiment of Formula Ia, $R^1$ is methyl and $R^2$ is cyclopropyl.
In one embodiment of Formula Ia, $R^{22}$ is methyl.
In one embodiment of Formula Ia, $R^{22}$ is ethyl.
In one embodiment of Formula Ia, $R^{22}$ is $NH_2$.
In one embodiment of Formula Ia, $R^{22}$ is $N_3$.
In one embodiment of Formula Ia, $R^{22}$ is CN.
In one embodiment of Formula Ia, $R^{22}$ is —$CH_2F$.
In one embodiment of Formula Ia, $R^{22}$ is —$CF_3$.
In one embodiment of Formula Ia, $R^{22}$ is —$CH_2Cl$.
In an alternative embodiment of Formula Ia, $R^1$ is cyclopropyl and $R^2$ is hydrogen.
In an alternative embodiment, the compound of Formula Ia is a pharmaceutically acceptable sulfate salt, such as $H_2SO_4$.
In another embodiment, compounds of Formula Ib are disclosed:

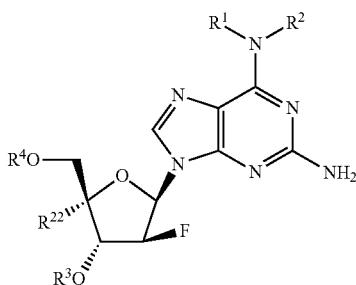

Formula Ib or a pharmaceutically acceptable composition, salt, or prodrug thereof,
wherein:
$R^1$, $R^2$, $R^3$, $R^4$ and $R^{22}$ are as defined above.
In one embodiment of Formula Ib, $R^3$ is hydrogen.
In one embodiment of Formula Ib, $R^1$ is methyl and $R^2$ is hydrogen.
In one embodiment of Formula Ib, both $R^1$ and $R^2$ are methyl.

In one embodiment of Formula Ib, $R^1$ is methyl and $R^2$ is cyclopropyl.
In one embodiment of Formula Ib, $R^{22}$ is methyl.
In one embodiment of Formula Ib, $R^{22}$ is ethyl.
In one embodiment of Formula Ib, $R^{22}$ is $NH_2$.
In one embodiment of Formula Ib, $R^{22}$ is $N_3$.
In one embodiment of Formula Ib, $R^{22}$ is CN.
In one embodiment of Formula Ib, $R^{22}$ is —$CH_2F$.
In one embodiment of Formula Ib, $R^{22}$ is —$CF_3$.
In one embodiment of Formula Ib, $R^{22}$ is —$CH_2Cl$.
In an alternative embodiment of Formula Ib, $R^1$ is cyclopropyl and $R^2$ is hydrogen.
In an alternative embodiment, the compound of Formula Ib is a pharmaceutically acceptable sulfate salt, such as $H_2SO_4$.
In another embodiment, compounds of Formula IIa are disclosed:

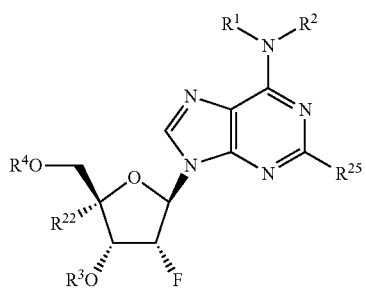

Formula IIa or a pharmaceutically acceptable composition, salt, or prodrug thereof,
wherein:
$R^1$, $R^2$, $R^3$, $R^4$, $R^{22}$ and $R^{25}$ are as defined above.
In one embodiment of Formula IIa, $R^3$ is hydrogen.
In one embodiment of Formula IIa, $R^1$ is methyl and $R^2$ is hydrogen.
In one embodiment of Formula IIa, both $R^1$ and $R^2$ are methyl.
In one embodiment of Formula IIa, $R^1$ is methyl and $R^2$ is cyclopropyl.
In one embodiment of Formula IIa, $R^{22}$ is methyl.
In one embodiment of Formula IIa, $R^{22}$ is ethyl.
In one embodiment of Formula IIa, $R^{22}$ is $NH_2$.
In one embodiment of Formula IIa, $R^{22}$ is $N_3$.
In one embodiment of Formula IIa, $R^{22}$ is CN.
In one embodiment of Formula IIa, $R^{22}$ is —$CH_2F$.
In one embodiment of Formula IIa, $R^{22}$ is —$CF_3$.
In one embodiment of Formula IIa, $R^{22}$ is —$CH_2Cl$.
In an alternative embodiment of Formula IIa, $R^{25}$ is NHC(O)iPr.
In an alternative embodiment of Formula IIa, $R^{25}$ is F.
In an alternative embodiment of Formula IIa, $R^{25}$ is Cl.
In an alternative embodiment of Formula IIa, $R^{25}$ is OMe.
In an alternative embodiment of Formula IIa, $R^1$ is cyclopropyl.
In an alternative embodiment of Formula IIa, $R^1$ is cyclopropyl and $R^2$ is hydrogen.
In an alternative embodiment of Formula IIa, $R^1$ is cyclopropyl and $R^2$ is methyl.
In an alternative embodiment, the compound of Formula IIa is a pharmaceutically acceptable sulfate salt, such as $H_2SO_4$.
In another embodiment, compounds of Formula IIb are disclosed:

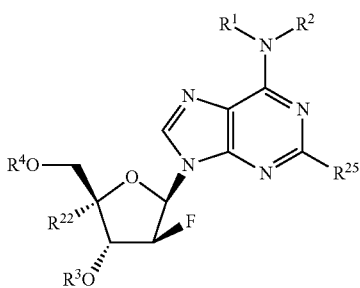

Formula IIb or a pharmaceutically acceptable composition, salt, or prodrug thereof,
wherein:
$R^1$, $R^2$, $R^3$, $R^{22}$ and $R^{25}$ are as defined above.
In one embodiment of Formula IIb, $R^3$ is hydrogen.
In one embodiment of Formula IIb, $R^1$ is methyl and $R^2$ is hydrogen.
In one embodiment of Formula IIb, both $R^1$ and $R^2$ are methyl.
In one embodiment of Formula IIb, $R^1$ is methyl and $R^2$ is cyclopropyl.
In one embodiment of Formula IIb, $R^{22}$ is methyl.
In one embodiment of Formula IIb, $R^{22}$ is ethyl.
In one embodiment of Formula IIb, $R^{22}$ is $NH_2$.
In one embodiment of Formula IIb, $R^{22}$ is $N_3$.
In one embodiment of Formula IIb, $R^{22}$ is CN.
In one embodiment of Formula IIb, $R^{22}$ is —$CH_2F$.
In one embodiment of Formula IIb, $R^{22}$ is —$CF_3$.
In one embodiment of Formula IIb, $R^{22}$ is —$CH_2Cl$.
In an alternative embodiment of Formula IIb, $R^{25}$ is NHC(O)iPr.
In an alternative embodiment of Formula IIb, $R^{25}$ is F.
In an alternative embodiment of Formula IIb, $R^{25}$ is Cl.
In an alternative embodiment of Formula IIb, $R^{25}$ is OMe.
In an alternative embodiment of Formula IIb, $R^1$ is cyclopropyl.
In an alternative embodiment of Formula IIb, $R^1$ is cyclopropyl and $R^2$ is hydrogen.
In an alternative embodiment of Formula IIb, $R^1$ is cyclopropyl and $R^2$ is methyl.
In an alternative embodiment, the compound of Formula IIb is a pharmaceutically acceptable sulfate salt, such as $H_2SO_4$.
In one embodiment, compounds of Formula III are disclosed:

Formula III

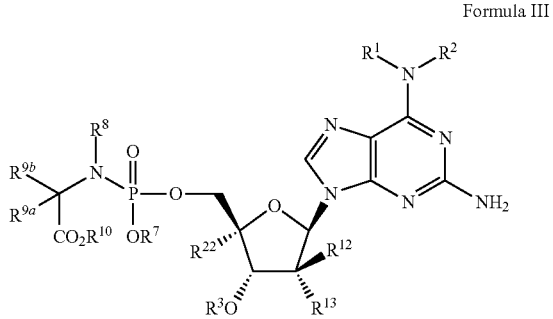

or a pharmaceutically acceptable composition, salt, or prodrug thereof, wherein the variables $R^1$, $R^2$, $R^3$, $R^{12}$, $R^{13}$ and $R^{22}$ are described above;
$R^7$ is hydrogen, $C_{1-6}$alkyl, $C_{3-7}$cycloalkyl, heteroaryl, heterocyclic, or aryl, which includes, but is not limited to, phenyl or naphthyl, where phenyl or naphthyl are optionally substituted with $C_{1-6}$alkyl, $C_{2-6}$alkenyl, $C_{2-6}$ alkynyl, $C_{1-6}$alkoxy, F, Cl, Br, I, nitro, cyano, $C_{1-6}$haloalkyl, —N($R^{7'}$)$_2$, $C_{1-6}$acylamino, $NHSO_2C_{1-6}$alkyl, —$SO_2N(R^{7'})_2$, $COR^{7''}$, and —$SO_2C_{1-6}$alkyl; ($R^{7'}$ is independently selected from hydrogen or $C_{1-6}$alkyl; $R^{7''}$ is —$OR^{11}$ or —$N(R^{7'})_2$);
$R^8$ is hydrogen, $C_{1-6}$alkyl, or $R^{9a}$ or $R^{9b}$ and $R^8$ together are $(CH_2)_n$ so as to form a cyclic ring that includes the adjoining N and C atoms; where n is 2 to 4;
$R^{9a}$ and $R^{9b}$ are (i) independently selected from hydrogen, $C_{1-6}$alkyl, cycloalkyl, —$(CH_2)_c(NR^{9'})_2$, $C_{1-6}$hydroxyalkyl, —$CH_2SH$, —$(CH_2)_2S(O)(Me)$, —$(CH_2)_3NHC(=NH)NH_2$, (1H-indol-3-yl)methyl, (1H-imidazol-4-yl)methyl, —$(CH_2)_c COR^{9''}$, aryl and aryl($C_{1-3}$alkyl)-, wherein the aryl groups can be optionally substituted with a group selected from hydroxyl, $C_{1-6}$alkyl, $C_{1-6}$alkoxy, halogen, nitro and cyano; (ii) $R^{9a}$ and $R^{9b}$ both are $C_{1-6}$alkyl; (iii) $R^{9a}$ and $R^{9b}$ together are $(CH_2)_r$ so as to form a spiro ring; (iv) $R^{9a}$ is hydrogen and $R^{9b}$ and $R^8$ together are $(CH_2)_n$ so as to form a cyclic ring that includes the adjoining N and C atoms (v) $R^{9b}$ is hydrogen and $R^{9a}$ and $R^8$ together are $(CH_2)_n$ so as to form a cyclic ring that includes the adjoining N and C atoms, wherein c is 1 to 6; n is 2 to 4; r is 2 to 5; and wherein $R^{9'}$ is independently hydrogen or $C_{1-6}$ alkyl and $R^{9''}$ is —$OR^{11}$ or —$N(R^{11'})_2$); (vi) $R^{9a}$ is hydrogen and $R^{9b}$ is hydrogen, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (vii) $R^{9a}$ is $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{9b}$ is hydrogen; and
$R^{10}$ is hydrogen, $C_{1-6}$alkyl optionally substituted with an alkoxy, di(lower alkyl)-amino, or halogen; $C_{1-6}$haloalkyl, $(C_0-C_2)(C_{3-7}$cycloalkyl), $(C_0-C_2)$(heterocycloalkyl), aminoacyl, $(C_0-C_2)$(aryl), such as $(C_0-C_2)$(phenyl), $(C_0-C_2)$(heteroaryl), such as $(C_0-C_2)$(pyridinyl), substituted $(C_0-C_2)$(aryl), or substituted $(C_0-C_2)$(heteroaryl).
In one embodiment of Formula III, $R^3$ is hydrogen.
In one embodiment of Formula III, $R^1$ is methyl and $R^2$ is hydrogen.
In one embodiment of Formula III, both $R^1$ and $R^2$ are methyl.
In one embodiment of Formula III, $R^1$ is methyl and $R^2$ is cyclopropyl.
In one embodiment of Formula III, $R^{22}$ is methyl.
In one embodiment of Formula III, $R^{22}$ is ethyl.
In one embodiment of Formula III, $R^{22}$ is $NH_2$.
In one embodiment of Formula III, $R^{22}$ is $N_3$.
In one embodiment of Formula III, $R^{22}$ is CN.
In one embodiment of Formula III, $R^{22}$ is —$CH_2F$.
In one embodiment of Formula III, $R^{22}$ is —$CF_3$.
In one embodiment of Formula III, $R^{22}$ is —$CH_2Cl$.
In an alternative embodiment of Formula III, $R^1$ is cyclopropyl and $R^2$ is hydrogen.
In an alternative embodiment of Formula III, $R^8$ is H.
In an alternative embodiment of Formula III, $R^7$ is phenyl.

In an alternative embodiment of Formula III, $R^{9a}$ is hydrogen and $R^{9b}$ is methyl.

In an alternative embodiment of Formula III, $R^{9a}$ is methyl and $R^{9b}$ is hydrogen.

In an alternative embodiment of Formula III, $R^{10}$ is isopropyl.

In an alternative embodiment, the compound of Formula III is a pharmaceutically acceptable sulfate salt, such as $H_2SO_4$.

In one embodiment, compounds of Formula IIIa are disclosed:

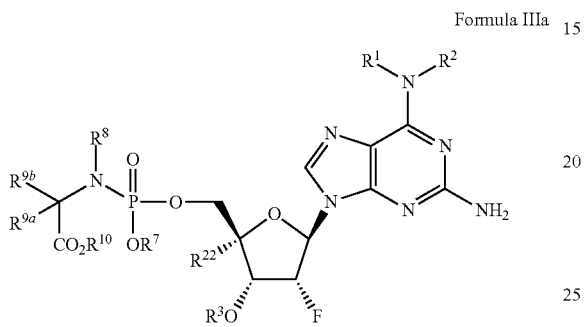

Formula IIIa or a pharmaceutically acceptable composition, salt, or prodrug thereof, wherein the variables $R^1$, $R^2$, $R^3$, $R^7$, $R^8$, $R^{9a}$, $R^{9b}$, $R^{10}$ and $R^{22}$ are described above.

In one embodiment of Formula IIa, $R^3$ is hydrogen.

In one embodiment of Formula IIIa, $R^1$ is methyl and $R^2$ is hydrogen.

In one embodiment of Formula IIIa, both $R^1$ and $R^2$ are methyl.

In one embodiment of Formula IIIa, $R^1$ is methyl and $R^2$ is cyclopropyl.

In one embodiment of Formula IIIa, $R^{22}$ is methyl.

In one embodiment of Formula IIIa, $R^{22}$ is ethyl.

In one embodiment of Formula IIIa, $R^{22}$ is $NH_2$.

In one embodiment of Formula IIIa, $R^{22}$ is $N_3$.

In one embodiment of Formula IIIa, $R^{22}$ is CN.

In one embodiment of Formula IIIa, $R^{22}$ is —$CH_2F$.

In one embodiment of Formula IIIa, $R^{22}$ is —$CF_3$.

In one embodiment of Formula IIIa, $R^{22}$ is —$CH_2Cl$.

In an alternative embodiment of Formula IIIa, $R^1$ is cyclopropyl and $R^2$ is hydrogen.

In an alternative embodiment of Formula IIIa, $R^8$ is H.

In an alternative embodiment of Formula IIIa, $R^7$ is phenyl.

In an alternative embodiment of Formula IIIa, $R^{9a}$ is hydrogen and $R^{9b}$ is methyl.

In an alternative embodiment of Formula IIIa, $R^{9a}$ is methyl and $R^9b$ is hydrogen.

In an alternative embodiment of Formula IIIa, $R^{10}$ is isopropyl.

In an alternative embodiment, the compound of Formula IIIa is a pharmaceutically acceptable sulfate salt, such as $H_2SO_4$.

In one embodiment, compounds of Formula IIIb are disclosed:

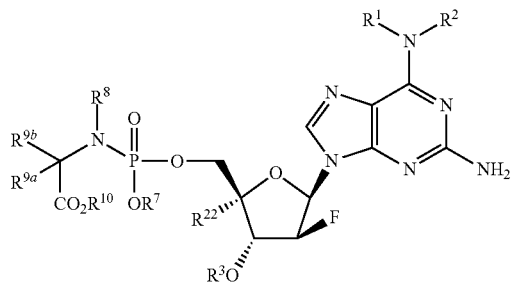

Formula IIIb or a pharmaceutically acceptable composition, salt, or prodrug thereof, wherein the variables $R^1$, $R^2$, $R^3$, $R^7$, $R^8$, $R^{9a}$, $R^{9b}$, $R^{10}$ and $R^{22}$ are described above.

In one embodiment of Formula IIIb, $R^1$ is methyl and $R^2$ is hydrogen.

In one embodiment of Formula IIIb, both $R^1$ and $R^2$ are methyl.

In one embodiment of Formula IIIb, $R^1$ is methyl and $R^2$ is cyclopropyl.

In one embodiment of Formula IIIb, $R^{22}$ is methyl.

In one embodiment of Formula IIIb, $R^{22}$ is ethyl.

In one embodiment of Formula IIIb, $R^{22}$ is $NH_2$.

In one embodiment of Formula IIIb, $R^{22}$ is $N_3$.

In one embodiment of Formula IIIb, $R^{22}$ is CN.

In one embodiment of Formula IIIb, $R^{22}$ is —$CH_2F$.

In one embodiment of Formula IIIb, $R^{22}$ is —$CF_3$.

In one embodiment of Formula IIIb, $R^{22}$ is —$CH_2Cl$.

In an alternative embodiment of Formula IIIb, $R^8$ is H.

In an alternative embodiment of Formula IIIb, $R^1$ is cyclopropyl and $R^2$ is hydrogen.

In an alternative embodiment of Formula IIIb, $R^7$ is phenyl.

In an alternative embodiment of Formula IIIb, $R^{9a}$ is hydrogen and $R^{9b}$ is methyl.

In an alternative embodiment of Formula IIIb, $R^{9a}$ is methyl and $R^{9b}$ is hydrogen.

In an alternative embodiment of Formula IIIb, $R^{10}$ is isopropyl.

In an alternative embodiment, the compound of Formula IIIb is a pharmaceutically acceptable sulfate salt, such as $H_2SO_4$.

In one embodiment, the compound is according to Formula IV:

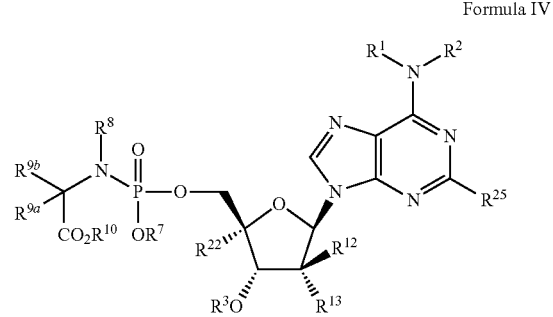

Formula IV or a pharmaceutically acceptable composition, salt, or prodrug thereof, wherein:

$R^1$, $R^2$, $R^3$, $R^7$, $R^8$, $R^{9a}$, $R^{9b}$, $R^{10}$, $R^{12}$, $R^{13}$, $R^{22}$ and $R^{25}$ are as defined above.

In one embodiment of Formula IV, $R^1$ is methyl and $R^2$ is hydrogen.

In one embodiment of Formula IV, both $R^1$ and $R^2$ are methyl.

In one embodiment of Formula IV, $R^1$ is methyl and $R^2$ is cyclopropyl.

In one embodiment of Formula IV, $R^{22}$ is methyl.
In one embodiment of Formula IV, $R^{22}$ is ethyl.
In one embodiment of Formula IV, $R^{22}$ is $NH_2$.
In one embodiment of Formula IV, $R^{22}$ is $N_3$.
In one embodiment of Formula IV, $R^{22}$ is CN.
In one embodiment of Formula IV, $R^{22}$ is —$CH_2F$.
In one embodiment of Formula IV, $R^{22}$ is —$CF_3$.
In one embodiment of Formula IV, $R^{22}$ is —$CH_2Cl$.
In an alternative embodiment of Formula IV, $R^8$ is H.
In an alternative embodiment of Formula IV, $R^7$ is phenyl.
In an alternative embodiment of Formula IV, $R^{9a}$ is hydrogen and $R^{9b}$ is methyl.
In an alternative embodiment of Formula IV, $R^{9a}$ is methyl and $R^{9b}$ is hydrogen.
In an alternative embodiment of Formula IV, $R^{10}$ is isopropyl.
In an alternative embodiment of Formula IV, $R^{25}$ is NHC(O)iPr.
In an alternative embodiment of Formula IV, $R^{25}$ is F.
In an alternative embodiment of Formula IV, $R^{25}$ is Cl.
In an alternative embodiment of Formula IV, $R^{25}$ is OMe.
In an alternative embodiment of Formula IV, $R^1$ is cyclopropyl.
In an alternative embodiment of Formula IV, $R^1$ is cyclopropyl and $R^2$ is hydrogen.
In an alternative embodiment of Formula IV, $R^1$ is cyclopropyl and $R^2$ is methyl.

In an alternative embodiment, the compound of Formula IV is a pharmaceutically acceptable sulfate salt, such as $H_2SO_4$.

In one embodiment, compounds of Formula IVa are disclosed:

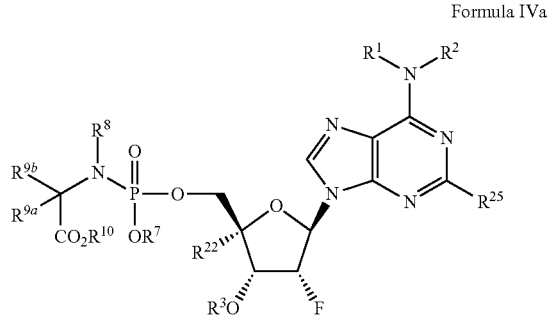

Formula IVa or a pharmaceutically acceptable composition, salt, or prodrug thereof, wherein the variables $R^1$, $R^2$, $R^3$, $R^7$, $R^8$, $R^{9a}$, $R^{9b}$, $R^{10}$, $R^{22}$ and $R^{25}$ are described above.

In one embodiment of Formula IVa, $R^1$ is methyl and $R^2$ is hydrogen.

In one embodiment of Formula IVa, both $R^1$ and $R^2$ are methyl.

In one embodiment of Formula IVa, $R^1$ is methyl and $R^2$ is cyclopropyl.

In one embodiment of Formula IVa, $R^{22}$ is methyl.
In one embodiment of Formula IVa, $R^{22}$ is ethyl.
In one embodiment of Formula IVa, $R^{22}$ is $NH_2$.
In one embodiment of Formula IVa, $R^{22}$ is $N_3$.
In one embodiment of Formula IVa, $R^{22}$ is CN.
In one embodiment of Formula IVa, $R^{22}$ is —$CH_2F$.
In one embodiment of Formula IVa, $R^{22}$ is —$CF_3$.
In one embodiment of Formula IVa, $R^{22}$ is —$CH_2Cl$.
In an alternative embodiment of Formula IVa, $R^8$ is H.
In an alternative embodiment of Formula IVa, $R^7$ is phenyl.
In an alternative embodiment of Formula IVa, $R^{9a}$ is hydrogen and $R^{9b}$ is methyl.
In an alternative embodiment of Formula IVa, $R^{9a}$ is methyl and $R^{9b}$ is hydrogen.
In an alternative embodiment of Formula IVa, $R^{10}$ is isopropyl.
In an alternative embodiment of Formula IVa, $R^{25}$ is NHC(O)iPr.
In an alternative embodiment of Formula IVa, $R^{25}$ is F.
In an alternative embodiment of Formula IVa, $R^{25}$ is Cl.
In an alternative embodiment of Formula IVa, $R^{25}$ is OMe.
In an alternative embodiment of Formula IVa, $R^1$ is cyclopropyl.
In an alternative embodiment of Formula IVa, $R^1$ is cyclopropyl and $R^2$ is hydrogen.
In an alternative embodiment of Formula IVa, $R^1$ is cyclopropyl and $R^2$ is methyl.

In an alternative embodiment, the compound of Formula IVa is a pharmaceutically acceptable sulfate salt, such as $H_2SO_4$.

In one embodiment, compounds of Formula IVb are disclosed:

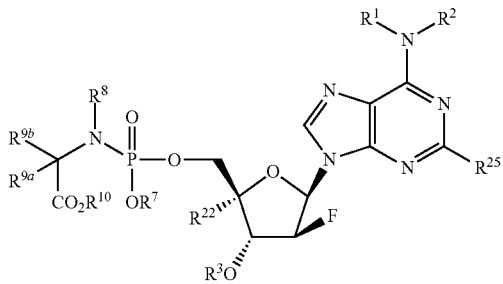

Formula IVb or a pharmaceutically acceptable composition, salt, or prodrug thereof, wherein the variables $R^1$, $R^2$, $R^3$, $R^7$, $R^8$, $R^{9a}$, $R^{9b}$, $R^{10}$, $R^{22}$ and $R^{25}$ are described above.

In one embodiment of Formula IVb, $R^1$ is methyl and $R^2$ is hydrogen.

In one embodiment of Formula IVb, both $R^1$ and $R^2$ are methyl.

In one embodiment of Formula IVb, $R^1$ is methyl and $R^2$ is cyclopropyl.

In one embodiment of Formula IVb, $R^{22}$ is methyl.
In one embodiment of Formula IVb, $R^{22}$ is ethyl.
In one embodiment of Formula IVb, $R^{22}$ is $NH_2$.
In one embodiment of Formula IVb, $R^{22}$ is $N_3$.
In one embodiment of Formula IVb, $R^{22}$ is CN.
In one embodiment of Formula IVb, $R^{22}$ is —$CH_2F$.
In one embodiment of Formula IVb, $R^{22}$ is —$CF_3$.

In one embodiment of Formula IVb, $R^{22}$ is —$CH_2Cl$.

In an alternative embodiment of Formula IVb, $R^{25}$ is NHC(O)iPr.

In an alternative embodiment of Formula IVb, $R^{25}$ is F.

In an alternative embodiment of Formula IVb, $R^{25}$ is Cl.

In an alternative embodiment of Formula IVb, $R^{25}$ is OMe.

In an alternative embodiment of Formula IVb, $R^1$ is cyclopropyl.

In an alternative embodiment of Formula IVb, $R^1$ is cyclopropyl and $R^2$ is hydrogen.

In an alternative embodiment of Formula IVb, $R^1$ is cyclopropyl and $R^2$ is methyl.

In an alternative embodiment, the compound of Formula IVb is a pharmaceutically acceptable sulfate salt, such as $H_2SO_4$.

In one embodiment, compounds of Formula V are disclosed:

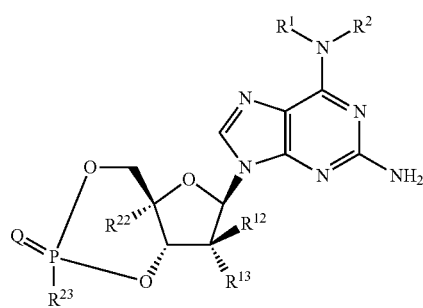

Formula V or a pharmaceutically acceptable composition, salt, or prodrug thereof, wherein the variables $R^1$, $R^2$, $R^{12}$, $R^{13}$ and $R^{22}$ are described above;

Q is oxygen or sulfur; and $R^{23}$ is —OH, —O⁻ an optionally substituted —O-alkyl, an optionally substituted —O-alkenyl, an optionally substituted —O-alkynyl, an optionally substituted —O—$(C_0\text{-}C_2)$(cycloalkyl), an optionally substituted —O—$(C_0\text{-}C_2)$(heterocyclo), an optionally substituted —O—$(C_0\text{-}C_2)$(aryl), an optionally substituted —O—$(C_0\text{-}C_2)$(heteroaryl), -an optionally substituted N-linked amino acid, or an optionally substituted N-linked amino acid ester.

In one embodiment of Formula V, $R^1$ is methyl and $R^2$ is hydrogen.

In one embodiment of Formula V, both $R^1$ and $R^2$ are methyl.

In one embodiment of Formula V, $R^1$ is methyl and $R^2$ is cyclopropyl.

In one embodiment of Formula V, $R^{22}$ is methyl.
In one embodiment of Formula V, $R^{22}$ is ethyl.
In one embodiment of Formula V, $R^{22}$ is $NH_2$.
In one embodiment of Formula V, $R^{22}$ is $N_3$.
In one embodiment of Formula V, $R^{22}$ is CN.
In one embodiment of Formula V, $R^{22}$ is —$CH_2F$.
In one embodiment of Formula V, $R^{22}$ is —$CF_3$.
In one embodiment of Formula V, $R^{22}$ is —$CH_2Cl$.

In an alternative embodiment of Formula V, $R^{12}$ is F and $R^{13}$ is hydrogen.

In an alternative embodiment of Formula V, $R^{12}$ is hydrogen and $R^{13}$ is F.

In an alternative embodiment of Formula V, $R^1$ is cyclopropyl and $R^2$ is hydrogen.

In an alternative embodiment, the compound of Formula V is a pharmaceutically acceptable sulfate salt, such as $H_2SO_4$.

In one embodiment, compounds of Formula VI are disclosed:

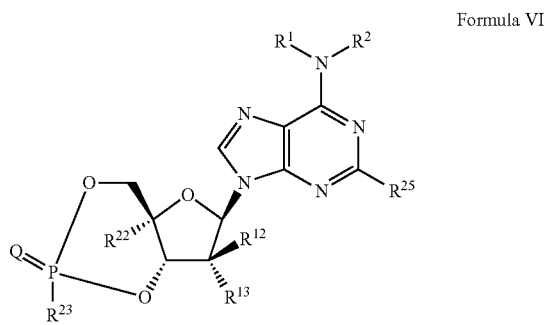

Formula VI or a pharmaceutically acceptable composition, salt, or prodrug thereof, wherein the variables $R^1$, $R^2$, $R^{12}$, $R^{13}$, $R^{22}$, $R^{23}$, $R^{25}$ and Q are described above.

In one embodiment of Formula VI, $R^1$ is methyl and $R^2$ is hydrogen.

In one embodiment of Formula VI, both $R^1$ and $R^2$ are methyl.

In one embodiment of Formula VI, $R^1$ is methyl and $R^2$ is cyclopropyl.

In one embodiment of Formula VI, $R^{22}$ is methyl.
In one embodiment of Formula VI, $R^{22}$ is ethyl.
In one embodiment of Formula VI, $R^{22}$ is $NH_2$.
In one embodiment of Formula VI, $R^{22}$ is $N_3$.
In one embodiment of Formula VI, $R^{22}$ is CN.
In one embodiment of Formula VI, $R^{22}$ is —$CH_2F$.
In one embodiment of Formula VI, $R^{22}$ is —$CF_3$.
In one embodiment of Formula VI, $R^{22}$ is —$CH_2Cl$.

In an alternative embodiment of Formula VI, $R^{12}$ is F and $R^{13}$ is hydrogen.

In an alternative embodiment of Formula VI, $R^{12}$ is hydrogen and $R^{13}$ is F.

In an alternative embodiment of Formula VI, $R^1$ is cyclopropyl and $R^2$ is hydrogen.

In an alternative embodiment, the compound of Formula VI is a pharmaceutically acceptable sulfate salt, such as $H_2SO_4$.

The phosphorus in any of the Formulas above may be chiral and thus can be provided as an R or S enantiomer or mixture thereof, including a racemic mixture.

In one embodiment, compounds, methods, and compositions are provided for the treatment of a host infected with or exposed to respiratory syncytial virus described herein. The compounds of the invention can be administered in an effective amount alone or in combination with another anti-RSV drug, to treat the infected host. In certain embodiments, it is useful to administer a combination of drugs that modulates the same or a different pathway or inhibits a different target in the virus. As the disclosed β-D-2'-deoxy-2'-substituted-4'-substituted-2-substituted-$N^6$-substituted-6-aminopurine nucleotides are RSV polymerase inhibitors, it may be useful to administer the compound to a host in combination with an immune globulin such as, but not limited to, RespiGram® (RSV-IGIV, Medimmune). The compounds of the invention can also be administered in combination with another nucleoside compound such as, but not limited to, Virzole® (ribavirin by aerosol, ICN pharmaceuticals). The compounds of the invention can also be administered in combination with an antibody to RSV such as, but not limited to, Synagis® (palivizumab, Medimmune).

The β-D-2'-deoxy-2'-substituted-4'-substituted-2-substituted-$N^6$-substituted-6-aminopurine nucleotides of the invention are typically administered orally, for example in pill or tablet form, but may be administered via another route which the attending physician considers appropriate, including via intravenous, transdermal, subcutaneous, topical, parenteral, or other suitable route.

DETAILED DESCRIPTION OF THE INVENTION

The invention disclosed herein is a compound, method, and composition for the treatment of infections of the Paramyxoviridae or Orthomyxoviridae families of viruses that includes the administration of an effective amount of a compound of Formula I-VI as described herein to a human or other host animal or a pharmaceutically acceptable salt or prodrug thereof, optionally in a pharmaceutically acceptable carrier. The compounds of this invention either possess antiviral activity, or are metabolized to a compound that exhibits such activity.

The compounds and compositions can also be used to treat conditions related to or occurring as a result of an RSV viral exposure. For example, the active compound can be used to treat RSV antibody-positive and RSV antigen-positive conditions. In one embodiment, the compounds or formulations that include the compounds can also be used prophylactically to prevent or retard the progression of clinical illness in individuals who are RSV antibody or RSV antigen positive or who have been exposed to respiratory syncytial virus.

In particular embodiments, it has been discovered that a 5'-stabilized phosphate prodrug or derivative of a β-D-2'-deoxy-2'-substituted-4'-substituted-2-substituted-$N^6$-methyl-6-aminopurine nucleotide, as well as a β-D-2'-deoxy-2'-substituted-4'-substituted-2-substituted-$N^6$-dimethyl-6-aminopurine nucleotide, and β-D-2'-deoxy-2'-substituted-4'-substituted-2-substituted-$N^6$-cyclopropyl-6-aminopurine nucleotide as described below, are advantageous against RSV.

Unless otherwise specified, the compounds described herein are provided in the β-D-configuration. In an alternative embodiment, the compounds can be provided in a β-L-configuration. Likewise, any substituent group that exhibits chirality can be provided in racemic, enantiomeric, diastereomeric form or any mixture thereof. Where a phosphoramidate, thiophosphoramidate or other stabilized phosphorus prodrug in which the phosphorus exhibits chirality is used as the $R^4$ stabilized phosphate prodrug, it can be provided as an R or S chiral phosphorus derivative or a mixture thereof, including a racemic mixture. The amino acid of the phosphoramidate or thiophosphoramidate can be in the D- or L-configuration, or a mixture thereof, including a racemic mixture. All of the combinations of these stereo configurations are included in the invention described herein.

The present invention includes the following features:

(a) a compound of Formula I-VI as described herein, and pharmaceutically acceptable salts and prodrugs thereof;

(b) Formulas I-VI as described herein, and pharmaceutically acceptable salts and prodrugs thereof for use in the treatment or prophylaxis of a Paramyxoviridae family or an Orthomyxoviridae family virus infection, and in particular respiratory syncytial virus;

(c) use of Formulas I-VI, and pharmaceutically acceptable salts and prodrugs thereof in the manufacture of a medicament for treatment of a Paramyxoviridae family or an Orthomyxoviridae family virus infection and in particular respiratory syncytial virus in a human or other host animal in need thereof;

(d) a method for manufacturing a medicament intended for the therapeutic use for treating a Paramyxoviridae family or an Orthomyxoviridae family virus infection and in particular respiratory syncytial virus, characterized in that a compound of Formulas I-VI as described herein is used in the manufacture;

(e) a pharmaceutical formulation comprising an effective host-treating amount of the compound of Formulas I-VI or a pharmaceutically acceptable salt or prodrug thereof together with a pharmaceutically acceptable carrier or diluent;

(f) Formulas I-VI as described herein substantially in the absence of stereoisomers of the described compound, or substantially isolated from other chemical entities; and, (g) processes for the preparation of therapeutic products that contain an effective amount of a compound of Formulas I-VI, as described herein.

I. β-D-2'-Deoxy-2'-Substituted-4'-Substituted-2-Substituted-$N^6$-Substituted-Aminopurine Nucleotides of the Invention In one embodiment, the active compounds of the invention are those depicted, for example, in Formula I, which can be provided in a pharmaceutically acceptable composition, salt or prodrug thereof:

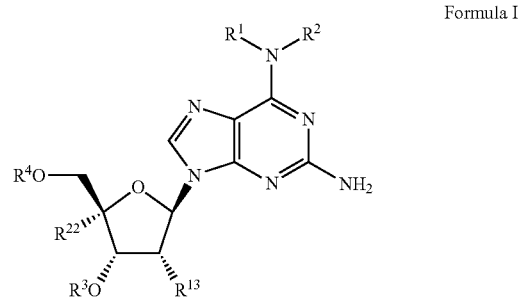

Formula I

A stabilized phosphate prodrug is any moiety that can deliver a mono, di, or triphosphate. In another embodiment, compounds of Formula Ia are disclosed:

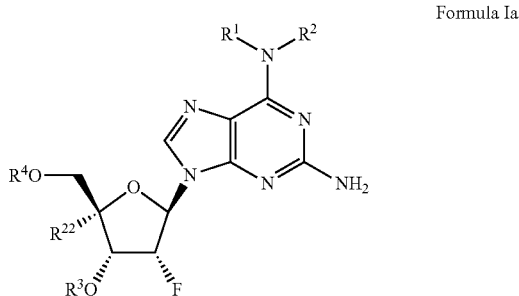

Formula Ia or a pharmaceutically acceptable composition, salt, or prodrug thereof,
wherein:
$R^1$, $R^2$, $R^3$, $R^4$ and $R^{22}$ are as defined above.

In another embodiment, compounds of Formula Ib are disclosed:

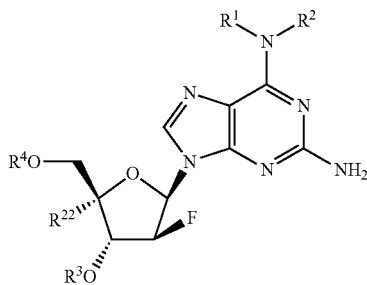

Formula Ib wherein:
$R^1$, $R^2$, $R^3$, $R^4$ and $R^{22}$ are as defined above.

In yet another embodiment, compounds of Formula II are disclosed:

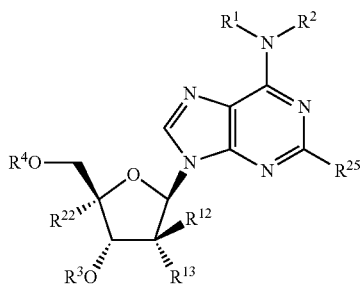

Formula II or a pharmaceutically acceptable composition, salt, or prodrug thereof,
wherein:
$R^{25}$ is Cl, Br, F, CN, $N_3$, $C_1$-$C_6$ alkyl, $C_2$-$C_6$ alkenyl, $C_2$-$C_6$ alkynyl, —($C_1$-$C_2$alkyl)($C_3$-$C_6$cycloalkyl), —($C_0$-$C_2$alkyl)($C_3$-$C_6$heterocycle), —($C_0$-$C_2$alkyl)(aryl), —($C_0$-$C_2$alkyl)(heteroaryl), —ONHC(=O)O$R^{26}$, —NHO$R^{27}$, —S$R^{28}$, —NH(CH$_2$)$_{1-4}$N($R^{29}$)$_2$, —NHNH$R^{29}$, —N=N$R^{30}$, —NHC(O)NHNH$R^{30}$, —NHC(S)NHNH$R^{30}$, —C(O)NHNH$R^{30}$, —N$R^{30}$SO$_2$$R^{31}$, —SO$_2$N$R^{30}$$R^{32}$, —C(O)N$R^{30}$$R^{32}$, —CO$_2$$R^{32}$, —SO$_2$$R^{32}$,

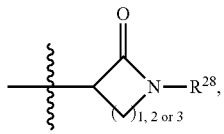

—P(O)H(O$R^{32}$), —P(O)(O$R^{32}$)(O$R^{33}$), —P(O)(O$R^{32}$)(N$R^{32}$$R^{33}$) or —N$R^5$$R^6$;
for example including but not limited to the following embodiments, Cl, Br, Fl, cyano, azido, methyl, ethyl, n-propyl, iso-propyl, n-butyl, iso-butyl, sec-butyl, tert-butyl and n-pentyl, 1,1-dimethylpropyl, 2,2-dimtheylpropyl, 3-methylbutyl, 1-methylbutyl, 1-ethylpropyl, vinyl, allyl, 1-butynyl, 2-butynyl, acetylenyl, cyclopropyl, cyclobutyl, cyclopentyl, cyclohexyl, —(CH$_2$)-cyclopropyl, —(CH$_2$)-cyclobutyl, —(CH$_2$)-cyclopentyl, —(CH$_2$)-cyclohexyl, aziridine, oxirane, thiirane, azetidine, oxetane, thietane, pyrrolidine, tetrahydrofuran, thiolane, pyrazolidine, piperidine, oxane, thiane, —(CH$_2$)-aziridine, —(CH$_2$)-oxirane, —(CH$_2$)-thiirane, —(CH$_2$)-azetidine, —(CH$_2$)-oxetane, —(CH$_2$)-thietane, —(CH$_2$)-pyrrolidine, —(CH$_2$)-tetrahydrofuran, —(CH$_2$)-thiolane, —(CH$_2$)-pyrazolidine, —(CH$_2$)-piperidine, —(CH$_2$)-oxane, —(CH$_2$)-thiane, phenyl, pyridyl, —ONHC(=O)OCH$_3$, —ONHC(=O)OCH$_2$CH$_3$, —NHOH, NHOCH$_3$, —OCH$_3$, OC$_2$H$_5$, —OPh, OCH$_2$Ph, —SCH$_3$, —SC$_2$H$_5$, —SPh, SCH$_2$Ph, —NH(CH$_2$)$_2$NH$_2$, —NH(CH$_2$)$_2$N(CH$_3$)$_2$, —NHNH$_2$, —NHNHCH$_3$, —N=NH, —N=NCH$_3$, —N=NCH$_2$CH$_3$, —NHC(O)NHNH$_2$, —NHC(S)NHNH$_2$, —C(O)NHNH$_2$, —NHSO$_2$CH$_3$, —NHSO$_2$CH$_2$CH$_3$, —SO$_2$NHCH$_3$, —SO$_2$N(CH$_3$)$_2$, —C(O)NH$_2$, —C(O)NHCH$_3$, —C(O)N(CH$_3$)$_2$, —CO$_2$CH$_3$, —CO$_2$CH$_2$CH$_3$, —CO$_2$Ph, —CO$_2$CH$_2$Ph, —SO$_2$CH$_3$, —SO$_2$CH$_2$CH$_3$, —SO$_2$Ph, —SO$_2$CH$_2$Ph,

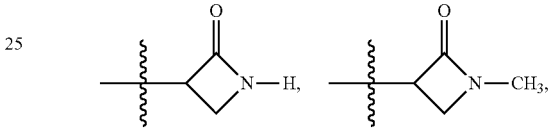

—P(O)H(OH), —P(O)H(OCH$_3$), —P(O)(OH)(OH), —P(O)(OH)(OCH$_3$), —P(O)(OCH$_3$)(OCH$_3$), —P(O)(OH)(NH$_2$), —P(O)(OH)(NHCH$_3$), —P(O)(OH)N(CH$_3$)$_2$, —NHC(O)CH$_3$, —NHC(O)CH$_2$CH$_3$, —NHC(O)CH(CH$_3$)$_2$, —NHC(O)OCH$_3$, —NHC(O)OCH$_2$CH$_3$, —NHC(O)OCH(CH$_3$)$_2$, —NHC(O)OCH$_2$CH$_2$CH$_3$, —NHC(O)OCH$_2$CH$_2$CH$_2$CH$_3$ and —NHC(O)OCH$_2$CH$_2$CH$_2$CH$_2$CH$_3$;

$R^{26}$ is $C_1$-$C_5$alkyl, —($C_0$-$C_2$alkyl)($C_3$-$C_6$cycloalkyl), —($C_0$-$C_2$alkyl)(heterocycle)-($C_{0-2}$alkyl)(aryl) or —($C_0$-$C_2$alkyl)(heteroaryl) each of which can be optionally substituted;

$R^{27}$ is hydrogen, $C_1$-$C_6$ alkyl, —($C_1$-$C_2$alkyl)($C_3$-$C_6$cycloalkyl), —($C_1$-$C_2$alkyl)($C_3$-$C_6$heterocycle) —($C_0$-$C_2$alkyl)(aryl) or —($C_0$-$C_2$alkyl)(heteroaryl) wherein except for the hydrogen each of which can be optionally substituted;

$R^{28}$ is hydrogen, $C_1$-$C_6$ alkyl, $C_2$-$C_6$ alkenyl, $C_2$-$C_6$ alkynyl, —($C_0$-$C_2$alkyl)($C_3$-$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) wherein except for the hydrogen each of which can be optionally substituted;

$R^{29}$ is independently selected from hydrogen, $C_1$-$C_6$alkyl, —($C_0$-$C_2$alkyl)($C_3$-$C_6$cycloalkyl), —($C_0$-$C_2$alkyl)(heterocycle), —($C_0$-$C_2$alkyl)(aryl), or —($C_0$-$C_2$alkyl)(heteroaryl) wherein except for the hydrogen each of which can be optionally substituted;

$R^{30}$ hydrogen or optionally substituted $C_1$-$C_6$ alkyl;

$R^{31}$ is $C_1$-$C_6$ alkyl, $C_2$-$C_6$ alkenyl, $C_2$-$C_6$ alkynyl, —($C_0$-$C_2$alkyl)($C_3$-$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) each of which can be optionally substituted;

$R^{32}$ is hydrogen, $C_1$-$C_6$ alkyl, $C_2$-$C_6$ alkenyl, $C_2$-$C_6$ alkynyl, —($C_0$-$C_2$alkyl)($C_3$-$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) wherein except for the hydrogen each of which can be optionally substituted; or $R^{30}$ and $R^{32}$ together with the nitrogen that they are bonded to can form a heterocyclic ring;

$R^{33}$ is hydrogen, $C_1$-$C_6$ alkyl, $C_2$-$C_6$ alkenyl, $C_2$-$C_6$ alkynyl, —($C_0$-$C_2$alkyl)($C_3C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) wherein except for the hydrogen each of which can be optionally substituted; or $R^{32}$ and $R^{33}$ can be bonded together to form a heterocyclic ring.

$R^1$, $R^2$, $R^3$, $R^4$, $R^{12}$, $R^{13}$ and $R^{22}$ are as defined above.

In another embodiment, compounds of Formula IIa are disclosed:

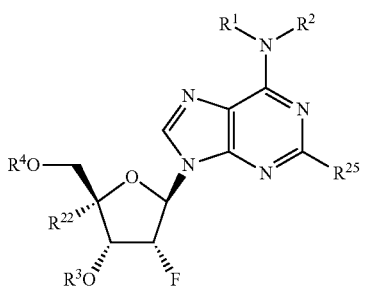

Formula IIa or a pharmaceutically acceptable composition, salt, or prodrug thereof, wherein:

$R^1$, $R^2$, $R^3$, $R^4$, $R^{22}$ and $R^{25}$ are as defined above.

In another embodiment, compounds of Formula IIb are disclosed:

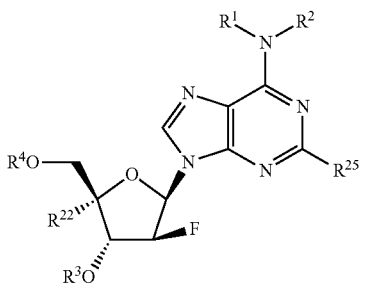

Formula IIb or a pharmaceutically acceptable composition, salt, or prodrug thereof, wherein:

$R^1$, $R^2$, $R^3$, $R^4$, $R^{22}$ and $R^{25}$ are as defined above.

In a typical embodiment, the compound is a β-D isomer with reference to the corresponding nucleoside (i.e., in the naturally occurring configuration). In an alternative configuration, the compound is provided as a β-L isomer. The compound is typically at least 90% free of the opposite enantiomer, and can be at least 98%, 99% or even 100% free of the opposite enantiomer. Unless described otherwise, the compound is at least 90% free of the opposite enantiomer.

In another embodiment, the compound is according to Formula III:

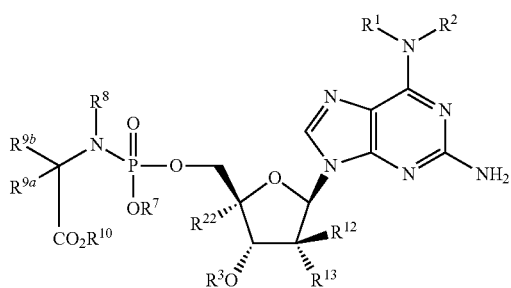

Formula III or a pharmaceutically acceptable composition, salt, or prodrug thereof, wherein:

$R^7$ is hydrogen, $C_{1-6}$alkyl, $C_{3-7}$cycloalkyl; heteroaryl, heterocyclic, or aryl, which includes, but is not limited to, phenyl or naphthyl, wherein phenyl or naphthyl are optionally substituted with $C_{1-6}$alkyl, $C_{2-6}$alkenyl, $C_{2-6}$ alkynyl, $C_{1-6}$alkoxy, F, Cl, Br, I, nitro, cyano, $C_{1-6}$haloalkyl, —N($R^{7'}$)$_2$, $C_{1-6}$acylamino, NHSO$_2$$C_{1-6}$alkyl, —SO$_2$N($R^{7'}$)$_2$, COR$^{7''}$, and —SO$_2$$C_{1-6}$alkyl; ($R^{7'}$ is independently hydrogen or $C_{1-6}$alkyl; $R^{7''}$ is —OR$^{11}$ or —N($R^{7'}$)$_2$);

$R^8$ is hydrogen, $C_{1-6}$alkyl, or $R^{9a}$ or $R^{9b}$ and $R^8$ together are (CH$_2$)$_n$ so as to form a cyclic ring that includes the adjoining N and C atoms; where n is 2 to 4;

$R^{9a}$ and $R^{9b}$ are (i) independently selected from hydrogen, $C_{1-6}$alkyl, cycloalkyl, —(CH$_2$)$_c$(NR$^{9'}$)$_2$, $C_{1-6}$hydroxyalkyl, —CH$_2$SH, —(CH$_2$)$_2$S(O)(Me, —(CH$_2$)$_3$NHC(=NH)NH$_2$, (1H-indol-3-yl)methyl, (1H-imidazol-4-yl)methyl, —(CH$_2$)$_c$ COR$^{9'''}$, aryl and aryl($C_{1-3}$alkyl)-, the aryl groups can be optionally substituted with a group selected from hydroxyl, $C_{1-6}$alkyl, $C_{1-6}$alkoxy, halogen, nitro and cyano; (ii) $R^{9a}$ and $R^{9b}$ both are $C_{1-6}$alkyl; (iii) $R^{9a}$ and $R^{9b}$ together are (CH$_2$)$_r$ so as to form a spiro ring; (iv) $R^{9a}$ is hydrogen and $R^{9b}$ and $R^8$ together are (CH$_2$)$_n$ so as to form a cyclic ring that includes the adjoining N and C atoms (v) $R^{9b}$ is hydrogen and $R^{9a}$ and $R^8$ together are (CH$_2$)$_n$ so as to form a cyclic ring that includes the adjoining N and C atoms, where c is 1 to 6, n is 2 to 4, r is 2 to 5 and where $R^{9'}$ is independently hydrogen or $C_{1-6}$ alkyl and $R^{9''}$ is —OR$^{11}$ or —N($R^{11'}$)$_2$); (vi) $R^{9a}$ is hydrogen and $R^{9b}$ is hydrogen, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl; or (vii) $R^{9a}$ is CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and $R^{9b}$ is hydrogen;

$R^{10}$ is hydrogen, $C_{1-6}$alkyl optionally substituted with an alkoxy, di(lower alkyl)-amino, or halogen; $C_{1-6}$haloalkyl, ($C_0$-$C_2$)($C_{3-7}$cycloalkyl), ($C_0$-$C_2$)(heterocycloalkyl), aminoacyl, ($C_0$-$C_2$)(aryl), such as ($C_0$-$C_2$)(phenyl), ($C_0$-$C_2$)(heteroaryl), such as ($C_0$-$C_2$)(pyridinyl), substituted ($C_0$-$C_2$) (aryl), or substituted ($C_0$-$C_2$)(heteroaryl);

$R^{11}$ is an optionally substituted $C_{1-6}$alkyl, an optionally substituted cycloalkyl; an optionally substituted $C_{2-6}$alkynyl, an optionally substituted $C_{2-6}$alkenyl, or optionally substituted acyl, which includes but is not limited to C(O) ($C_{1-6}$ alkyl); and $R^1$, $R^2$, $R^3$, $R^{12}$, $R^{13}$ and $R^{22}$ are as defined above.

In one embodiment, compounds of Formula IIIa are disclosed:

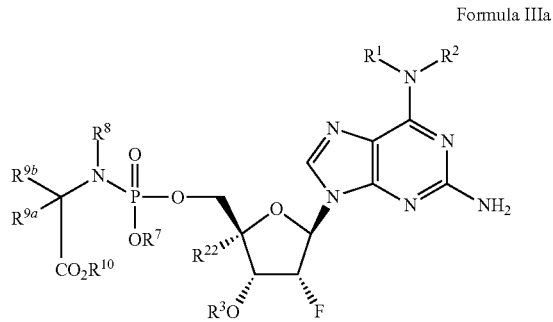

Formula IIIa or a pharmaceutically acceptable composition, salt, or prodrug thereof, wherein the variables $R^1$, $R^2$, $R^3$, $R^7$, $R^8$, $R^{9a}$, $R^{9b}$, $R^{10}$ and $R^{22}$ are described above.

In one embodiment, compounds of Formula IIIb are disclosed:

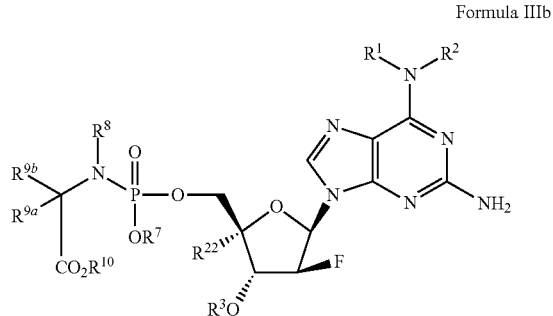

Formula IIIb or a pharmaceutically acceptable composition, salt, or prodrug thereof, wherein the variables $R^1$, $R^2$, $R^3$, $R^7$, $R^8$, $R^{9a}$, $R^{9b}$, $R^{10}$ and $R^{22}$ are described above.

In one embodiment, the compound is according to Formula IV:

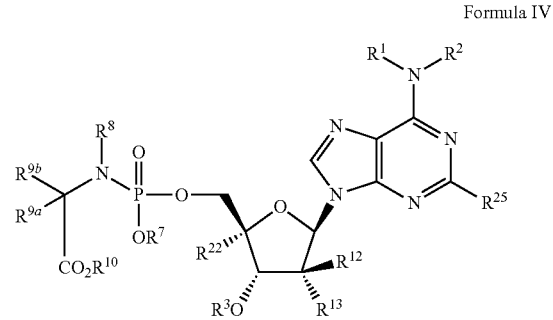

Formula IV or a pharmaceutically acceptable composition, salt, or prodrug thereof, wherein:
$R^1$, $R^2$, $R^3$, $R^7$, $R^8$, $R^{9a}$, $R^{9b}$, $R^{10}$, $R^{12}$, $R^{13}$, $R^{22}$ and $R^{25}$ are as defined above.

In one embodiment, compounds of Formula IVa are disclosed:

Formula IVa or a pharmaceutically acceptable composition, salt, or prodrug thereof, wherein the variables $R^1$, $R^2$, $R^3$, $R^7$, $R^8$, $R^{9a}$, $R^{9b}$, $R^{10}$, $R^{22}$ and $R^{25}$ are described above.

In one embodiment, compounds of Formula IVb are disclosed:

Formula IVb or a pharmaceutically acceptable composition, salt, or prodrug thereof, wherein the variables $R^1$, $R^2$, $R^3$, $R^7$, $R^8$, $R^{9a}$, $R^{9b}$, $R^{10}$, $R^{22}$ and $R^{25}$ are described herein.

In one embodiment, compounds of Formula V are disclosed:

Formula V or a pharmaceutically acceptable composition, salt, or prodrug thereof, wherein the variables $R^1$, $R^2$, $R^{12}$, $R^{13}$ and $R^{22}$ are described herein.

Q is oxygen or sulfur; and $R^{23}$ is —OH, —O⁻, optionally substituted —O-alkyl, an optionally substituted —O-alkenyl, an optionally substituted —O-alkynyl, an optionally substituted —O—($C_0$-$C_2$)(cycloalkyl), an optionally substituted —O—($C_0$-$C_2$)(heterocyclo), an optionally substituted —O—($C_0$-$C_2$)(aryl), an optionally substituted —O—($C_0$-$C_2$)(heteroaryl), -an optionally substituted N-linked amino acid, or an optionally substituted N-linked amino acid ester.

In one embodiment, compounds of Formula VI are disclosed:

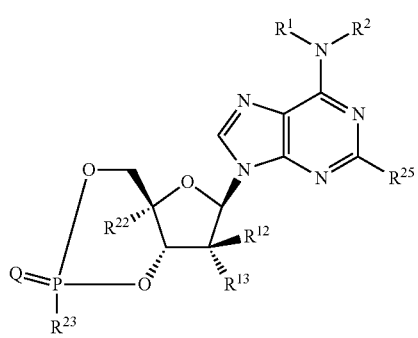

Formula VI or a pharmaceutically acceptable composition, salt, or prodrug thereof, wherein the variables $R^1$, $R^2$, $R^{12}$, $R^{13}$, $R^{22}$, $R^{23}$, $R^{25}$ and Q are described herein.

In an alternative embodiment, compounds, methods, and compositions are provided for the treatment of a host infected with or exposed to a paramyxovirus or an orthomyxovirus.

Metabolism of β-D-2'-deoxy-2'-substituted-4'-substituted-$N^6$-substituted-2,6-diaminopurine nucleotides The metabolism of the β-D-2'-deoxy-2'-substituted-4'-substituted-$N^6$-methyl-2,6-diaminopurine nucleoside phosphoramidate involves the production of a 5'-monophosphate and the subsequent anabolism of the $N^6$-methyl-2,6-diaminopurine base to generate the β-D-2'-deoxy-2'-substituted-4'-substituted-$N^6$-methyl-2,6-diaminopurine-guanine nucleoside as the 5'-monophosphate. The monophosphate is then further anabolized to the active species; the 5'-triphosphate. The metabolic pathway for the β-D-2'-deoxy-2'-substituted-4'-substituted-$N^6$-methyl-2,6-diaminopurine nucleoside phosphoramidate is illustrated in Scheme 1 below.

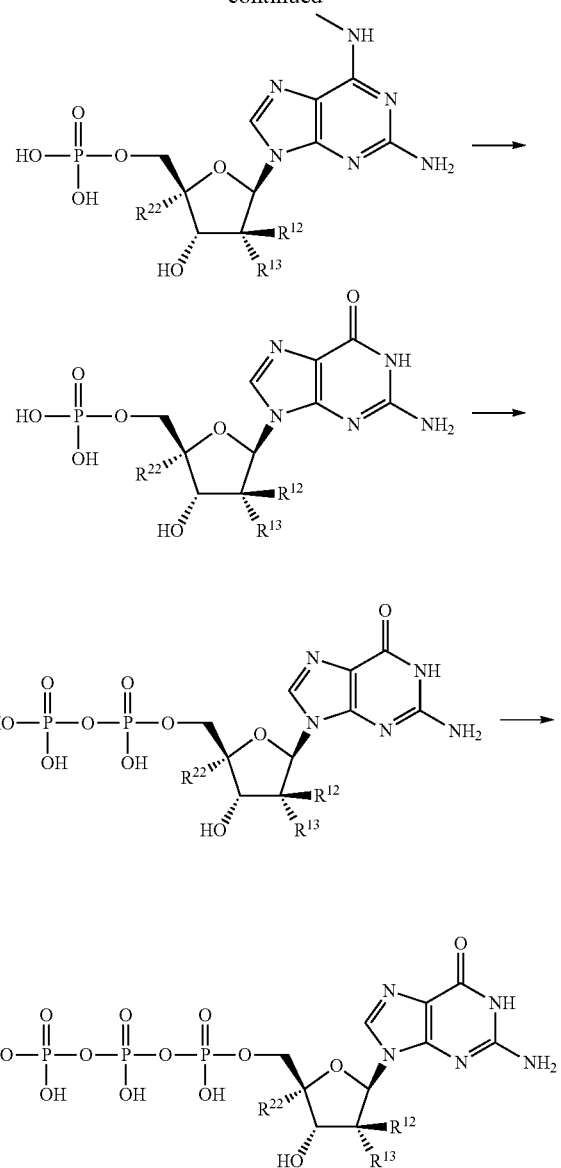

The metabolism of the β-D-2'-deoxy-2'-substituted-4'-substituted-$N^6$-dimethyl-2,6-diaminopurine nucleotide involves both the formation of the β-D-2'-deoxy-2'-substituted-4'-substituted-$N^6$-dimethyl-2,6-diaminopurine triphosphate as well as the generation of the corresponding guanine nucleoside triphosphate. These metabolic pathways are illustrated in Schemes 2 and 3 below.

Scheme 1

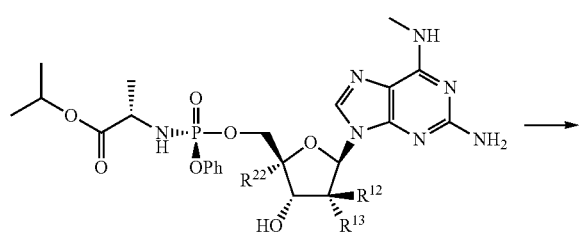

Scheme 2

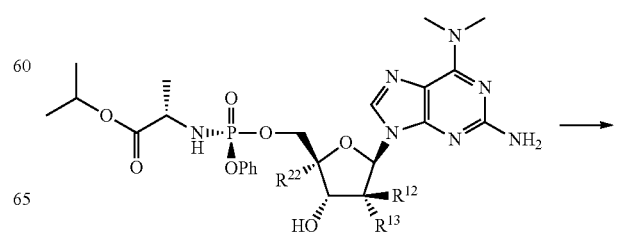

29
-continued
30
-continued
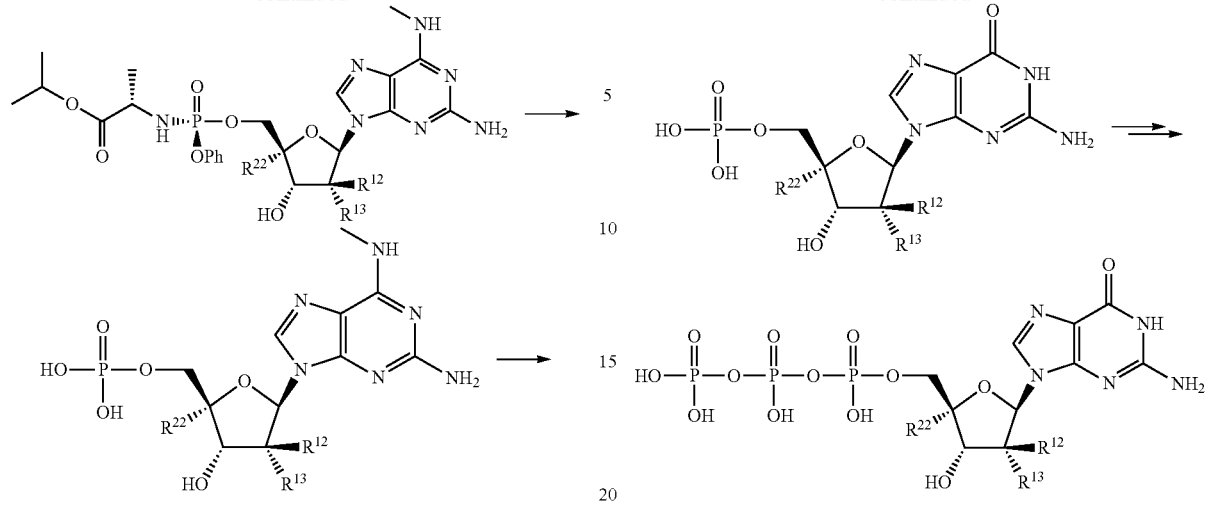
Scheme 3
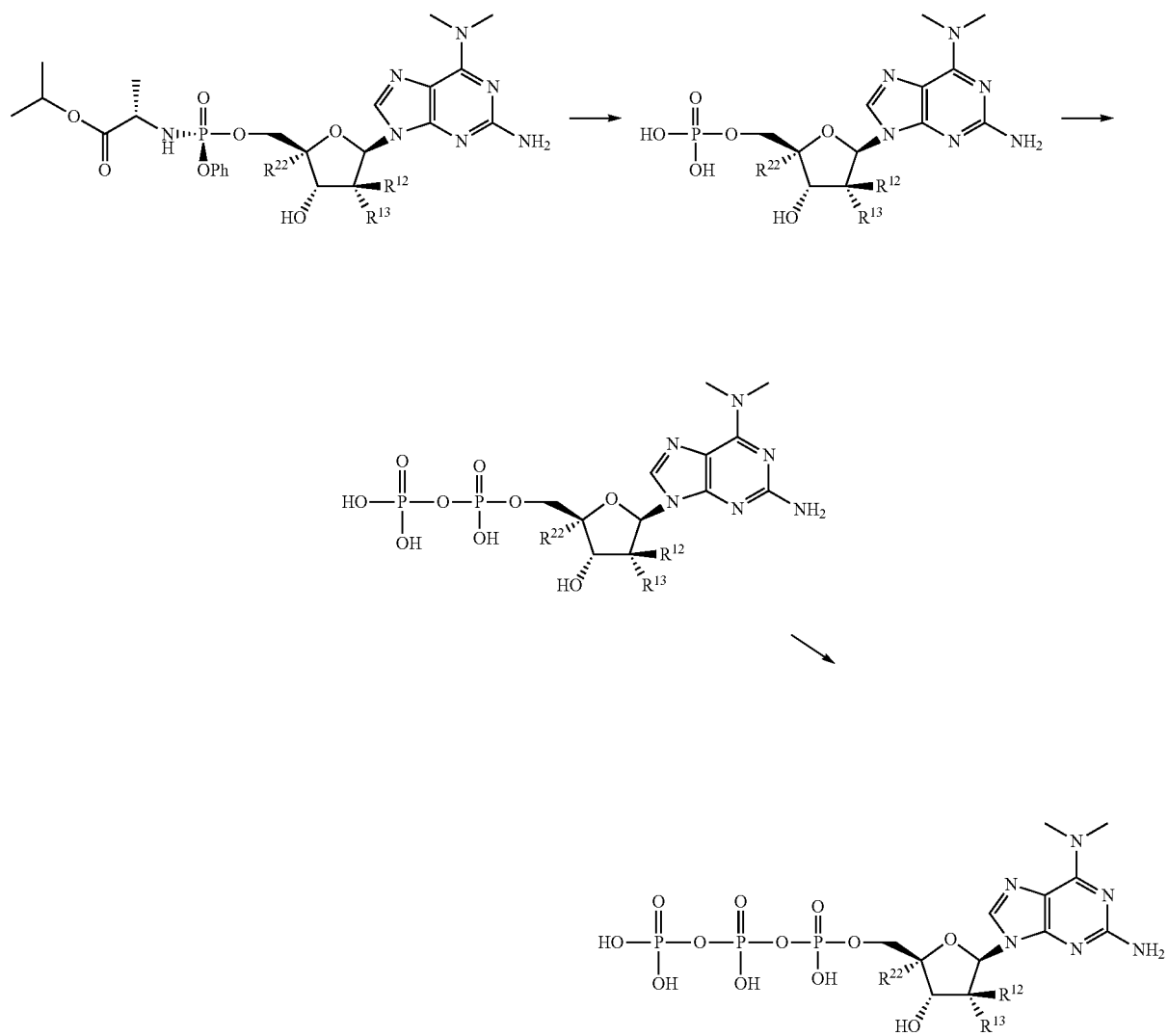

Stabilized Phosphate Prodrugs

Stabilized phosphate prodrugs are moieties that can deliver a mono, di, or triphosphate in vivo, for example in a human. For example, McGuigan has disclosed phosphoramidates in U.S. Pat. Nos. 8,933,053; 8,759,318; 8,658,616; 8,263,575; 8,119,779; 7,951,787 and 7,115,590. Alios has disclosed thiophosphoramidates in U.S. Pat. Nos. 8,895,723 and 8,871,737. Alios has also disclosed cyclic nucleotides in U.S. Pat. No. 8,772,474. Idenix has disclosed cyclic phosphoramidates and phosphoramidate/SATE derivatives in WO 2013/177219. Idenix has also disclosed substituted carbonyloxymethylphosphoramidate compounds in WO 2013/039920. Hostetler has disclosed lipid phosphate prodrugs, see, for example, U.S. Pat. No. 7,517,858. Hostetler has also disclosed lipid conjugates of phosphonate prodrugs, see, for example, U.S. Pat. Nos. 8,889,658; 8,846,643; 8,710,030; 8,309,565; 8,008,308; and 7,790,703. Emory University has disclosed nucleotide sphingoid and lipid derivatives in WO 2014/124430. RFS Pharma has disclosed purine nucleoside monophosphate prodrugs in WO 2010/091386. HepDirect™ technology is disclosed in the article "Design, Synthesis, and Characterization of a Series of Cytochrome P(450) 3A-Activated Prodrugs (HepDirect Prodrugs) Useful for Targeting Phosph(on)ate-Based Drugs to the Liver," (J. Am. Chem. Soc. 126, 5154-5163 (2004). Additional phosphate prodrugs include, but are not limited to phosphate esters, 3',5'-cyclic phosphates including CycloSAL, SATE derivatives (S-acyl-2thioesters) and DTE (dithiodiethyl) prodrugs. For literature reviews that disclose non-limiting examples see: A. Ray and K. Hostetler, "Application of kinase bypass strategies to nucleoside antivirals," Antiviral Research (2011) 277-291; M. Sofia, "Nucleotide prodrugs for HCV therapy," Antiviral Chemistry and Chemotherapy 2011; 22-23-49; and S. Peyrottes et al., "SATE Pronucleotide Approaches: An Overview," Mini Reviews in Medicinal Chemistry 2004, 4, 395. In one embodiment, a 5'-prodrug described in any of these patent filings or literature can be used in the $R^4$ position of the presented compounds.

Embodiments

In particular embodiments:
(i) in Formula Ia, $R^1$ is methyl, $R^2$ is hydrogen, $R^3$ is hydrogen, $R^4$ is a stabilized phosphate prodrug;
(ii) in Formula Ia, $R^1$ is methyl, $R^2$ is hydrogen, $R^3$ is hydrogen, and $R^4$ is a stabilized thiophosphate prodrug;
(iii) in Formula Ia, $R^1$ is methyl, $R^2$ is hydrogen, $R^3$ is hydrogen, and $R^4$ is a phosphoramidate;
(iv) in Formula Ia, $R^1$ is methyl, $R^2$ is hydrogen, $R^3$ is hydrogen, and $R^4$ is a thiophosphoramidate:
(v) in Formula Ia, $R^1$ is methyl, $R^2$ is hydrogen, $R^3$ is hydrogen, and $R^4$ is a monophosphate;
(vi) in Formula Ia, $R^1$ is methyl, $R^2$ is hydrogen, $R^3$ is hydrogen, and $R^4$ is a diphosphate;
(vii) in Formula Ia, $R^1$ is methyl, $R^2$ is hydrogen, $R^3$ is hydrogen, and $R^4$ is a triphosphate;
(viii) in Formula Ia, $R^1$ is methyl, $R^2$ is methyl, $R^3$ is hydrogen, $R^4$ is a stabilized phosphate prodrug;
(ix) in Formula Ia, $R^1$ is methyl, $R^2$ is methyl, $R^3$ is hydrogen, and $R^4$ is a stabilized thiophosphate prodrug;
(x) in Formula Ia, $R^1$ is methyl, $R^2$ is methyl, $R^3$ is hydrogen, and $R^4$ is a phosphoramidate;
(xi) in Formula Ia, $R^1$ is methyl, $R^2$ is methyl, $R^3$ is hydrogen, and $R^4$ is a thiophosphoramidate:
(xii) in Formula Ia, $R^1$ is methyl, $R^2$ is methyl, $R^3$ is hydrogen, and $R^4$ is a monophosphate;
(xiii) in Formula Ia, $R^1$ is methyl, $R^2$ is methyl, $R^3$ is hydrogen, and $R^4$ is a diphosphate;
(xiv) in Formula Ia, $R^1$ is methyl, $R^2$ is methyl, $R^3$ is hydrogen, and $R^4$ is a triphosphate;
(xv) in Formula Ia, $R^1$ is methyl, $R^2$ is cyclopropyl, $R^3$ is hydrogen, $R^4$ is a stabilized phosphate prodrug;
(xvi) in Formula Ia, $R^1$ is methyl, $R^2$ is cyclopropyl, $R^3$ is hydrogen, and $R^4$ is a stabilized thiophosphate prodrug;
(xvii) in Formula Ia, $R^1$ is methyl, $R^2$ is cyclopropyl, $R^3$ is hydrogen, and $R^4$ is a phosphoramidate;
(xviii) in Formula Ia, $R^1$ is methyl, $R^2$ is cyclopropyl, $R^3$ is hydrogen, and $R^4$ is a thiophosphoramidate:
(xix) in Formula Ia, $R^1$ is methyl, $R^2$ is cyclopropyl, $R^3$ is hydrogen, and $R^4$ is a monophosphate;
(xx) in Formula Ia, $R^1$ is methyl, $R^2$ is cyclopropyl, $R^3$ is hydrogen, and $R^4$ is a diphosphate;
(xxi) in Formula Ia, $R^1$ is methyl, $R^2$ is cyclopropyl, $R^3$ is hydrogen, and $R^4$ is a triphosphate;
(xxii) in Formula Ia, $R^1$ is ethyl, $R^2$ is hydrogen, $R^3$ is hydrogen, $R^4$ is a stabilized phosphate prodrug;
(xxiii) in Formula Ia, $R^1$ is ethyl, $R^2$ is hydrogen, $R^3$ is hydrogen, and $R^4$ is a stabilized thiophosphate prodrug;
(xxiv) in Formula Ia, $R^1$ is ethyl, $R^2$ is hydrogen, $R^3$ is hydrogen, and $R^4$ is a phosphoramidate;
(xxv) in Formula Ia, $R^1$ is ethyl, $R^2$ is hydrogen, $R^3$ is hydrogen, and $R^4$ is a thiophosphoramidate:
(xxvi) in Formula Ia, $R^1$ is ethyl, $R^2$ is hydrogen, $R^3$ is hydrogen, and $R^4$ is a monophosphate;
(xxvii) in Formula Ia, $R^1$ is ethyl, $R^2$ is hydrogen, $R^3$ is hydrogen, and $R^4$ is a diphosphate;
(xxviii) in Formula Ia, $R^1$ is ethyl, $R^2$ is hydrogen, $R^3$ is hydrogen, and $R^4$ is a triphosphate;
(xxix) in Formula Ia, $R^1$ is propyl, $R^2$ is hydrogen, $R^3$ is hydrogen, $R^4$ is a stabilized phosphate prodrug;
(xxx) in Formula Ia, $R^1$ is propyl, $R^2$ is hydrogen, $R^3$ is hydrogen, and $R^4$ is a stabilized thiophosphate prodrug;
(xxxi) in Formula Ia, $R^1$ is propyl, $R^2$ is hydrogen, $R^3$ is hydrogen, and $R^4$ is a phosphoramidate;
(xxxii) in Formula Ia, $R^1$ is propyl, $R^2$ is hydrogen, $R^3$ is hydrogen, and $R^4$ is a thiophosphoramidate:
(xxxiii) in Formula Ia, $R^1$ is propyl, $R^2$ is hydrogen, $R^3$ is hydrogen, and $R^4$ is a monophosphate;
(xxxiv) in Formula Ia, $R^1$ is propyl, $R^2$ is hydrogen, $R^3$ is hydrogen, and $R^4$ is a diphosphate;
(xxxv) in Formula Ia, $R^1$ is propyl, $R^2$ is hydrogen, $R^3$ is hydrogen, and $R^4$ is a triphosphate;
(xxxvi) in Formula Ia, $R^1$ is isopropyl, $R^2$ is hydrogen, $R^3$ is hydrogen, and $R^4$ is a stabilized phosphate prodrug;
(xxxvii) in Formula Ia, $R^1$ is isopropyl, $R^2$ is hydrogen, $R^3$ is hydrogen, and $R^4$ is a stabilized thiophosphate prodrug;
(xxxviii) in Formula Ia, $R^1$ is isopropyl, $R^2$ is hydrogen, $R^3$ is hydrogen, and $R^4$ is a phosphoramidate;
(xxxix) in Formula Ia, $R^1$ is isopropyl, $R^2$ is hydrogen, $R^3$ is hydrogen, and $R^4$ is a thiophosphoramidate:
(xl) in Formula Ia, $R^1$ is isopropyl, $R^2$ is hydrogen, $R^3$ is hydrogen, and $R^4$ is a monophosphate;
(xli) in Formula Ia, $R^1$ is isopropyl, $R^2$ is hydrogen, $R^3$ is hydrogen, and $R^4$ is a diphosphate;
(xlii) in Formula Ia, $R^1$ is isopropyl, $R^2$ is hydrogen, $R^3$ is hydrogen, and $R^4$ is a triphosphate;
(xliii) in Formula Ia, $R^1$ is ethyl, $R^2$ is ethyl, $R^3$ is hydrogen, $R^4$ is a stabilized phosphate prodrug;
(xliv) in Formula Ia, $R^1$ is ethyl, $R^2$ is ethyl, $R^3$ is hydrogen, and $R^4$ is a stabilized thiophosphate prodrug;
(xlv) in Formula Ia, $R^1$ is ethyl, $R^2$ is ethyl, $R^3$ is hydrogen, and $R^4$ is a phosphoramidate;
(xlvi) in Formula Ia, $R^1$ is ethyl, $R^2$ is ethyl, $R^3$ is hydrogen, and $R^4$ is a thiophosphoramidate:

(xlvii) in Formula Ia, $R^1$ is ethyl, $R^2$ is ethyl, $R^3$ is hydrogen, and $R^4$ is a monophosphate;
(xlviii) in Formula Ia, $R^1$ is ethyl, $R^2$ is ethyl, $R^3$ is hydrogen, and $R^4$ is a diphosphate;
(xlix) in Formula Ia, $R^1$ is ethyl, $R^2$ is ethyl, $R^3$ is hydrogen, and $R^4$ is a triphosphate;
(l) in Formula Ia, $R^1$ is methyl, $R^2$ is propyl, $R^3$ is hydrogen, $R^4$ is a stabilized phosphate prodrug;
(li) in Formula Ia, $R^1$ is methyl, $R^2$ is propyl, $R^3$ is hydrogen, and $R^4$ is a stabilized thiophosphate prodrug;
(lii) in Formula Ia, $R^1$ is methyl, $R^2$ is propyl, $R^3$ is hydrogen, and $R^4$ is a phosphoramidate;
(liii) in Formula Ia, $R^1$ is methyl, $R^2$ is propyl, $R^3$ is hydrogen, and $R^4$ is a thiophosphoramidate:
(liv) in Formula Ia, $R^1$ is methyl, $R^2$ is propyl, $R^3$ is hydrogen, and $R^4$ is a monophosphate;
(lv) in Formula Ia, $R^1$ is methyl, $R^2$ is propyl, $R^3$ is hydrogen, and $R^4$ is a diphosphate;
(lvi) in Formula Ia, $R^1$ is methyl, $R^2$ is propyl, $R^3$ is hydrogen, and $R^4$ is a triphosphate;
(lvii) in Formula Ia, $R^1$ and $R^2$ together with the nitrogen to which they are bonded to form a 5-membered heterocyclic ring, $R^3$ is hydrogen, $R^4$ is a stabilized phosphate prodrug;
(lviii) in Formula Ia, $R^1$ and $R^2$ together with the nitrogen to which they are bonded to form a 5-membered heterocyclic ring, $R^3$ is hydrogen, and $R^4$ is a stabilized thiophosphate prodrug;
(lix) in Formula Ia, $R^1$ and $R^2$ together with the nitrogen to which they are bonded to form a 5-membered heterocyclic ring, $R^3$ is hydrogen, and $R^4$ is a phosphoramidate;
(lx) in Formula Ia, $R^1$ and $R^2$ together with the nitrogen to which they are bonded to form a 5-membered heterocyclic ring, $R^3$ is hydrogen, and $R^4$ is a thiophosphoramidate:
(lxi) in Formula Ia, $R^1$ and $R^2$ together with the nitrogen to which they are bonded to form a 5-membered heterocyclic ring, $R^3$ is hydrogen, and $R^4$ is a monophosphate;
(lxii) in Formula Ia, $R^1$ and $R^2$ together with the nitrogen to which they are bonded to form a 5-membered heterocyclic ring, $R^3$ is hydrogen, and $R^4$ is a diphosphate;
(lxiii) in Formula Ia, $R^1$ and $R^2$ together with the nitrogen to which they are bonded to form a 5-membered heterocyclic ring, $R^3$ is hydrogen, and $R^4$ is a triphosphate;
(lxiv) in Formula Ia, $R^1$ is cyclopentyl, $R^2$ is hydrogen, $R^3$ is hydrogen, $R^4$ is a stabilized phosphate prodrug;
(lxv) in Formula Ia, $R^1$ is cyclopentyl, $R^2$ is hydrogen, $R^3$ is hydrogen, and $R^4$ is a stabilized thiophosphate prodrug;
(lxvi) in Formula Ia, $R^1$ is cyclopentyl, $R^2$ is hydrogen, $R^3$ is hydrogen, and $R^4$ is a phosphoramidate;
(lxvii) in Formula Ia, $R^1$ is cyclopentyl, $R^2$ is hydrogen, $R^3$ is hydrogen, and $R^4$ is a thiophosphoramidate:
(lxviii) in Formula Ia, $R^1$ is cyclopentyl, $R^2$ is hydrogen, $R^3$ is hydrogen, and $R^4$ is a monophosphate;
(lxix) in Formula Ia, $R^1$ is cyclopentyl, $R^2$ is hydrogen, $R^3$ is hydrogen, and $R^4$ is a diphosphate;
(lxx) in Formula Ia, $R^1$ is cyclopentyl, $R^2$ is hydrogen, $R^3$ is hydrogen, and $R^4$ is a triphosphate;
(lxxi) in Formula Ia, $R^1$ is cyclopropyl, $R^2$ is cyclopropyl, $R^3$ is hydrogen, $R^4$ is a stabilized phosphate prodrug;
(lxxii) in Formula Ia, $R^1$ is cyclopropyl, $R^2$ is cyclopropyl, $R^3$ is hydrogen, and $R^4$ is a stabilized thiophosphate prodrug;
(lxxiii) in Formula Ia, $R^1$ is cyclopropyl, $R^2$ is cyclopropyl, $R^3$ is hydrogen, and $R^4$ is a phosphoramidate;
(lxxiv) in Formula Ia, $R^1$ is cyclopropyl, $R^2$ is cyclopropyl, $R^3$ is hydrogen, and $R^4$ is a thiophosphoramidate:
(lxxv) in Formula Ia, $R^1$ is cyclopropyl, $R^2$ is cyclopropyl, $R^3$ is hydrogen, and $R^4$ is a monophosphate;
(lxxvi) in Formula Ia, $R^1$ is cyclopropyl, $R^2$ is cyclopropyl, $R^3$ is hydrogen, and $R^4$ is a diphosphate;
(lxxvii) in Formula Ia, $R^1$ is cyclopropyl, $R^2$ is cyclopropyl, $R^3$ is hydrogen, and $R^4$ is a triphosphate;
(lxxviii) in Formula Ia, $R^1$ is methyl, $R^2$ is ethyl, $R^3$ is hydrogen, $R^4$ is a stabilized phosphate prodrug;
(lxxix) in Formula Ia, $R^1$ is methyl, $R^2$ is ethyl, $R^3$ is hydrogen, and $R^4$ is a stabilized thiophosphate prodrug;
(lxxx) in Formula Ia, $R^1$ is methyl, $R^2$ is ethyl, $R^3$ is hydrogen, and $R^4$ is a phosphoramidate;
(lxxxi) in Formula Ia, $R^1$ is methyl, $R^2$ is ethyl, $R^3$ is hydrogen, and $R^4$ is a thiophosphoramidate:
(lxxxii) in Formula Ia, $R^1$ is methyl, $R^2$ is ethyl, $R^3$ is hydrogen, and $R^4$ is a monophosphate;
(lxxxiii) in Formula Ia, $R^1$ is methyl, $R^2$ is ethyl, $R^3$ is hydrogen, and $R^4$ is a diphosphate;
(lxxxiv) in Formula Ia, $R^1$ is methyl, $R^2$ is ethyl, $R^3$ is hydrogen, and $R^4$ is a triphosphate;
(lxxxv) in Formula Ia, $R^1$ is cyclobutyl, $R^2$ is hydrogen, $R^3$ is hydrogen, $R^4$ is a stabilized phosphate prodrug;
(lxxxvi) in Formula Ia, $R^1$ is cyclobutyl, $R^2$ is hydrogen, $R^3$ is hydrogen, and $R^4$ is a stabilized thiophosphate prodrug;
(lxxxvii) in Formula Ia, $R^1$ is cyclobutyl, $R^2$ is hydrogen, $R^3$ is hydrogen, and $R^4$ is a phosphoramidate;
(lxxxviii) in Formula Ia, $R^1$ is cyclobutyl, $R^2$ is hydrogen, $R^3$ is hydrogen, and $R^4$ is a thiophosphoramidate:
(lxxxix) in Formula Ia, $R^1$ is cyclobutyl, $R^2$ is hydrogen, $R^3$ is hydrogen, and $R^4$ is a monophosphate;
(xc) in Formula Ia, $R^1$ is cyclobutyl, $R^2$ is hydrogen, $R^3$ is hydrogen, and $R^4$ is a diphosphate;
(xci) in Formula Ia, $R^1$ is cyclobutyl, $R^2$ is hydrogen, $R^3$ is hydrogen, and $R^4$ is a triphosphate;
(xcii) in Formula Ib, $R^1$ is methyl, $R^2$ is methyl, $R^3$ is hydrogen, $R^4$ is a stabilized phosphate prodrug;
(xciii) in Formula Ib, $R^1$ is methyl, $R^2$ is methyl, $R^3$ is hydrogen, and $R^4$ is a stabilized thiophosphate prodrug;
(xciv) in Formula Ib, $R^1$ is methyl, $R^2$ is methyl, $R^3$ is hydrogen, and $R^4$ is a phosphoramidate;
(xcv) in Formula Ib, $R^1$ is methyl, $R^2$ is methyl, $R^3$ is hydrogen, and $R^4$ is a thiophosphoramidate:
(xcvi) in Formula Ib, $R^1$ is methyl, $R^2$ is methyl, $R^3$ is hydrogen, and $R^4$ is a monophosphate;
(xcvii) in Formula Ib, $R^1$ is methyl, $R^2$ is methyl, $R^3$ is hydrogen, and $R^4$ is a diphosphate;
(xcviii) in Formula Ib, $R^1$ is methyl, $R^2$ is methyl, $R^3$ is hydrogen, and $R^4$ is a triphosphate;
(xcix) in Formula Ib, $R^1$ is methyl, $R^2$ is hydrogen, $R^3$ is hydrogen, $R^4$ is a stabilized phosphate prodrug;
(c) in Formula Ib, $R^1$ is methyl, $R^2$ is hydrogen, $R^3$ is hydrogen, and $R^4$ is a stabilized thiophosphate prodrug;
(ci) in Formula Ib, $R^1$ is methyl, $R^2$ is hydrogen, $R^3$ is hydrogen, and $R^4$ is a phosphoramidate;
(cii) in Formula Ib, $R^1$ is methyl, $R^2$ is hydrogen, $R^3$ is hydrogen, and $R^4$ is a thiophosphoramidate:
(ciii) in Formula Ib, $R^1$ is methyl, $R^2$ is hydrogen, $R^3$ is hydrogen, and $R^4$ is a monophosphate;

(civ) in Formula Ib, $R^1$ is methyl, $R^2$ is hydrogen, $R^3$ is hydrogen, and $R^4$ is a diphosphate;
(cv) in Formula Ib, $R^1$ is methyl, $R^2$ is hydrogen, $R^3$ is hydrogen, and $R^4$ is a triphosphate;
(cvi) in Formula Ib, $R^1$ is cyclopentyl, $R^2$ is hydrogen, $R^3$ is hydrogen, $R^4$ is a stabilized phosphate prodrug;
(cvii) in Formula Ib, $R^1$ is cyclopentyl, $R^2$ is hydrogen, $R^3$ is hydrogen, and $R^4$ is a stabilized thiophosphate prodrug;
(cviii) in Formula Ib, $R^1$ is cyclopentyl, $R^2$ is hydrogen, $R^3$ is hydrogen, and $R^4$ is a phosphoramidate;
(cix) in Formula Ib, $R^1$ is cyclopentyl, $R^2$ is hydrogen, $R^3$ is hydrogen, and $R^4$ is a thiophosphoramidate:
(cx) in Formula Ib, $R^1$ is cyclopentyl, $R^2$ is hydrogen, $R^3$ is hydrogen, and $R^4$ is a monophosphate;
(cxi) in Formula Ib, $R^1$ is cyclopentyl, $R^2$ is hydrogen, $R^3$ is hydrogen, and $R^4$ is a diphosphate;
(cxii) in Formula Ib, $R^1$ is cyclopentyl, $R^2$ is hydrogen, $R^3$ is hydrogen, and $R^4$ is a triphosphate;
(cxiii) in Formula Ib, $R^1$ and $R^2$ together with the nitrogen to which they are bonded to form a 5-membered heterocyclic ring, $R^3$ is hydrogen, $R^4$ is a stabilized phosphate prodrug;
(cxiv) in Formula Ib, $R^1$ and $R^2$ together with the nitrogen to which they are bonded to form a 5-membered heterocyclic ring, $R^3$ is hydrogen, and $R^4$ is a stabilized thiophosphate prodrug;
(cxv) in Formula Ib, $R^1$ and $R^2$ together with the nitrogen to which they are bonded to form a 5-membered heterocyclic ring, $R^3$ is hydrogen, and $R^4$ is a phosphoramidate;
(cxvi) in Formula Ib, $R^1$ and $R^2$ together with the nitrogen to which they are bonded to form a 5-membered heterocyclic ring, $R^3$ is hydrogen, and $R^4$ is a thiophosphoramidate:
(cxvii) in Formula Ib, $R^1$ and $R^2$ together with the nitrogen to which they are bonded to form a 5-membered heterocyclic ring, $R^3$ is hydrogen, and $R^4$ is a monophosphate;
(cxviii) in Formula Ib, $R^1$ and $R^2$ together with the nitrogen to which they are bonded to form a 5-membered heterocyclic ring, $R^3$ is hydrogen, and $R^4$ is a diphosphate;
(cxix) in Formula Ib, $R^1$ and $R^2$ together with the nitrogen to which they are bonded to form a 5-membered heterocyclic ring, $R^3$ is hydrogen, and $R^4$ is a triphosphate;
(cxx) in Formula Ib, $R^1$ is methyl, $R^2$ is cyclopropyl, $R^3$ is hydrogen, $R^4$ is a stabilized phosphate prodrug;
(cxxi) in Formula Ib, $R^1$ is methyl, $R^2$ is cyclopropyl, $R^3$ is hydrogen, and $R^4$ is a stabilized thiophosphate prodrug;
(cxxii) in Formula Ib, $R^1$ is methyl, $R^2$ is cyclopropyl, $R^3$ is hydrogen, and $R^4$ is a phosphoramidate;
(cxxiii) in Formula Ib, $R^1$ is methyl, $R^2$ is cyclopropyl, $R^3$ is hydrogen, and $R^4$ is a thiophosphoramidate:
(cxxiv) in Formula Ib, $R^1$ is methyl, $R^2$ is cyclopropyl, $R^3$ is hydrogen, and $R^4$ is a monophosphate;
(cxxv) in Formula Ib, $R^1$ is methyl, $R^2$ is cyclopropyl, $R^3$ is methyl, and $R^4$ is a diphosphate;
(cxxvi) in Formula Ia, $R^1$ is methyl, $R^2$ is cyclopropyl, $R^3$ is hydrogen, and $R^4$ is a triphosphate;
(cxxvii) in Formula Ib, $R^1$ is cyclopropyl, $R^2$ is cyclopropyl, $R^3$ is hydrogen, and $R^4$ is a stabilized phosphate prodrug;
(cxxviii) in Formula Ib, $R^1$ is cyclopropyl, $R^2$ is cyclopropyl, $R^3$ is hydrogen, and $R^4$ is a stabilized thiophosphate prodrug;
(cxxix) in Formula Ib, $R^1$ is cyclopropyl, $R^2$ is cyclopropyl, $R^3$ is hydrogen, and $R^4$ is a phosphoramidate;
(cxxx) in Formula Ib, $R^1$ is cyclopropyl, $R^2$ is cyclopropyl, $R^3$ is hydrogen, and $R^4$ is a thiophosphoramidate:
(cxxxi) in Formula Ib, $R^1$ is cyclopropyl, $R^2$ is cyclopropyl, $R^3$ is hydrogen, and $R^4$ is a monophosphate;
(cxxxii) in Formula Ib, $R^1$ is cyclopropyl, $R^2$ is cyclopropyl, $R^3$ is hydrogen, and $R^4$ is a diphosphate;
(cxxxiii) in Formula Ib, $R^1$ is cyclopropyl, $R^2$ is cyclopropyl, $R^3$ is hydrogen, and $R^4$ is a triphosphate;
(cxxxiv) in Formula I, $R^{12}$ is F;
(cxxxv) in Formula II, $R^{12}$ is F;
(cxxxvi) in Formula III, $R^{12}$ is F;
(cxxxvii) in Formula IV, $R^{12}$ is F;
(cxxxviii) in Formula V, $R^{12}$ is F;
(cxxxix) in Formula VI, $R^{12}$ is F;
(cxl) in Formula I, $R^{12}$ is Cl;
(cxli) in Formula II, $R^{12}$ is Cl;
(cxlii) in Formula III, $R^{12}$ is Cl;
(cxliii) in Formula IV, $R^{12}$ is Cl;
(cxliv) in Formula V, $R^{12}$ is Cl;
(cxlv) in Formula VI, $R^{12}$ is Cl;
(cxlvi) in Formula I, $R^{12}$ is Br;
(cxlvii) in Formula II, $R^{12}$ is Br;
(cxlviii) in Formula III, $R^{12}$ is Br;
(cxlix) in Formula IV, $R^{12}$ is Br;
(cl) in Formula V, $R^{12}$ is Br;
(cli) in Formula VI, $R^{12}$ is Br;
(clii) in Formula I, $R^{13}$ is F;
(cliii) in Formula II, $R^{13}$ is F;
(cliv) in Formula III, $R^{13}$ is F;
(clv) in Formula IV, $R^{13}$ is F;
(clvi) in Formula V, $R^{13}$ is F;
(clvii) in Formula VI, $R^{13}$ is F;
(clviii) in Formula I, $R^{13}$ is Cl;
(clix) in Formula II, $R^{13}$ is Cl;
(clx) in Formula III, $R^{13}$ is Cl;
(clxi) in Formula IV, $R^{13}$ is Cl;
(clxii) in Formula V, $R^{13}$ is Cl;
(clxiii) in Formula VI, $R^{13}$ is Cl;
(clxiv) in Formula I, $R^{13}$ is Br;
(clxv) in Formula II, $R^{13}$ is Cl;
(clxvi) in Formula III, $R^{13}$ is Br;
(clxvii) in Formula IV, $R^{13}$ is Br;
(clxviii) in Formula V, $R^{13}$ is Br;
(clxix) in Formula VI, $R^{13}$ is Br;
(clxx) in Formula I, $R^{12}$ and $R^{13}$ are F;
(clxxi) in Formula II, $R^{12}$ and $R^{13}$ are F;
(clxxii) in Formula III, $R^{12}$ and $R^{13}$ are F;
(clxxiii) in Formula IV, $R^{12}$ and $R^{13}$ are F;
(clxxiv) in Formula V, $R^{12}$ and $R^{13}$ are F;
(clxxv) in Formula VI, $R^{12}$ and $R^{13}$ are F.

In alternative embodiments:
(clxxvi) in Formula Ia, $R^1$ is cyclopropyl, $R^2$ is hydrogen, $R^3$ is hydrogen, $R^4$ is a stabilized phosphate prodrug;
(clxxvii) in Formula Ia, $R^1$ is cyclopropyl, $R^2$ is hydrogen, $R^3$ is hydrogen, and $R^4$ is a stabilized thiophosphate prodrug;
(clxxviii) in Formula Ia, $R^1$ is cyclopropyl, $R^2$ is hydrogen, $R^3$ is hydrogen, and $R^4$ is a phosphoramidate;
(clxxix) in Formula Ia, $R^1$ is cyclopropyl, $R^2$ is hydrogen, $R^3$ is hydrogen, and $R^4$ is a thiophosphoramidate:
(clxxx) in Formula Ia, $R^1$ is cyclopropyl, $R^2$ is hydrogen, $R^3$ is hydrogen, and $R^4$ is a monophosphate;

(clxxxi) in Formula Ia, R¹ is cyclopropyl, R² is hydrogen, R³ is hydrogen, and R⁴ is a diphosphate;
(clxxxii) in Formula Ia, R¹ is cyclopropyl, R² is hydrogen, R³ is hydrogen, and R⁴ is a triphosphate;
(clxxxiii) in Formula Ia, R¹ is cyclopropyl, R² is methyl, R³ is hydrogen, R⁴ is a stabilized phosphate prodrug;
(clxxxiv) in Formula Ib, R¹ is cyclopropyl, R² is hydrogen, R³ is hydrogen, R⁴ is a stabilized phosphate prodrug;
(clxxxv) in Formula Ib, R¹ is cyclopropyl, R² is hydrogen, R³ is hydrogen, and R⁴ is a stabilized thiophosphate prodrug;
(clxxxvi) in Formula Ib, R¹ is cyclopropyl, R² is hydrogen, R³ is hydrogen, and R⁴ is a phosphoramidate;
(clxxxvii) in Formula Ib, R¹ is cyclopropyl, R² is hydrogen, R³ is hydrogen, and R⁴ is a thiophosphoramidate:
(clxxxviii) in Formula Ib, R¹ is cyclopropyl, R² is hydrogen, R³ is hydrogen, and R⁴ is a monophosphate;
(clxxxix) in Formula Ib, R¹ is cyclopropyl, R² is hydrogen, R³ is hydrogen, and R⁴ is a diphosphate;
(cxc) in Formula Ib, R¹ is cyclopropyl, R² is hydrogen, R³ is hydrogen, and R⁴ is a triphosphate;
(cxci) in Formula Ib, R¹ is cyclopropyl, R² is methyl, R³ is hydrogen, R⁴ is a stabilized phosphate prodrug;
(cxcii) in Formula Ia, R¹ is cyclopropyl, R² is hydrogen, R³ is hydrogen, R⁴ is a phosphoramidate, and R²² is methyl;
(cxciii) in Formula Ia, R¹ is cyclopropyl, R² is hydrogen, R³ is hydrogen, R⁴ is a phosphoramidate, and R²² is CH₂Cl;
(cxciv) in Formula Ia, R¹ is methyl, R² is hydrogen, R³ is hydrogen, R⁴ is a phosphoramidate, and R²² is methyl;
(cxcv) in Formula Ia, R¹ is methyl, R² is hydrogen, R³ is hydrogen, R⁴ is a phosphoramidate, and R²² is CH₂Cl;
(cxcvi) in Formula Ia, R¹ is methyl, R² is methyl, R³ is hydrogen, R⁴ is a phosphoramidate, and R²² is methyl;
(cxcvii) in Formula Ia, R¹ is methyl, R² is methyl, R³ is hydrogen, R⁴ is a phosphoramidate, and R²² is CH₂Cl;
(cxcviii) in Formula Ia, R¹ is cyclopropyl, R² is methyl, R³ is hydrogen, R⁴ is a phosphoramidate, and R²² is methyl;
(cxcix) in Formula Ia, R¹ is cyclopropyl, R² is methyl, R³ is hydrogen, R⁴ is a phosphoramidate, and R²² is CH₂Cl;

In alternate embodiments of compounds (i) through (cxxxiii), an L-nucleoside is used in Formula I-VI.

In an alternate embodiment, the Formula I $R^{12}$ variable is F.

In an alternate embodiment, the Formula I $R^{12}$ variable is Cl.

In an alternate embodiment, the Formula I $R^{12}$ variable is Br.

In one embodiment, a compound of Formula I is provided. Non-limiting examples of compounds of Formula I include:

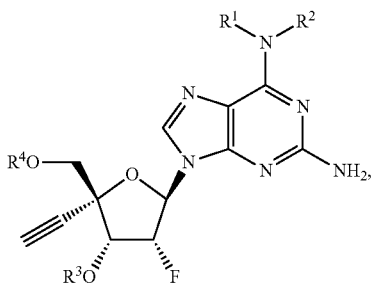

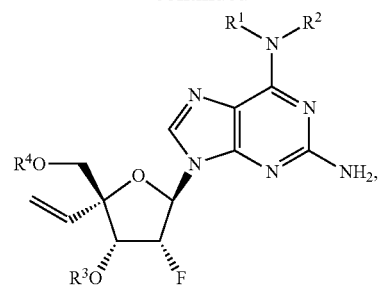

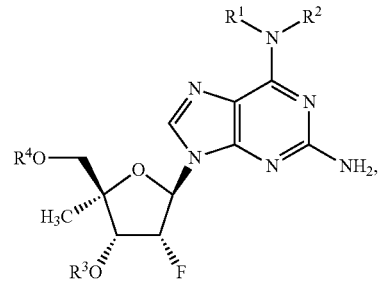

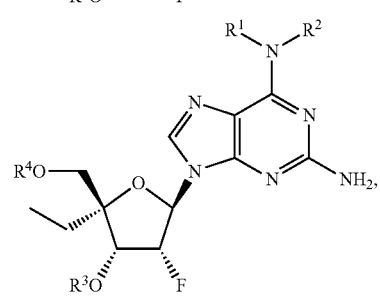

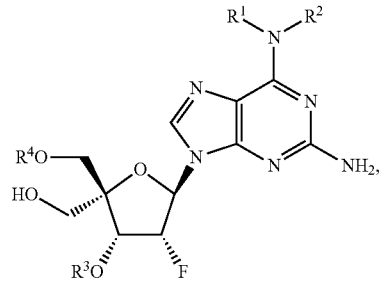

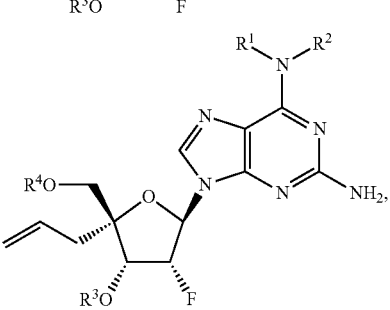

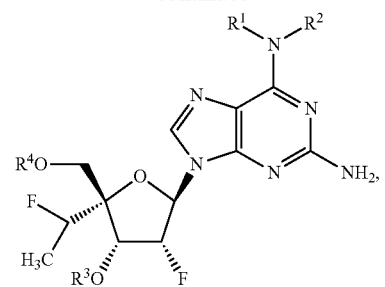
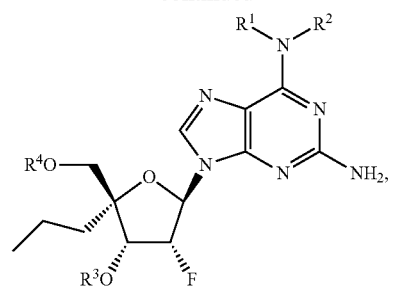

-continued
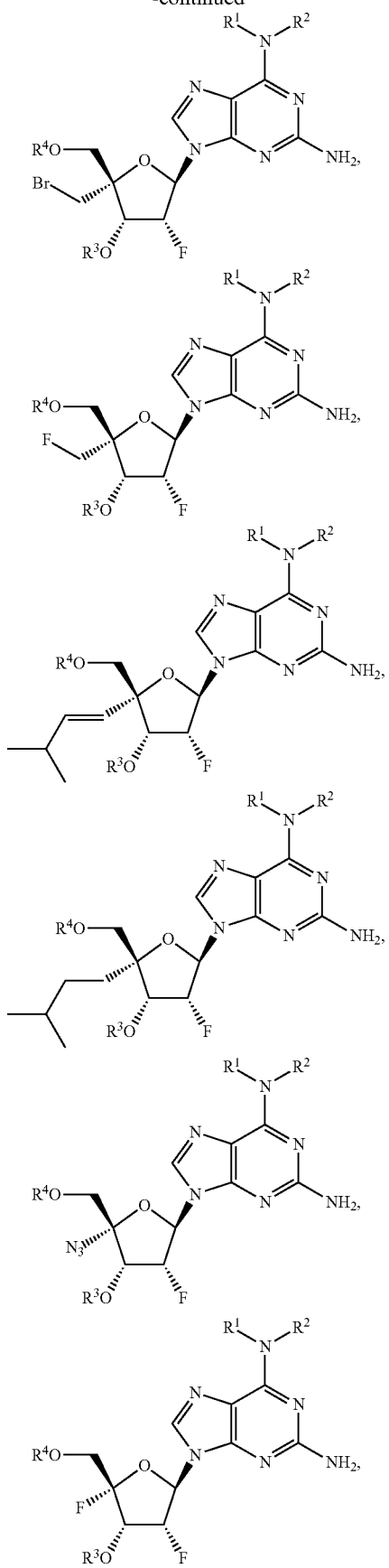
-continued
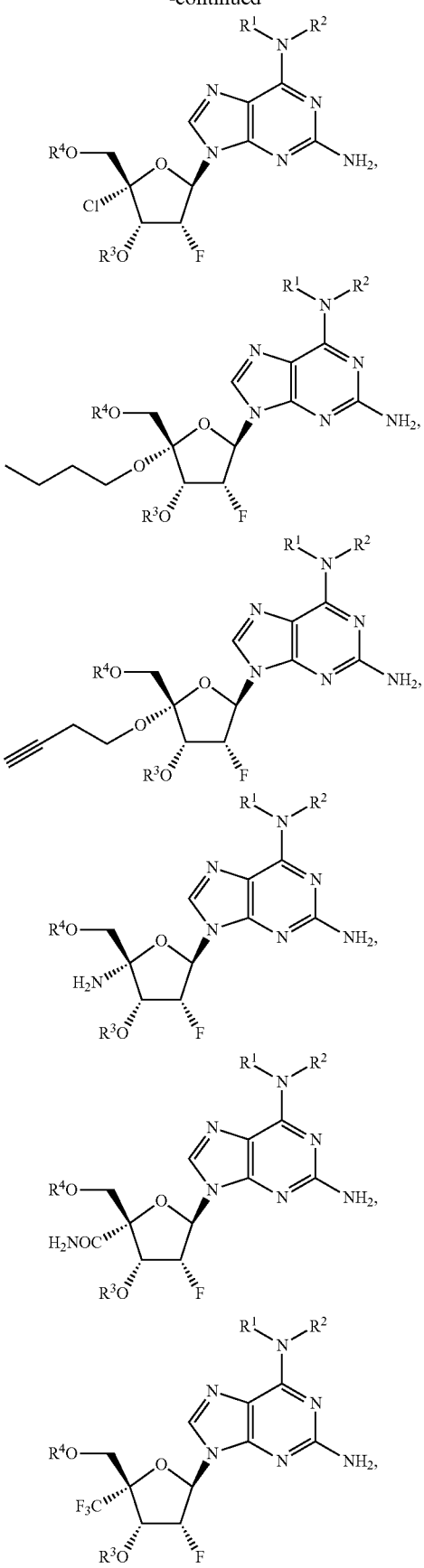

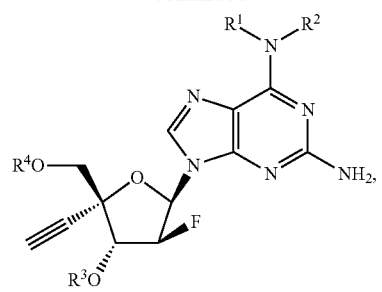
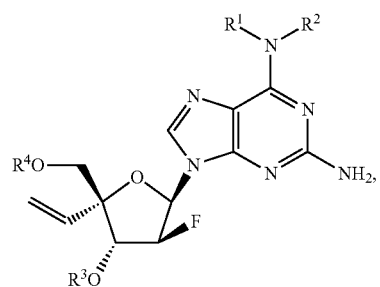
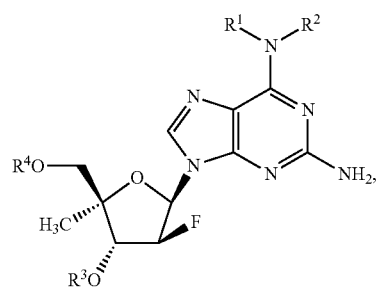
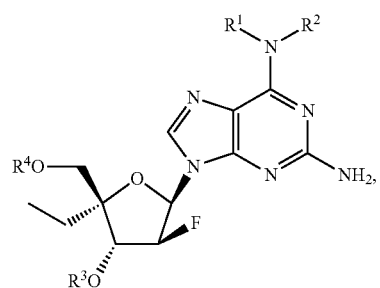
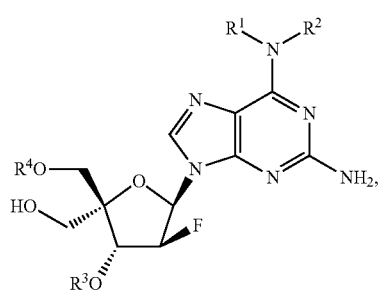
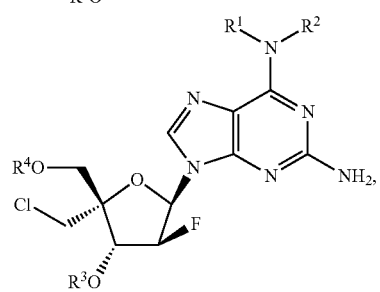
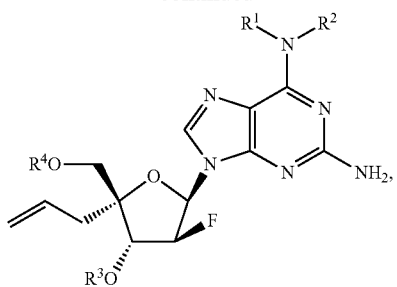
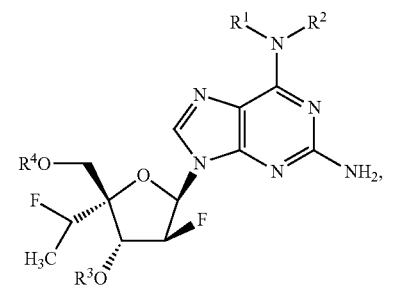
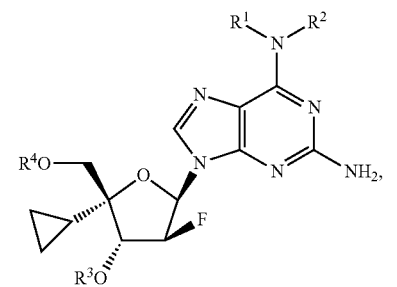
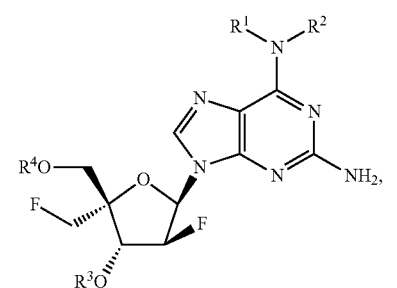
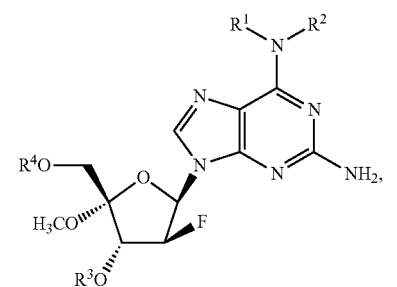

-continued
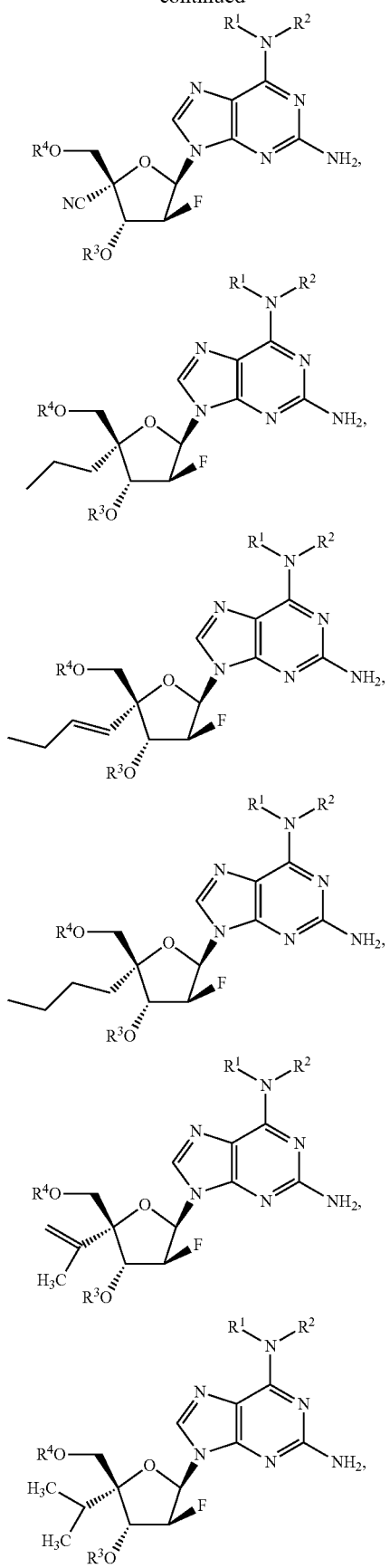
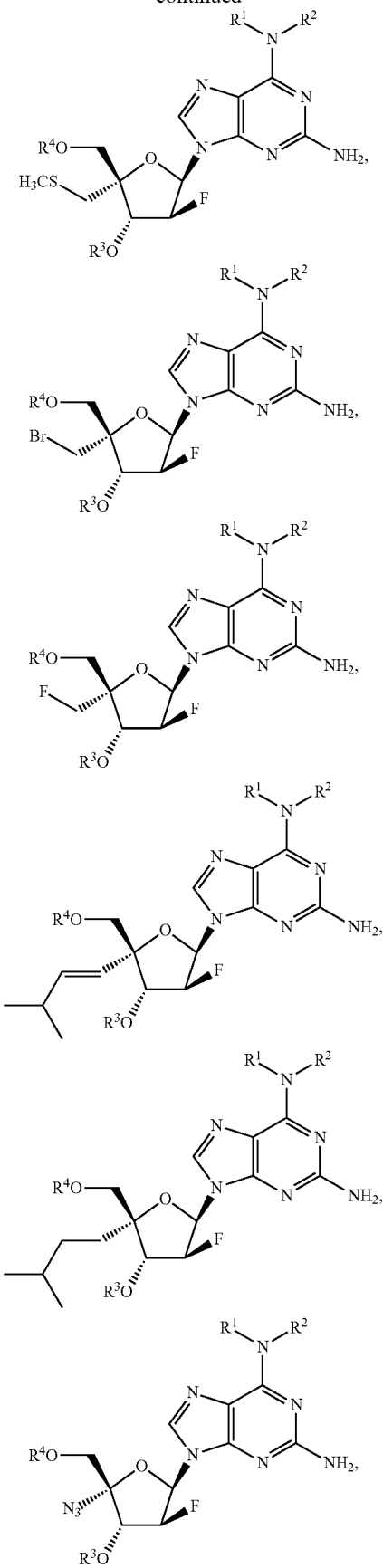

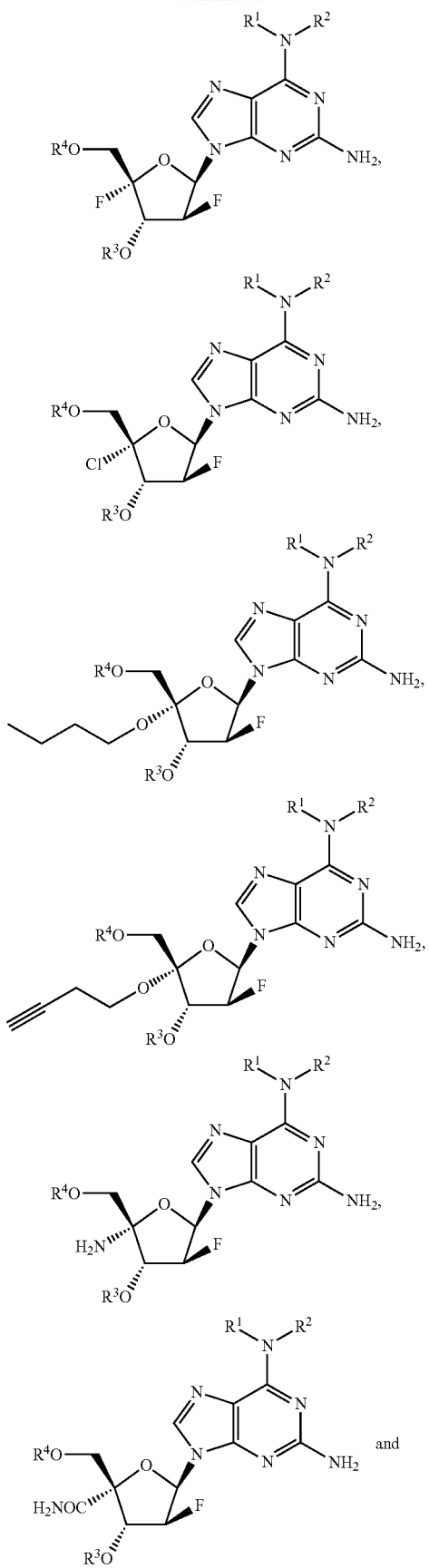
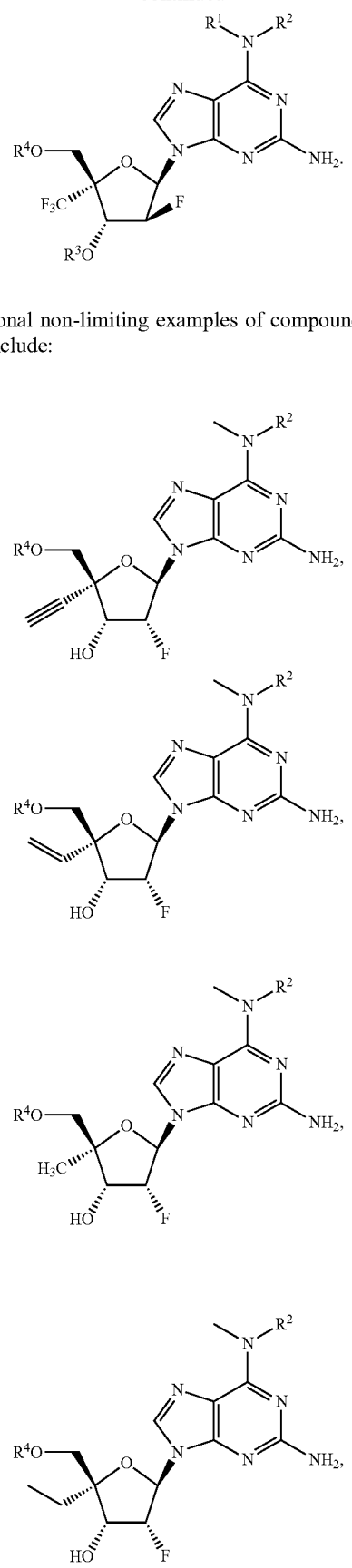
Additional non-limiting examples of compounds of Formula I include:

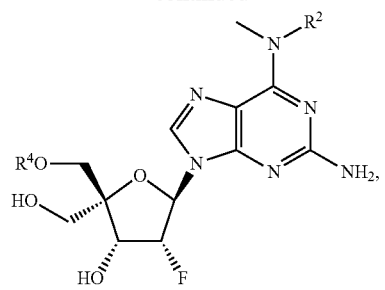
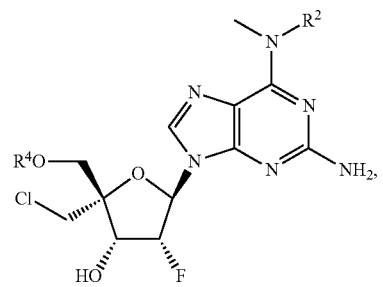
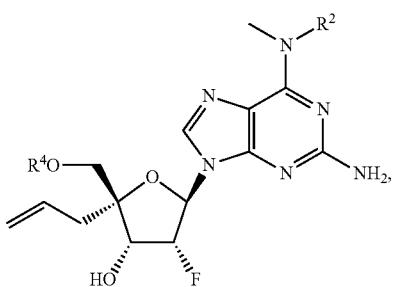
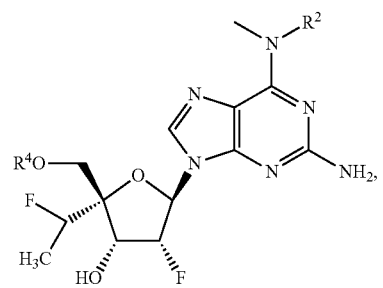
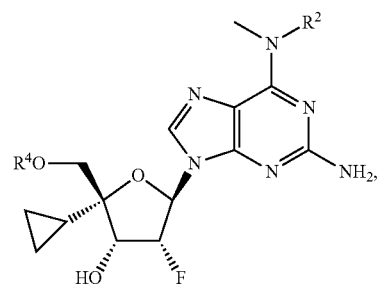
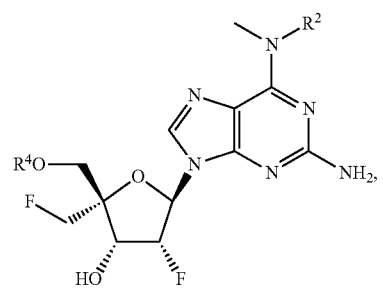
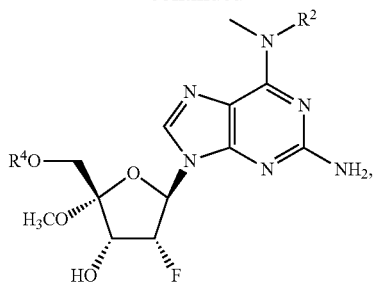
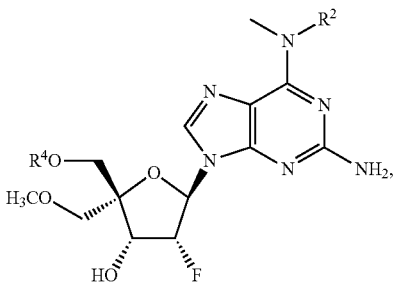
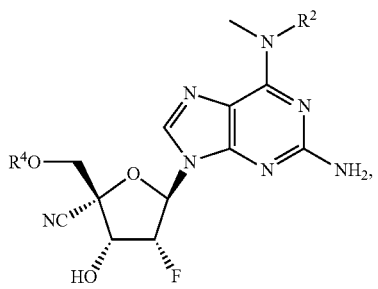
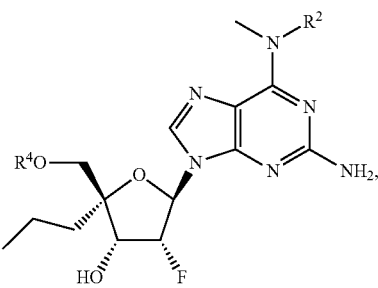
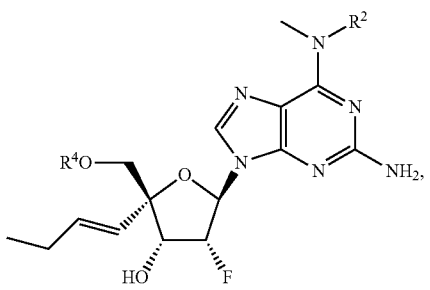
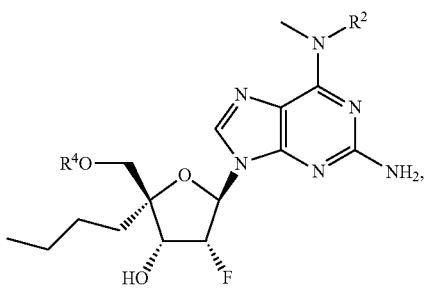

-continued
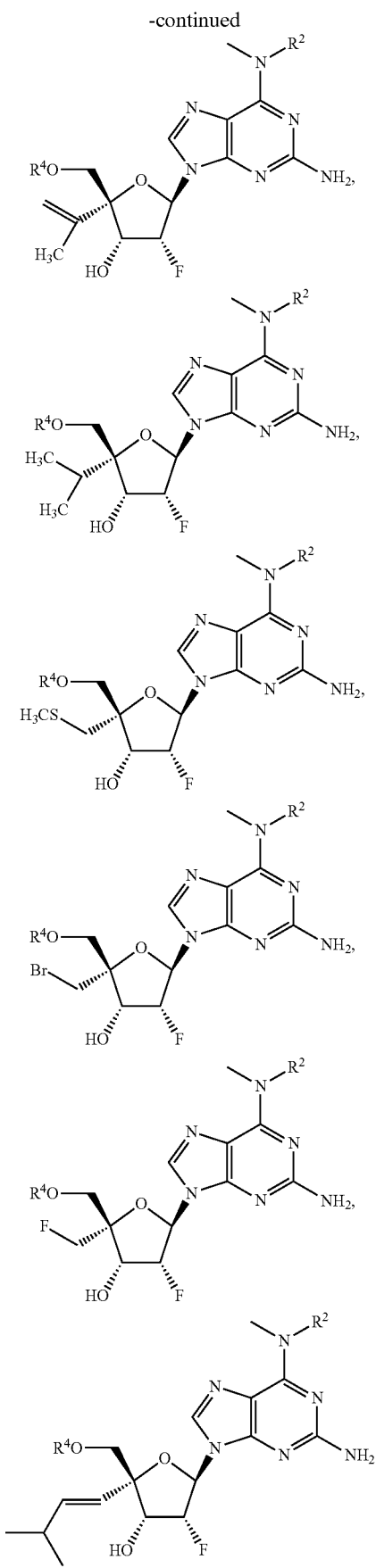
-continued
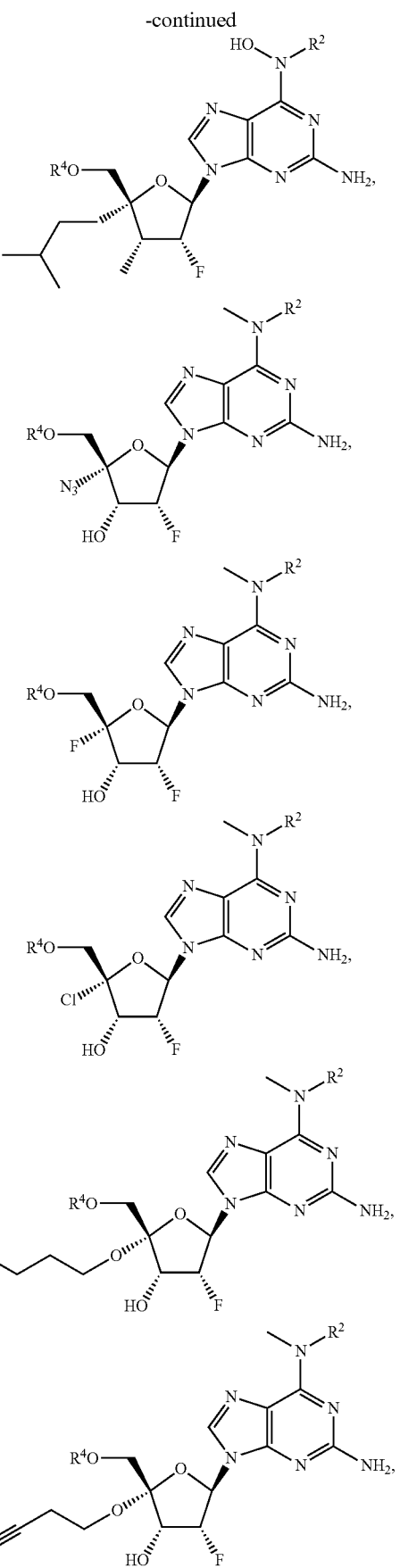

53
-continued
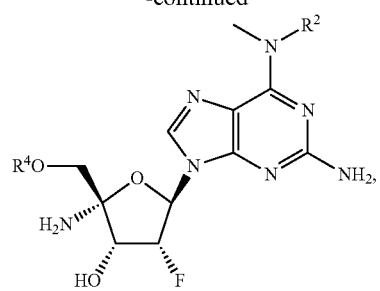
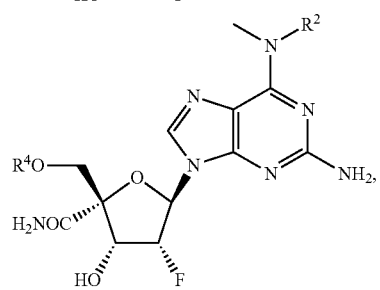
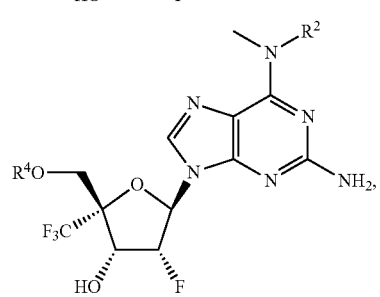
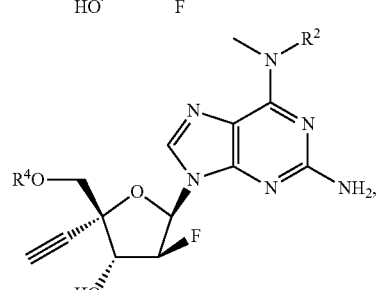
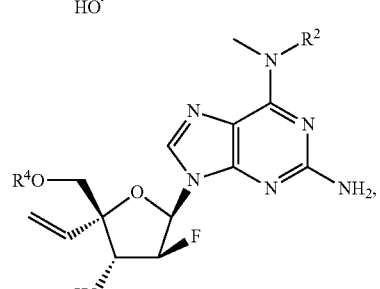
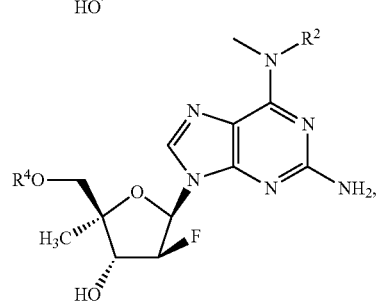
54
-continued
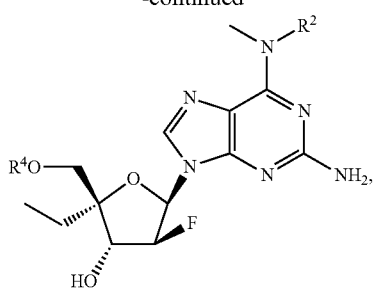
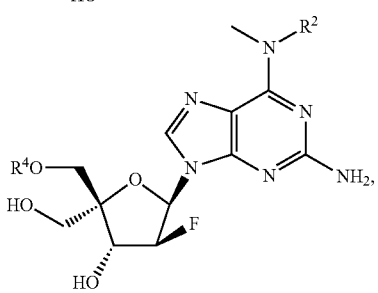
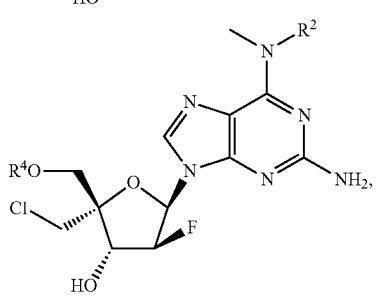
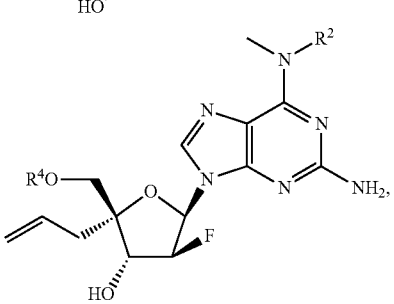
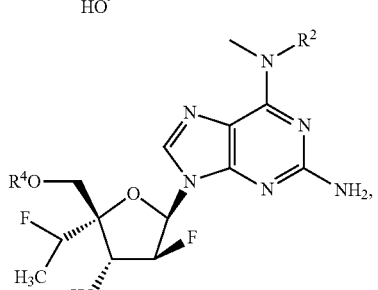
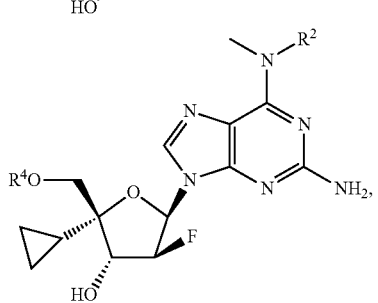

-continued
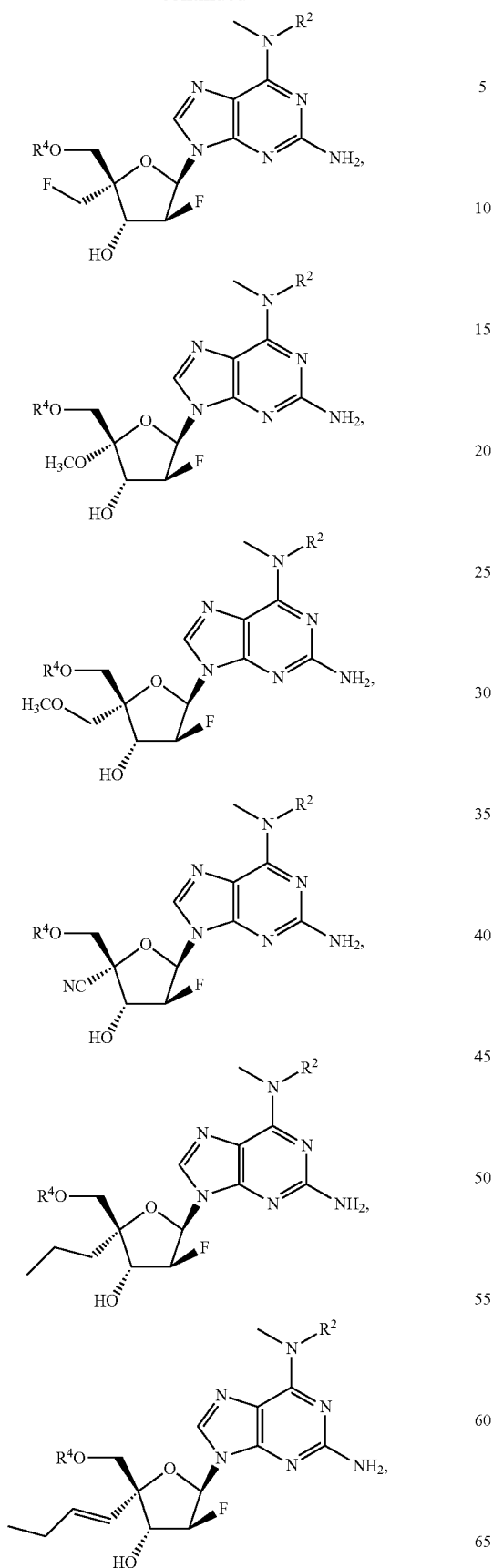
-continued
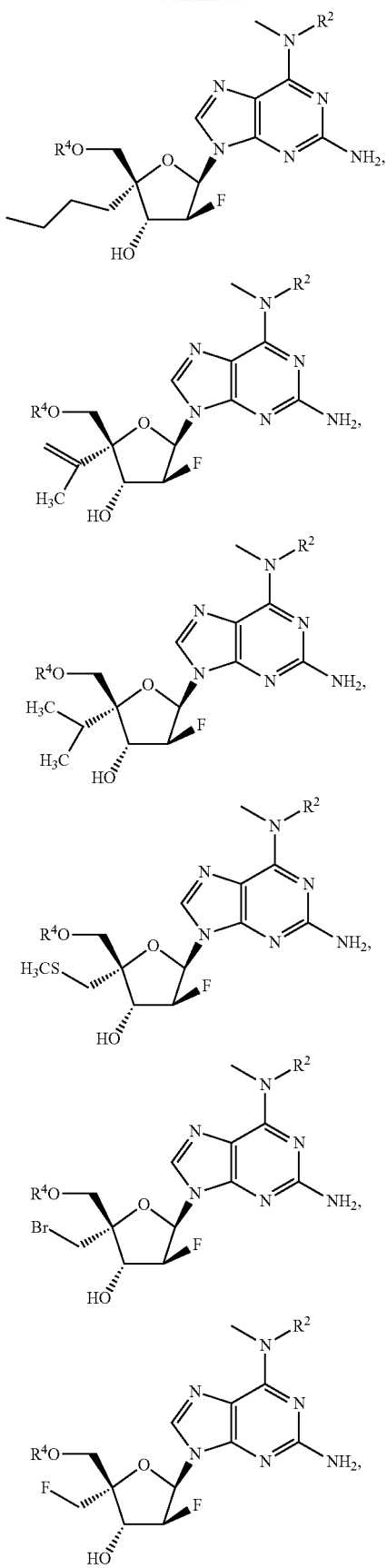

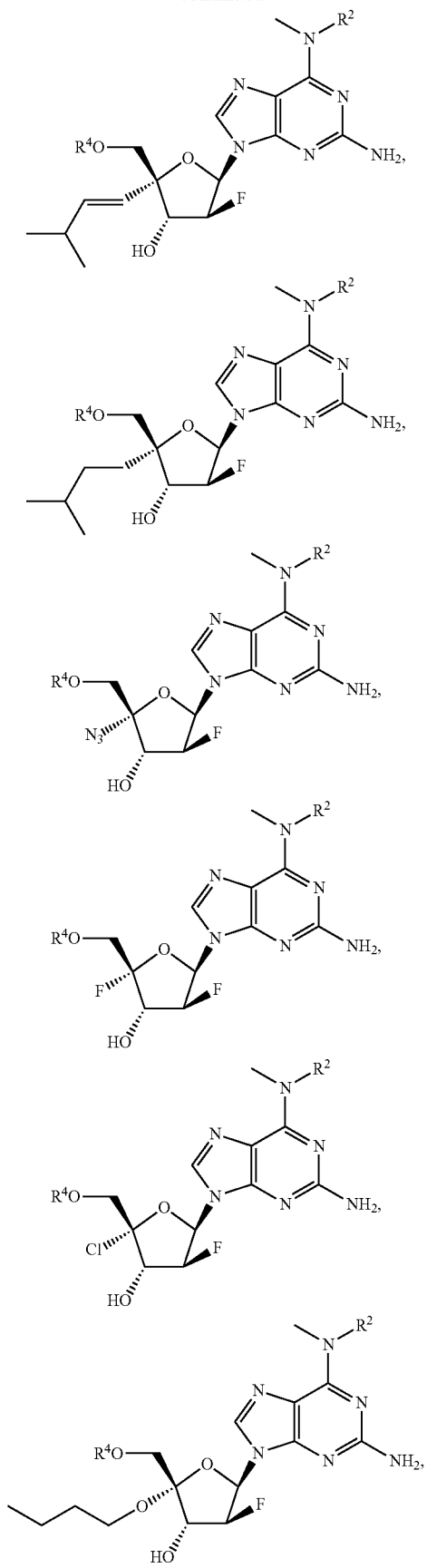
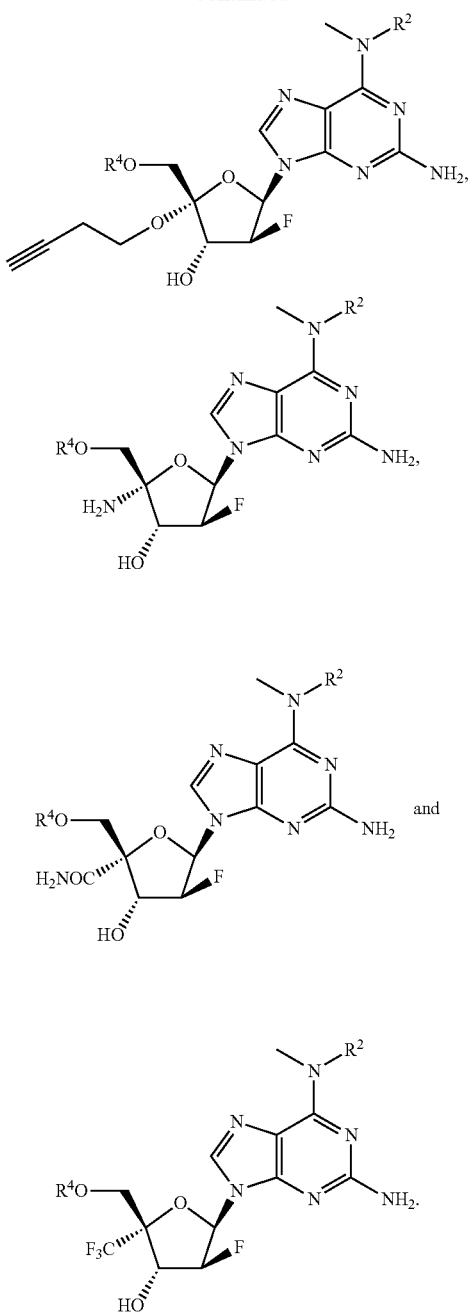
In one embodiment, $R^3$ is hydrogen and $R^4$ is
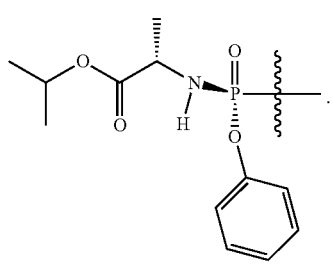 [SMILES: *[P@](=O)(N[C@@H](C)C(=O)OC(C)C)Oc1ccccc1]

In one embodiment, R³ is hydrogen and R⁴ is
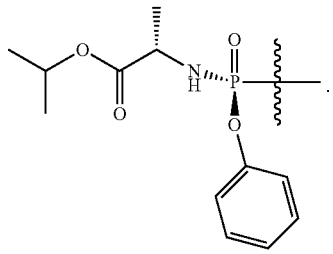 [SMILES: *[P@@](=O)(N[C@@H](C)C(=O)OC(C)C)Oc1ccccc1]
In one embodiment, R³ is hydrogen and R⁴ is
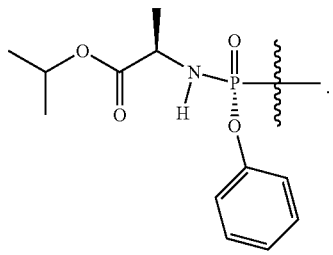 [SMILES: *[P@](=O)(N[C@H](C)C(=O)OC(C)C)Oc1ccccc1]
In one embodiment, R³ is hydrogen and R⁴ is
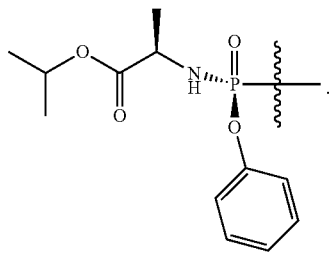 [SMILES: *[P@@](=O)(N[C@H](C)C(=O)OC(C)C)Oc1ccccc1]
In one embodiment, a compound of Formula II is provided. Non-limiting examples of compounds of Formula II include:
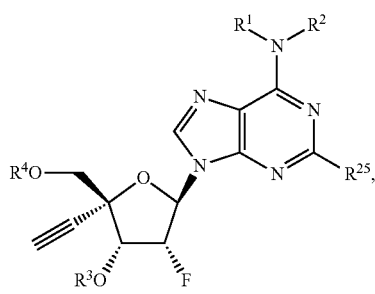
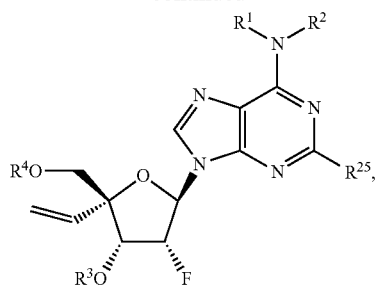
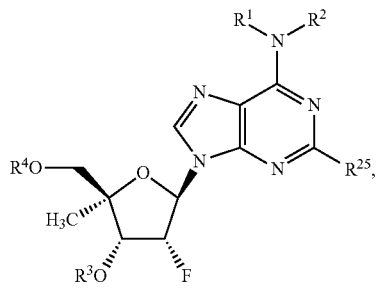
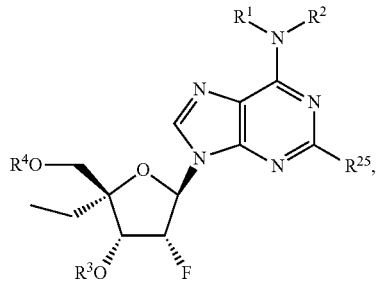
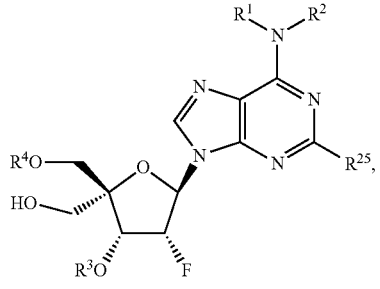
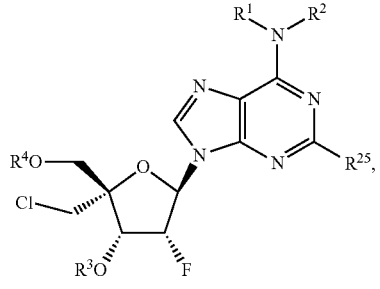
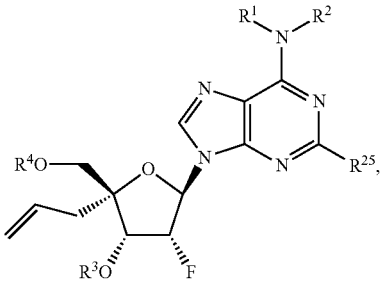

-continued
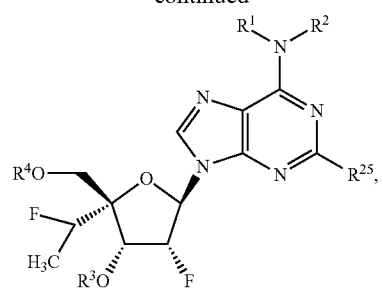
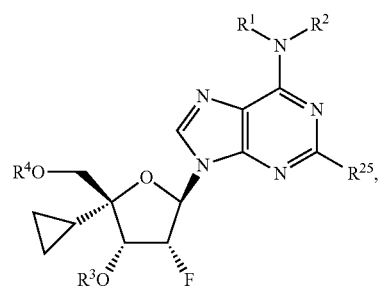
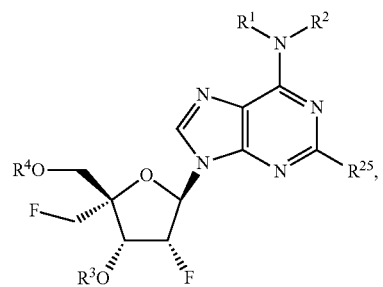
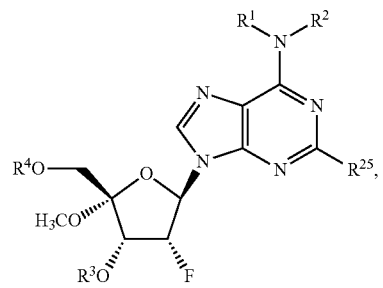
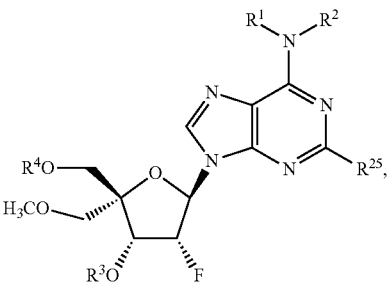
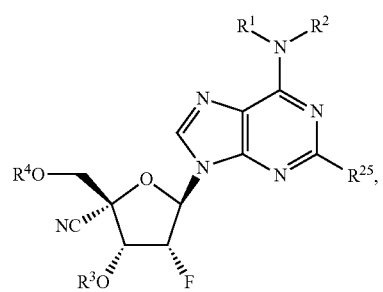
-continued
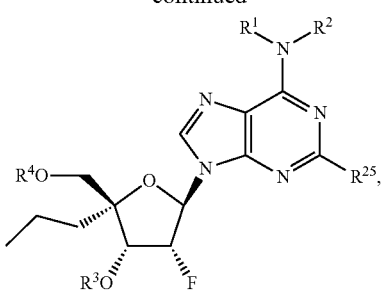
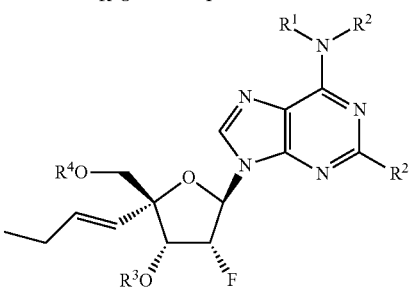
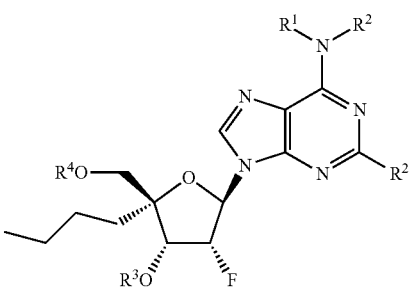
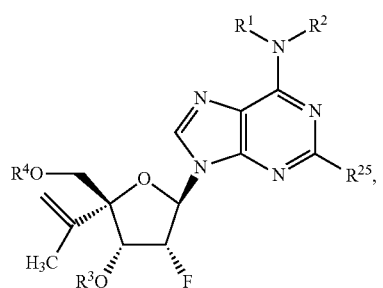
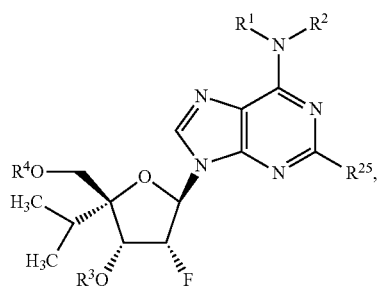
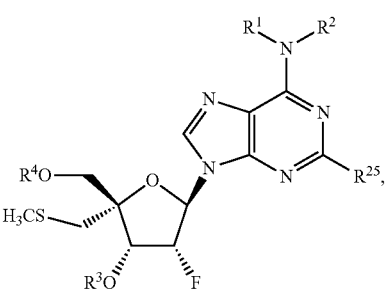

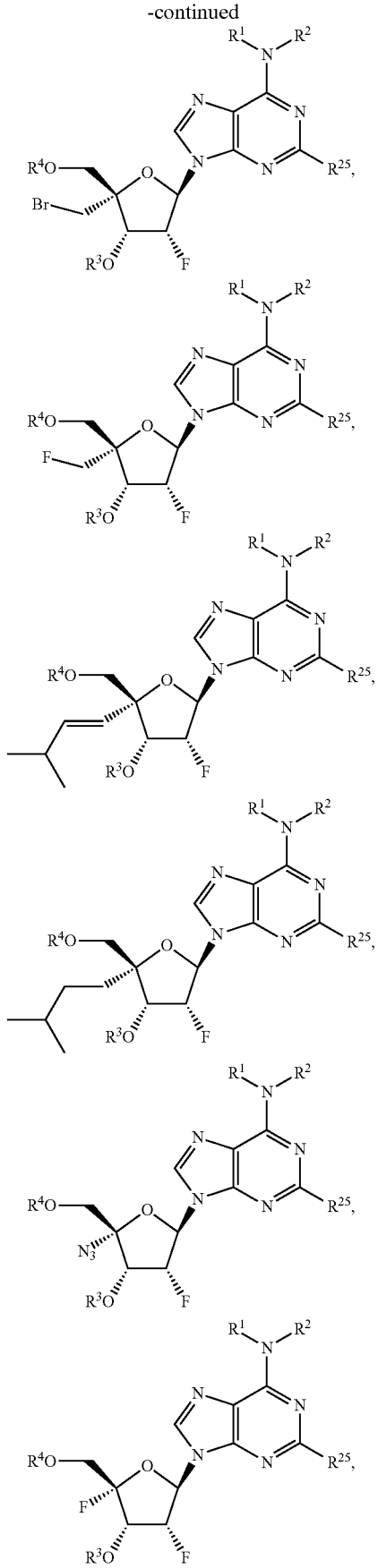
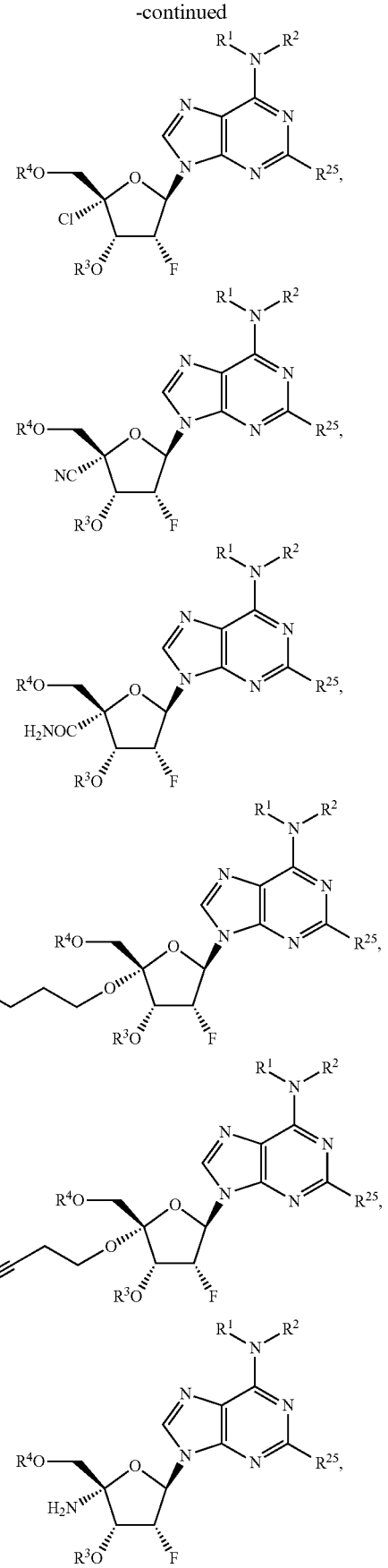

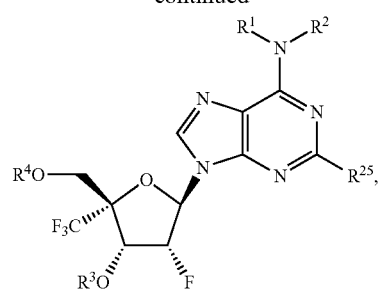
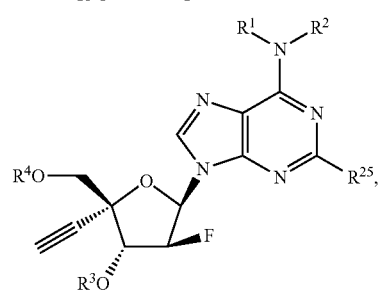
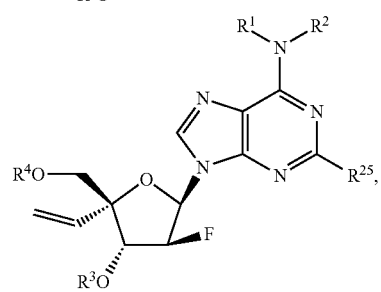
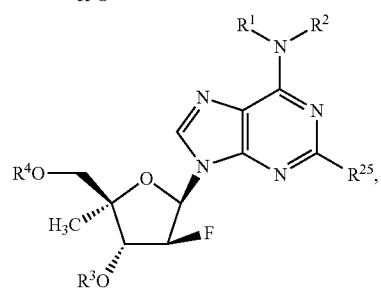
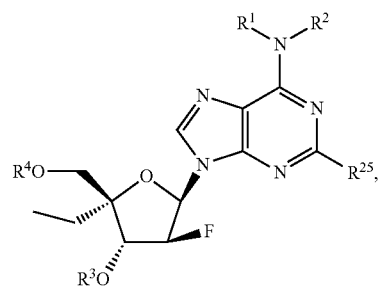
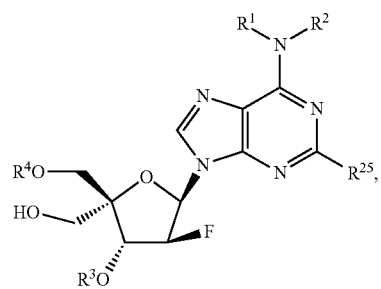
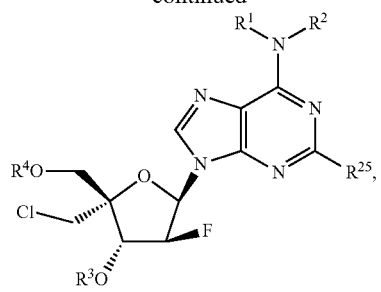
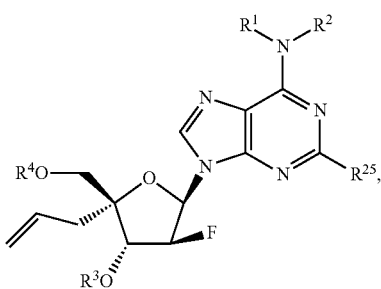
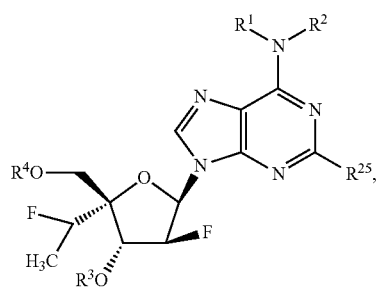
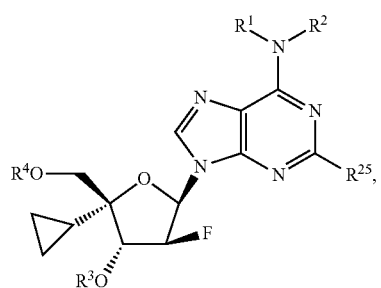
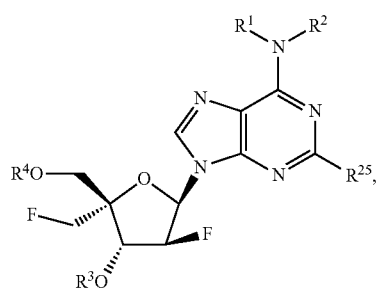
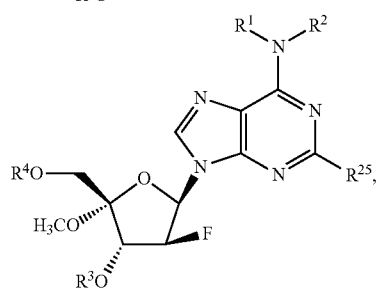

67
-continued

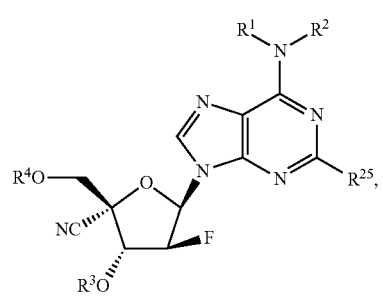
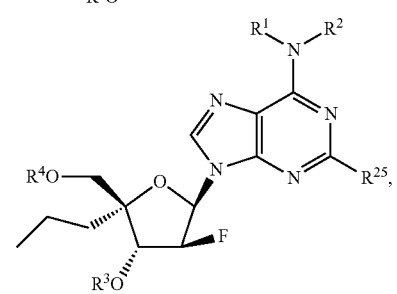
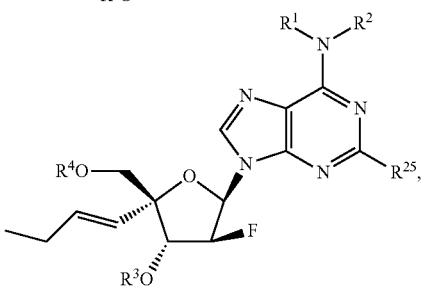
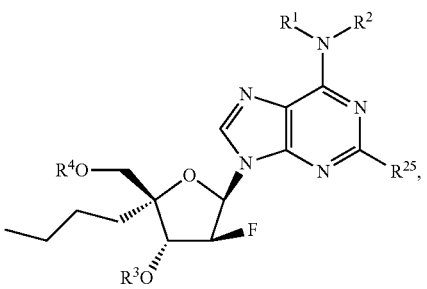
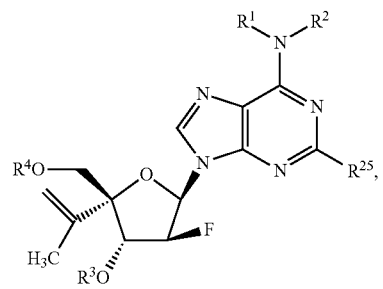
68
-continued
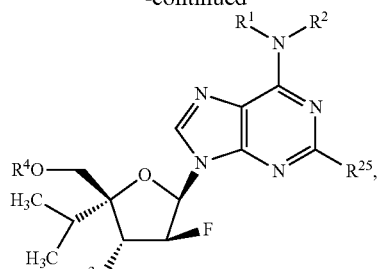
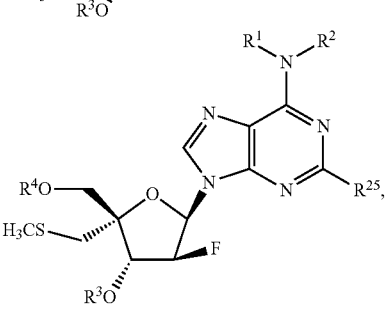
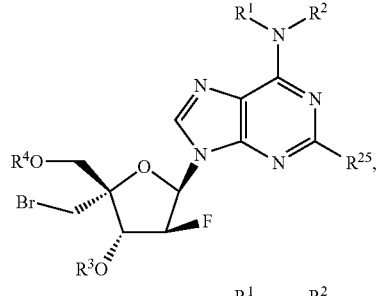
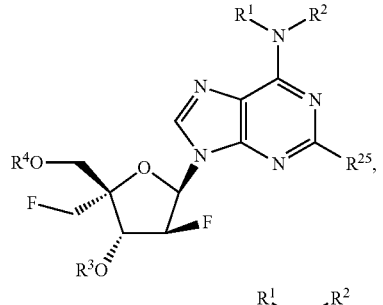
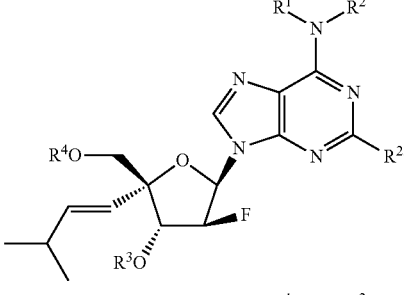
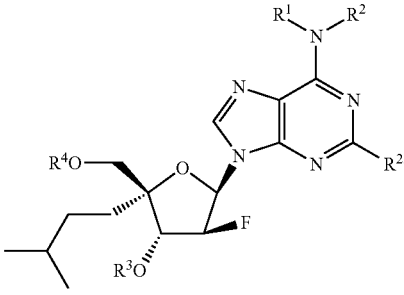

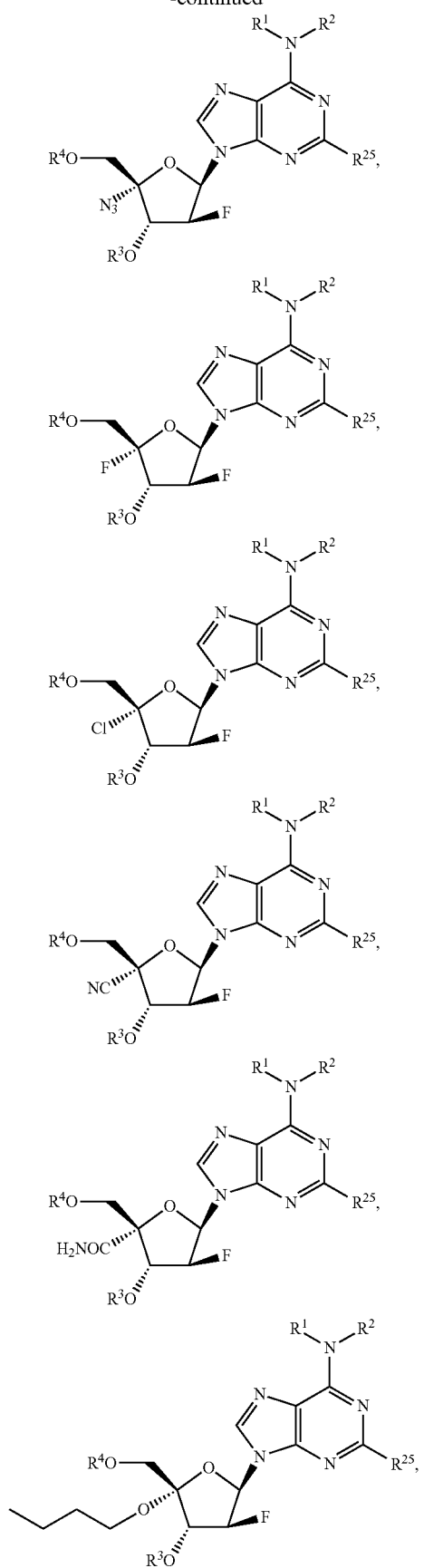
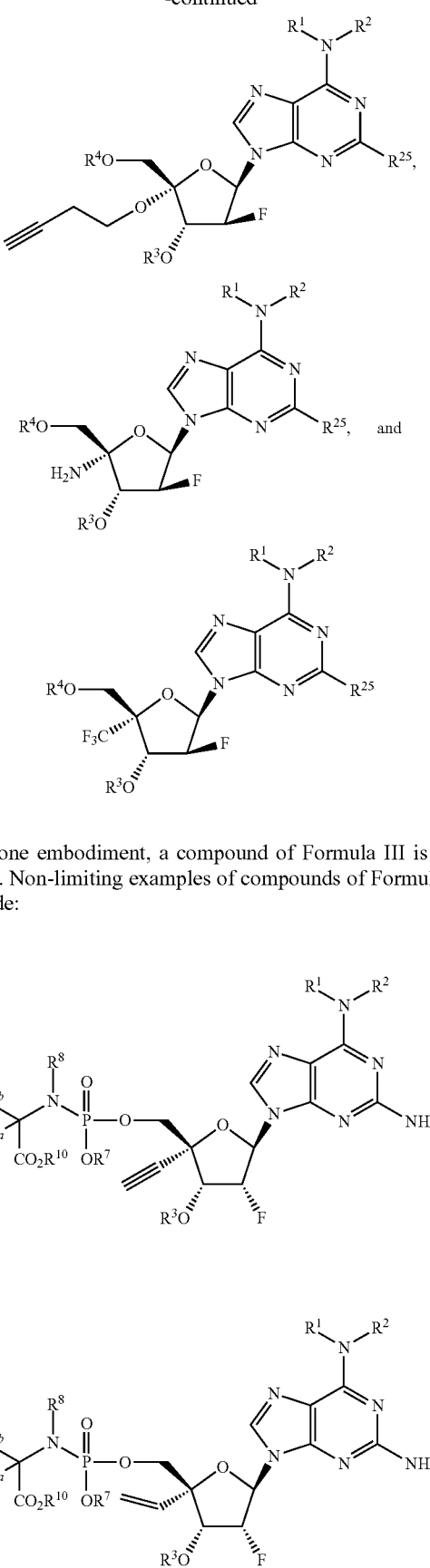
In one embodiment, a compound of Formula III is provided. Non-limiting examples of compounds of Formula III include:

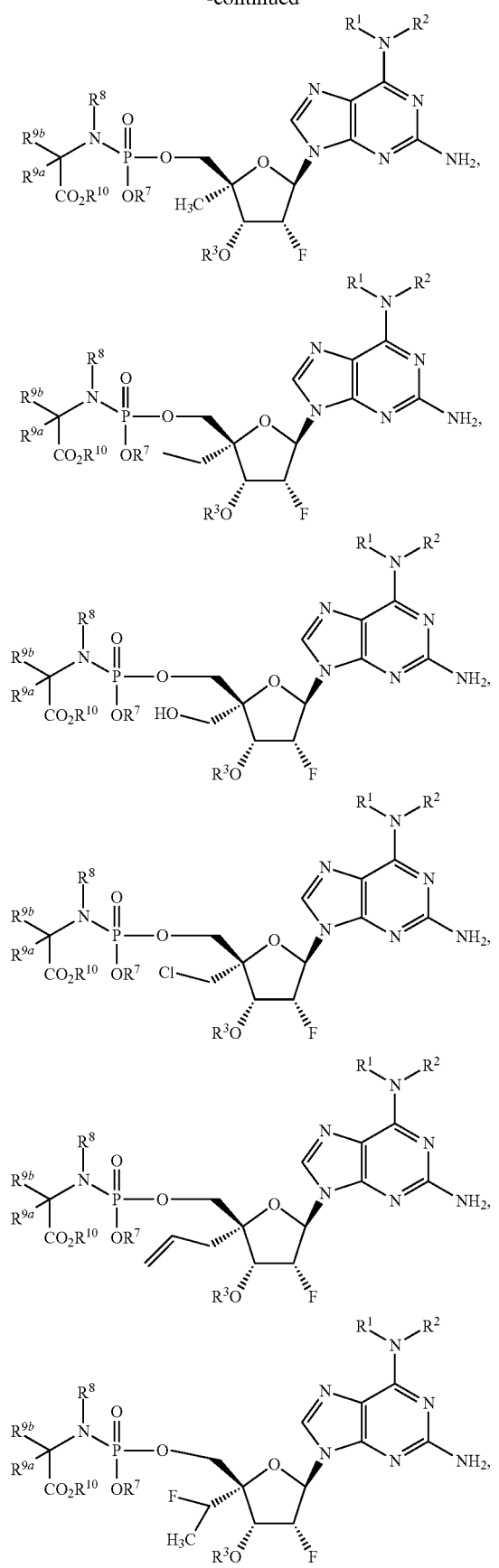
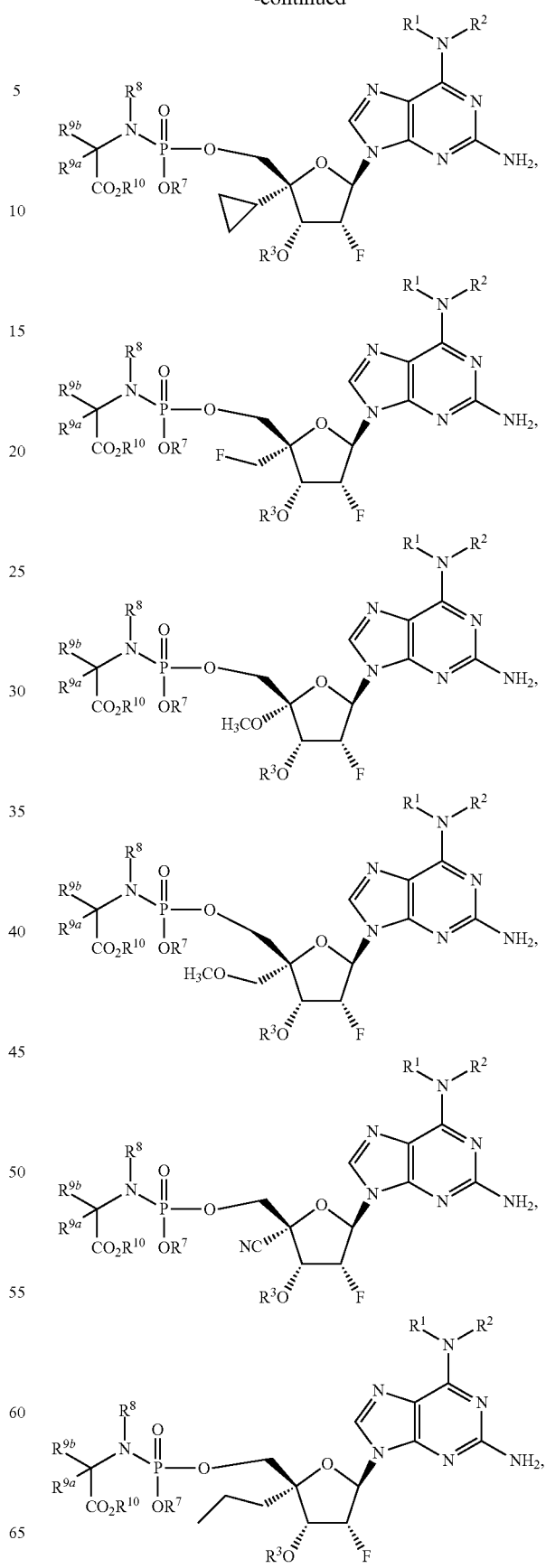

73
-continued
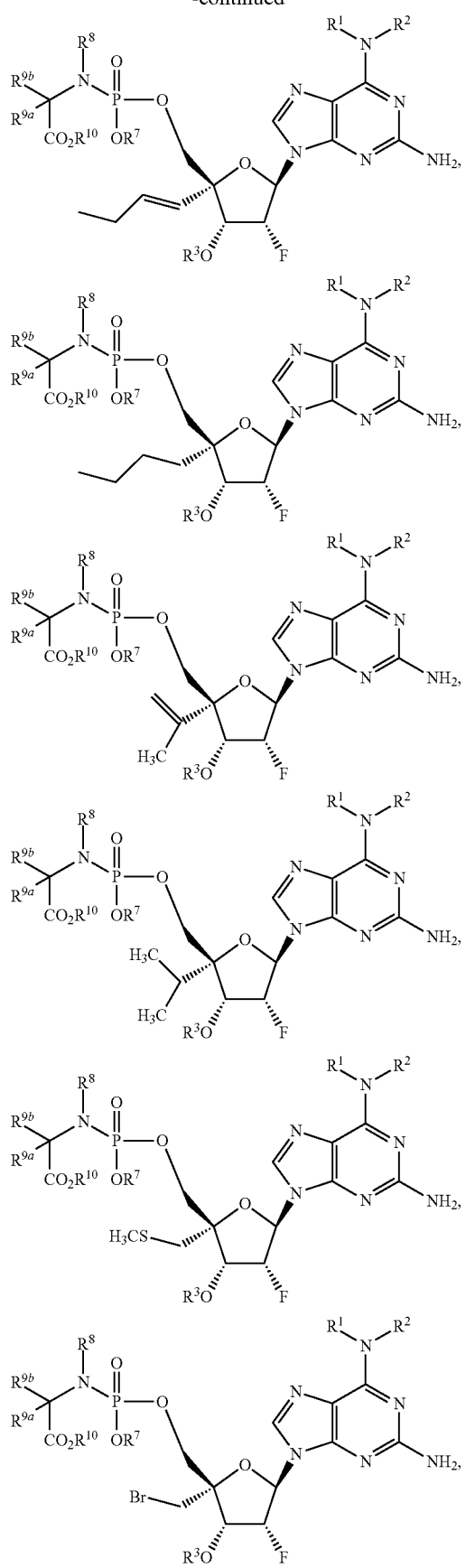
74
-continued
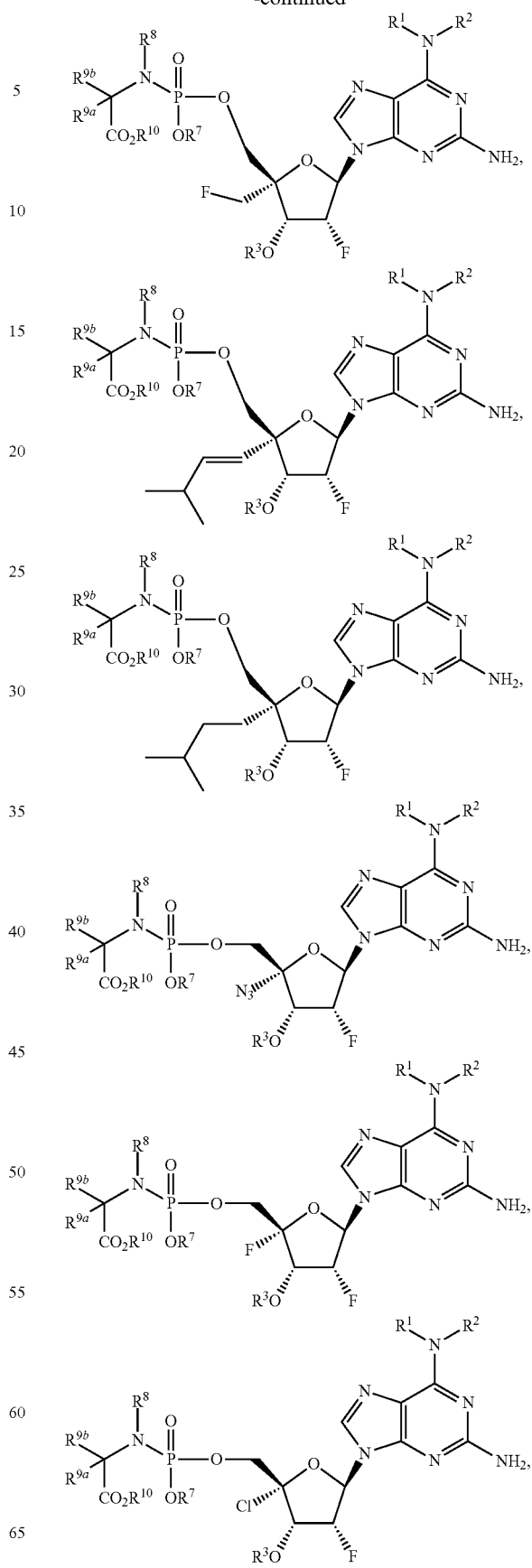

75
-continued
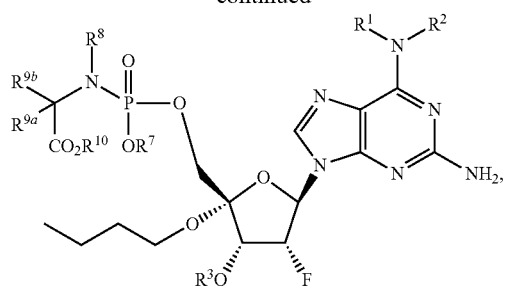
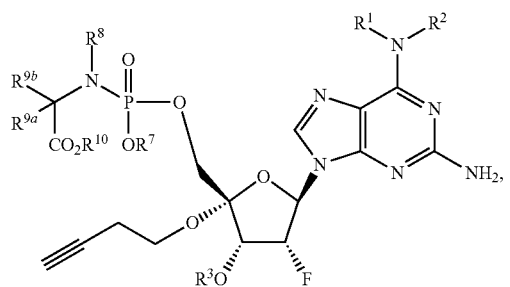
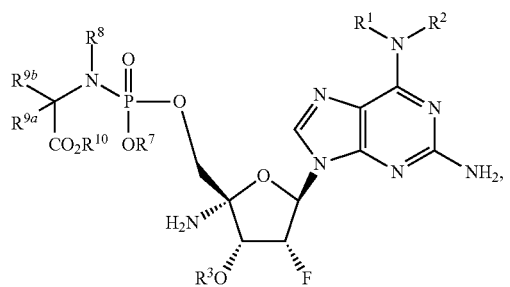
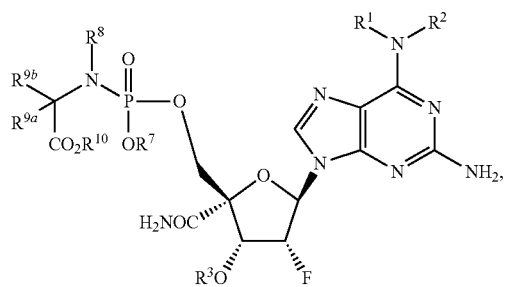
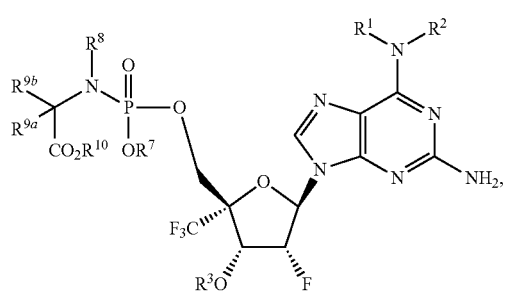
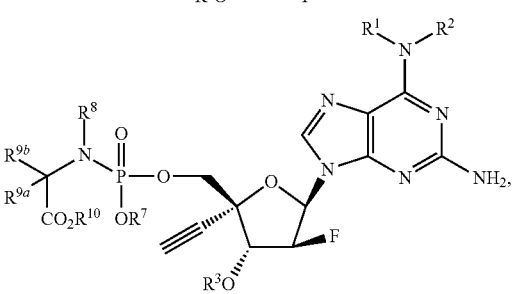
76
-continued
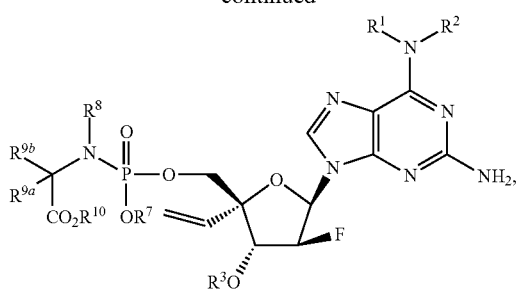
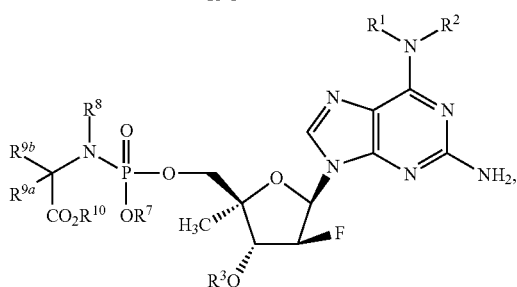
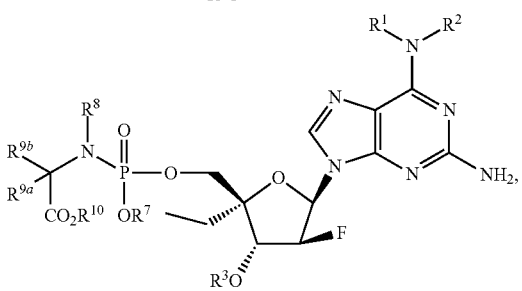
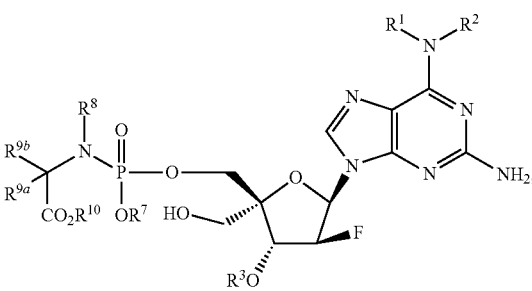
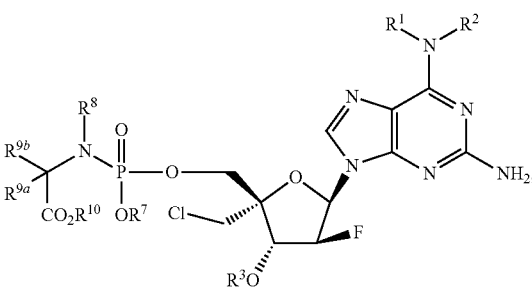
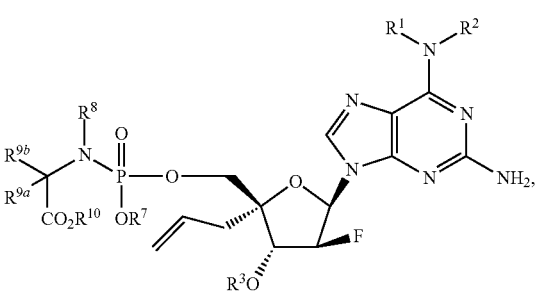

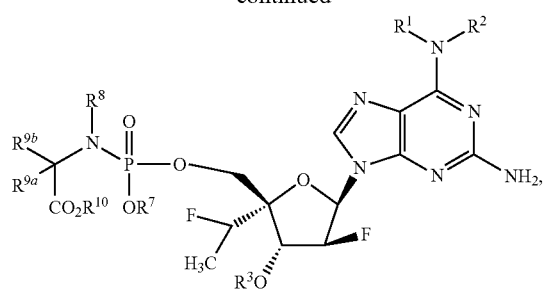
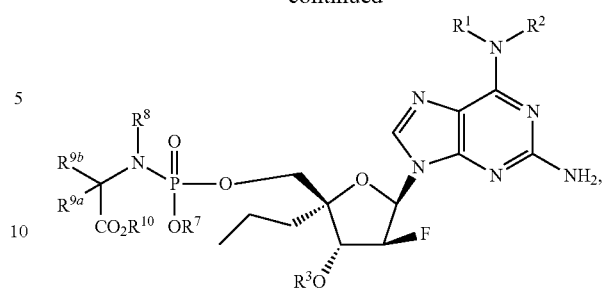
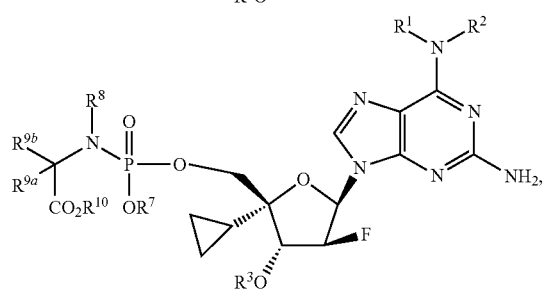
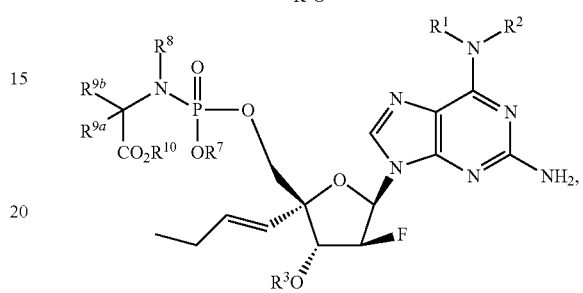
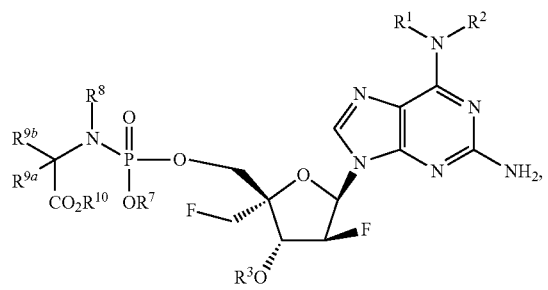
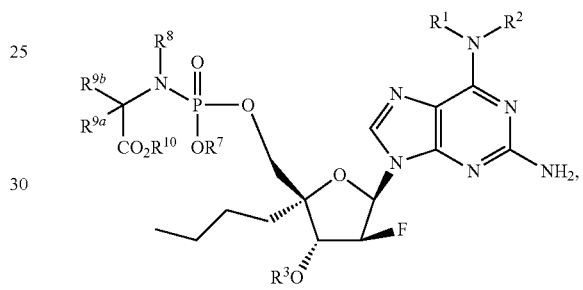
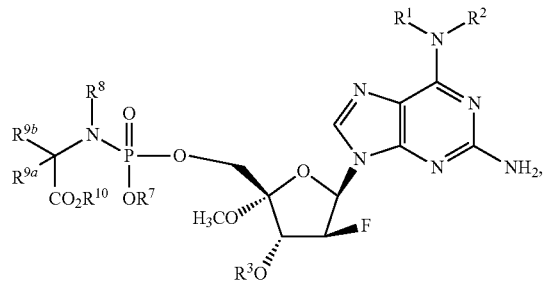
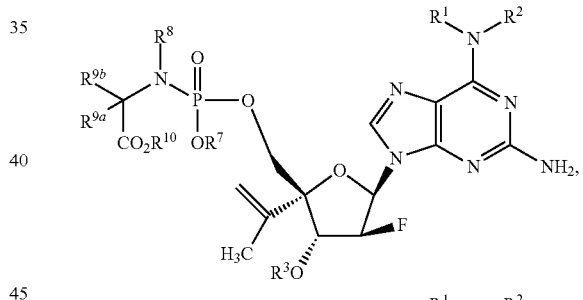
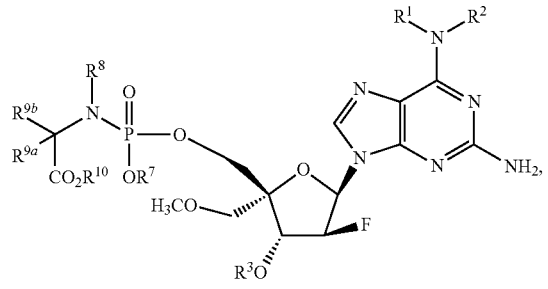

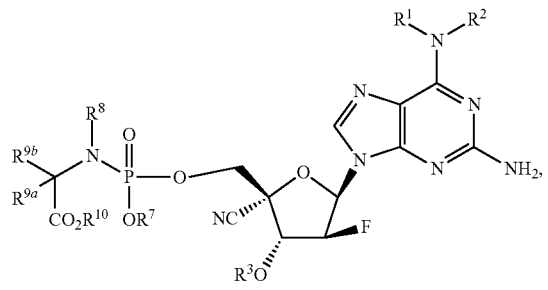
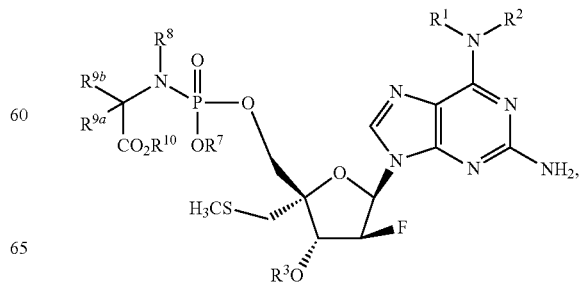

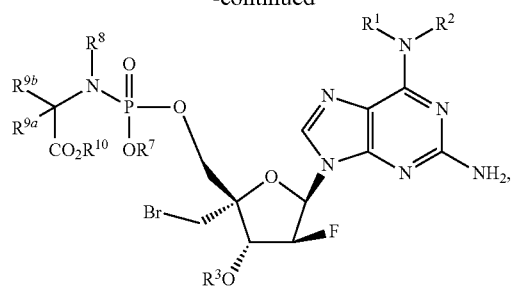
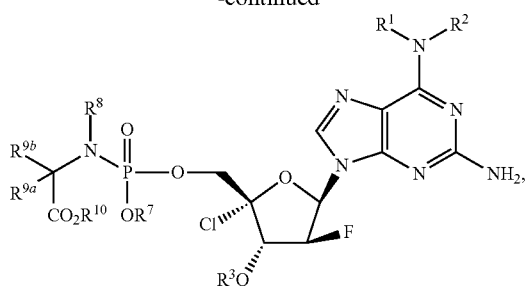
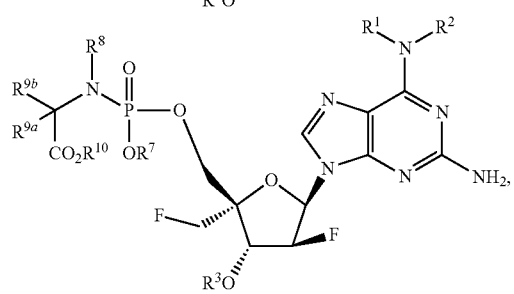
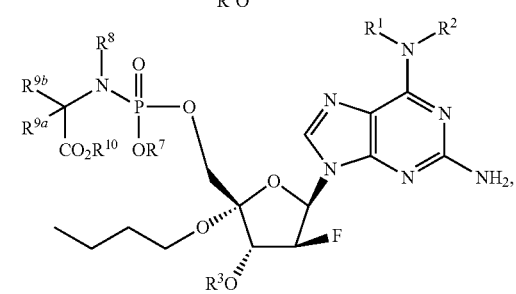
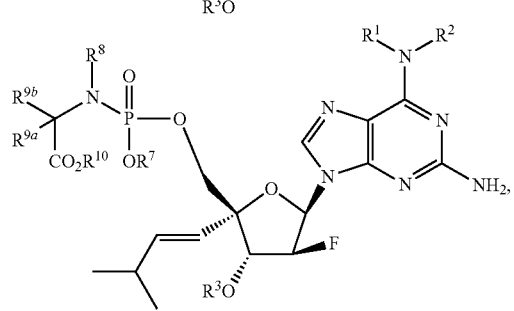
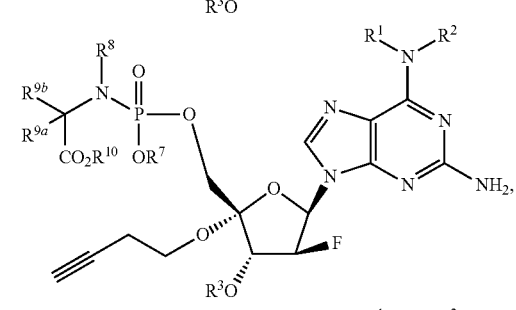
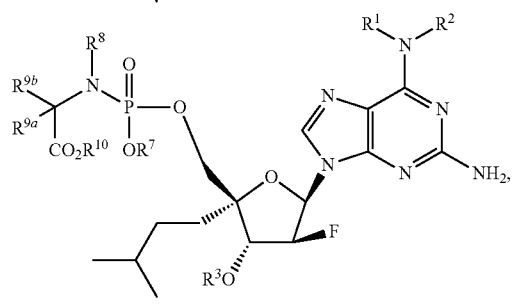
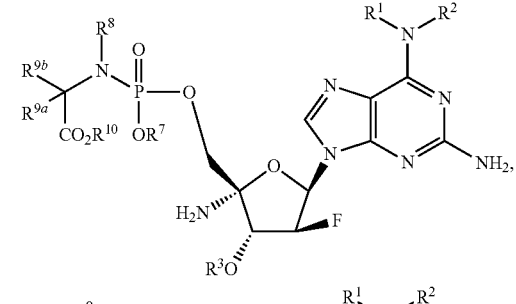
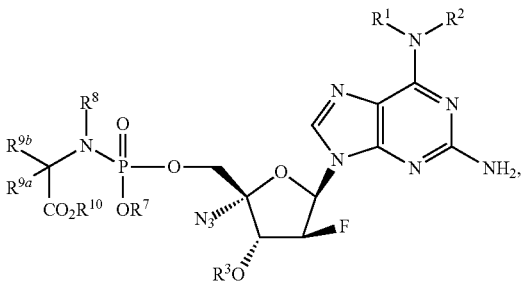
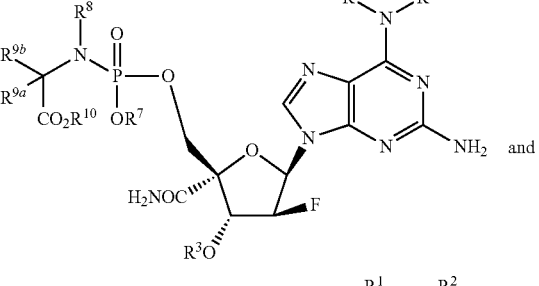
and
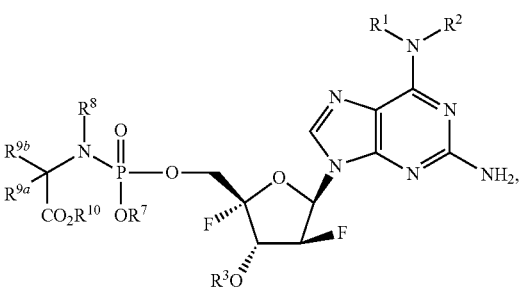
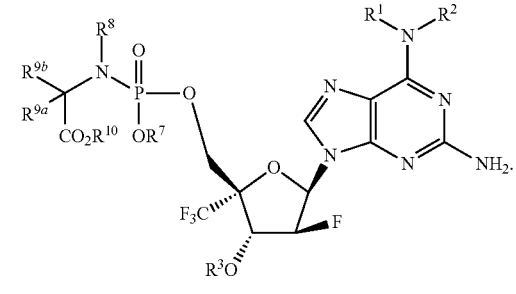

In one embodiment, a compound of Formula IV is provided. Non-limiting examples of compounds of Formula IV include:
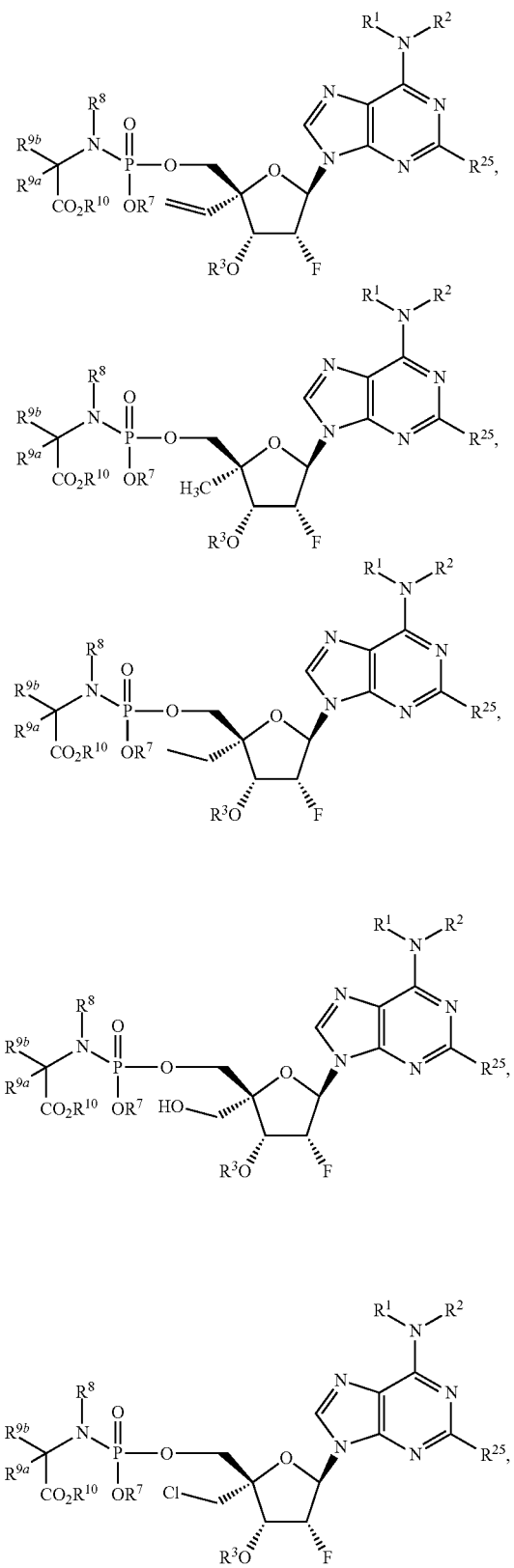
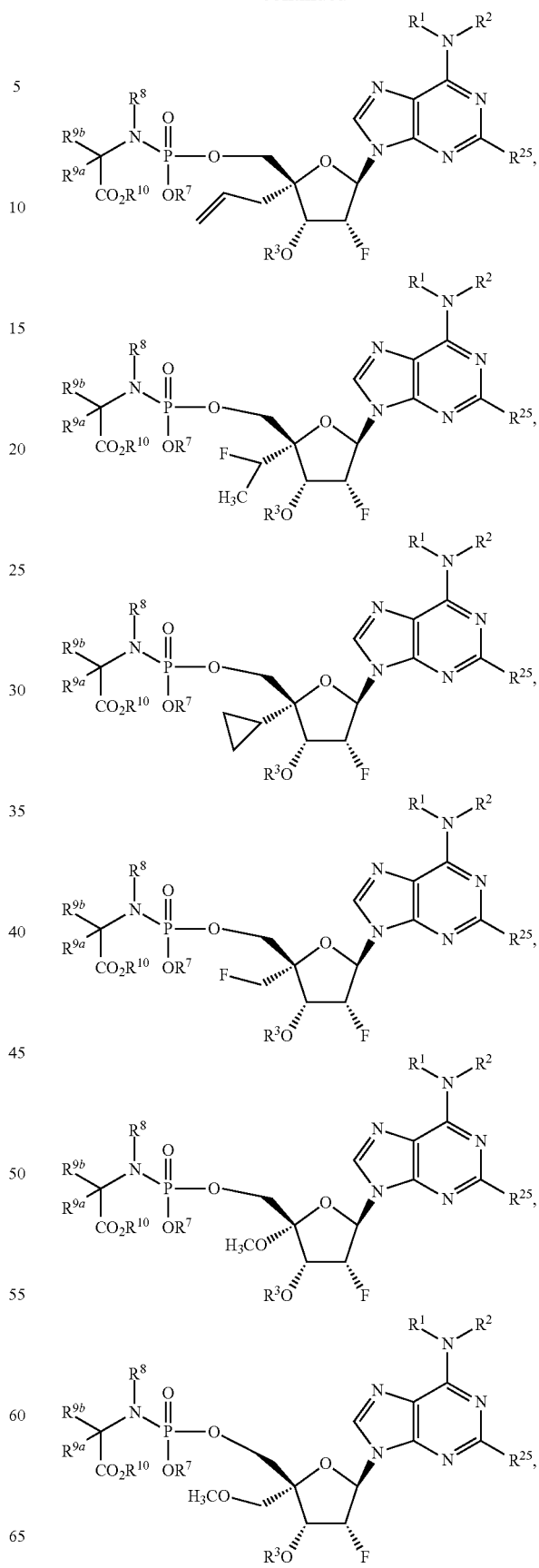
-continued 83
-continued
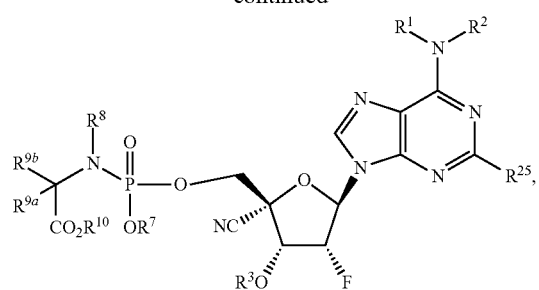
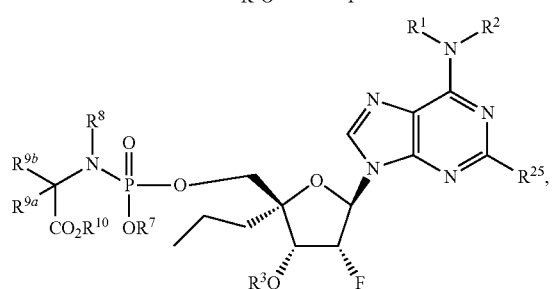
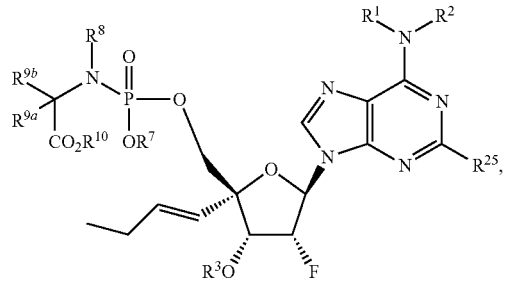
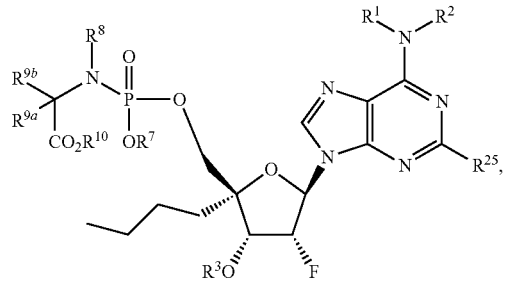
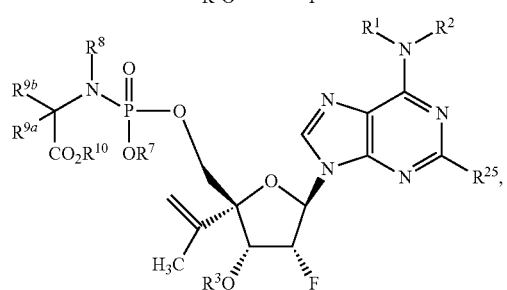
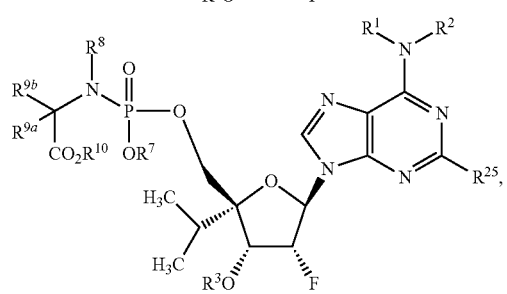
84
-continued
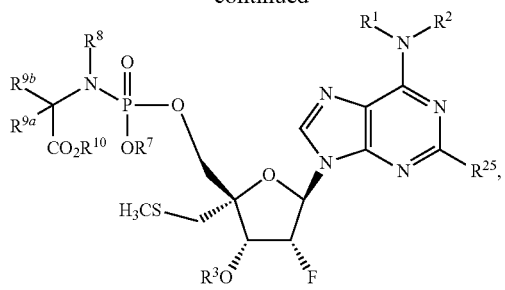
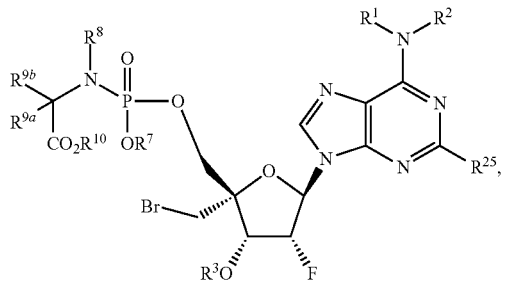
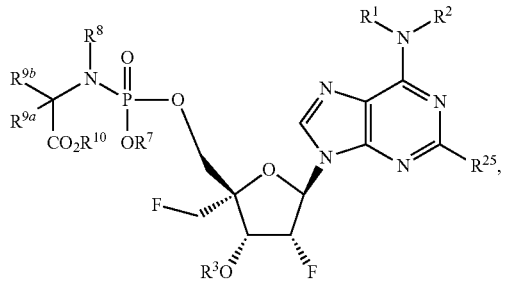
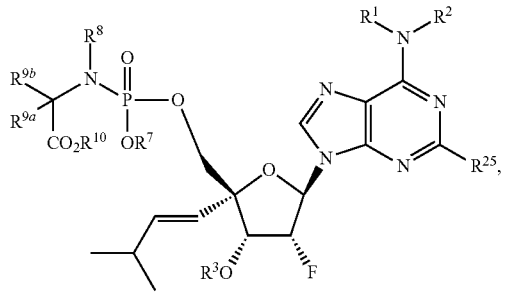
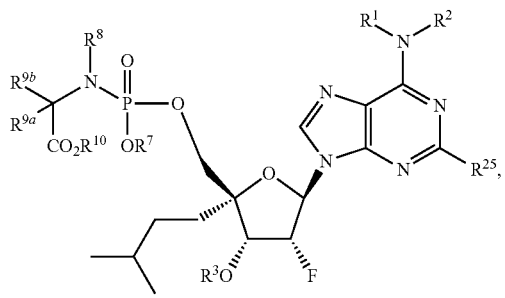
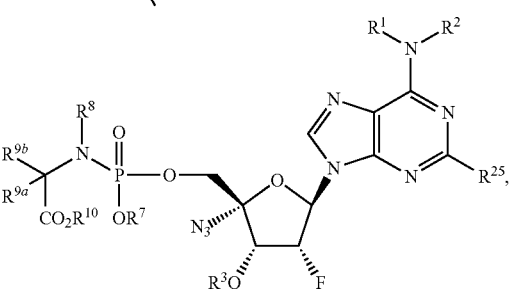

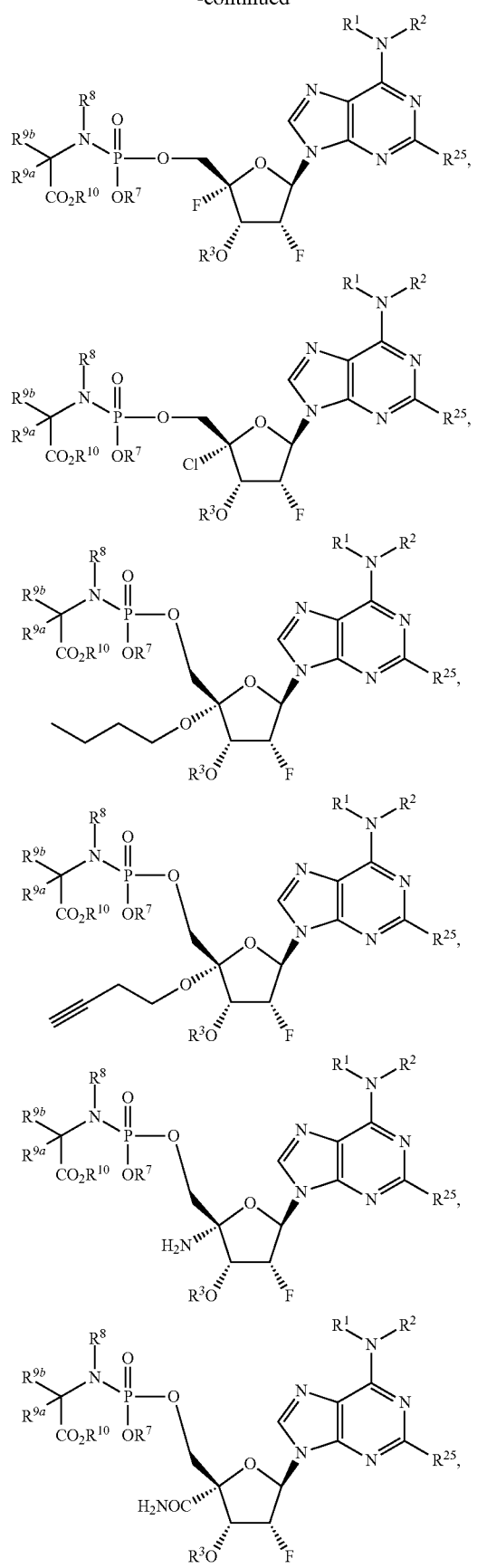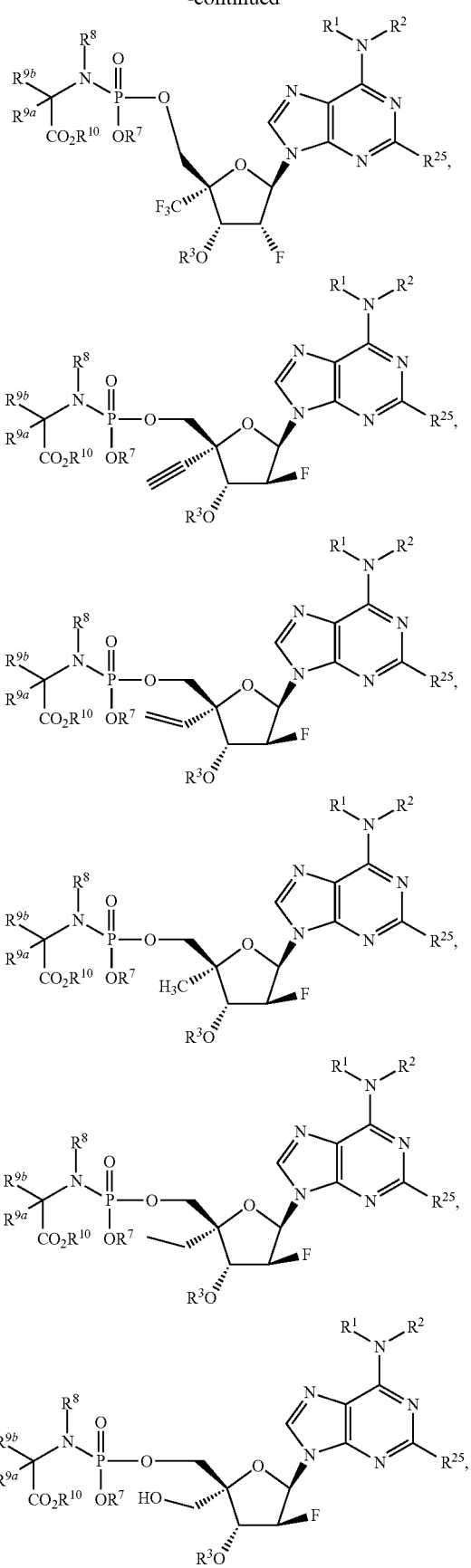

87
-continued
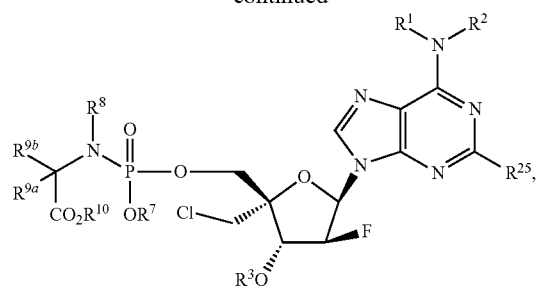
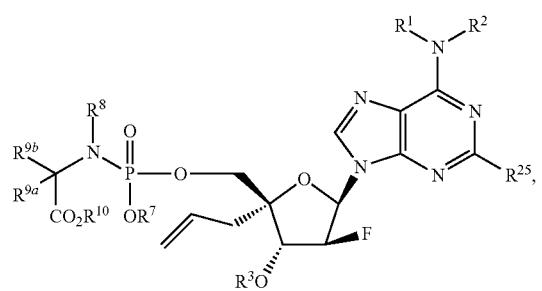
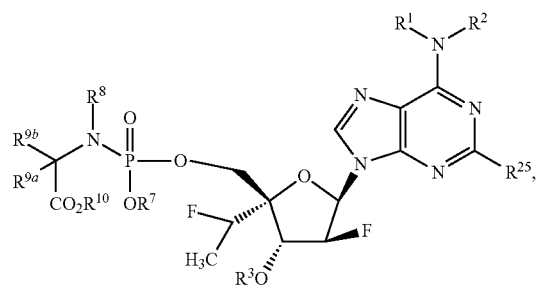
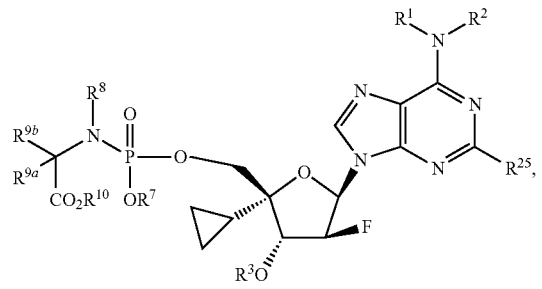
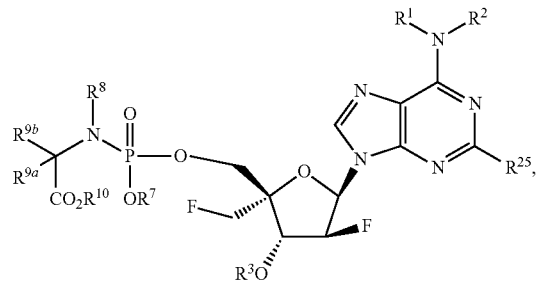
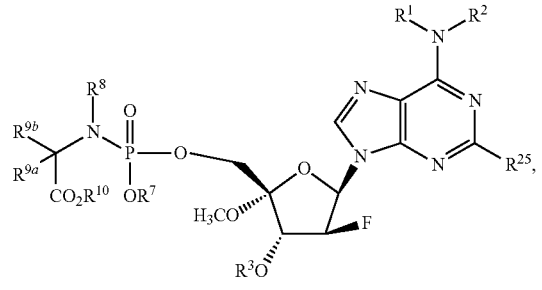
88
-continued
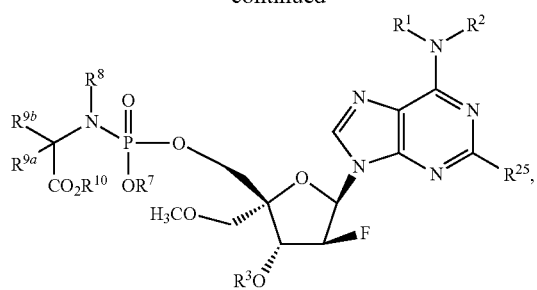
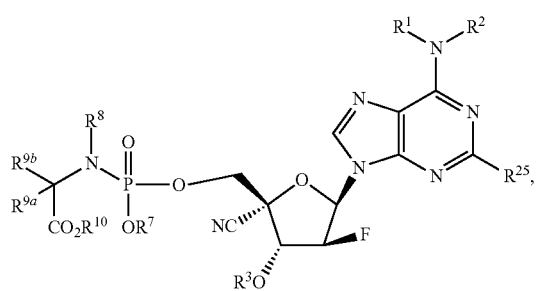
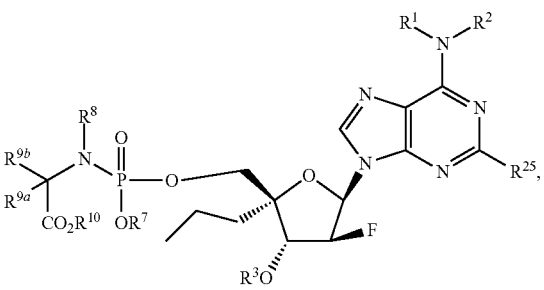
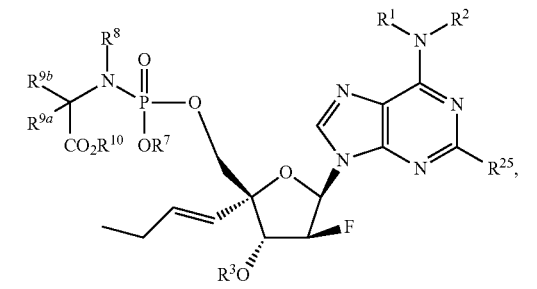
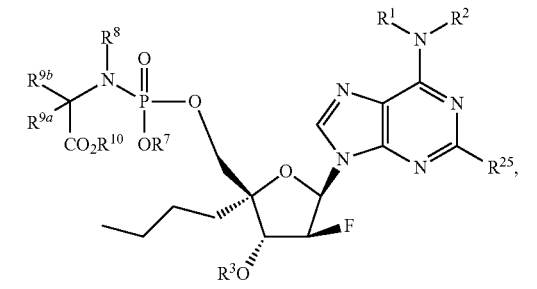
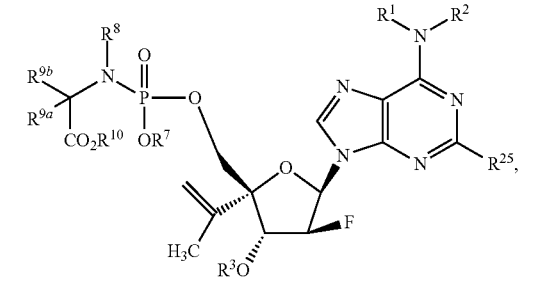

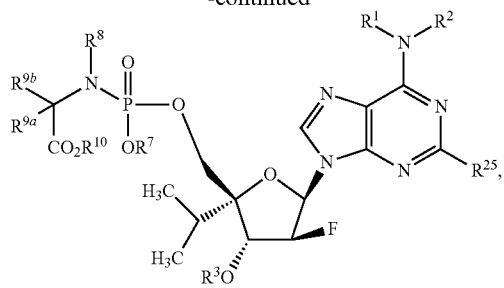
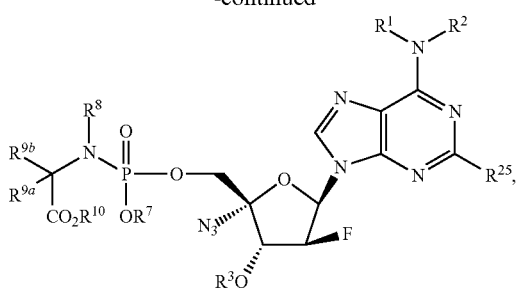
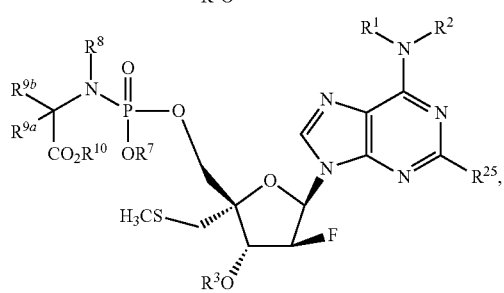
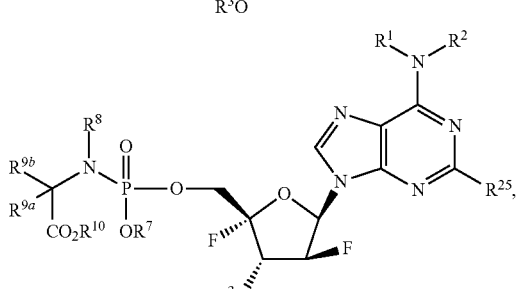
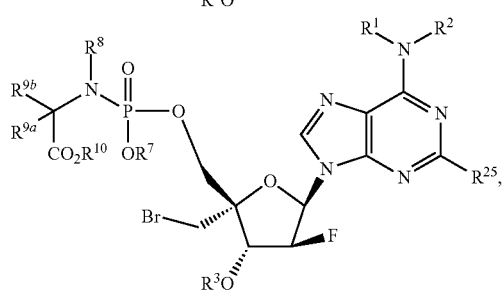
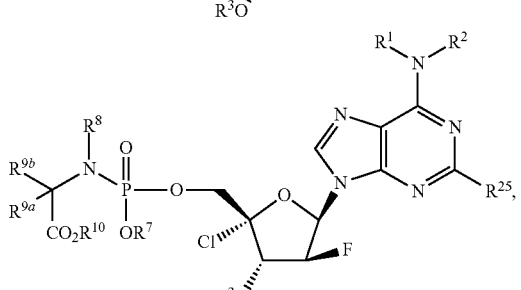
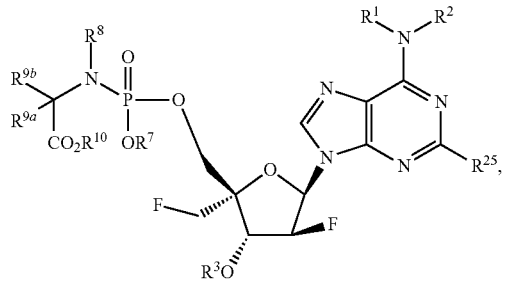
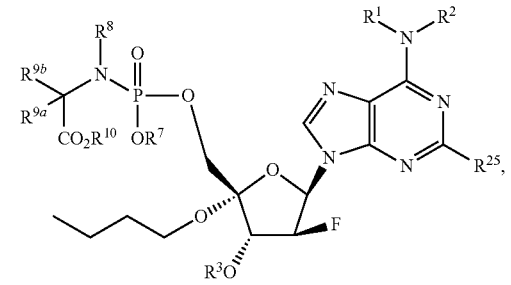
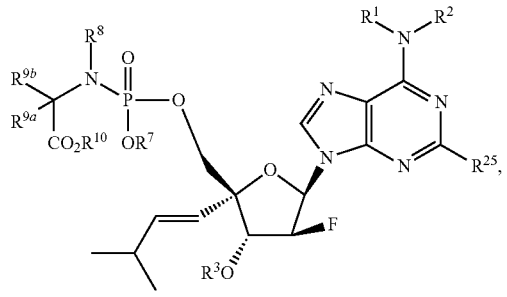
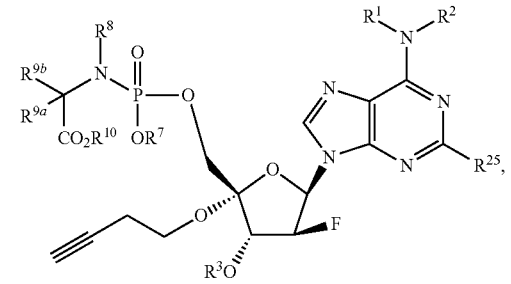
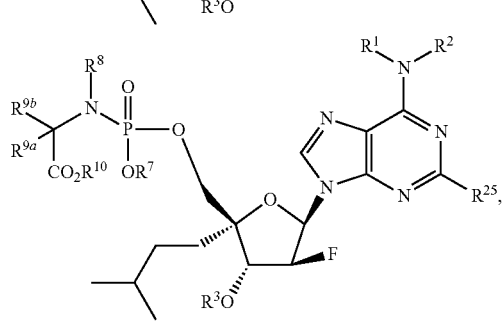
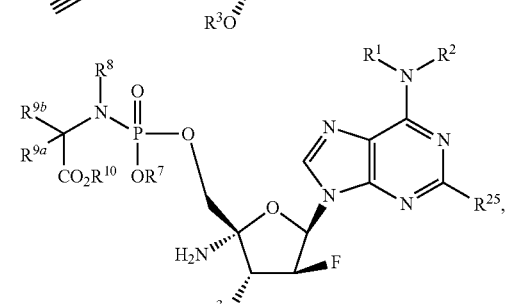

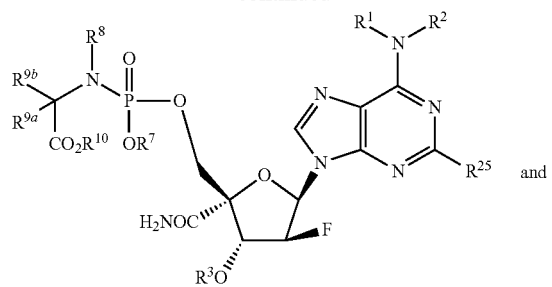
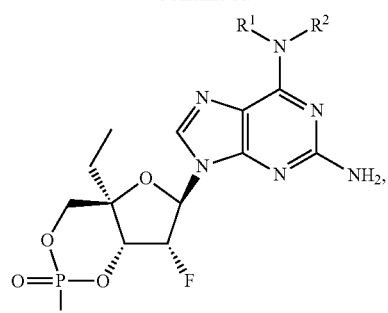
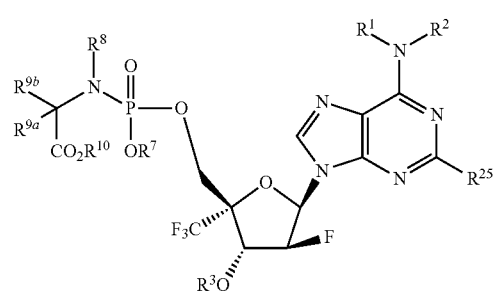
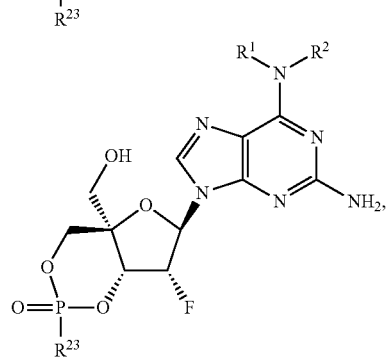
In one embodiment, a compound of Formula V is provided. Non-limiting examples of compounds of Formula V include:
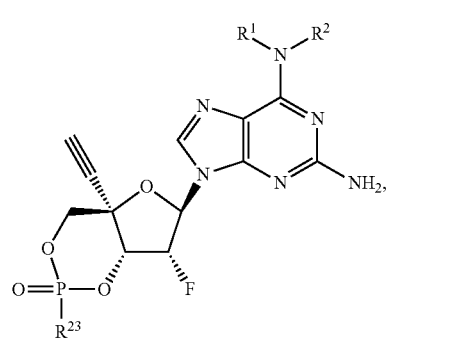
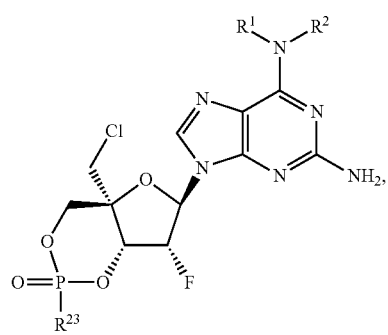
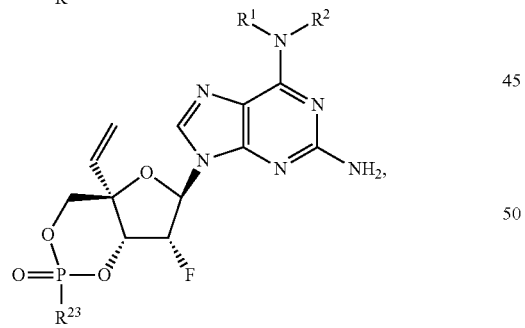
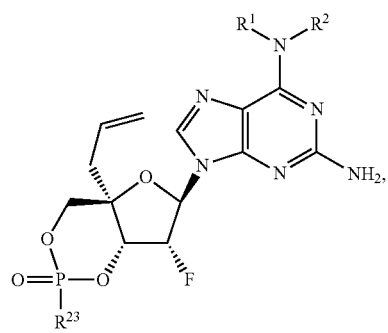
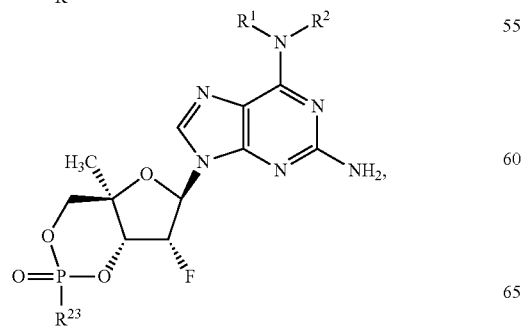
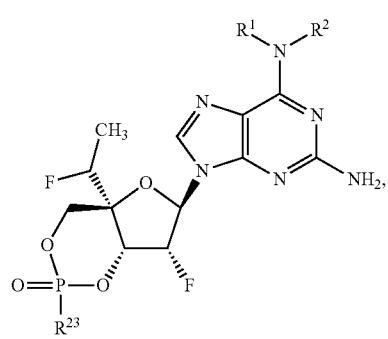

93
-continued
94
-continued
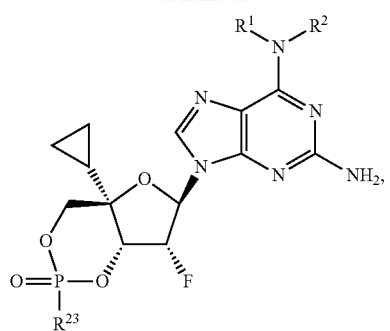

95
-continued
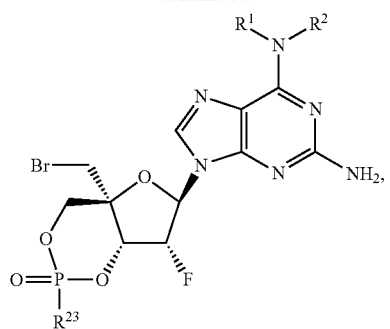
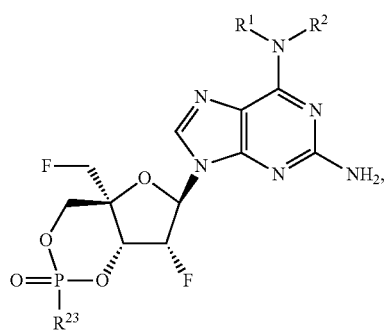
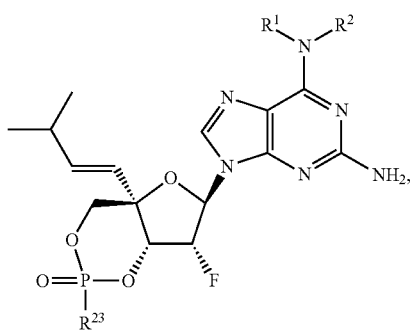
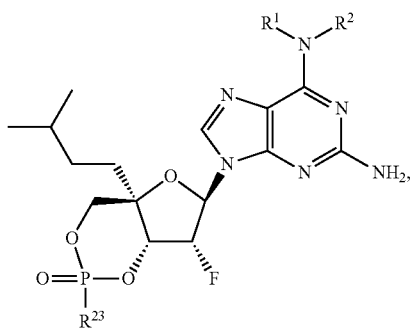
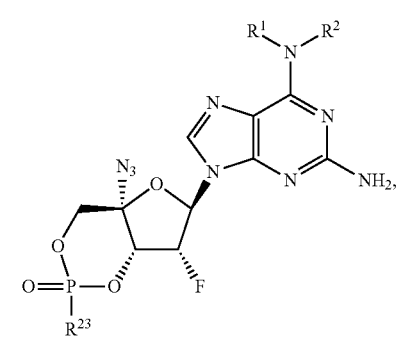
96
-continued
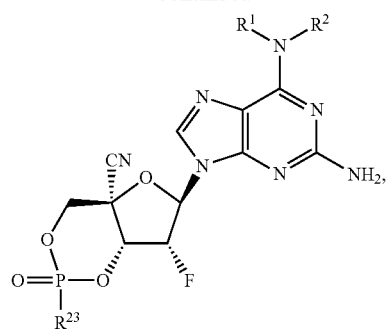
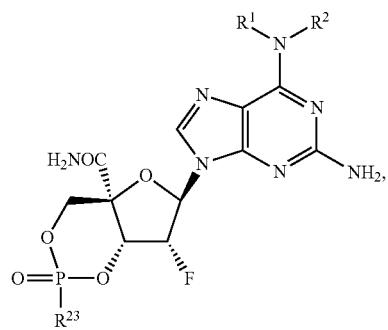
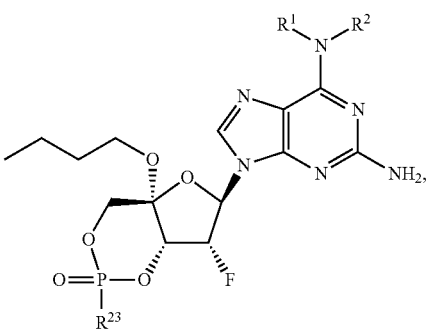
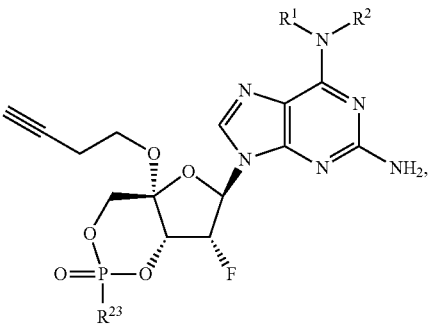
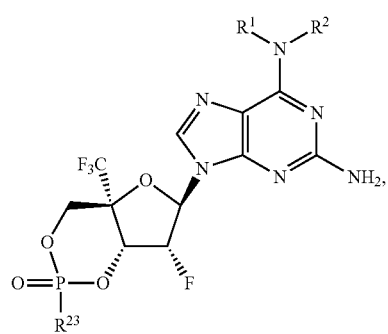

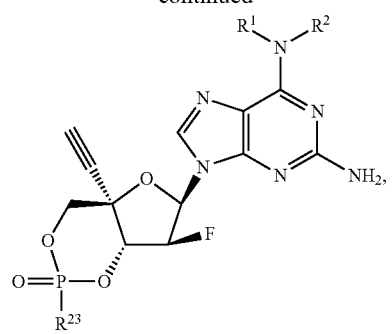
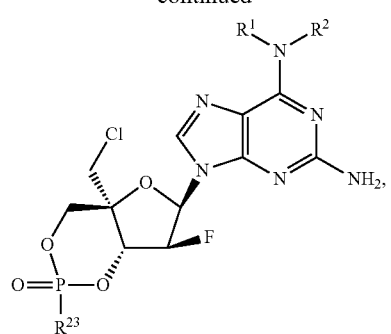
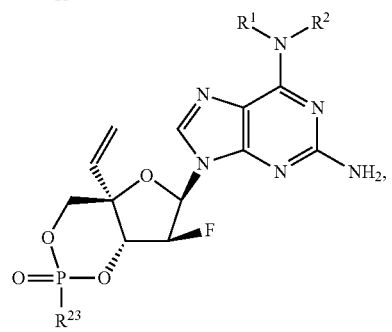
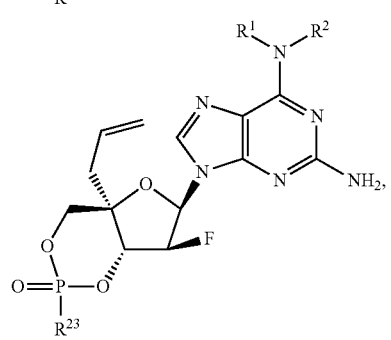
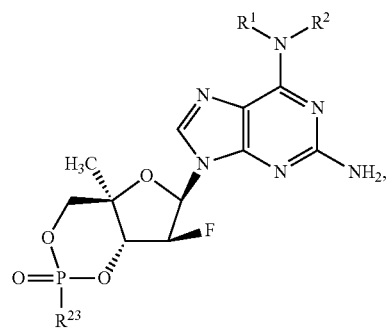
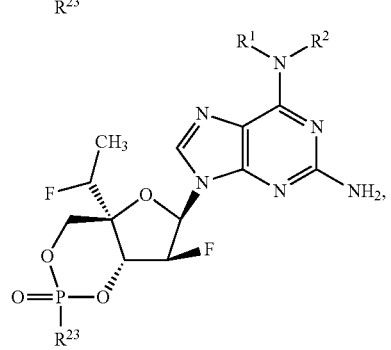
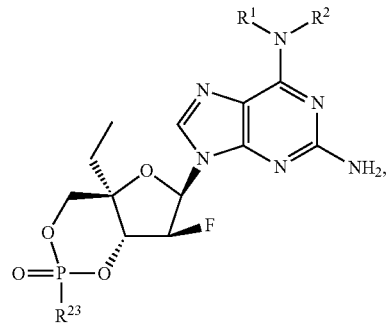
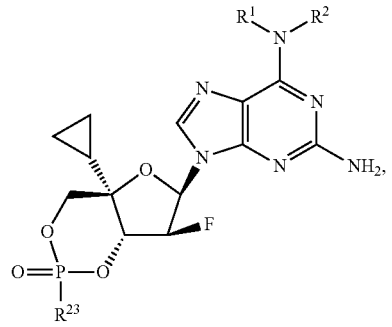
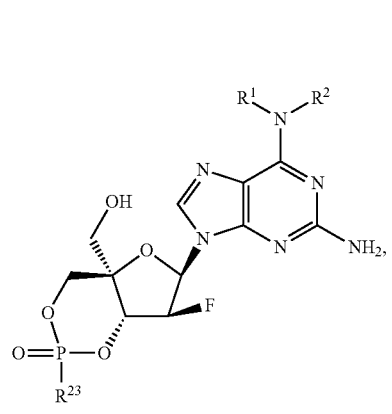
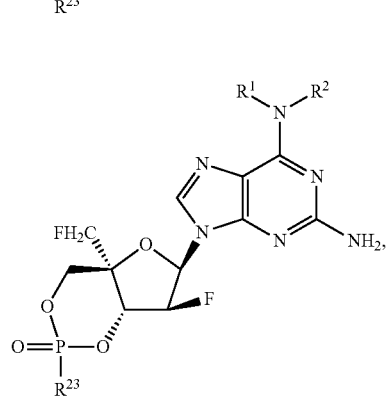

99
-continued
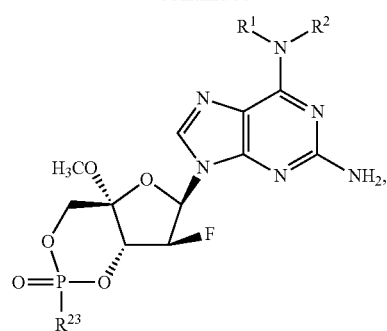
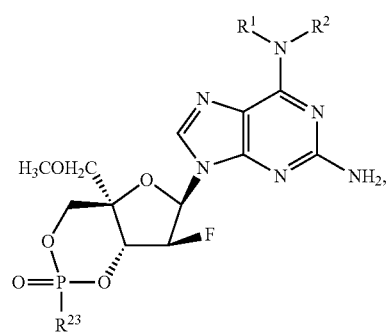
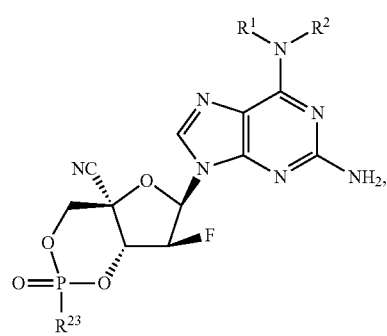
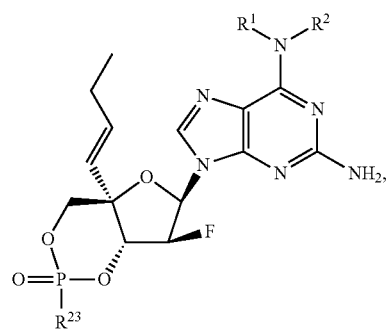
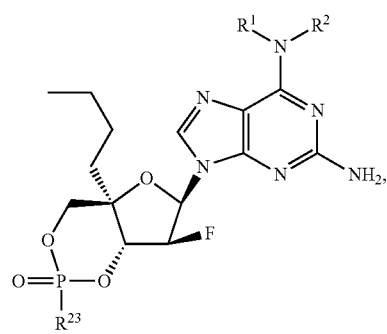
100
-continued
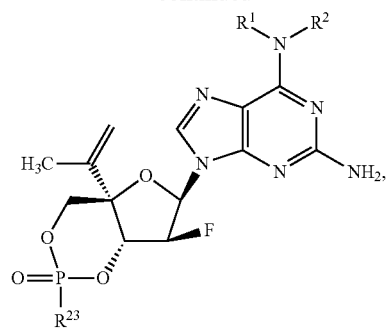
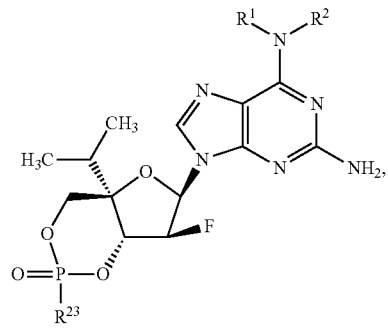
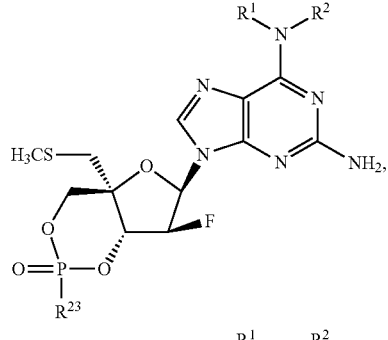
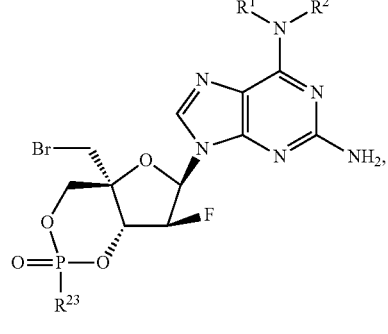
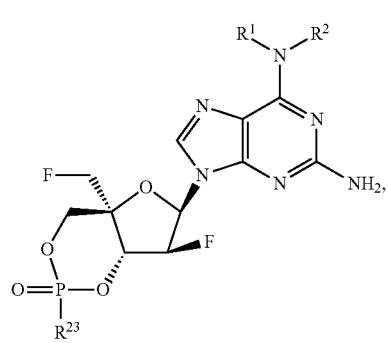

101
-continued

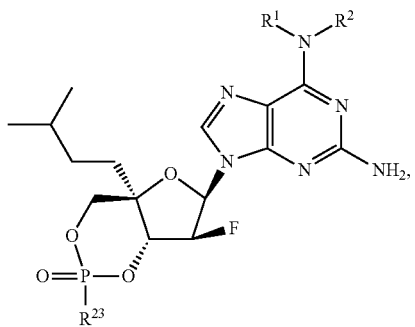
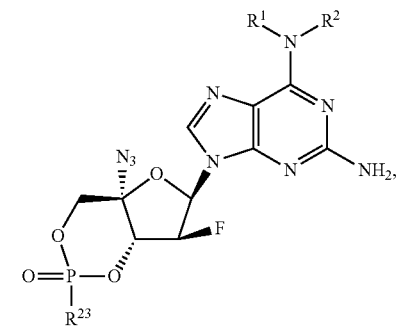
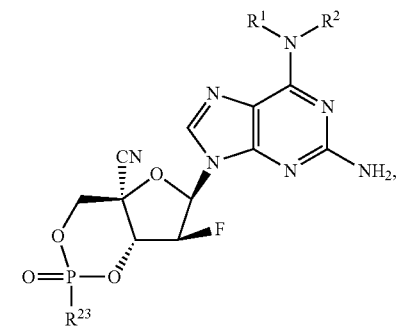
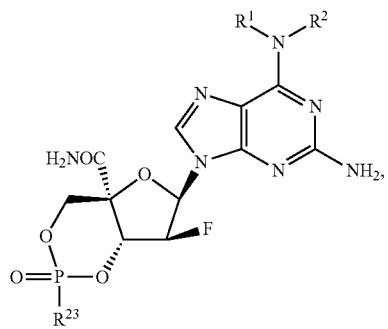
102
-continued
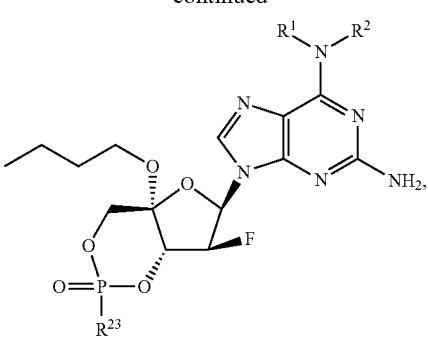
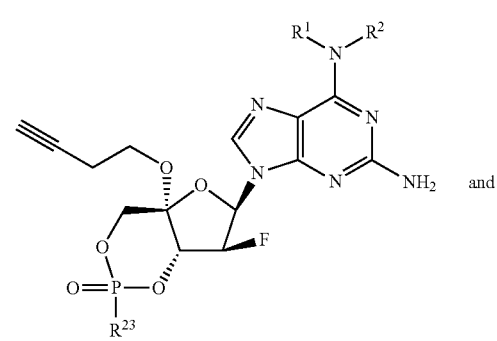
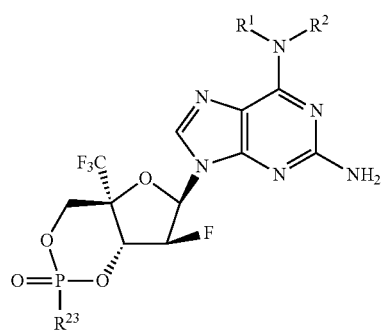
In one embodiment, a compound of Formula VI is provided. Non-limiting examples of compounds of Formula VI include:
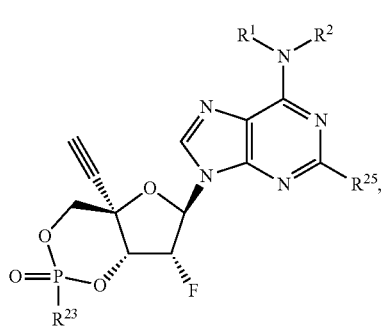

103
-continued
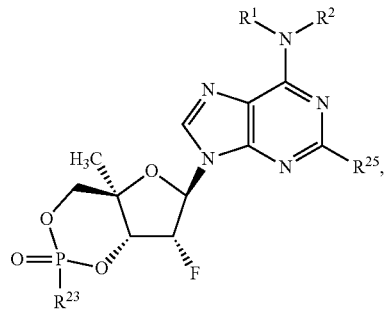
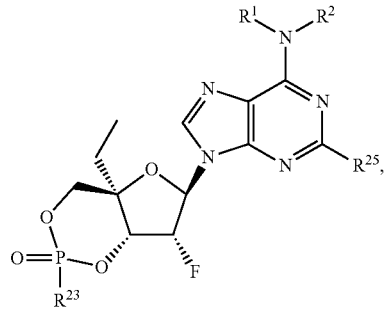
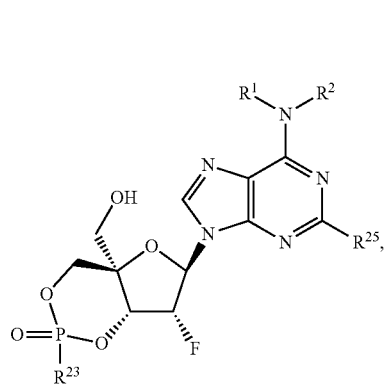
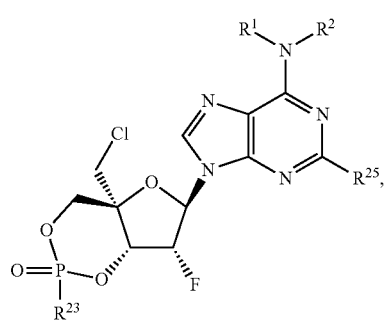
104
-continued
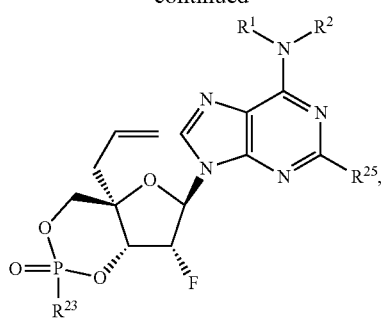
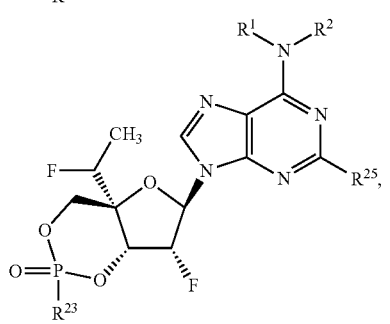
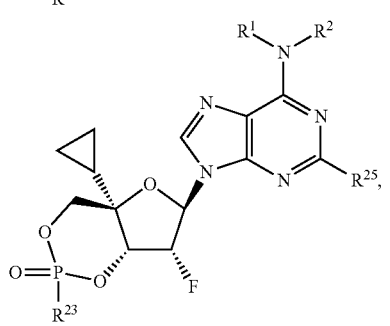
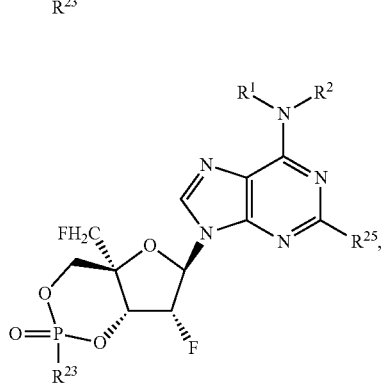
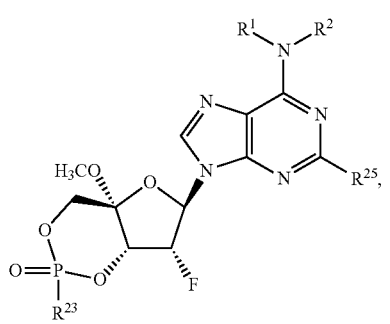

105
-continued

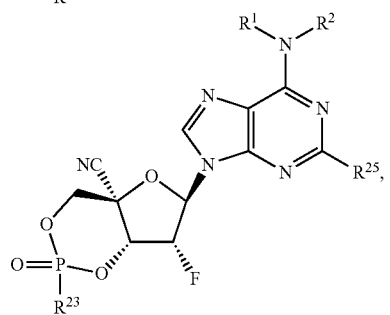
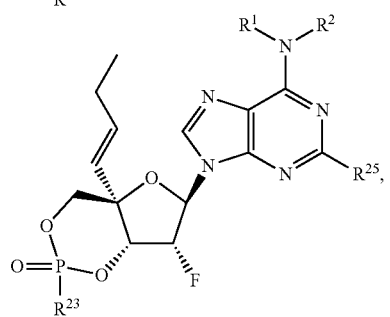
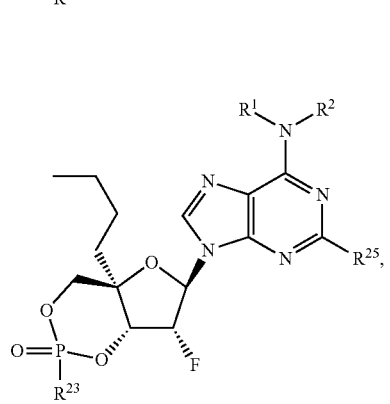
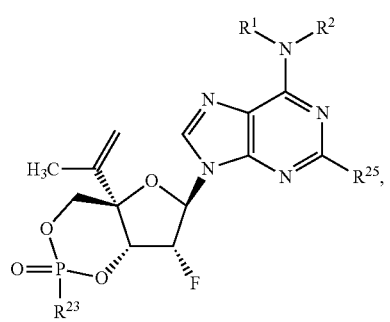
106
-continued
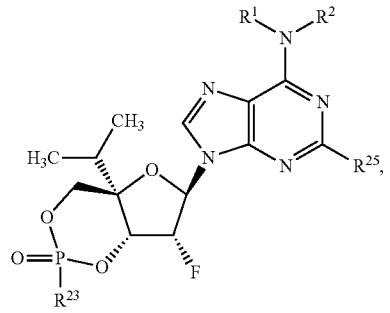
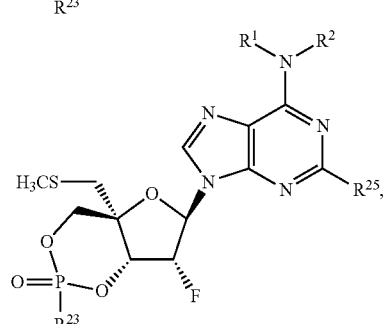
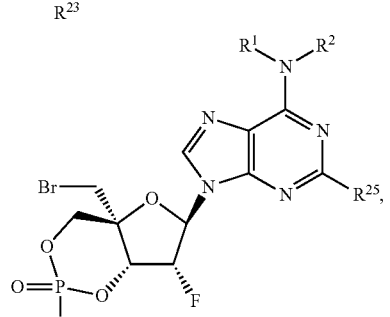
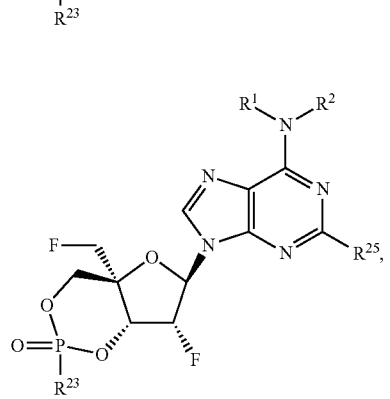
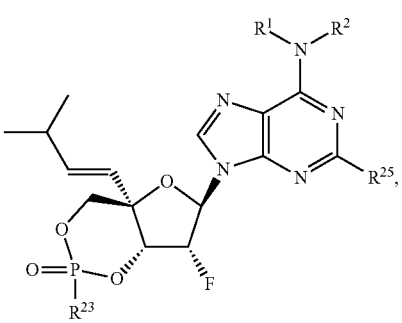

107
-continued
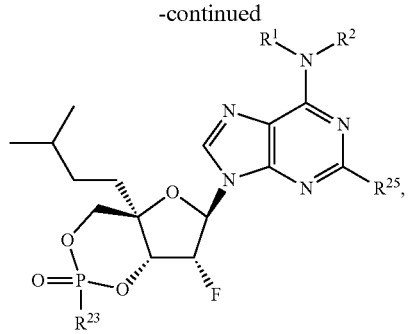
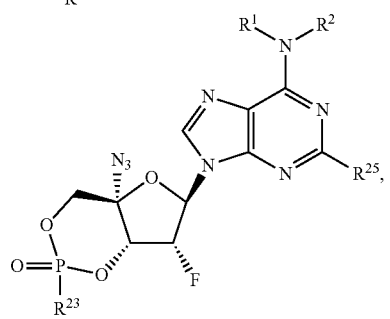
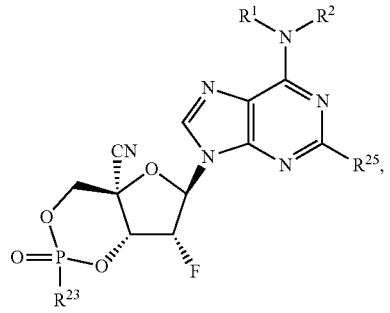
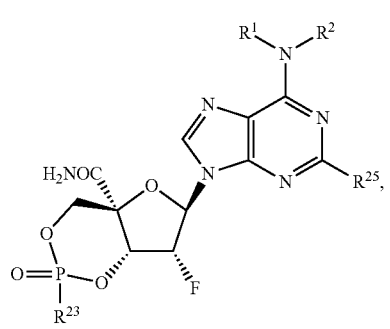
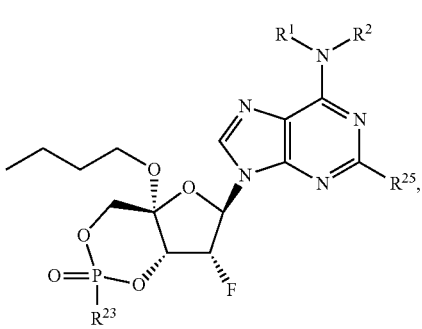
108
-continued
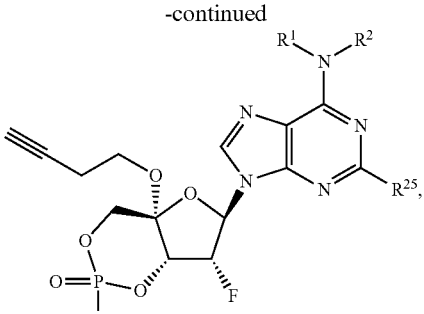
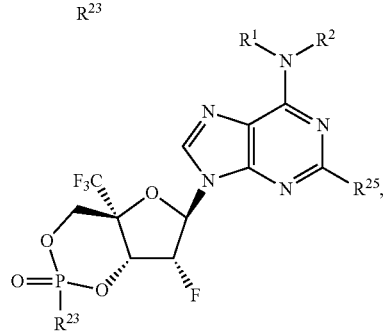
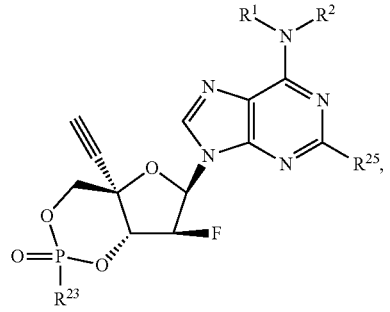
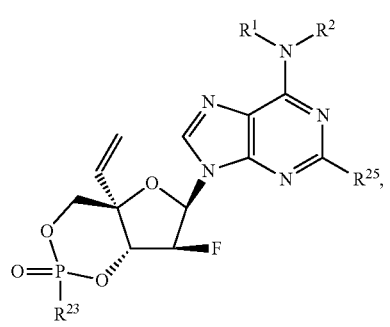
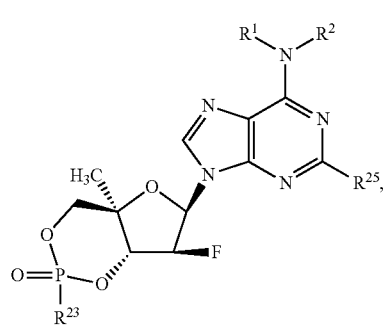

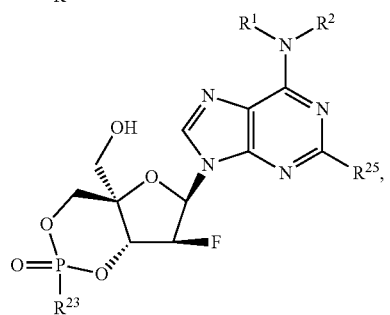
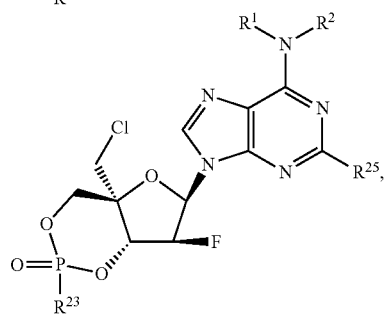
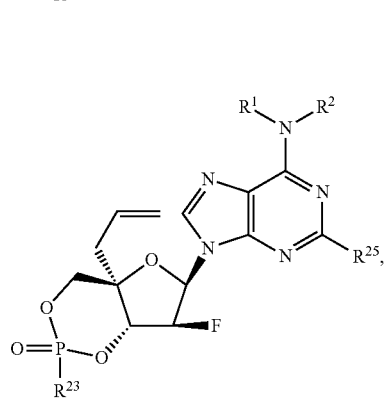
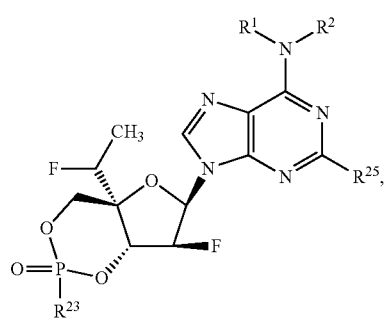
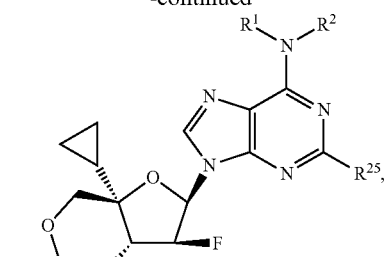
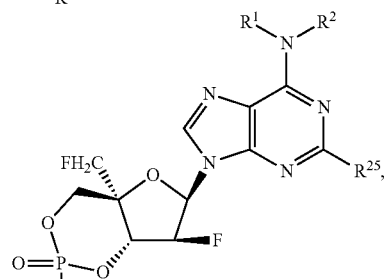
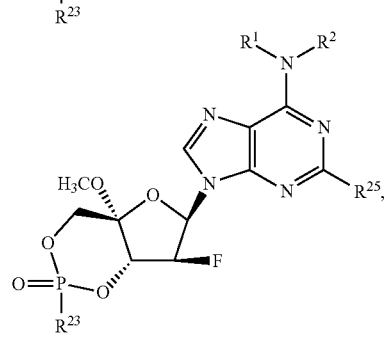
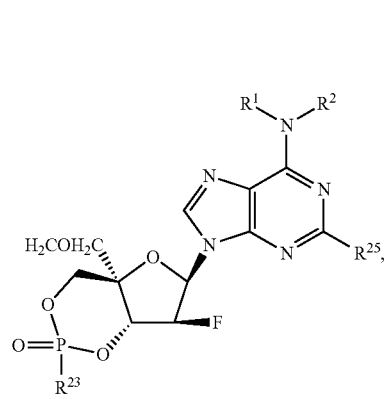
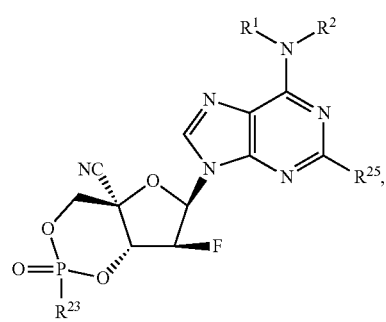

111
-continued
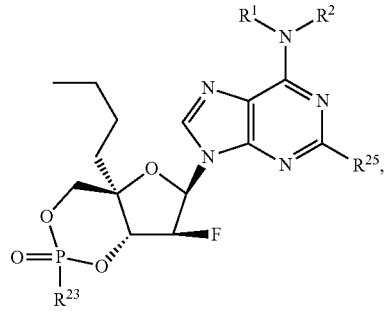
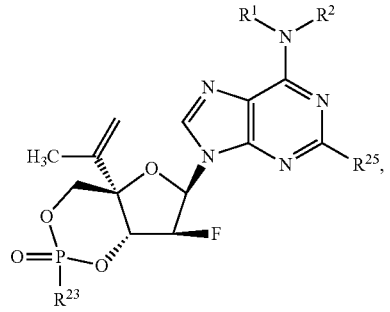
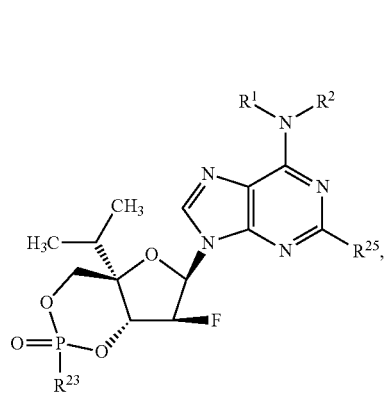
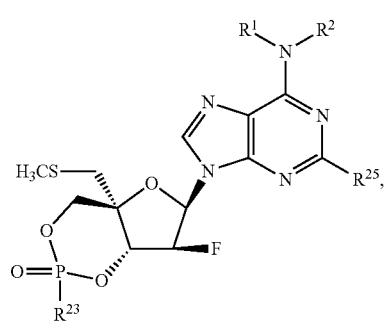
112
-continued
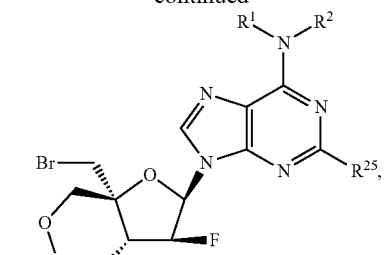
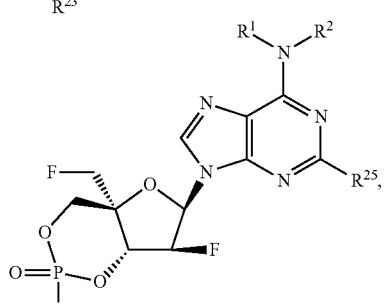
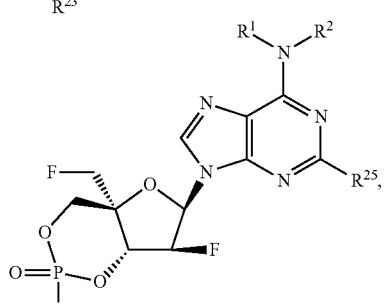
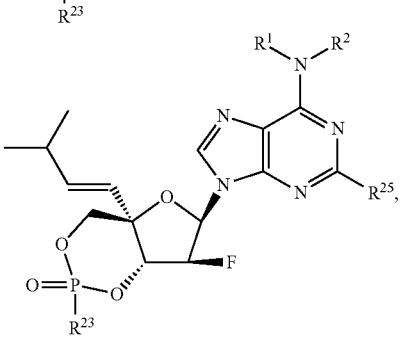
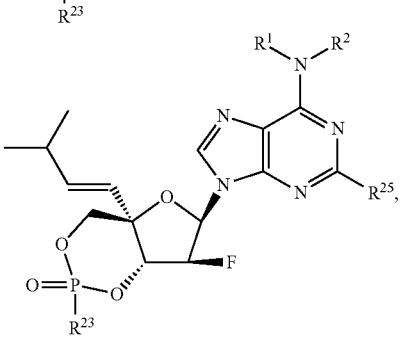

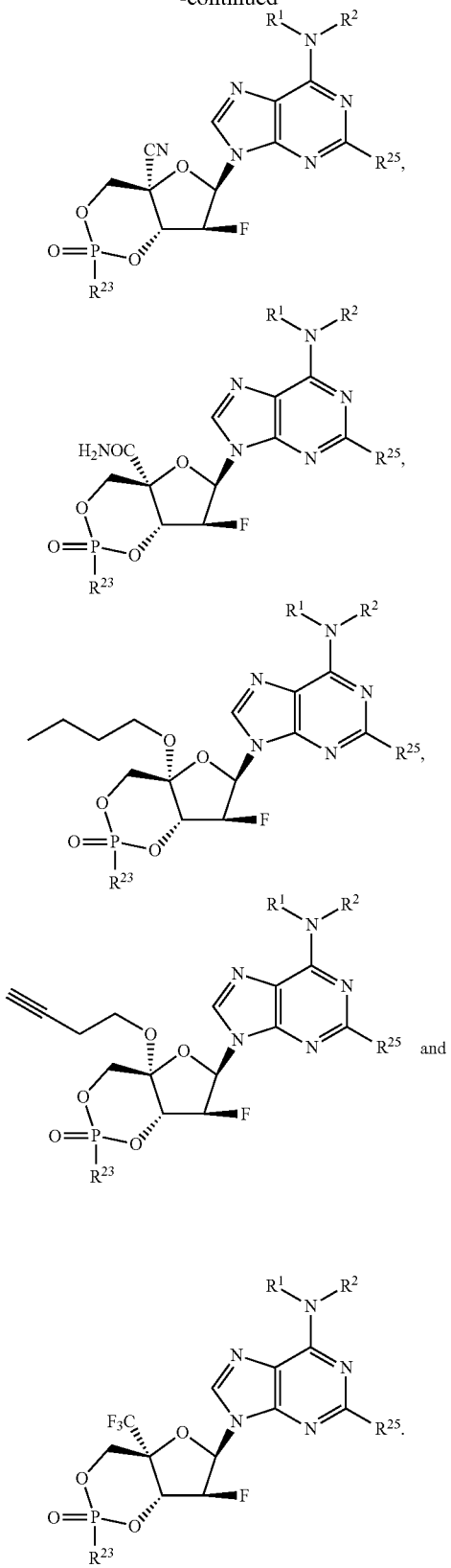
In one embodiment, a compound of Formula I is provided. Non-limiting examples of compounds of Formula I include:

115
-continued
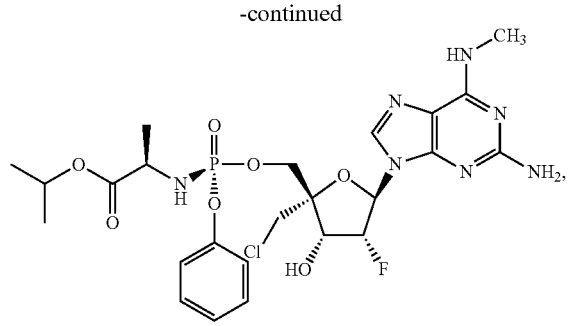
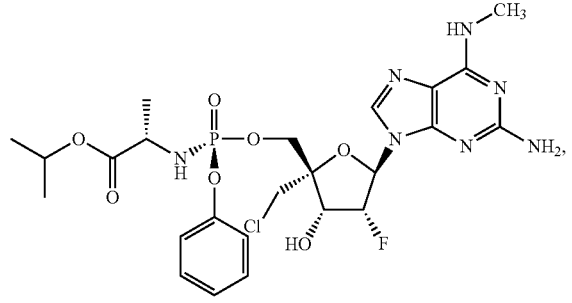
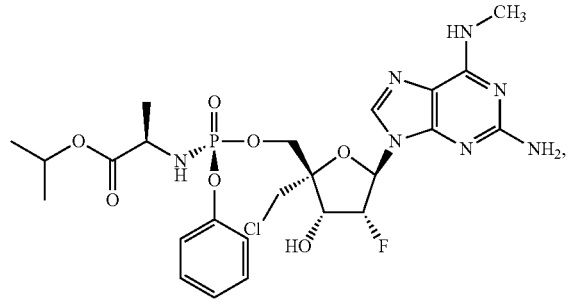
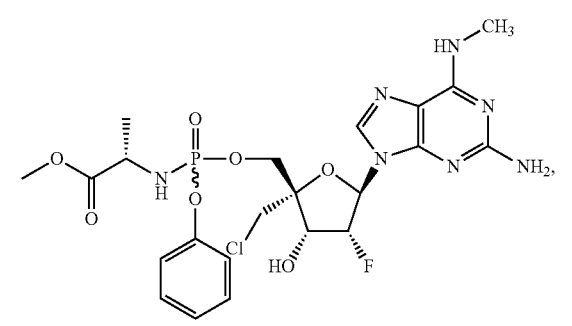
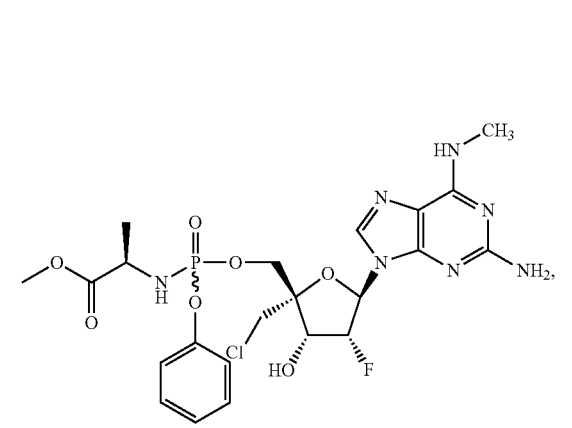
116
-continued
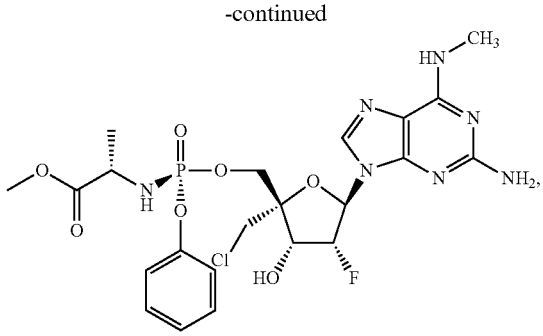
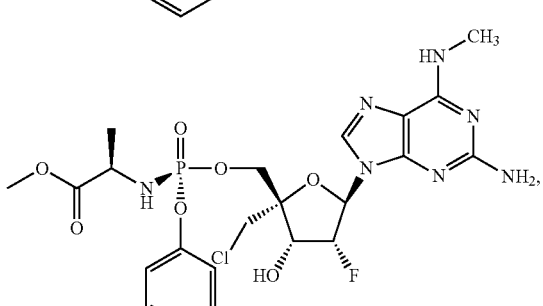
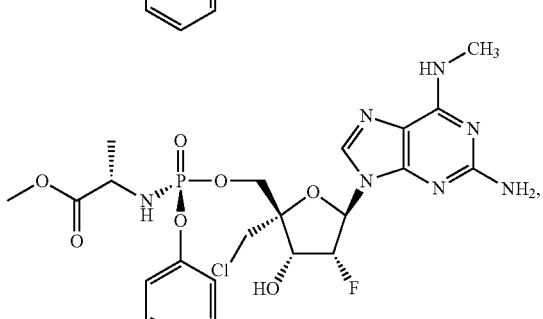
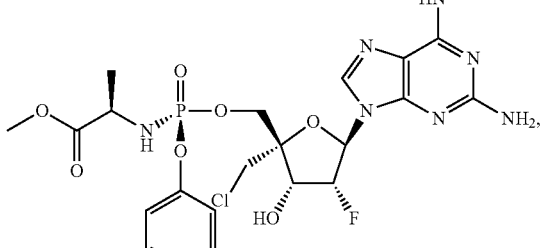
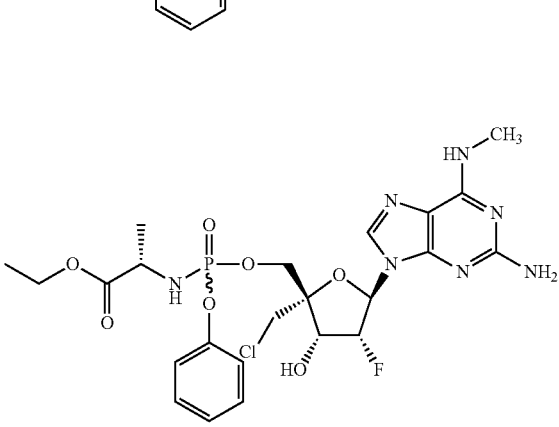

117
-continued
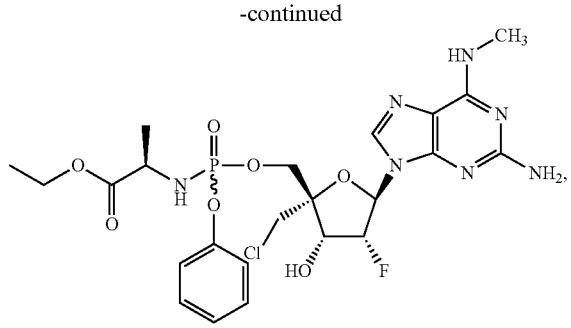
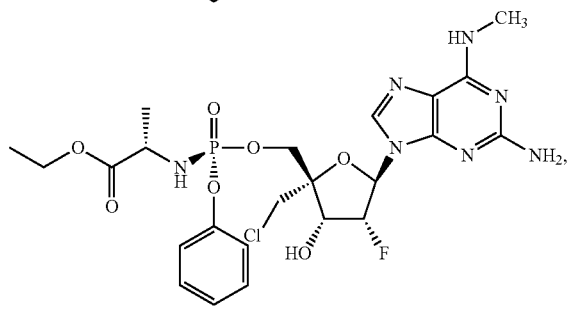
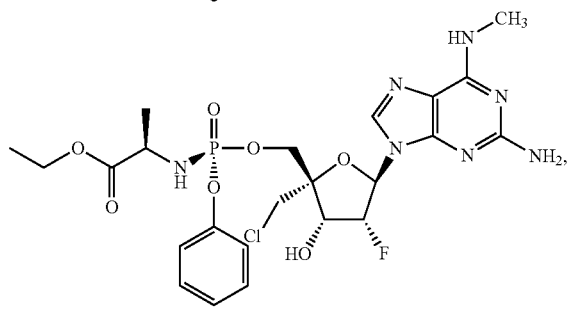
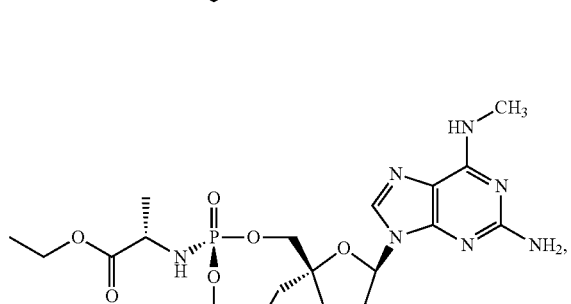
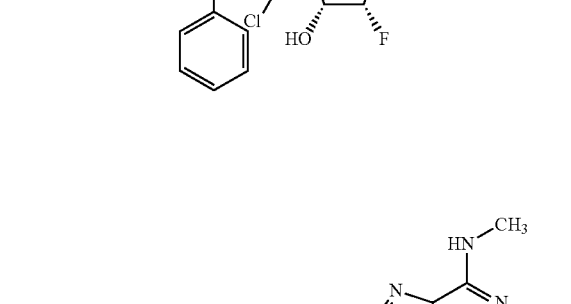
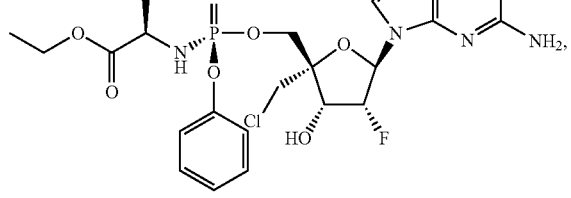
118
-continued
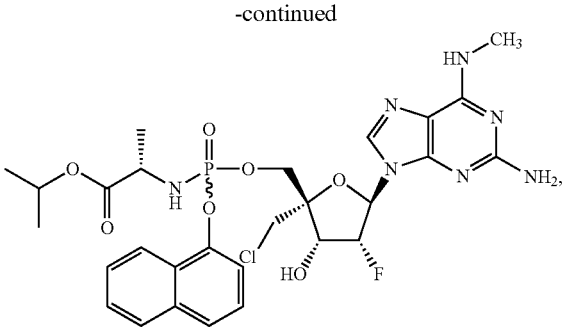

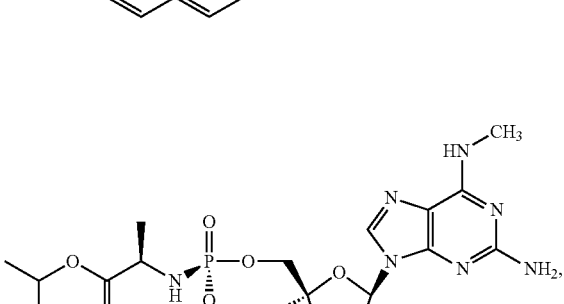
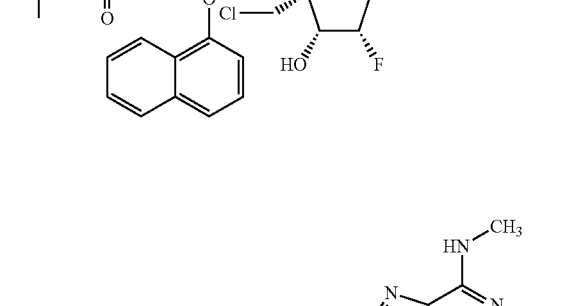
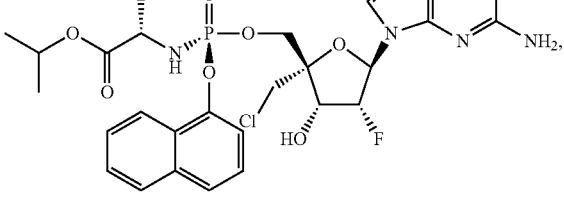

119
-continued
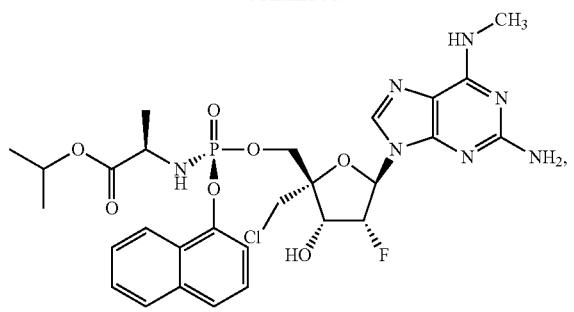
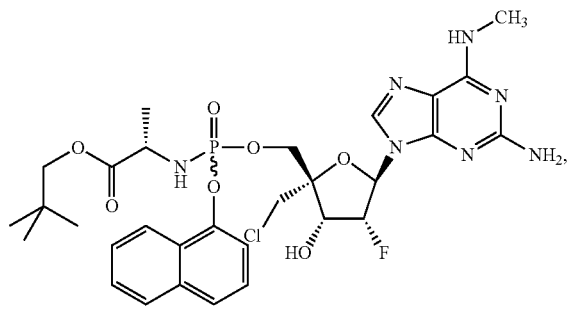
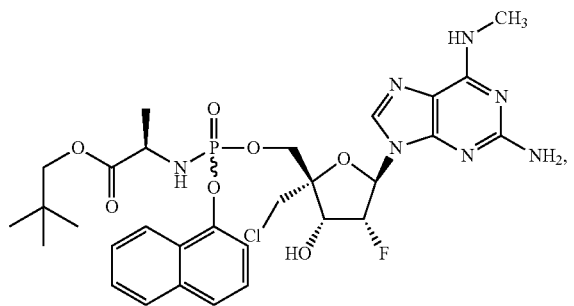
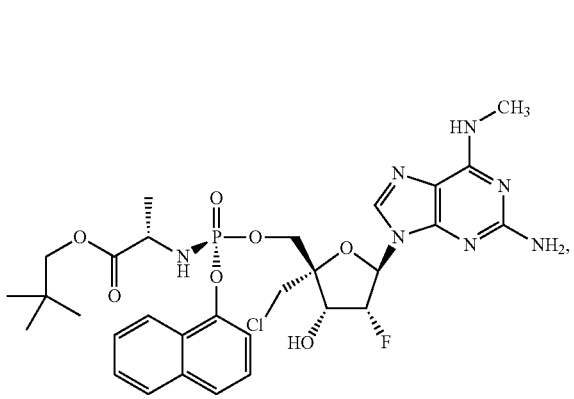
120
-continued
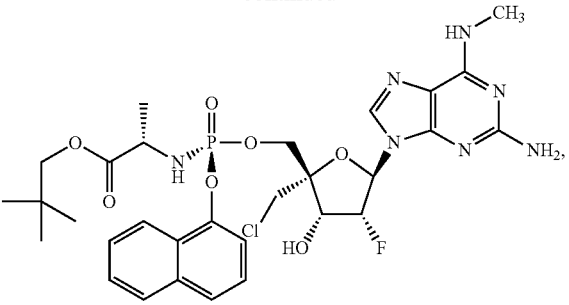
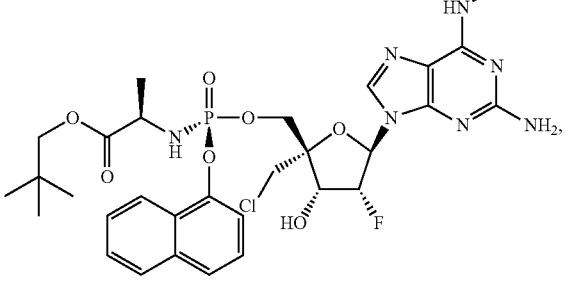
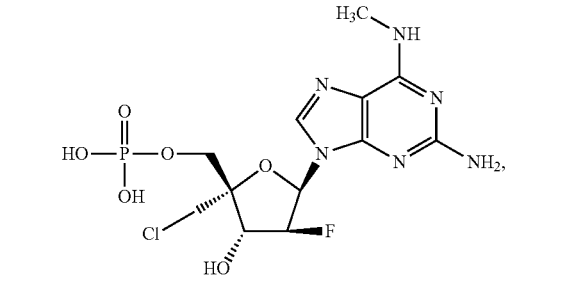
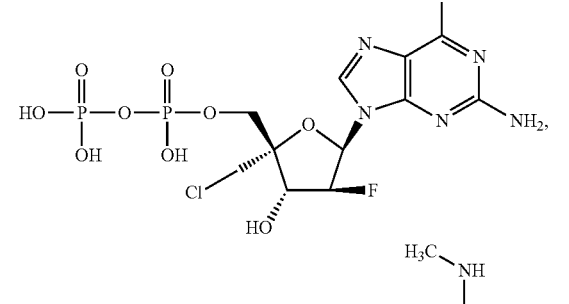
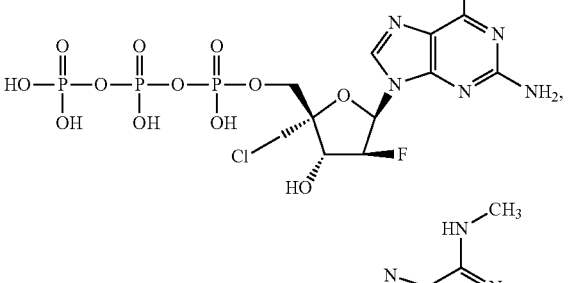
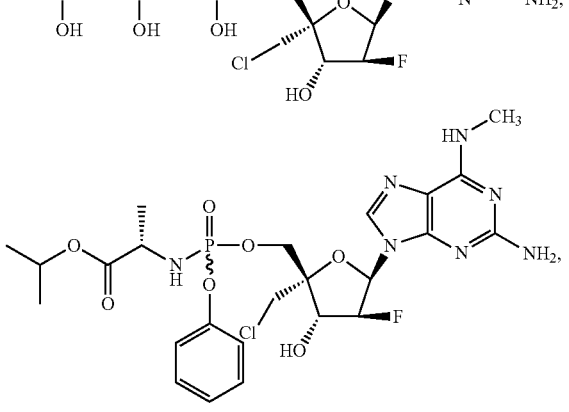

-continued
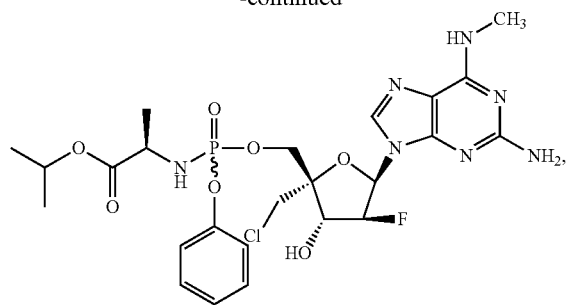
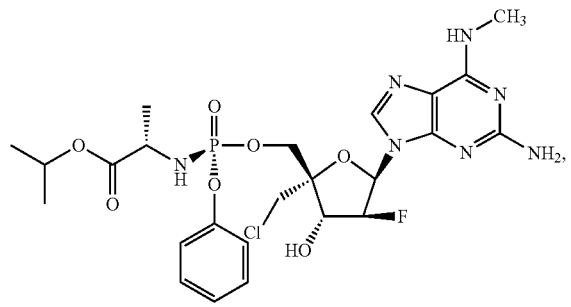
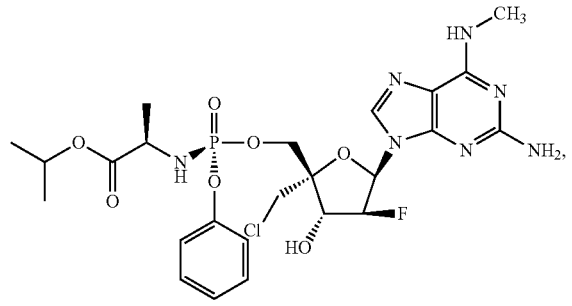
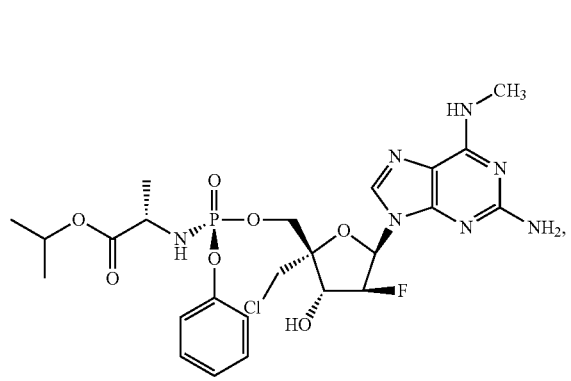
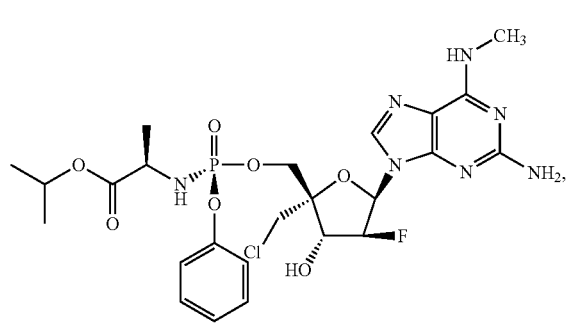
-continued
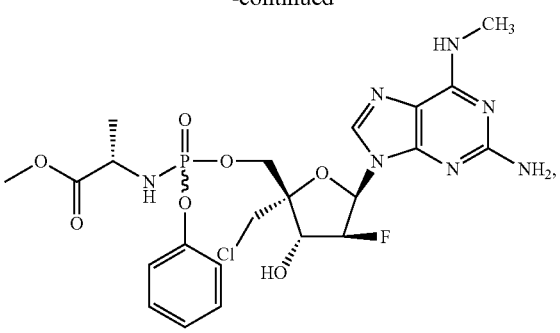
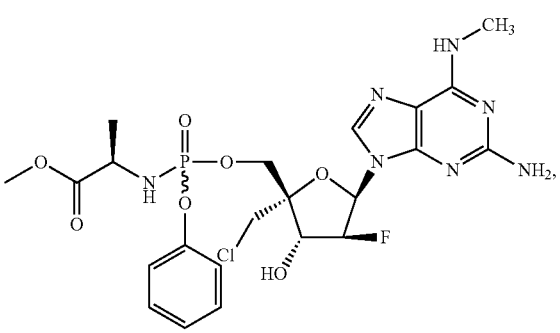
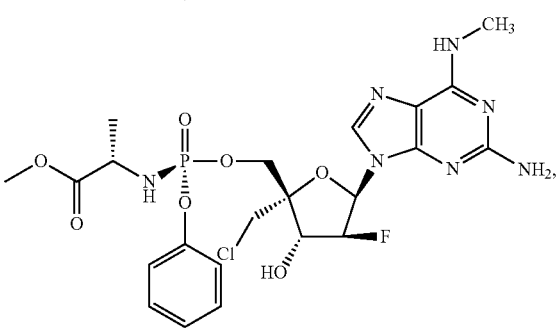
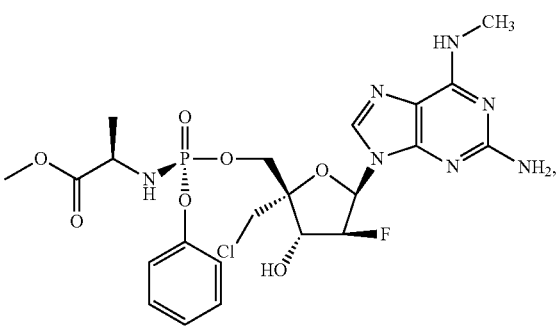
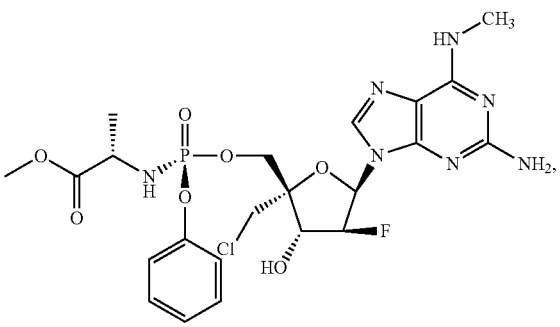

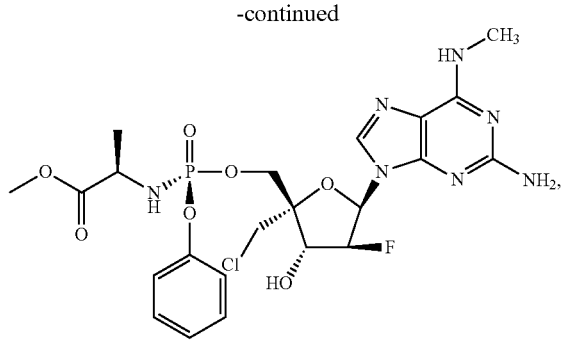
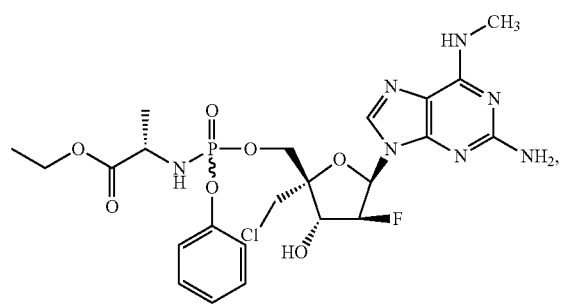
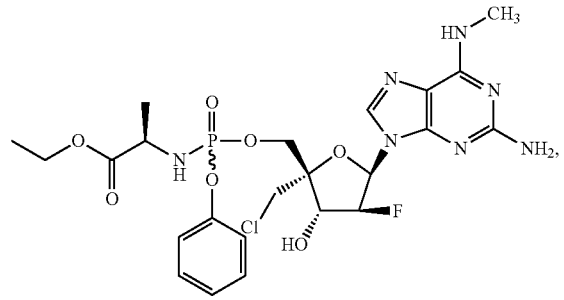
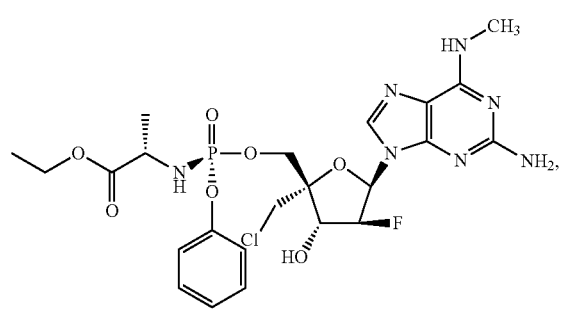
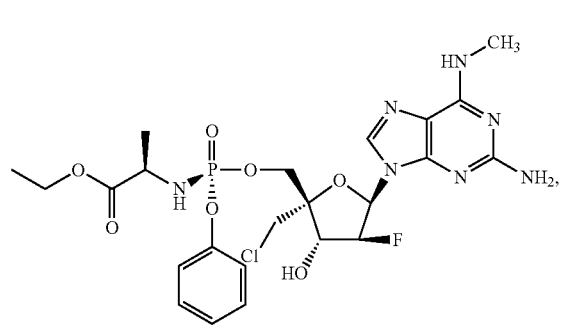
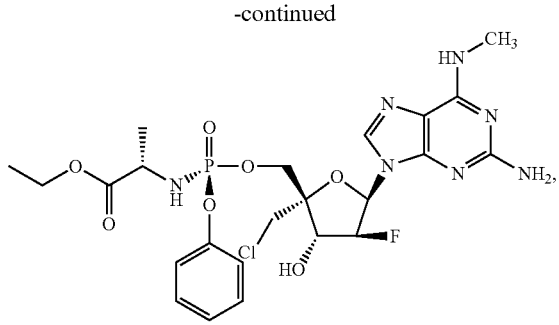
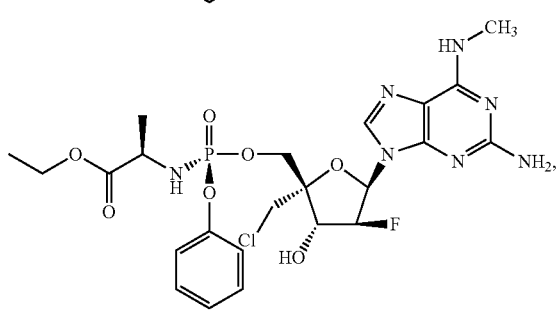
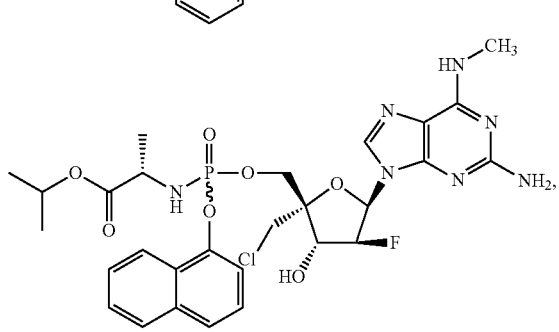
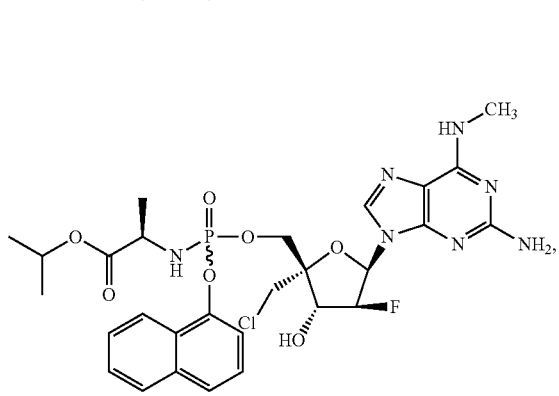
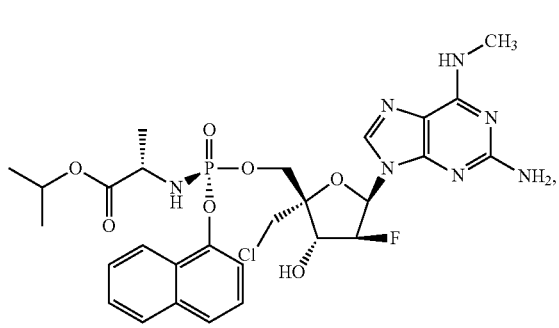

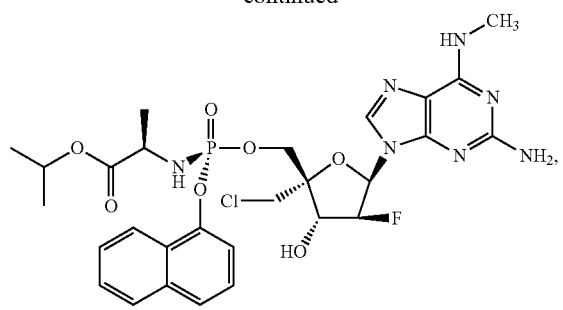
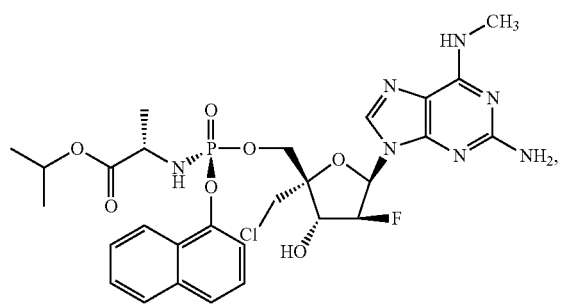
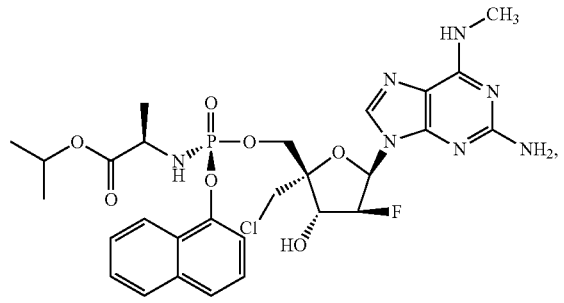
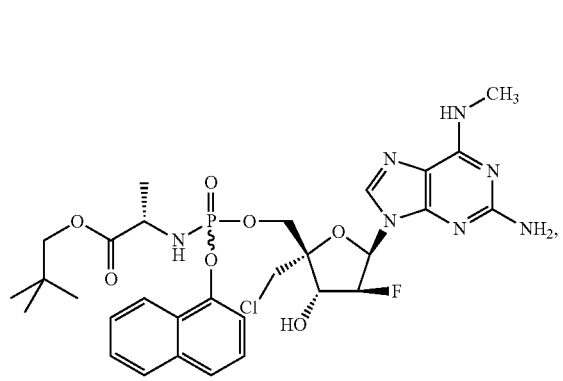
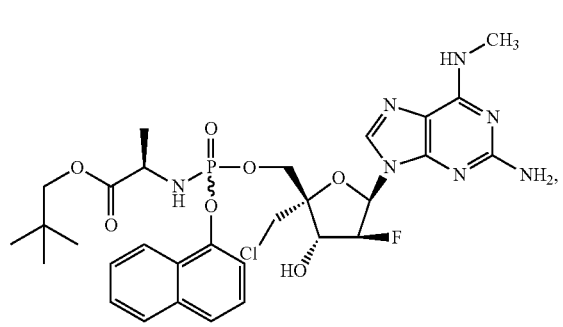
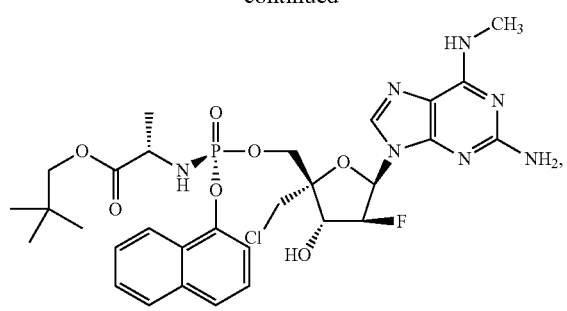
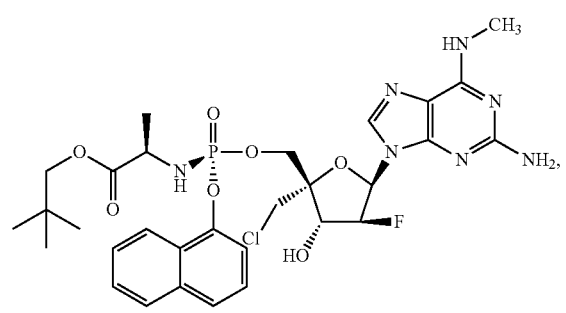
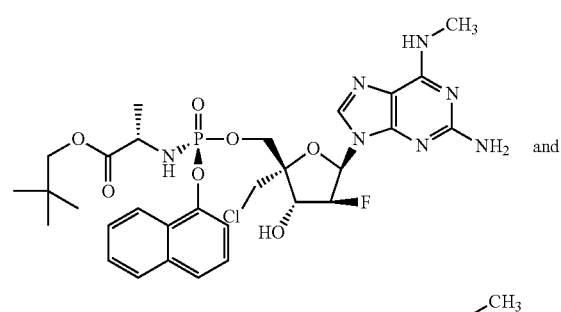
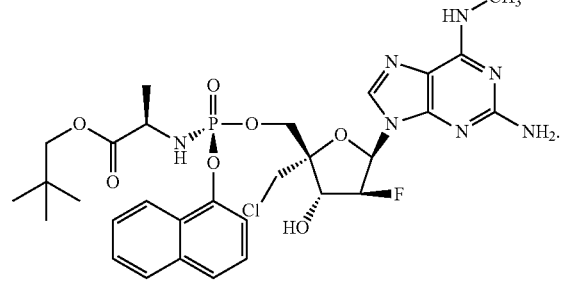 and
In one embodiment, a thiophosphoramidate of Formula I is provided. Non-limiting examples of thiophosphoramidates of Formula I include, but are not limited to:
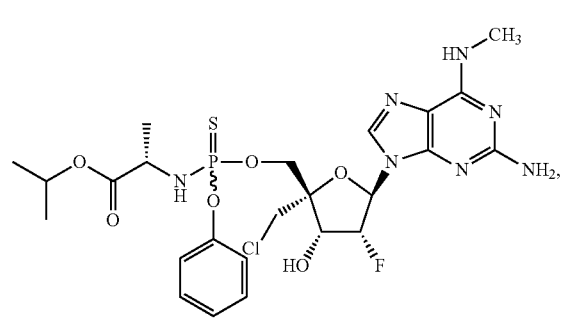

127
-continued
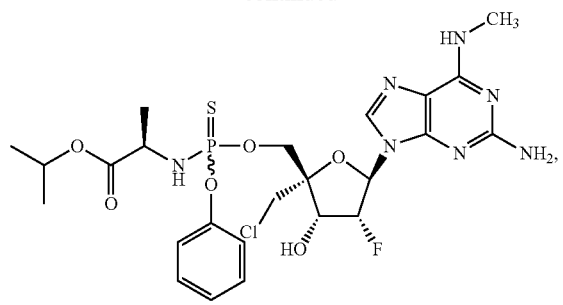
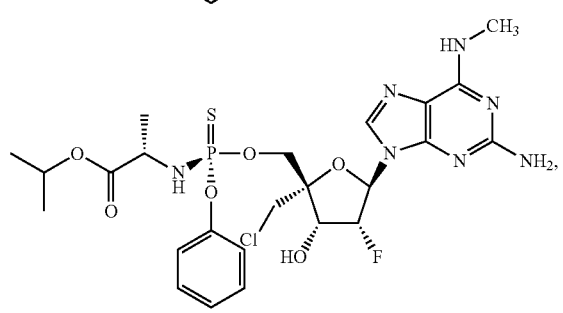
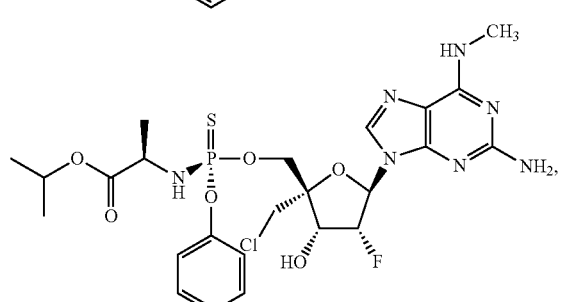
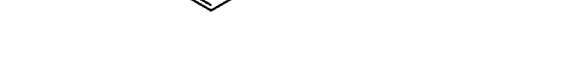
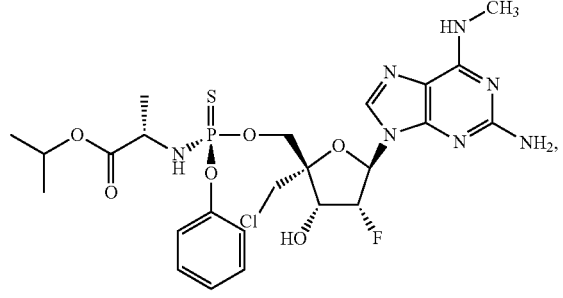
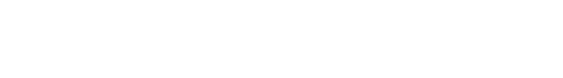
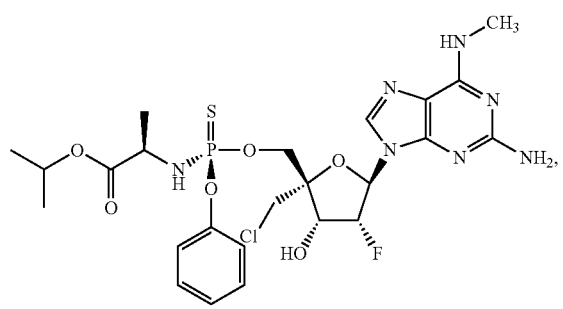
128
-continued
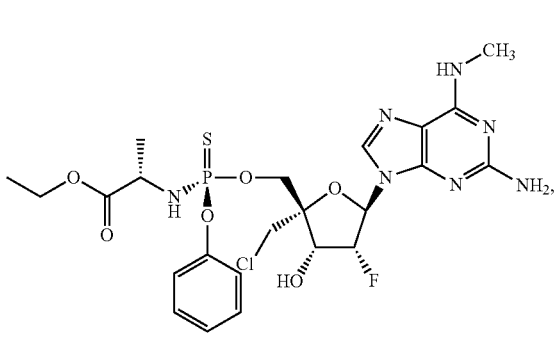

129
-continued
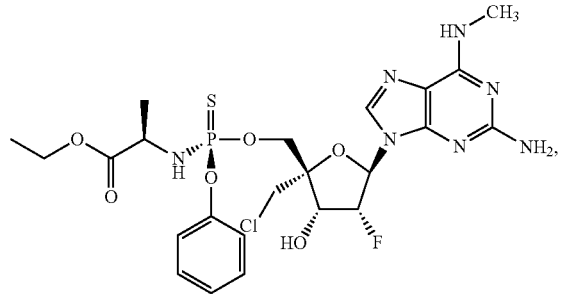
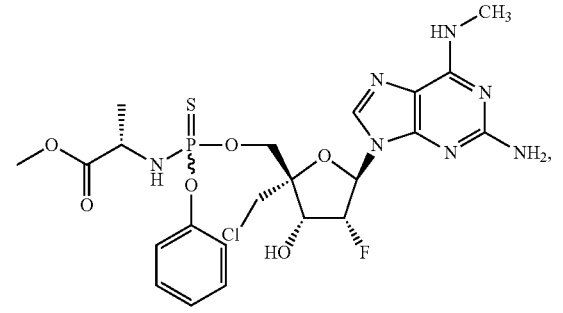
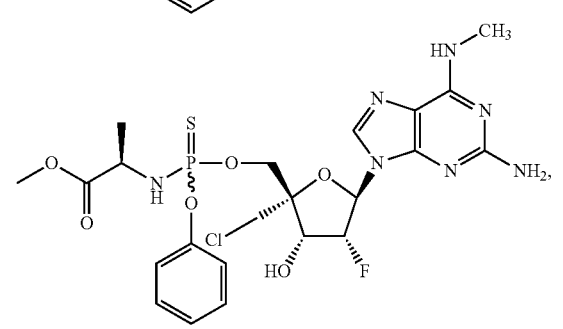
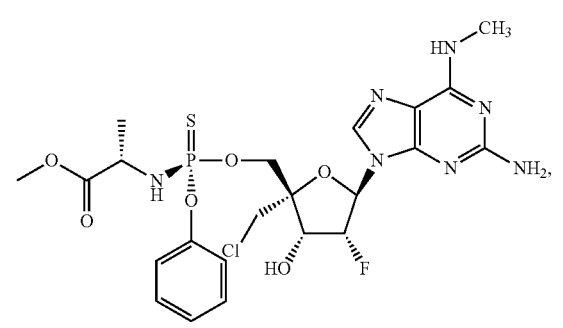
130
-continued
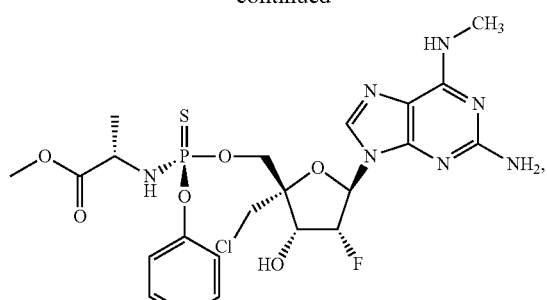
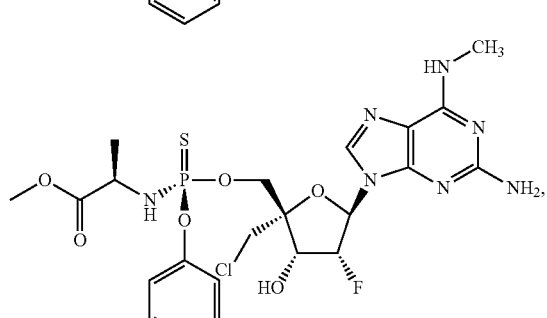
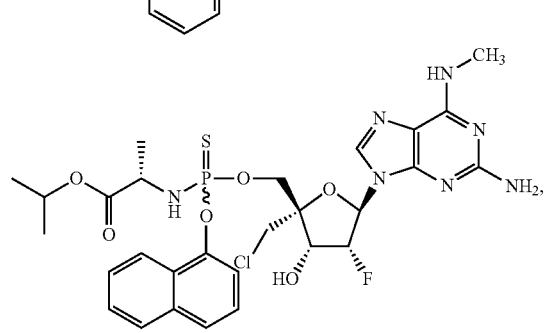
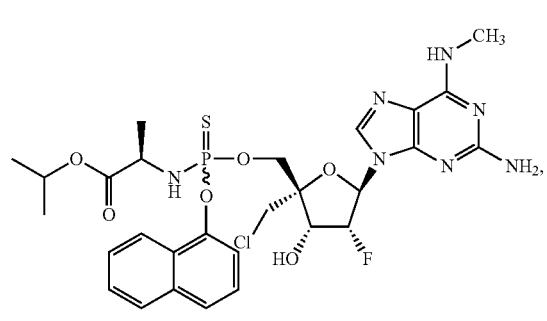
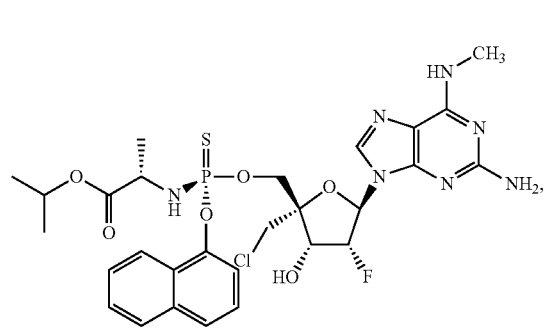

131
-continued
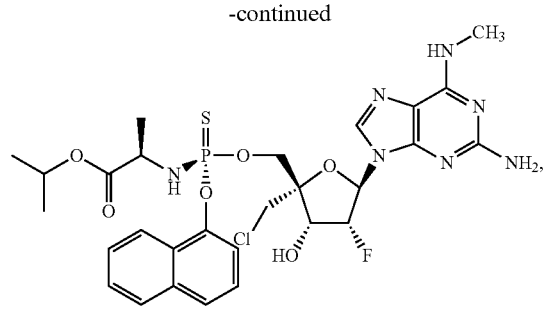
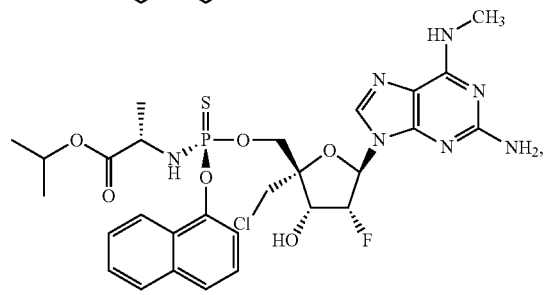
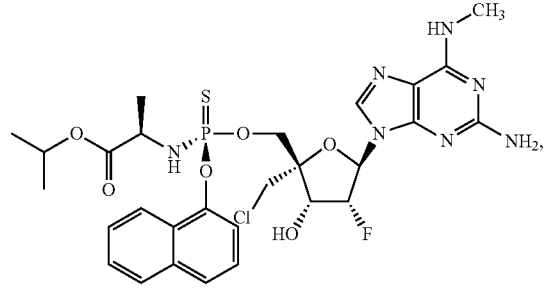
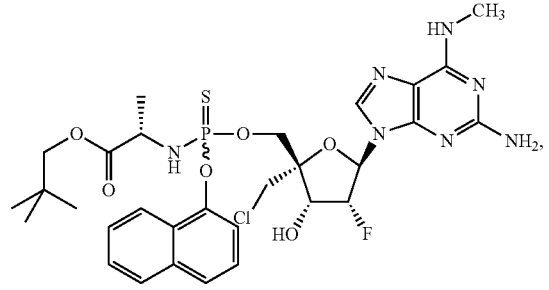
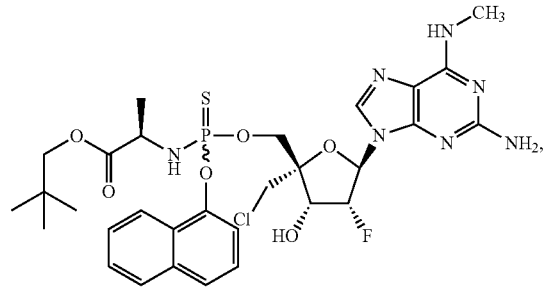
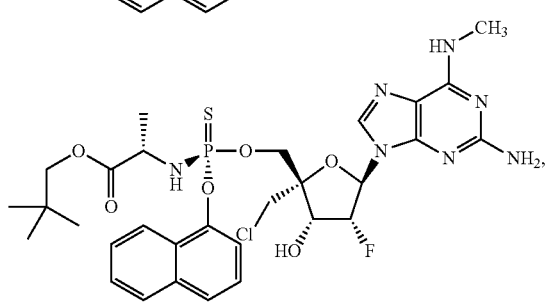
132
-continued
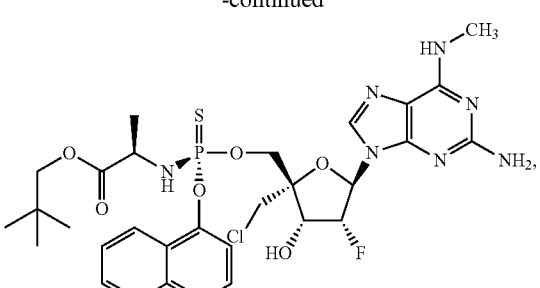
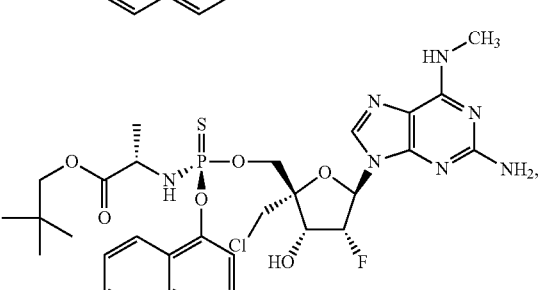
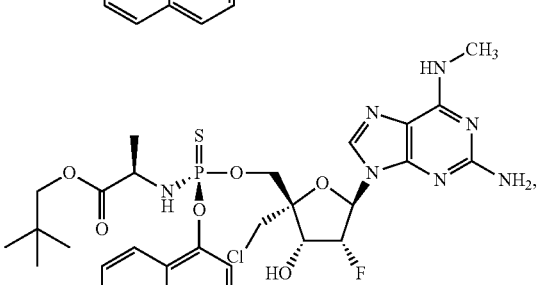
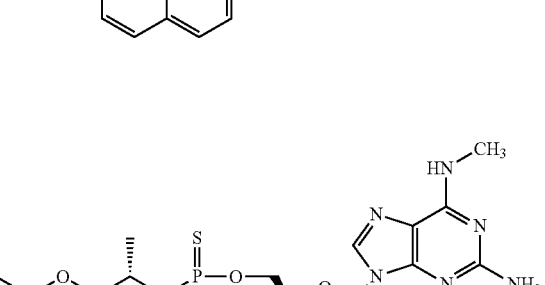
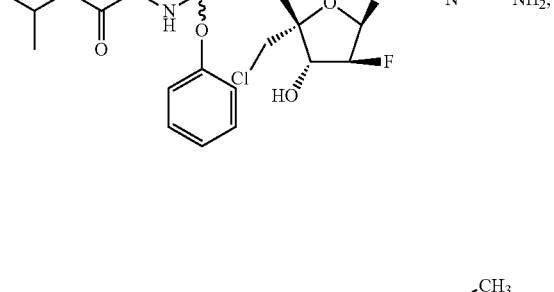
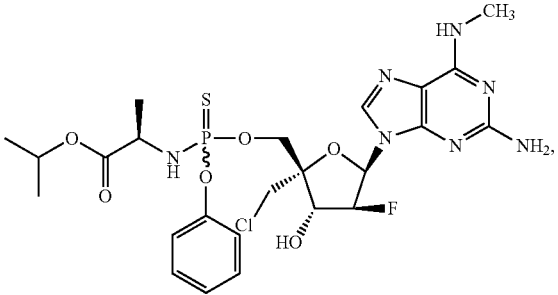

133
-continued
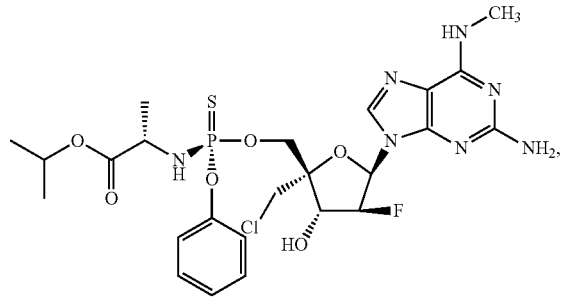
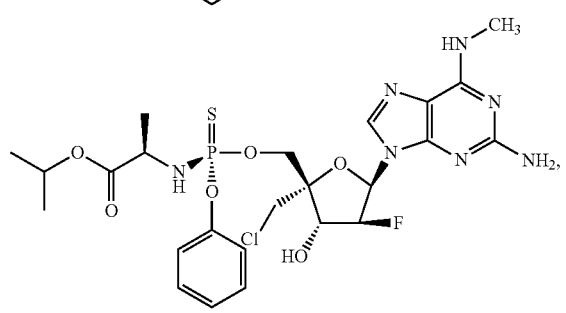
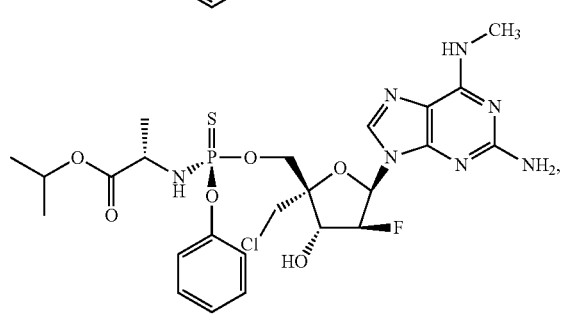
134
-continued
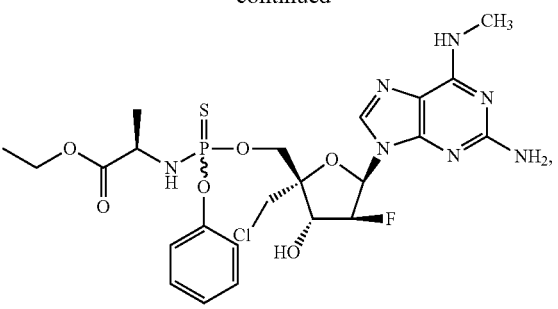
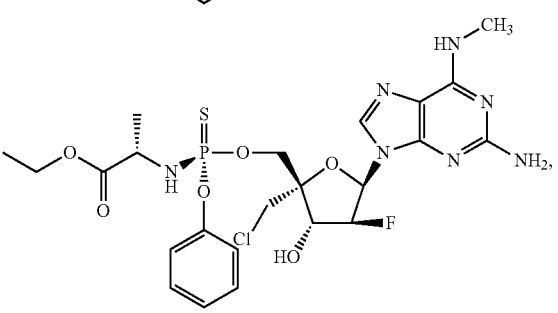
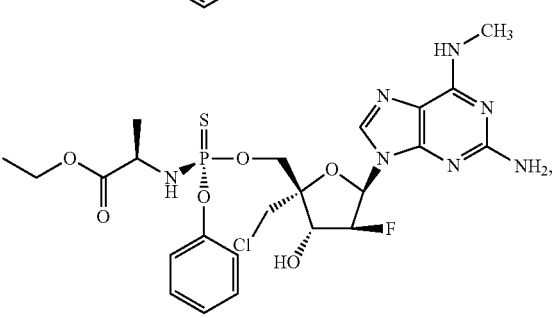
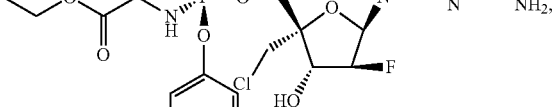

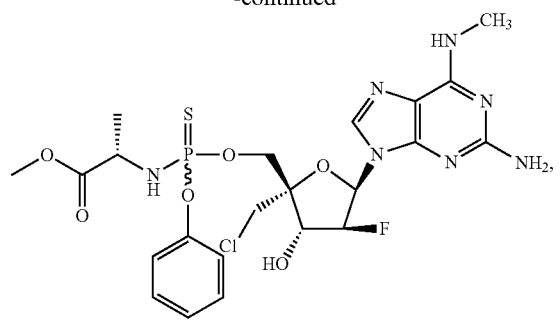
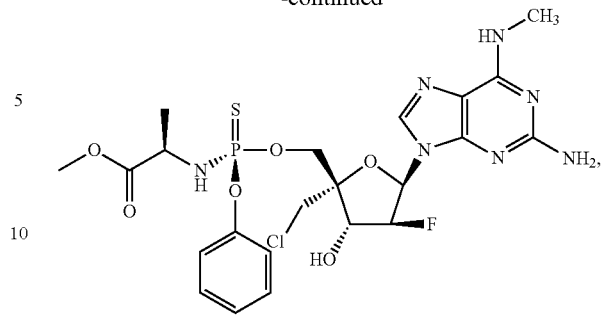
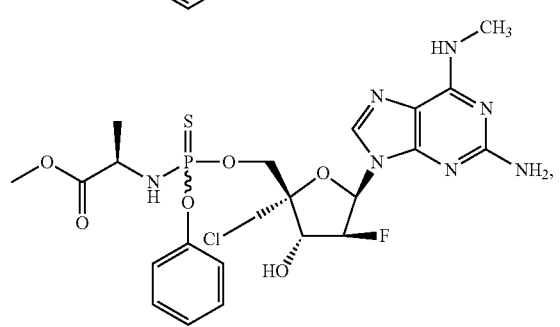
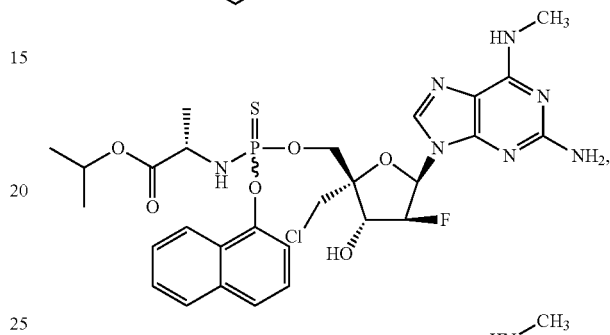
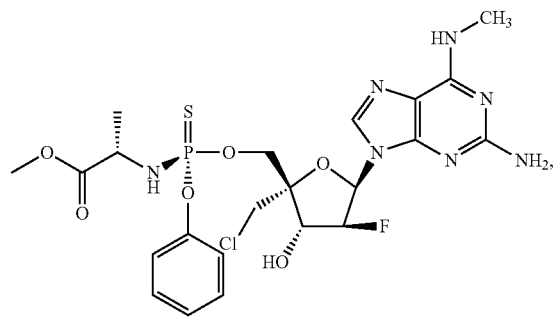
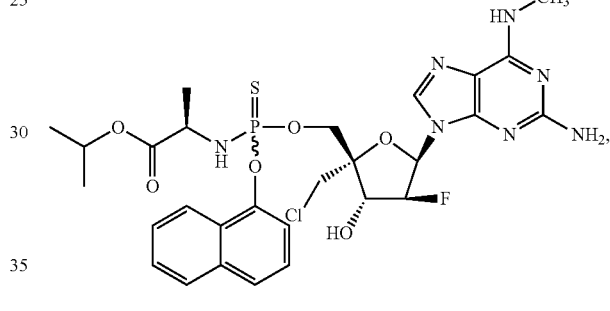
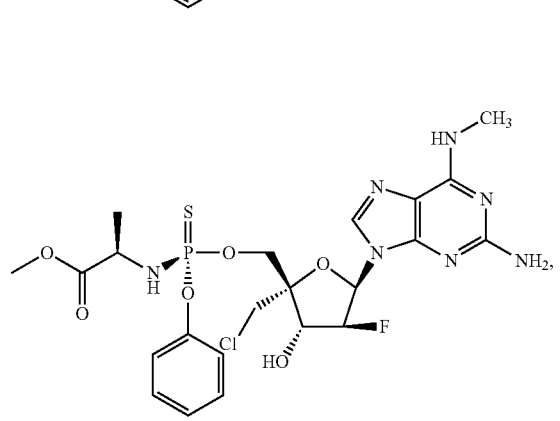
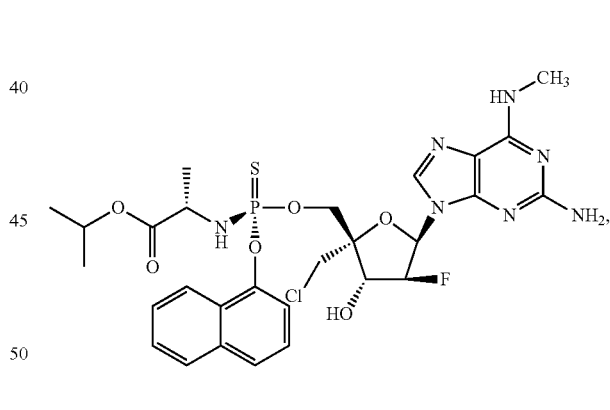
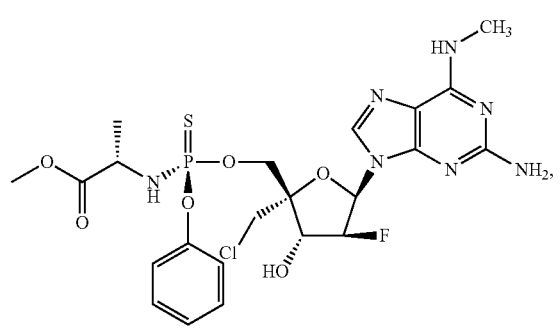
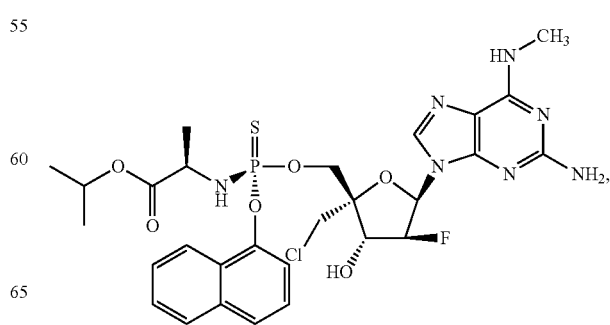

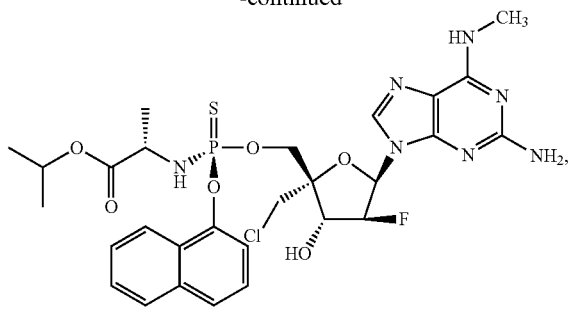
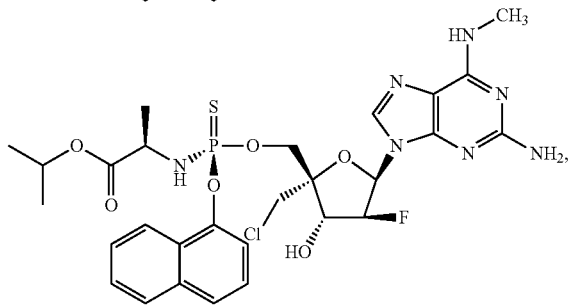
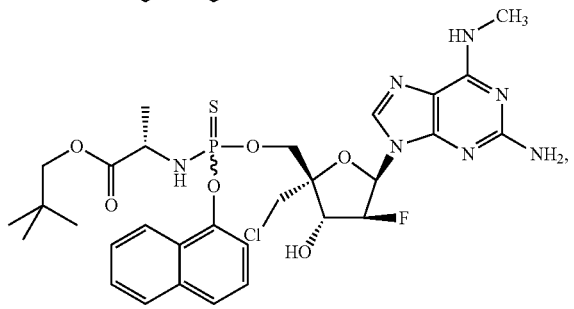
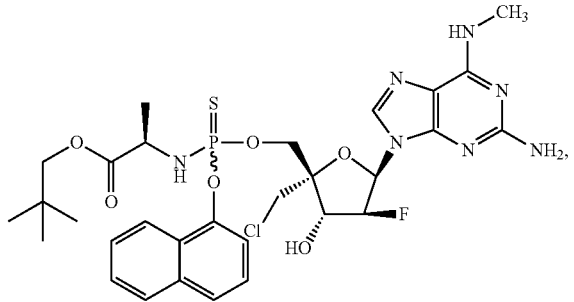
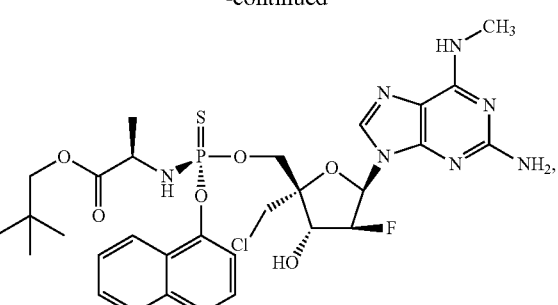
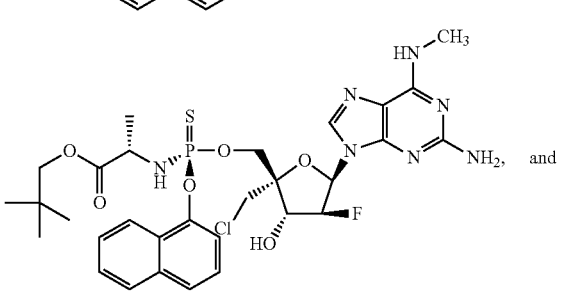
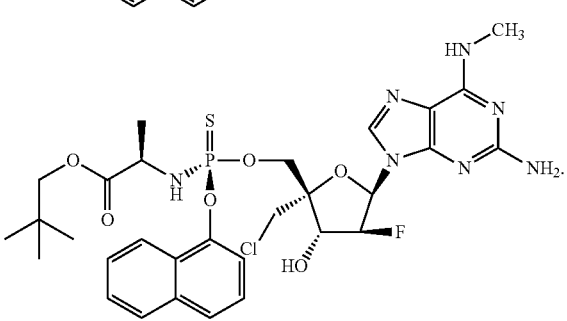
In one embodiment, a stabilized phosphate prodrug of Formula V is provided. Non-limiting examples of stabilized phosphate prodrugs of Formula V are illustrated below:
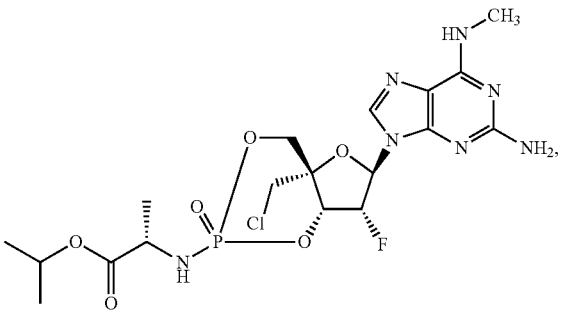
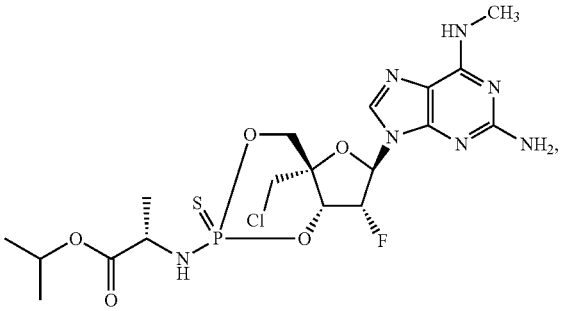

139
-continued
140
-continued
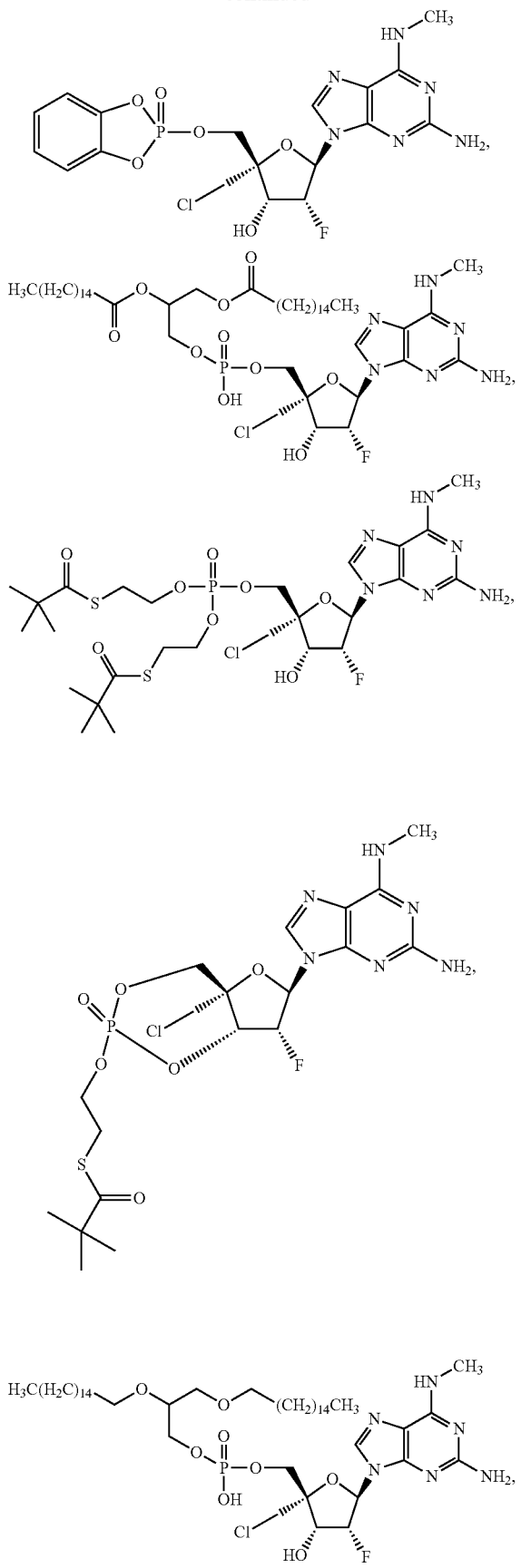
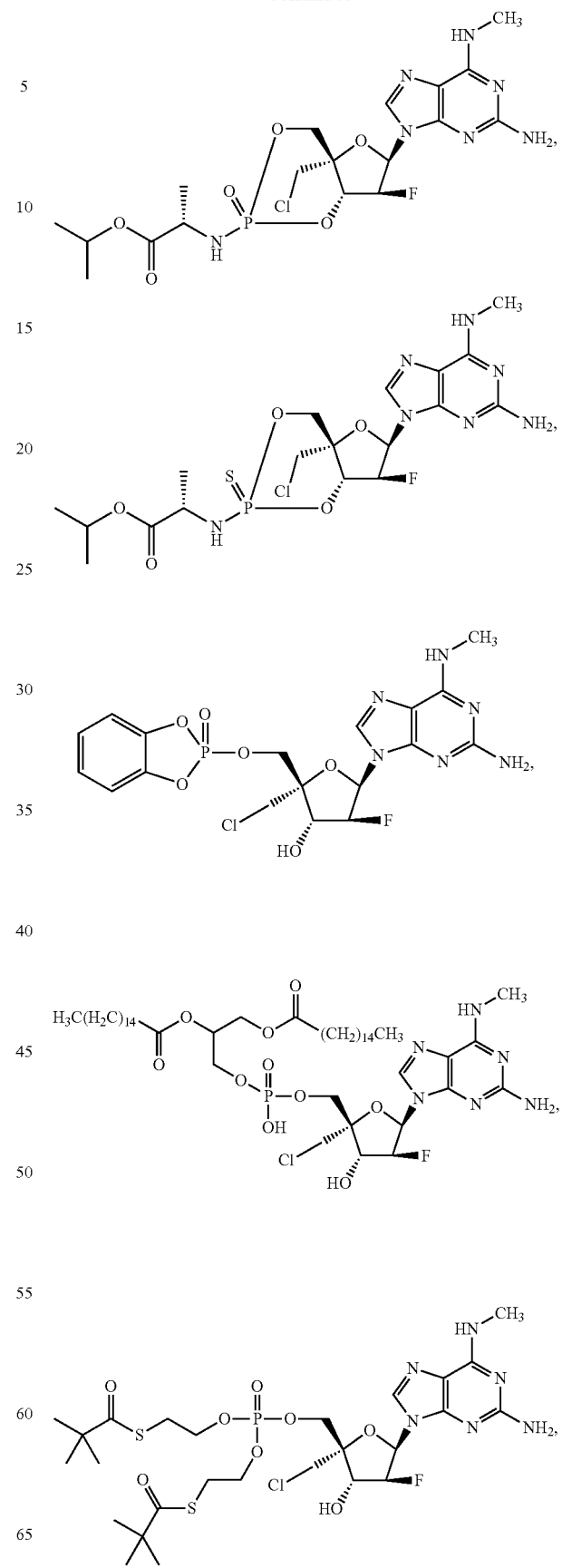

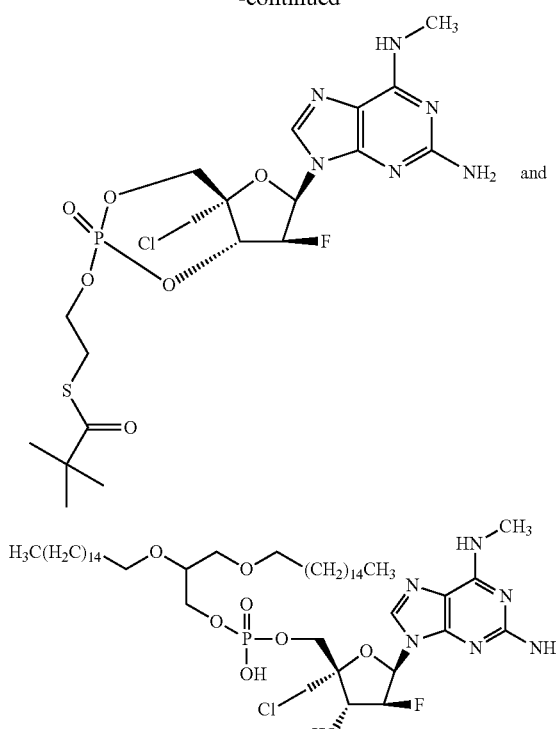
In another embodiment, a compound of Formula I is provided. Non-limiting examples of compounds of Formula I include:
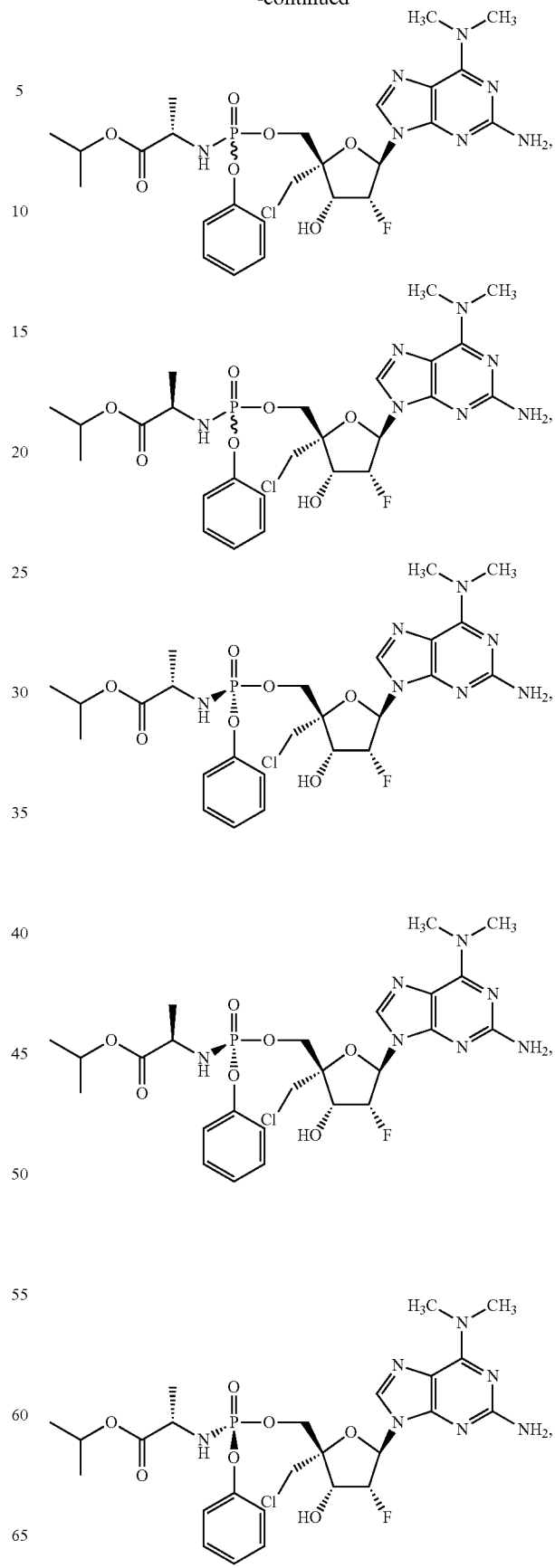

143
-continued
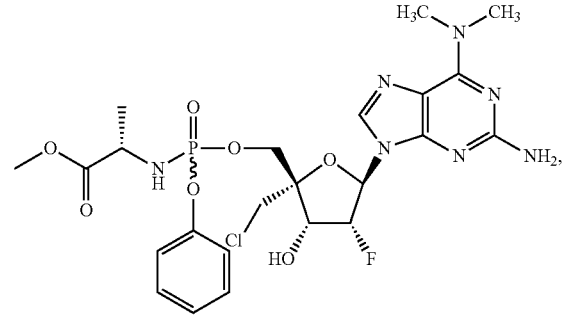
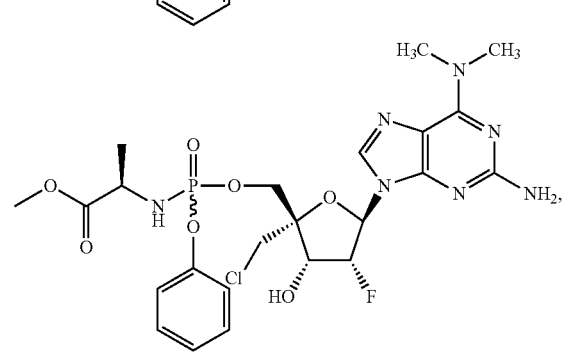
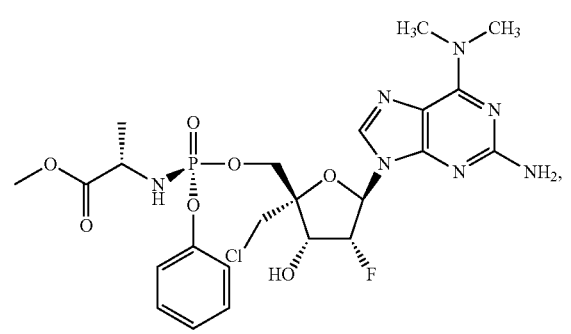
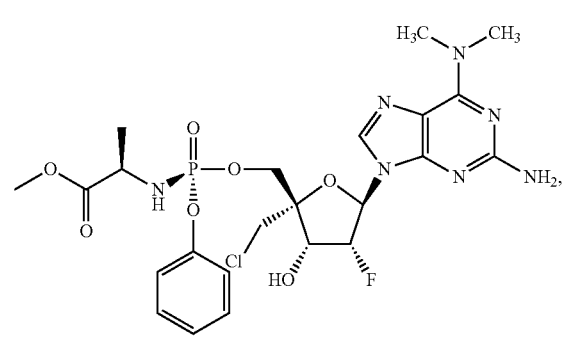
144
-continued
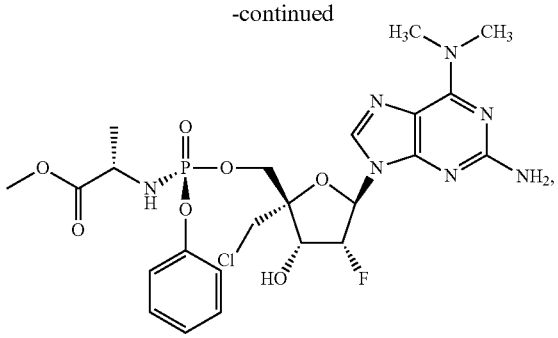

145
-continued
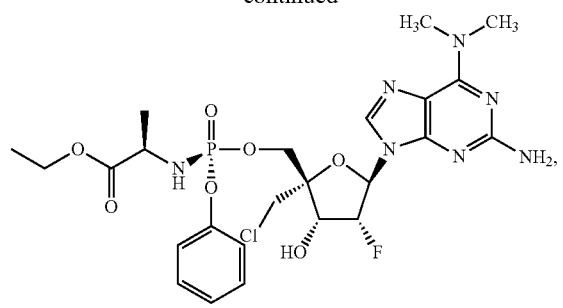
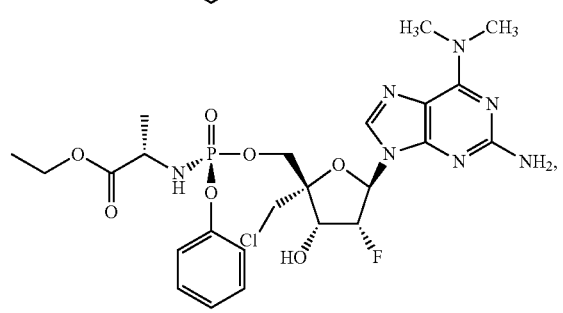
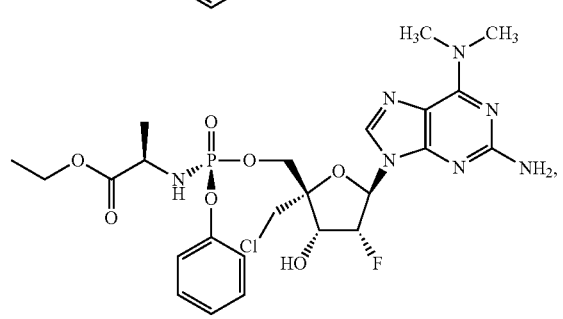
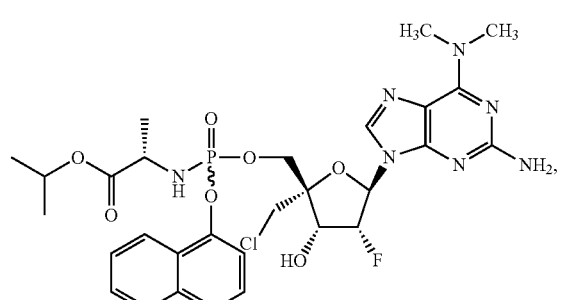
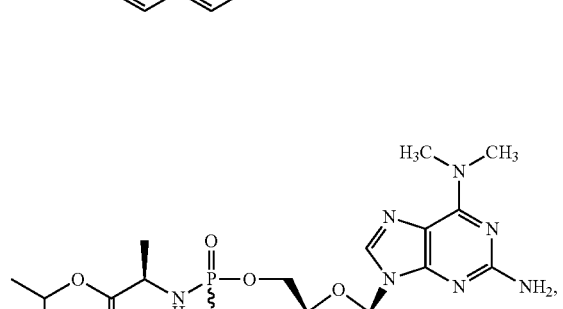
146
-continued
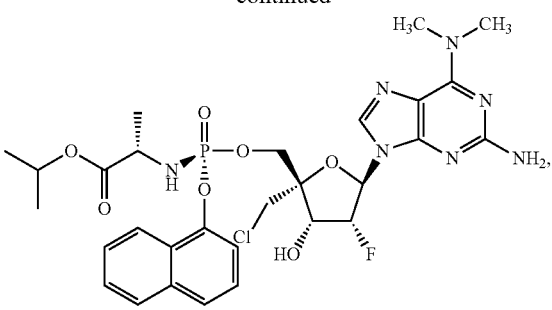
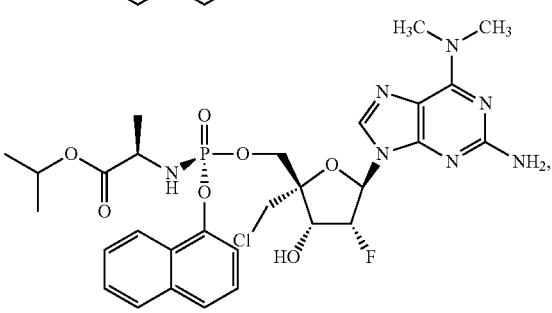
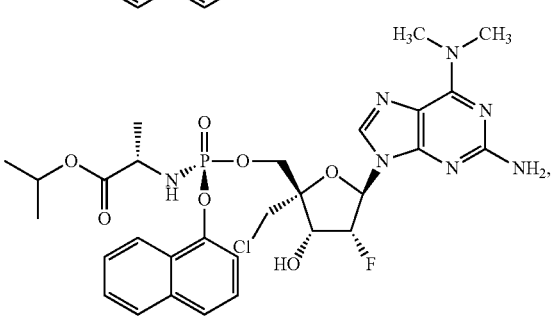
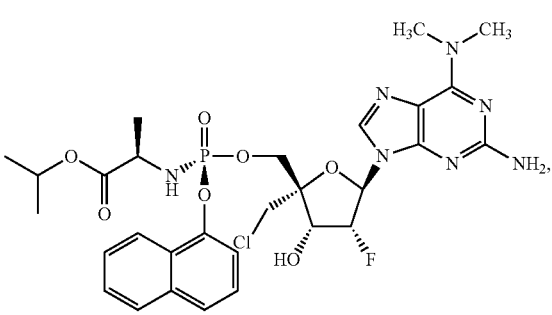
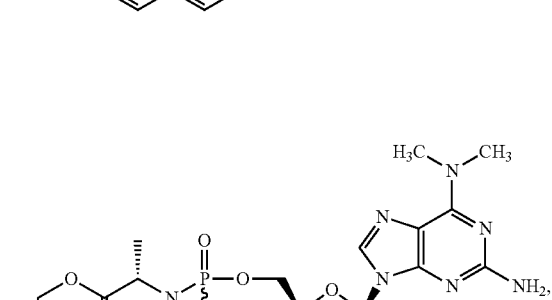

147
-continued
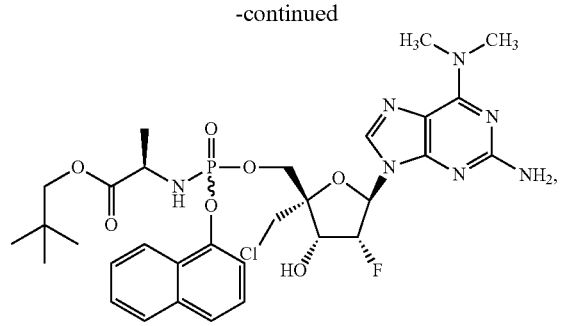
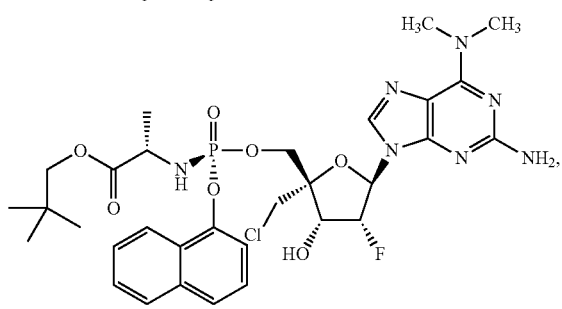
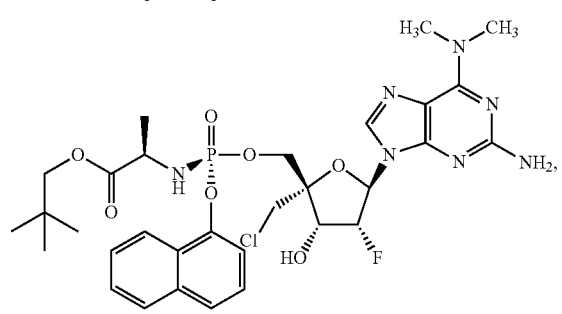
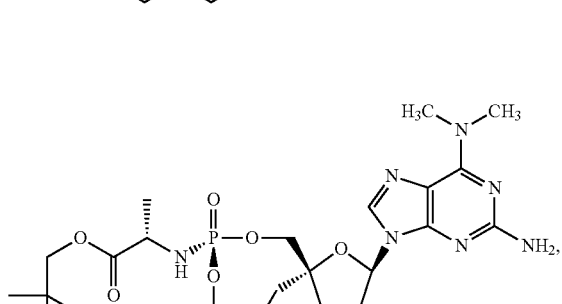
148
-continued
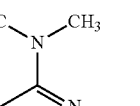
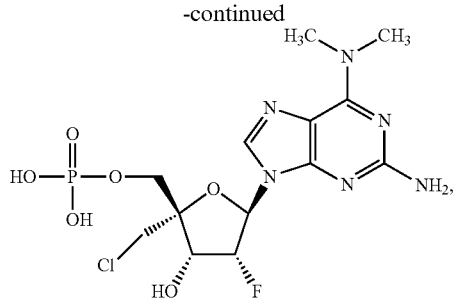
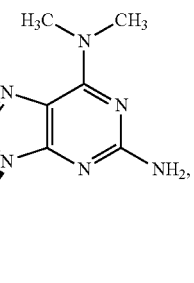
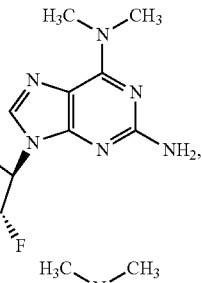
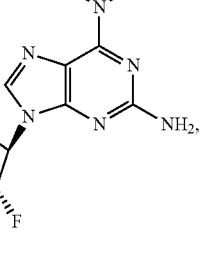
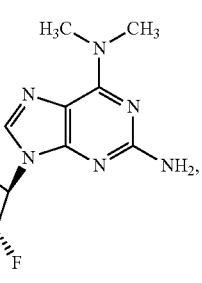
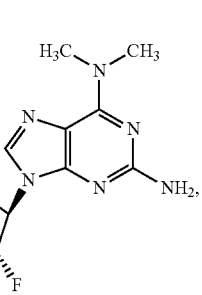

149
-continued
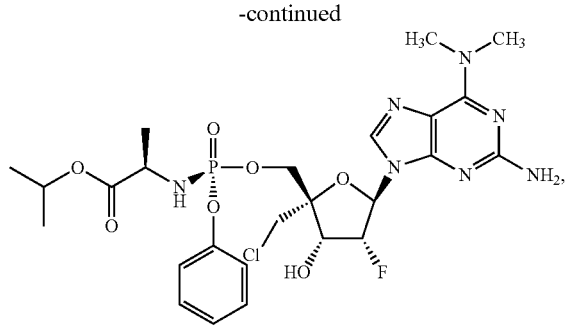
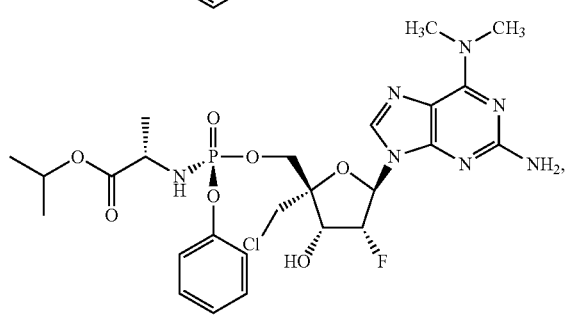
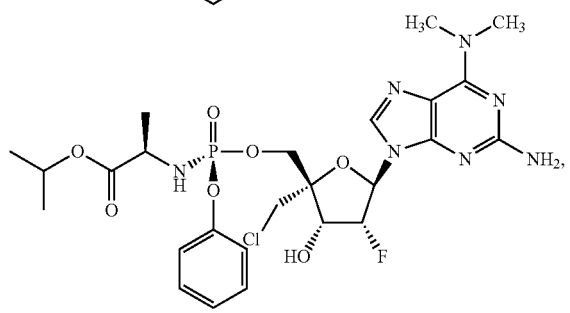
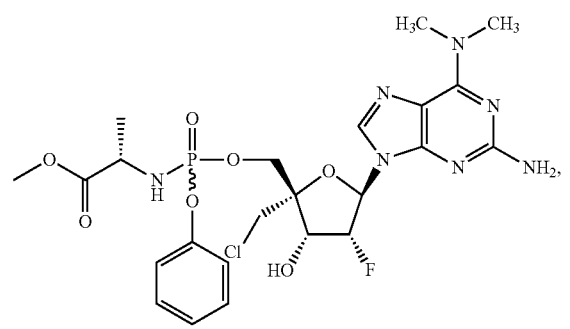
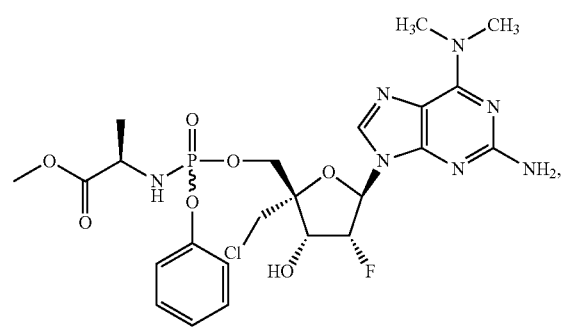
150
-continued
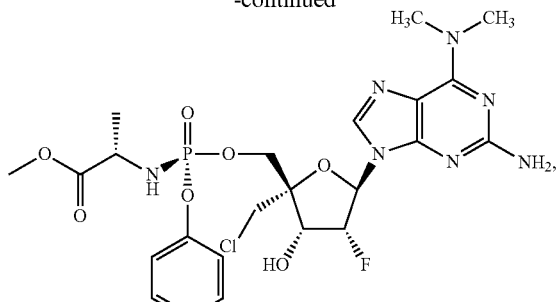
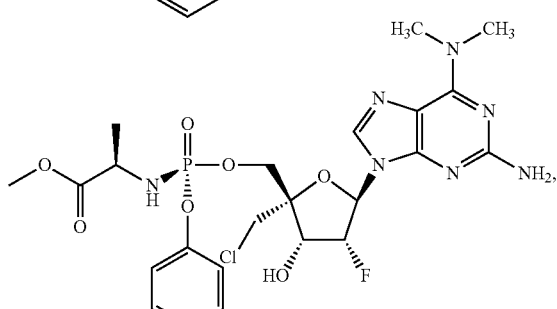
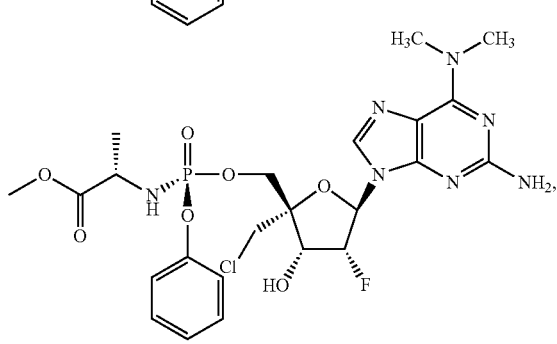
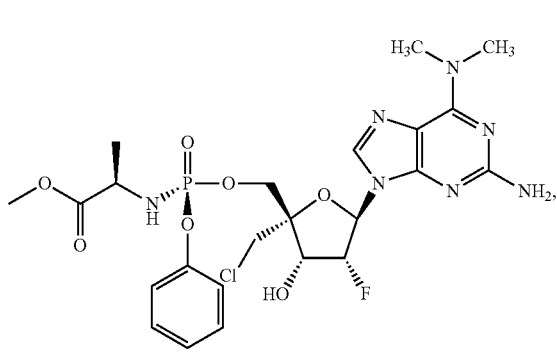
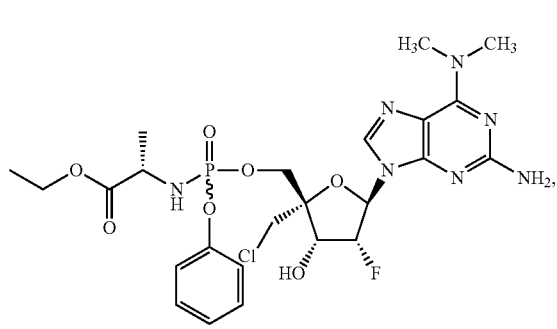

151
-continued
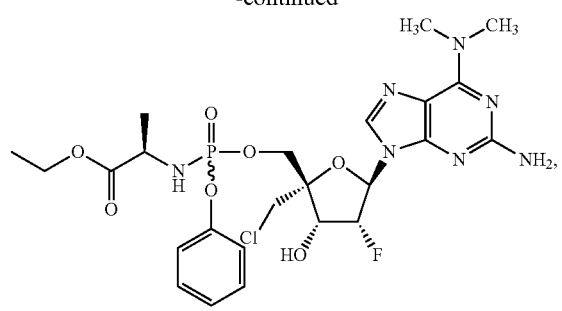
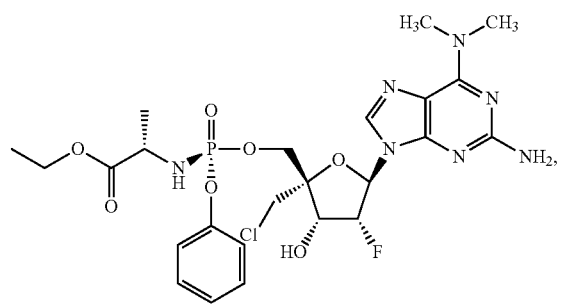
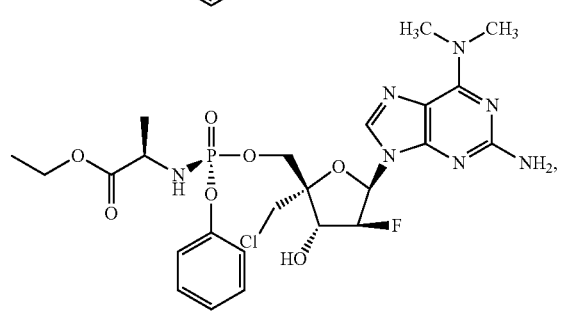
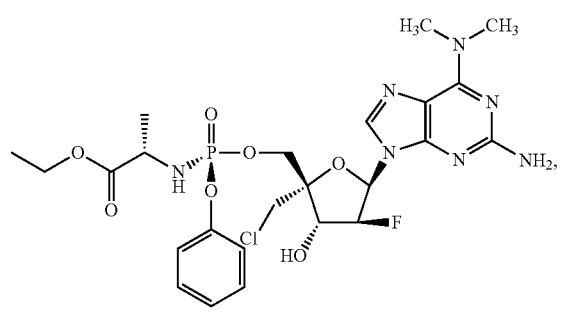
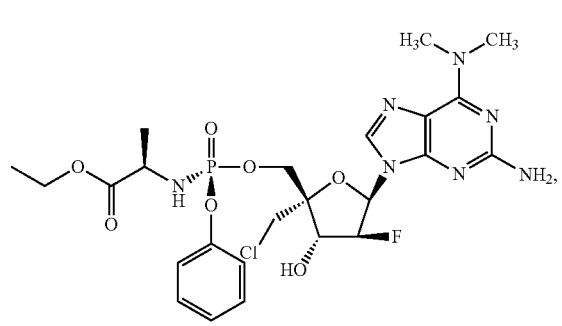
152
-continued
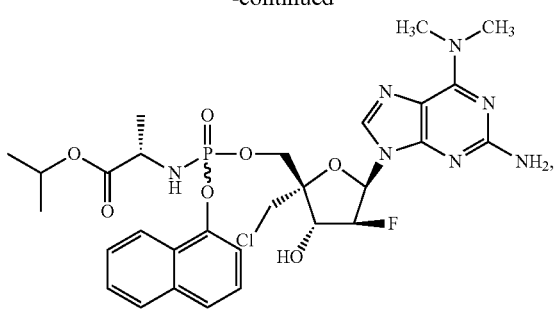
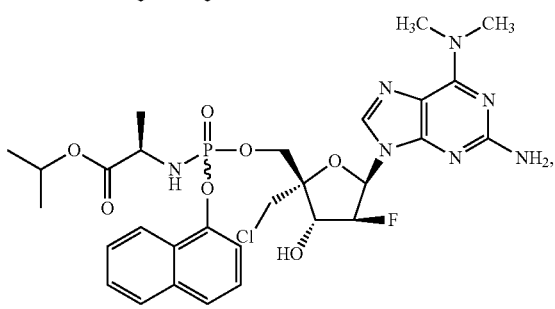
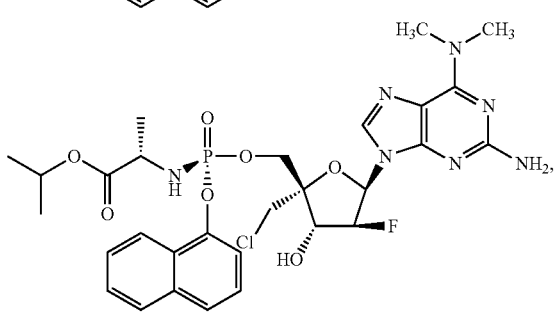
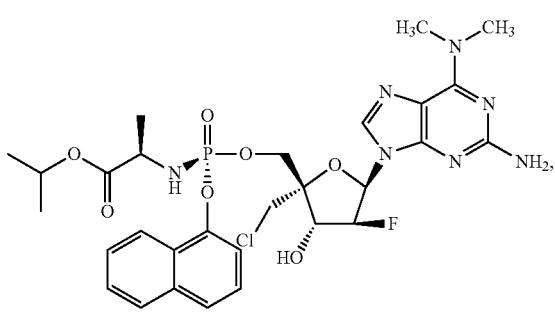
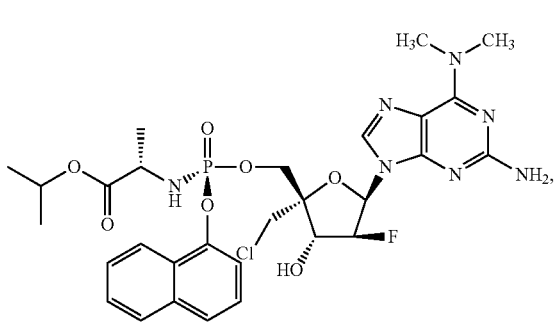

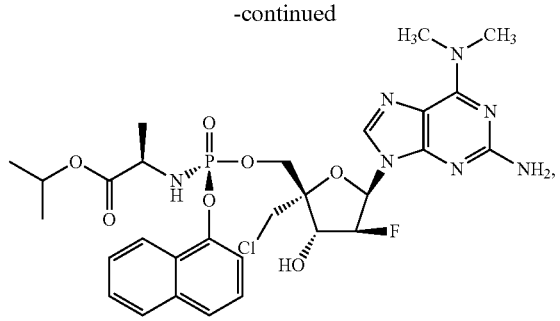
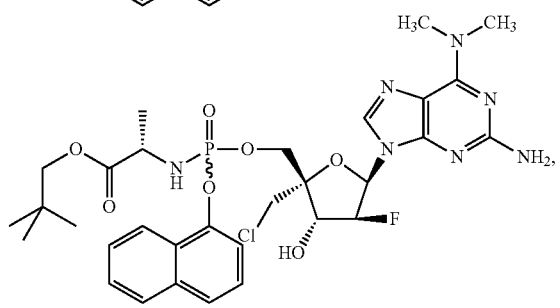
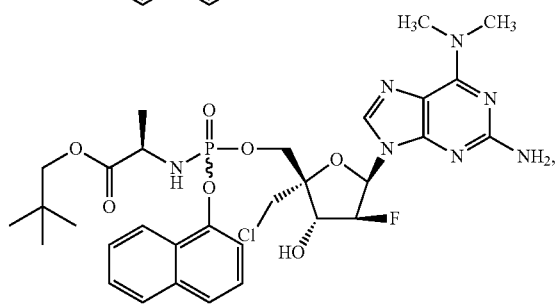
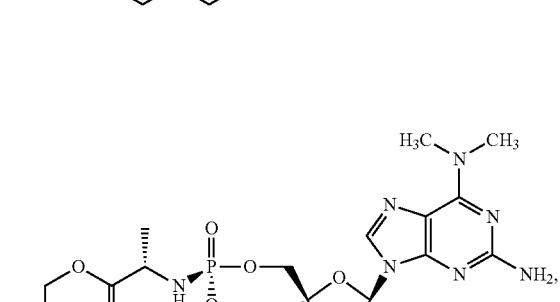
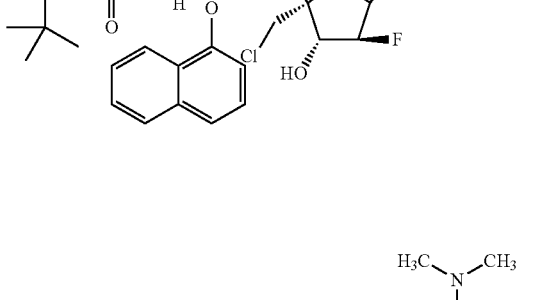
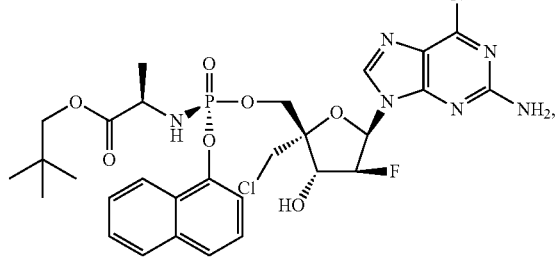
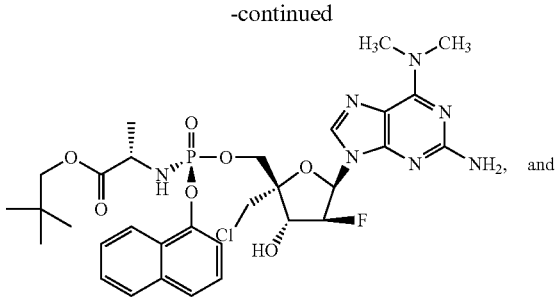
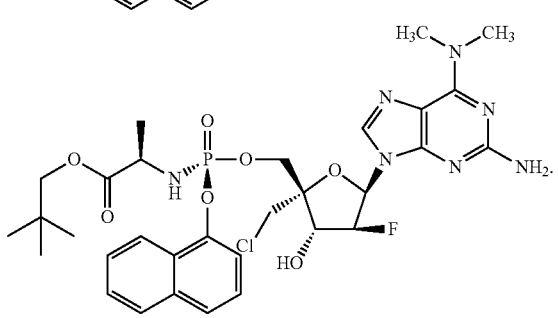
In one embodiment, a thiophosphoramidate of Formula I is provided. Non-limiting examples of thiophosphoramidates of Formula I include, but are not limited to:
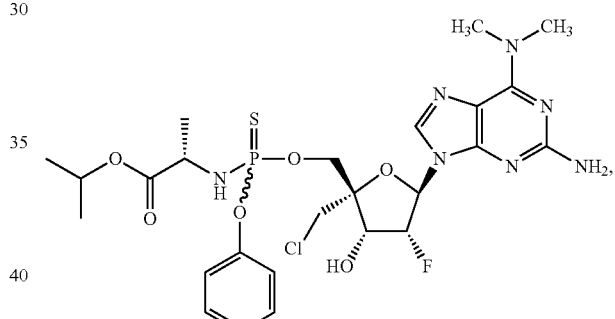
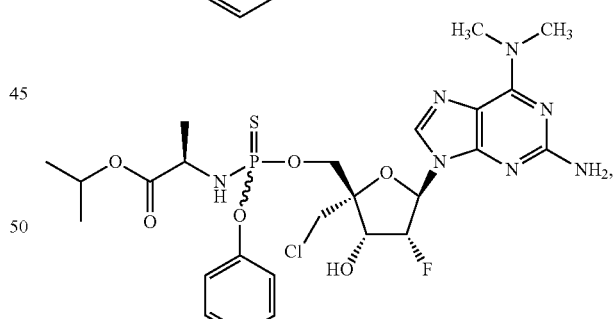
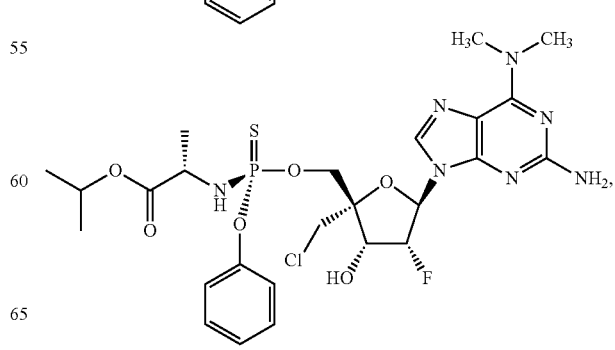

155
-continued
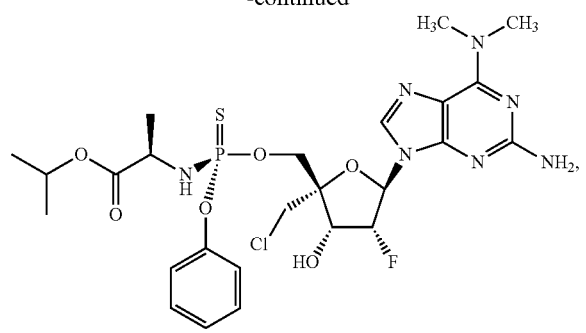
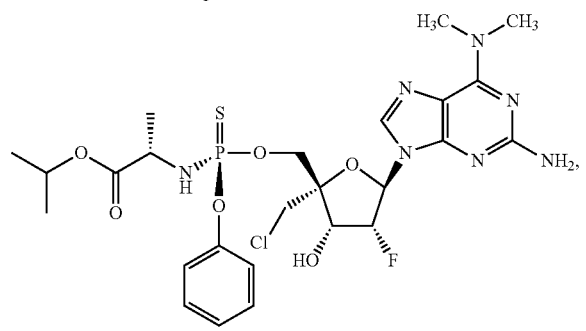
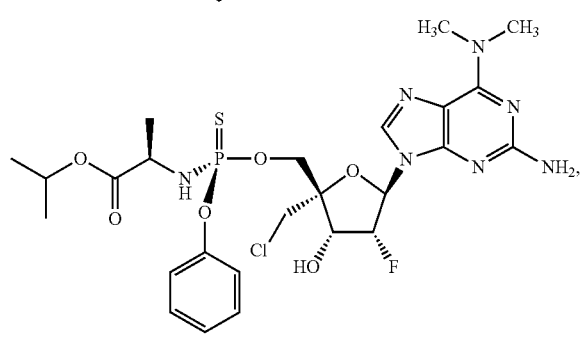
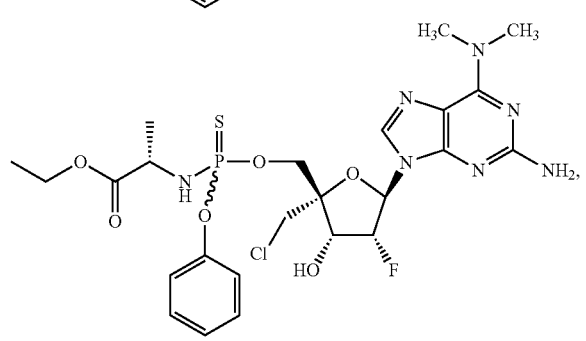
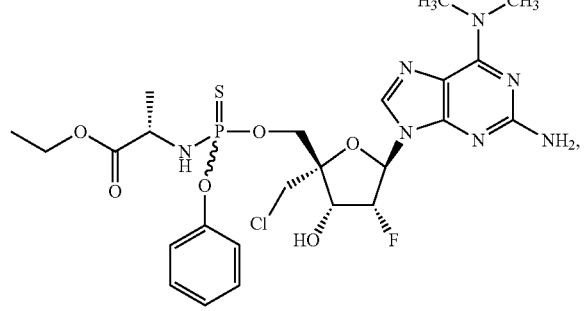
156
-continued
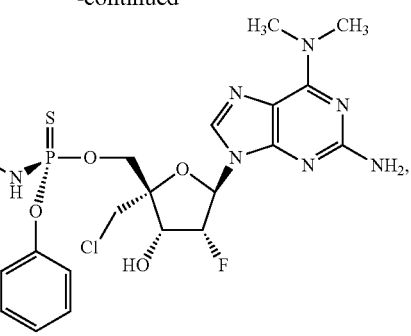
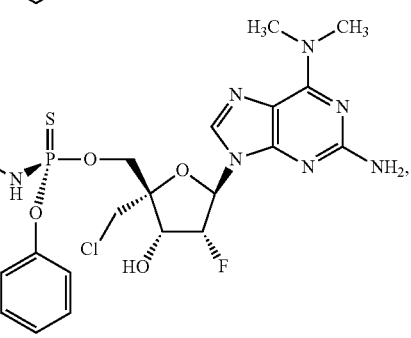
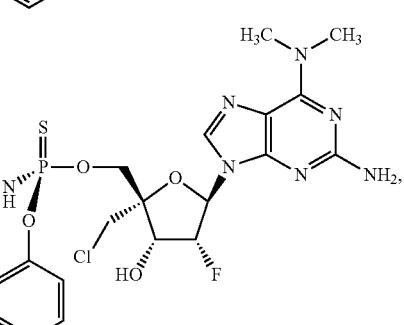
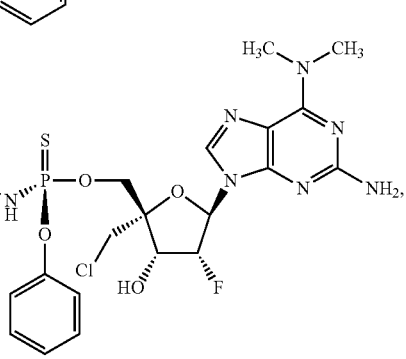

157
-continued
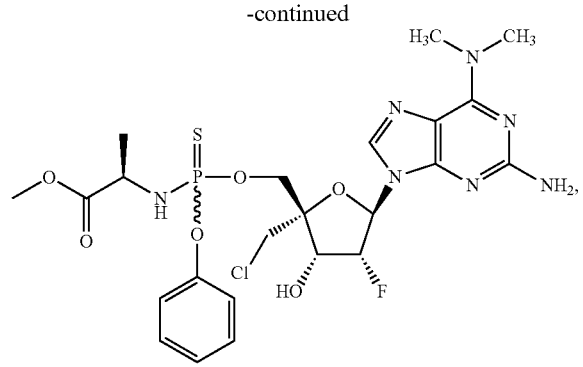
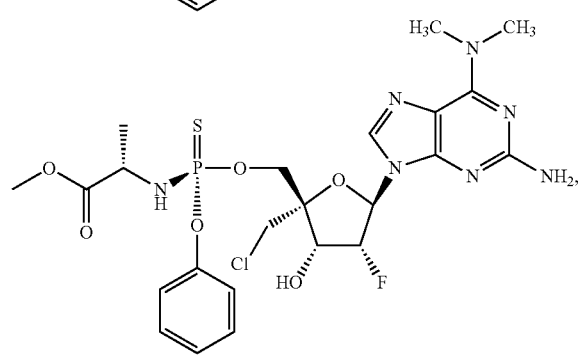
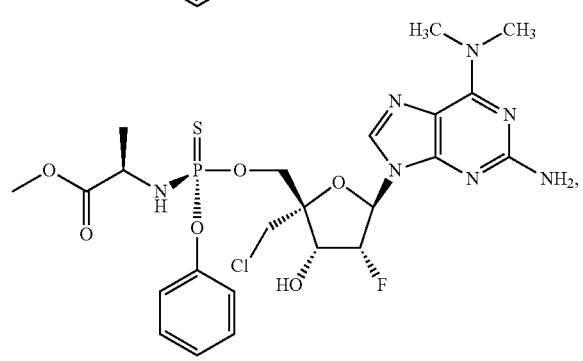
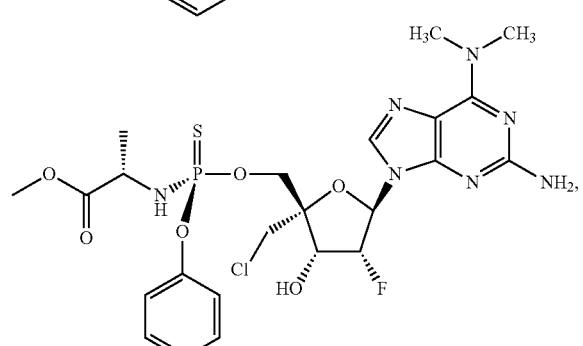
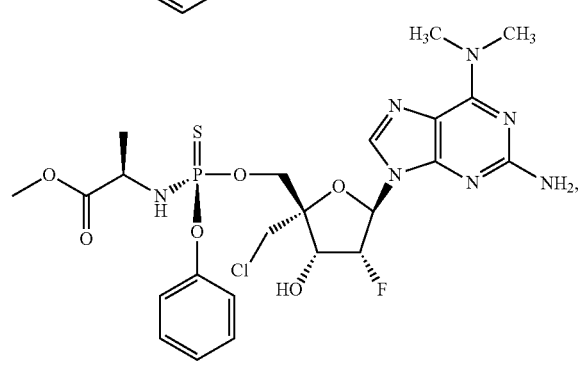
158
-continued
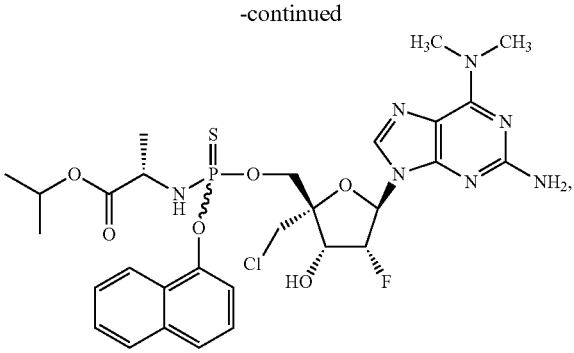
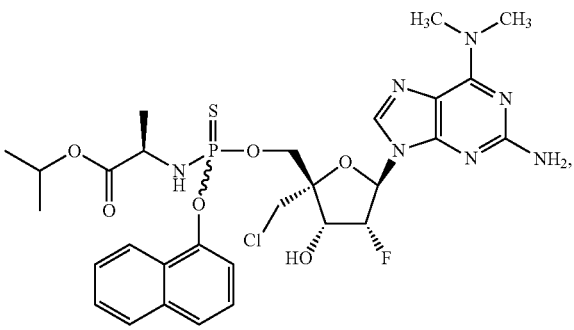
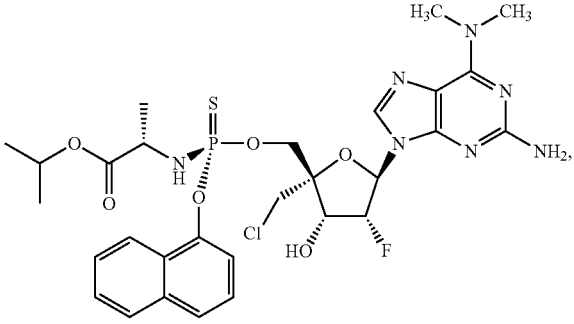
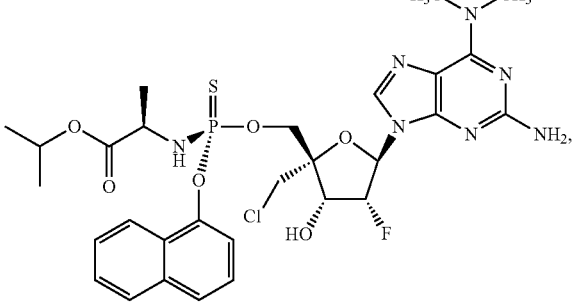
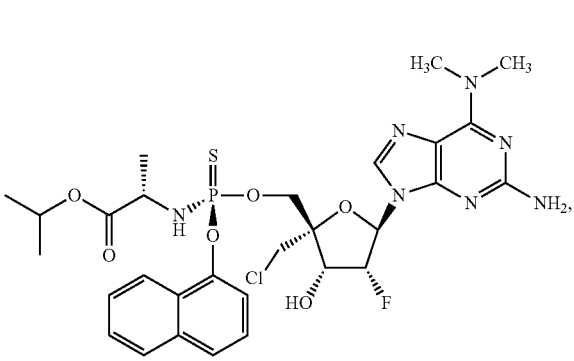

159
-continued
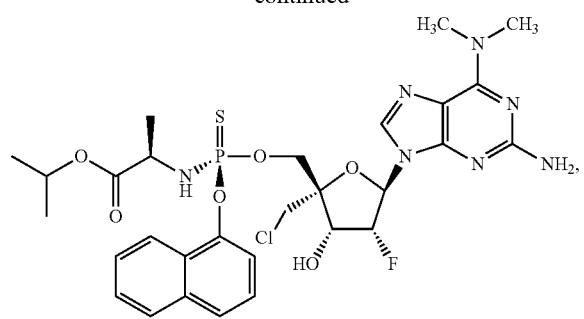
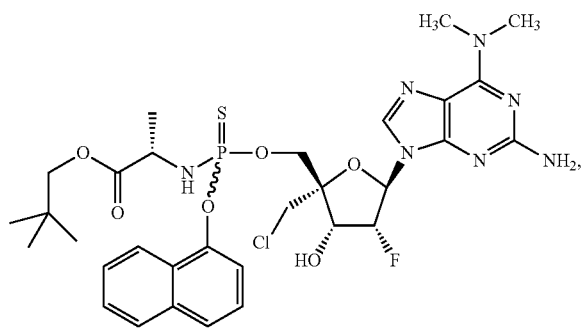
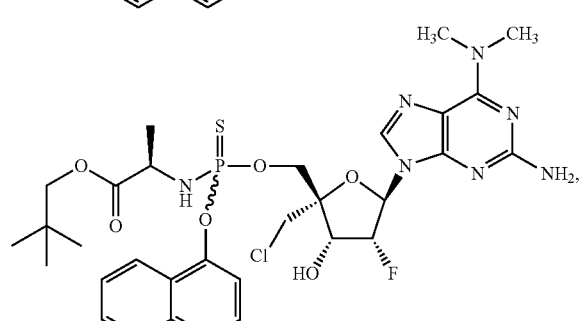
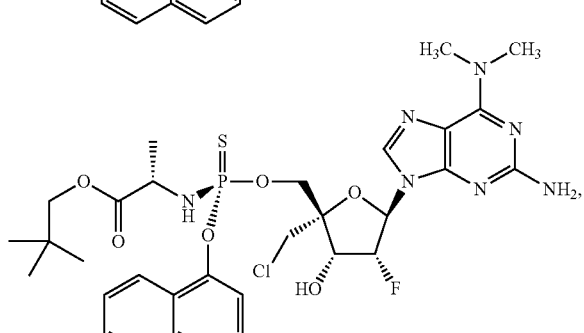
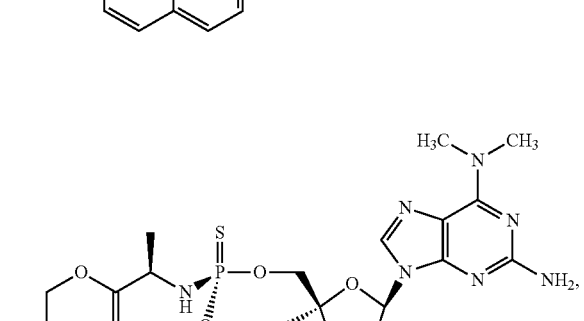
160
-continued
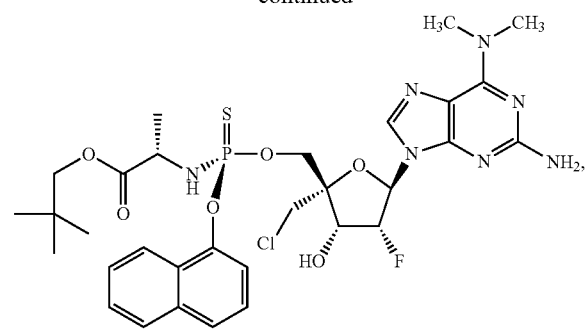
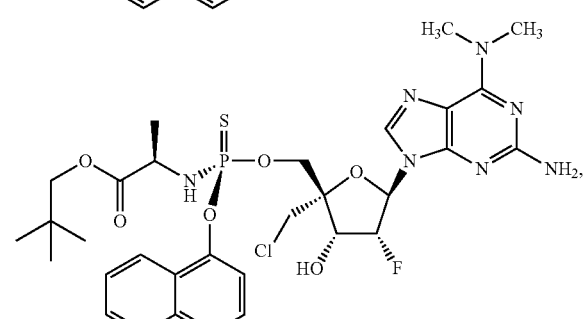
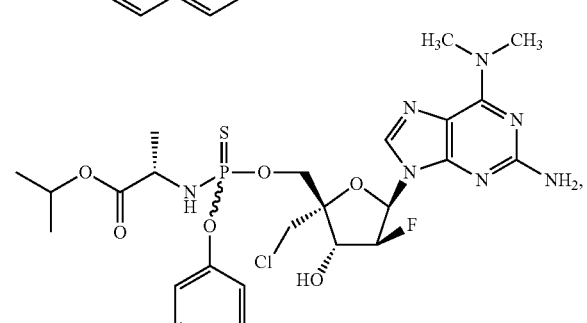
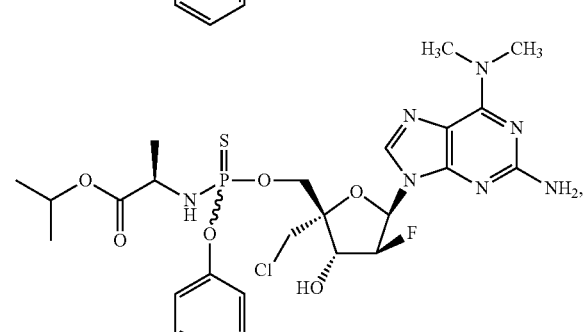
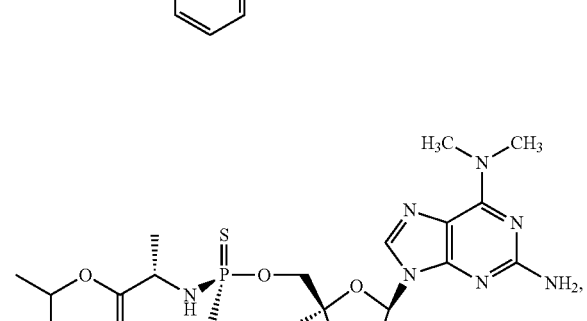

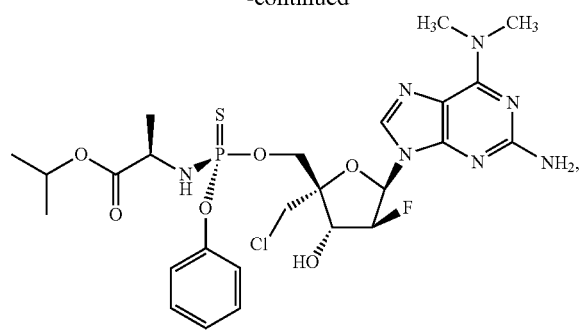
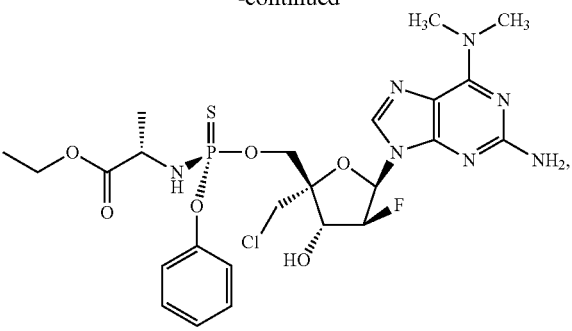

163
-continued
164
-continued
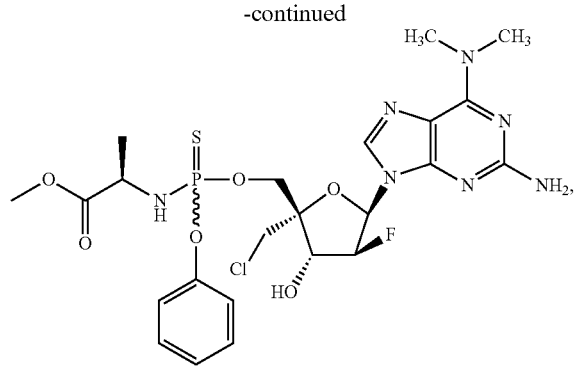
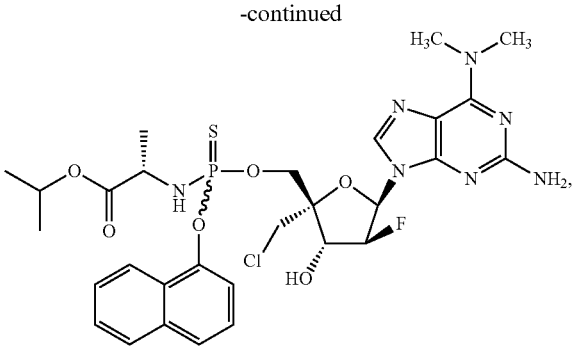

-continued
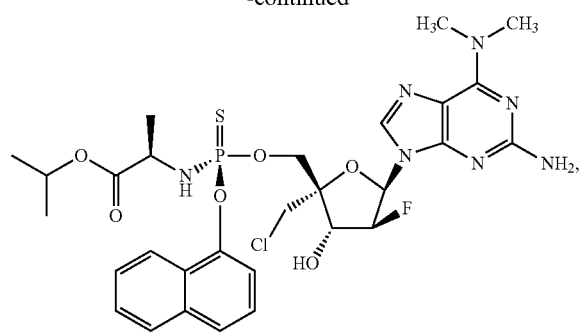
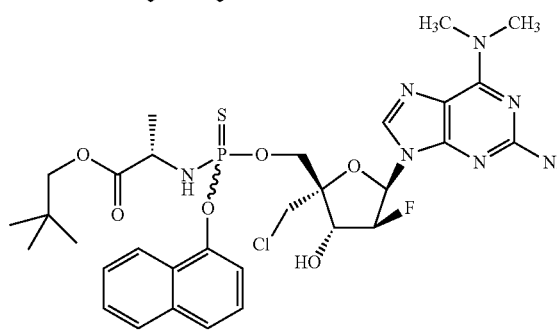
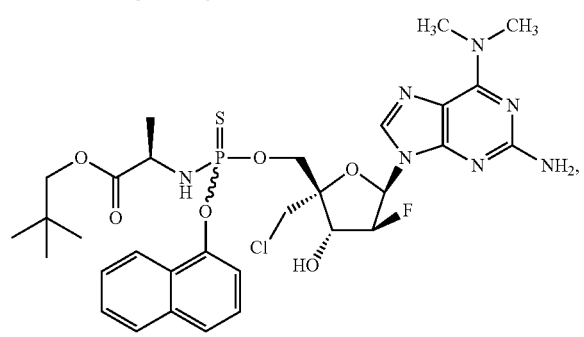
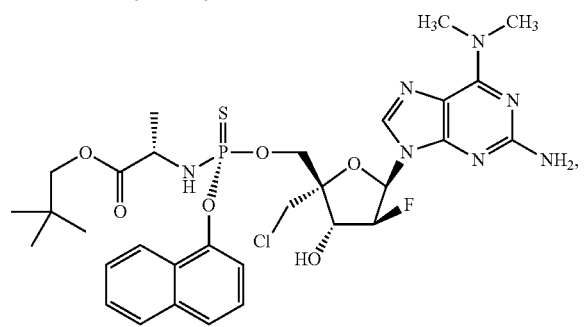
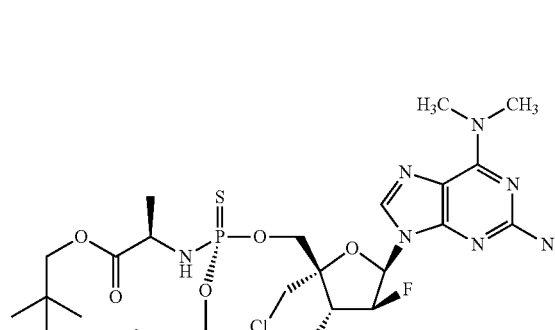
-continued
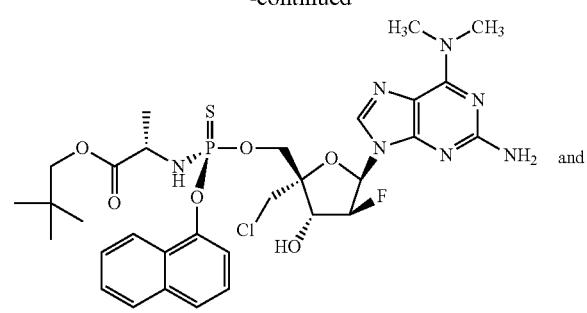
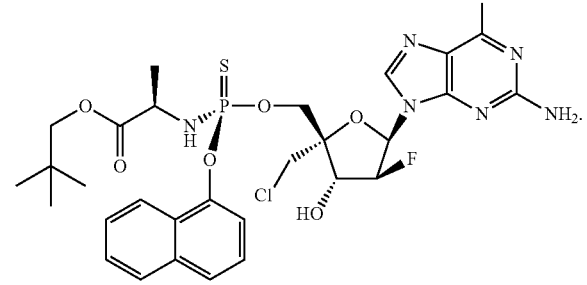
In one embodiment, a stabilized phosphate prodrug of Formula V is provided. Non-limiting examples of stabilized phosphate prodrugs of Formula V are illustrated below:
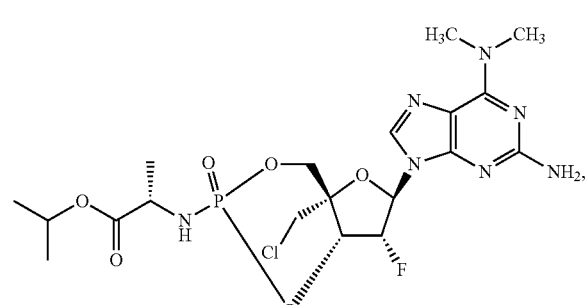
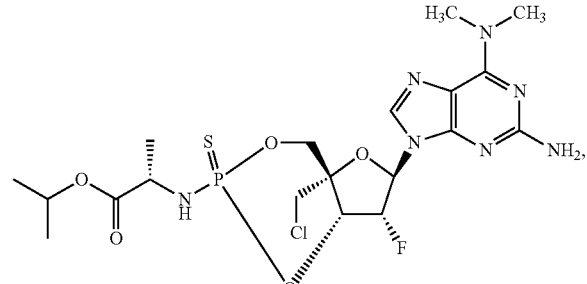
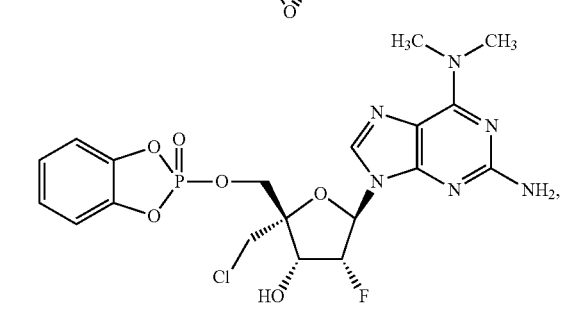

167
-continued
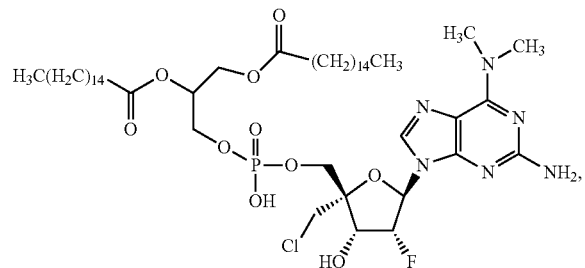
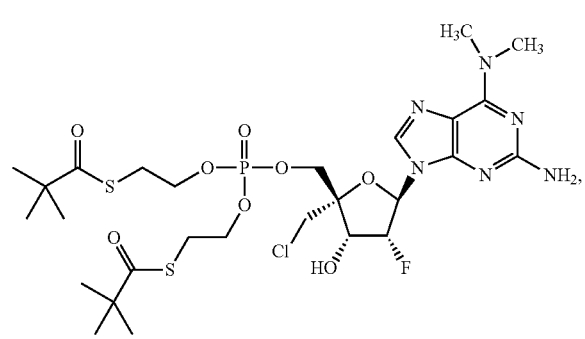
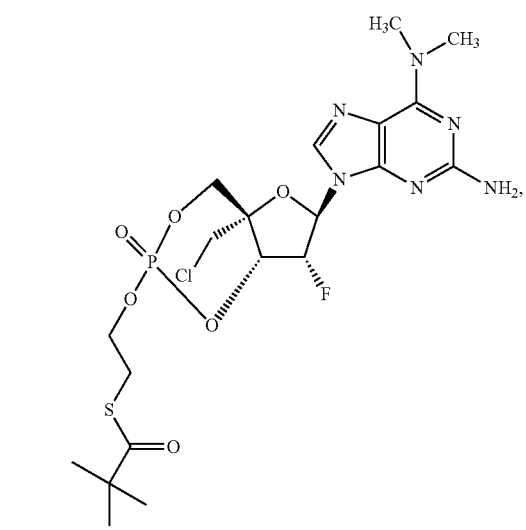
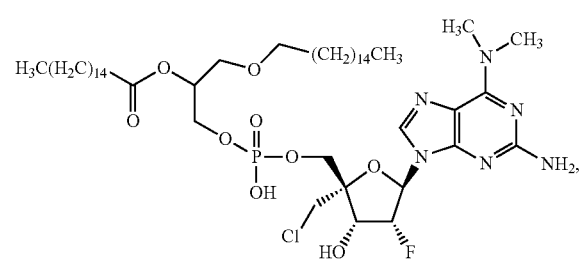
168
-continued
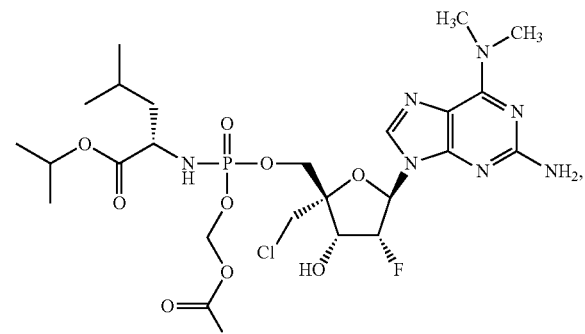
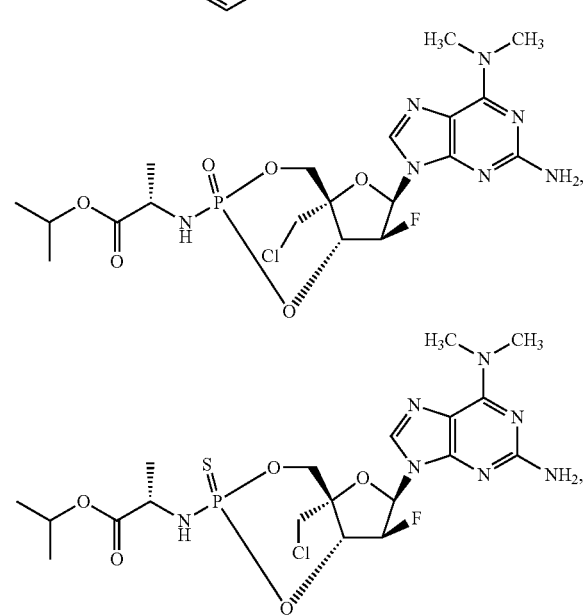
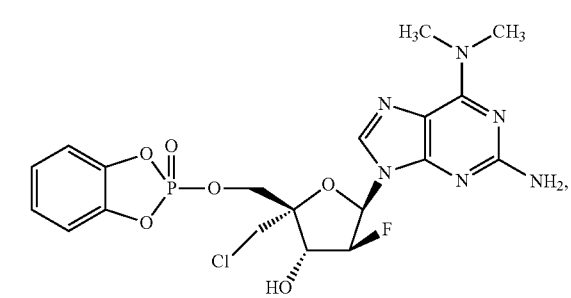

-continued
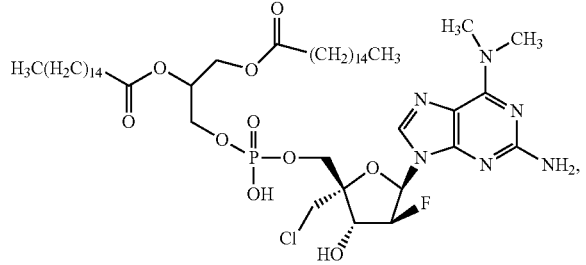
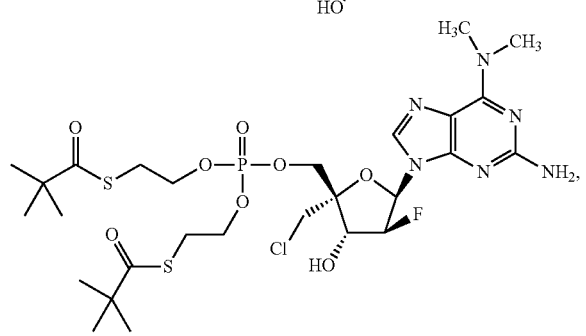
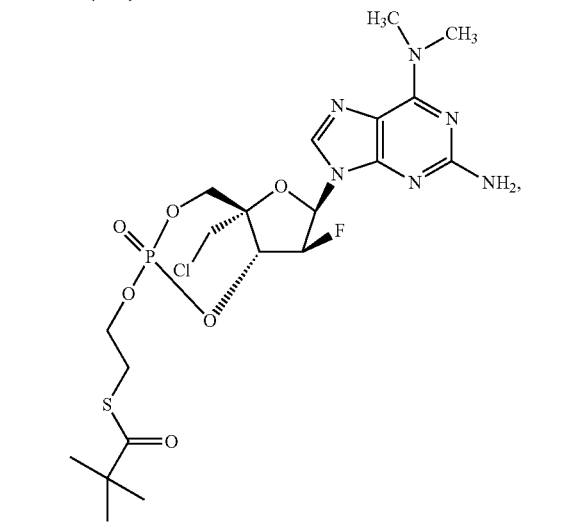
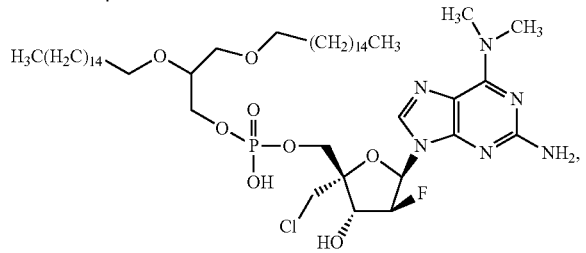
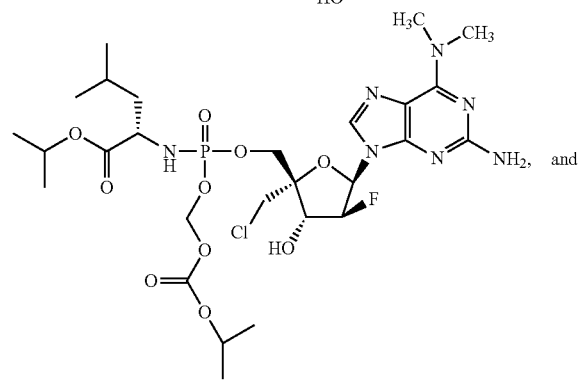
-continued
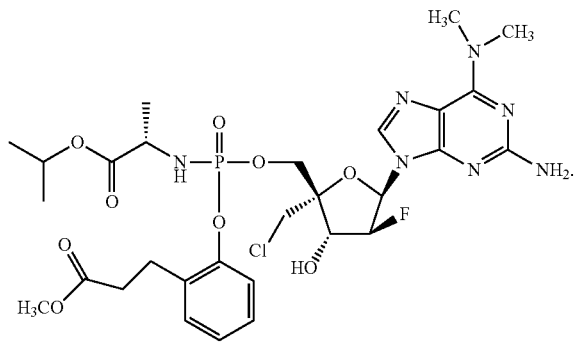
In one embodiment, a compound of Formula I is provided. Non-limiting examples of compounds of Formula I include:
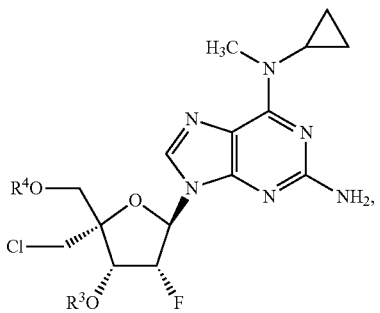
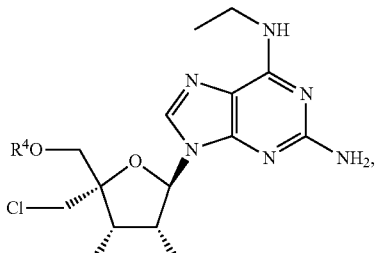
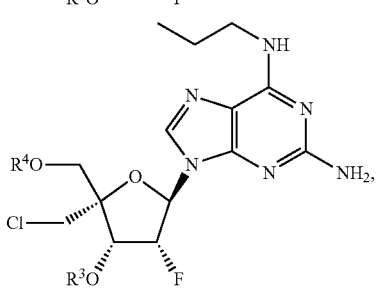
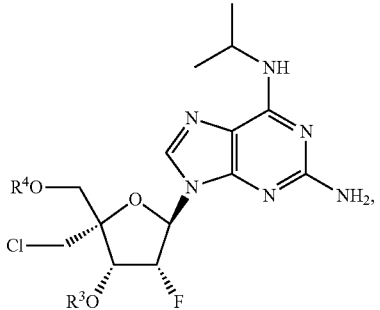

-continued
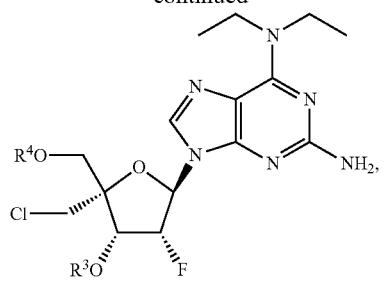
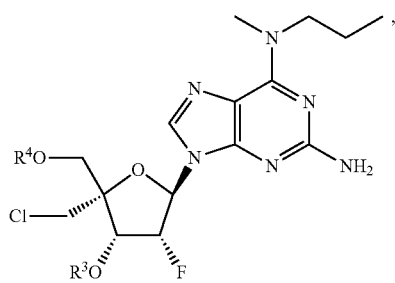
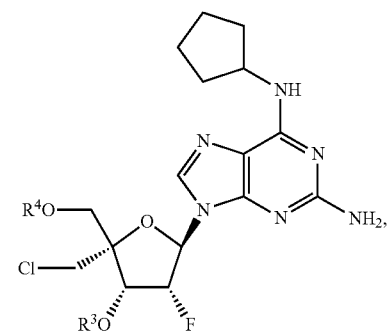
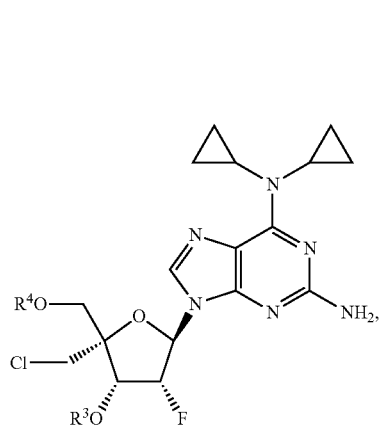
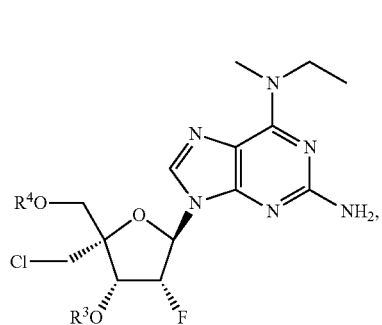
-continued
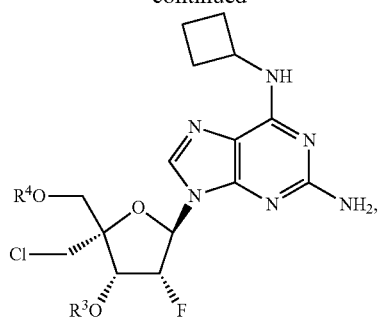
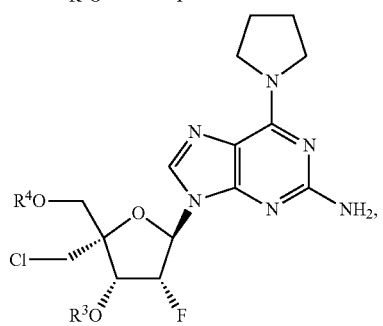
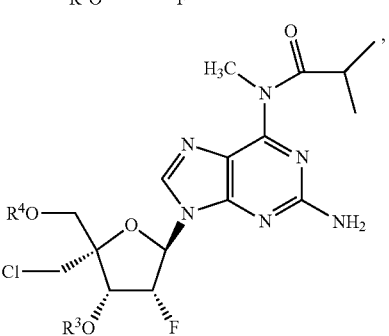
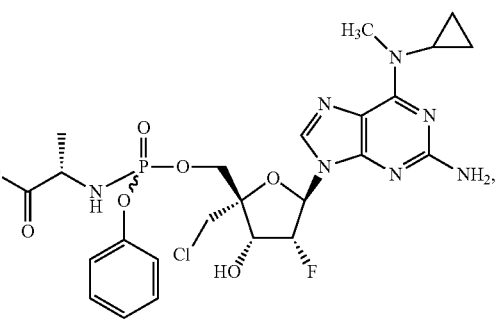

173
-continued
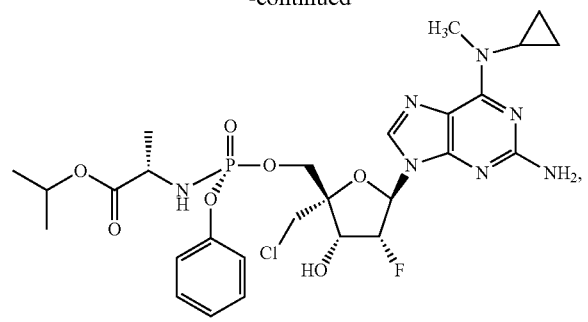
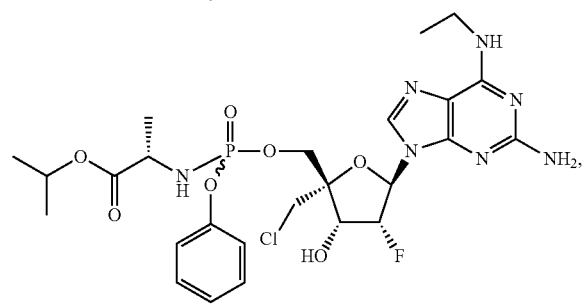
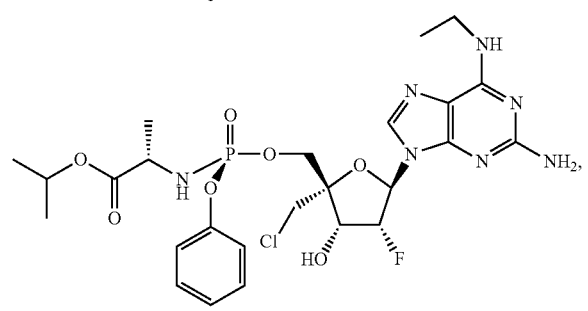
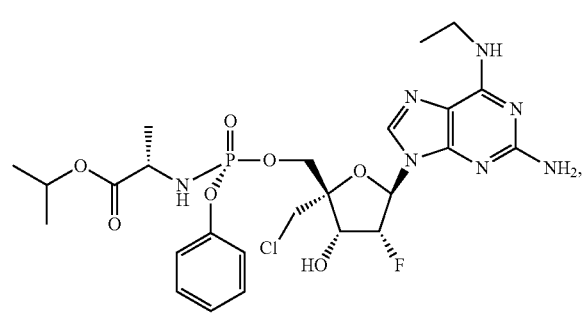
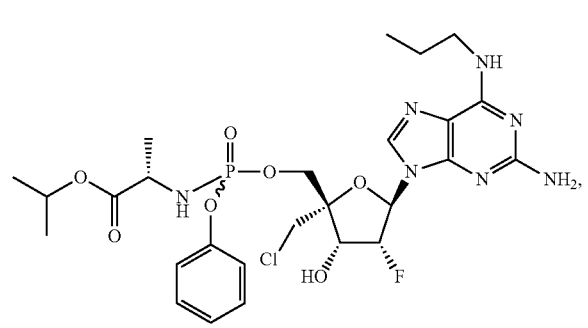
174
-continued
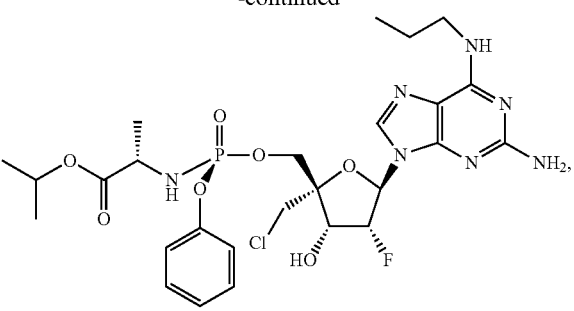
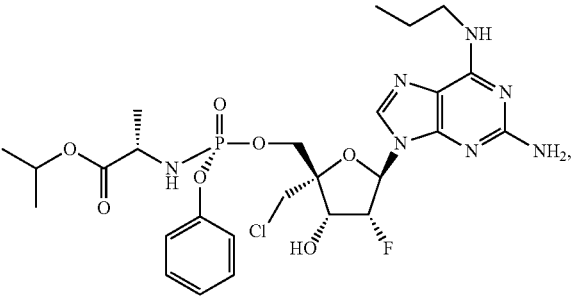
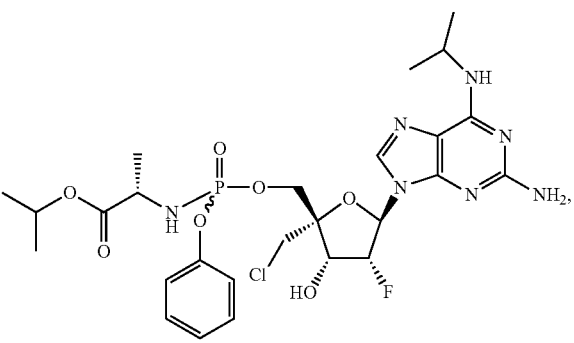
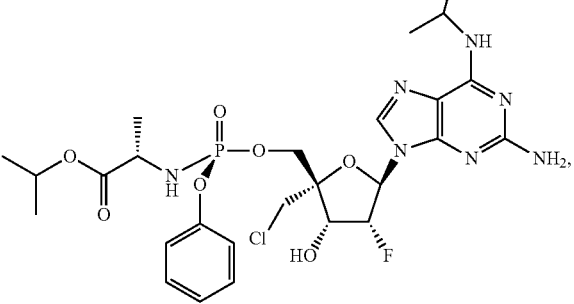
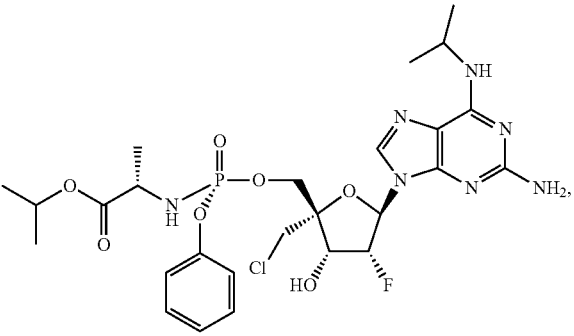

175
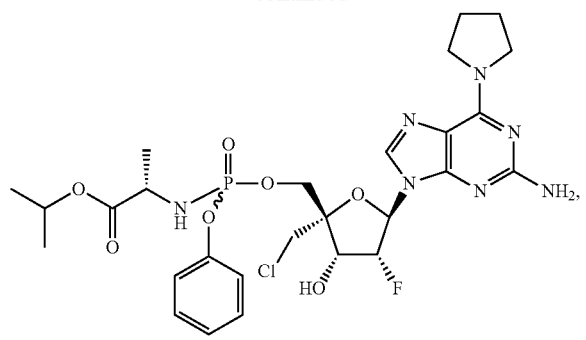
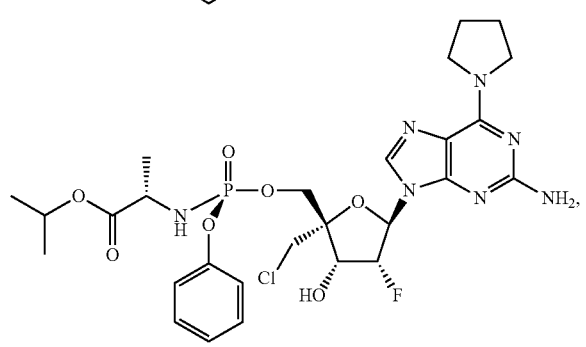
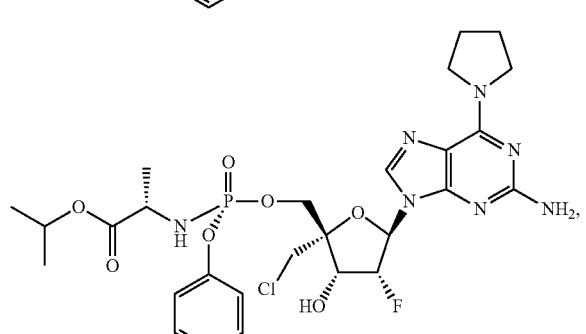
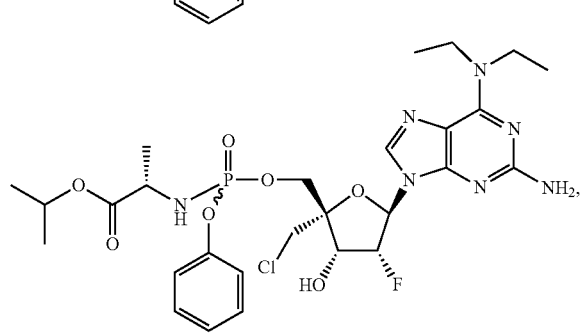
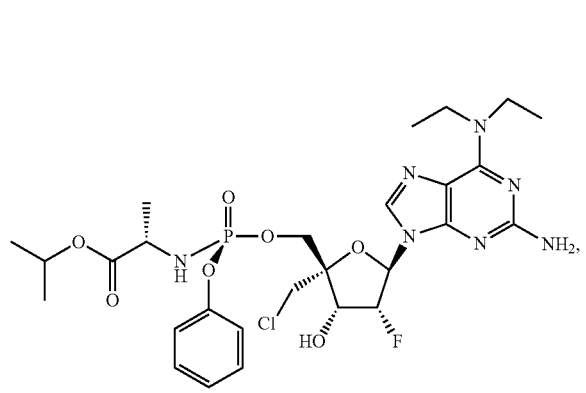
176
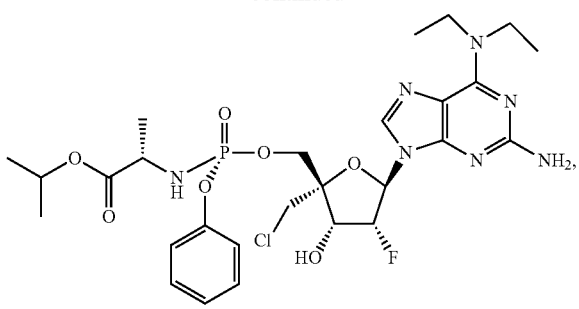
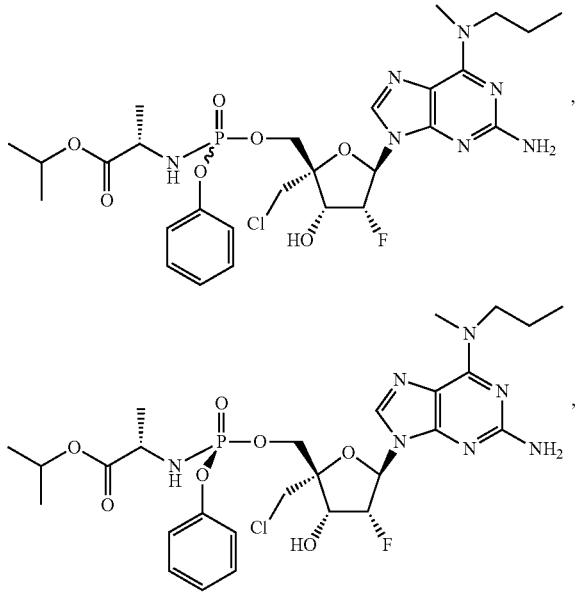
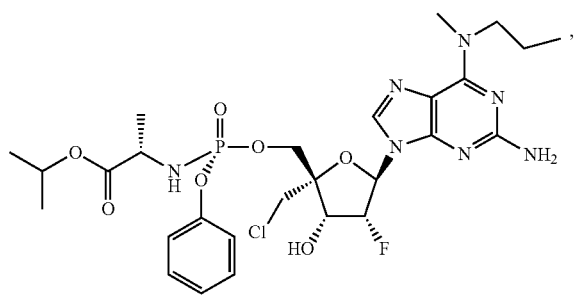
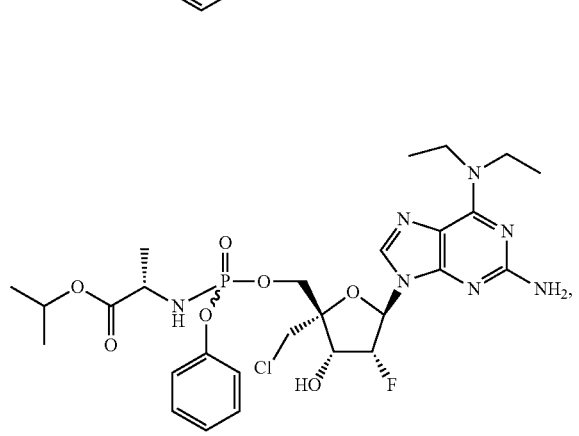

177
-continued
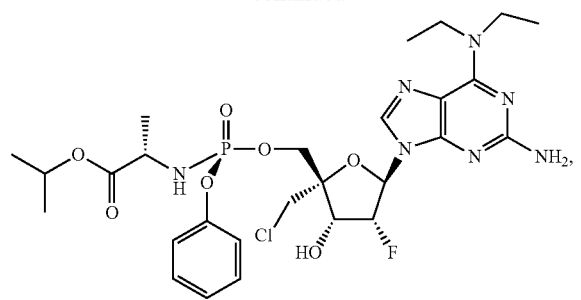
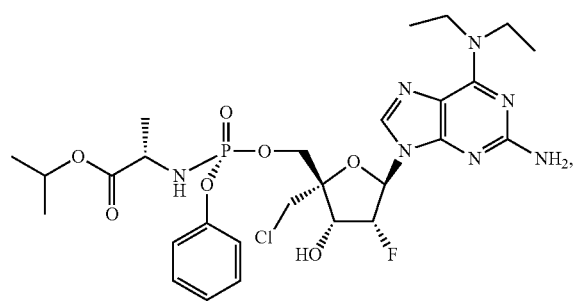
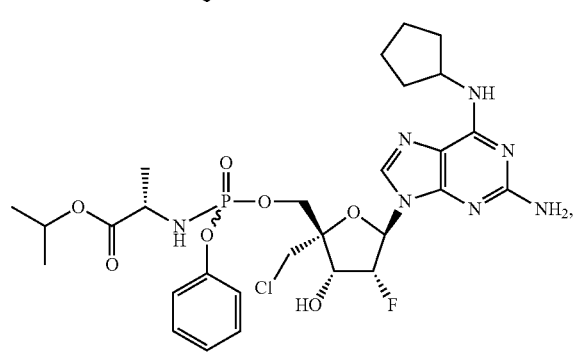
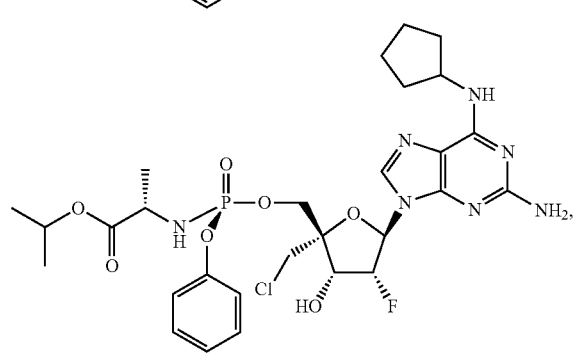
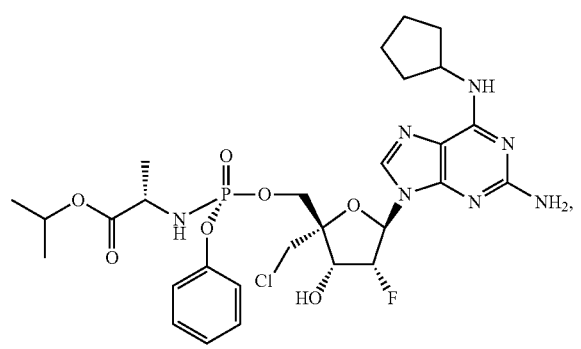
178
-continued
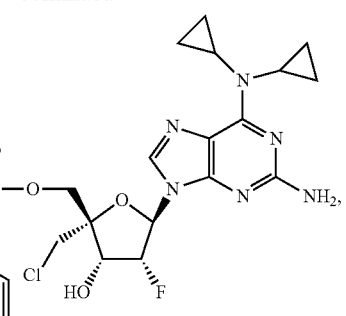
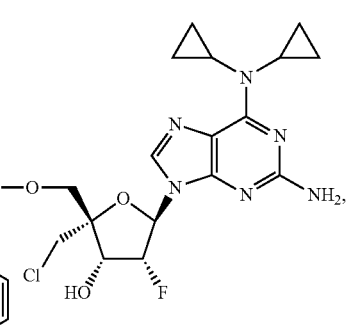
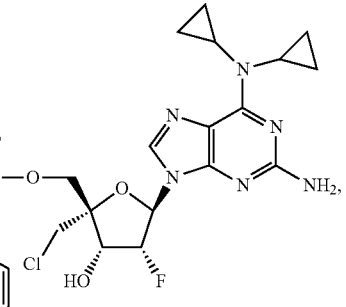
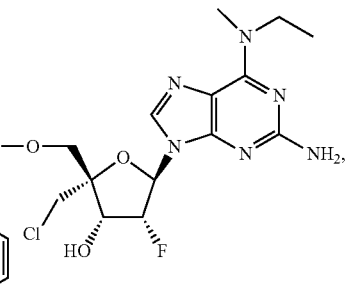
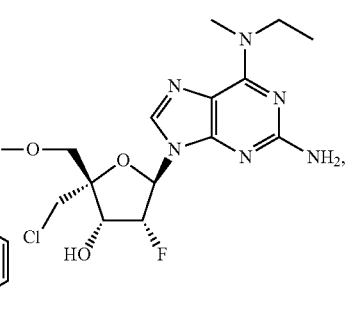

179
-continued
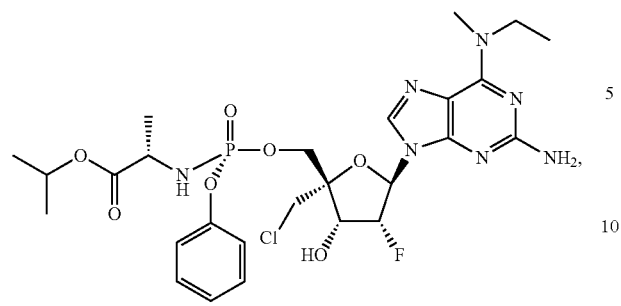
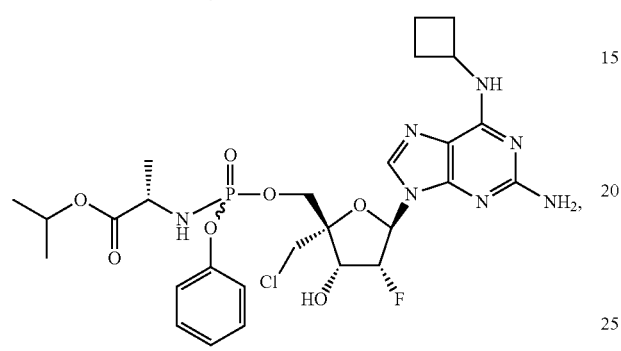
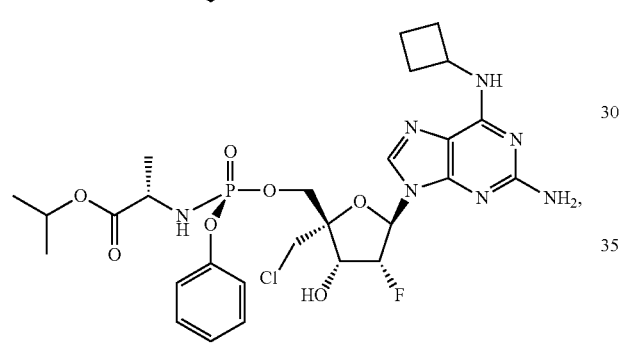
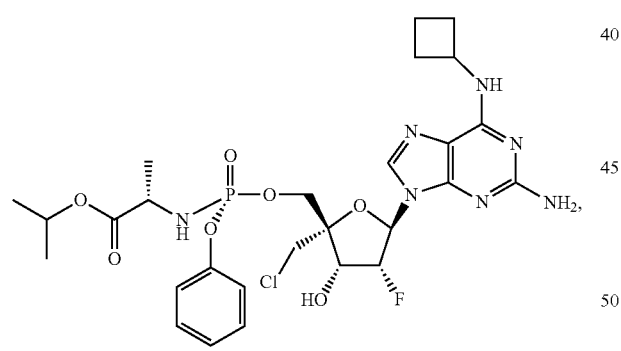
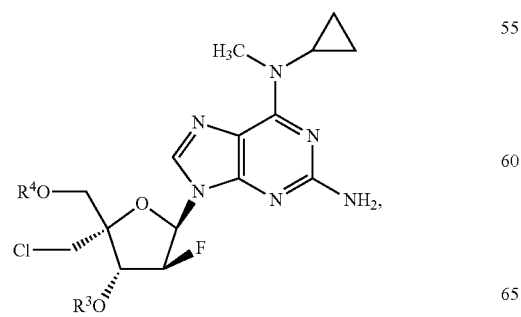
180
-continued
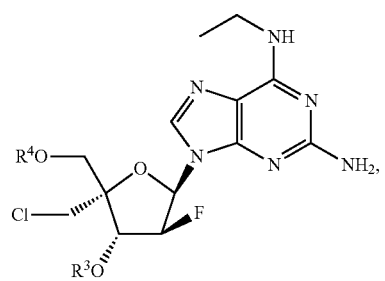
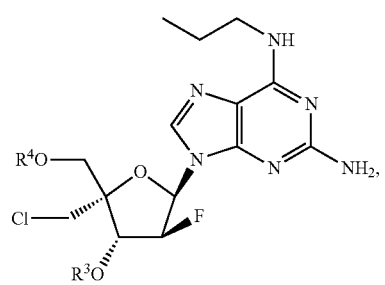
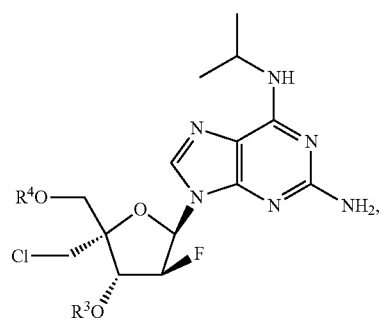
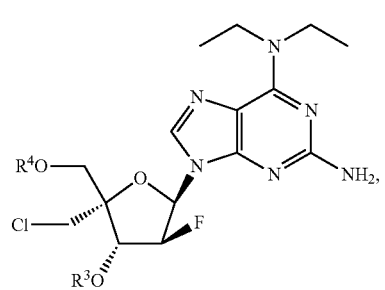
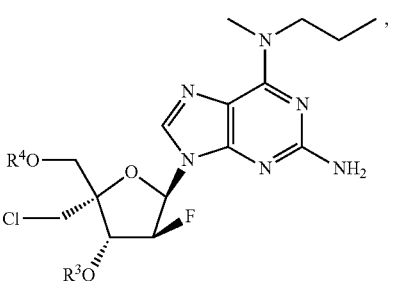

-continued
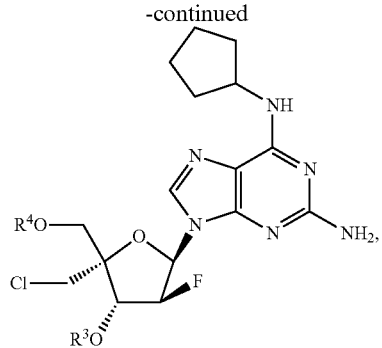
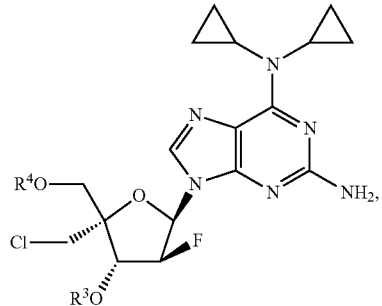
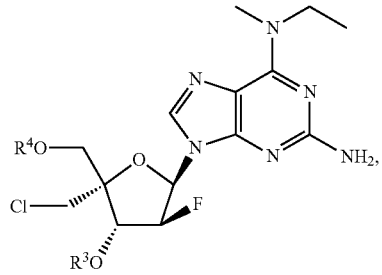
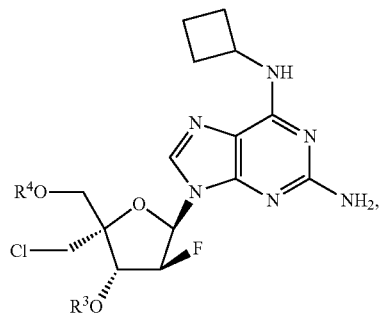
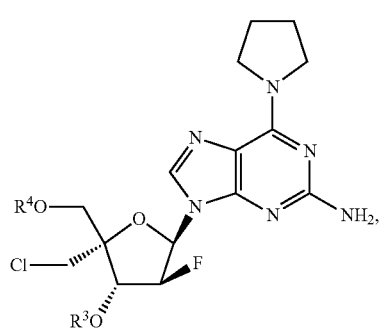
-continued
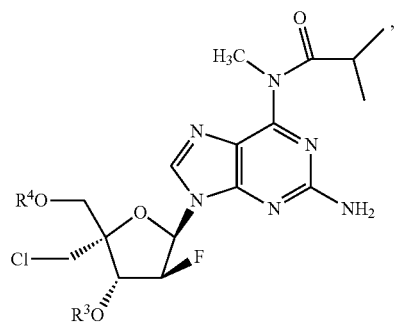
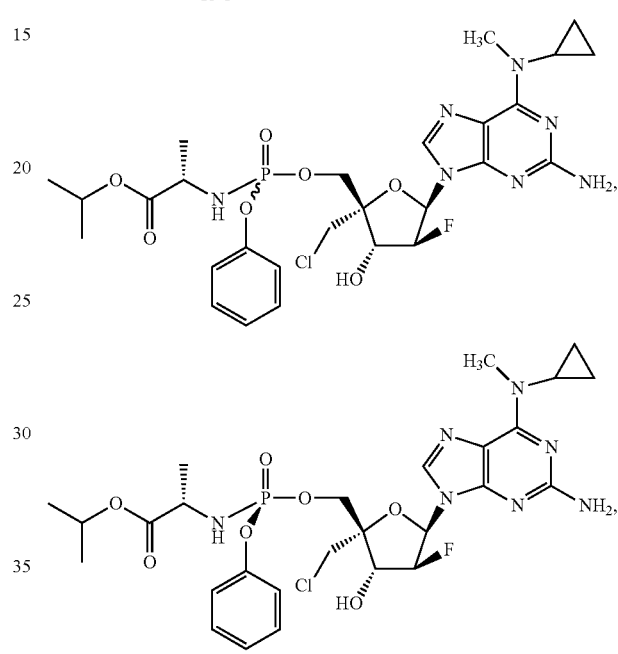
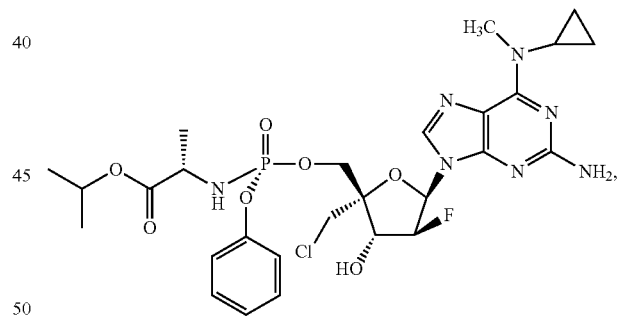
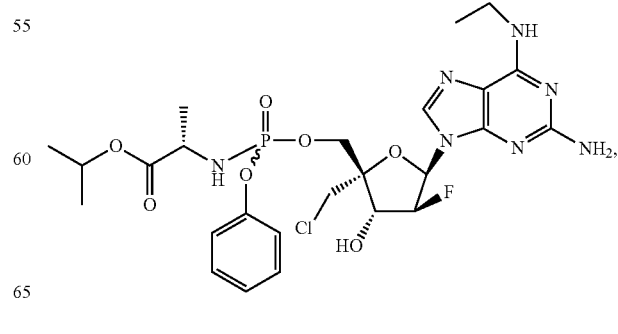

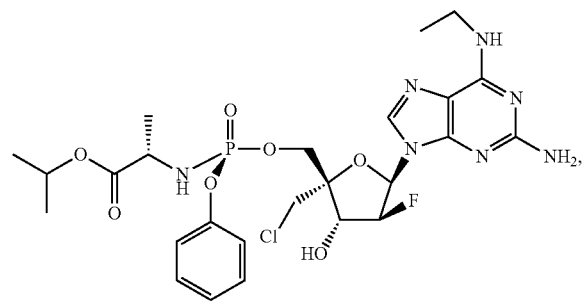
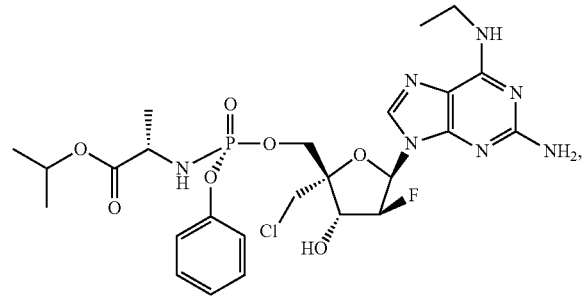
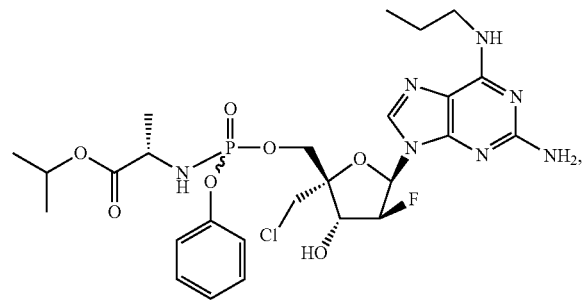
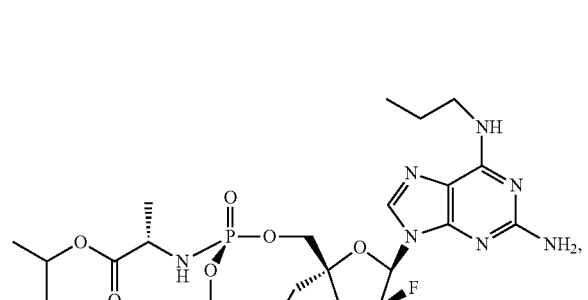

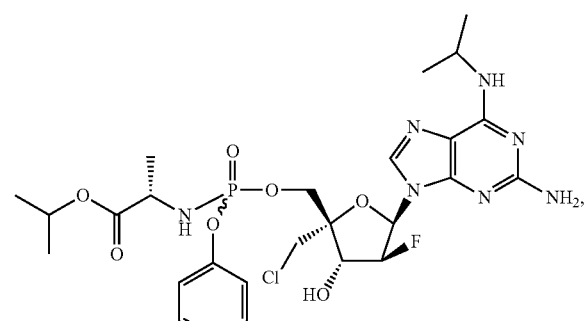
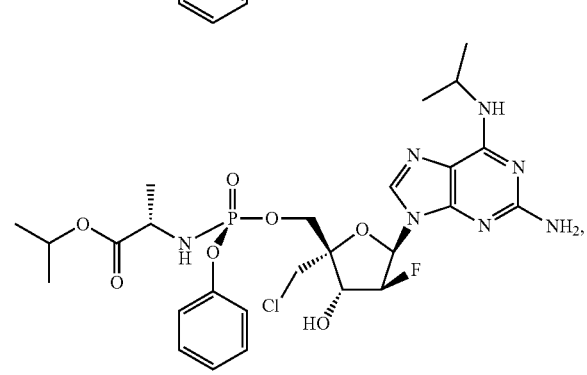
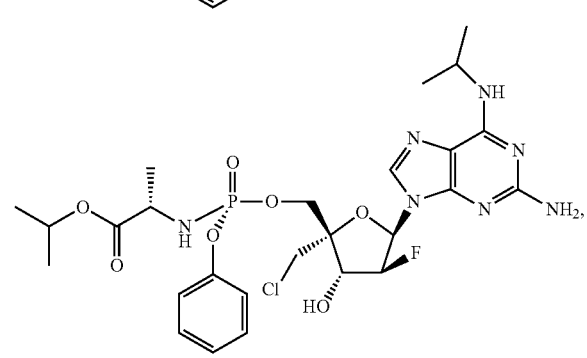
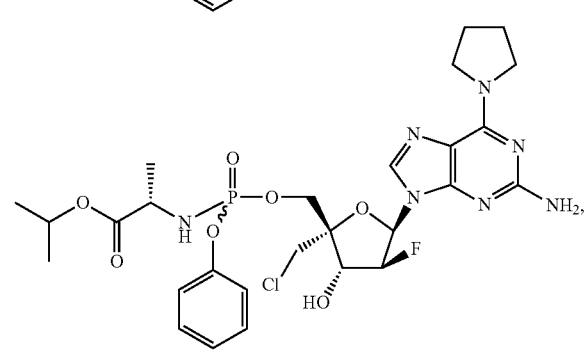
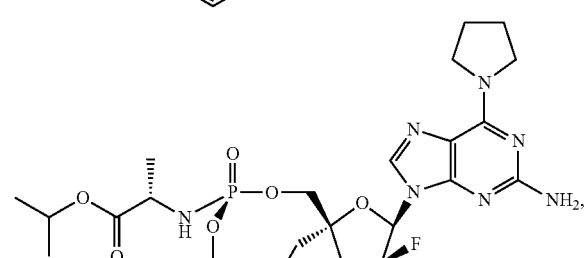

185
-continued
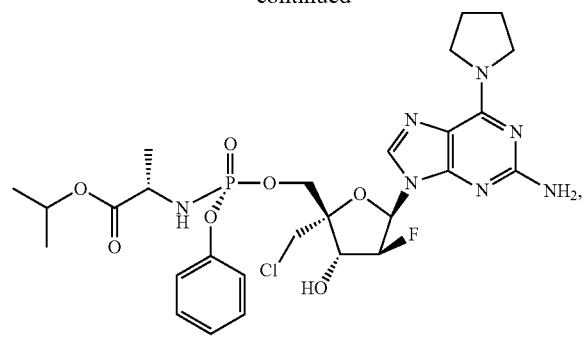
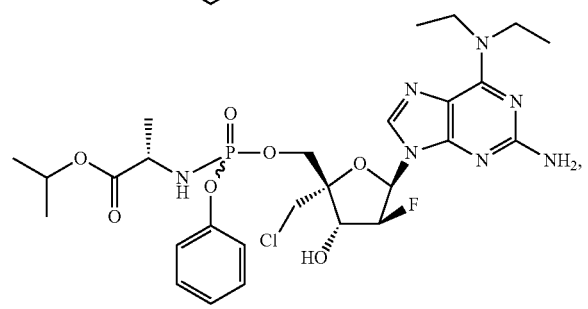
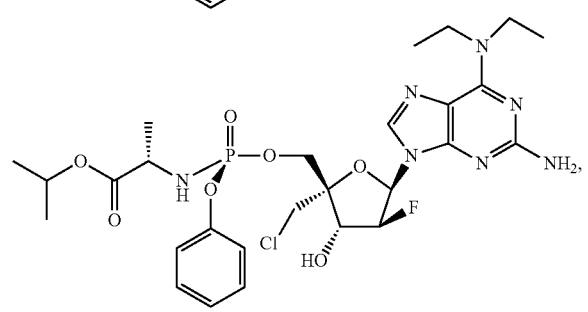
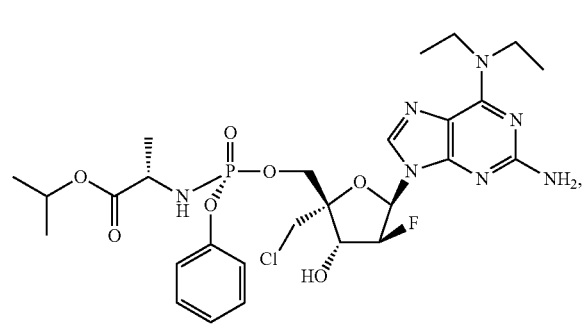
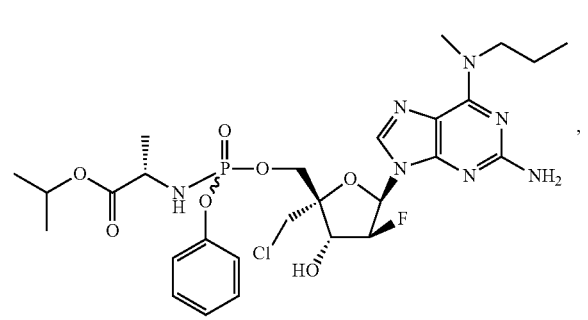
186
-continued
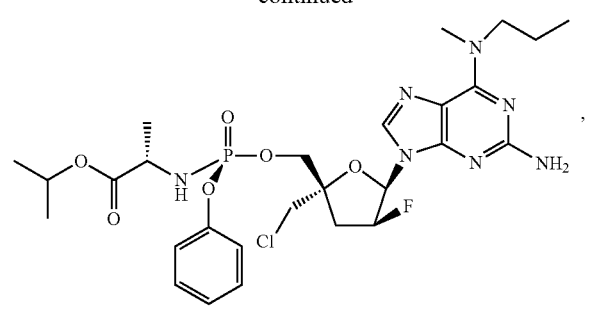
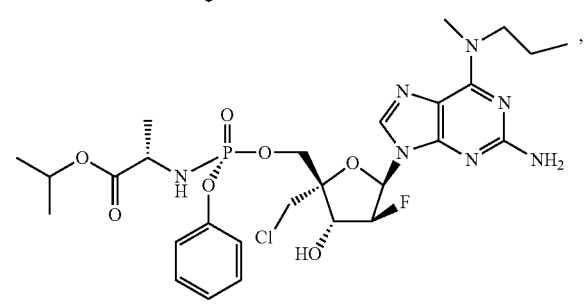
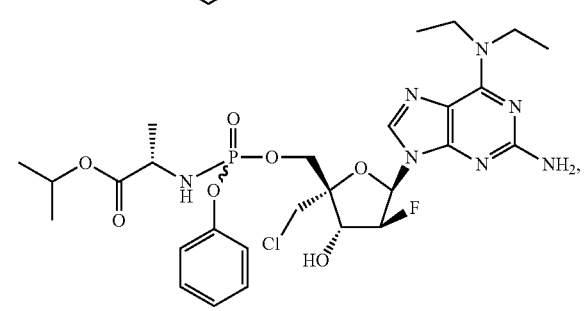
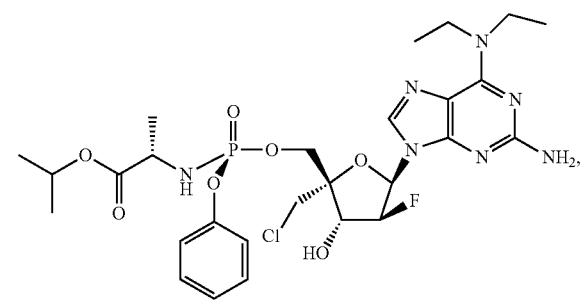
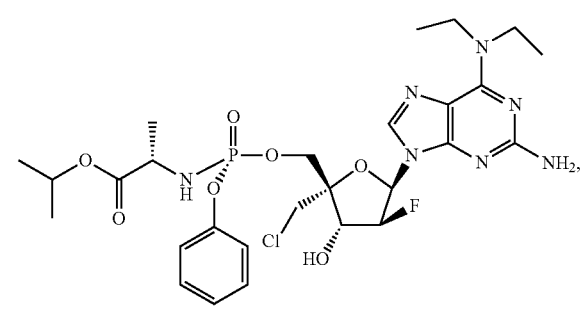

187
-continued
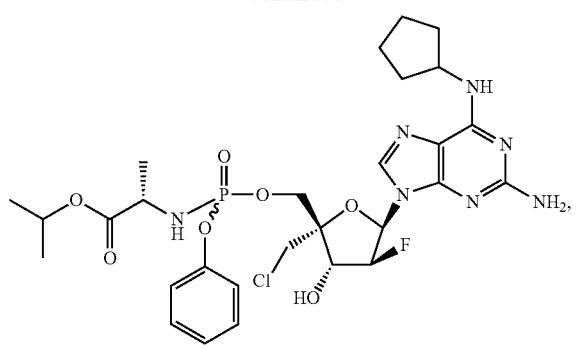
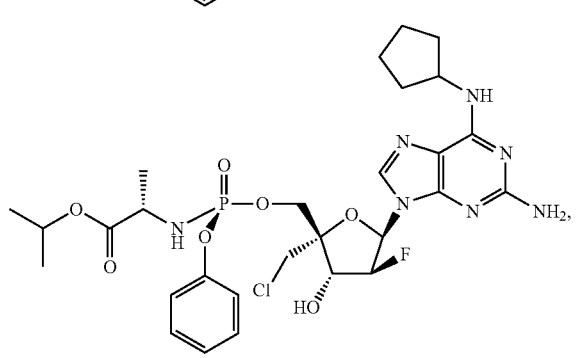
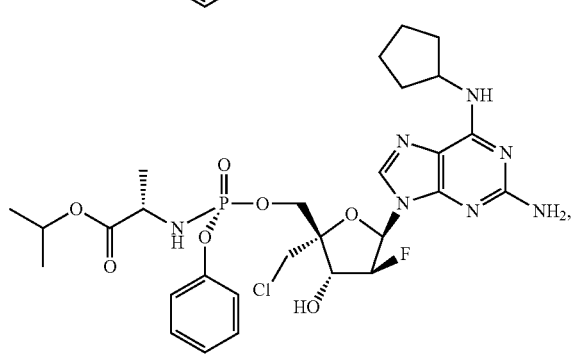
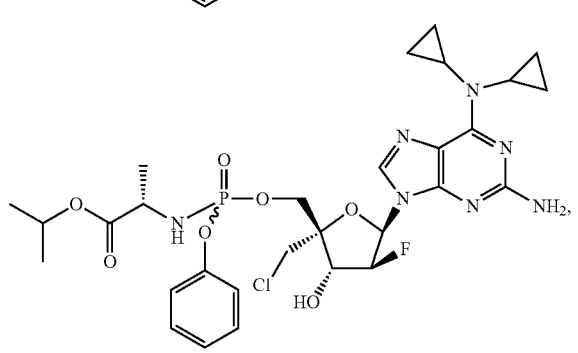
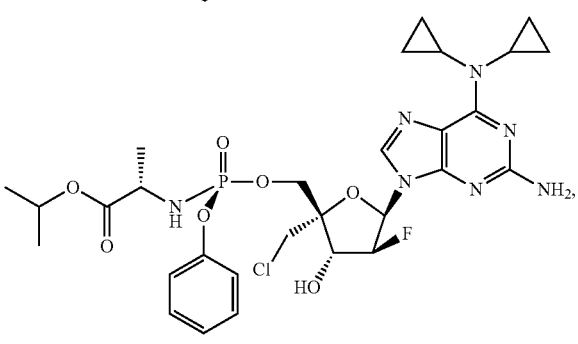
188
-continued
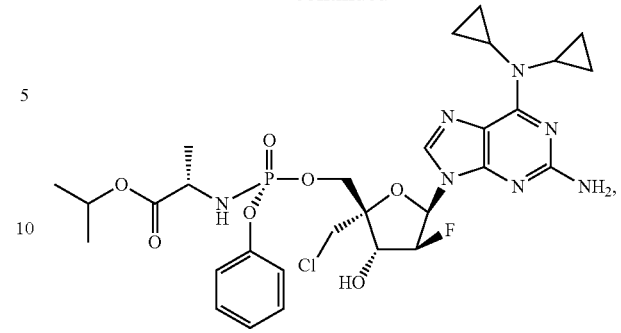
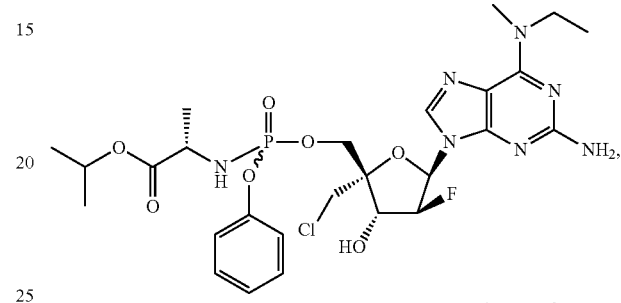
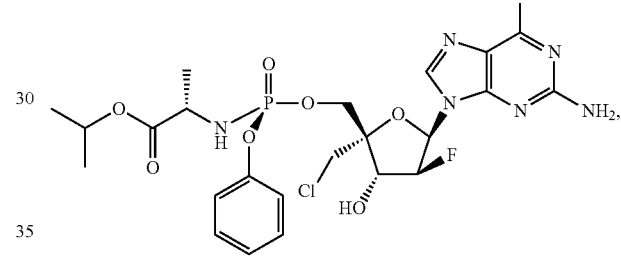
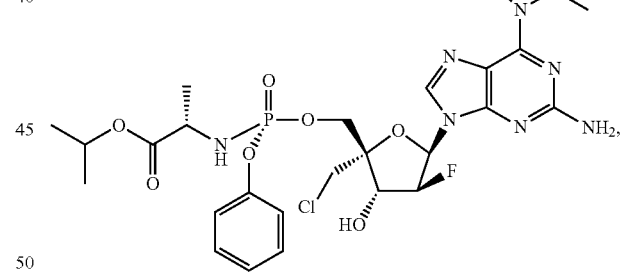
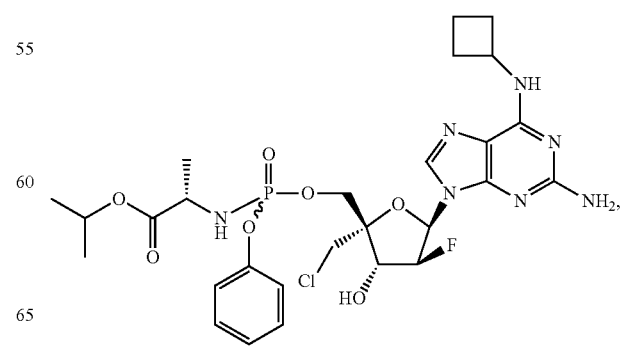

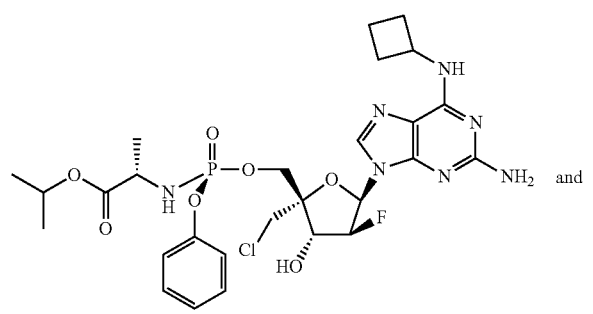
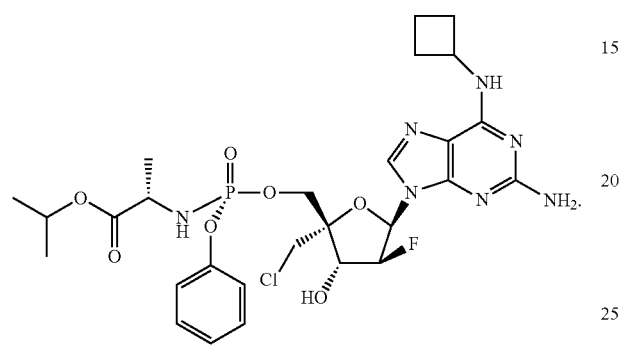
In one embodiment, a compound of Formula II is provided. Non-limiting examples of compounds of Formula II include:
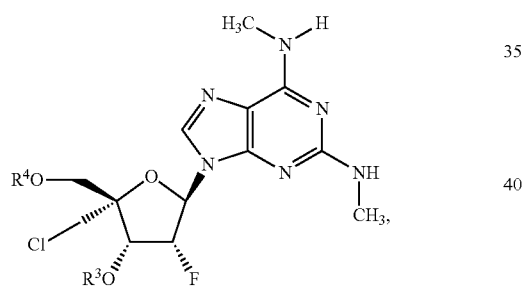
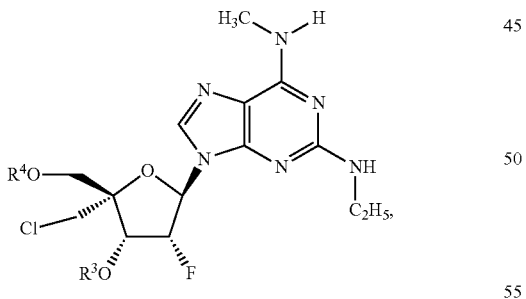
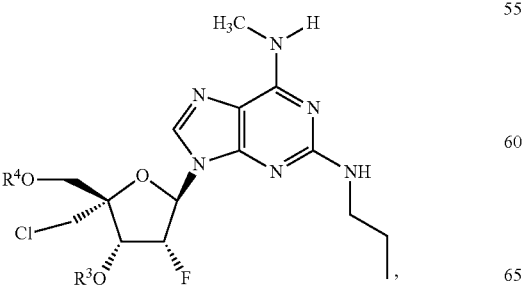
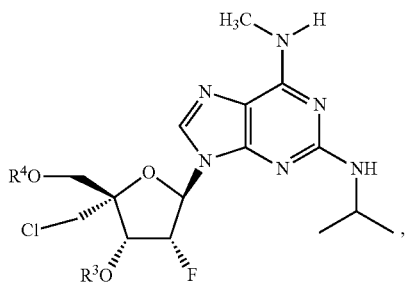
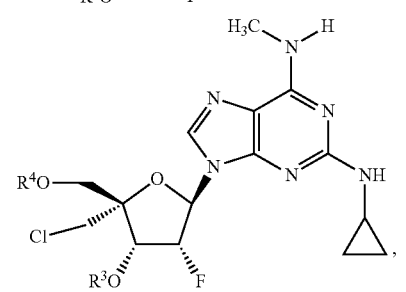
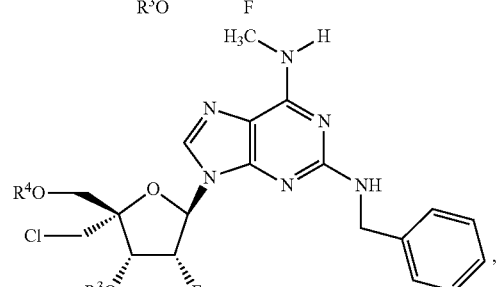
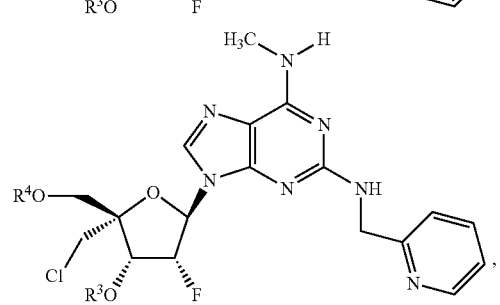
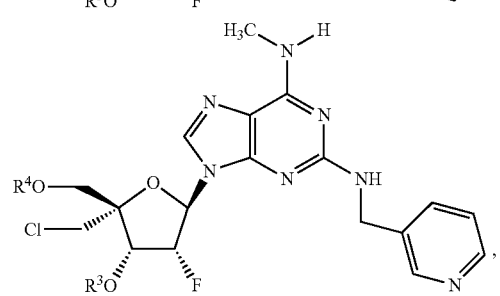
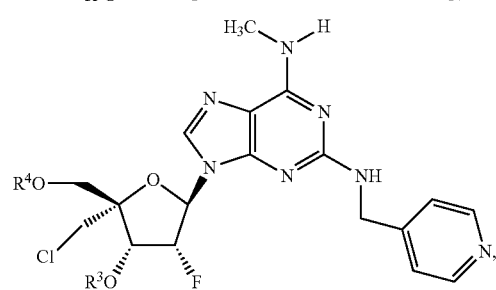

191
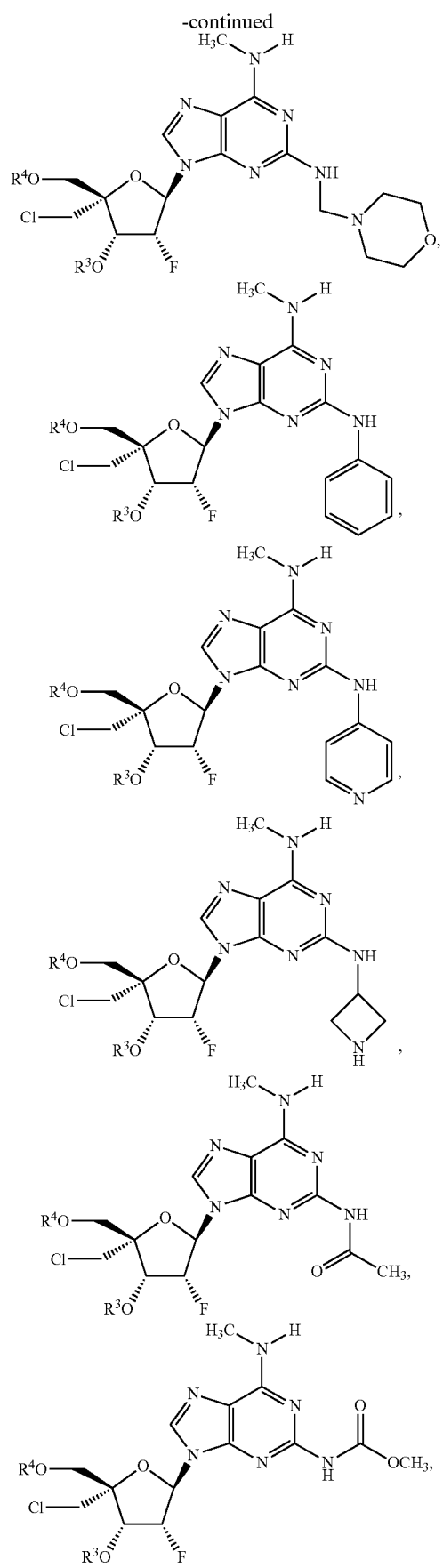
192
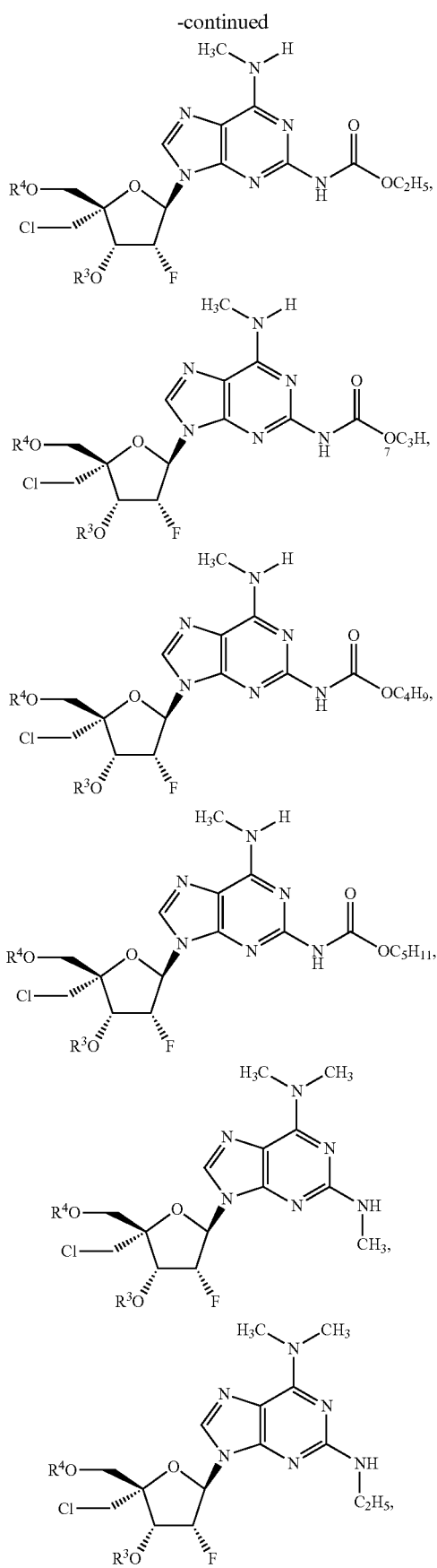

193
-continued
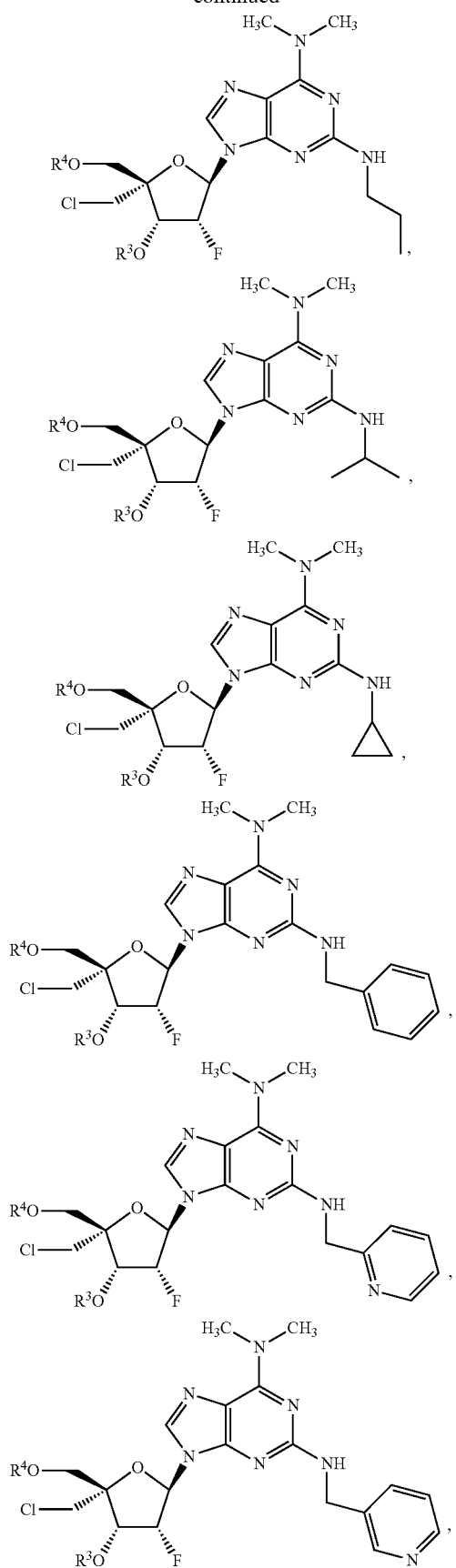
194
-continued
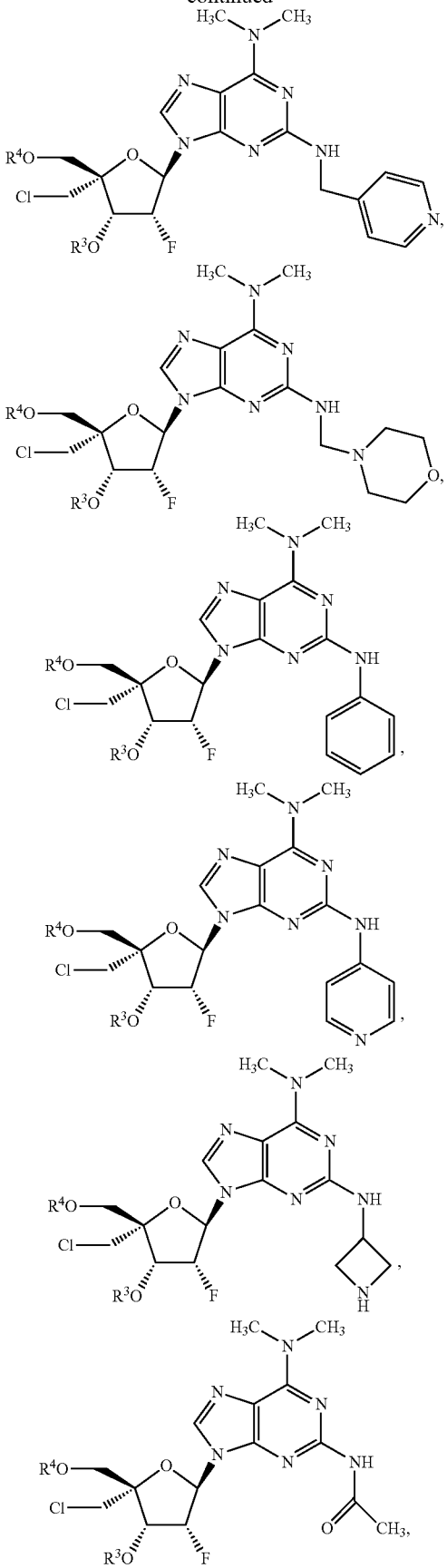

-continued
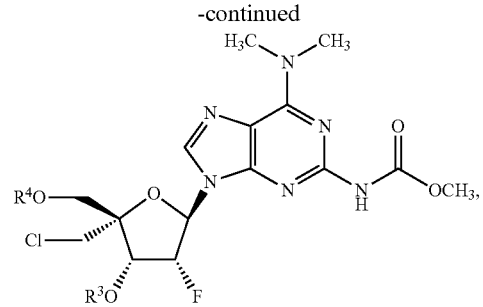
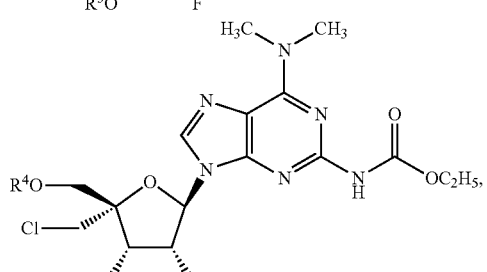
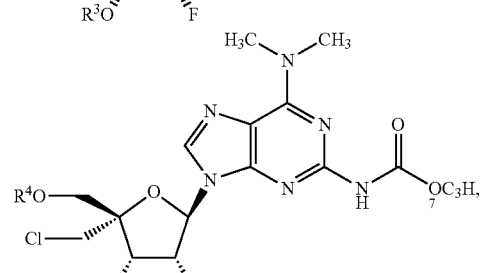
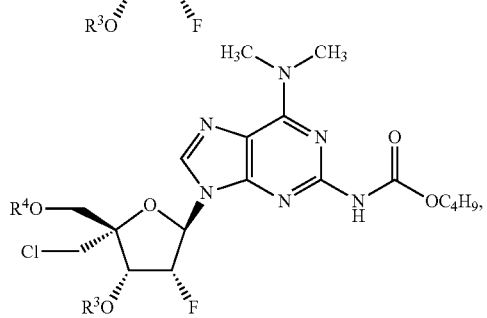
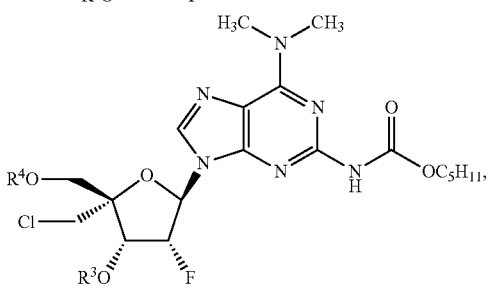
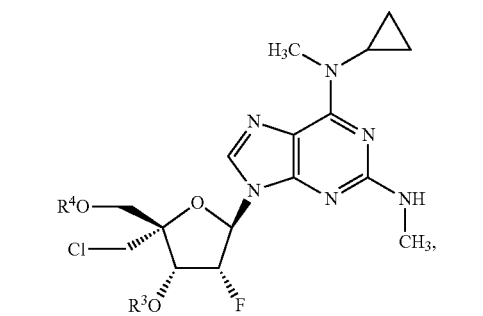
-continued
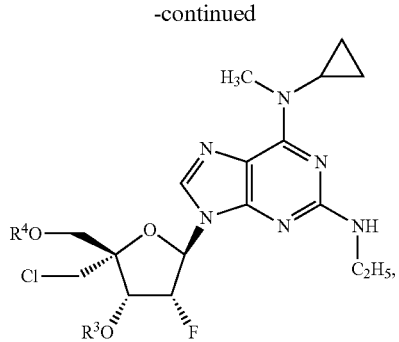
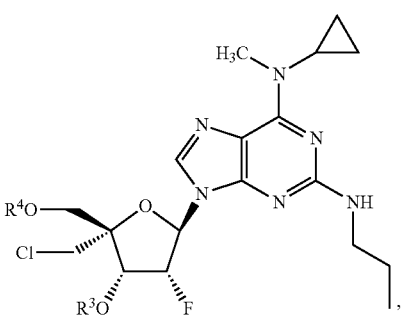
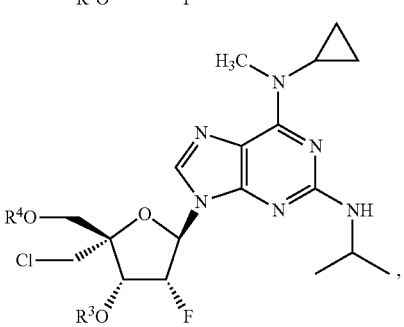
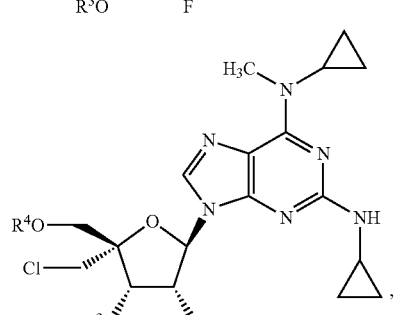
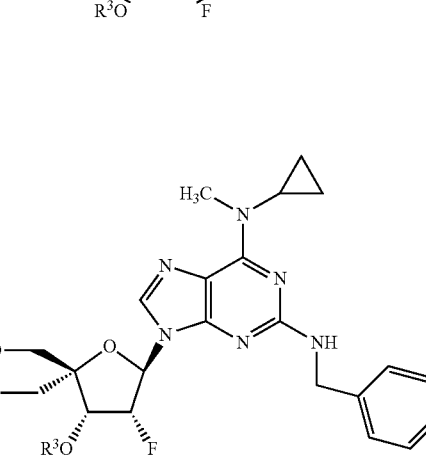

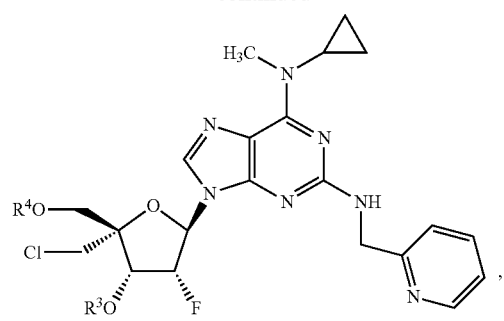
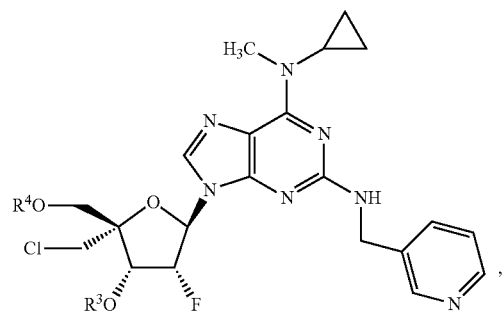
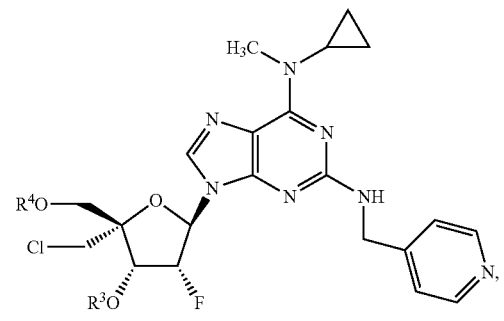
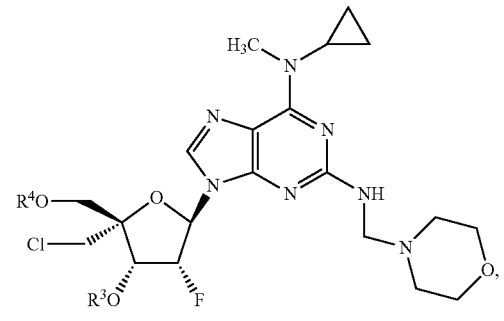
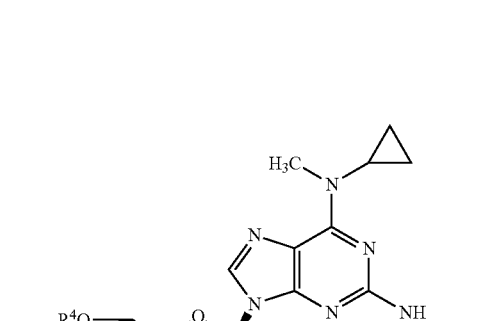
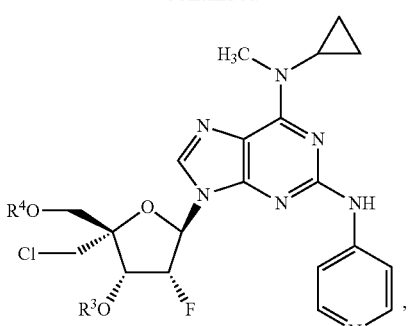
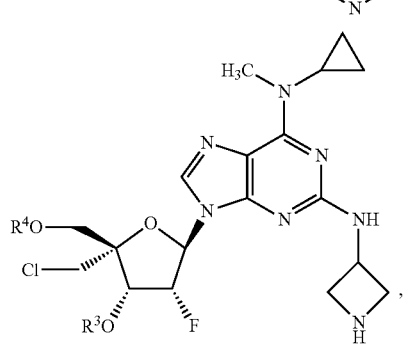
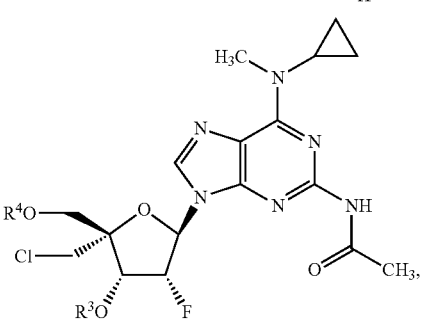
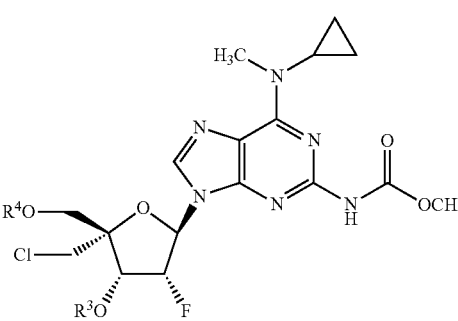

-continued
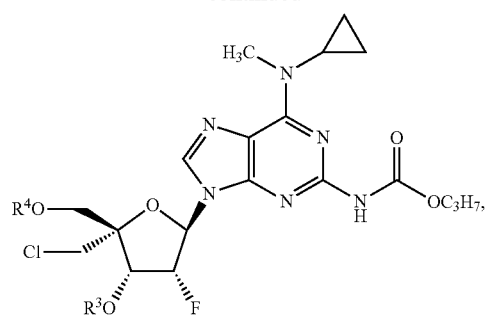
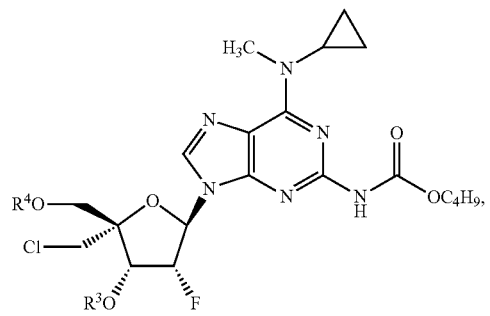
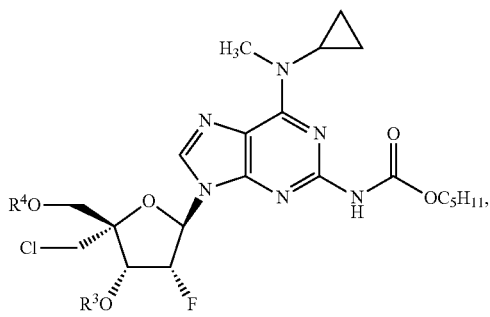
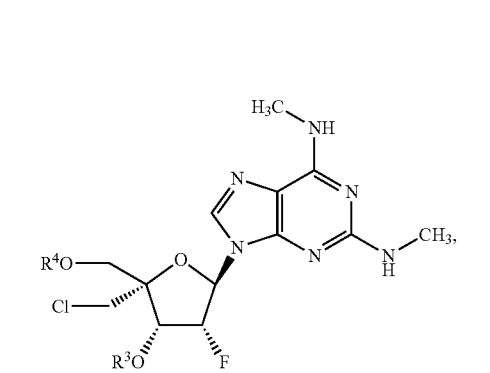
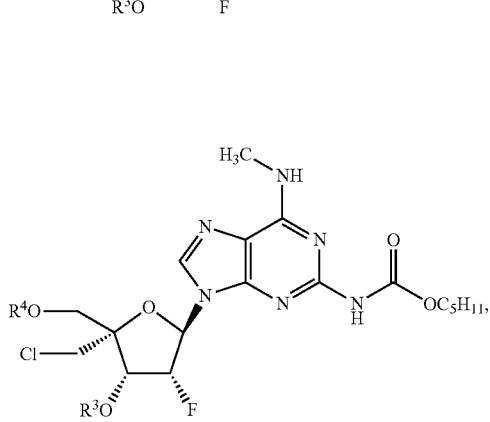
-continued
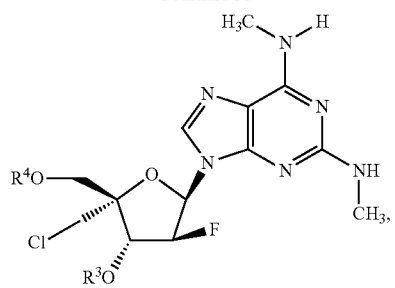
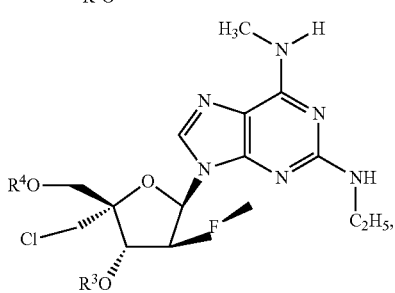
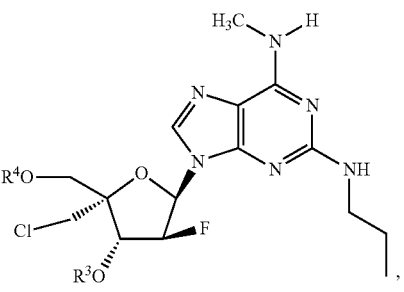
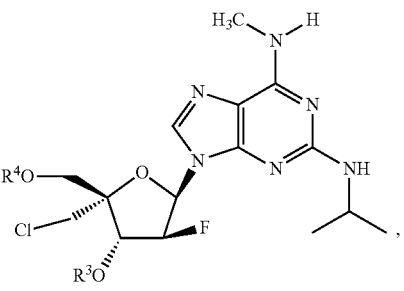
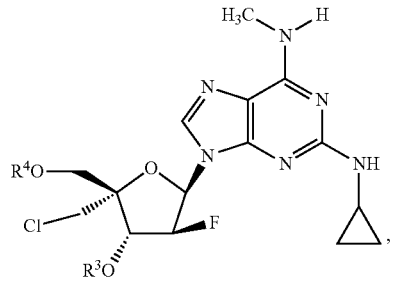
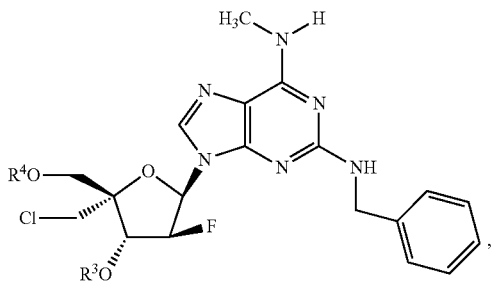

-continued
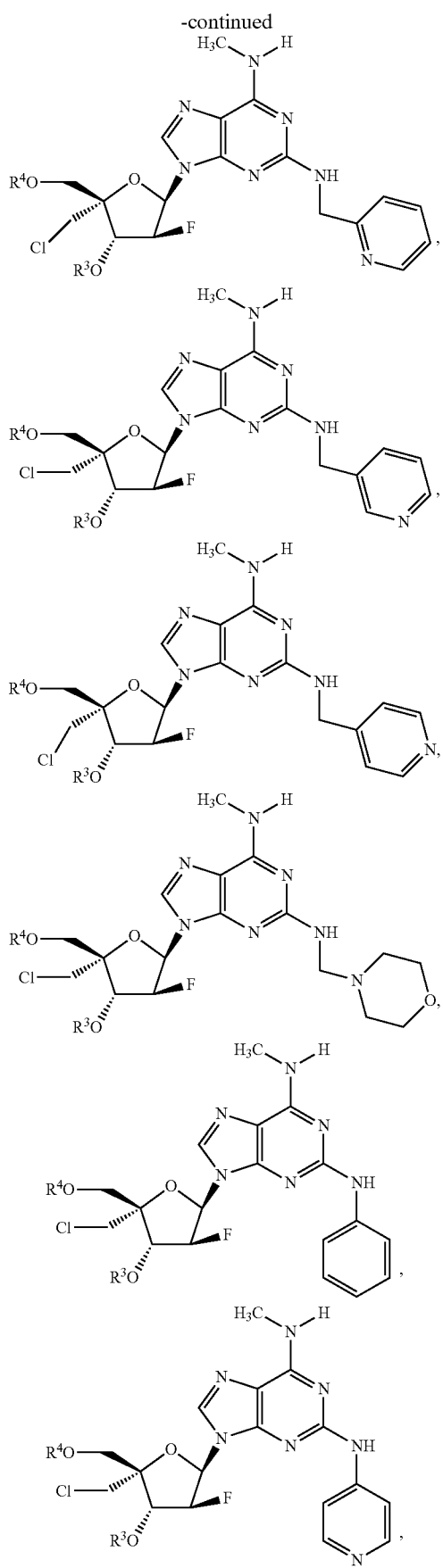
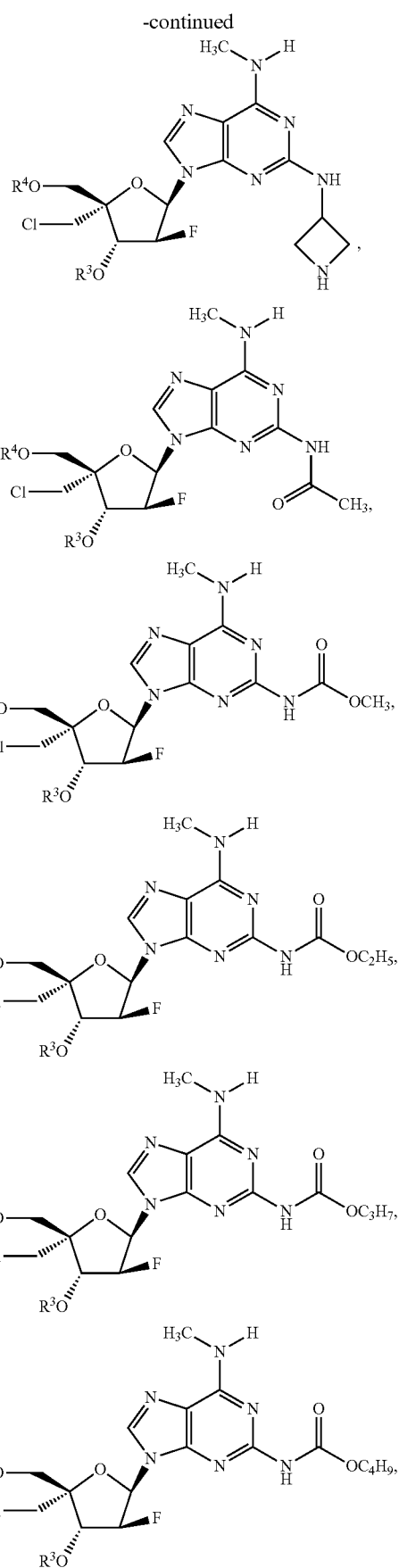

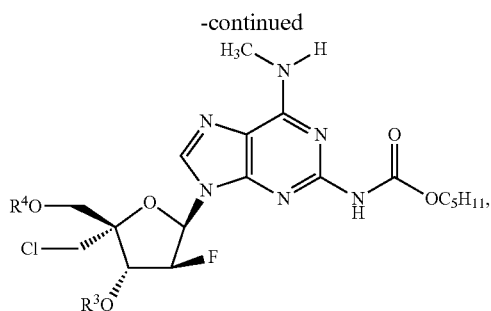
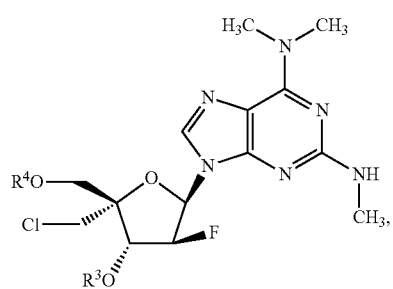
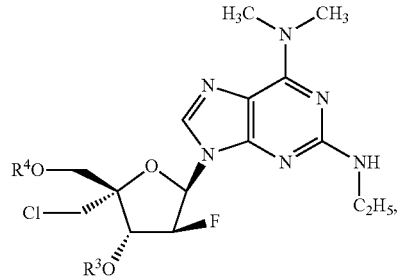
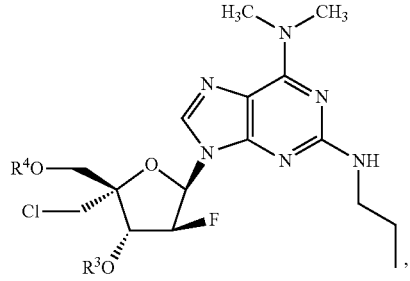
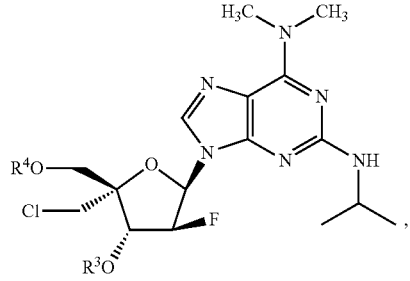
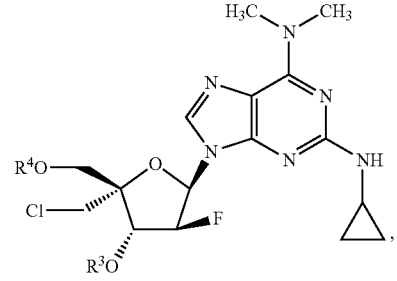
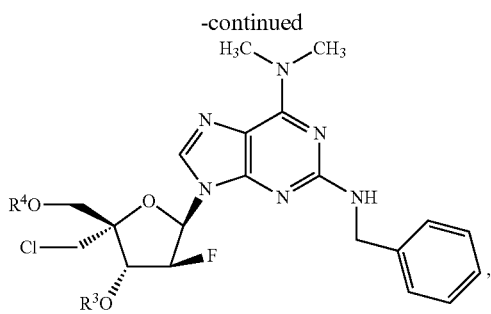
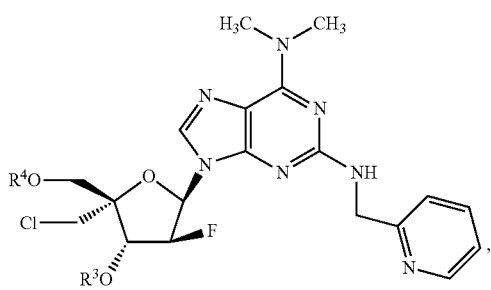
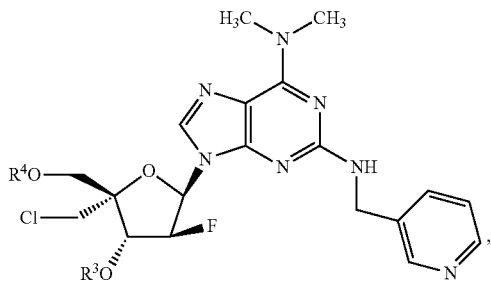
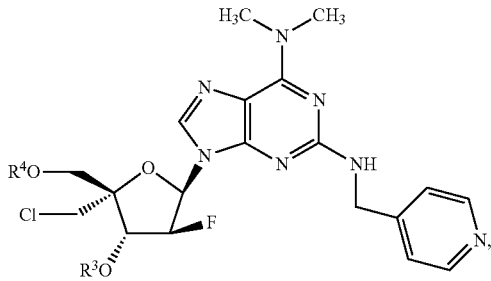
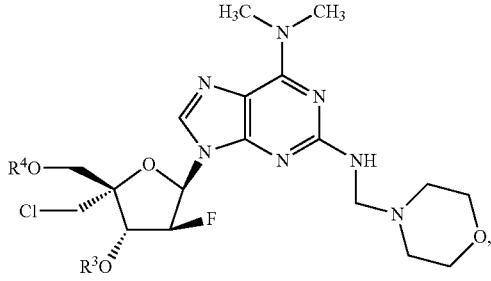
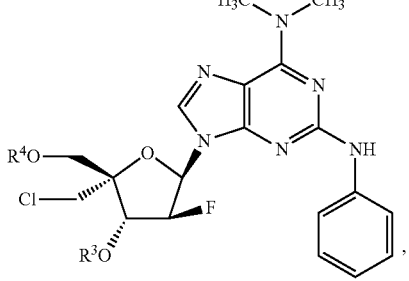

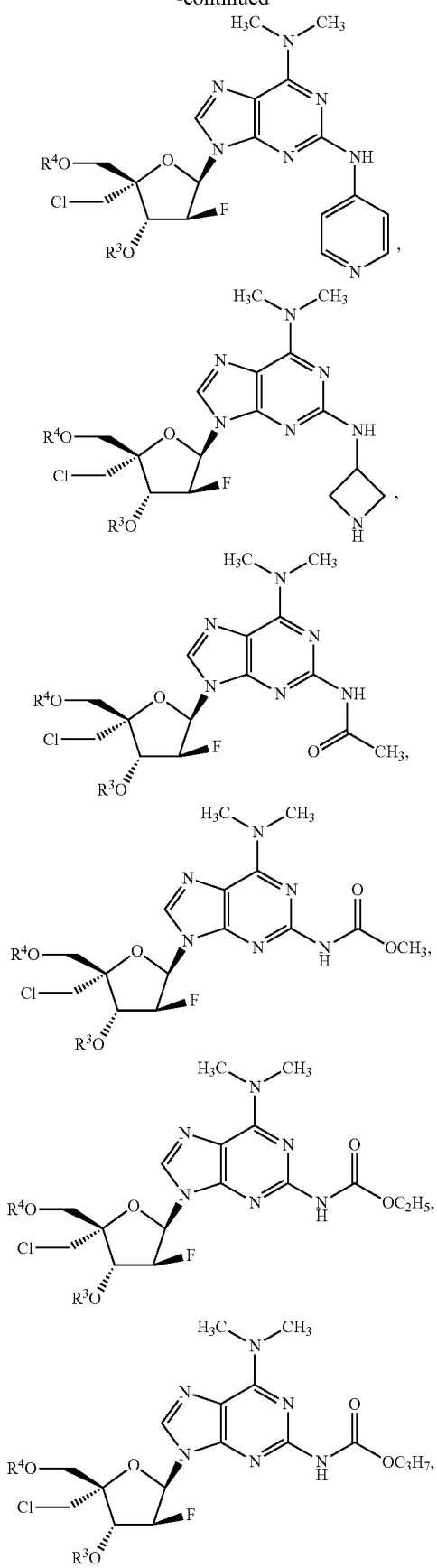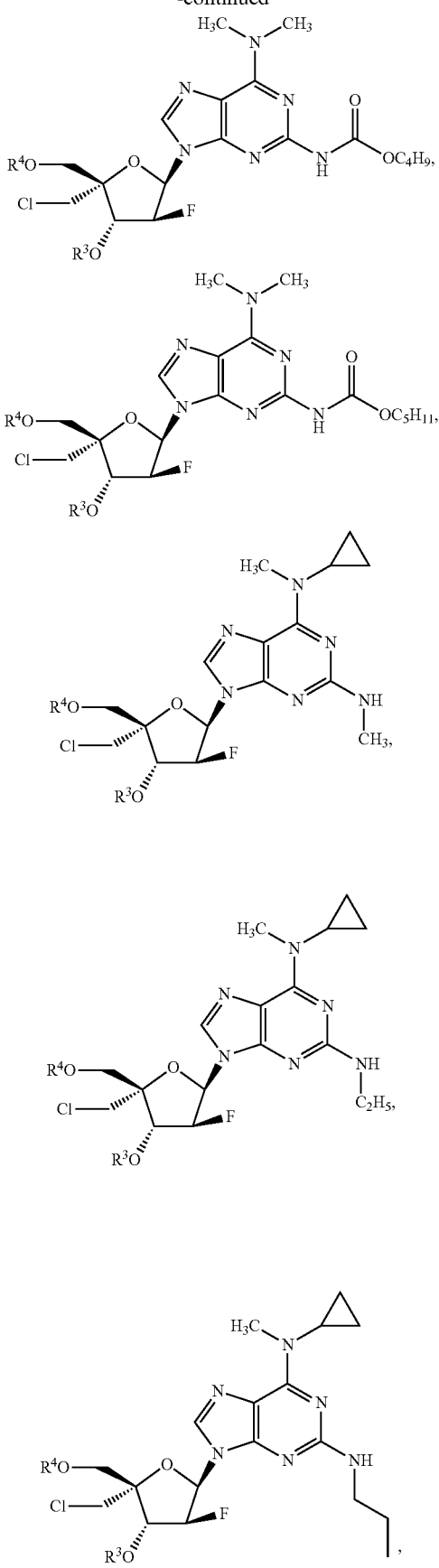

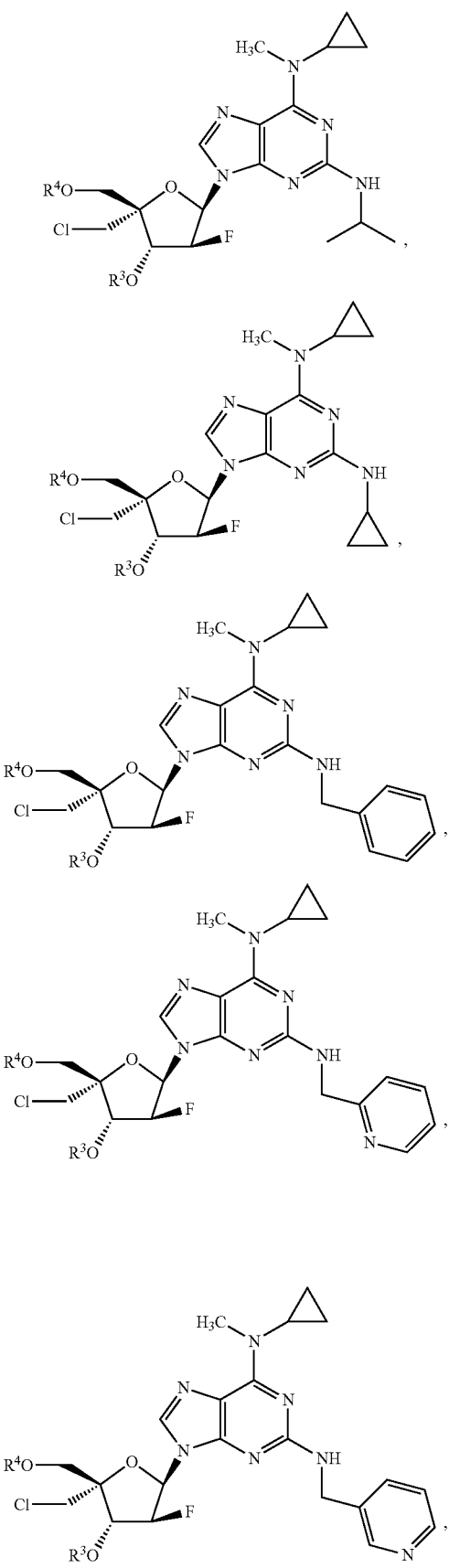
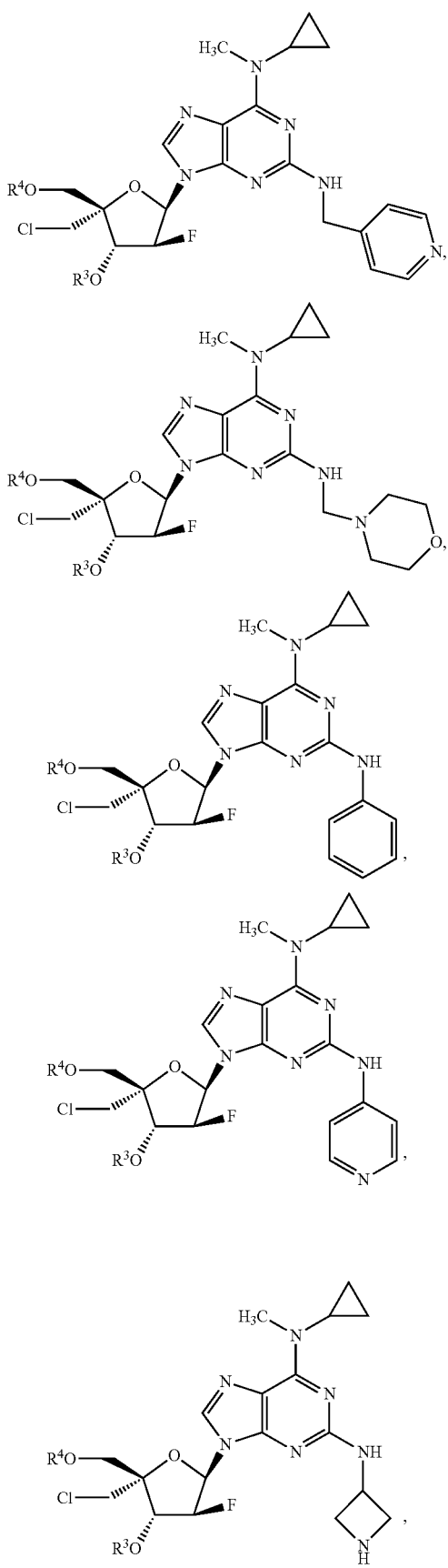

-continued
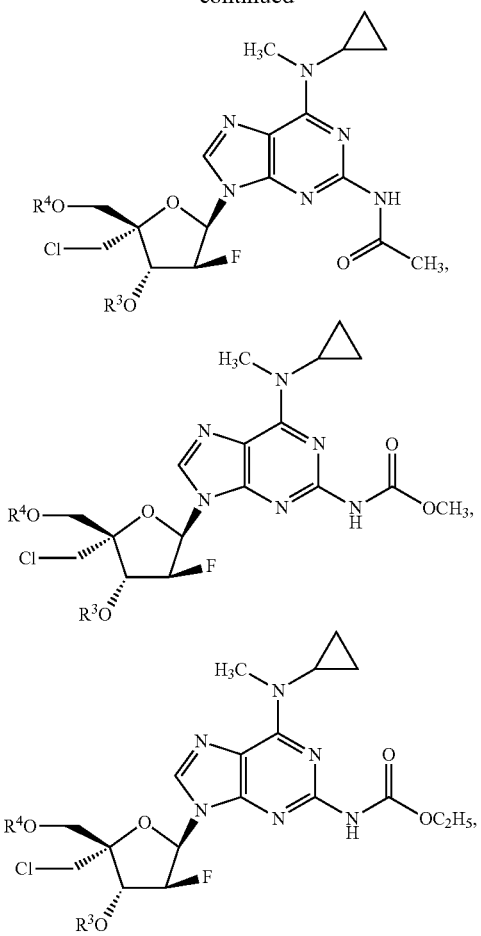
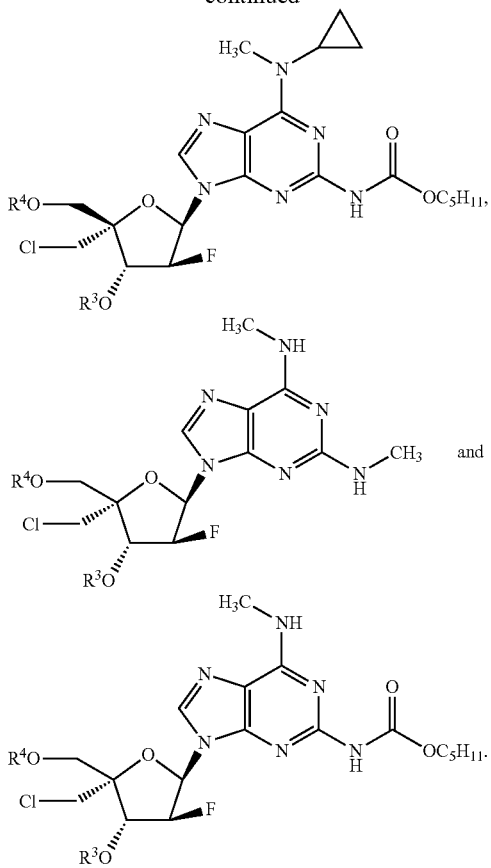
In one embodiment, $R^3$ is hydrogen and $R^4$ is
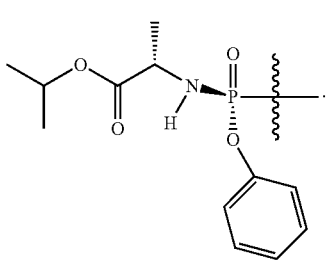 [SMILES: *[P@](=O)(N[C@@H](C)C(=O)OC(C)C)Oc1ccccc1]
In one embodiment, $R^3$ is hydrogen and $R^4$ is
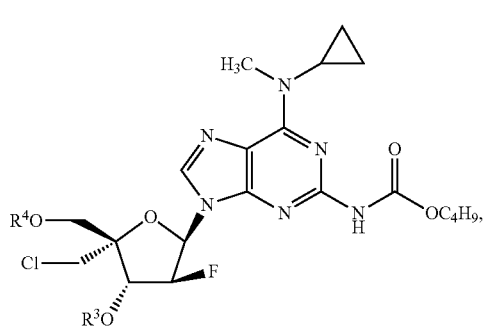
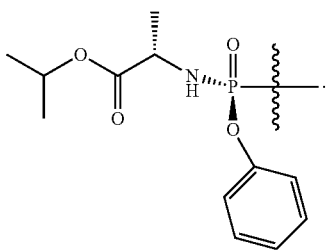 [SMILES: *[P@@](=O)(N[C@@H](C)C(=O)OC(C)C)Oc1ccccc1]

In one embodiment, R³ is hydrogen and R⁴ is
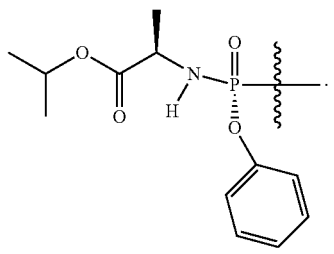 [SMILES: *[P@](=O)(N[C@H](C)C(=O)OC(C)C)Oc1ccccc1]
In one embodiment, R³ is hydrogen and R⁴ is
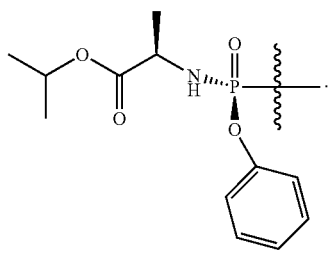 [SMILES: *[P@@](=O)(N[C@H](C)C(=O)OC(C)C)Oc1ccccc1]
In one embodiment, a compound of Formula II is provided. Non-limiting examples of compounds of Formula II include:
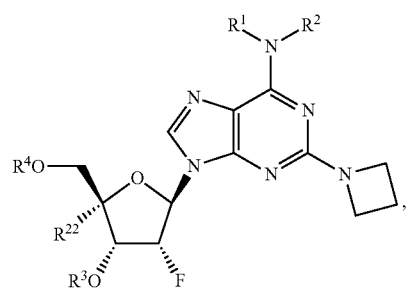
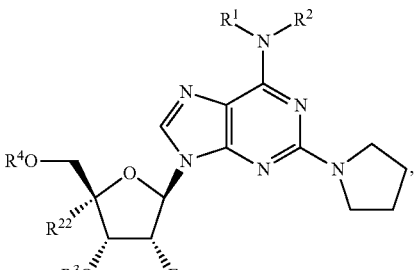
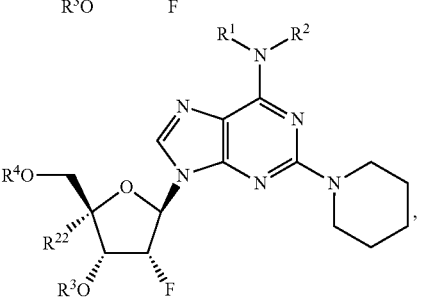
-continued
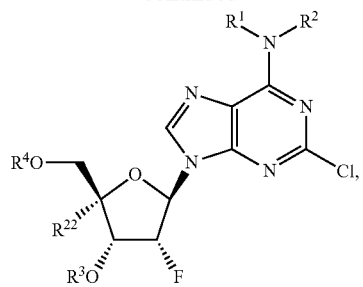
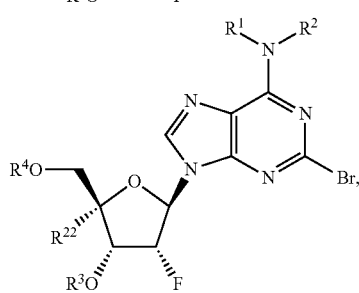
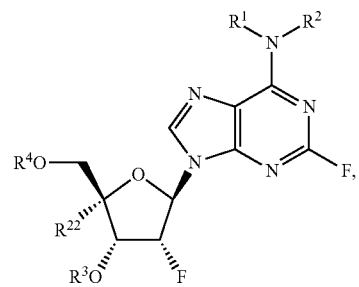
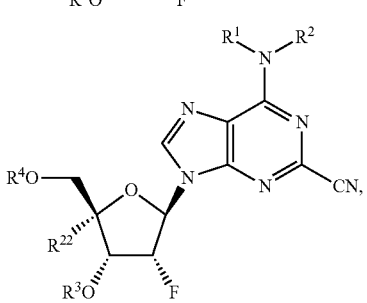
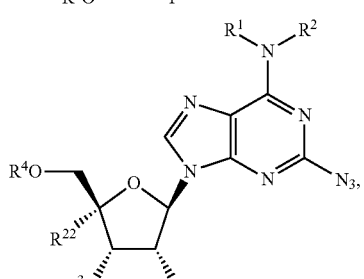
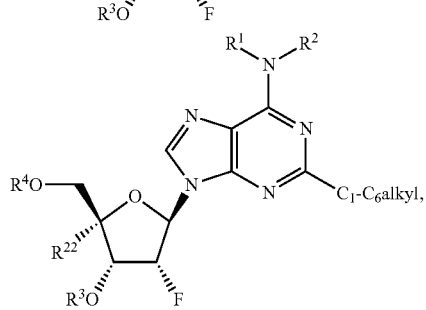

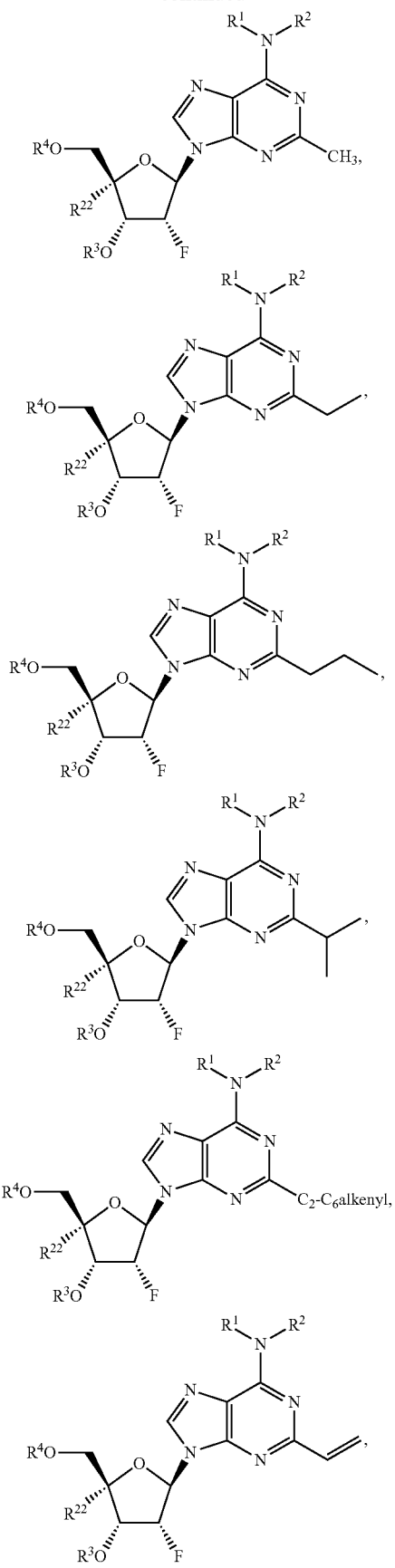
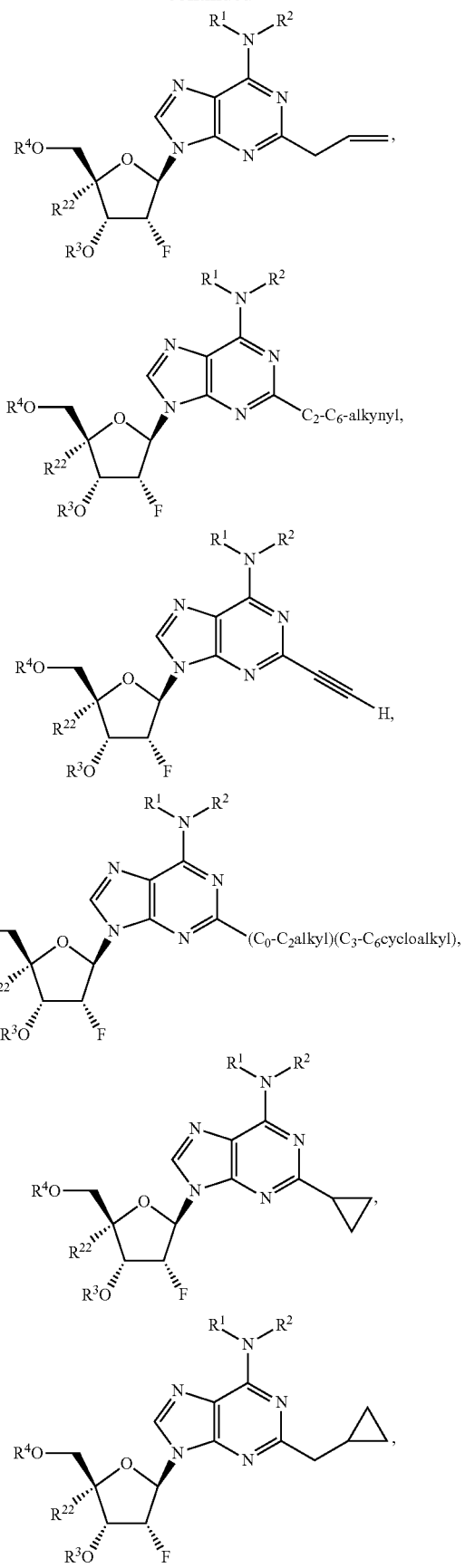

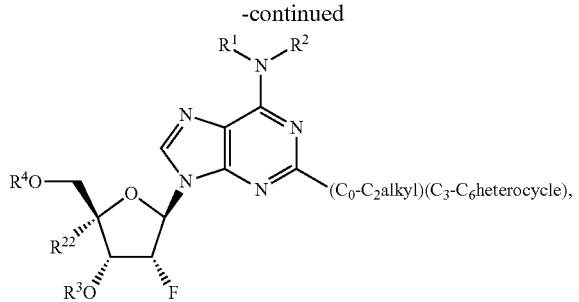
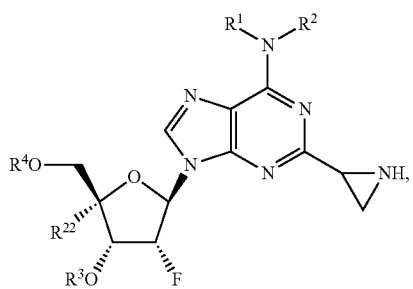
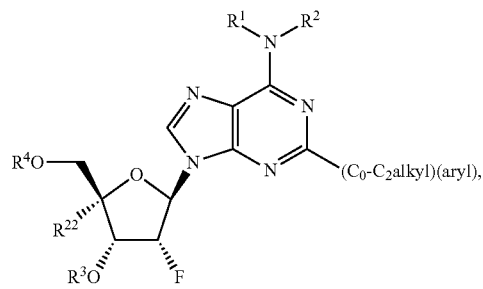
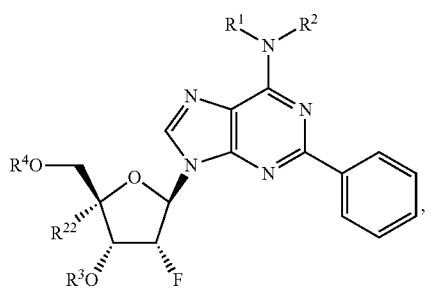
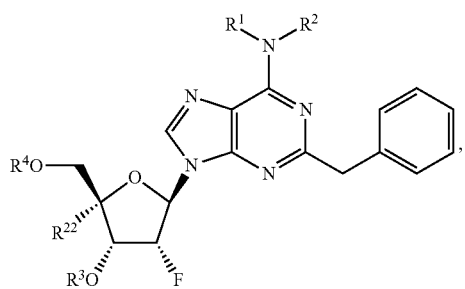
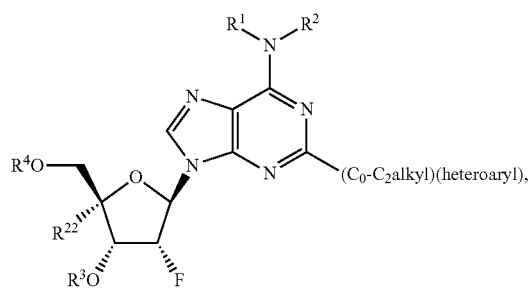
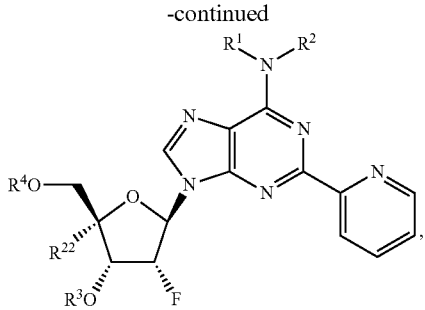
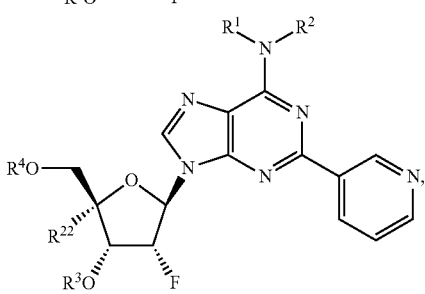
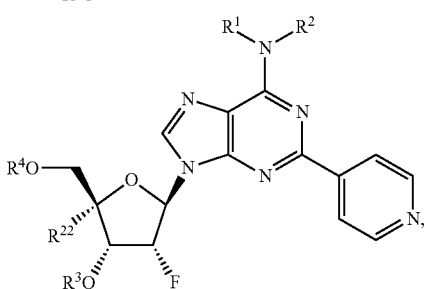
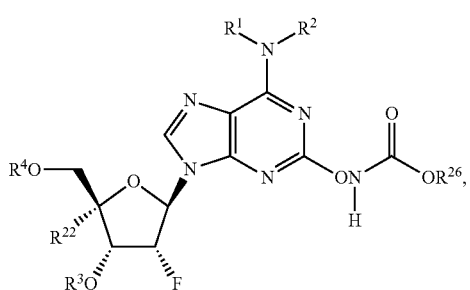
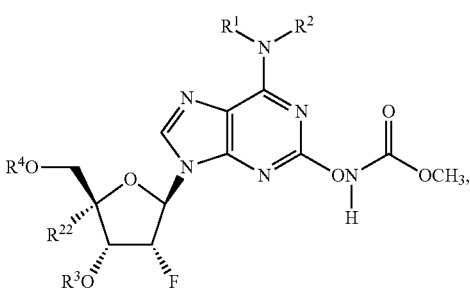
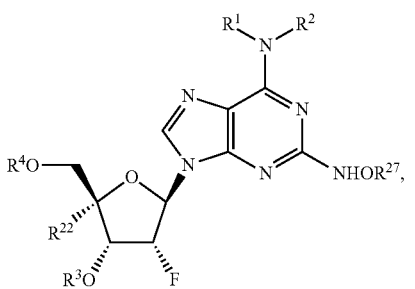

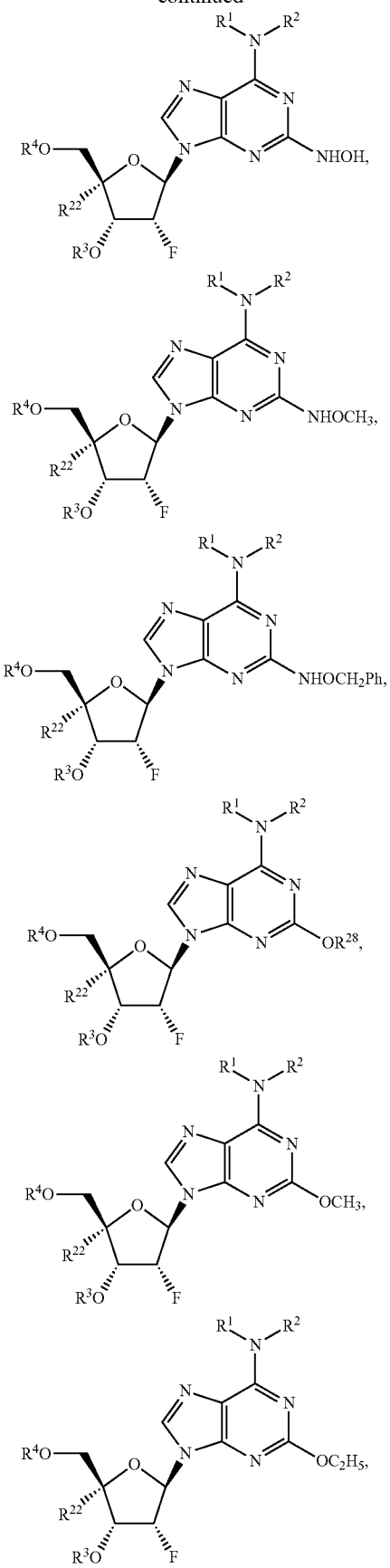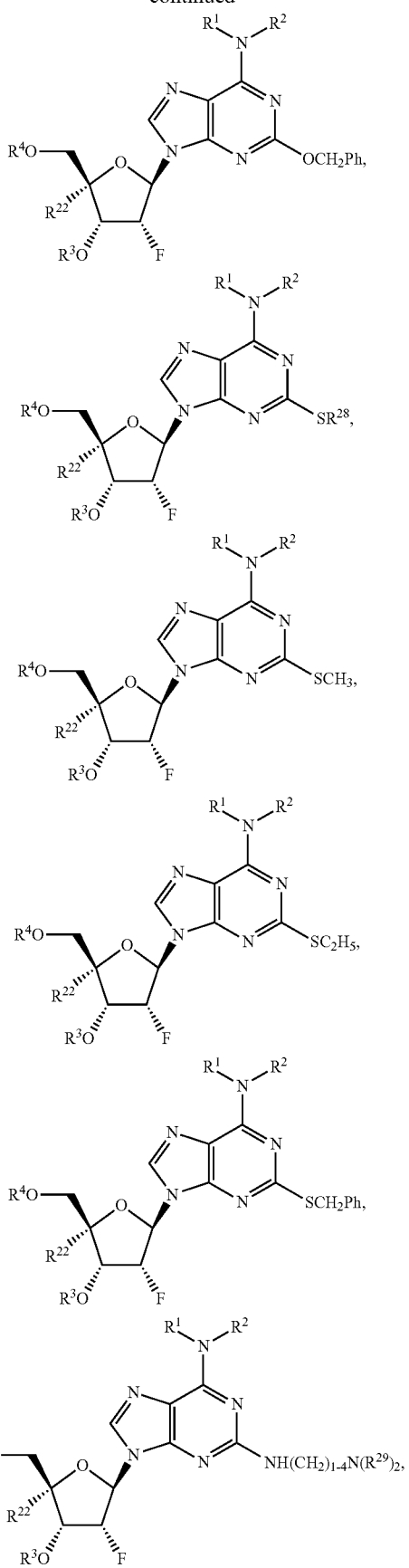

219
-continued
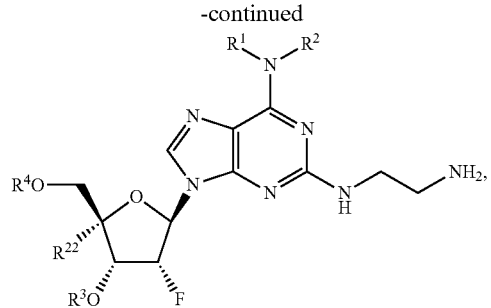
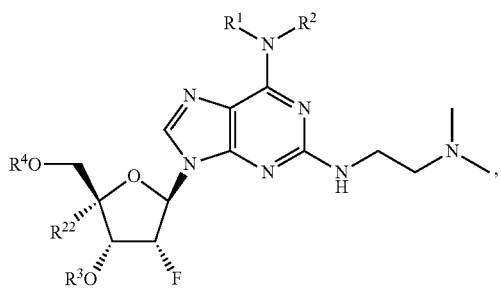
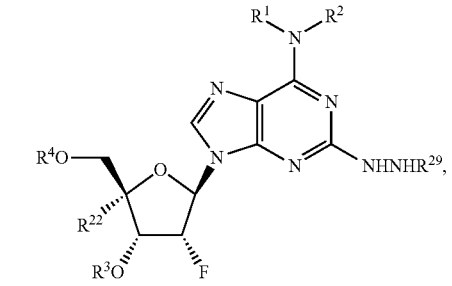
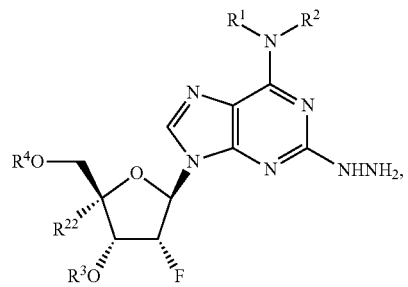
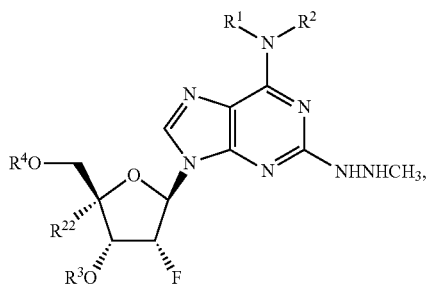
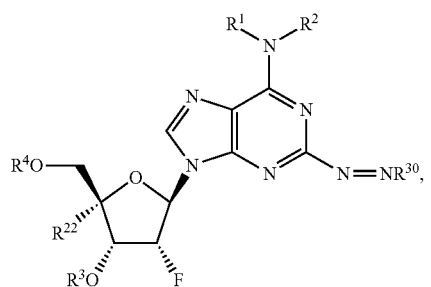
220
-continued
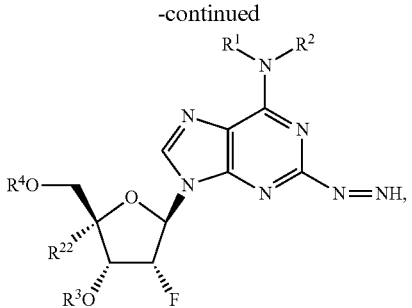
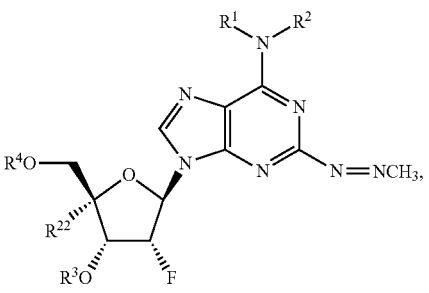
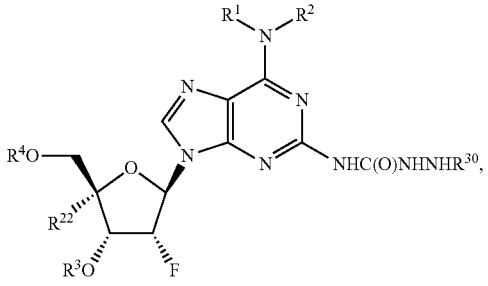
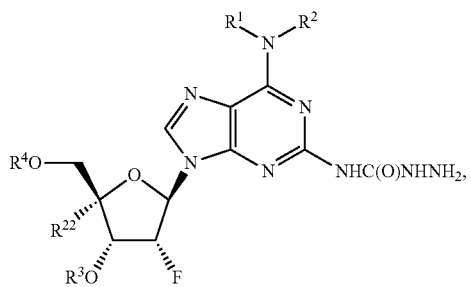
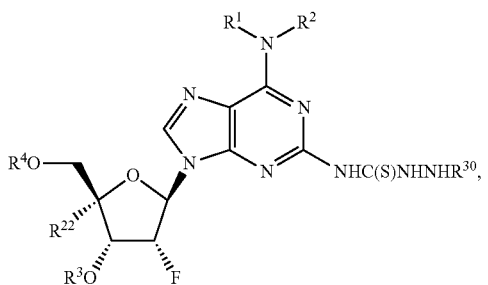
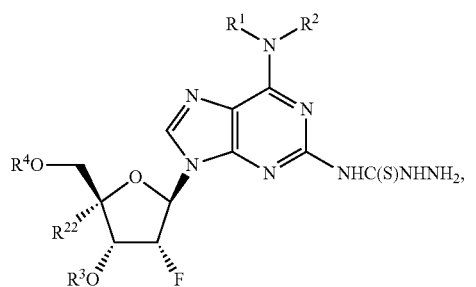

221
-continued
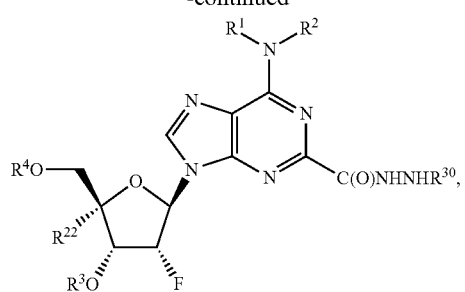
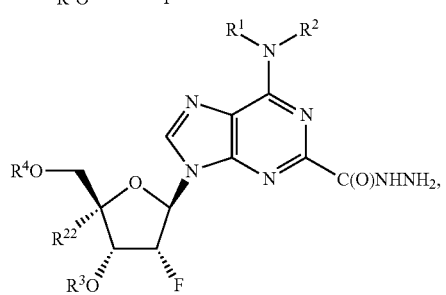
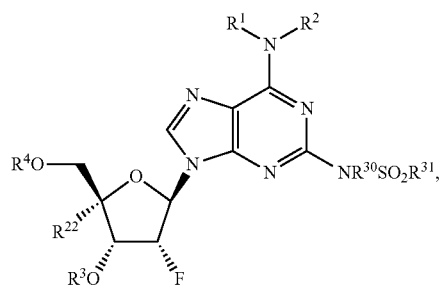
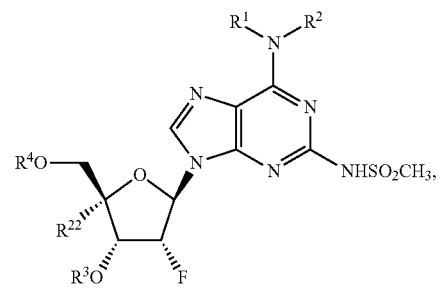
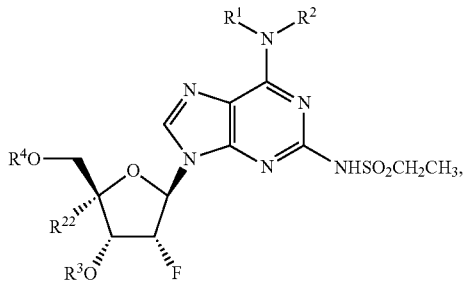
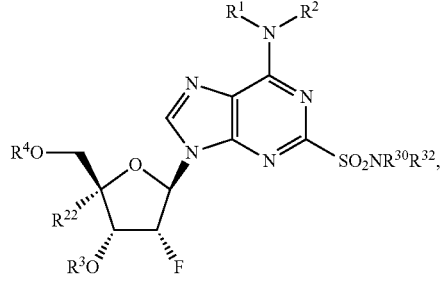
222
-continued
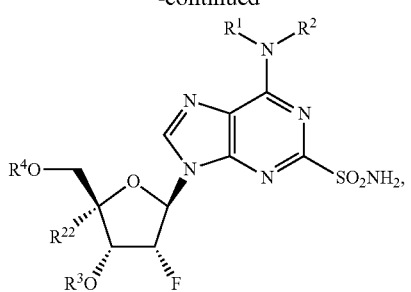
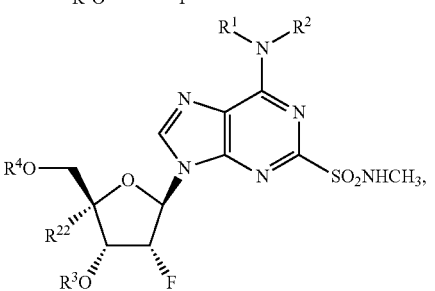
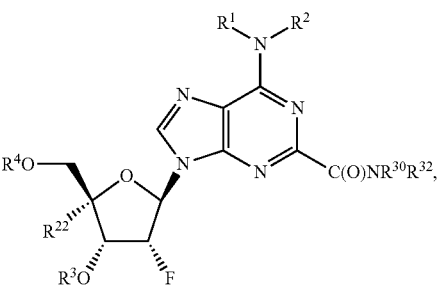
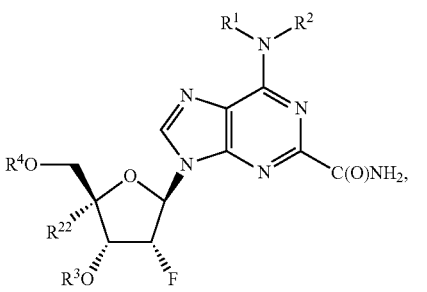
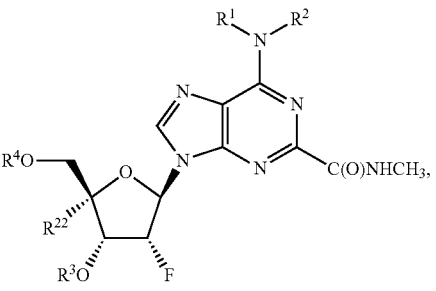
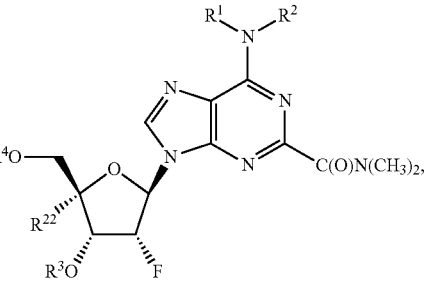

223
-continued
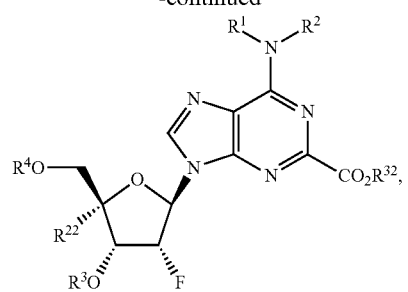
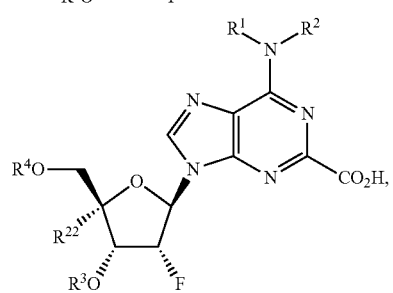
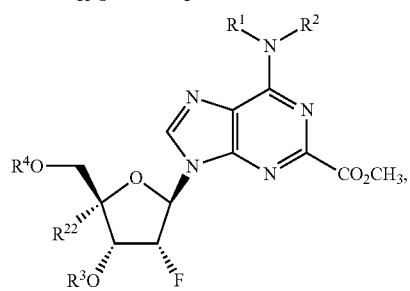
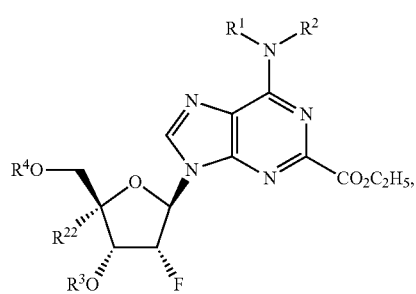
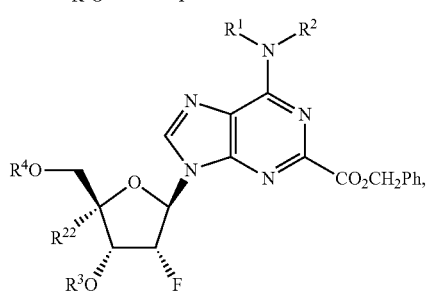
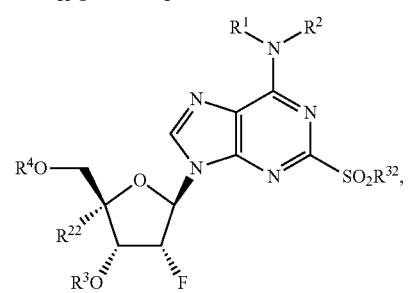
224
-continued
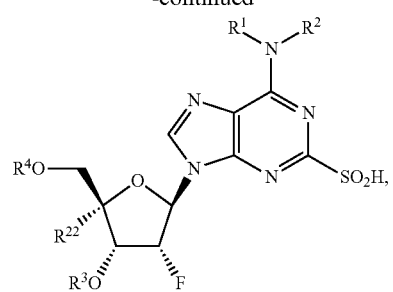
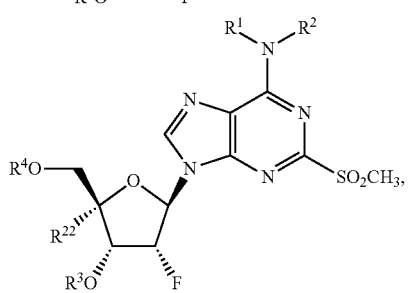
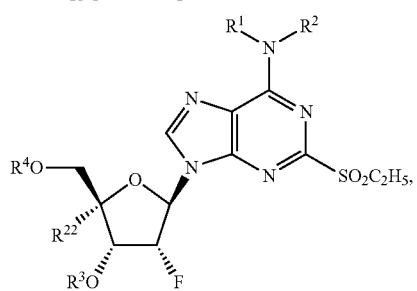
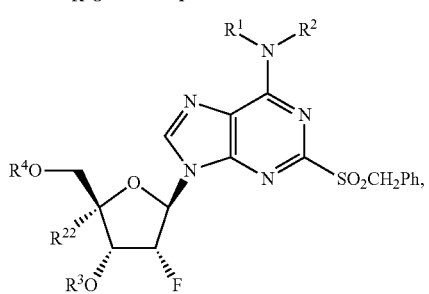
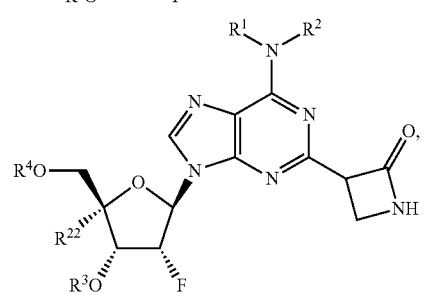
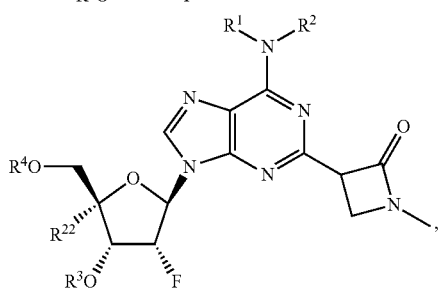

225
-continued
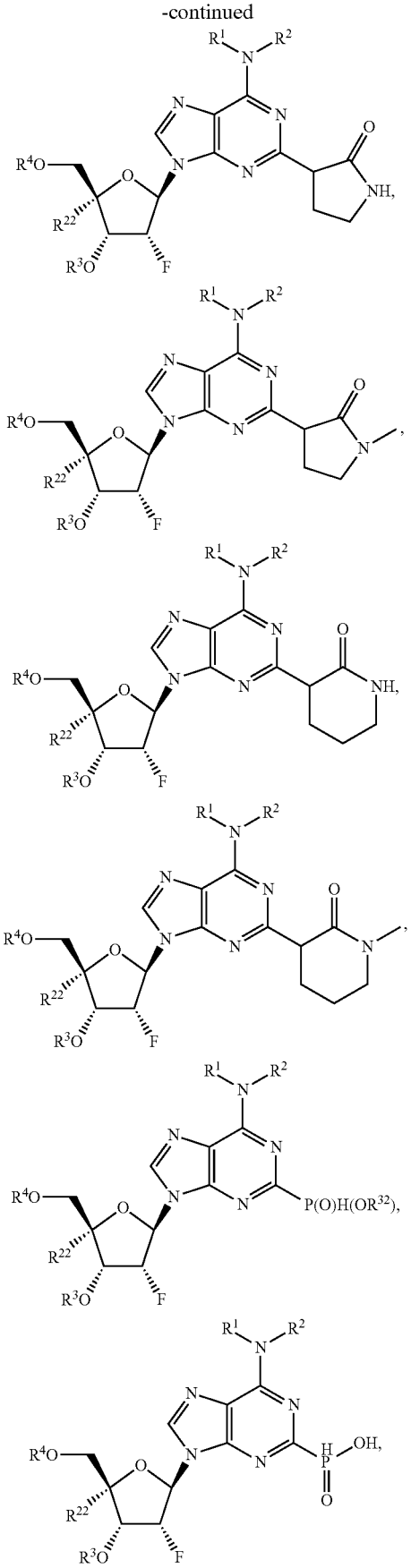
226
-continued
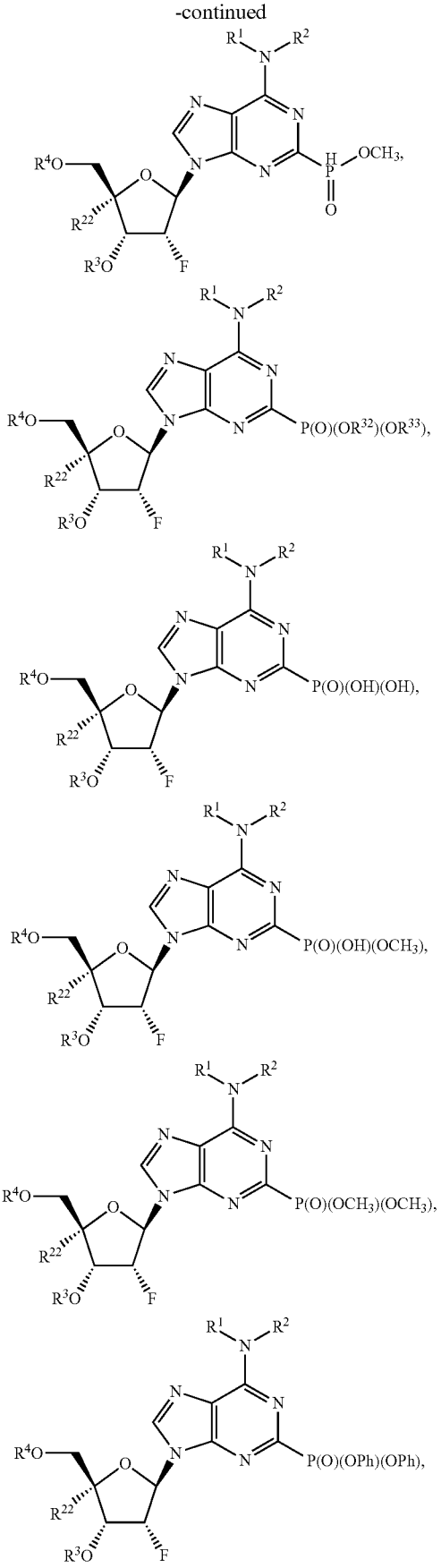

227
-continued
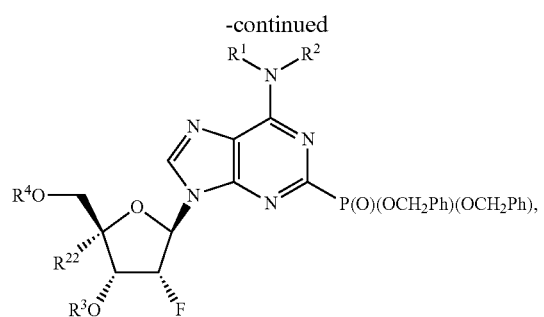
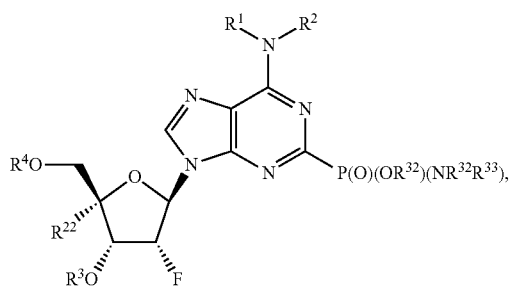
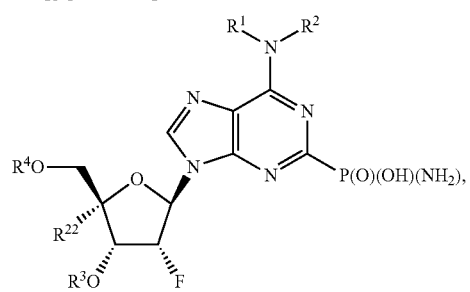
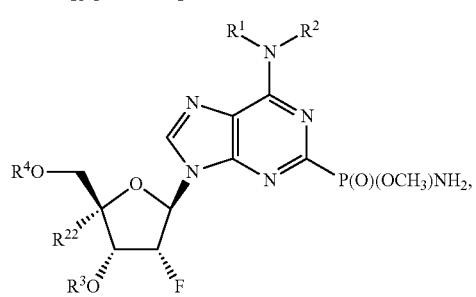
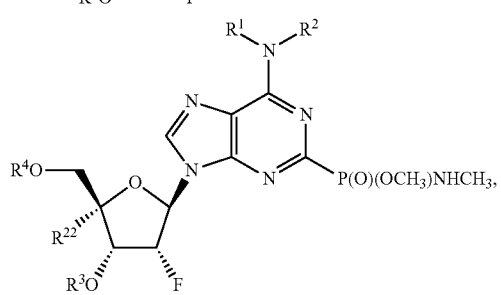
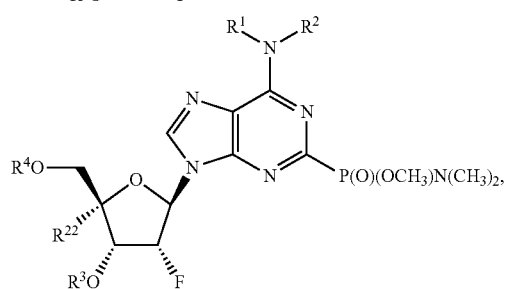
228
-continued
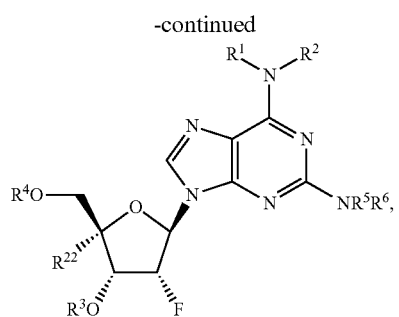
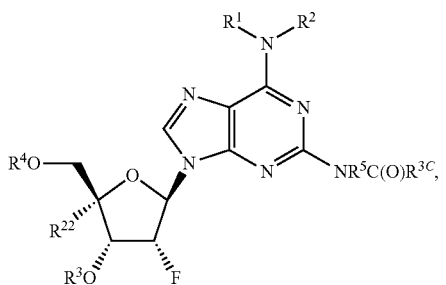
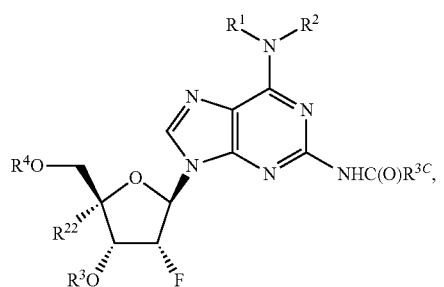
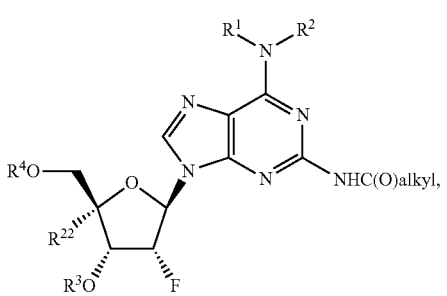
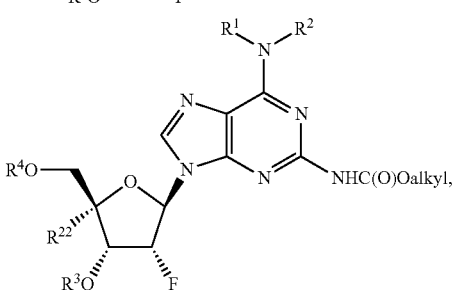
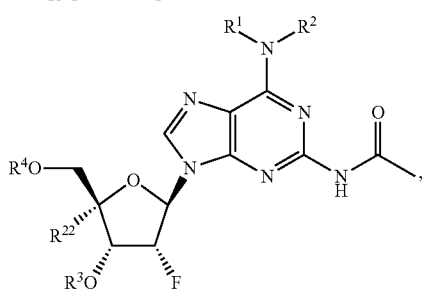

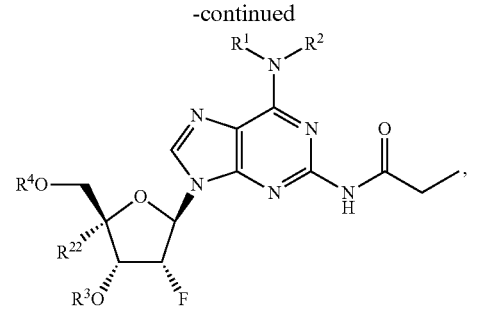
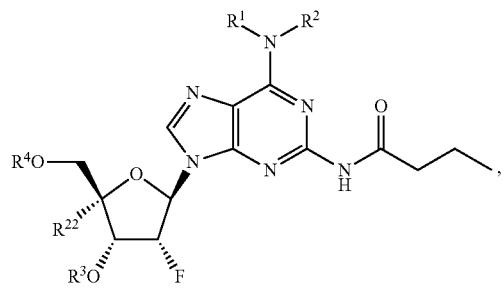
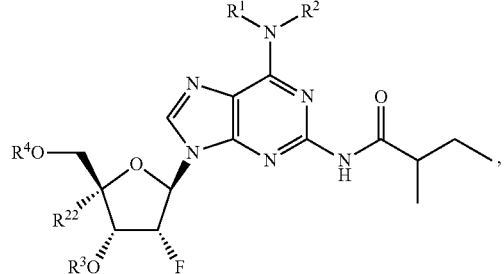
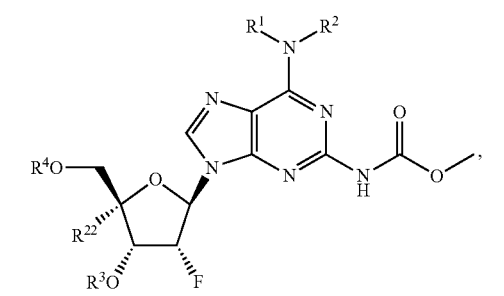
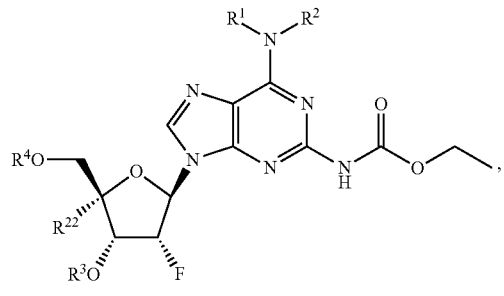
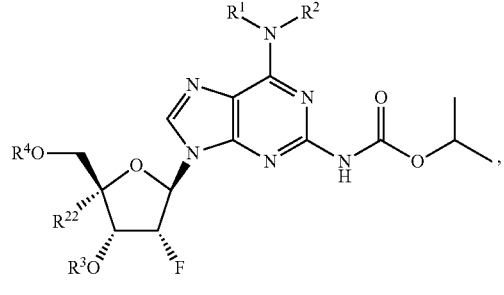
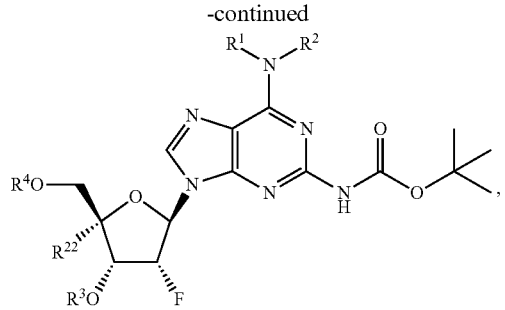
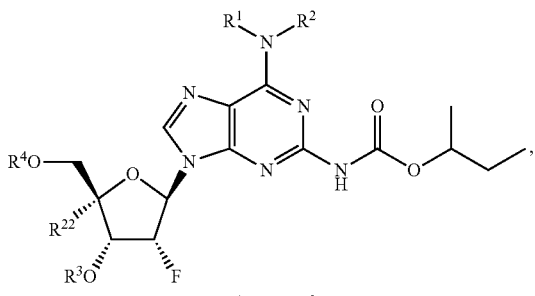
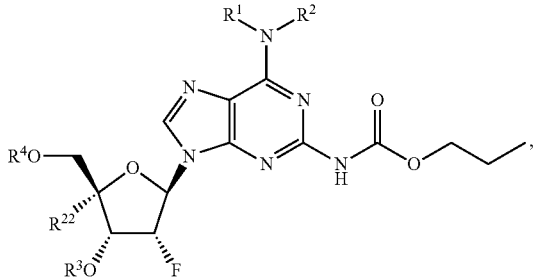
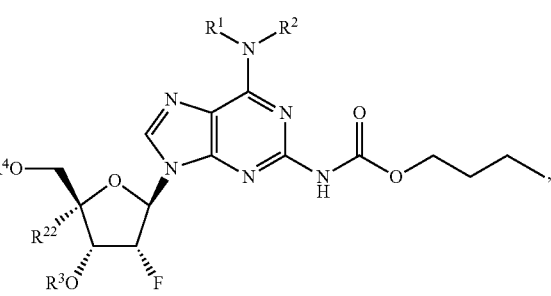
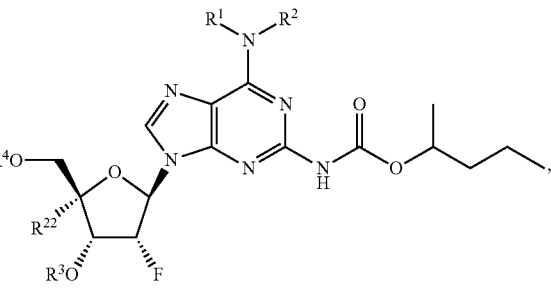
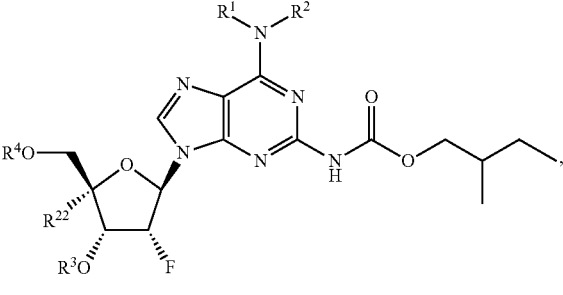

231
-continued
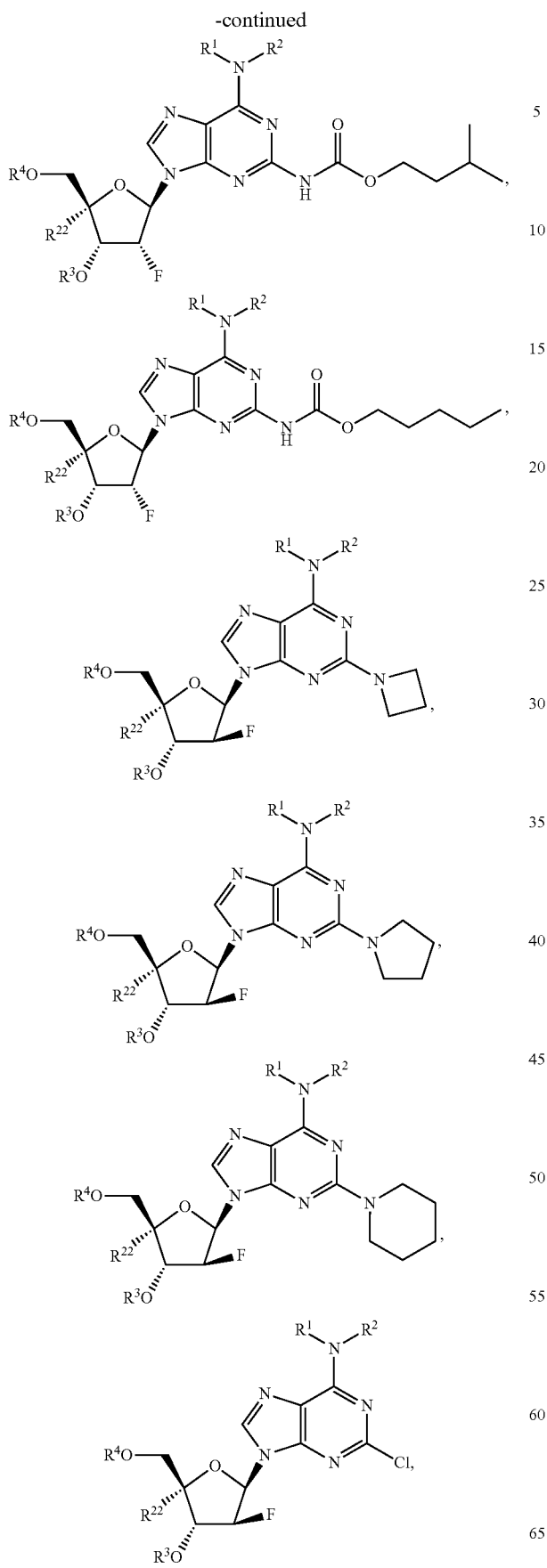
232
-continued
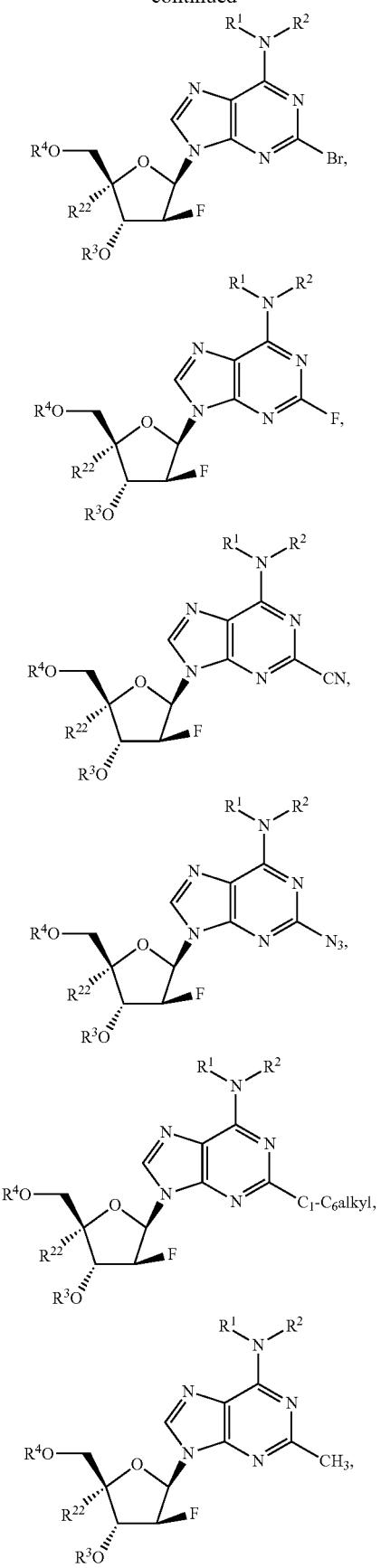

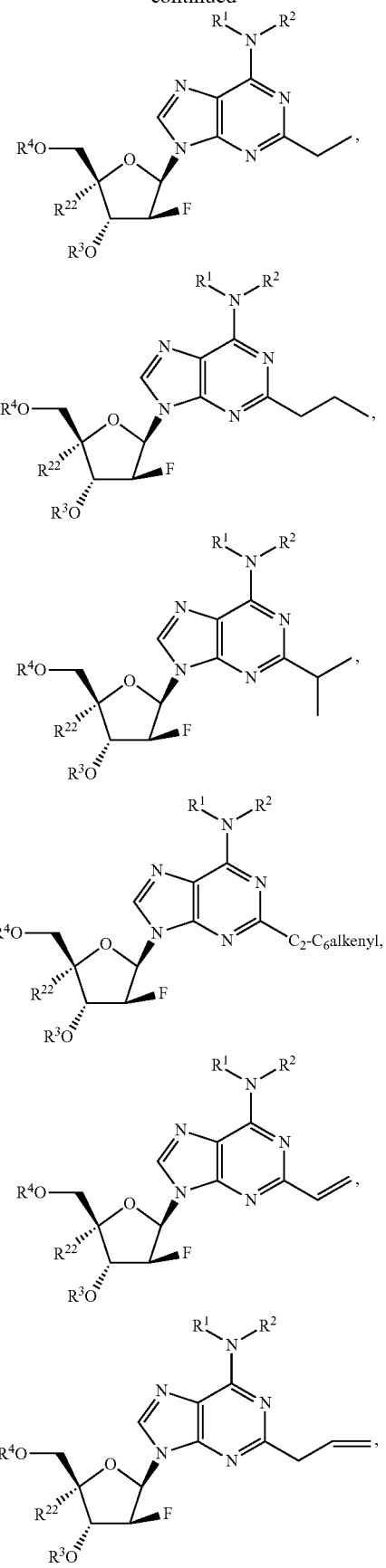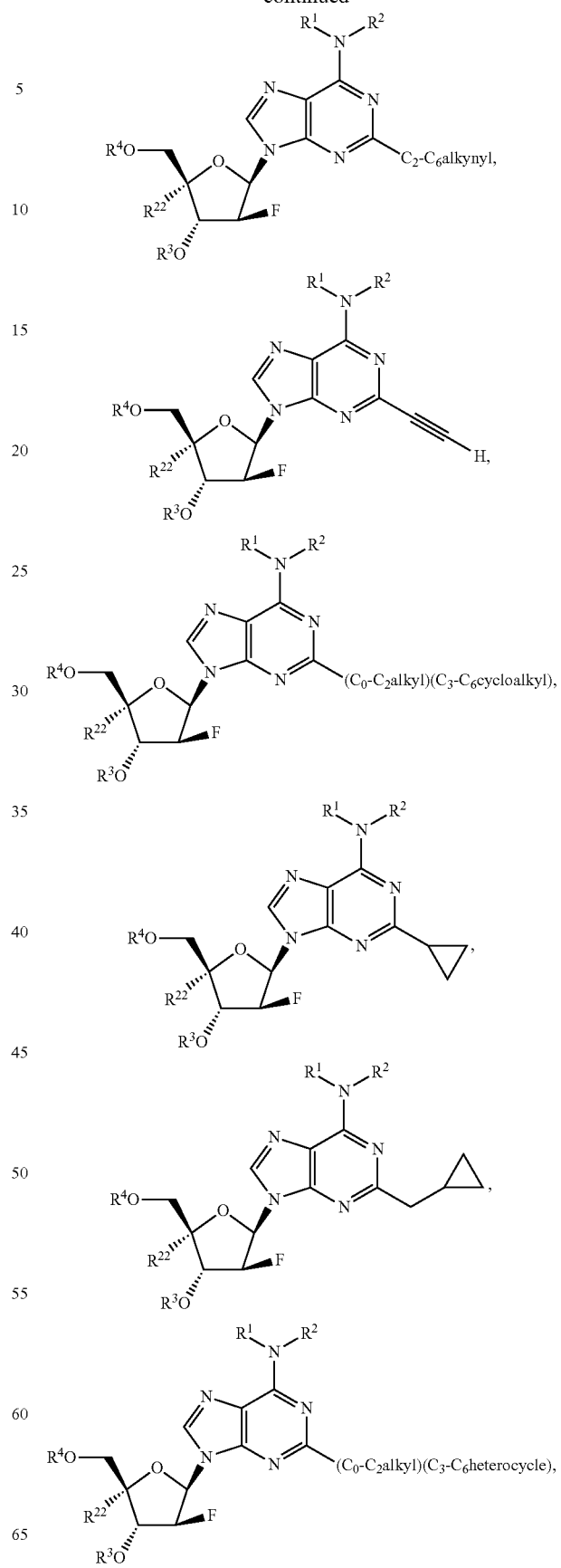

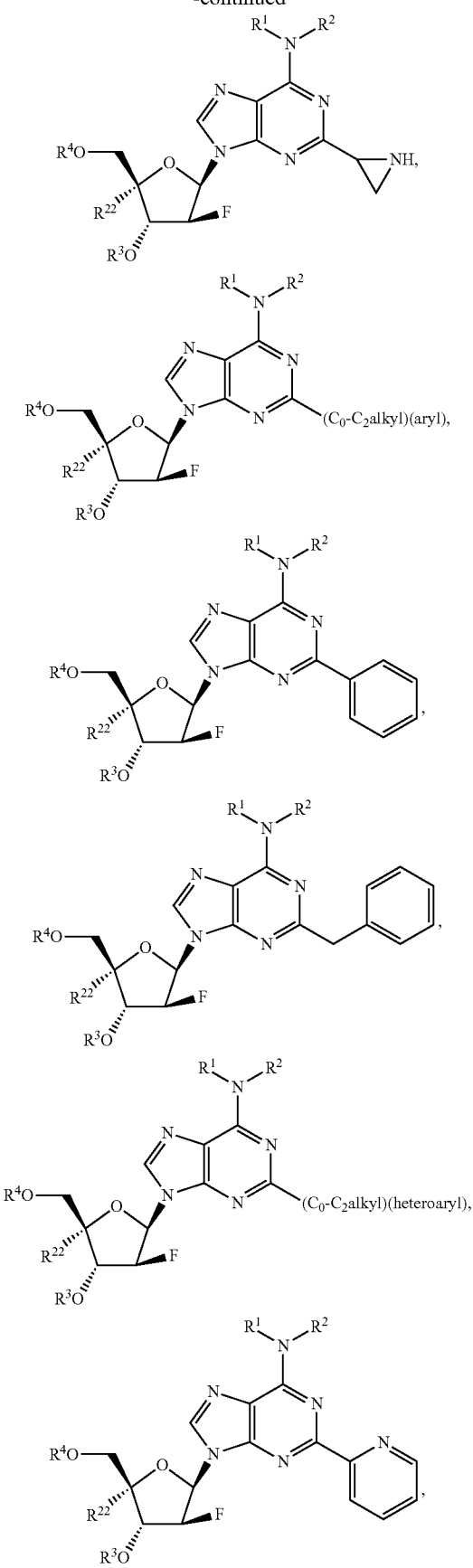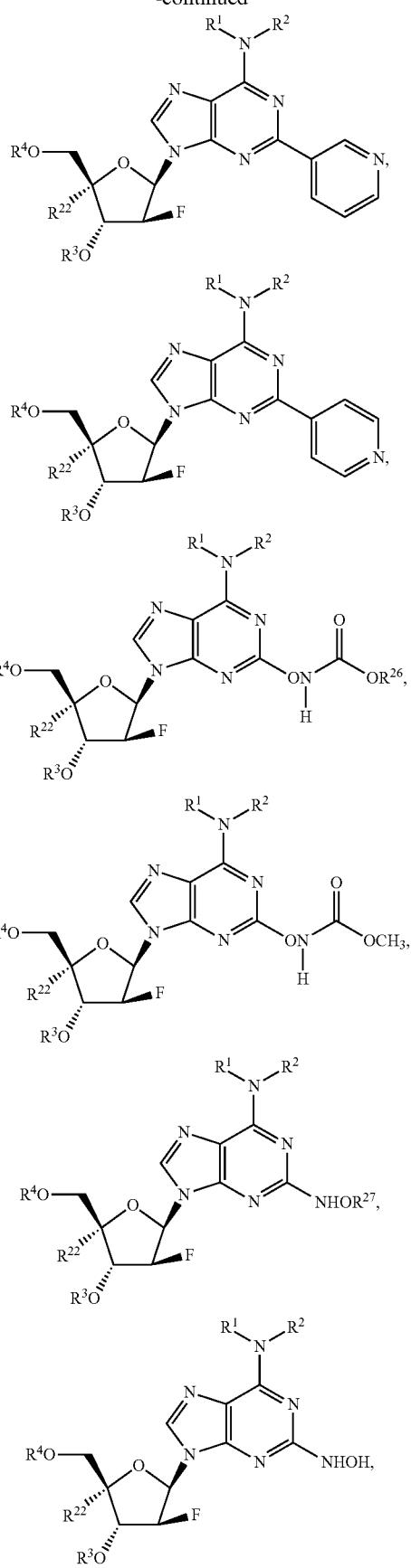

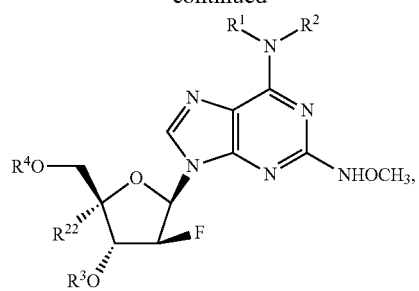
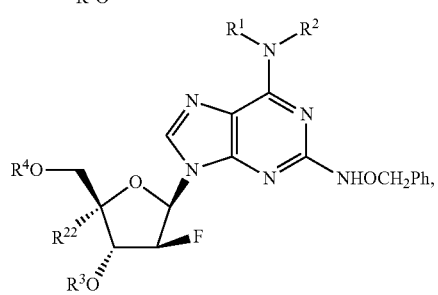
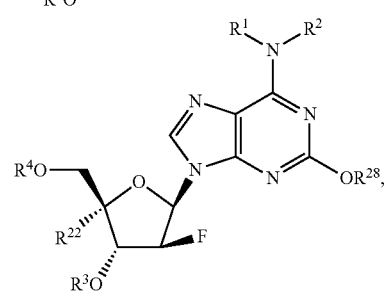
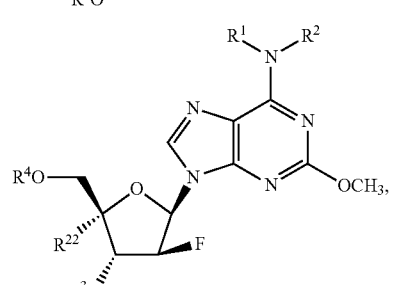
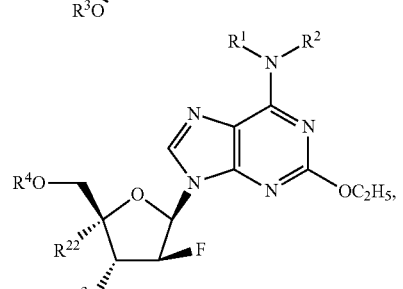
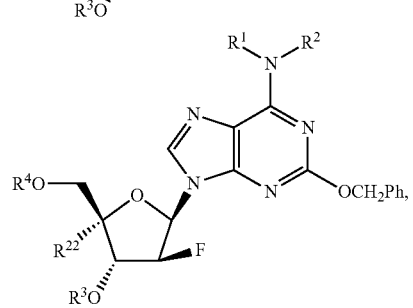
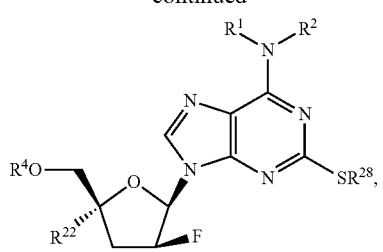
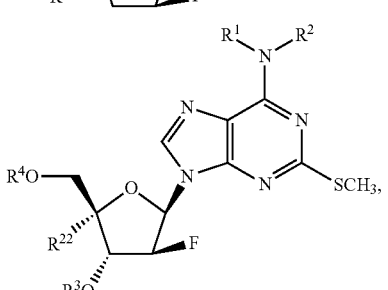
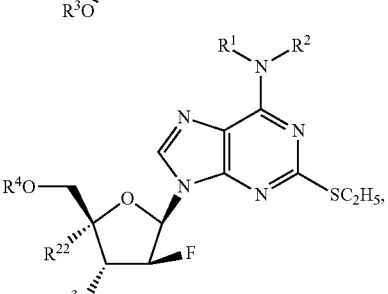
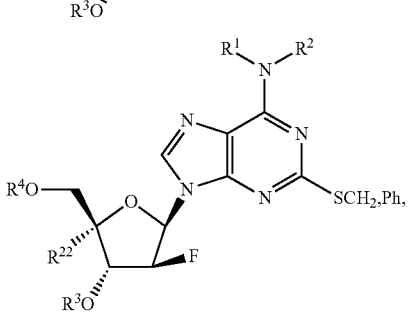
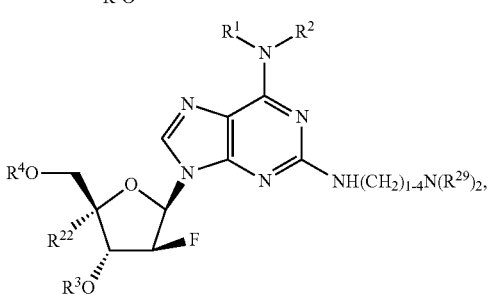
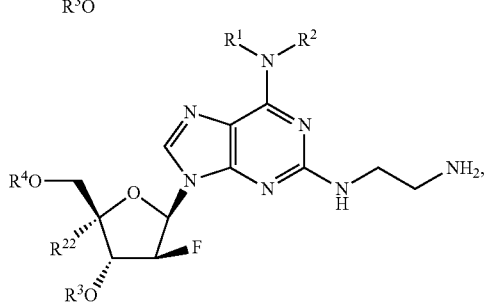

239
-continued
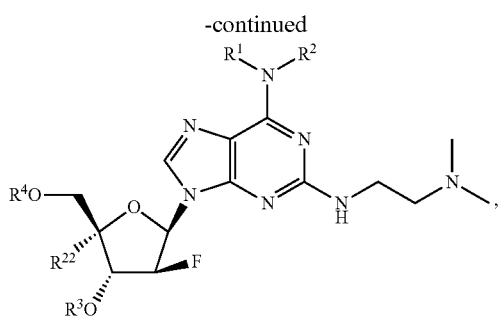
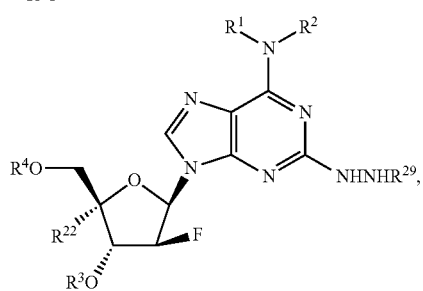
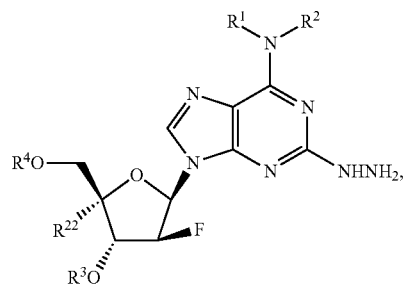
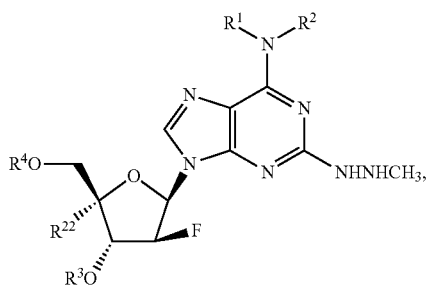
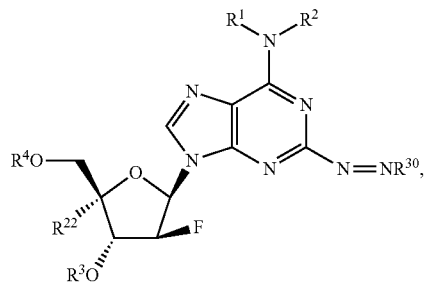
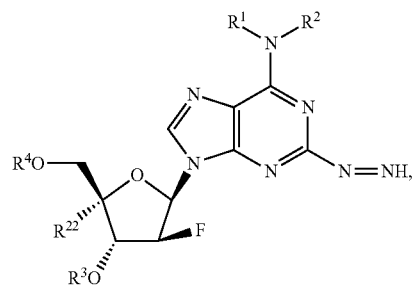
240
-continued
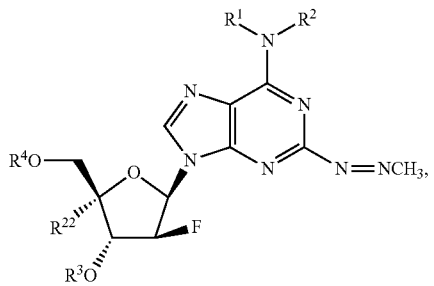
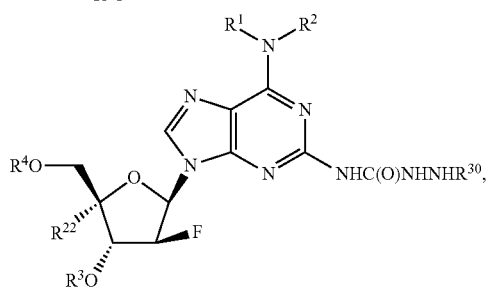
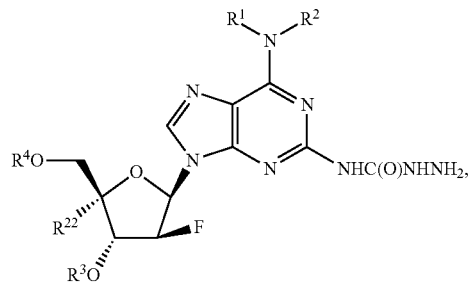
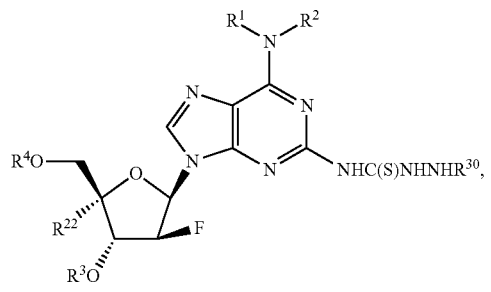
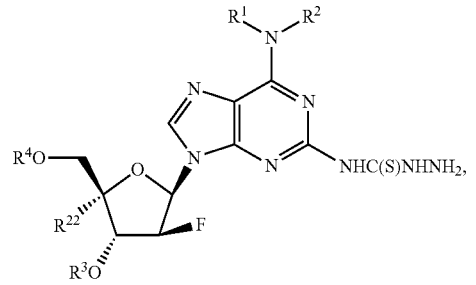
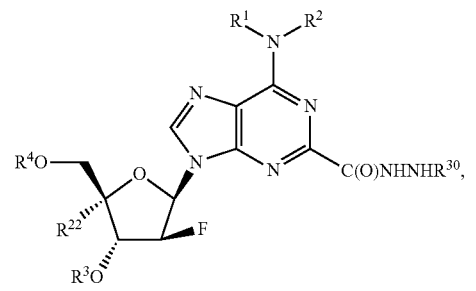

-continued
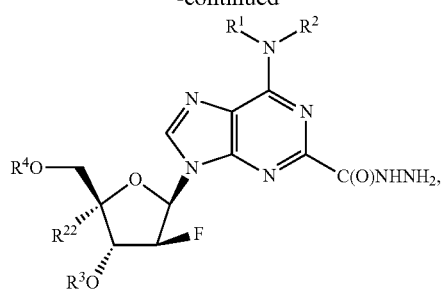
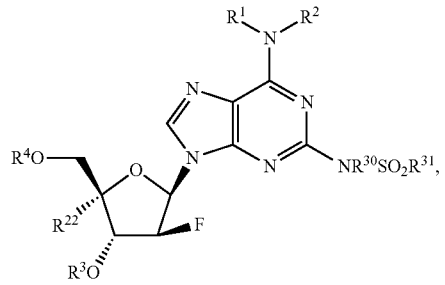
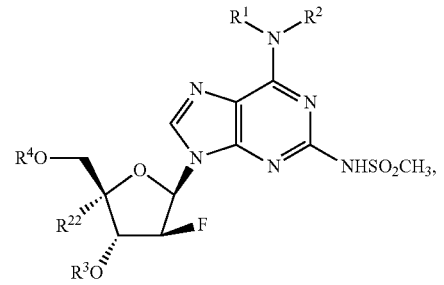
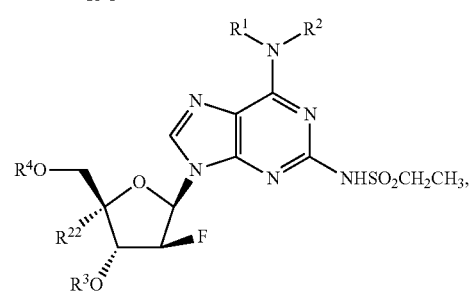
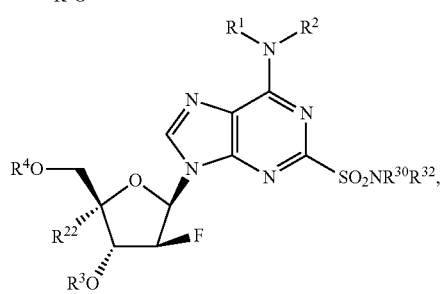
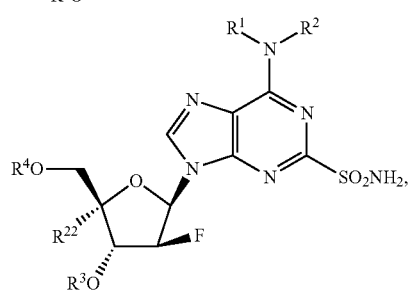
-continued
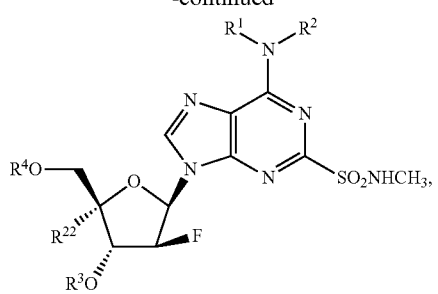
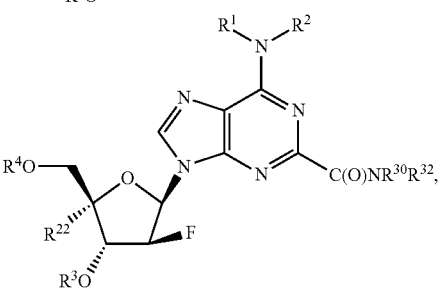
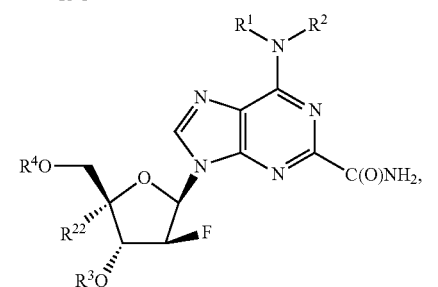
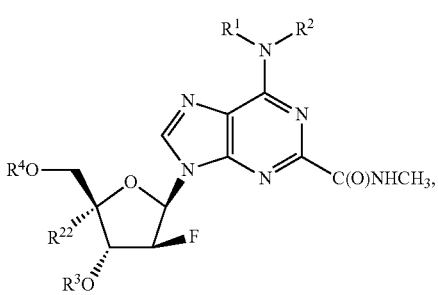
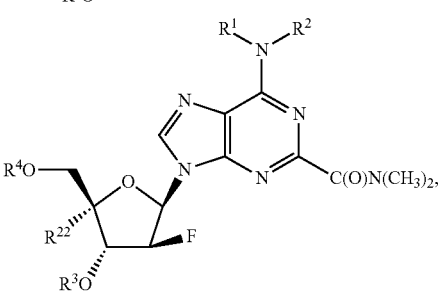
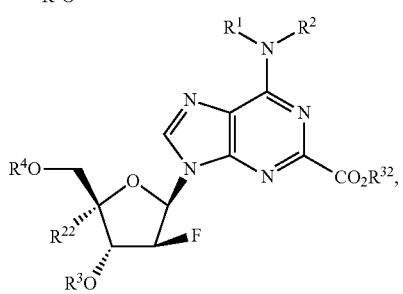

-continued
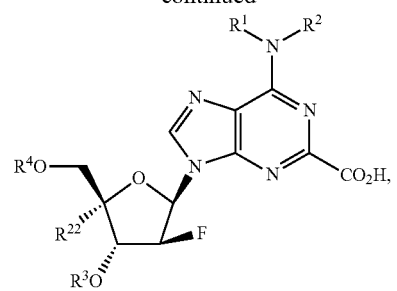
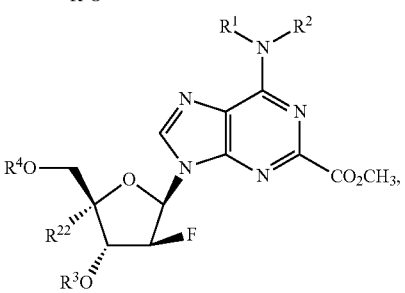
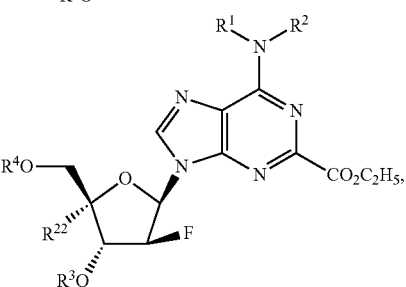
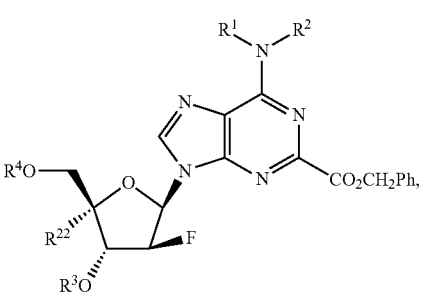
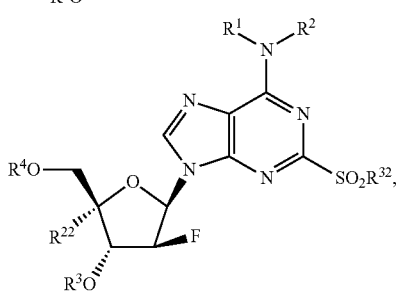
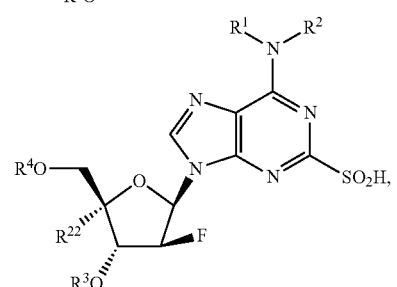
-continued
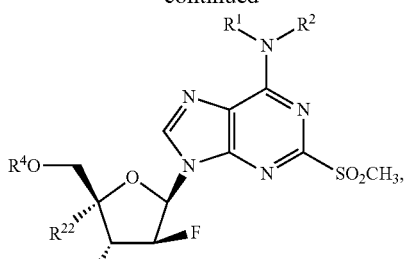
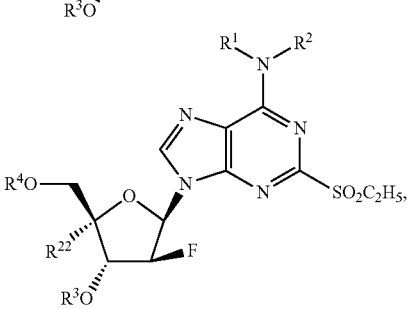
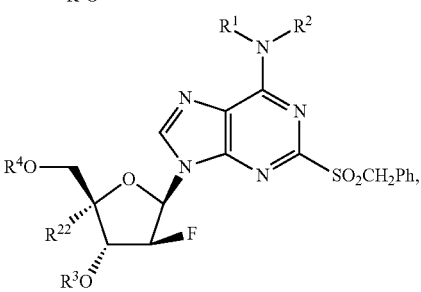
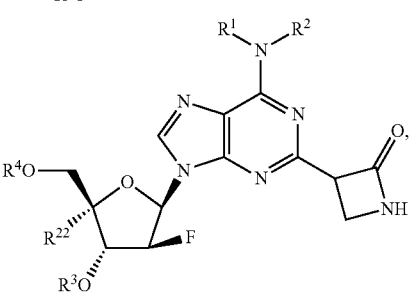
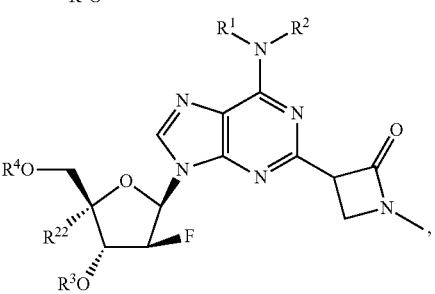
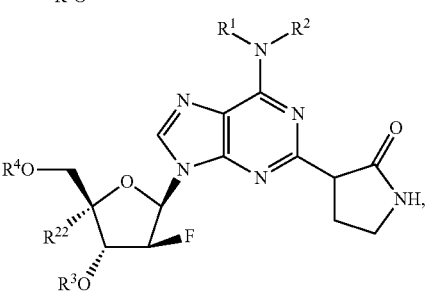

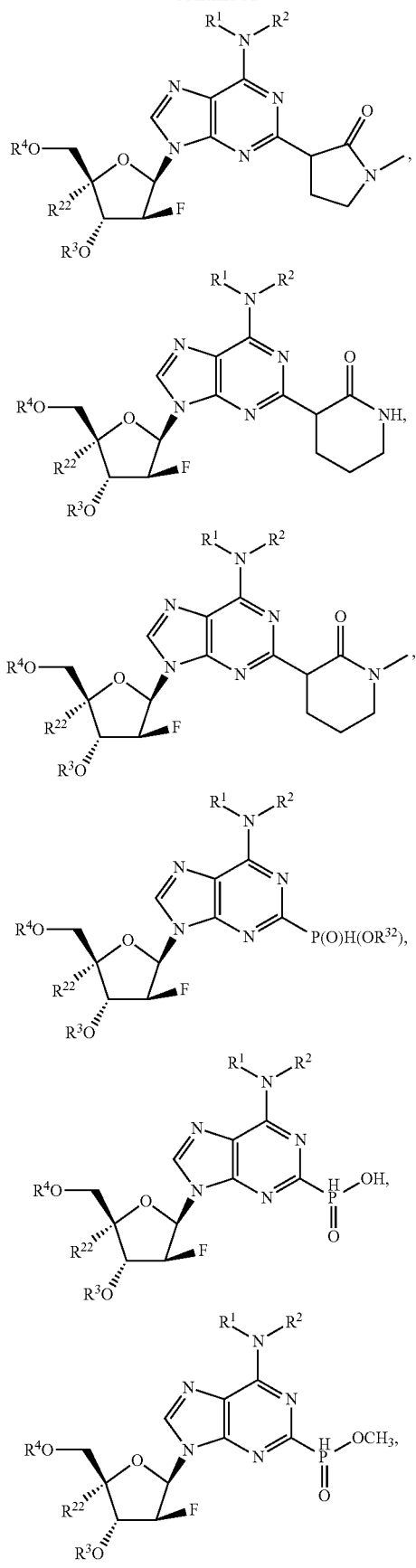
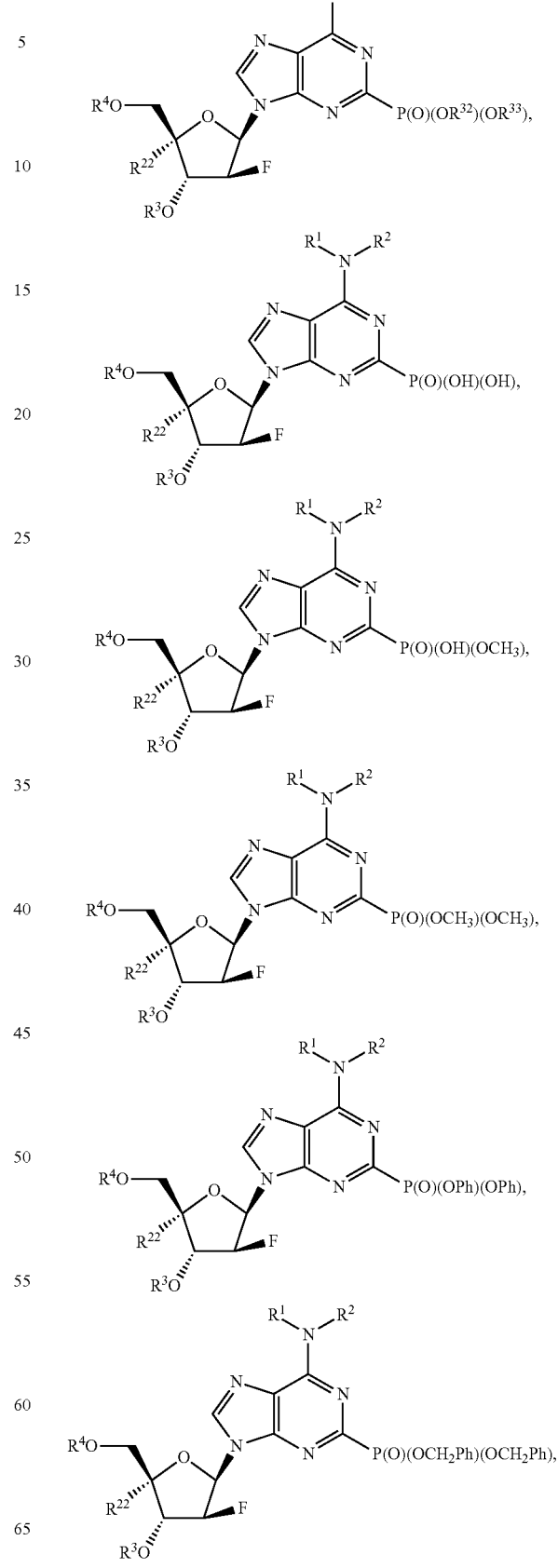

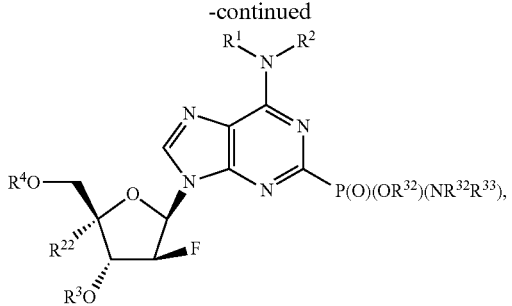
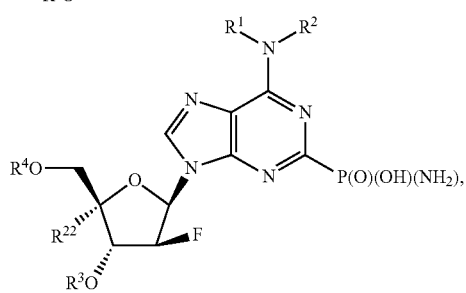
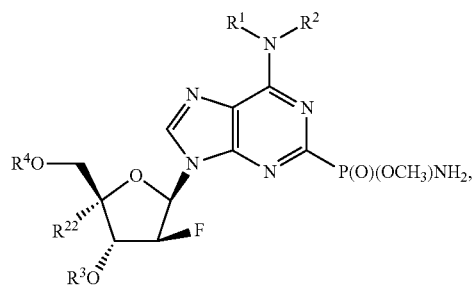
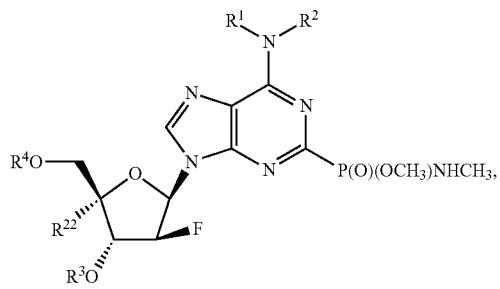
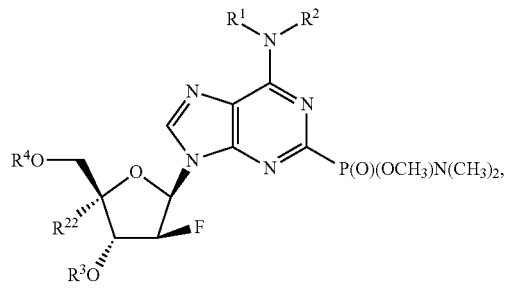
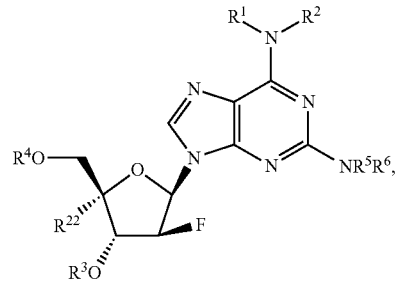
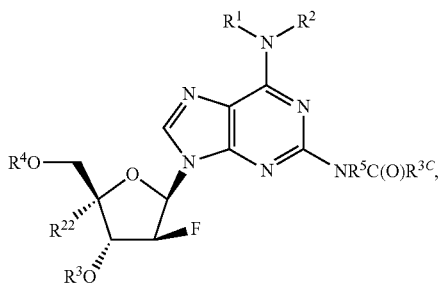
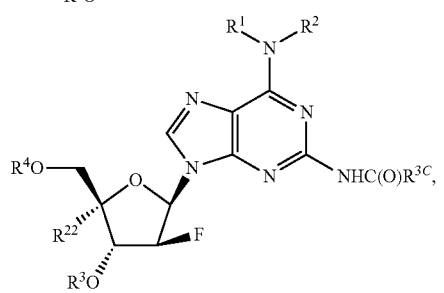
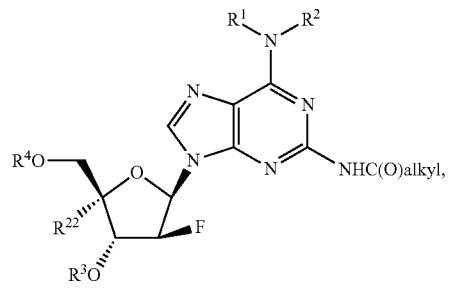
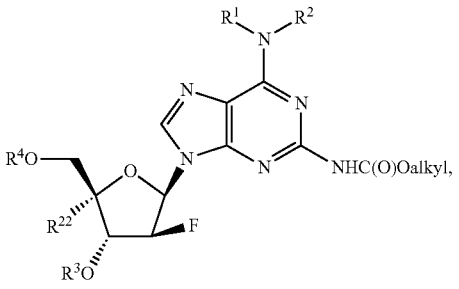
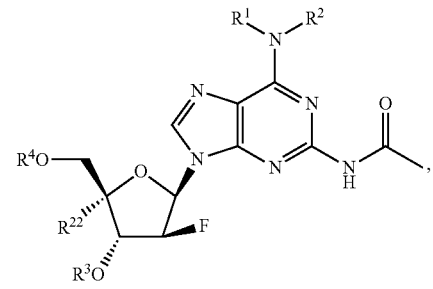
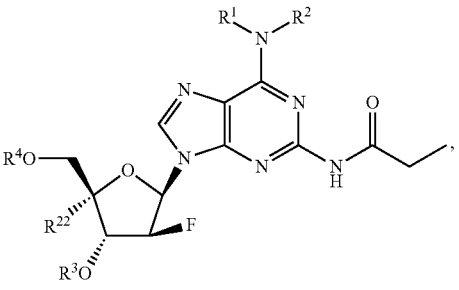

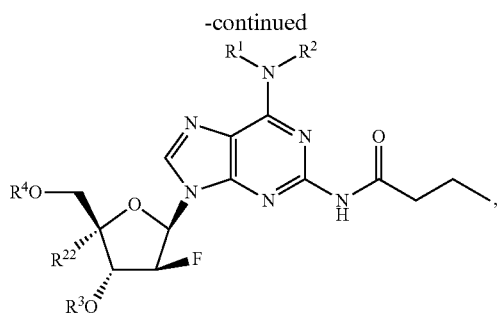
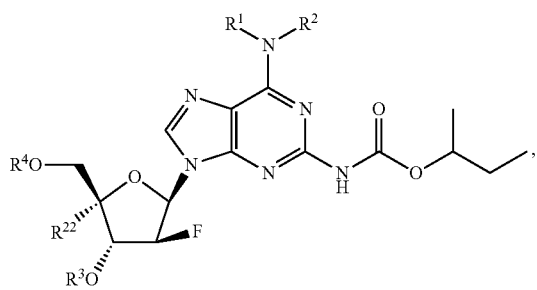
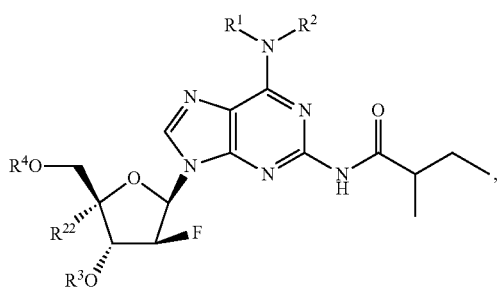
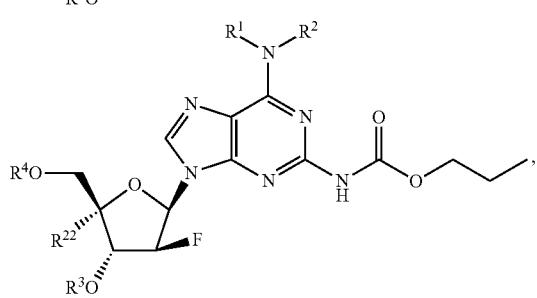
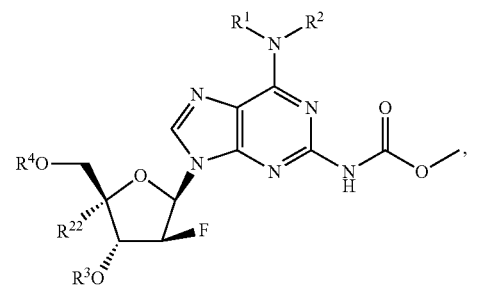
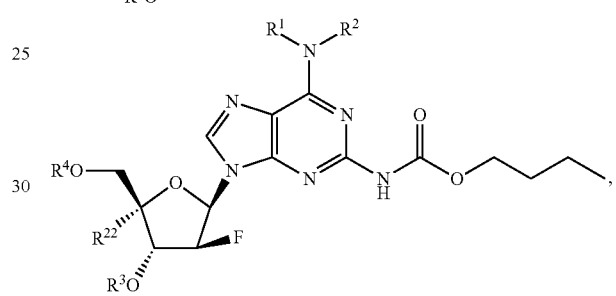
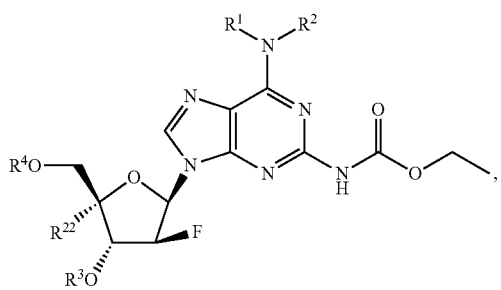
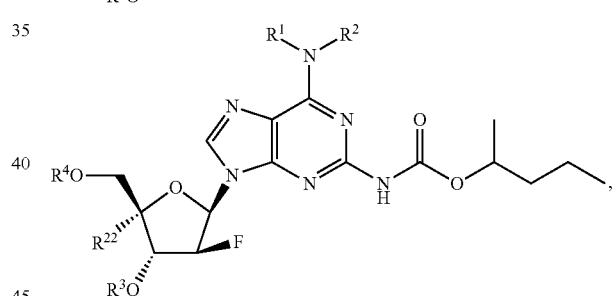
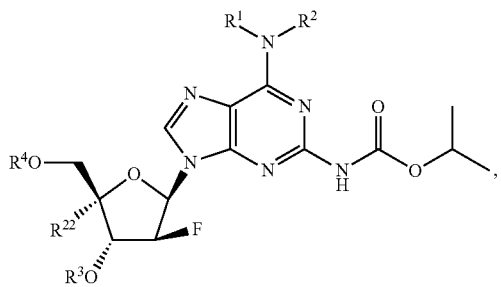
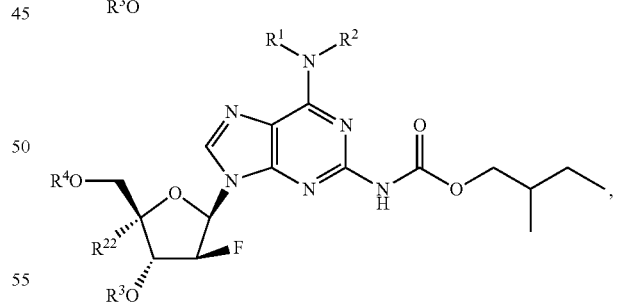
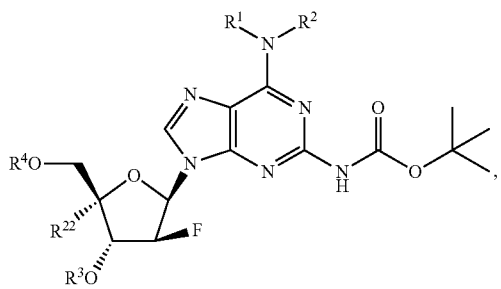
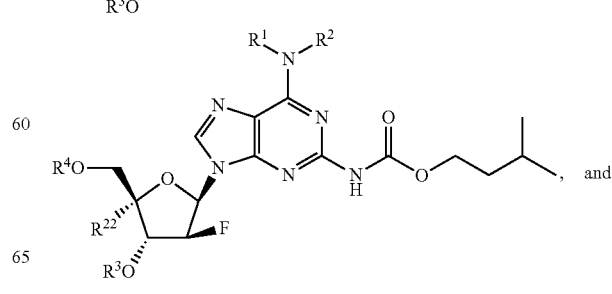

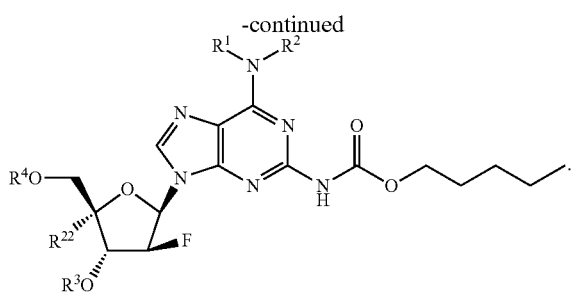

In some embodiments, $R^3$ is H and $R^4$ is

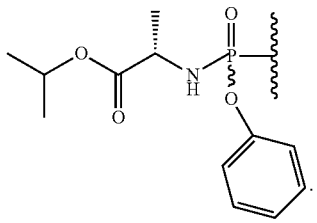

In some embodiments, $R^3$ is H and $R^4$ is

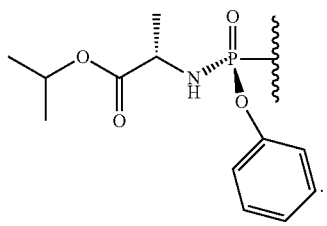

In some embodiments, $R^3$ is H and $R^4$ is

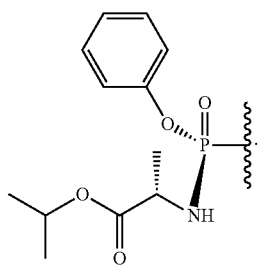 [SMILES: *[P@](=O)(N[C@@H](C)C(=O)OC(C)C)Oc1ccccc1]

In some embodiments, $R^1$ is $CH_3$, $R^2$ is H, $R^3$ is H and $R^4$ is

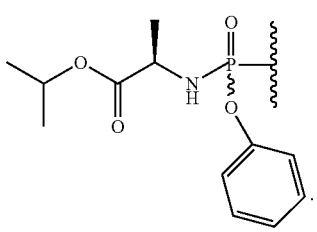

In some embodiments, $R^1$ is $CH_3$, $R^2$ is H, $R^3$ is H and $R^4$ is

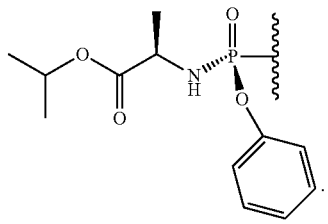

In some embodiments, $R^3$ is H and $R^4$ is

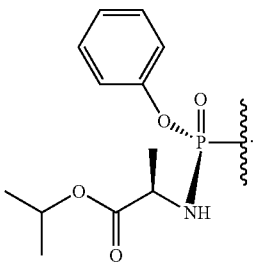 [SMILES: *[P@](=O)(N[C@H](C)C(=O)OC(C)C)Oc1ccccc1]

In one embodiment, a compound of Formula II is provided. Non-limiting examples of compounds of Formula II include:

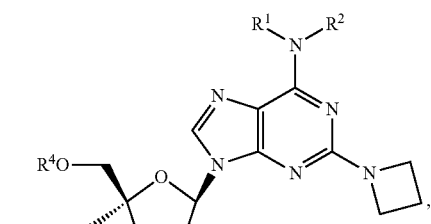

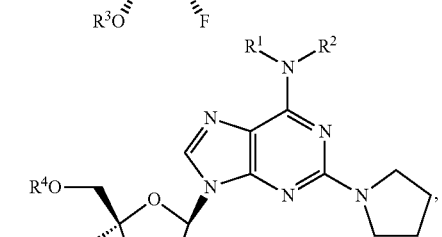

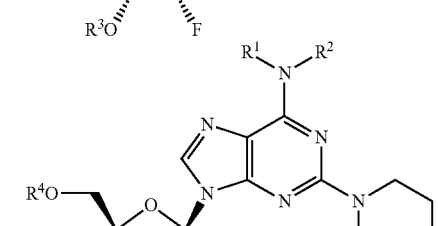

253
-continued
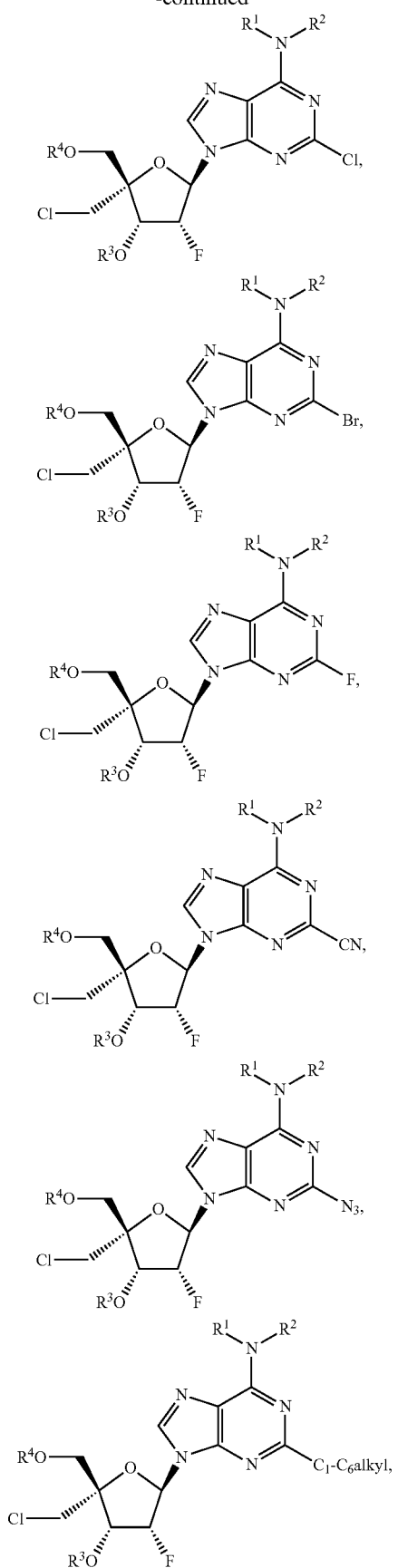
254
-continued
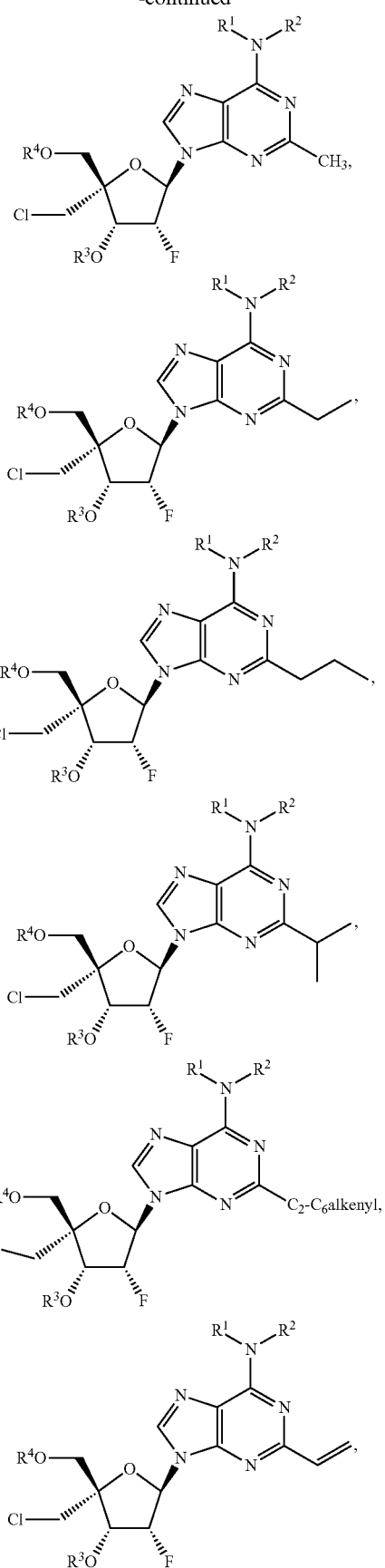

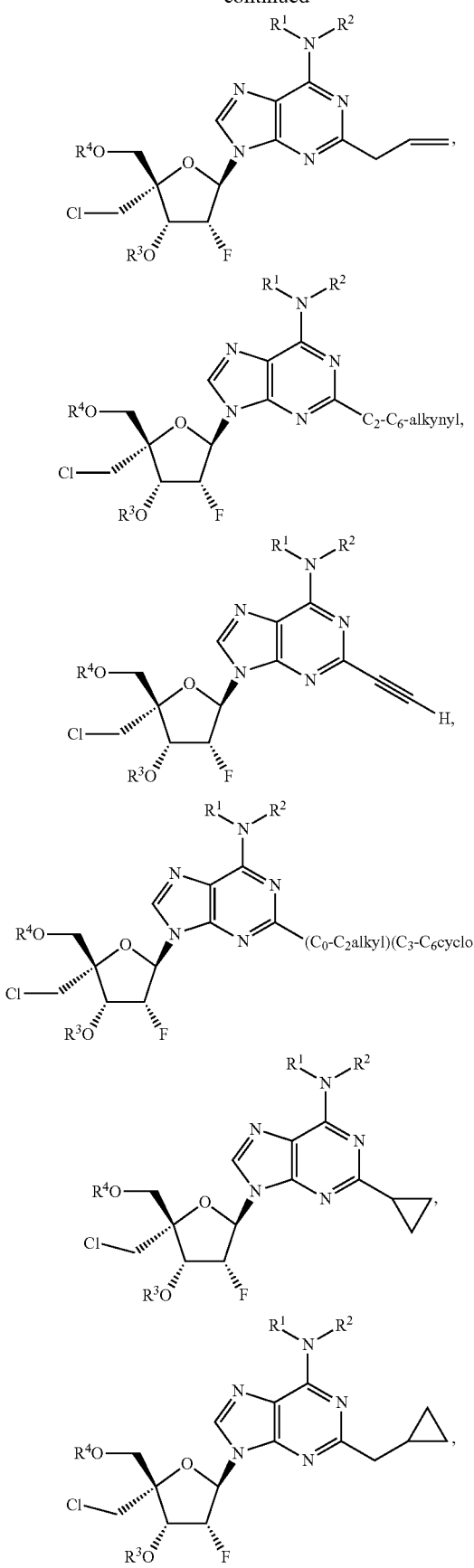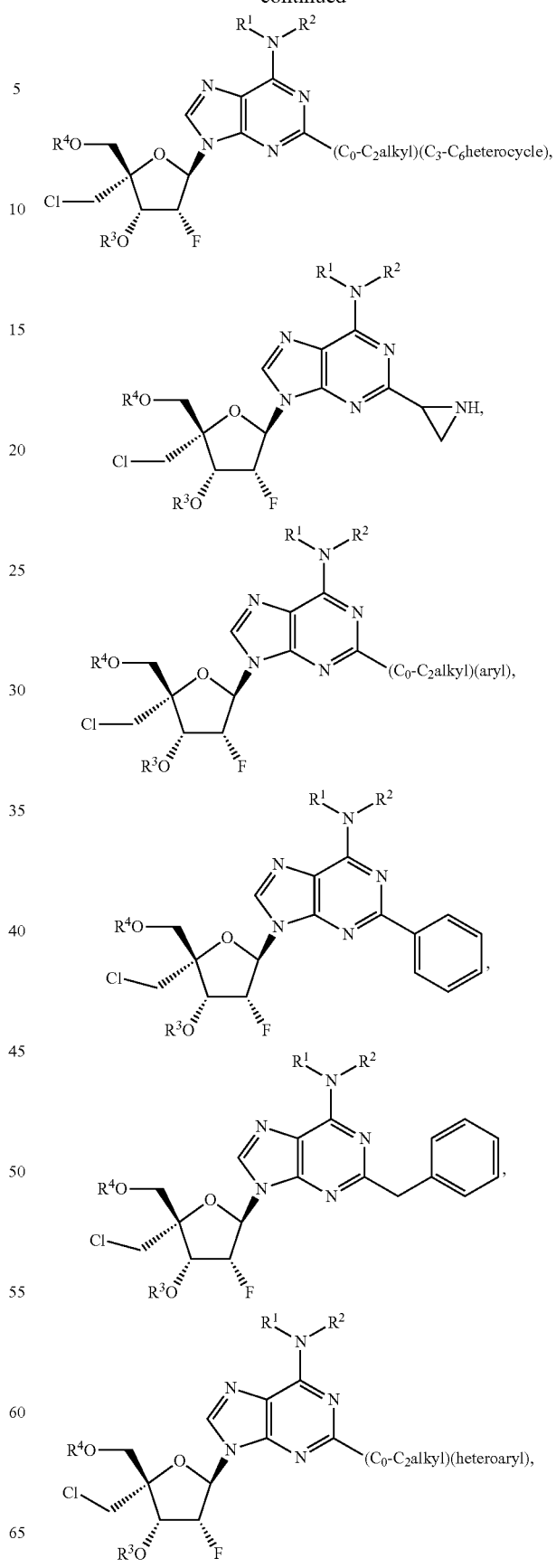

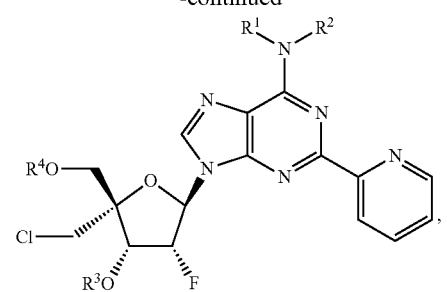
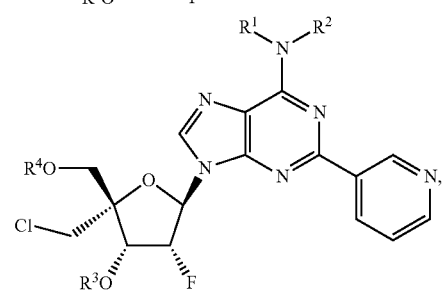
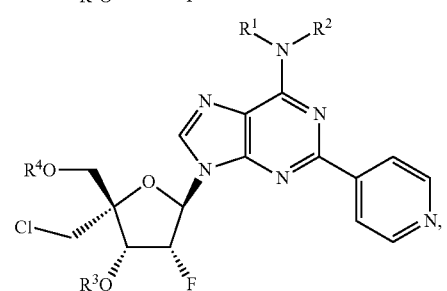
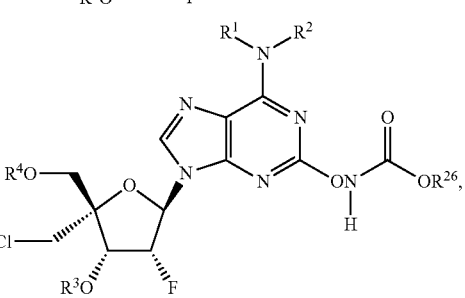
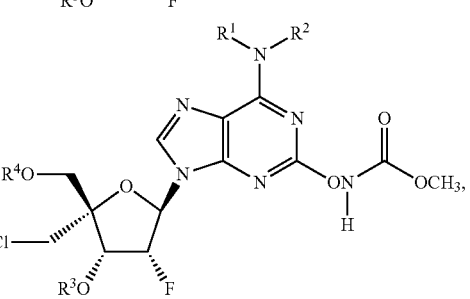
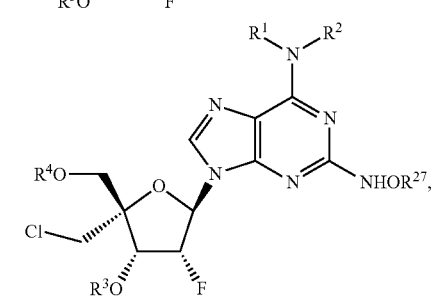
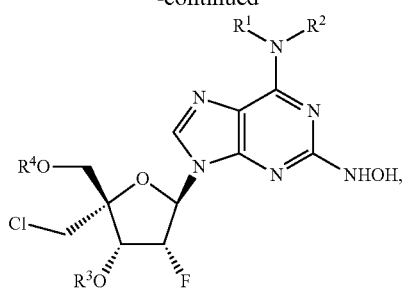
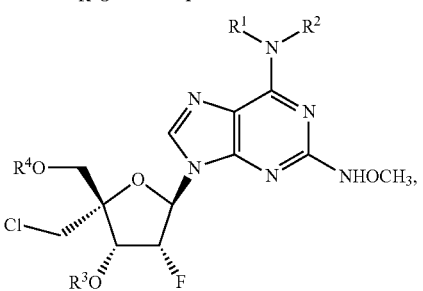
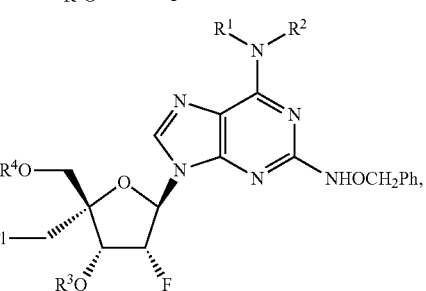
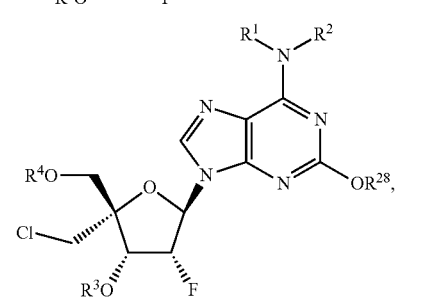
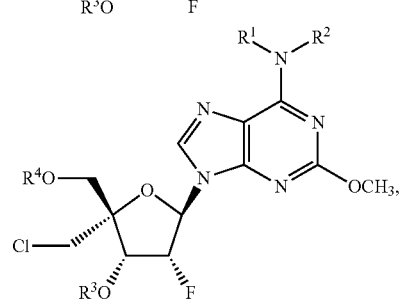
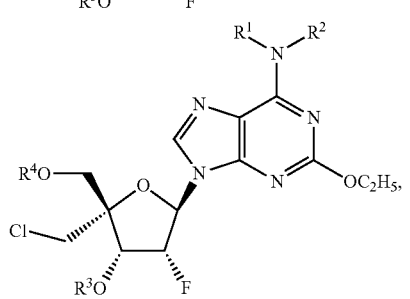

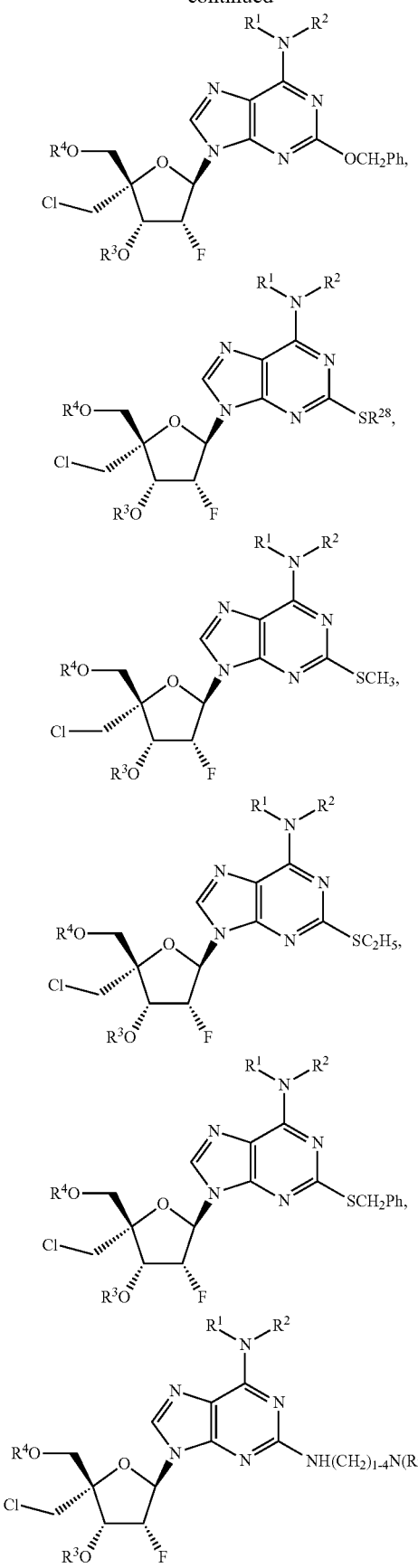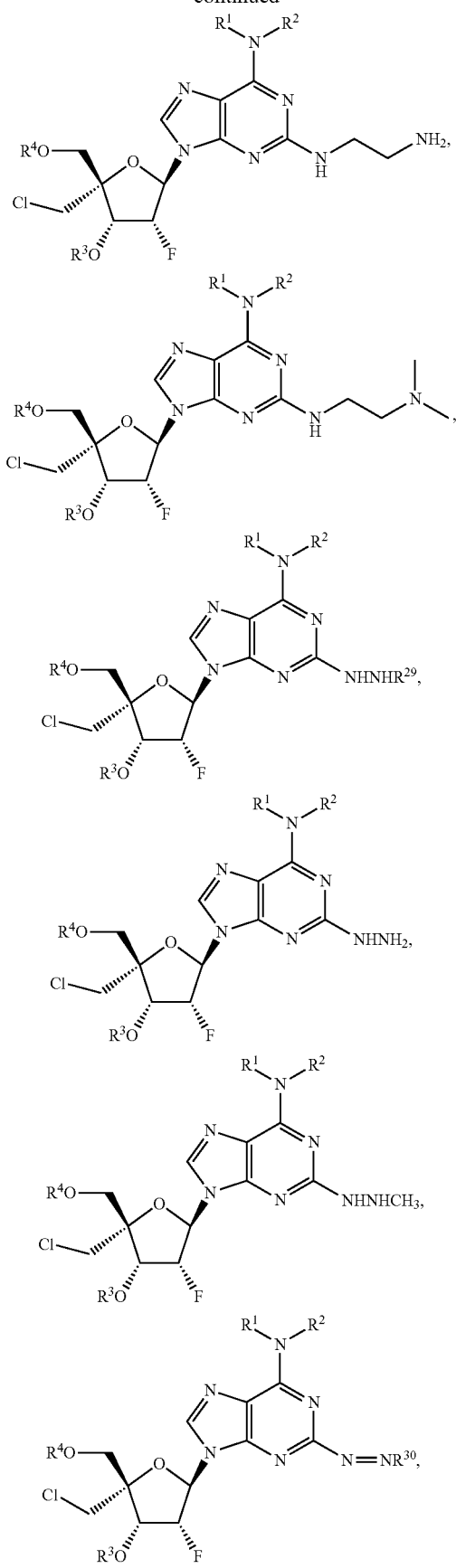

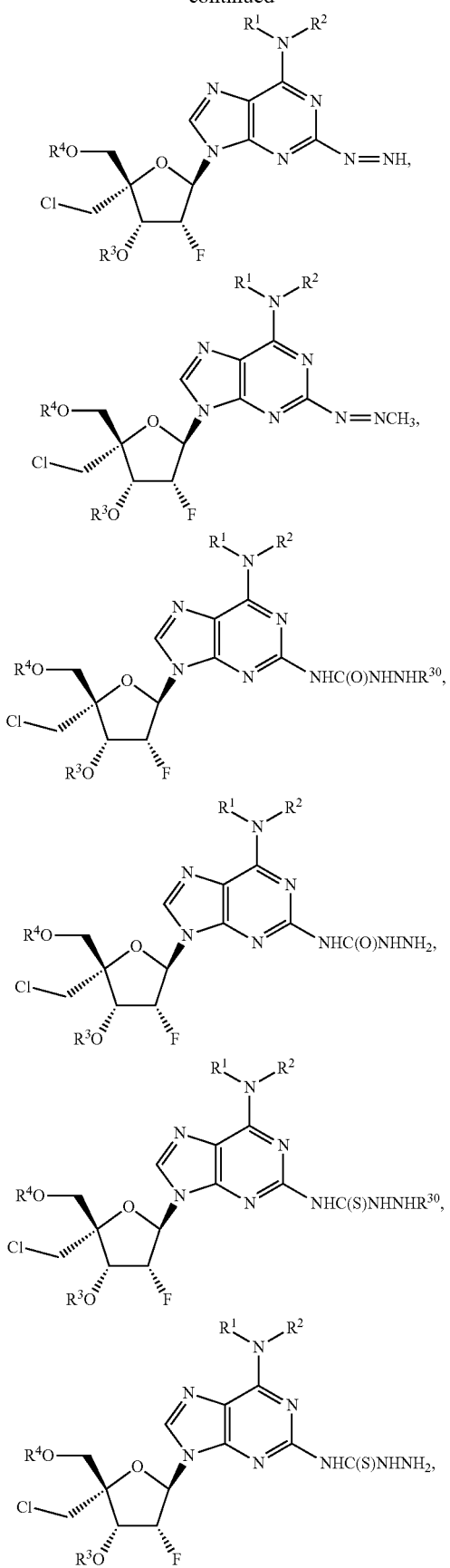
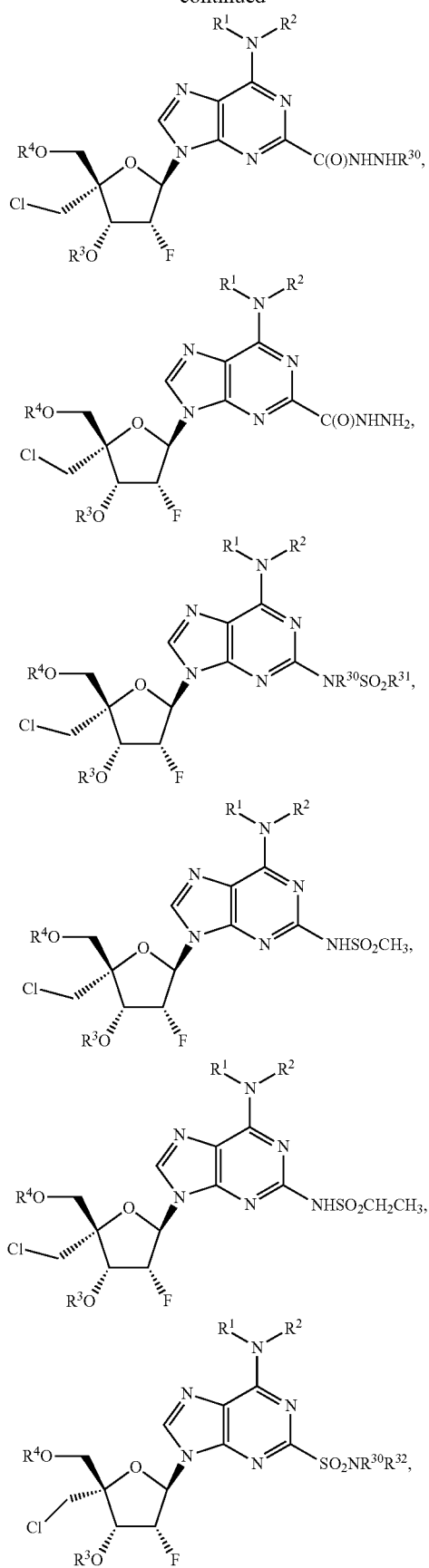

263
-continued
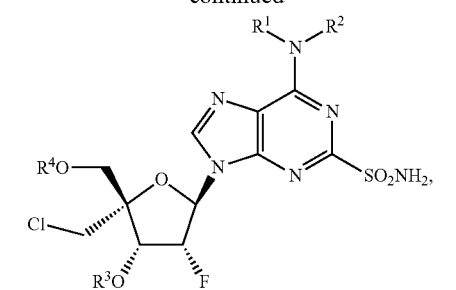
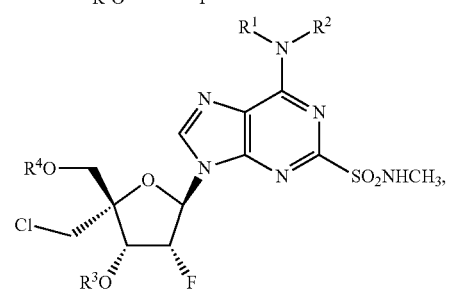
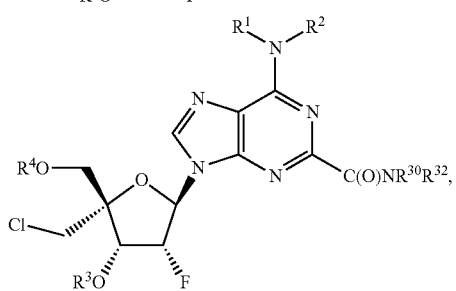
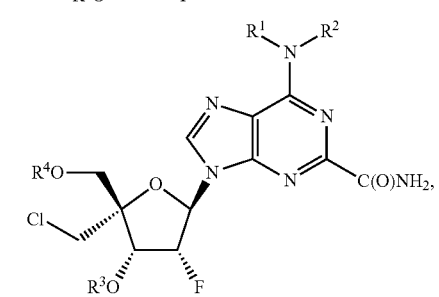
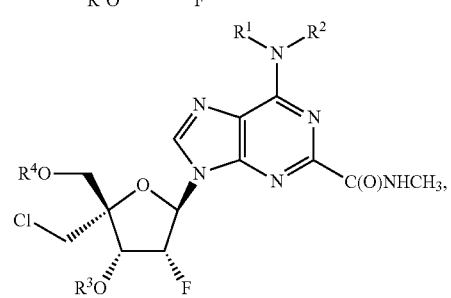
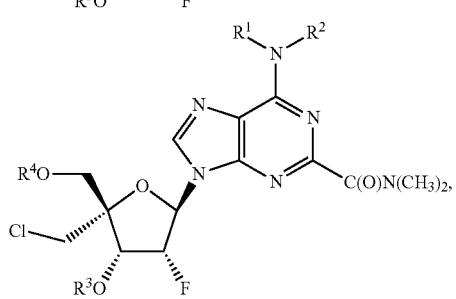
264
-continued
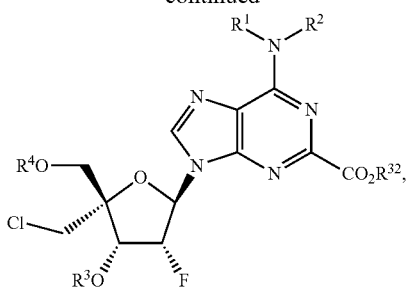
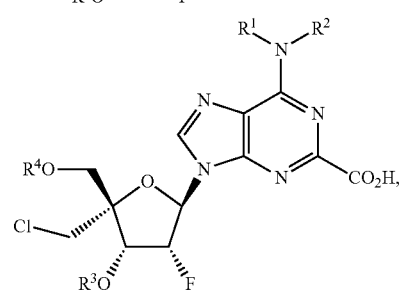
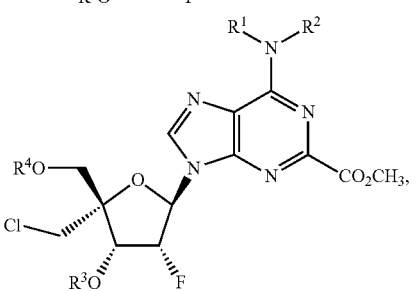
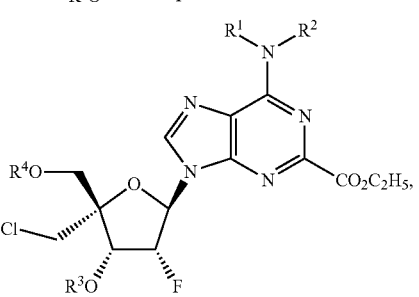
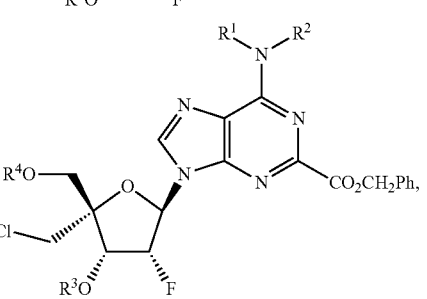
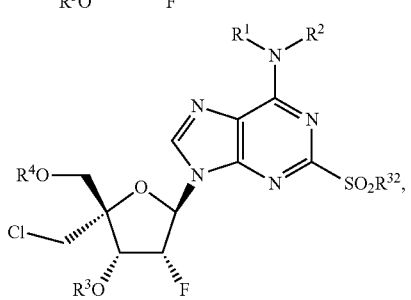

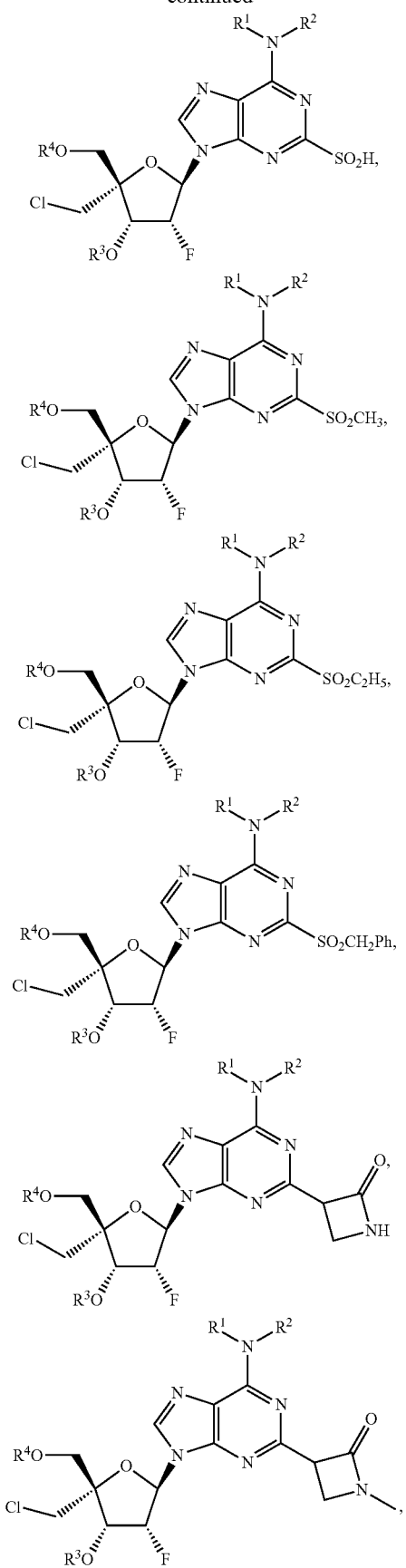
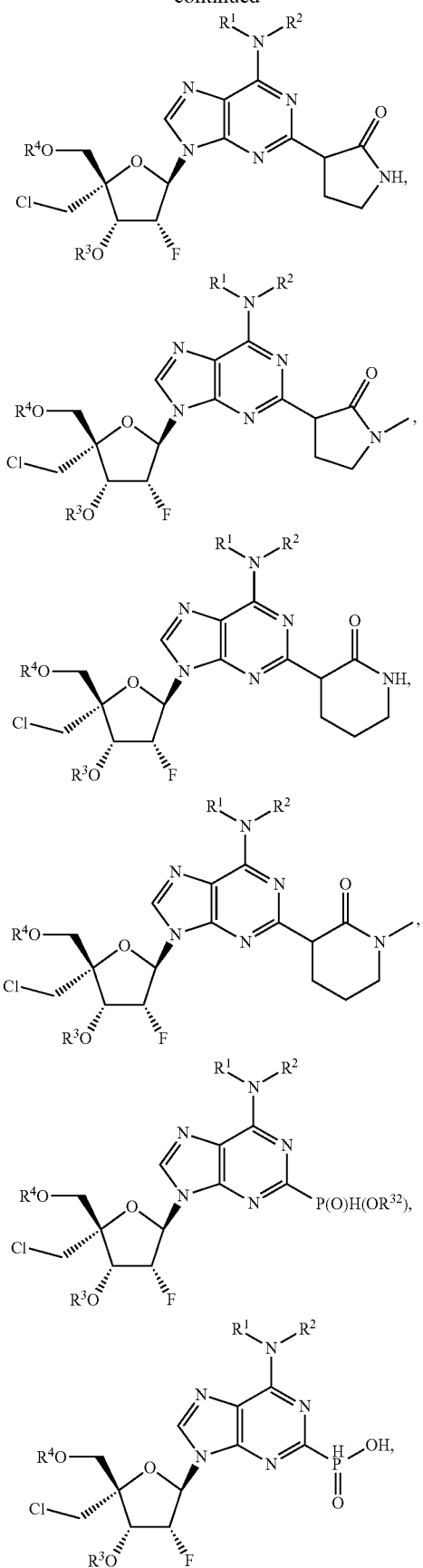

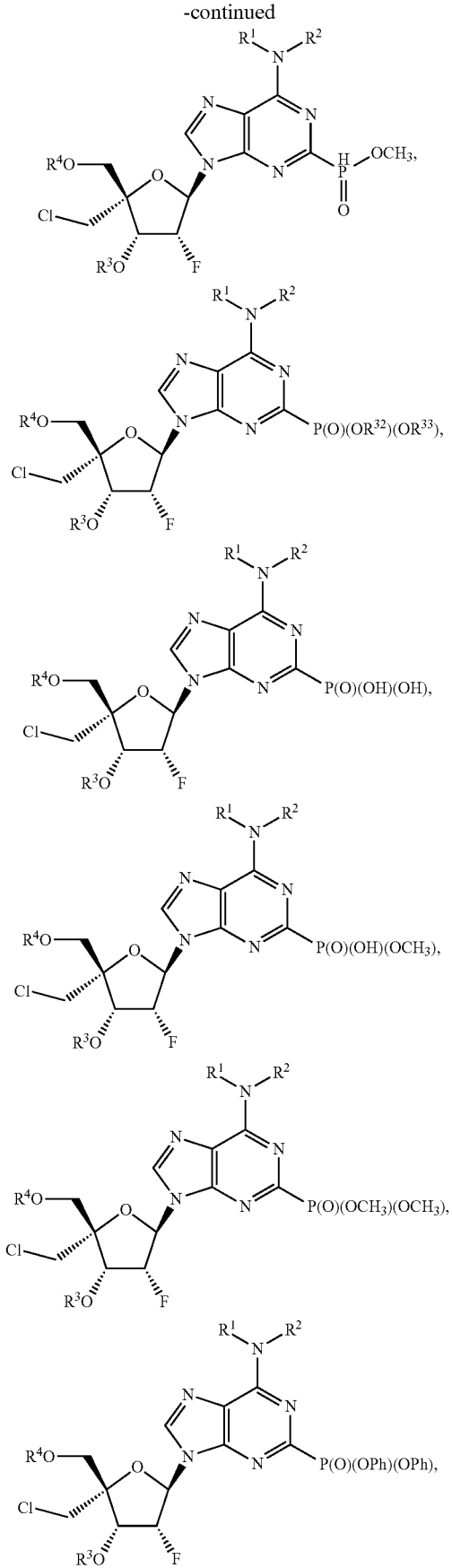
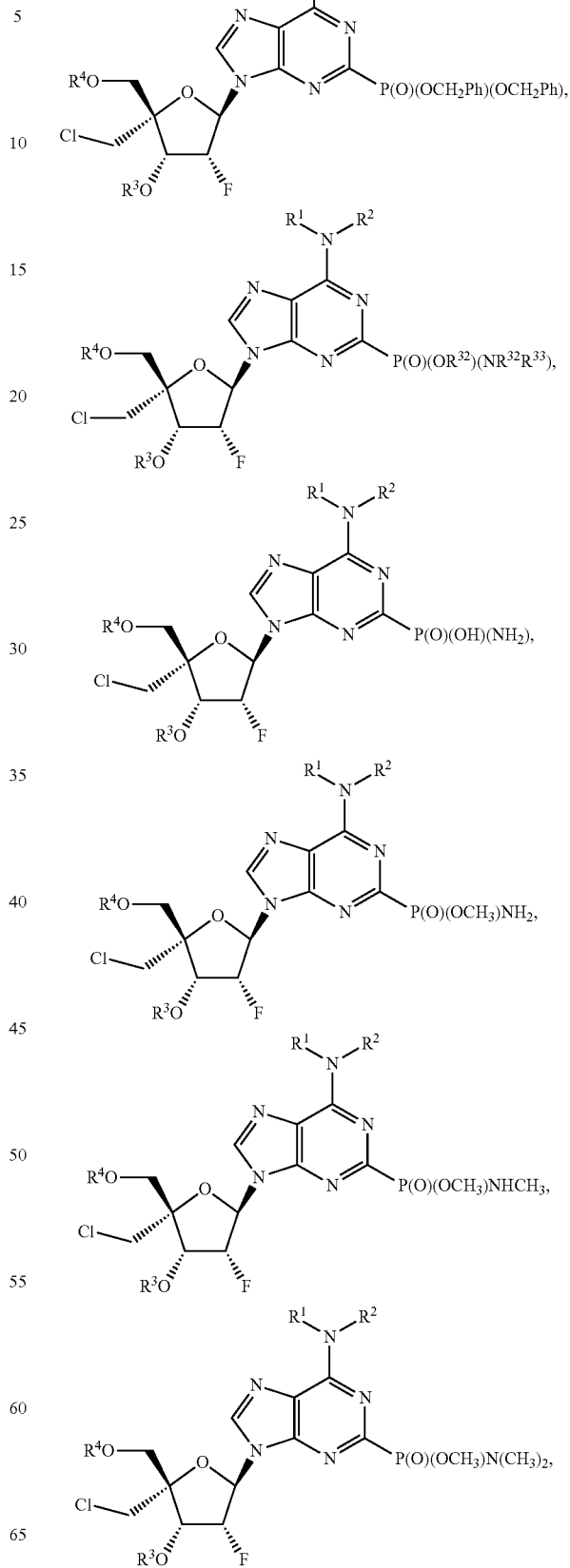

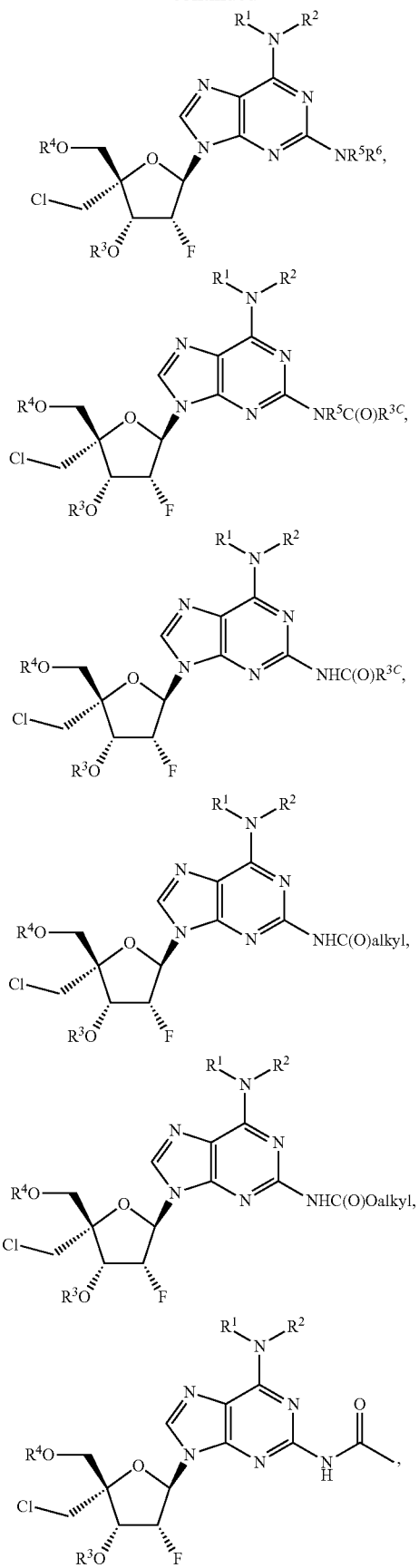
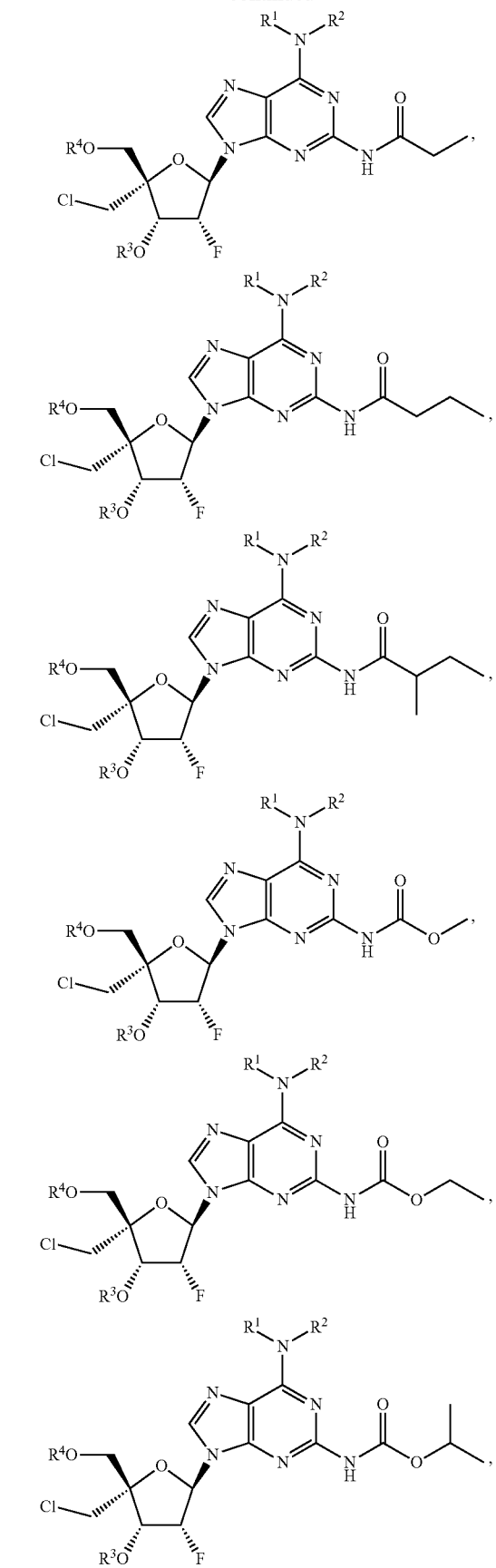

271
-continued
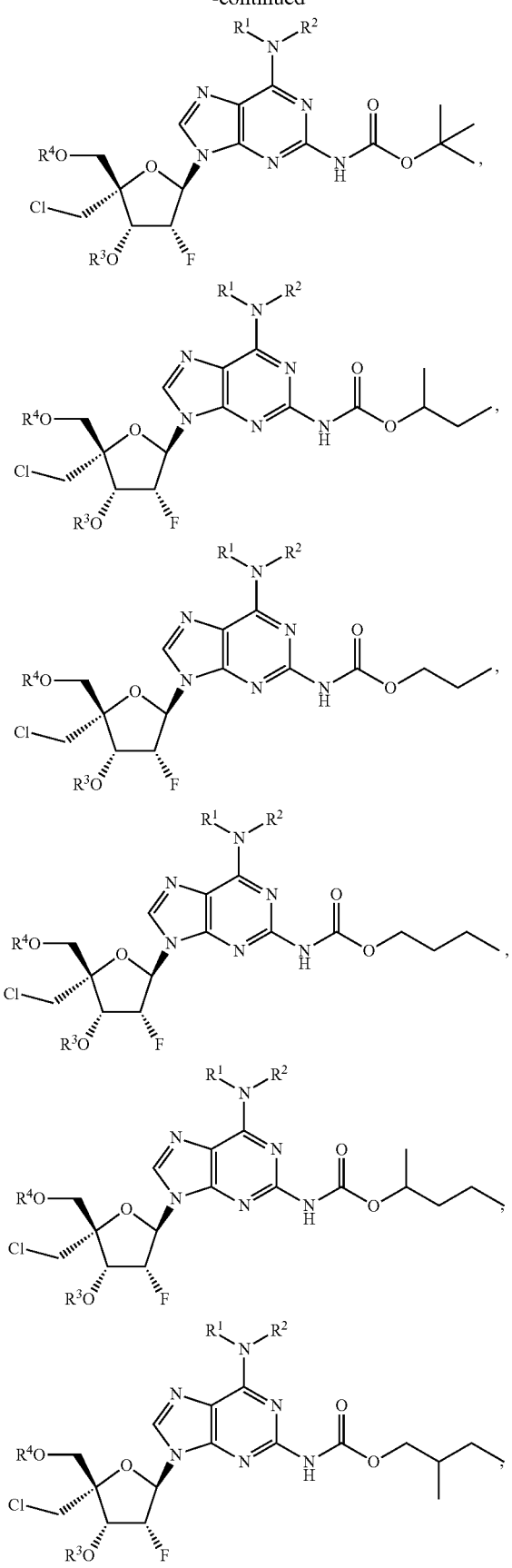
272
-continued
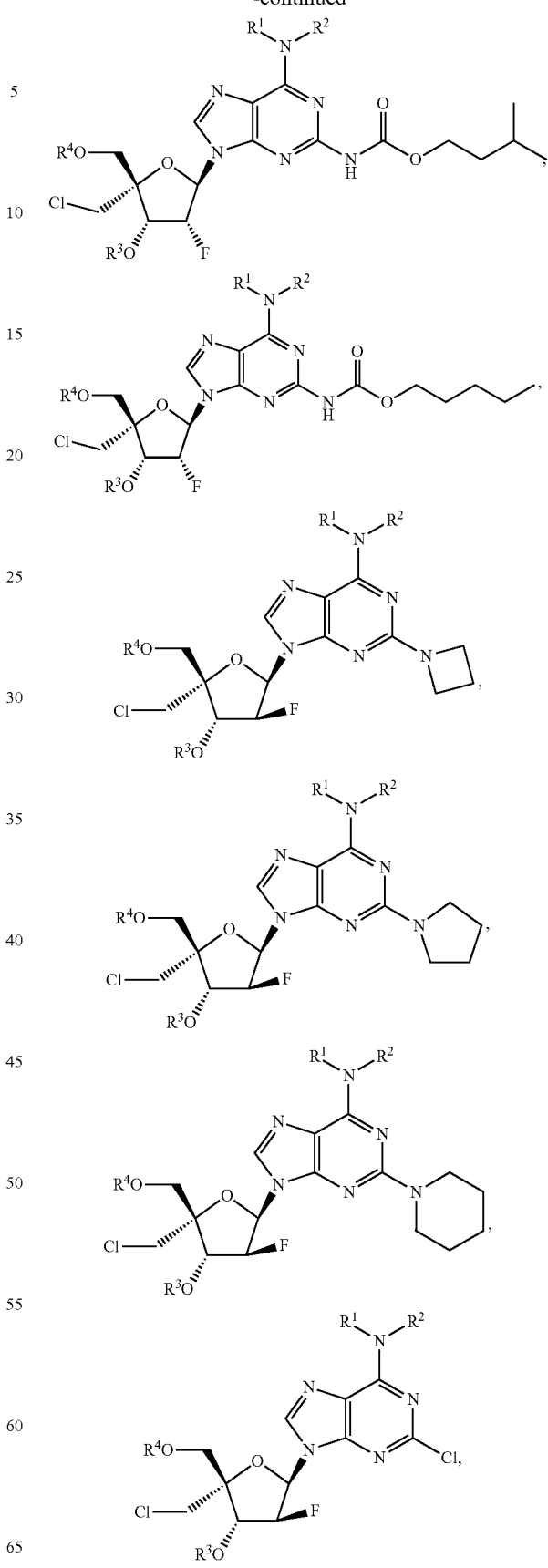

273
-continued
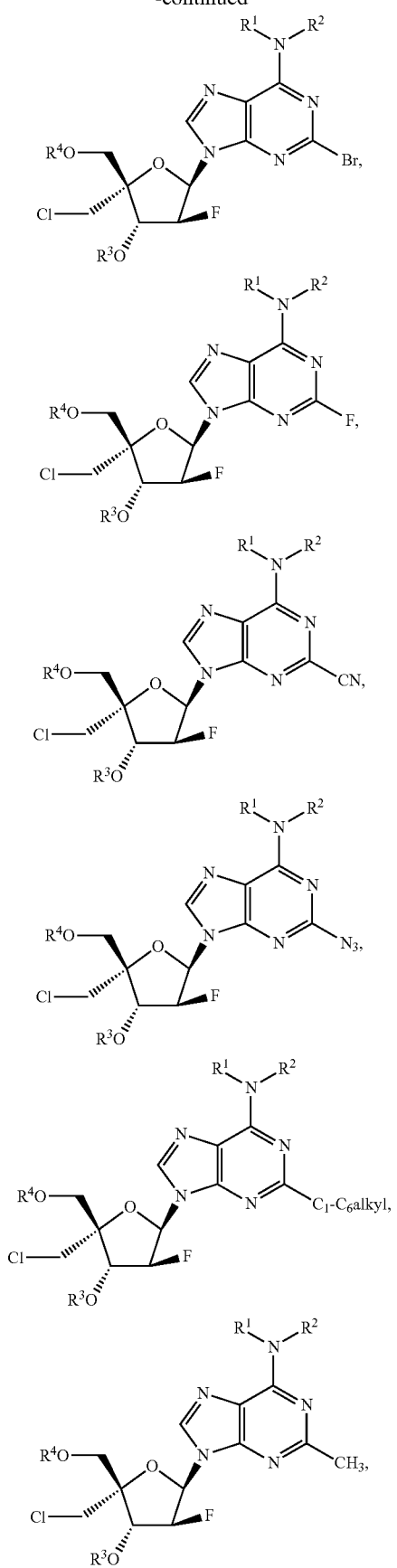
274
-continued
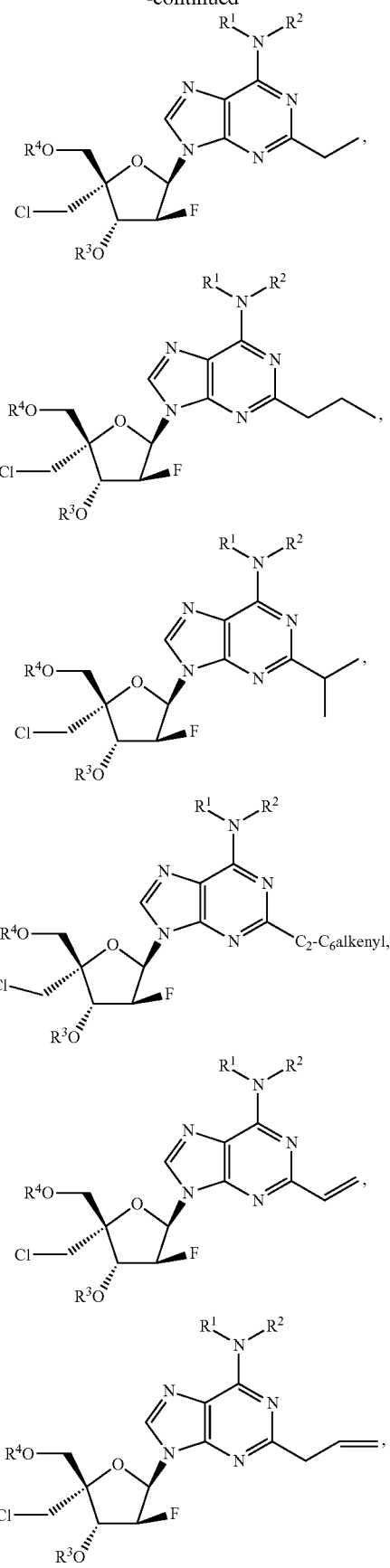

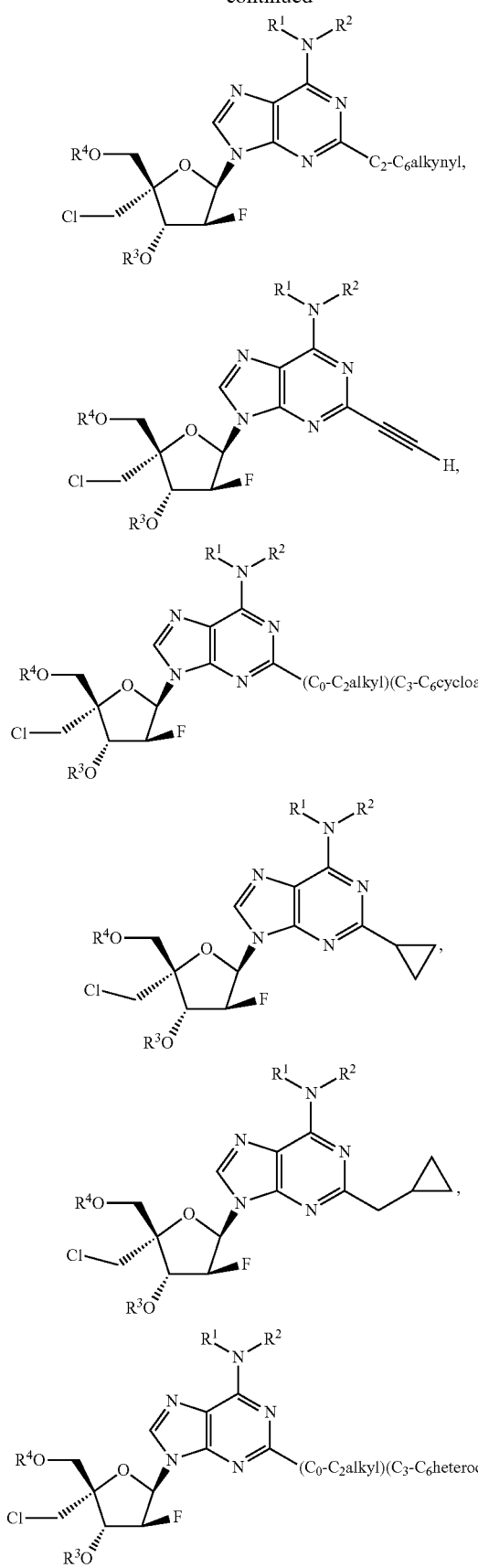
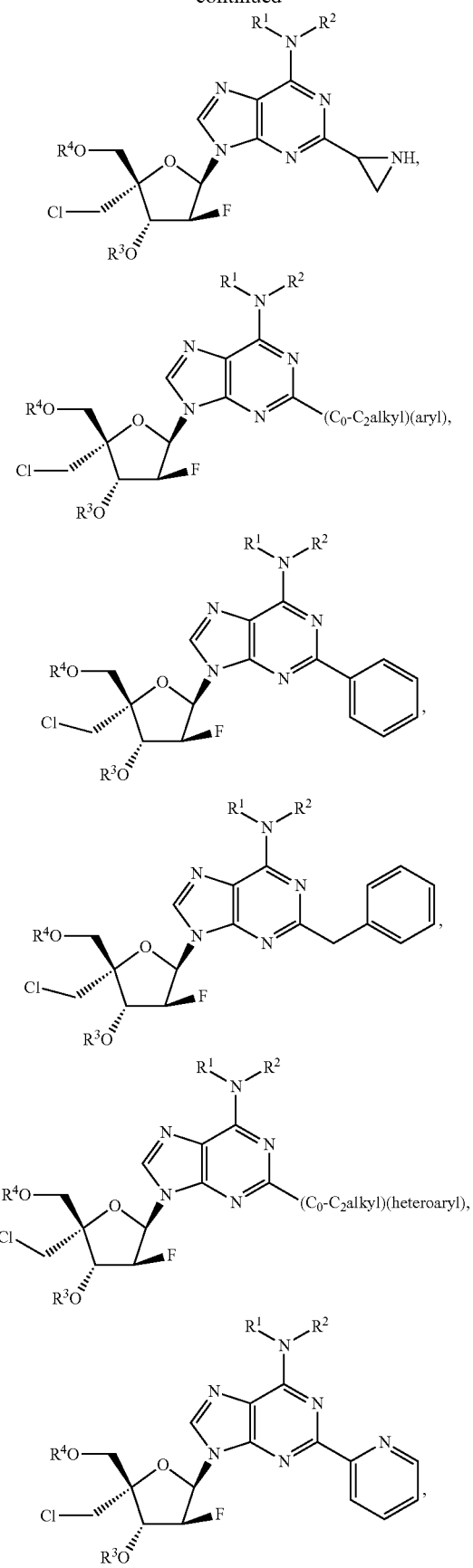

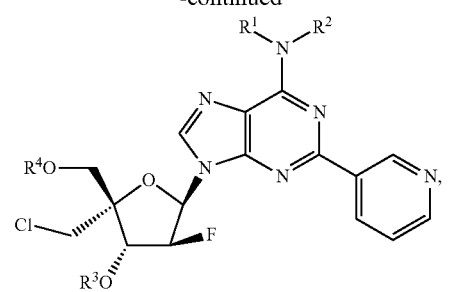
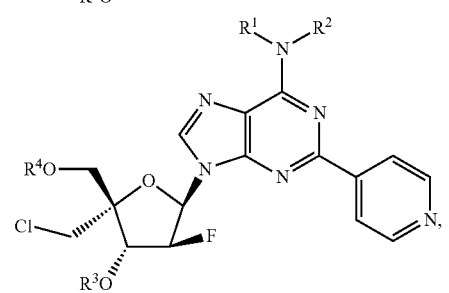
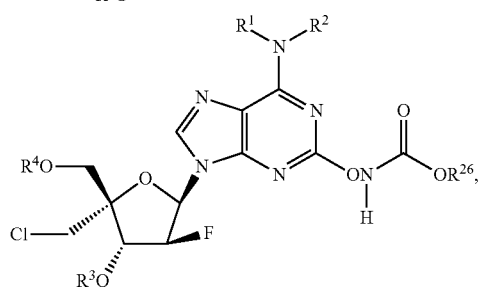
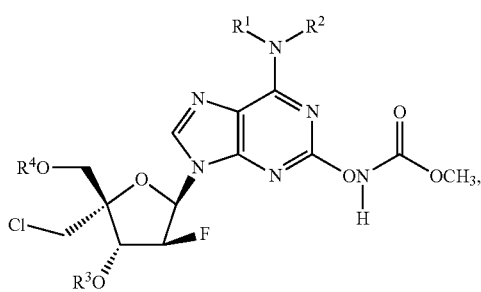
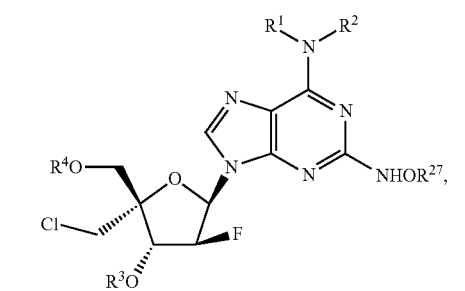
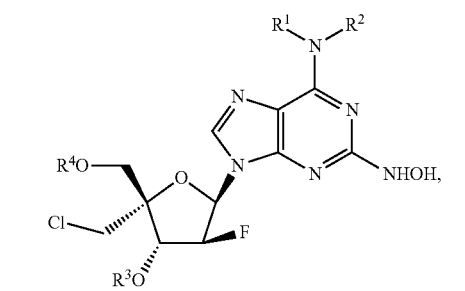
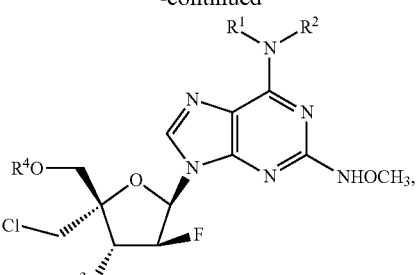
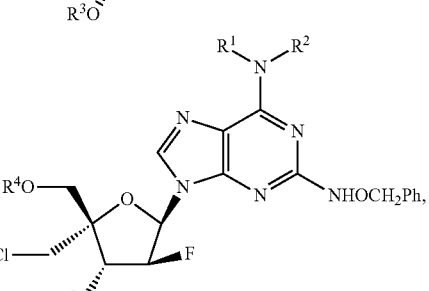
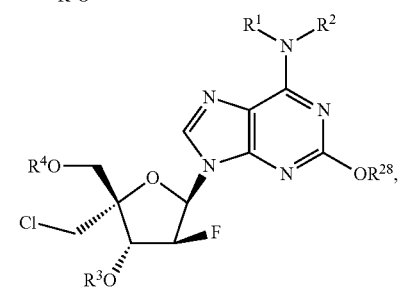
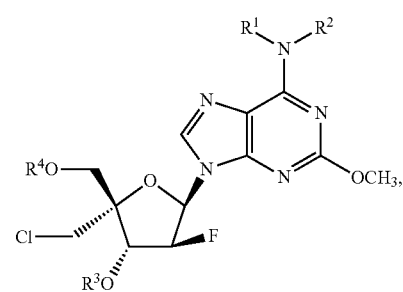
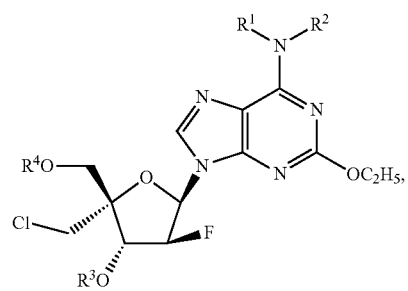
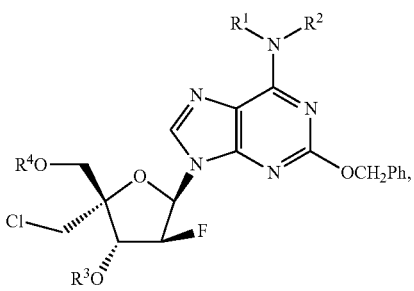

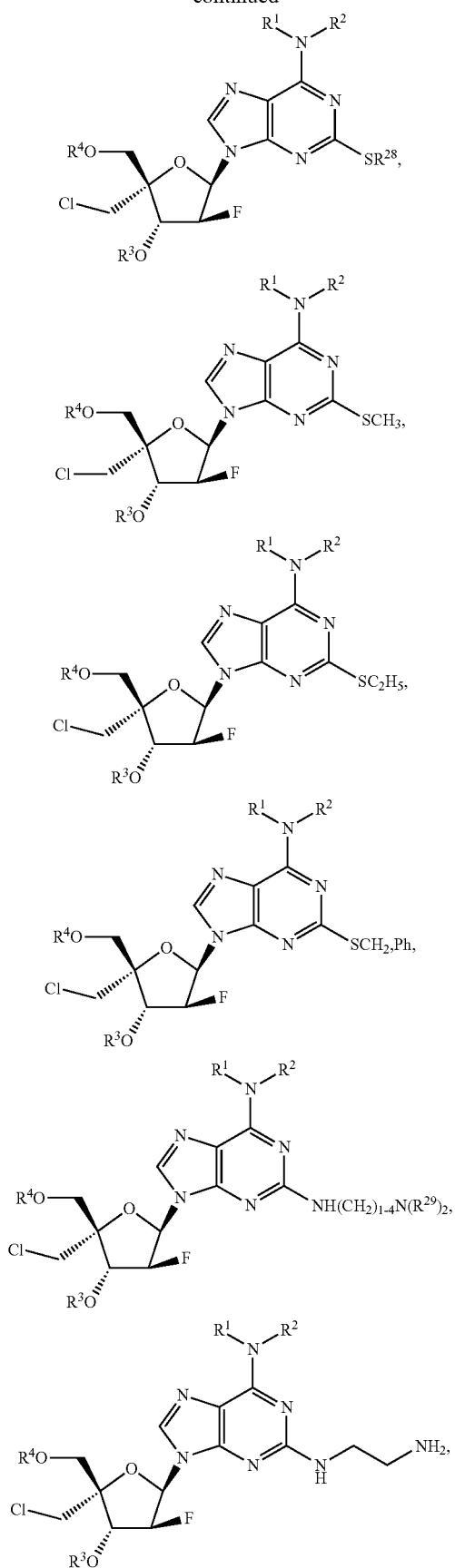
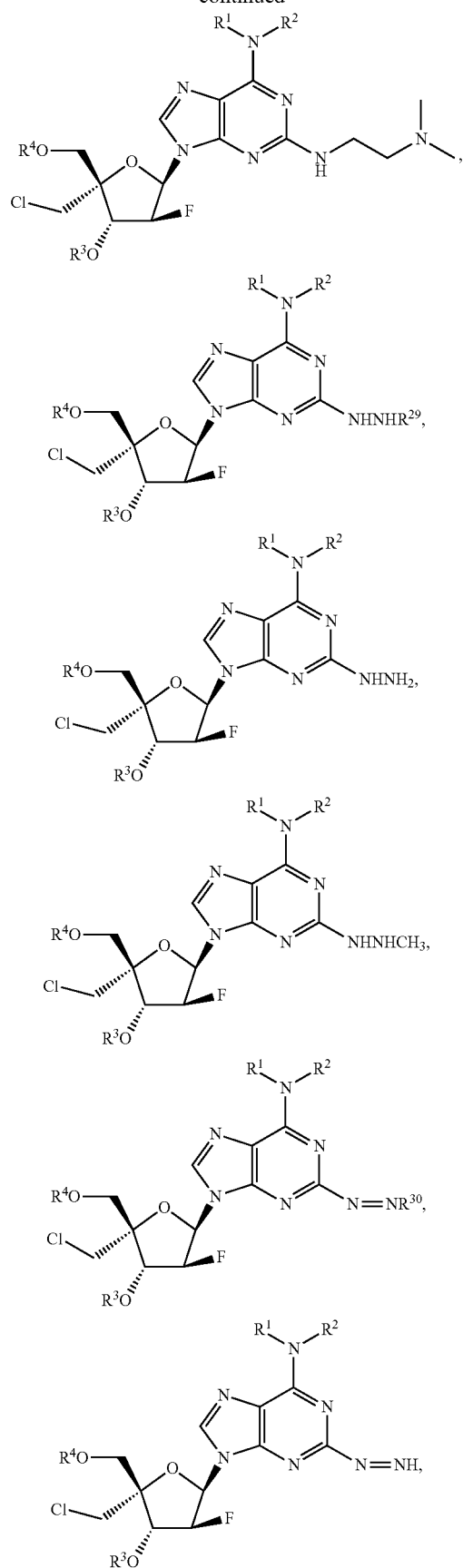

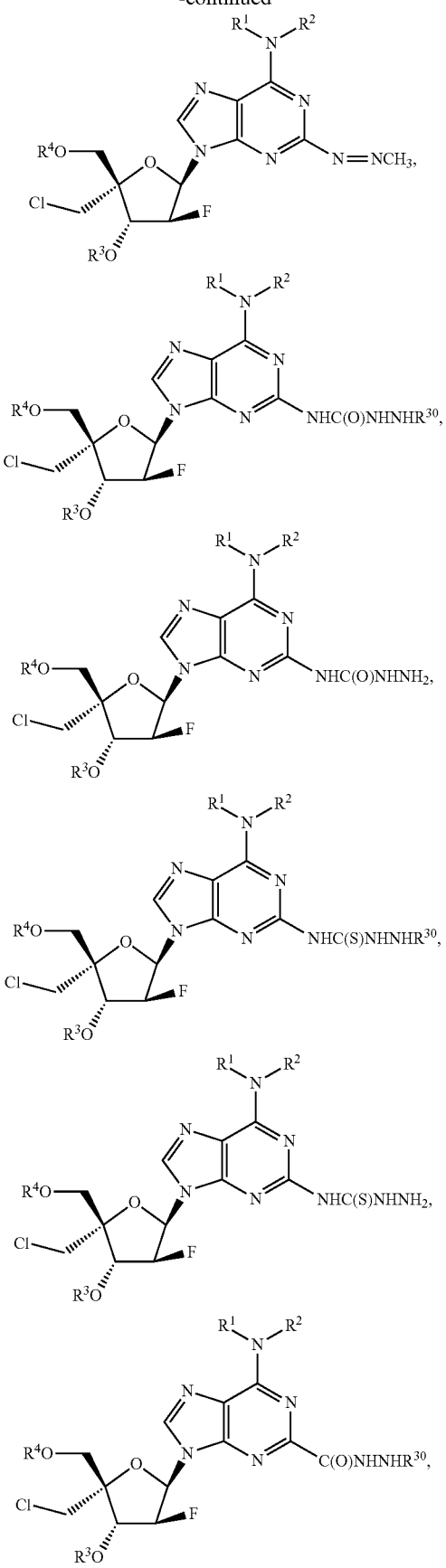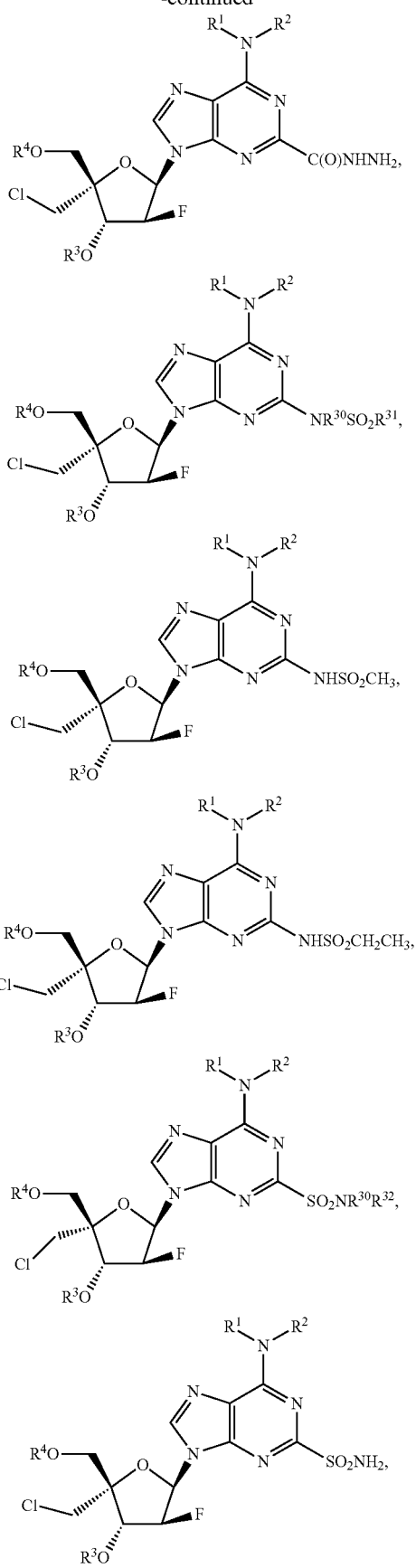

-continued
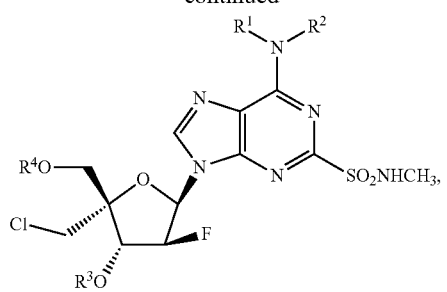
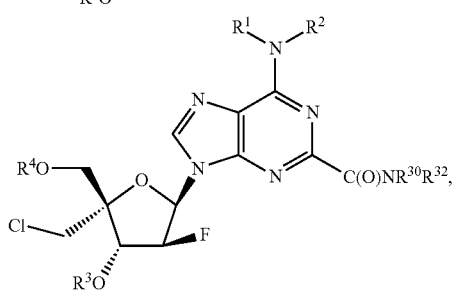
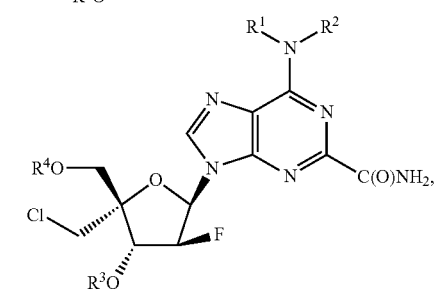
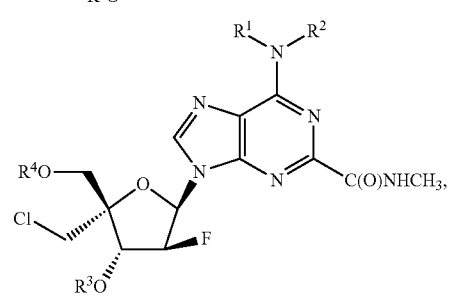
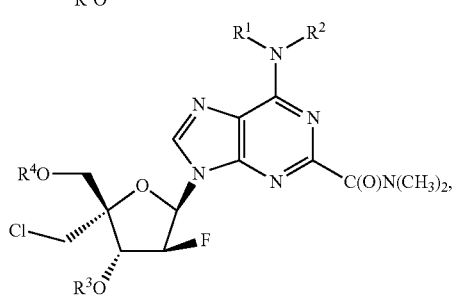
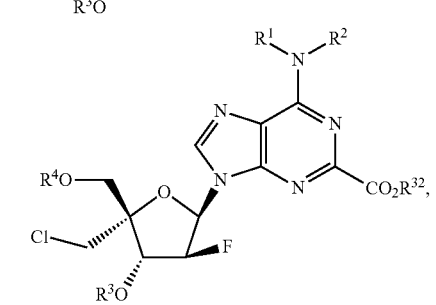
-continued
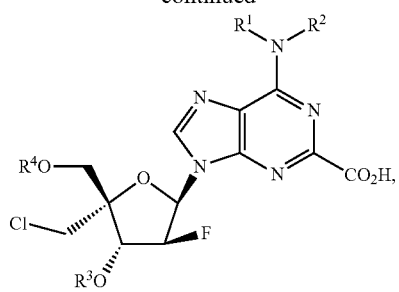
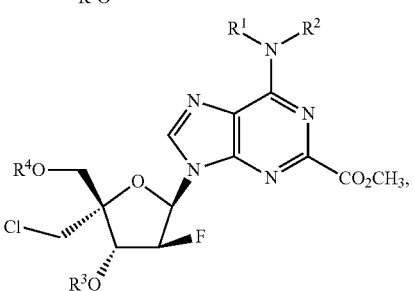
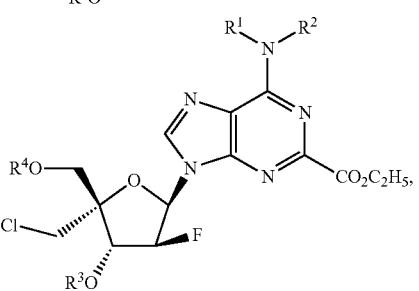
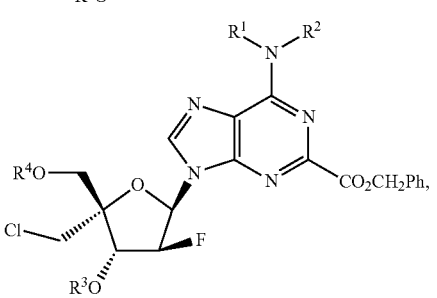
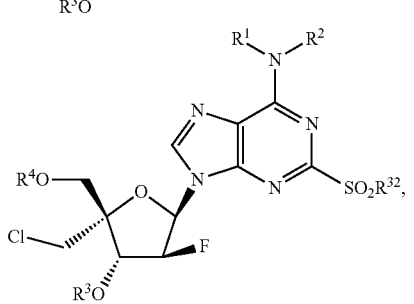
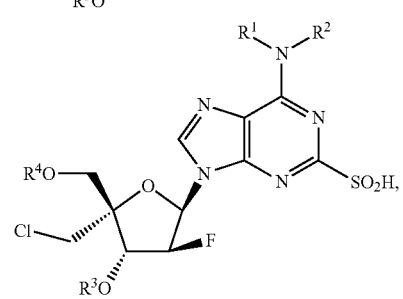

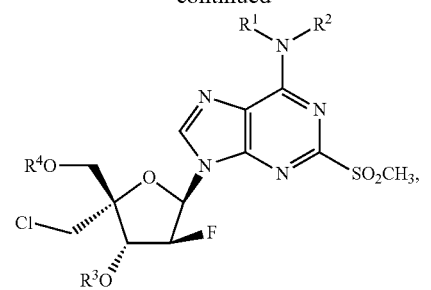
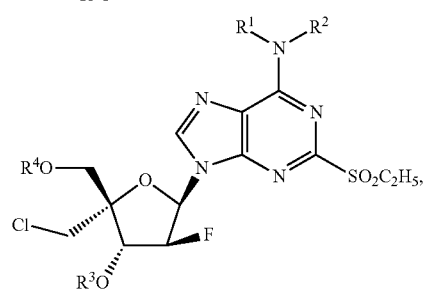
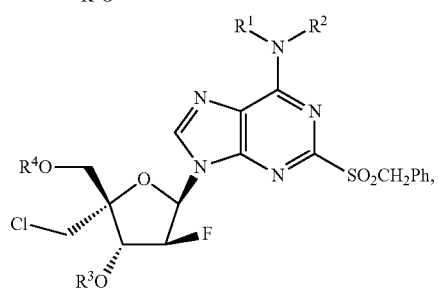
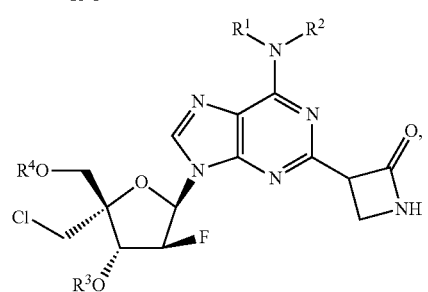
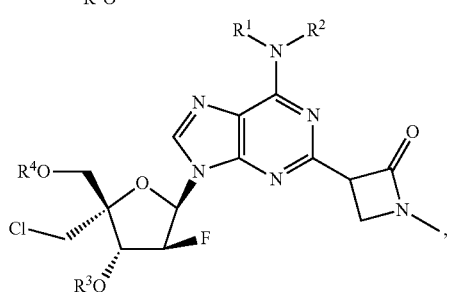
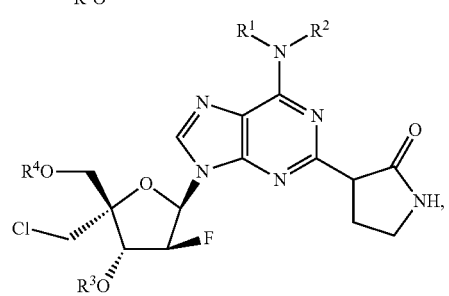
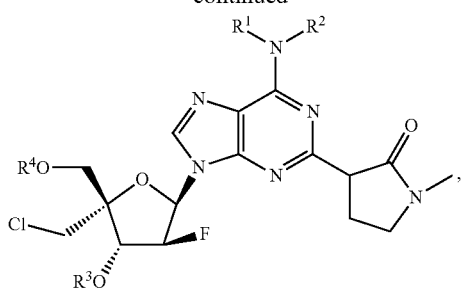
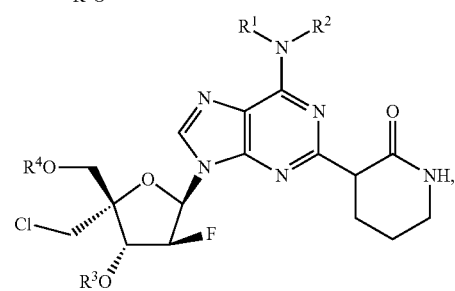
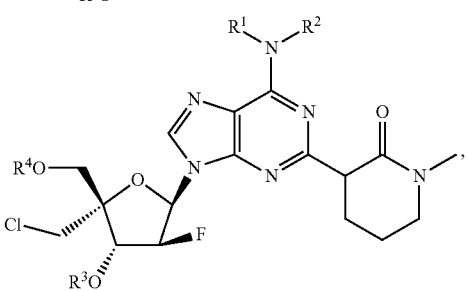
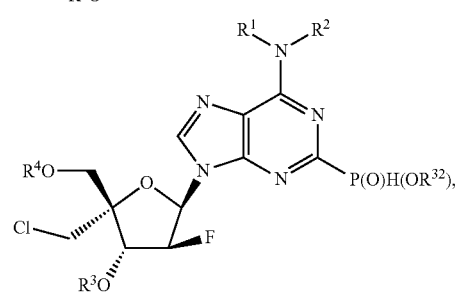
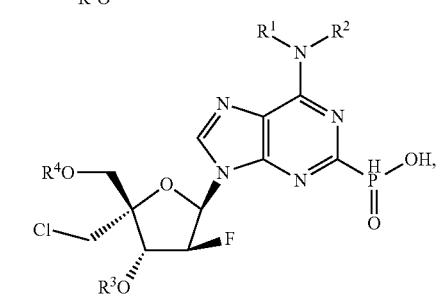
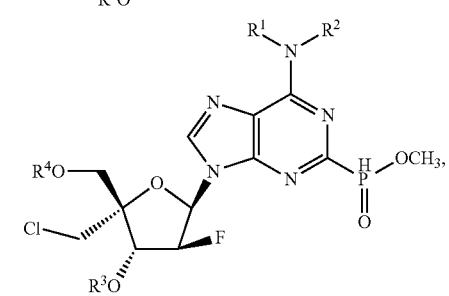

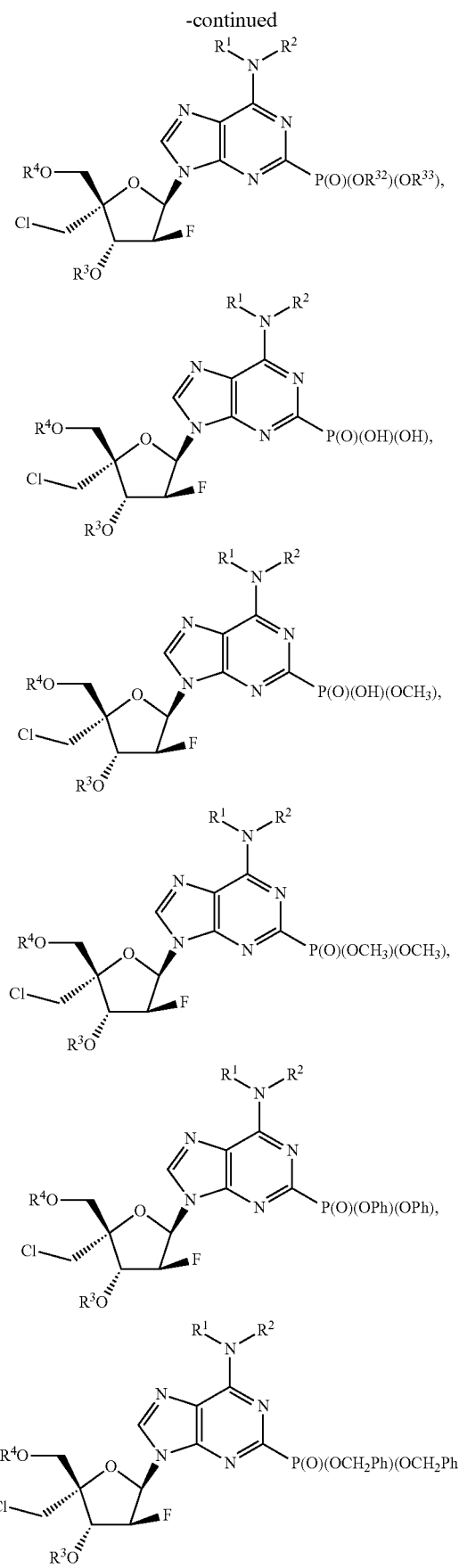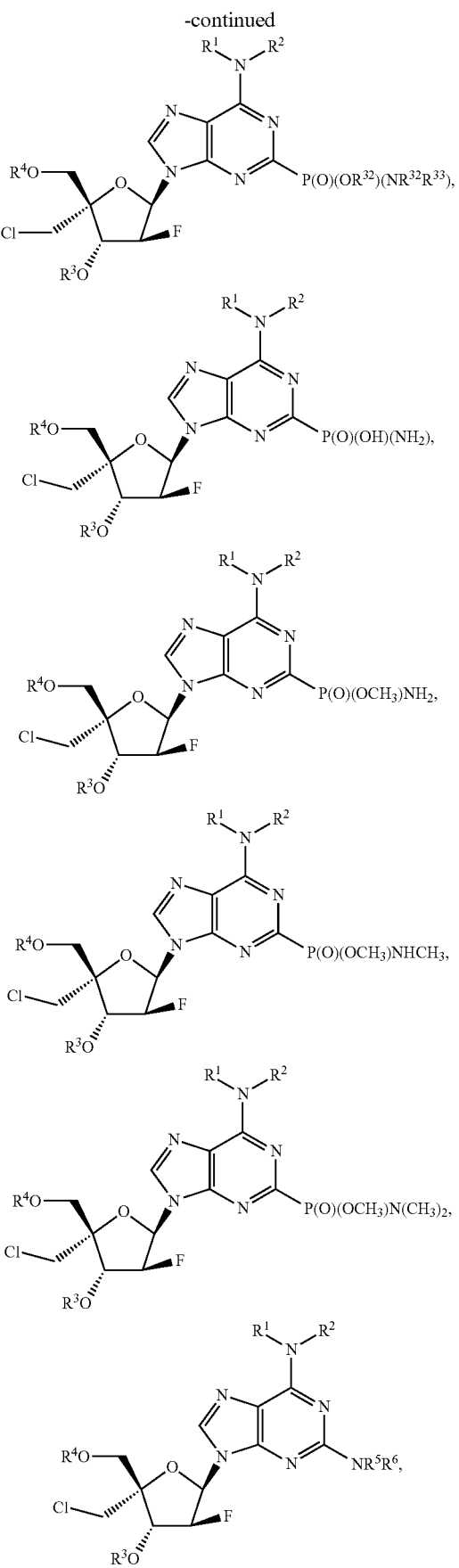

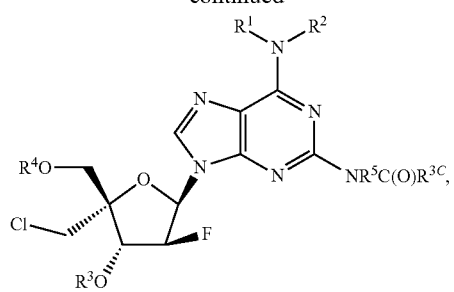
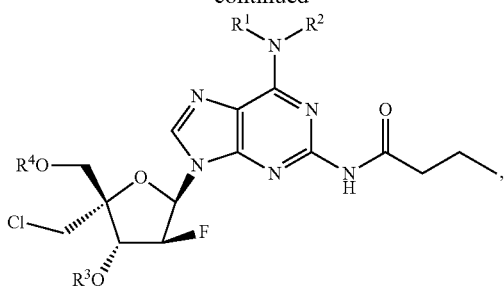
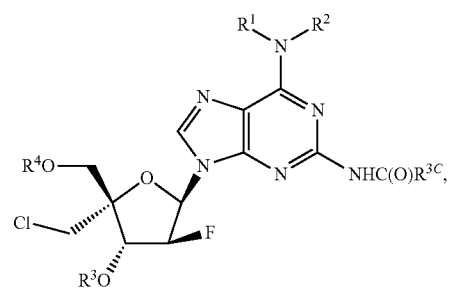
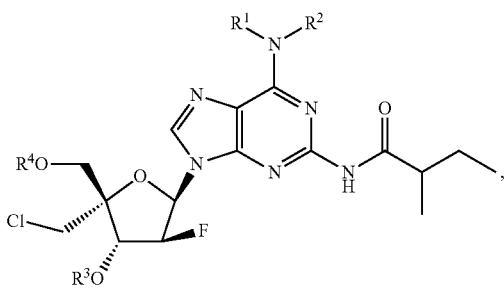
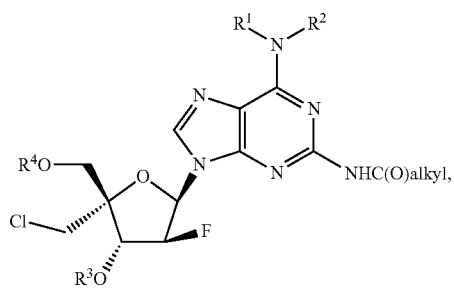
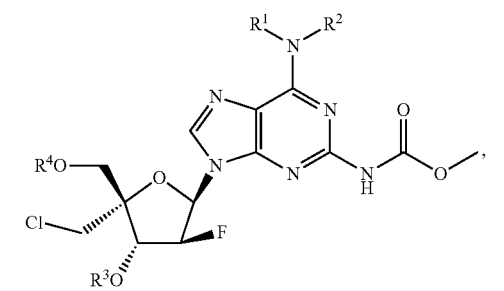
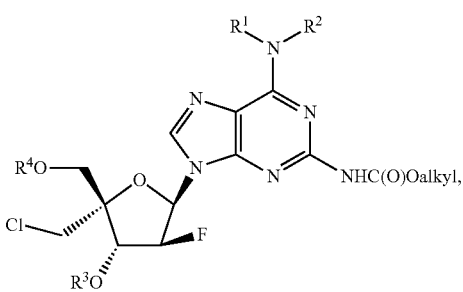
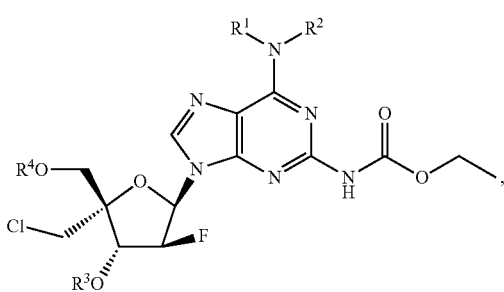
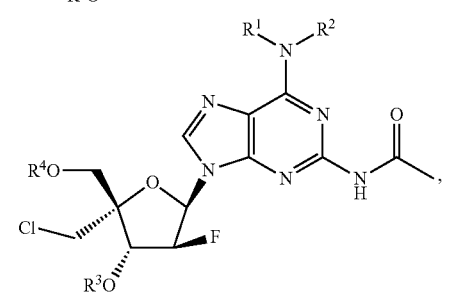
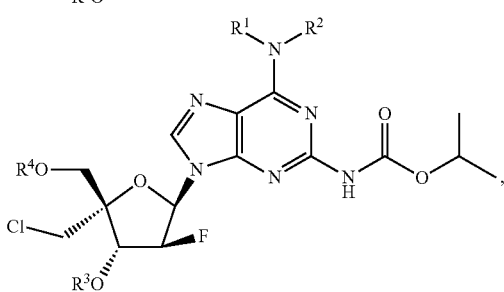
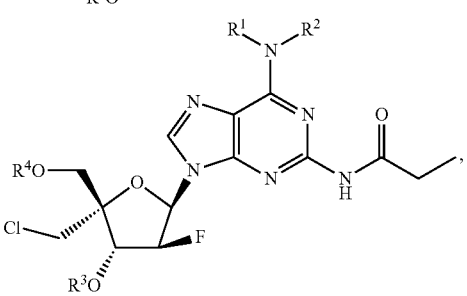
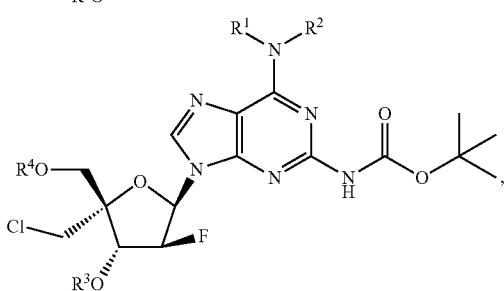

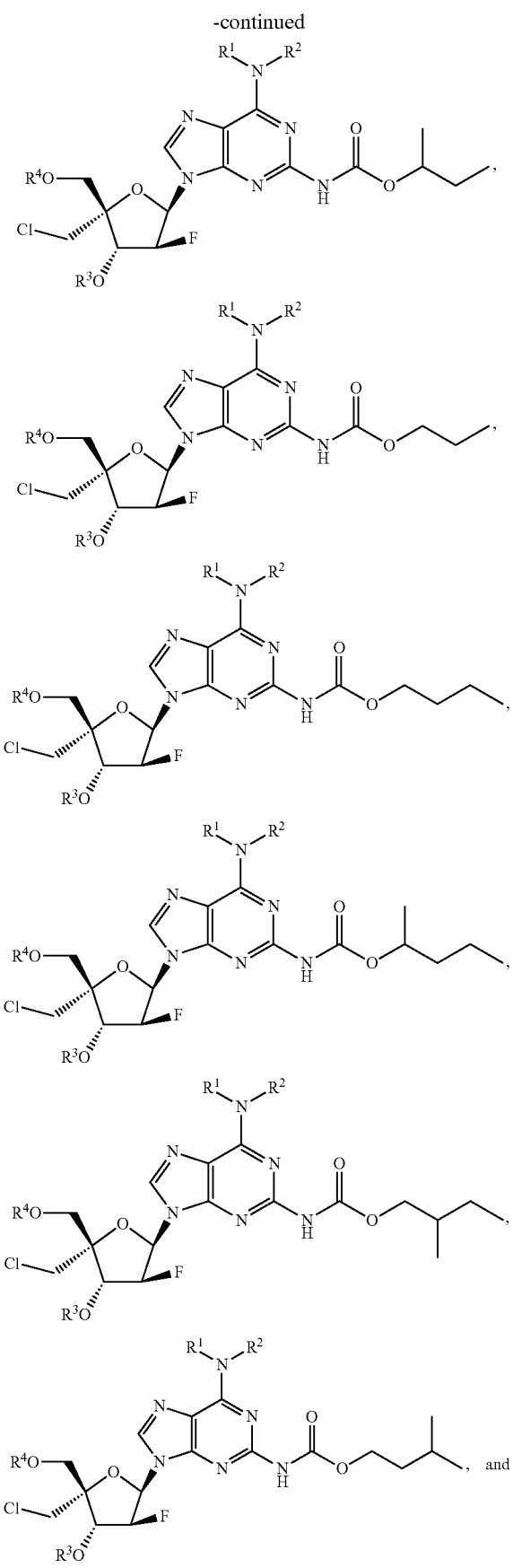
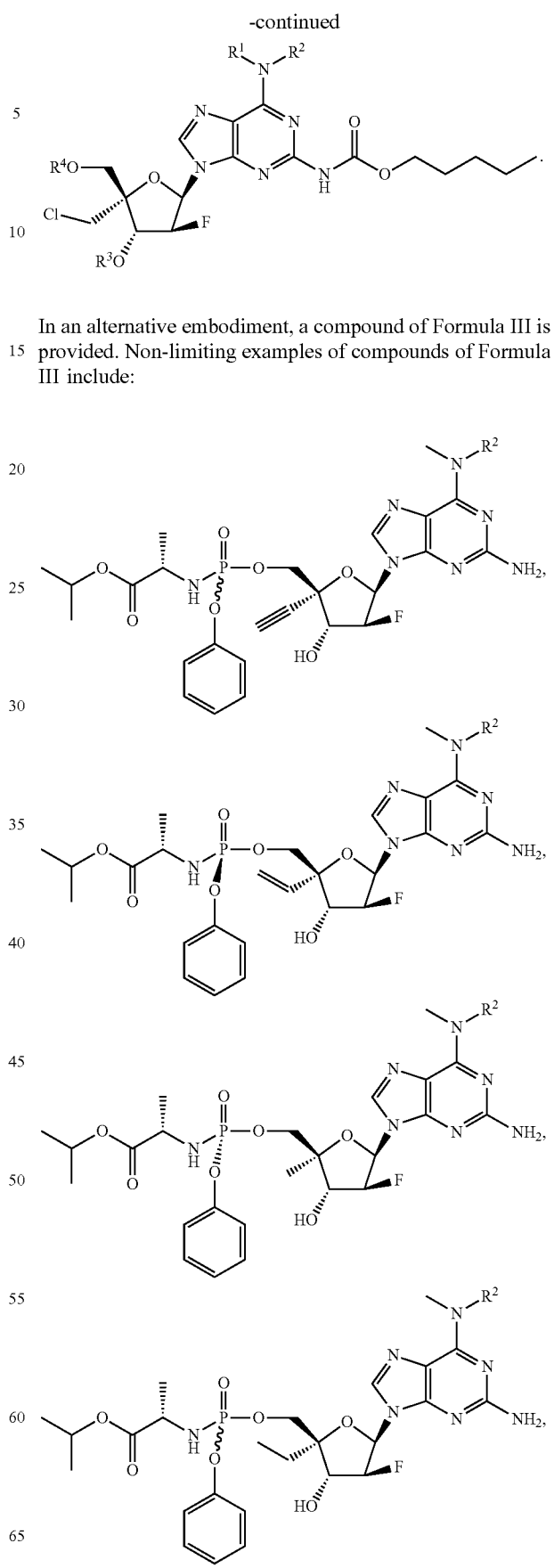
In an alternative embodiment, a compound of Formula III is provided. Non-limiting examples of compounds of Formula III include:

293
-continued
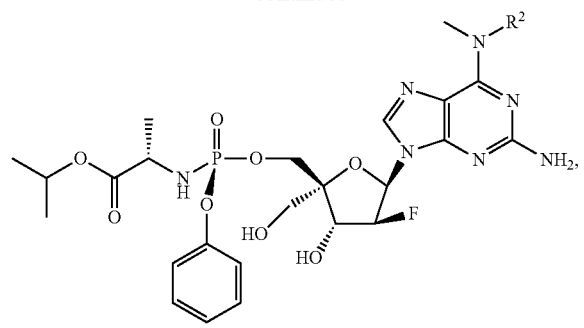
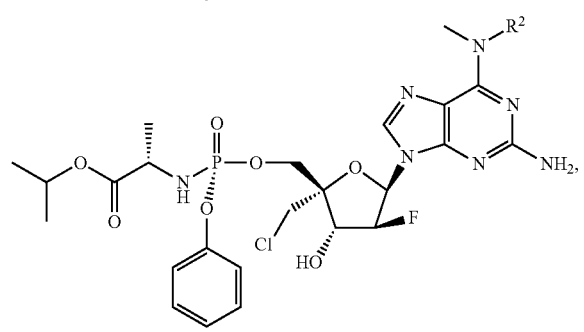
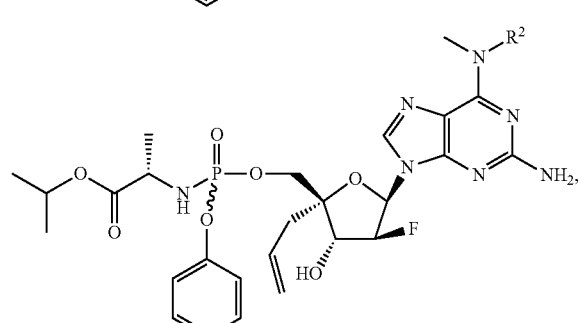
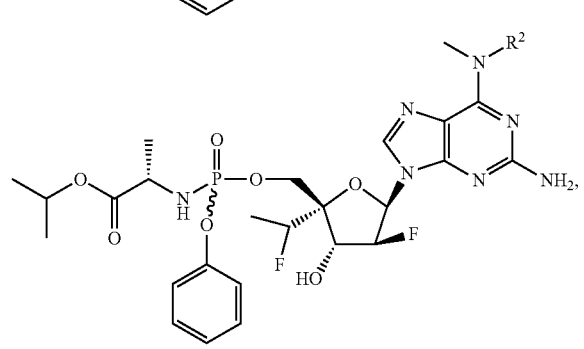
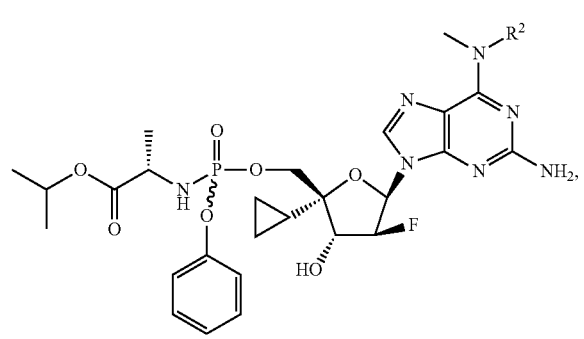
294
-continued
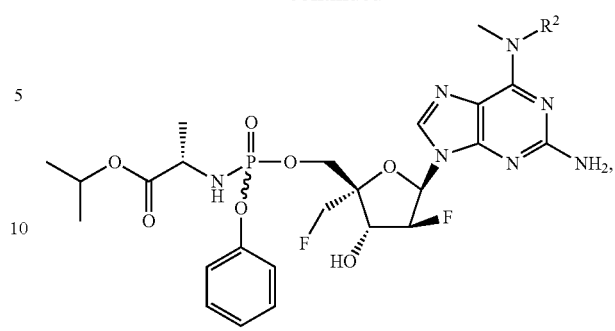
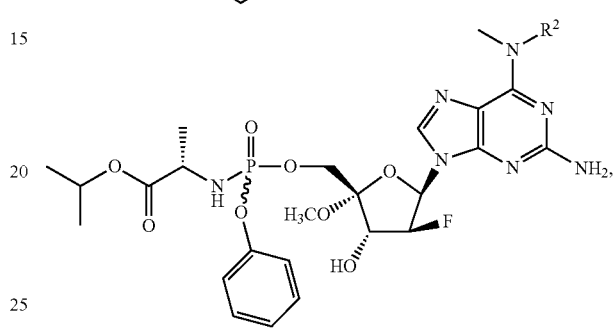
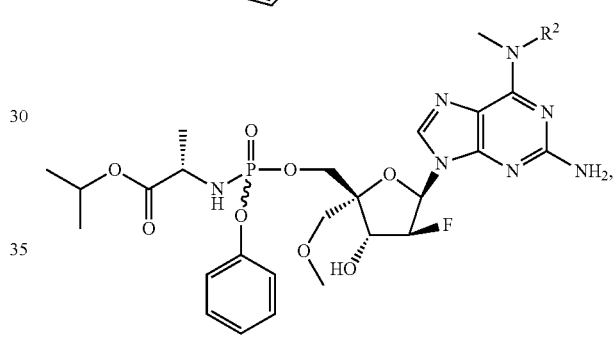
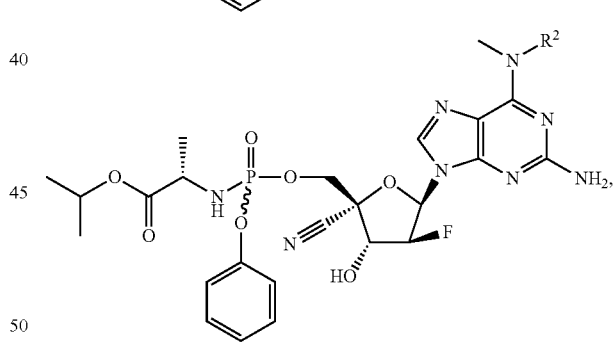
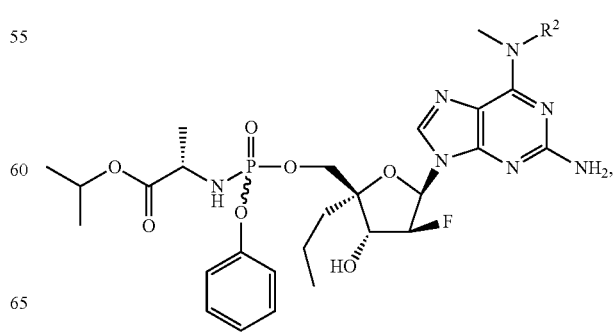

295
-continued
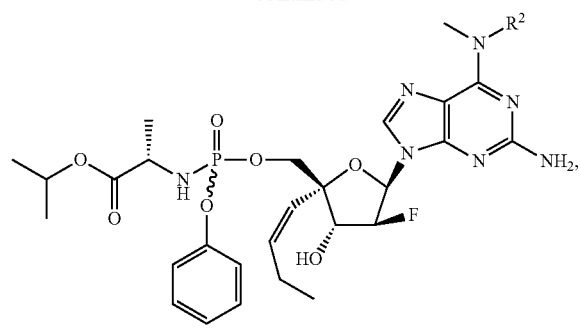
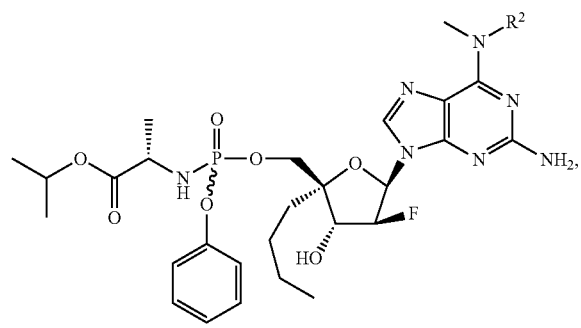
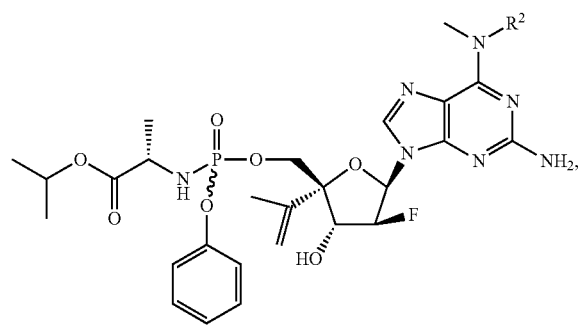
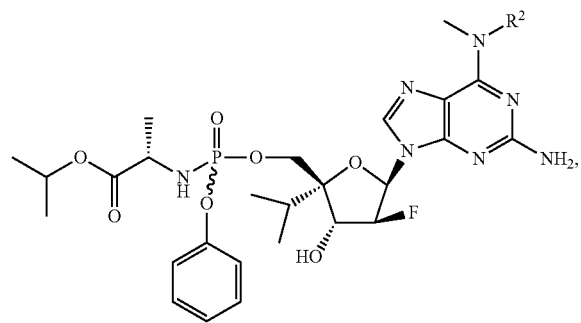
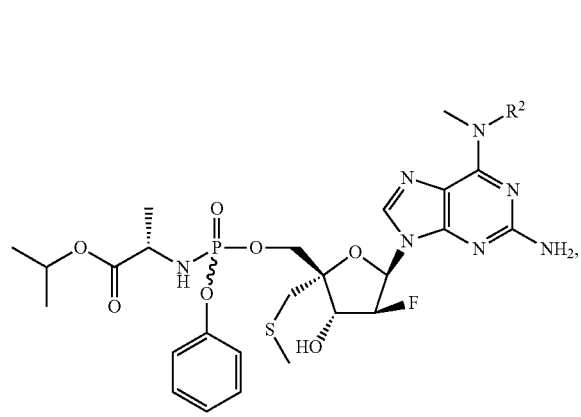
296
-continued
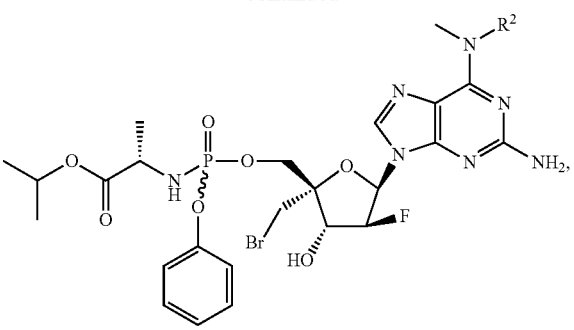
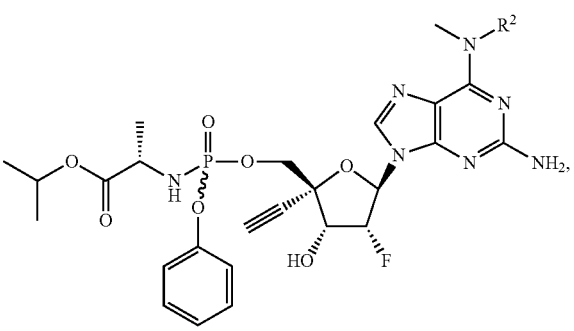
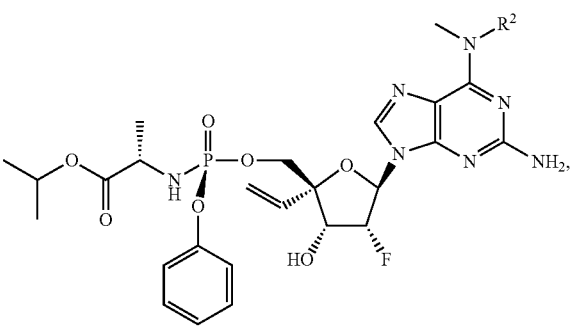
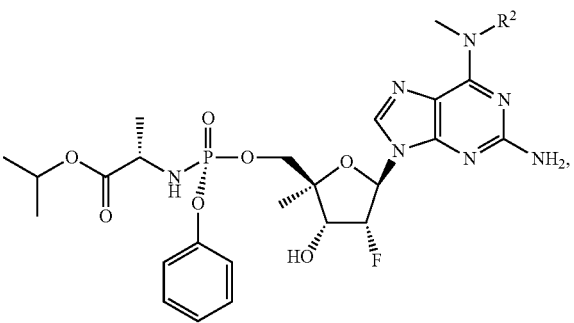
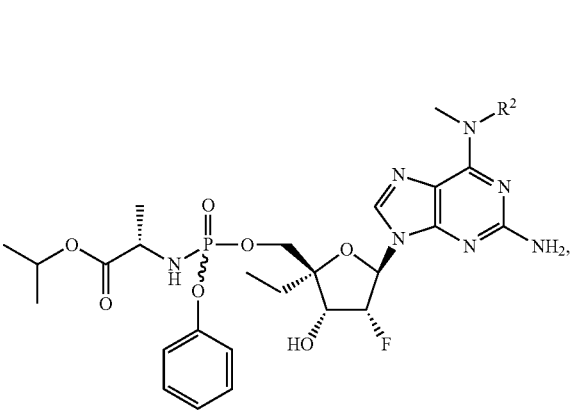

297
-continued
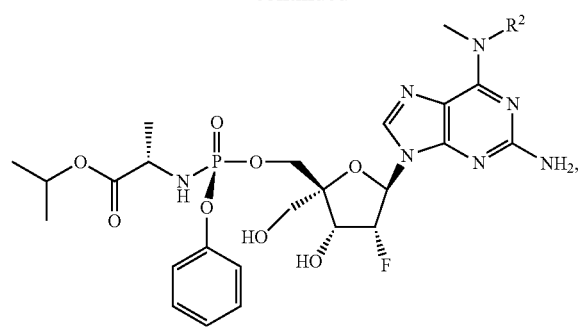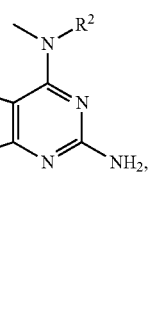
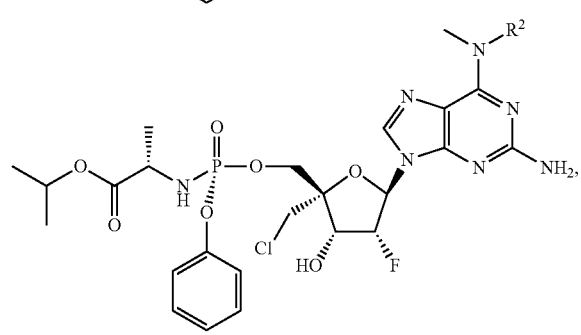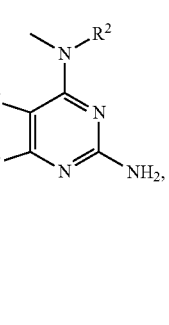
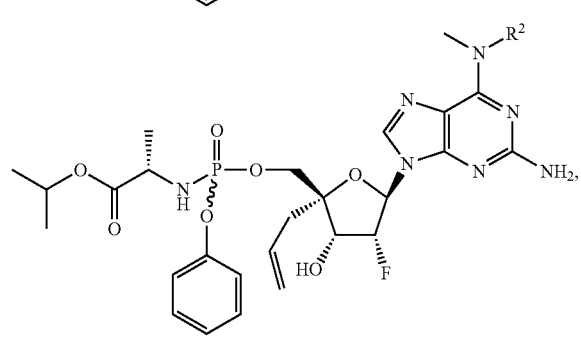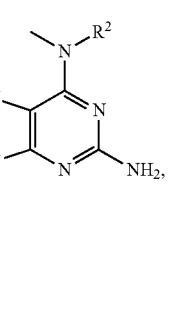
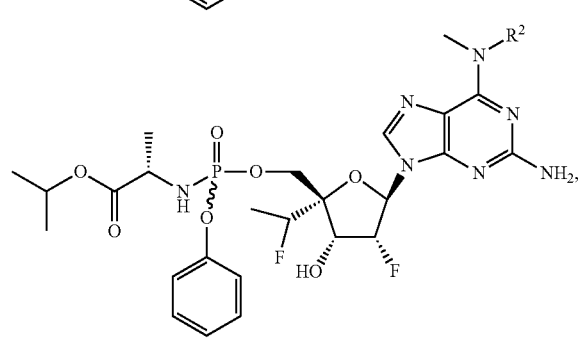
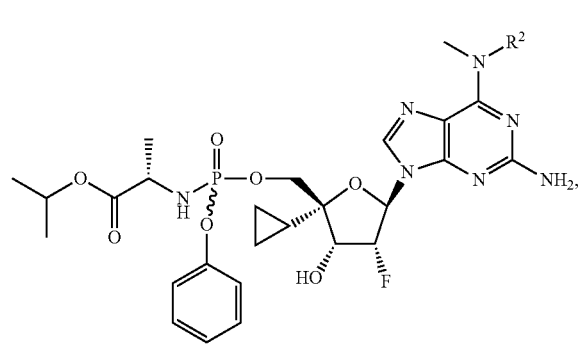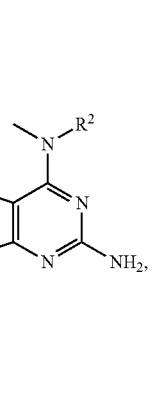
298
-continued
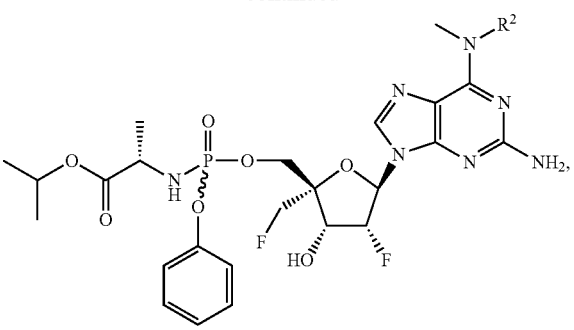
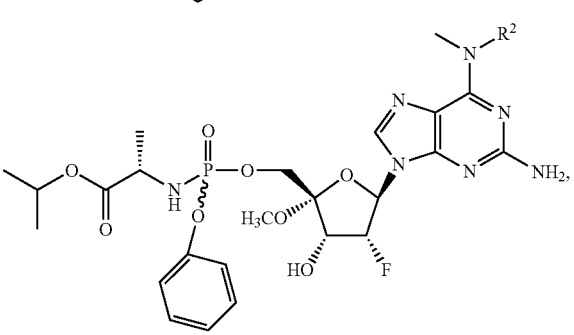
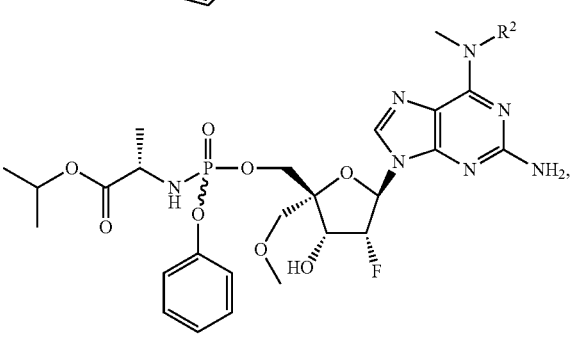
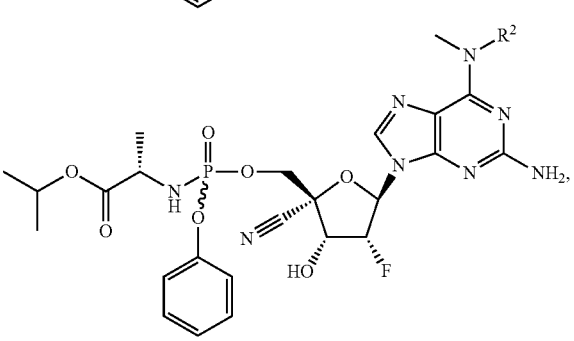
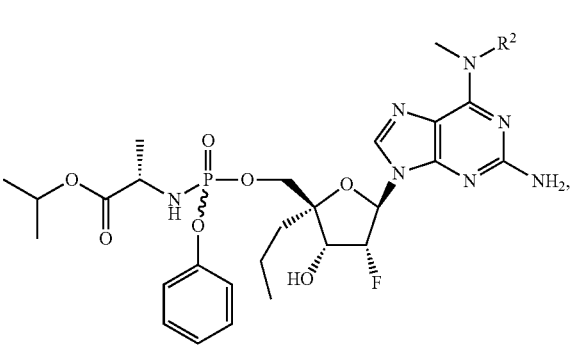

299
-continued
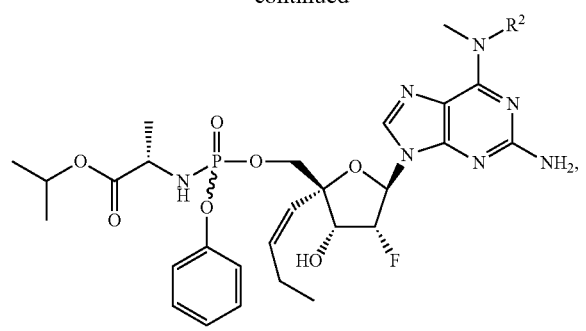
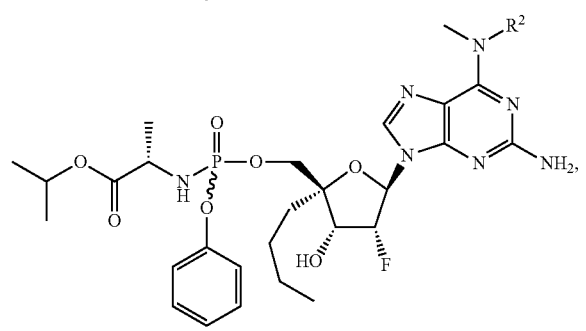
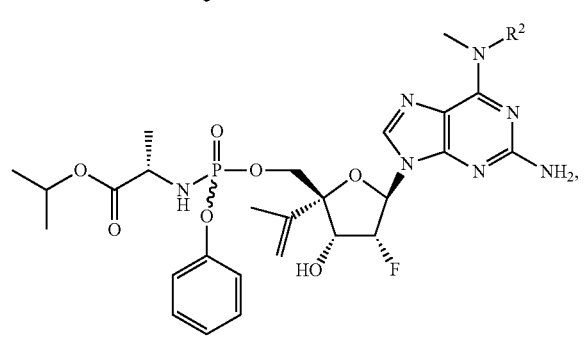
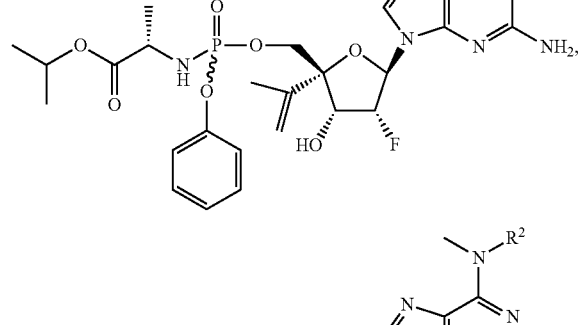
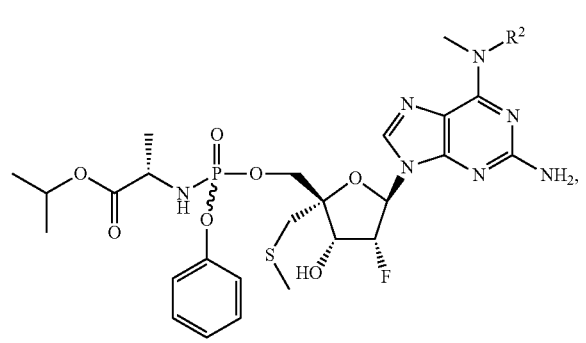
300
-continued
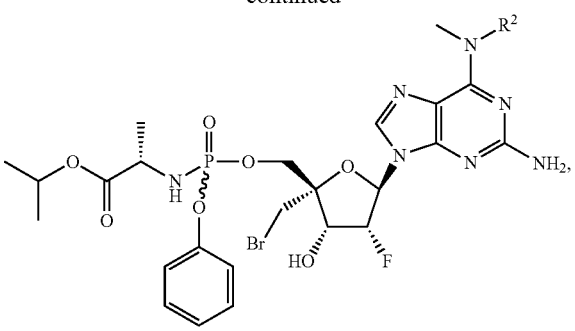
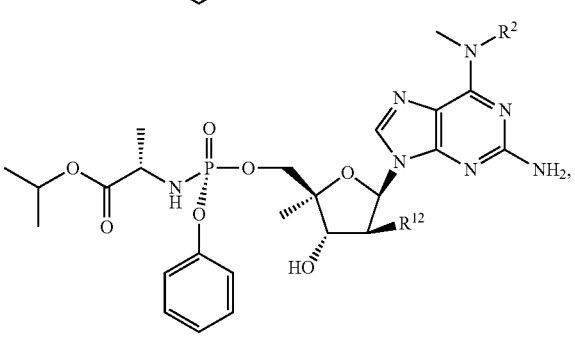
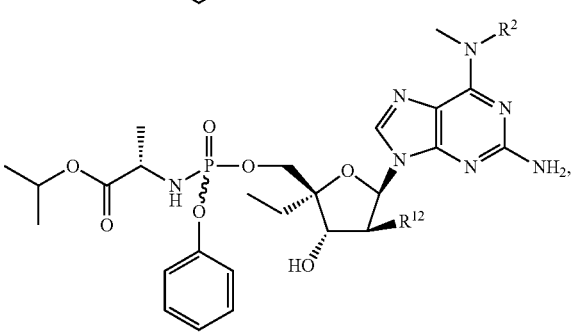
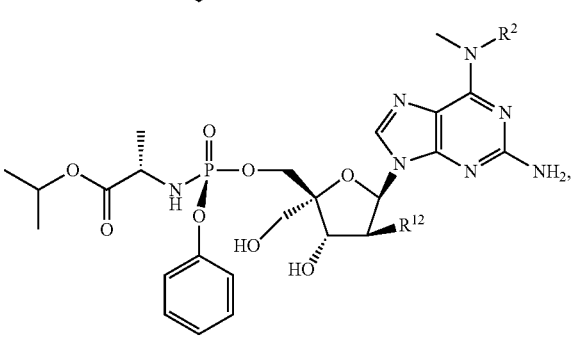
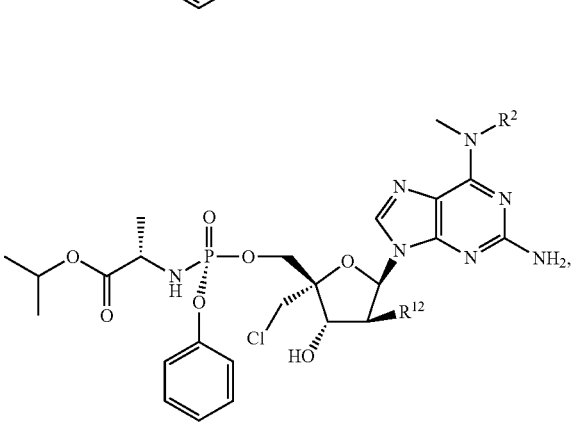

301
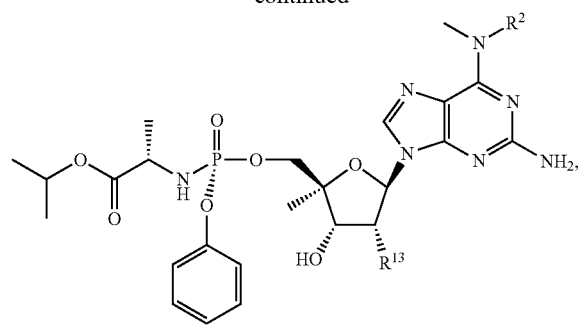
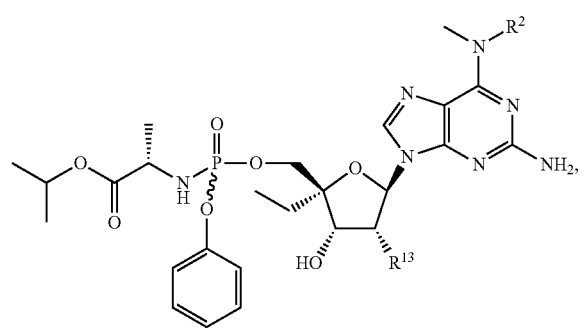
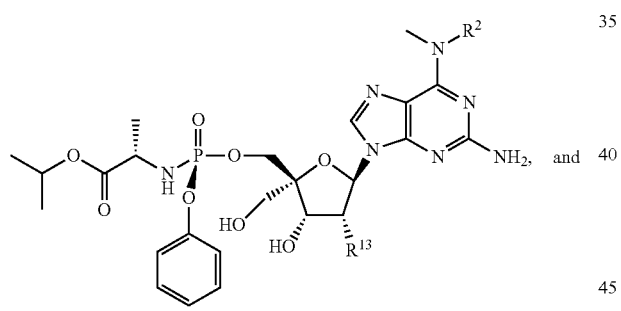
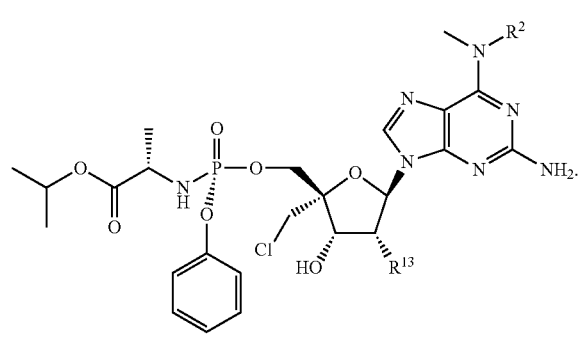
In an alternative embodiment, a compound of Formula III is provided. Non-limiting examples of compounds of Formula III include:
302
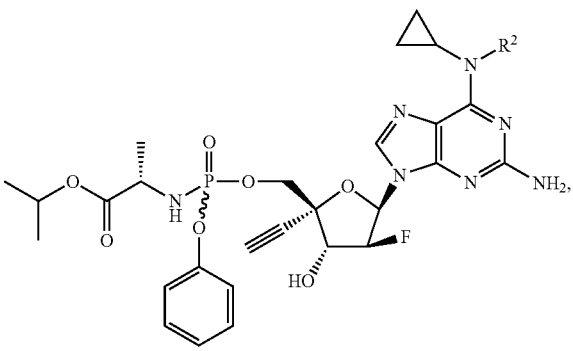
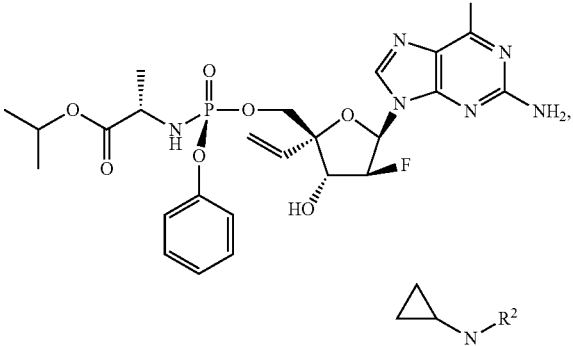
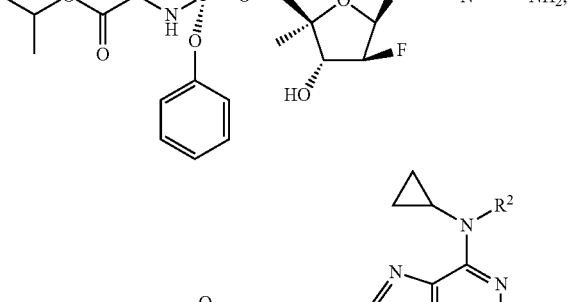
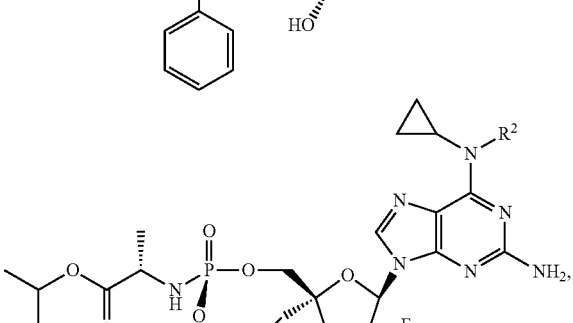

303
-continued
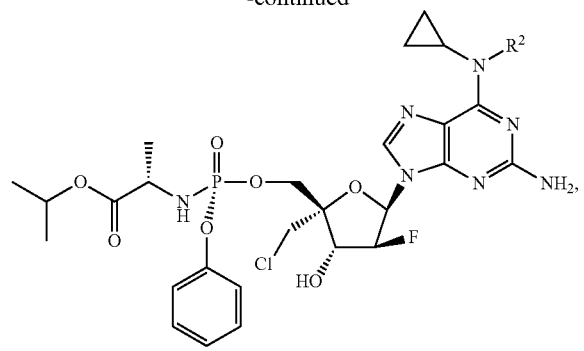
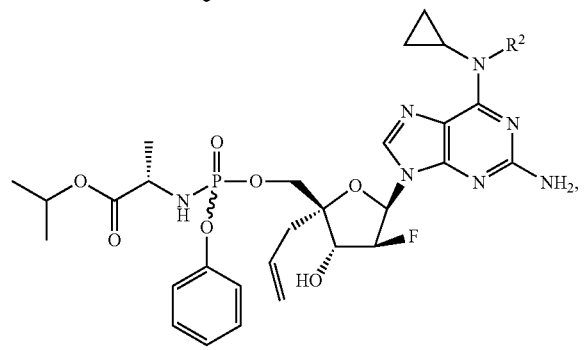
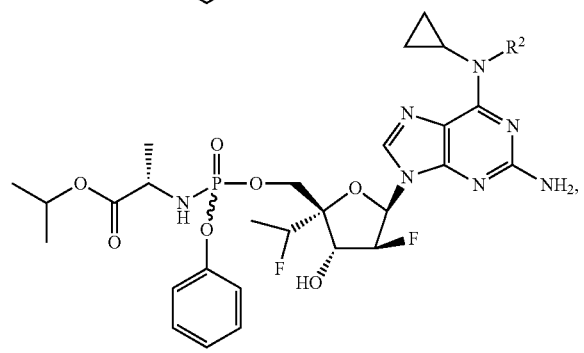
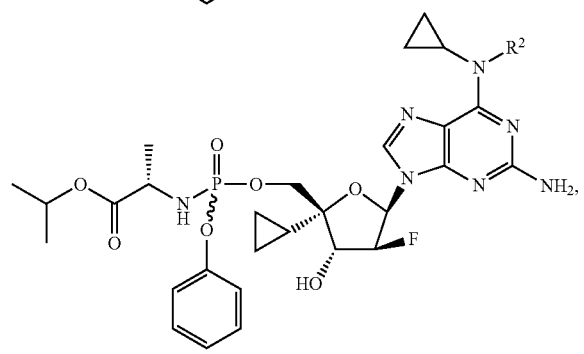
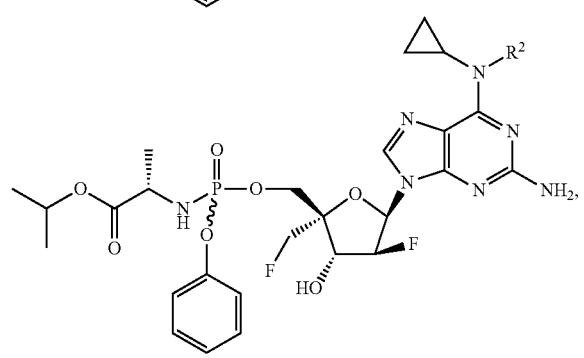
304
-continued
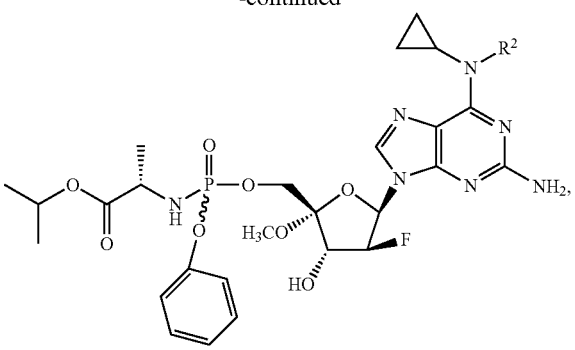
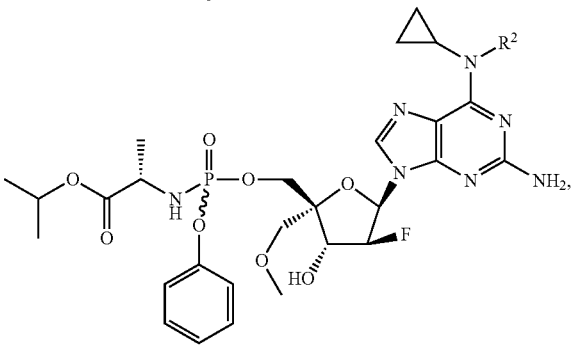
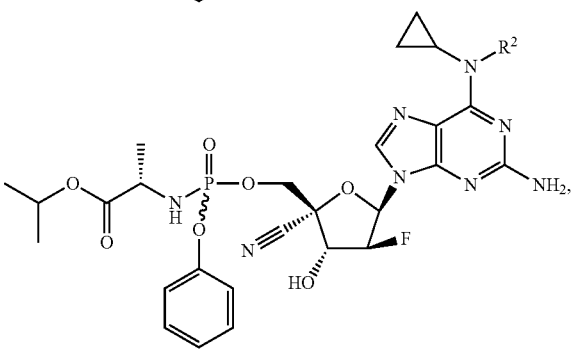
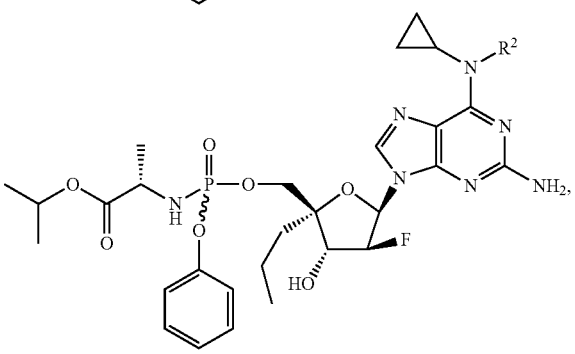
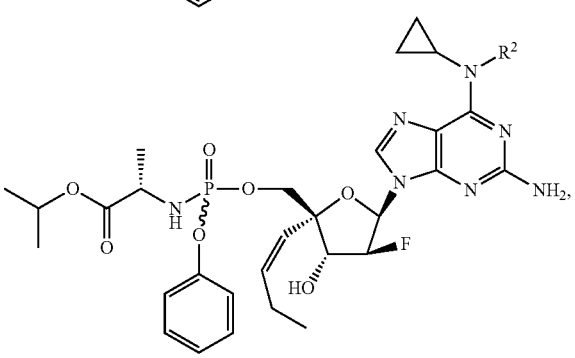

305
-continued
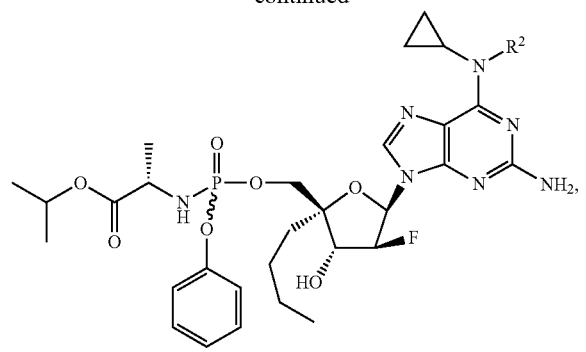
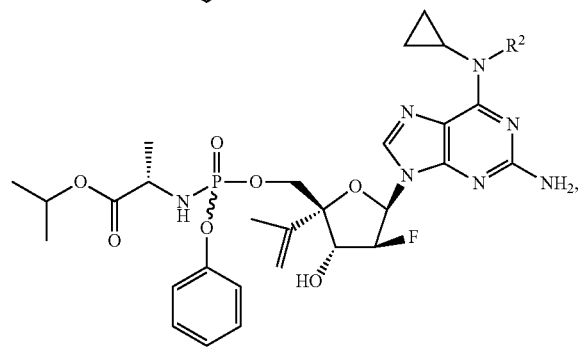
306
-continued
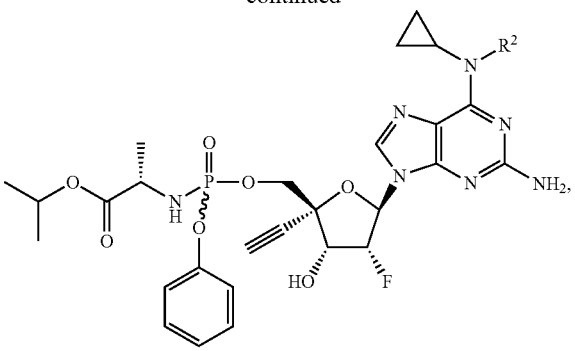
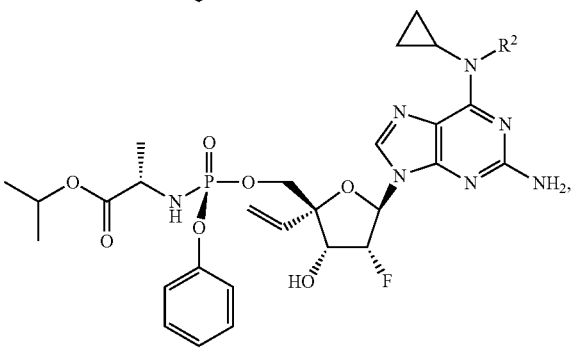
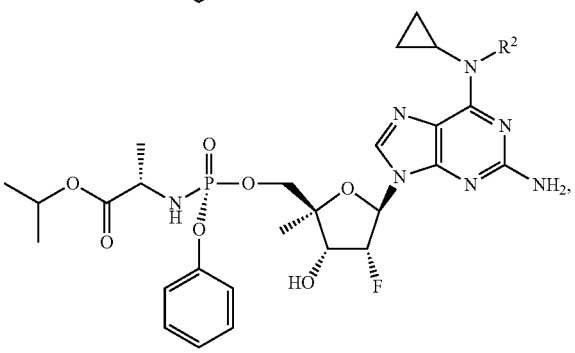
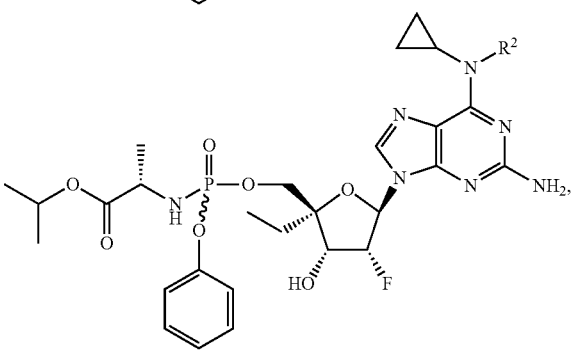
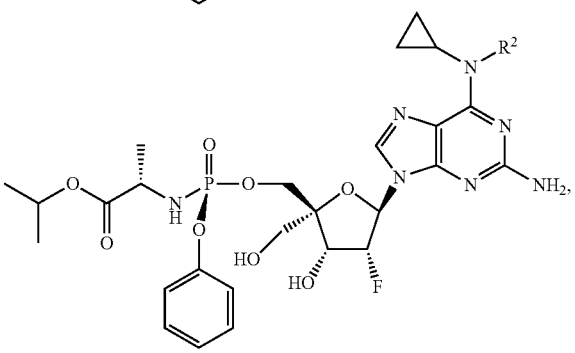

307
-continued
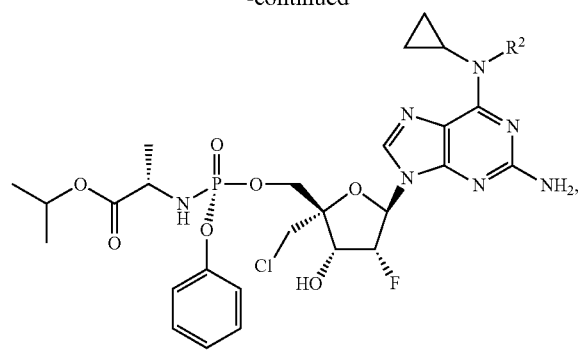
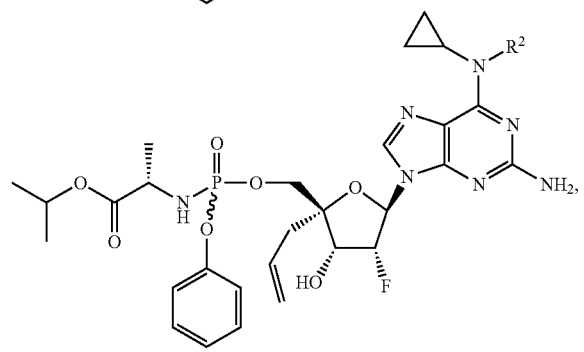
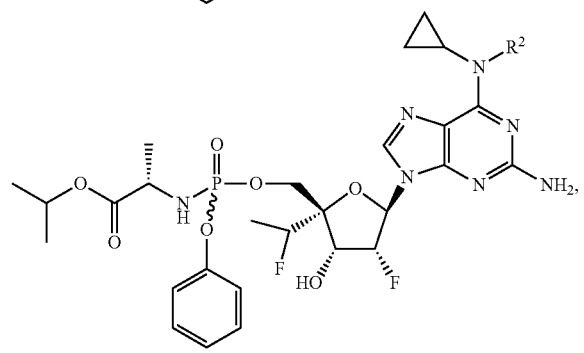
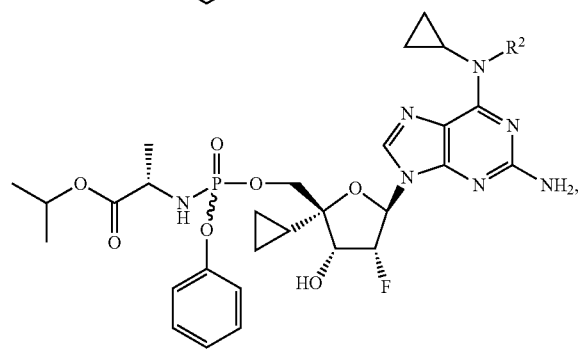
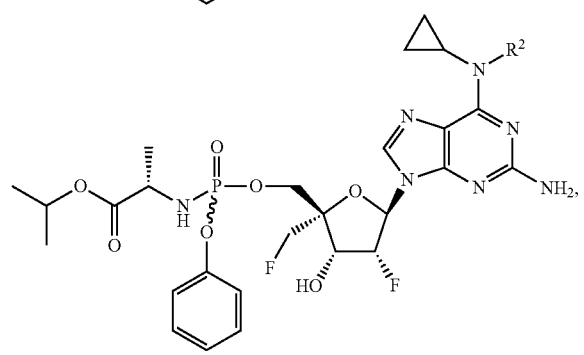
308
-continued
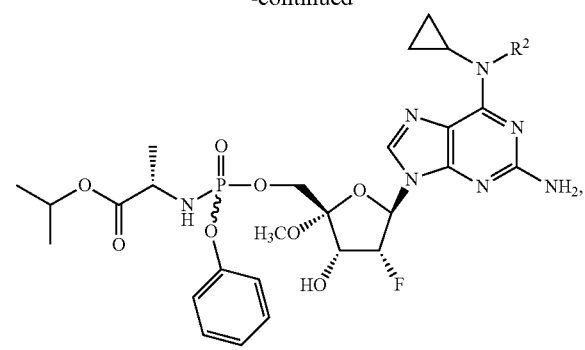
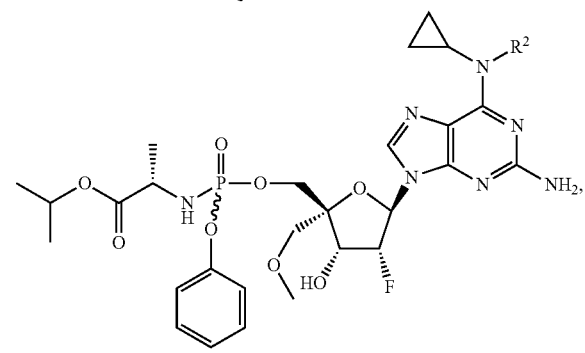
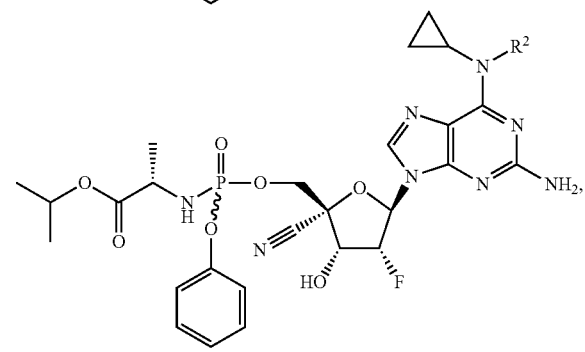
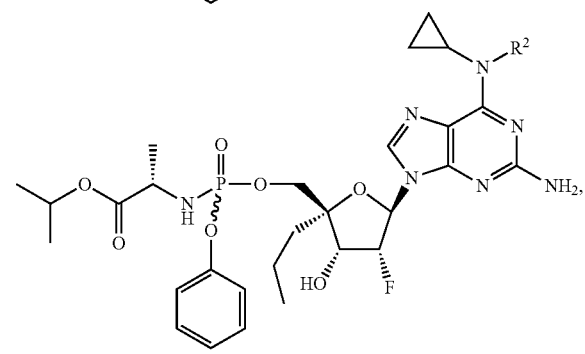
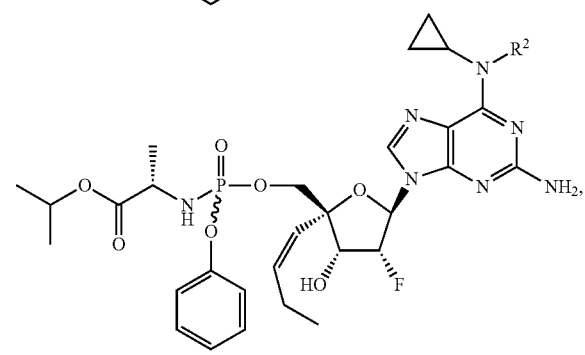

309
-continued
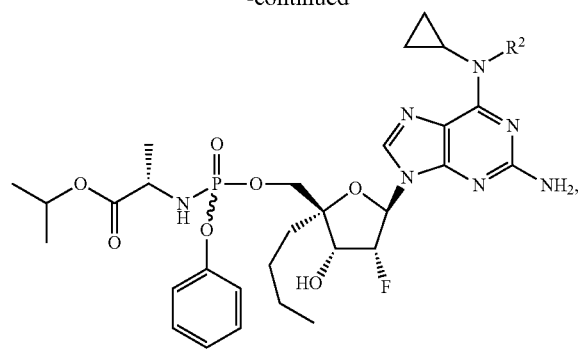
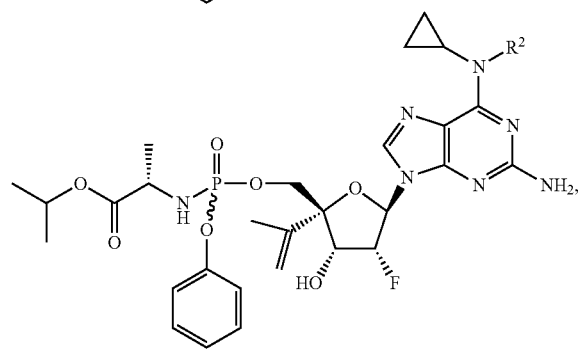
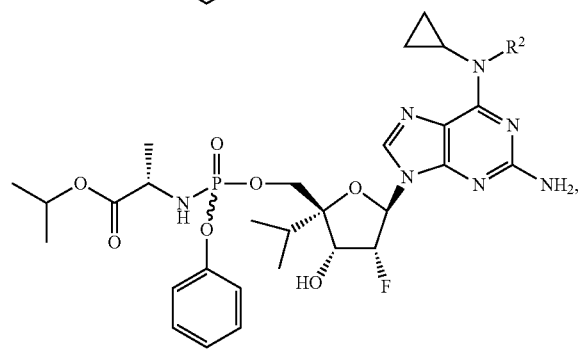
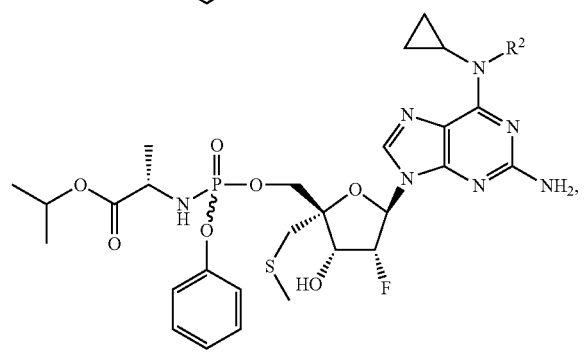
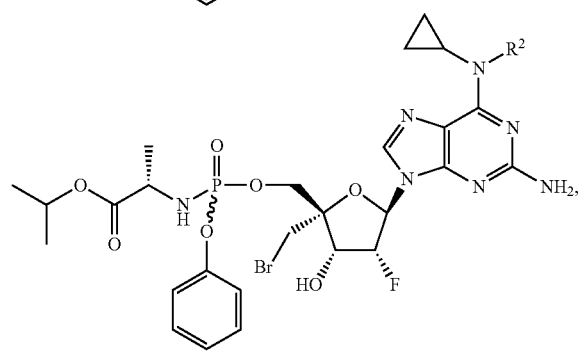
310
-continued
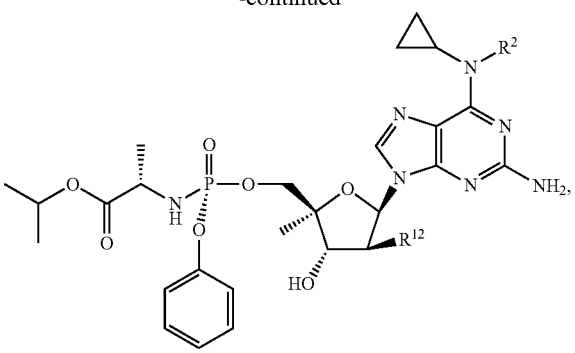
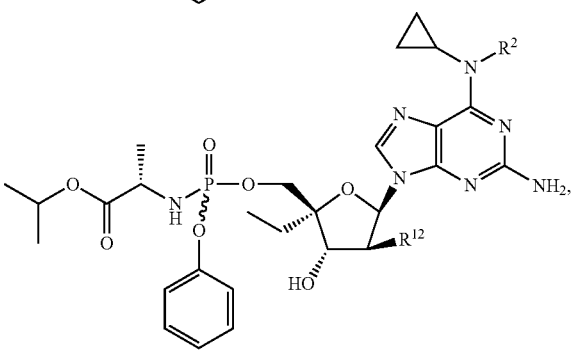
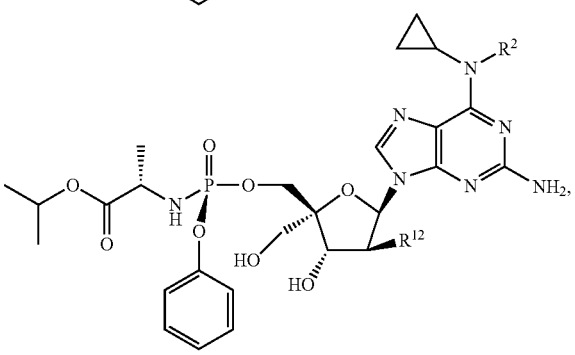
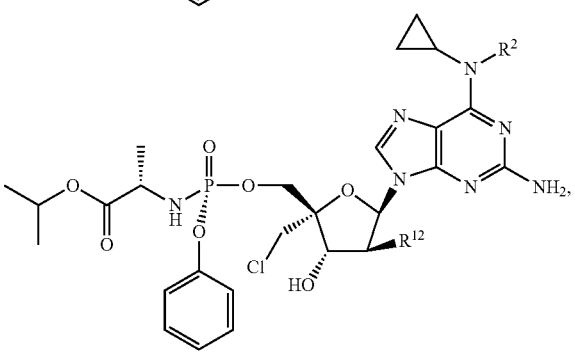
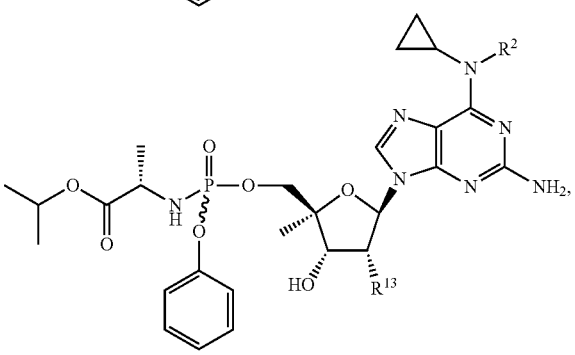

311
-continued
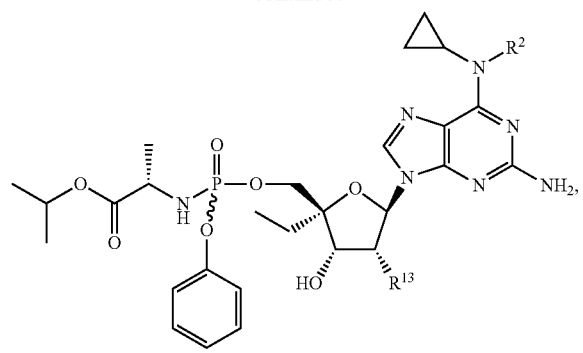
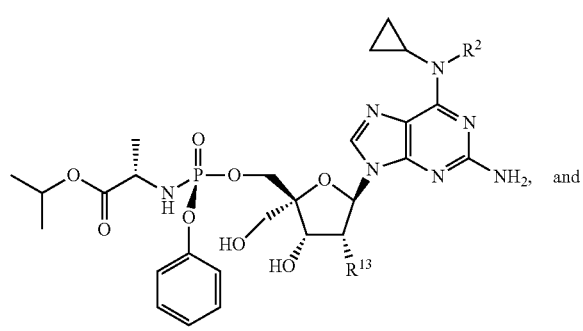
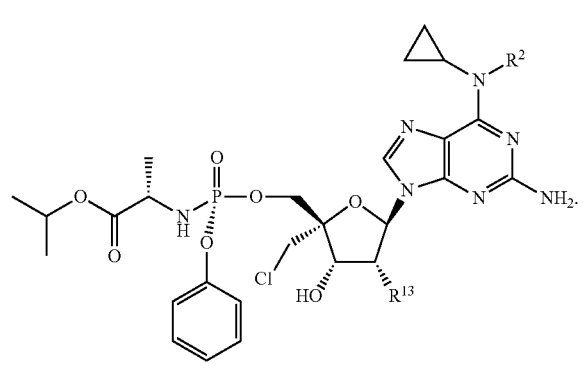
In an alternative embodiment, a compound of Formula III is provided. Non-limiting examples of compounds of Formula III include:
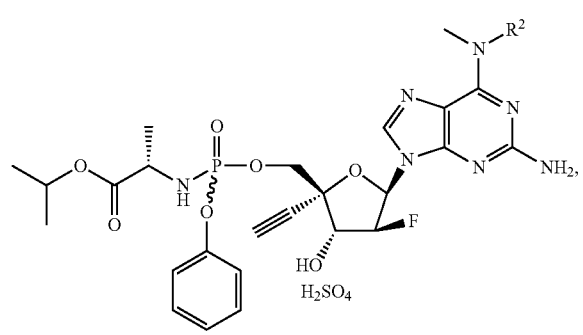
312
-continued
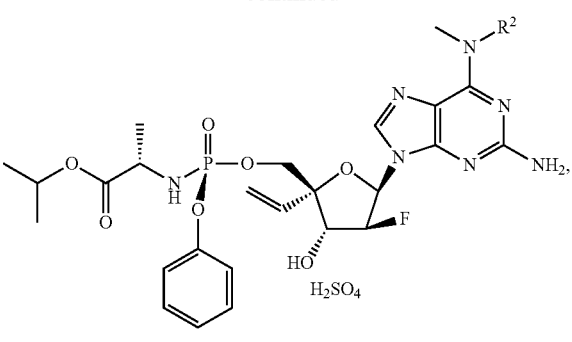
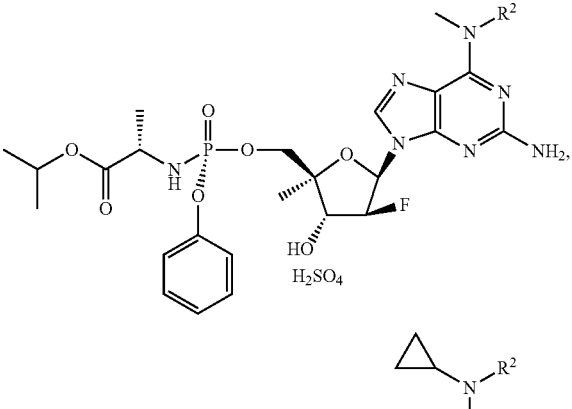
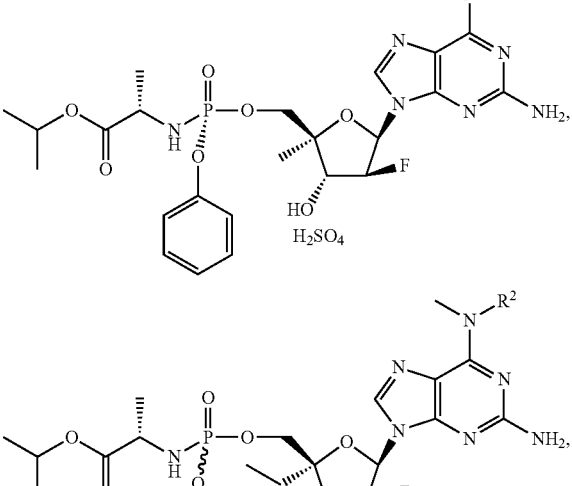
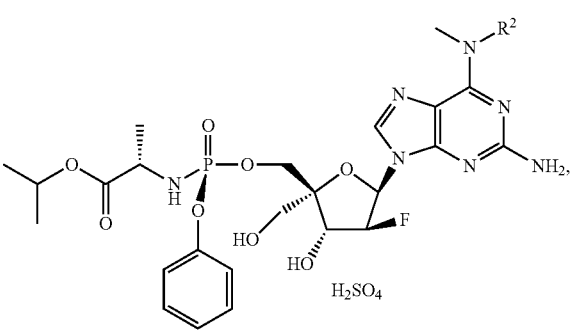

313
-continued
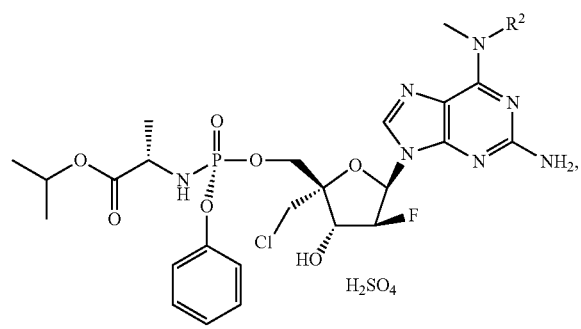
H2SO4
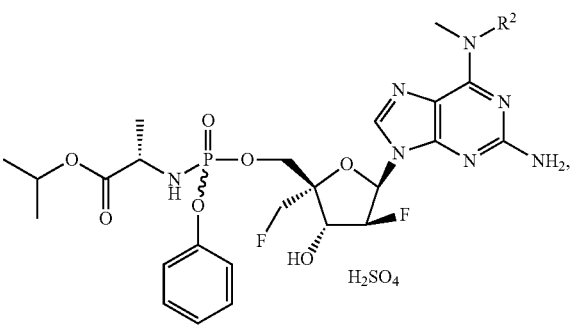
H2SO4
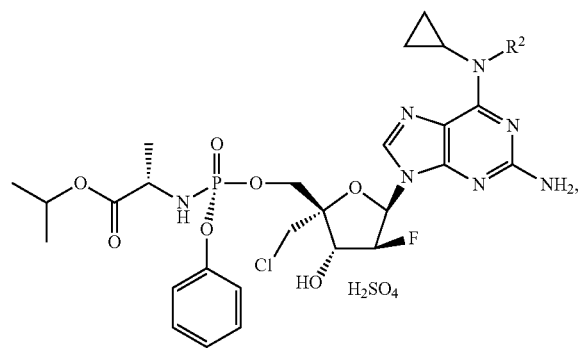
H2SO4
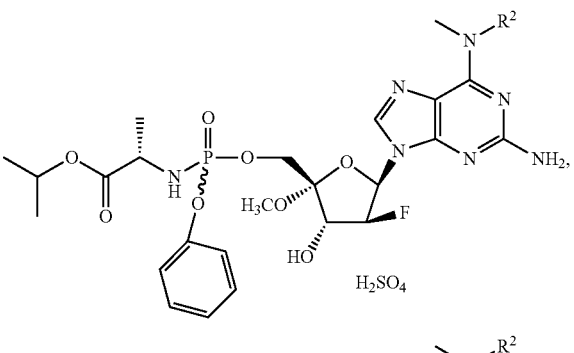
H2SO4
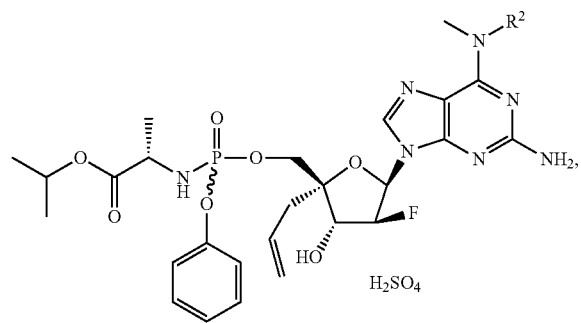
H2SO4
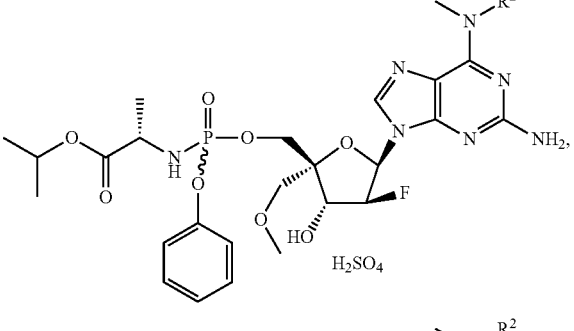
H2SO4
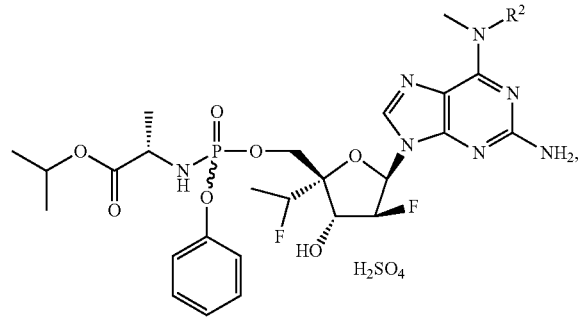
H2SO4
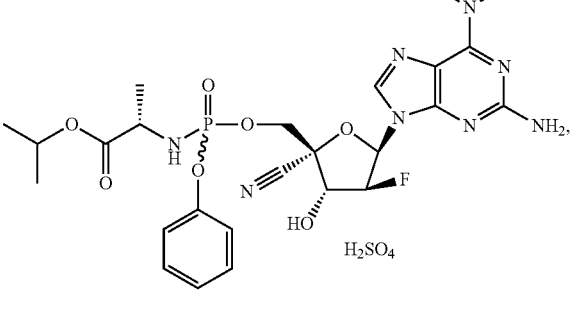
H2SO4
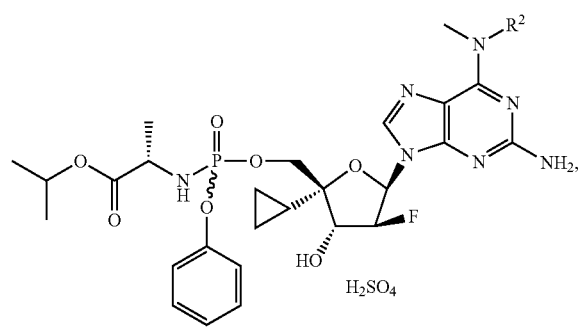
H2SO4
314
-continued
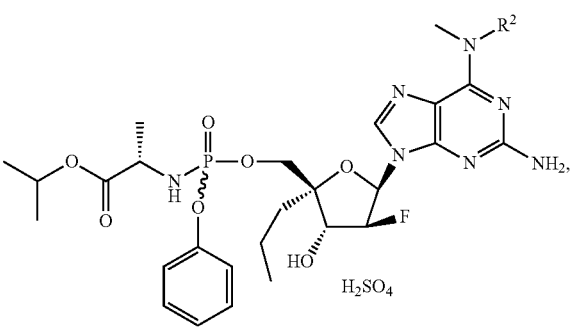
H2SO4

315
-continued
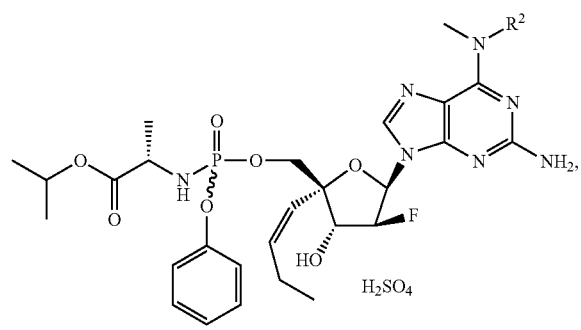
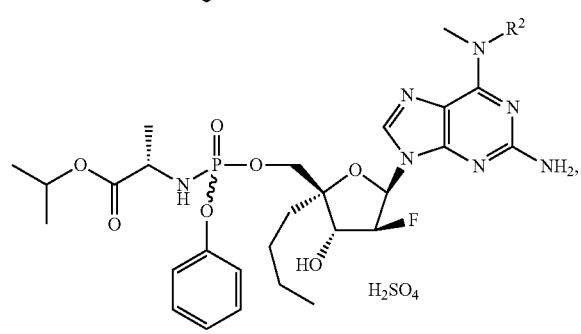
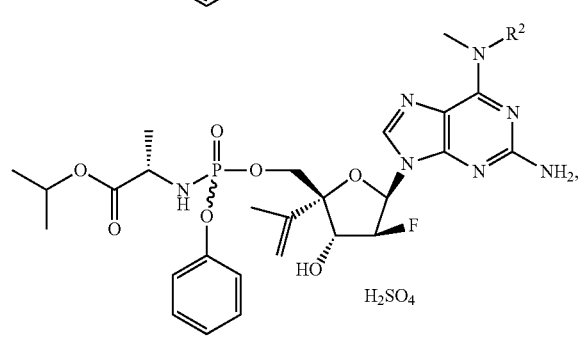
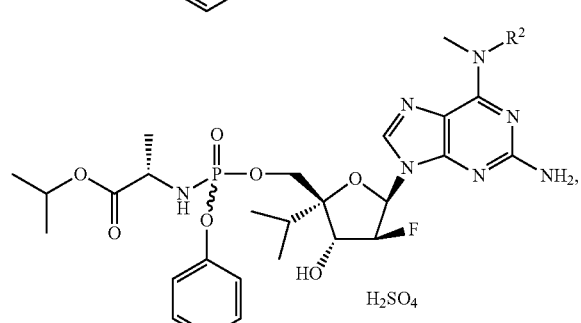
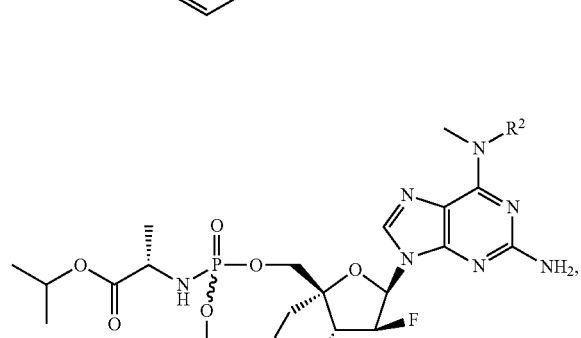
316
-continued
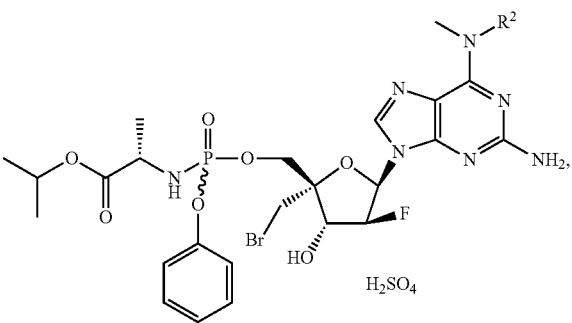
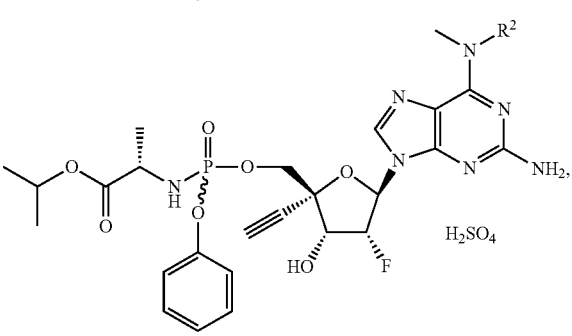
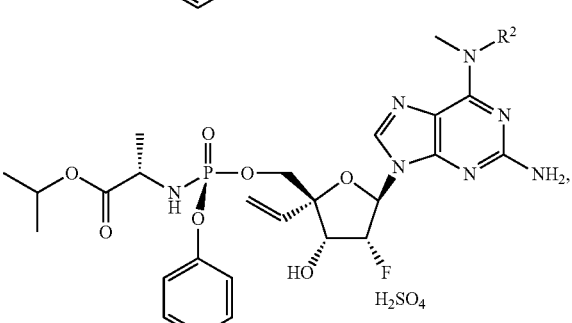
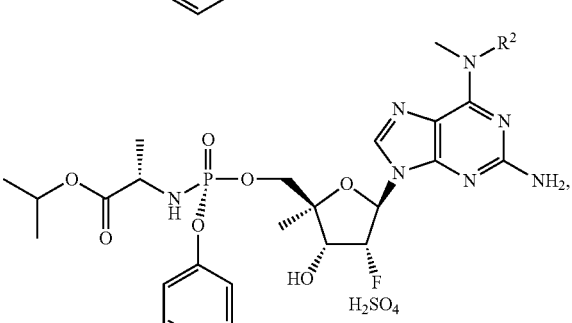
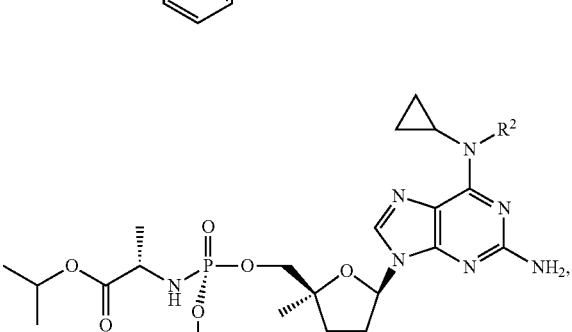

317
-continued
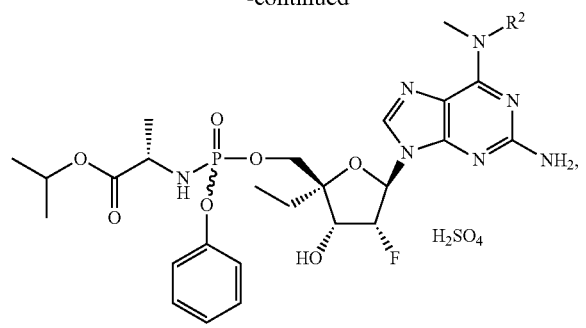
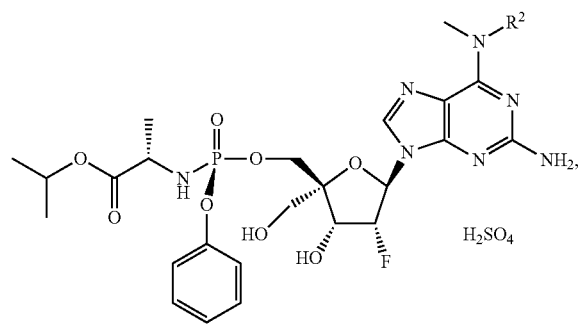
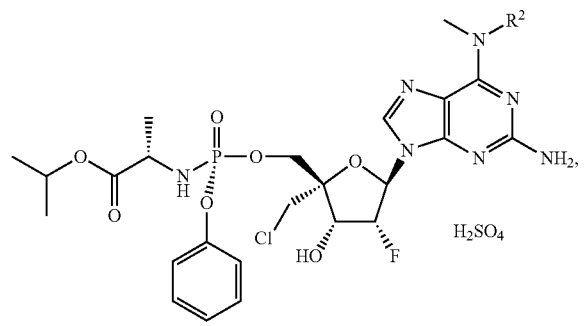
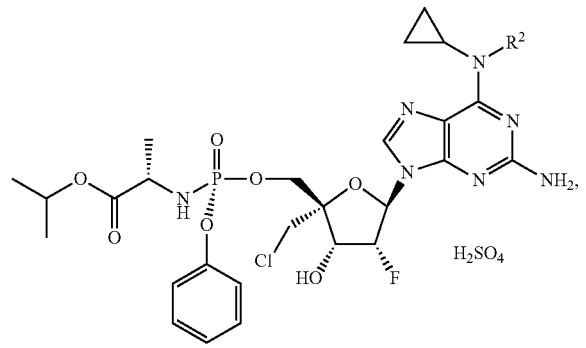
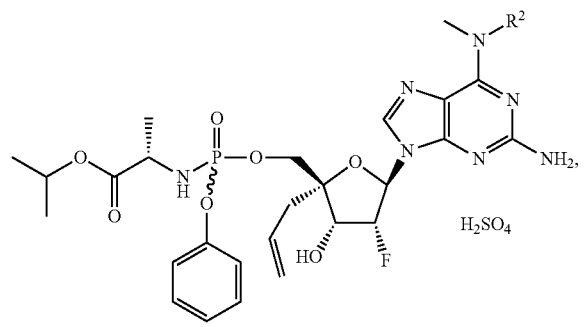
318
-continued
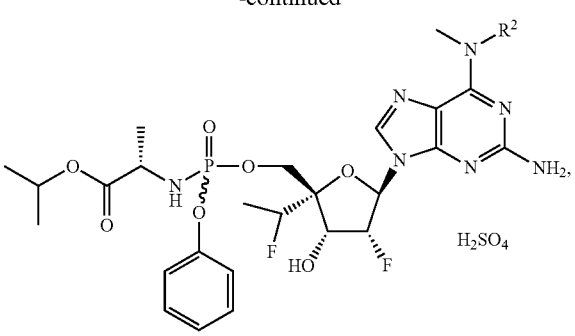
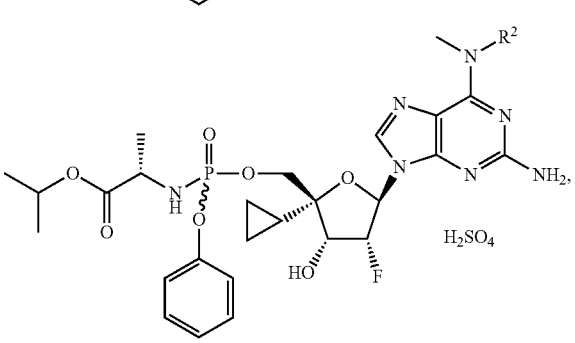
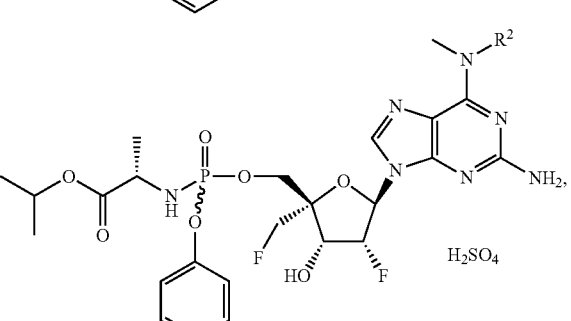
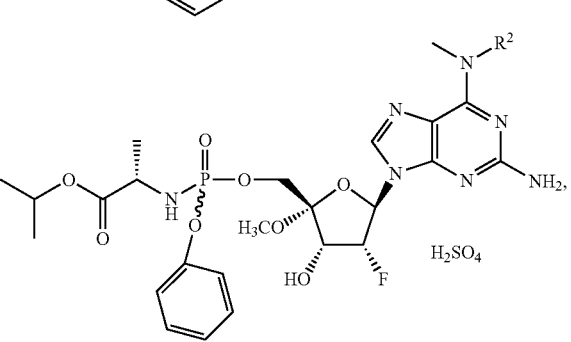

319
-continued
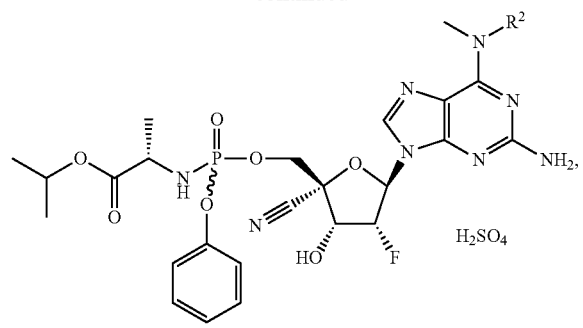
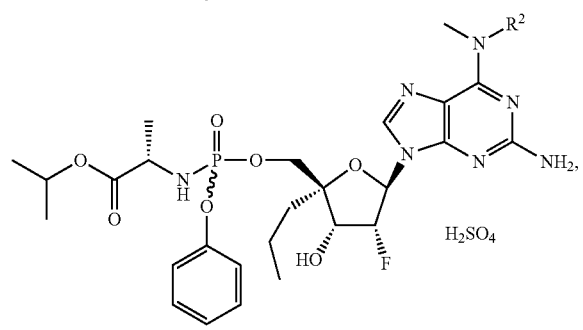
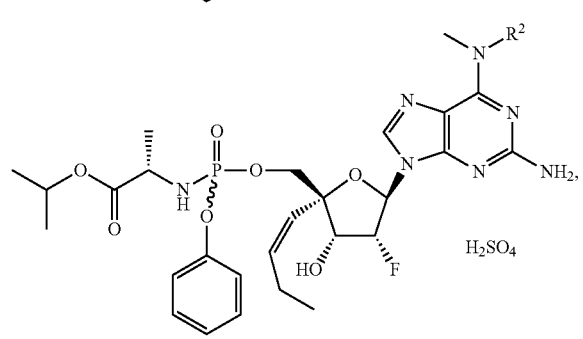
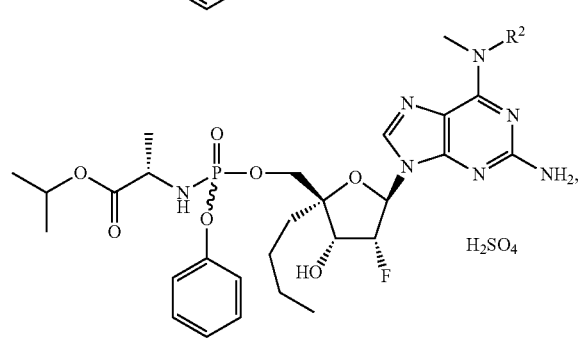
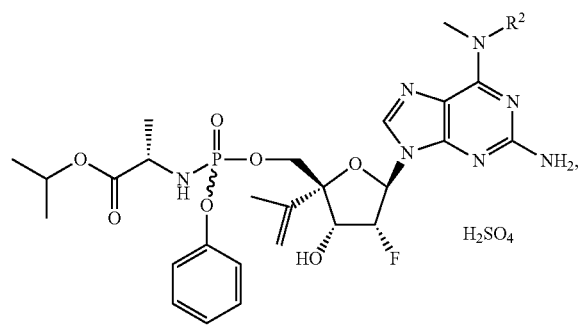
320
-continued
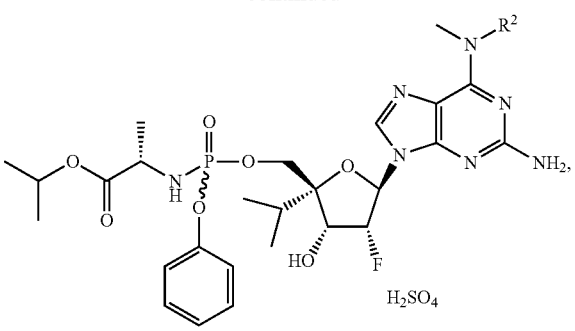
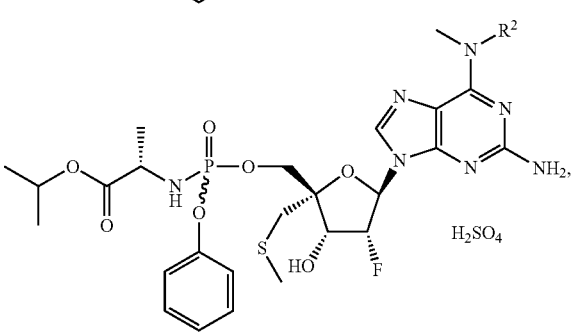
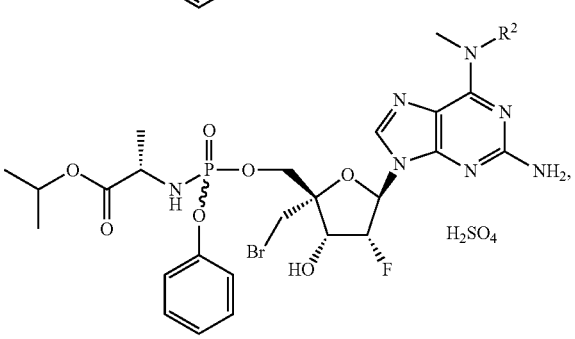
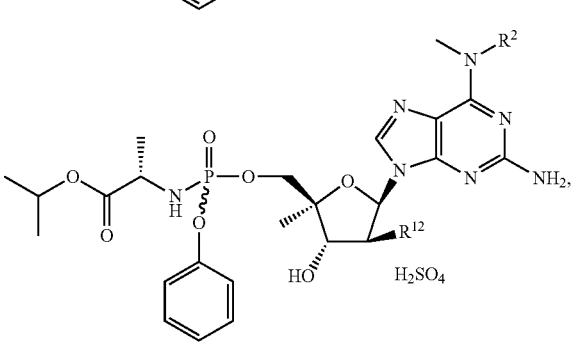
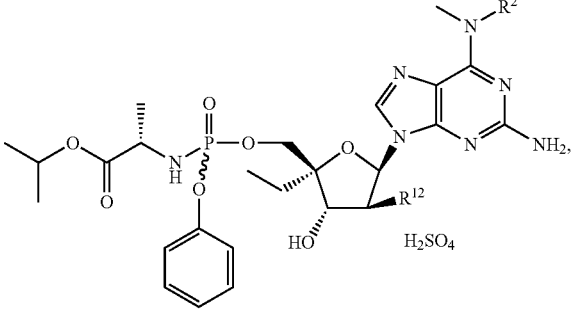

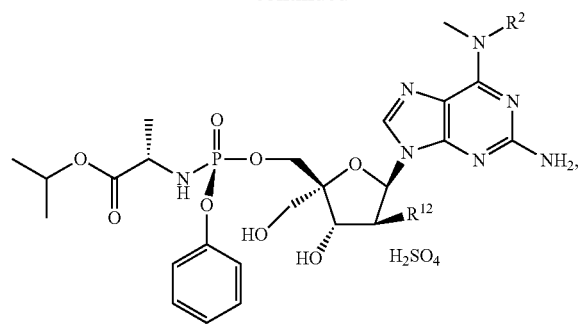
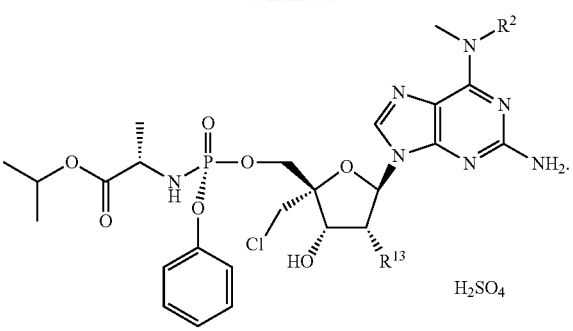
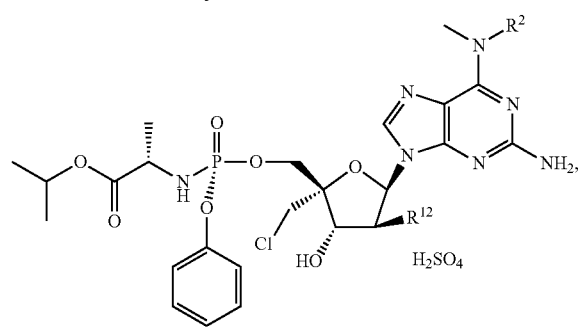
In an alternative embodiment, a compound of Formula IV is provided. Non-limiting examples of compounds of Formula IV include:
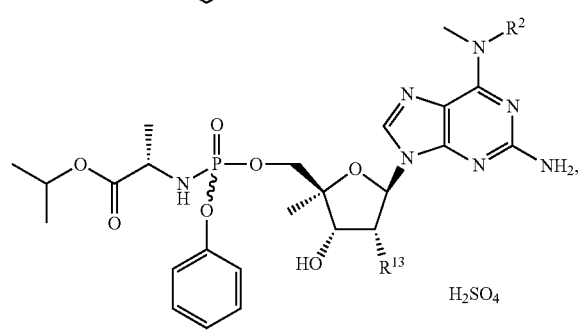
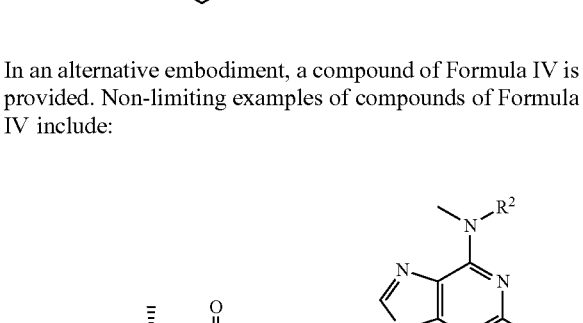
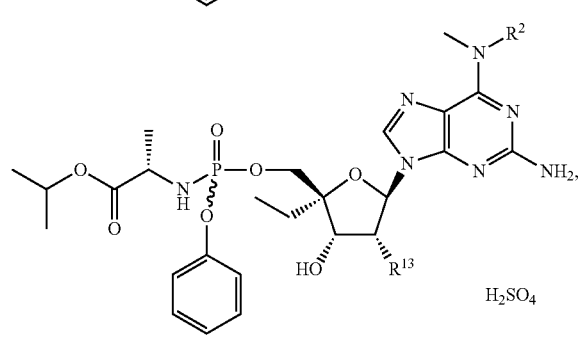
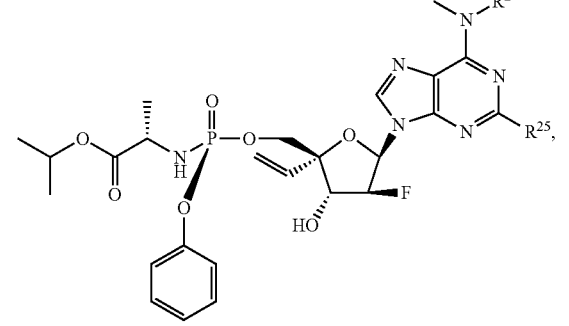
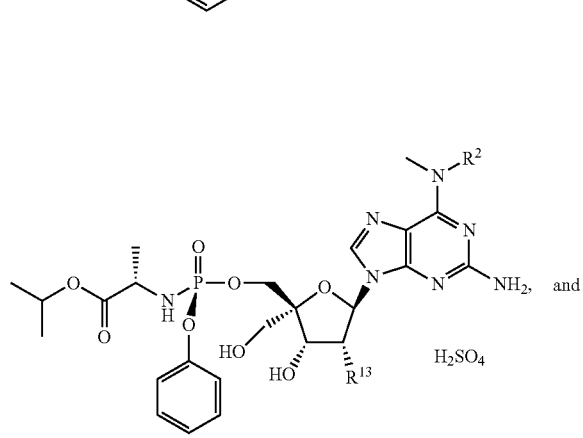
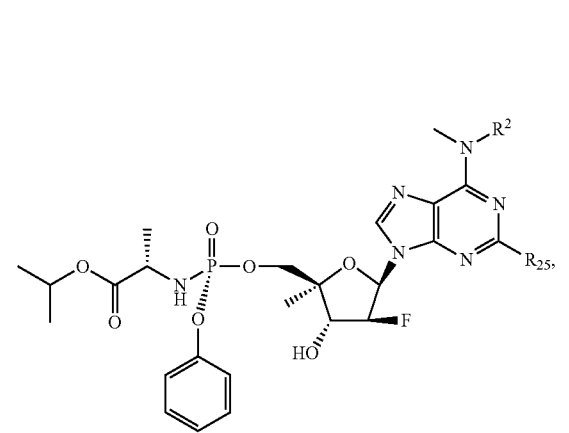

323
-continued
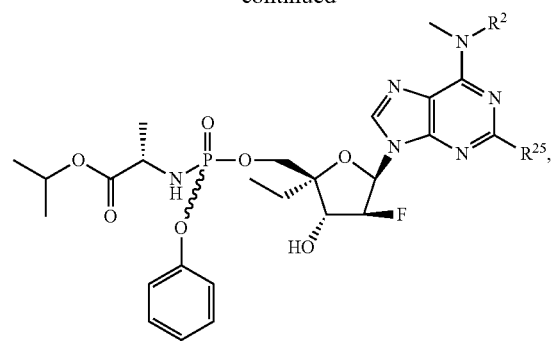
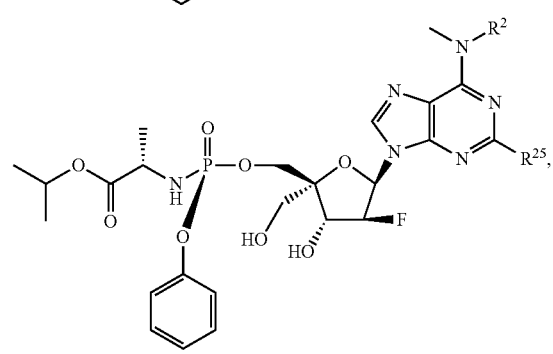
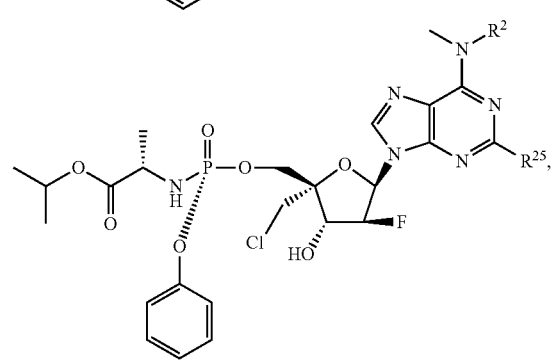
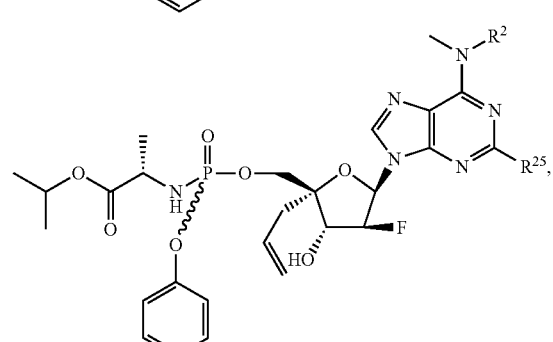
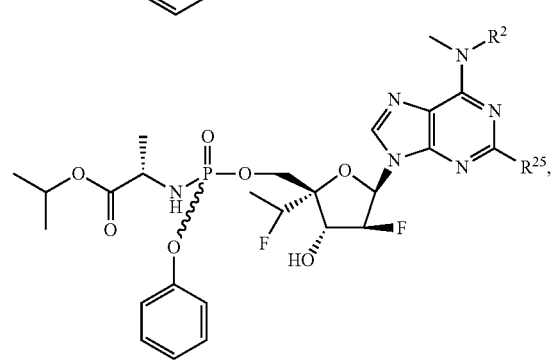
324
-continued
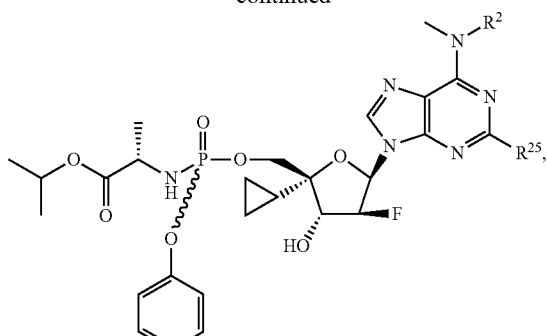
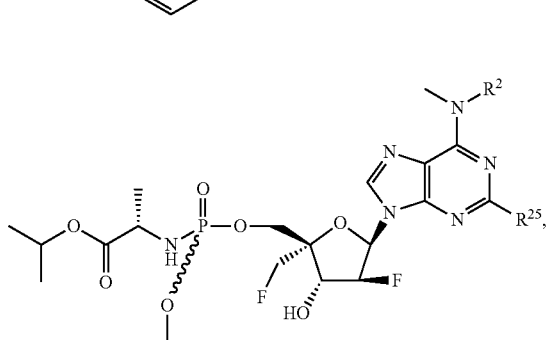
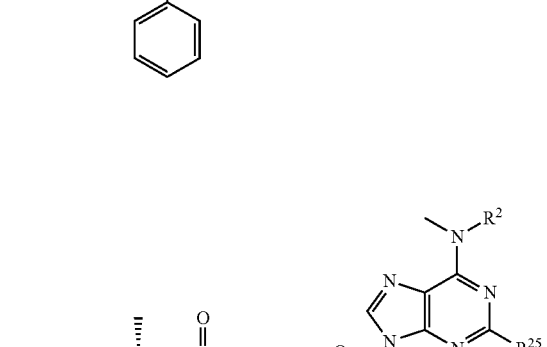
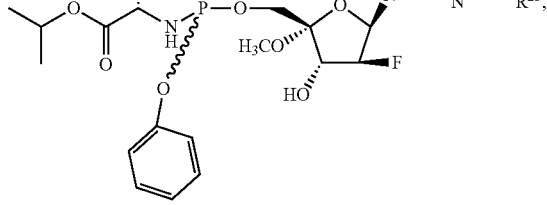
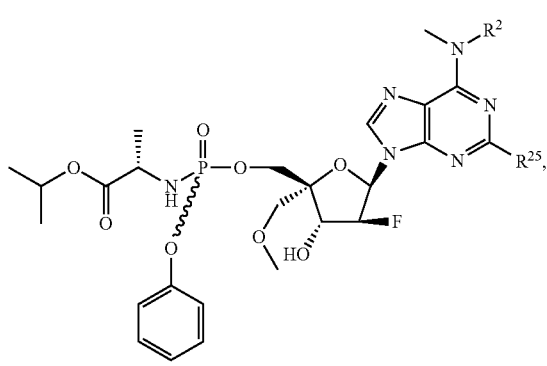

325
-continued
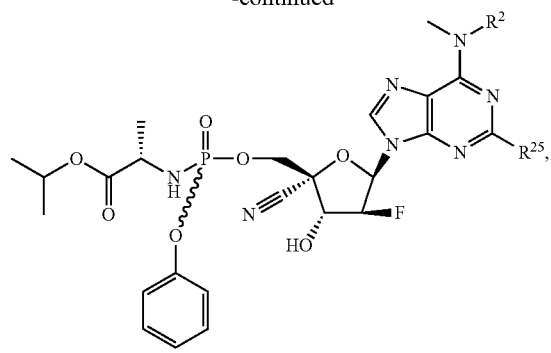
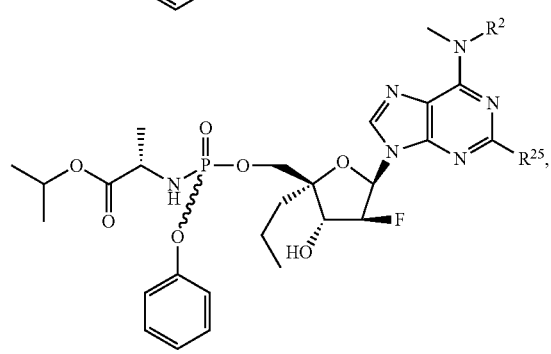
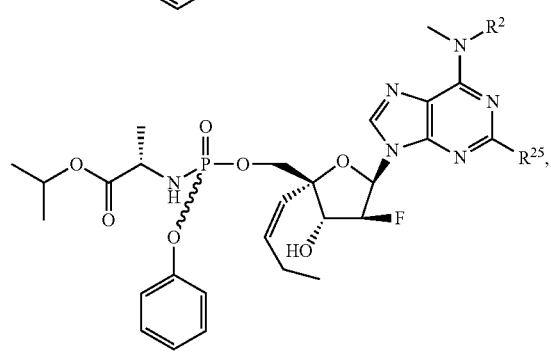
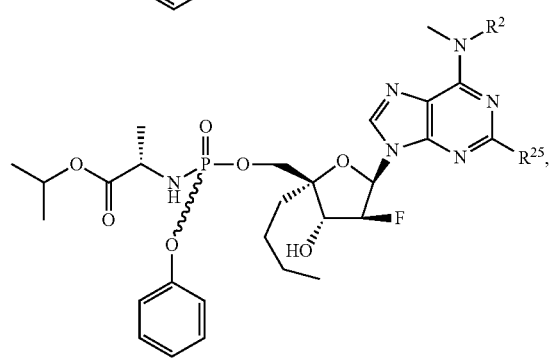
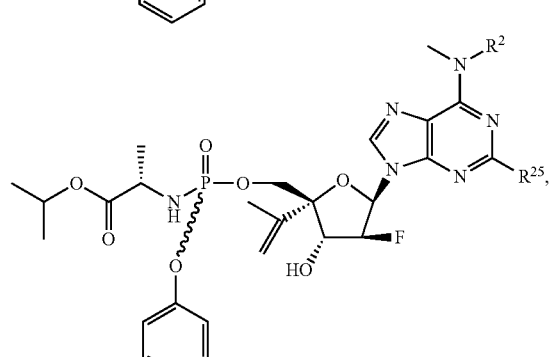
326
-continued
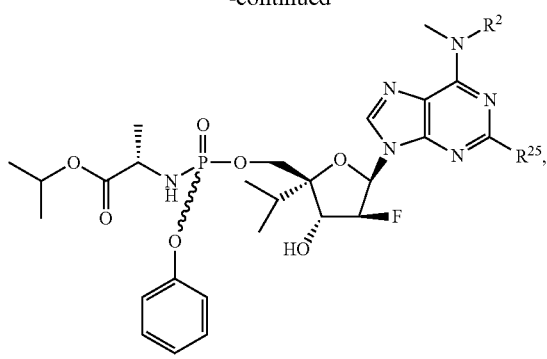
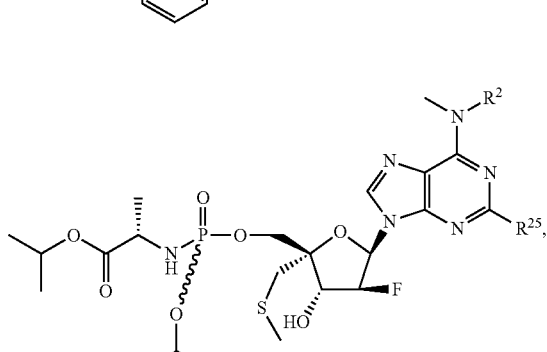
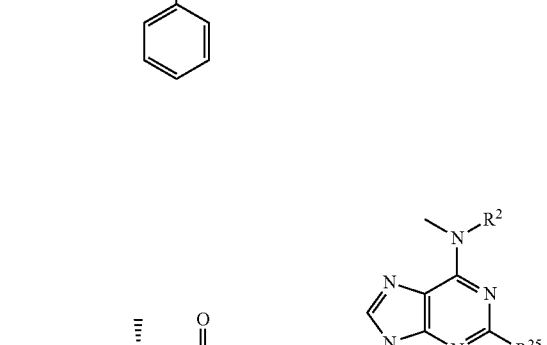
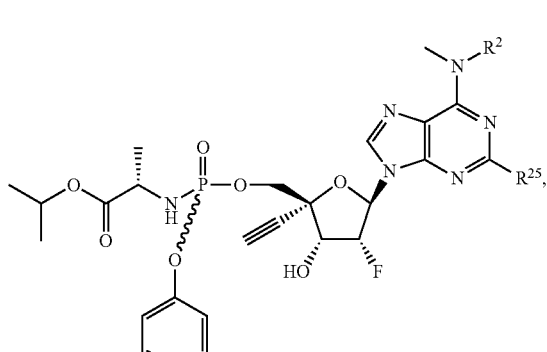

327
-continued
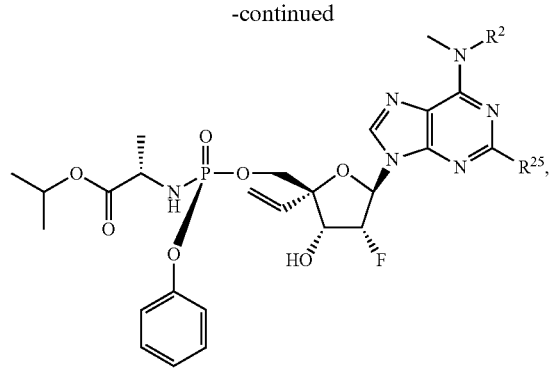
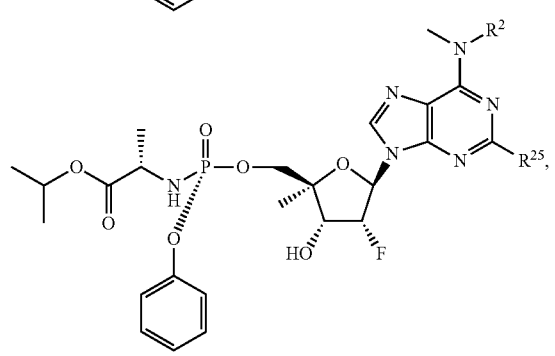
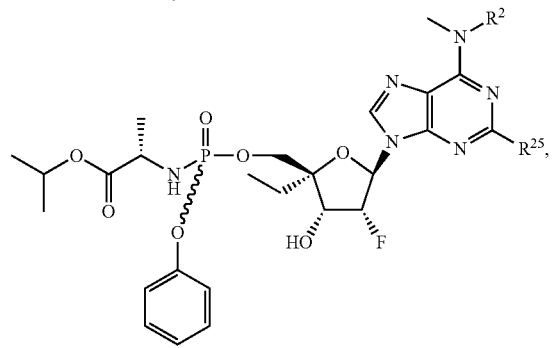
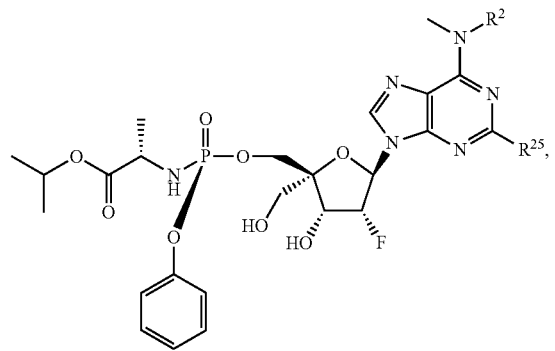
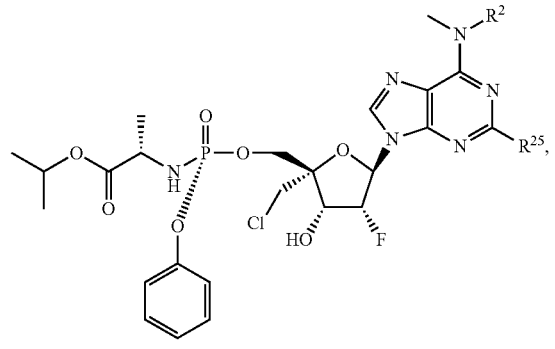
328
-continued
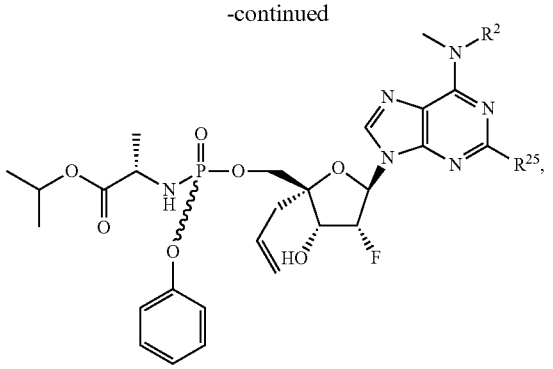
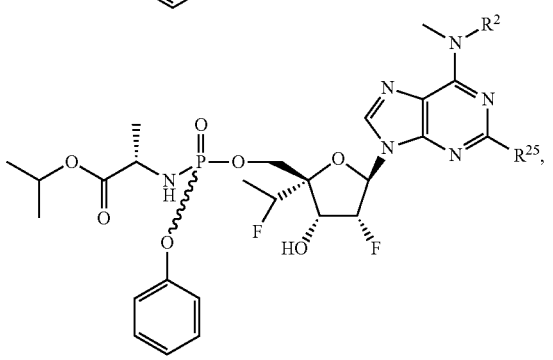
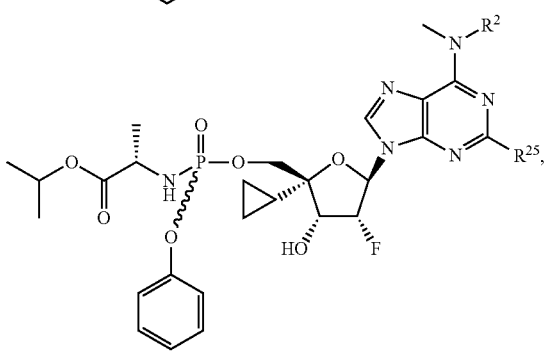
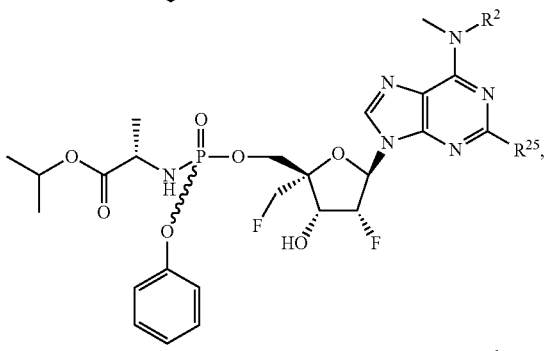
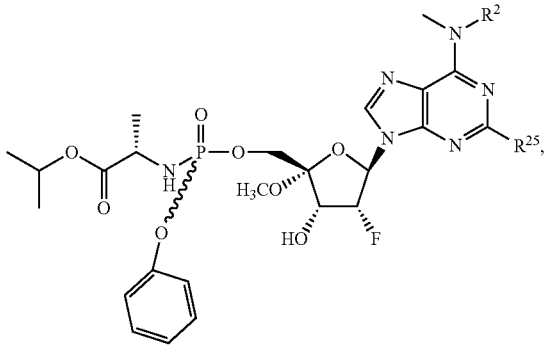

329
-continued
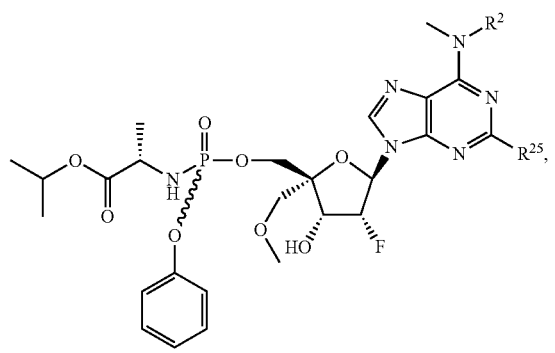
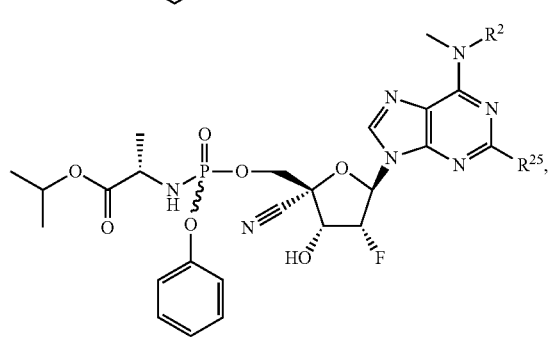
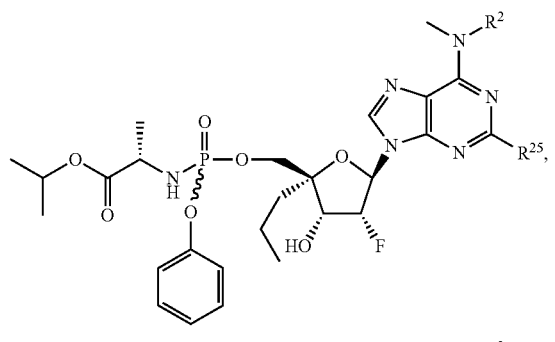
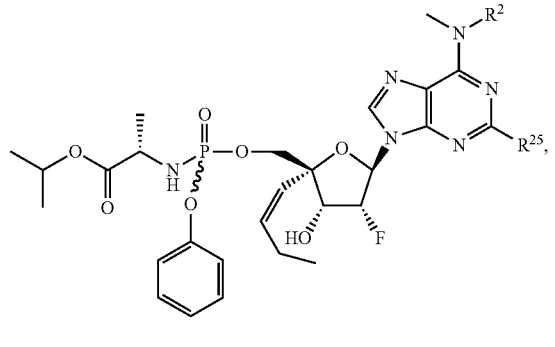
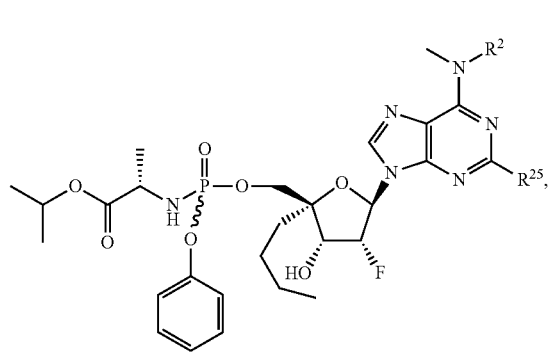
330
-continued
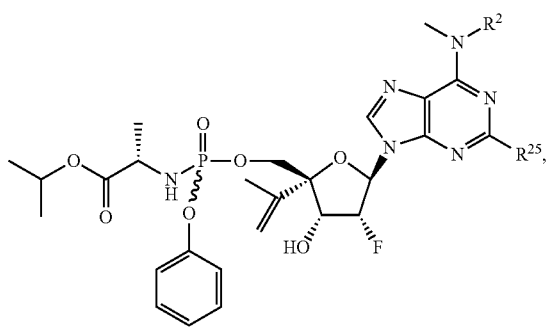
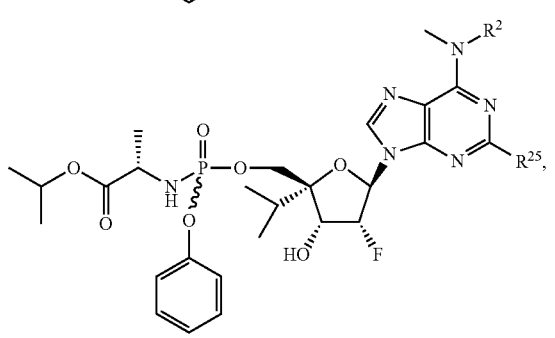
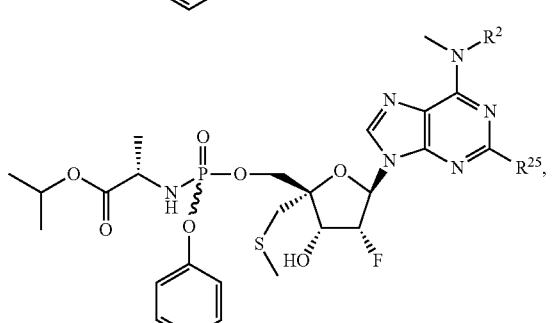
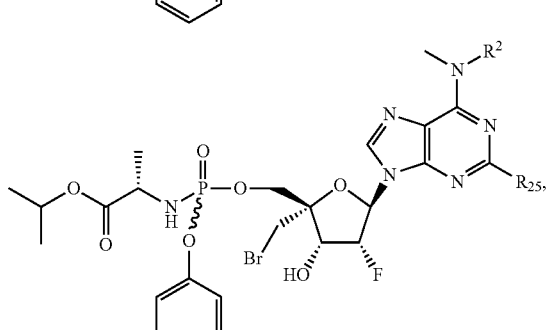
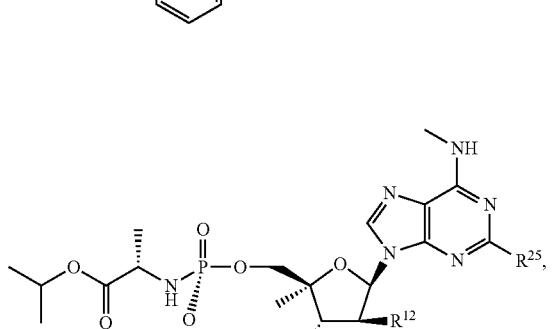

331
-continued
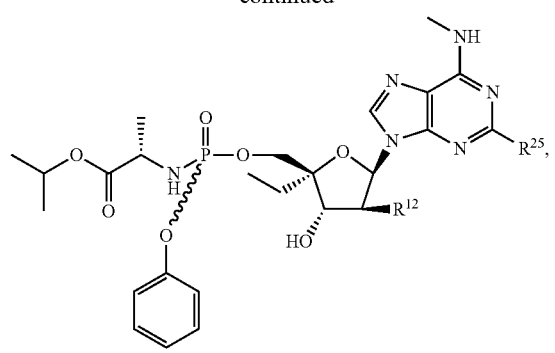
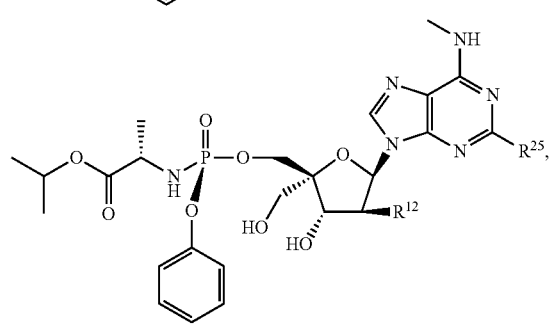
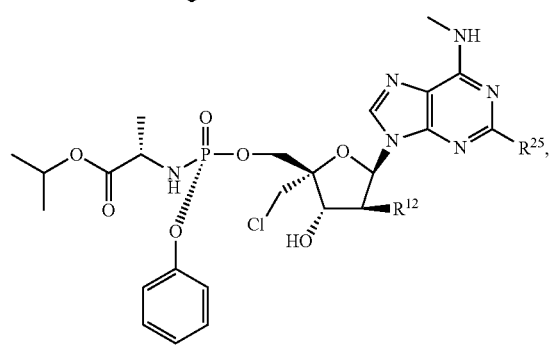
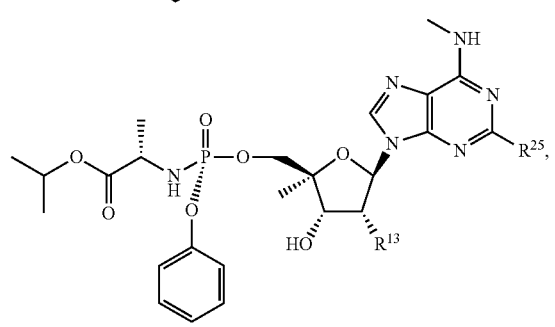
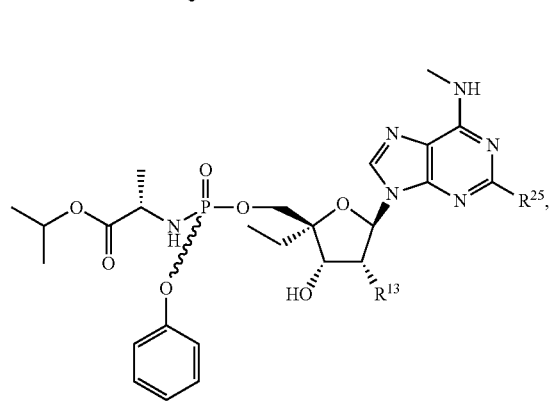
332
-continued
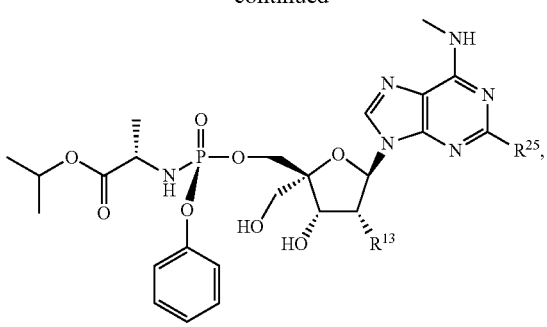
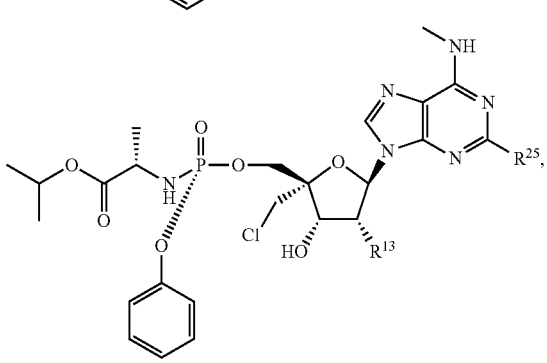
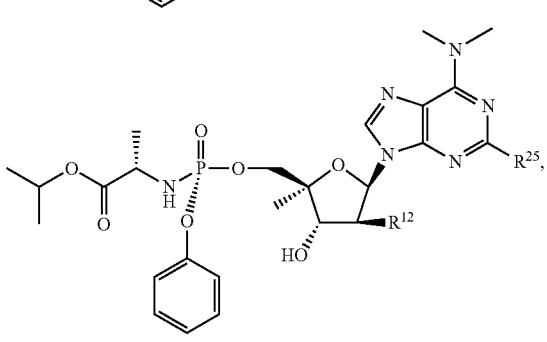
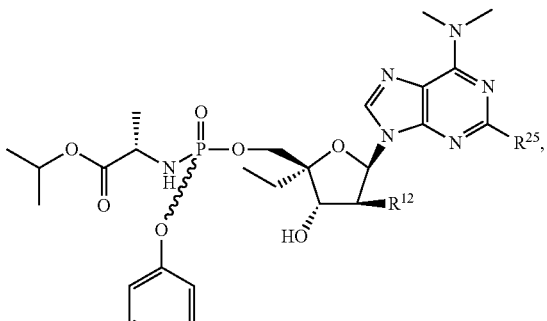
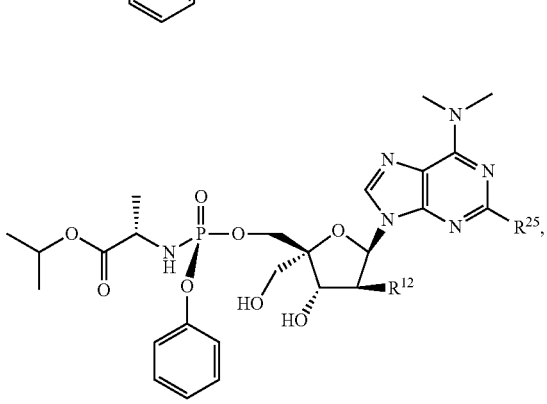

-continued

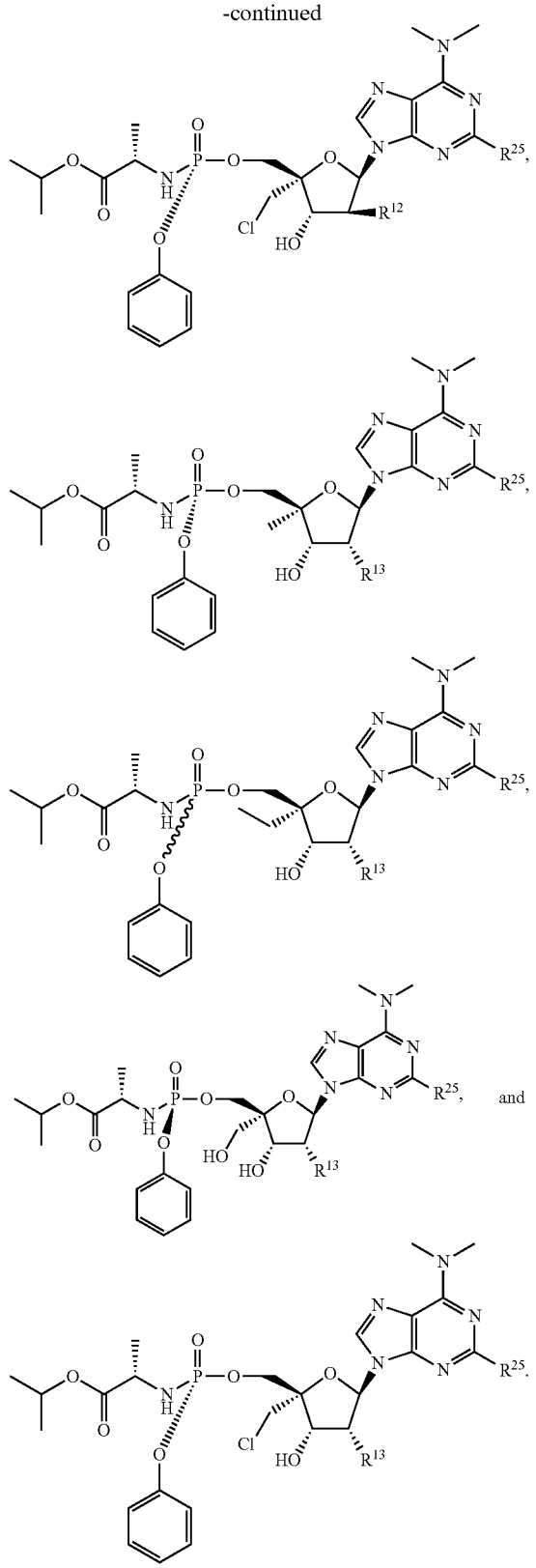

II. Definitions

The following terms are used to describe the present invention. In instances where a term is not specifically defined herein, that term is given an art-recognized meaning by those of ordinary skill applying that term in context to its use in describing the present invention.

The term "pharmaceutically acceptable salt" or prodrug" is used throughout the specification to describe any pharmaceutically acceptable form (such as an ester, phosphoramidate, thiophosphoramidate, phosphate ester, salt of an ester, or a related group) of a 2'-deoxy-2'-α-fluoro-2'-β-C-substituted-4'-fluoro-$N^6$-substituted-2,6-diaminopurine nucleotide or 2'-deoxy-2'-α-fluoro-2'-β-C-substituted-4'-fluoro-2-substituted-$N^6$-substituted-6-aminopurine nucleotide or β-D-2'-deoxy-2'-substituted-4'-substituted-2-substituted-$N^6$-substituted-6-aminopurine nucleotide which, upon administration to a patient, provides the desired active compound. Examples of pharmaceutically acceptable salts are organic acid addition salts formed with acids, which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium, or lithium) or alkaline earth metal (for example calcium) salts of carboxylic acids can also be made. The salts of the present compounds can be synthesized from a parent compound that contains a basic or acidic moiety by conventional chemical methods. Generally, such salt can be prepared by reacting free acid forms of these compounds with a stoichiometric amount of the appropriate base (such as Na, Ca, Mg, or K hydroxide, carbonate, bicarbonate, or the like), or by reacting a free base form of the compound with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

Additional non-limiting examples of salts include 1-hydroxy-2-naphthoic acid, 2,2-dichloroacetic acid, 2-oxoglutaric acid, 4-acetamidobenzoic acid, 4-aminosalicylic acid, adipic acid, aspartic acid, benzenesulfonic acid, camphoric acid, camphor-10-sulfonic acid, capric acid, caproic acid, caprylic acid, carbonic acid, cinnamic acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutaric acid, glycerophosphoric acid, hippuric acid, isobutyric acid, lactobionic acid, lauric acid, malonic acid, mandelic acid, naphthalene-1,5-disulfonic acid, naphthalene-2-sulfonic acid, nicotinic acid, nitric acid, oleic acid, palmitic acid, pyroglutamic acid, sebacic acid, thiocyanic acid, and undecylenic acid. Lists of additional suitable salts may be found, e.g., in *Remington's Pharmaceutical Sciences,* 17th ed., Mack Publishing Company, Easton, Pa., p. 1418 (1985).

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

"Pharmaceutically acceptable prodrug" refers to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated, thiophoshoramidated, dethiophoshoramidated, phoshoramidated or dephosphoramidated to produce the active compound. The compounds of this invention possess antiviral activity against RSV, or are metabolized to a compound that exhibits such activity. The β-D-2'-deoxy-2'-α-fluoro-4'-fluoro-2-substituted-$N^6$-substituted-6-aminopurine nucleoside or β-D-2'-deoxy-2'-substituted-4'-substituted-2-substituted-$N^6$-substituted-6-aminopurine nucleotide can also be administered as a 5'-phosphoether lipid, a bisphosphoramidate, a 3',5'-cyclic phosphoramidate, a 3',5'-cyclic thiophosphoramidate, a DTE conjugate, a mixed phosphoramidate-SATE derivative or a "SATE" derivative.

The term "substituted" or "optionally substituted" indicates that the moiety can have at least one additional substituent, including but not limited to amino, halogen (F, Cl, Br, I), OH, phenyl, benzyl, $N_3$, CN, alkyl, including methyl; alkenyl, alkynyl, alkoxy, —$SC_{1-6}$ alkyl, haloalkyl; including $CHF_2$, $CH_2F$ and $CF_3$; etc.

The term "alkyl" shall mean within its context, a linear, or branch-chained fully saturated hydrocarbon radical or alkyl group which can be optionally substituted (for example, with halogen, including F). For example, an alkyl group can have 1, 2, 3, 4, 5, 6, 7 or 8 carbon atoms (i.e., $C_1$-$C_8$ alkyl), 1, 2, 3, 4, 5 or 6 carbon atoms (i.e., $C_1$-$C_6$ alkyl) or 1 to 4 carbon atoms (i.e., $C_1$-$C_4$ alkyl). Examples of suitable alkyl groups include, but are not limited to, methyl, ethyl, n-propyl, iso-propyl, n-butyl, isobutyl, sec-butyl, tert-butyl, pentyl, isopentyl, tert-pentyl, neopentyl, hexyl, 2-methylpentyl, 3-methylpentyl, 2,2-dimethylbutyl and 2,3-dimethylbutyl.

The term "alkenyl" refers to a non-aromatic hydrocarbon group which contains at least one double bond between adjacent carbon atoms and a similar structure to an alkyl group as otherwise described herein. For example, an alkenyl group can have 2 to 8 carbon atoms (i.e., $C_2$-$C_8$ alkenyl), or 2 to 4 carbon atoms (i.e., $C_2$-$C_4$ alkenyl). Examples of suitable alkenyl groups include, but are not limited to, ethenyl or vinyl (—CH=$CH_2$), allyl (—$CH_2$CH=$CH_2$), 1-butenyl (—C=CH—$CH_2CH_3$) and 2-butenyl (—$CH_2$CH=$CHCH_2$). The alkenyl group can be optionally substituted as described herein.

The term "alkynyl" refers to a non-aromatic hydrocarbon group containing at least one triple bond between adjacent carbon atoms and a similar structure to an alkyl group as otherwise described herein. For example, an alkynyl group can have 2 to 8 carbon atoms (i.e., $C_2$-$C_8$ alkyne), or 2 to 4 carbon atoms (i.e., $C_2$-$C_4$ alkynyl). Examples of alkynyl groups include, but are not limited to, acetylenic or ethynyl and propargyl. The alkynyl group can be optionally substituted as described herein.

The term "aryl" or "aromatic", in context, refers to a substituted (as otherwise described herein) or unsubstituted monovalent aromatic radical having a single ring (e.g., phenyl or benzyl) or condensed rings (e.g., naphthyl, anthracenyl, phenanthrenyl, etc.) and can be bound to the compound according to the present invention at any available stable position on the ring(s) or as otherwise indicated in the chemical structure presented. The aryl group can be optionally substituted as described herein.

"Cycloalkyl", "carbocycle", or "carbocyclyl" refers to a saturated (i.e., cycloalkyl) or partially unsaturated (e.g., cycloakenyl, cycloalkadienyl, etc.) ring having 3 to 7 carbon atoms as a monocycle. Monocyclic carbocycles have 3 to 7 ring atoms, still more typically 5 or 6 ring atoms. Non-limiting examples of cycloalkyl groups include cyclopropyl, cyclobuty, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, and 1-cyclo-hex-3-enyl.

A heteroaryl ring system is a saturated or unsaturated ring with one or more nitrogen, oxygen, or sulfur atoms in the ring (monocyclic) including but not limited to imidazole, furyl, pyrrole, furanyl, thiene, thiazole, pyridine, pyrimidine, purine, pyrazine, triazole, oxazole, or fused ring systems such as indole, quinoline, etc., among others, which may be optionally substituted as described above. Heteroaryl groups include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazino-pyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising two or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" refers to a cyclic group which contains at least one heteroatom, i.e., O, N, or S, and may be aromatic (heteroaryl) or non-aromatic. Exemplary non-aromatic heterocyclic groups for use in the present invention include, for example, pyrrolidinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethylene urea, 1,3-dioxolane, 1,3-dioxane, 1,4-dioxane, phthalimide, and succinimide, among others, all of which may be optionally substituted.

In one embodiment, the term purine or pyrimidine base includes, but is not limited to, adenine, $N^6$-alkylpurines, $N^6$-acylpurines (wherein acyl is —C(O)alkyl, —C(O)(aryl) $C_0$-$C_4$alkyl, or —C(O)($C_0$-$C_4$alkyl)aryl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases include, but are not limited to, guanine, adenine, hypoxanthine, optionally substituted 2,6-diaminopurine, and 6-chloropurine. Functional oxygen and nitrogen groups on the base can be protected as necessary or desired. Suitable protecting groups are well known to those skilled in the art, and include benzyl, trimethylsilyl, dimethylhexylsilyl, t-butyldimethylsilyl, t-butyldiphenylsilyl, trityl, alkyl groups, and acyl groups such as acetyl and propionyl; methanesulfonyl, and p-toluenesulfonyl. Alternatively, the purine or pyrimidine base can optionally be substituted such that it forms a viable prodrug, which can be cleaved in vivo. Examples of appropriate substituents include an acyl moiety.

The term "acyl" refers to a the moiety in which the carbonyl moiety, for example, —C(O)alkyl, is selected from alkyl, cycloalkyl, lower alkyl (i.e., $C_1$-$C_4$); alkoxyalkyl, including methoxymethyl; aralkyl- including benzyl, aryloxyalkyl- such as phenoxymethyl; aryl including phenyl optionally substituted with halogen, $C_1$-$C_4$ alkyl or $C_1$-$C_4$ alkoxy. In one embodiment, the term "acyl" refers to a mono, di or triphosphate.

The term "lower acyl" refers to an acyl group in which the carbonyl moiety is lower alkyl (i.e., $C_1$-$C_4$).

The term sulfonate esters, represented by the formula, $R^{14}S(O)_2OR^{15}$, comprise $R^{14}$ wherein $R^{14}$ is alkyl, haloalkyl, aralkyl or aryl. $R^{15}$ is alkyl, aryl or aralkyl.

The term "amino acid" or "amino acid residue" refers to a D- or L-natural or non-naturally occurring amino acid. Representative amino acids include, but are not limited to, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine, among others.

The term "nitrogen-protecting group" as used herein refers to a moiety that is covalently attached to nitrogen and which can be removed, and typically replaced with hydrogen, when appropriate. For example, a nitrogen-protecting group may be a group that is removed in vivo after administration to a host, in vitro by a cell, or it may be removed during a manufacturing process. Suitable nitrogen-protecting groups useful in the present invention are described by Greene and Wuts in Protective Groups in Organic Synthesis (1991) New York, John Wiley and Sons, Inc.

The term "oxygen-protecting group" as used herein refers to a moiety that is covalently attached to oxygen and which can be removed, and typically replaced with hydrogen, when appropriate. For example, an oxygen-protecting group may be a group that is removed in vivo after administration to a host, in vitro by a cell, or it may be removed during a manufacturing process. Suitable oxygen-protecting groups useful in the present invention are described by Greene and Wuts in Protective Groups in Organic Synthesis (1991) New York, John Wiley and Sons, Inc.

Phosphate ester refers to mono, di, and tri phosphates unless otherwise indicated.

The term "phosphoamidate", "phosphoramidate", or "phosphoroamidate" is a moiety that has a phosphorus bound to three oxygen groups and an amine (which may optionally be substituted). Suitable phosphoramidates useful in the present invention are described by Madela, Karolina and McGuigan in 2012, "Progress in the development of anti-hepatitis C virus nucleoside and nucleotide prodrugs", *Future Medicinal Chemistry* 4(5), pages 625-650 10:1021/jm300074y and Dominique, McGuigan and Balzarini in 2004, "Aryloxy Phosphoramidate Triesters as Pro-Tides", *Mini Reviews in Medicinal Chemistry* 4(4), pages 371-381. Additional phosphoramidates useful in the present invention are described in U.S. Pat. Nos. 5,233,031, 7,115,590, 7,547,704, 7,879,815, 7,888,330, 7,902,202, 7,951,789, 7,964,580, 8,071,568; 8,148,349, 8,263,575, 8,324,179, 8,334,270, 8,552,021, 8,563,530, 8,580,765, 8,735,372, 8,759,318; EP 2120565; EP 1143995; 6,455,513; and 8,334,270. Other phosphoramidates are described in the nucleoside patents described in the Background of the Invention.

Phosphoramidate groups for use in the present invention include those of the structures:

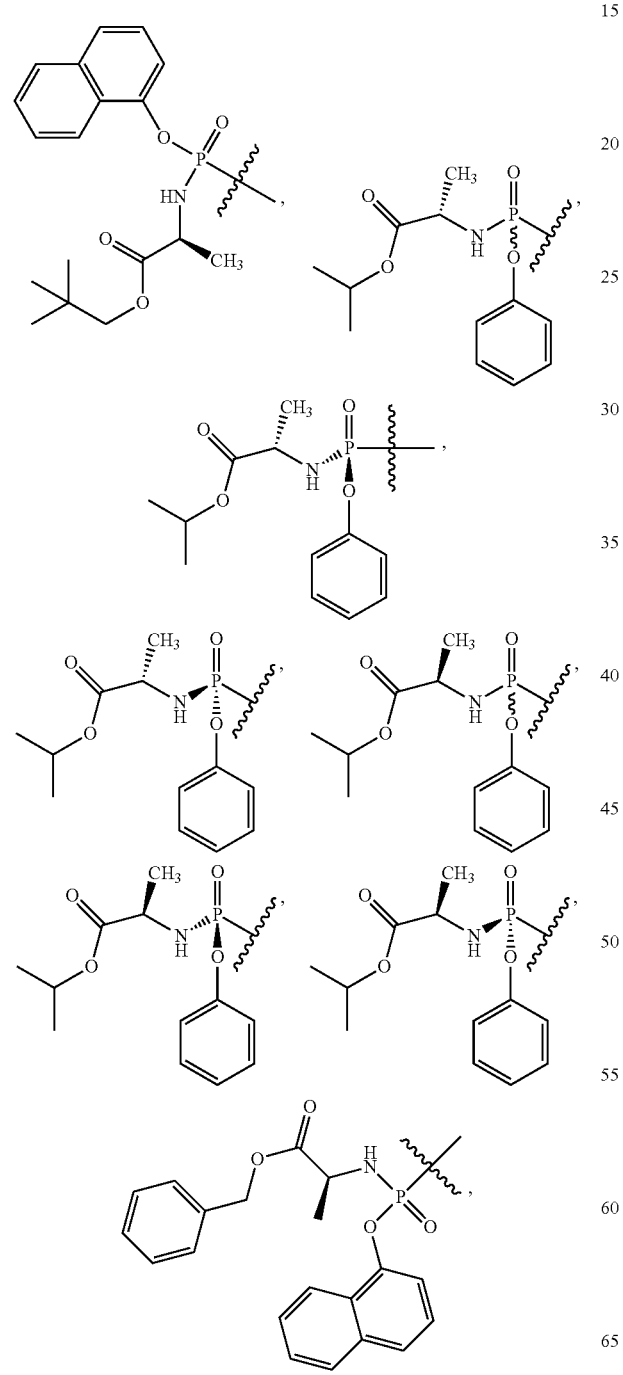
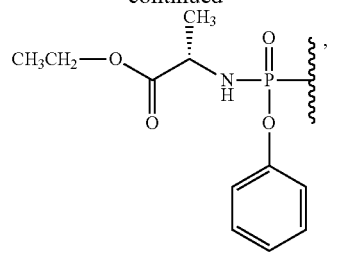
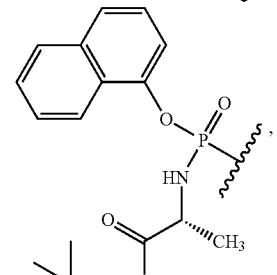
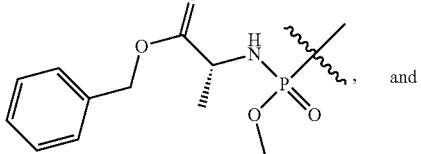
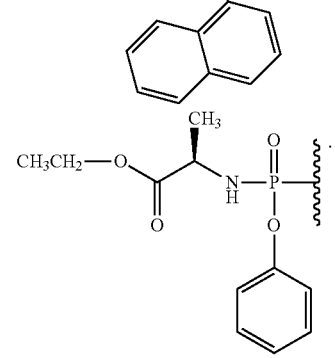

and

Other phosphoramidates for use in the present invention include those of the structure:

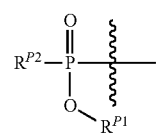

wherein:
$R^{P1}$ is an optionally substituted linear, branched, or cyclic alkyl group, or an optionally substituted aryl, heteroaryl or heterocyclic group or a linked combination thereof; and
$R^{P2}$ is a —$NR^{N1}R^{N2}$ group or a B' group;
wherein:
$R^{N1}$ and $R^{N2}$ are each independently H, $C_{1-8}$alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alkyl-; which may be optionally substituted;
$R^{N1}$ and $R^{N2}$ along with the nitrogen atom to which that are attached, join to form a 3 to 7 membered heterocyclic ring;

B' is a

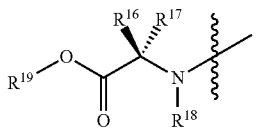

group;
wherein:
R$^{16}$ is hydrogen, (C$_1$-C$_8$)alkyl, (C$_2$-C$_8$)alkenyl, (C$_2$-C$_8$) alkynyl, (C$_3$-C$_8$cycloalkyl)C$_0$-C$_4$alkyl-, (aryl)C$_0$-C$_4$alkyl-, (C$_3$-C$_6$heterocyclo)C$_0$-C$_4$alkyl-, (heteroaryl)C$_0$-C$_4$alkyl-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often R$^{16}$ is hydrogen, methyl, isopropyl, or isobutyl);

R$^{17}$ is hydrogen, (C$_1$-C$_8$)alkyl, (C$_2$-C$_8$)alkenyl, (C$_2$-C$_8$) alkynyl, (C$_3$-C$_8$cycloalkyl)C$_0$-C$_4$alkyl-, (aryl)C$_0$-C$_4$alkyl-, (C$_3$-C$_6$heterocyclo)C$_0$-C$_4$alkyl-, (heteroaryl)C$_0$-C$_4$alkyl-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often R$^{17}$ is hydrogen, methyl, isopropyl, or isobutyl);

R$^{18}$ is hydrogen or C$_1$-C$_3$alkyl; or

R$^{16}$ and R$^{17}$ can form a (C$_3$-C$_7$)cycloalkyl or (C$_3$-C$_7$) heterocyclic group; or R$^{18}$ and R$^{16}$ or R$^{17}$ can form (C$_3$-C$_6$)heterocyclic group; and R$^{19}$ is hydrogen, (C$_1$-C$_6$)alkyl, (C$_3$-C$_6$)alkenyl, (C$_3$-C$_6$) alkynyl, (C$_3$-C$_8$cycloalkyl)C$_0$-C$_4$alkyl-, (aryl)C$_0$-C$_4$alkyl-, (C$_3$-C$_6$heterocyclo)C$_0$-C$_4$alkyl-, (heteroaryl)C$_0$-C$_4$alkyl-; or B' is a

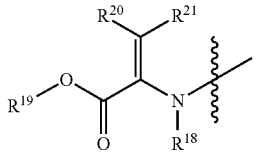

group;
wherein:
R$^{20}$ is hydrogen, (C$_1$-C$_3$)alkyl, (C$_3$-C$_8$cycloalkyl)C$_0$-C$_4$alkyl-, (aryl)C$_0$-C$_4$alkyl-, (C$_3$-C$_6$heterocyclo)C$_0$-C$_4$alkyl-, or (heteroaryl)C$_0$-C$_4$alkyl-;

R$^{21}$ is hydrogen, (C$_1$-C$_3$)alkyl, (C$_3$-C$_8$cycloalkyl)C$_0$-C$_4$alkyl-, (aryl)C$_0$-C$_4$alkyl-, (C$_3$-C$_6$heterocyclo)C$_0$-C$_4$alkyl-, or (heteroaryl)C$_0$-C$_4$alkyl-; and R$^{18}$ and R$^{19}$ are as defined above.

Preferred R$^{P1}$ groups include optionally substituted phenyl, naphthyl, and monocyclic heteroaryl groups, especially those groups (particularly lipophilic groups) which enhance bioavailability of the compounds in the cells of the patient and which exhibit reduced toxicity, enhanced therapeutic index and enhanced pharmacokinetics (the compounds are metabolized and excreted more slowly).

The term phosphoramidate is used throughout the specification to describe a group that is found at the 5'- or 3'-position of the furanose ring of the nucleoside compound and forms a prodrug form of the nucleoside compound. In one embodiment, phosphoramidates can be found at both the 5'- and 3'-position of the furanose ring of the nucleoside compound and form a prodrug form of the nucleoside compound. In another embodiment, the phosphoramidate found at the 5' position of the furanose ring of the nucleoside can form a cyclic phosphoramidate compound by forming a bond with the 3'-hydroxyl substituent at the 3' position of the furanose ring of the nucleoside compound and form a prodrug form of the nucleoside compound.

The term "thiophosphoamidate", "thiophosphoramidate", or "thiophosphoroamidate" is a moiety that has a phosphorus bound to sulfur (P=S), two oxygen groups and an amine (which may optionally be substituted). Thiophosphoramidates useful in the present invention are described in U.S. Pat. No. 8,772,474 and WO 2012/040124.

Thiophosphoramidate groups for use in the present invention include those of the structures:

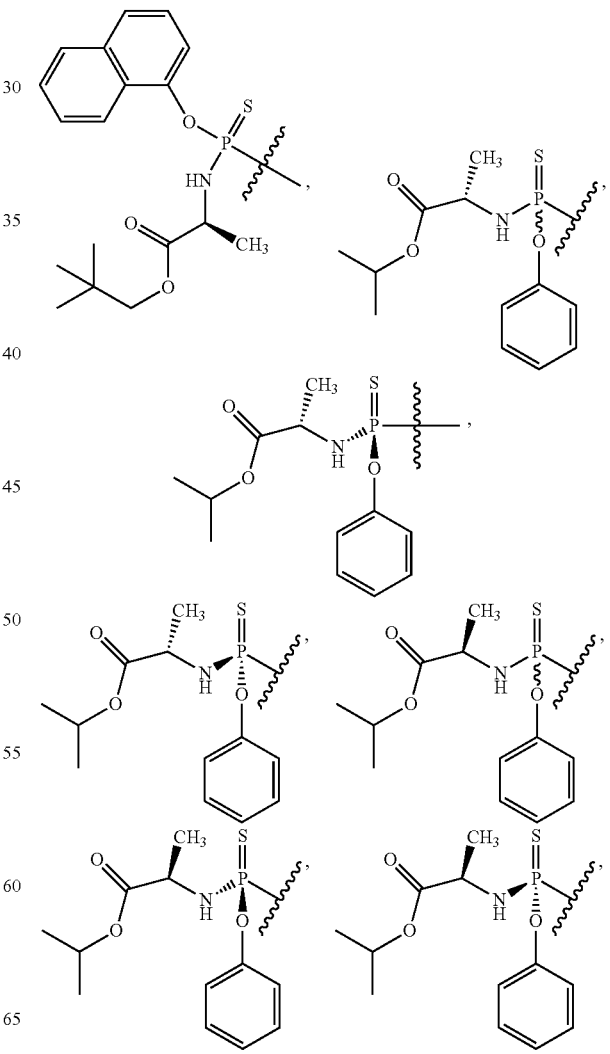

-continued

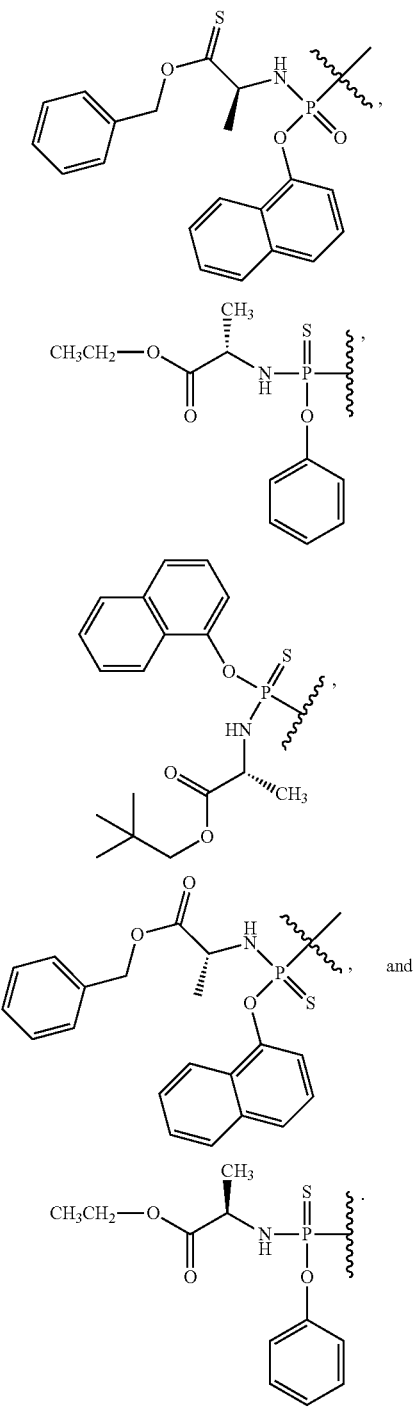

Other thiophosphoramidates include those of the structure:

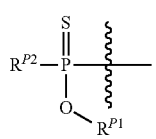

wherein:
$R^{P1}$ is an optionally substituted linear, branched, or cyclic alkyl group, or an optionally substituted aryl, heteroaryl or heterocyclic group or a linked combination thereof; and
$R^{P2}$ is a —$NR^{N1}R^{N2}$ group or a B' group;
wherein:
$R^{N1}$ and $R^{N2}$ are each independently H, $C_1$-$C_8$ alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alkyl-; or
$R^{N1}$ and $R^{N2}$ along with the nitrogen atom to which that are attached, join to form a 3 to 7 membered heterocyclic ring;
B' is a

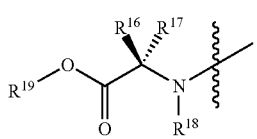

group;
wherein:
$R^{16}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alkyl-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{16}$ is hydrogen, methyl, isopropyl, or isobutyl);
$R^{17}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alkyl-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{17}$ is hydrogen, methyl, isopropyl, or isobutyl);
$R^{18}$ is hydrogen or $C_1$-$C_3$alkyl; or
$R^{16}$ and $R^{17}$ can form a ($C_3$-$C_7$)cycloalkyl or ($C_3$-$C_7$) heterocyclic group; or
$R^{18}$ and $R^{16}$ or $R^{17}$ can form ($C_3$-$C_6$) heterocyclic group; and
$R^{19}$ is hydrogen, ($C_1$-$C_6$)alkyl, ($C_3$-$C_6$)alkenyl, ($C_3$-$C_6$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alkyl-; or
B' is a

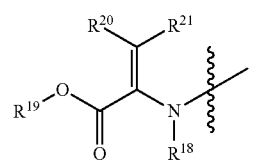

group; and
$R^{18}$, $R^{19}$, $R^{20}$ and $R^{21}$ are as defined above.

Preferred $R^{P1}$ groups include optionally substituted phenyl, naphthyl, and monocyclic heteroaryl groups, especially those groups (particularly lipophilic groups) which enhance bioavailability of the compounds into the cells of the patient and which exhibit reduced toxicity, enhanced therapeutic index and enhanced pharmacokinetics (the compounds are metabolized and excreted more slowly).

The thiophosphoramidate can be at the 5'- or 3'-position of the furanose ring of the nucleoside compound to form a prodrug form of the nucleoside compound. In one embodiment, thiophosphoramidates can be found at both the 5'- and 3'-position of the furanose ring of the nucleoside compound and form a prodrug form of the nucleoside compound. In another embodiment, the thiophosphoramidate found at the 5'-position of the furanose ring of the nucleoside can form a cyclic thiophosphoramidate compound by forming a bond with the 3'-hydroxyl substituent at the 3'-position of the furanose ring of the nucleoside compound and form a prodrug form of the nucleoside compound.

The term "D-configuration" as used in the context of the present invention refers to the principle configuration which mimics the natural configuration of sugar moieties as opposed to the unnatural occurring nucleosides or "L" configuration. The term "β" or "β anomer" is used with reference to nucleoside analogs in which the nucleoside base is configured (disposed) above the plane of the furanose moiety in the nucleoside analog.

The terms "coadminister" and "coadministration" or combination therapy are used to describe the administration of at least one of the 2'-deoxy-2'-substituted-4'-substituted nucleoside compounds according to the present invention in combination with at least one other active agent, for example where appropriate at least one additional anti-RSV agent, including other 2'-deoxy-2'-substituted-4'-substituted nucleoside agents which are disclosed herein. The timing of the coadministration is best determined by the medical specialist treating the patient. It is sometimes preferred that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

The term host, as used herein, refers to a unicellular or multicellular organism in which a RSV virus can replicate, including cell lines and animals, and typically a human. The term host specifically refers to infected cells, cells transfected with all or part of a RSV genome, and animals, in particular, primates (including chimpanzees) and humans. In most animal applications of the present invention, the host is a human patient. Veterinary applications, in certain indications, however, are clearly anticipated by the present invention. The host can be for example, bovine, equine, avian, canine, feline, etc.

Isotopic Substitution

The present invention includes compounds and the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an a-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetics or pharmacodynamics, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

III. Methods of Treatment or Prophylaxis

Treatment, as used herein, refers to the administration of an active compound to a host that is infected with a virus from either of the Paramyxoviridae and Orthomyxoviridae families. In one embodiment, the virus is a respiratory syncytial virus.

The term "prophylactic" or preventative, when used, refers to the administration of an active compound to prevent or reduce the likelihood of an occurrence of the viral disorder. The present invention includes both treatment and prophylactic or preventative therapies.

The invention is directed to a method of treatment or prophylaxis of a respiratory syncytial virus, including drug resistant and multidrug resistant forms of RSV and related disease states, conditions, or complications of an RSV infection, including breathing problems (coughing, sneezing or wheezing) pneumonia, bronchiolitis, middle ear infection, asthma, fever, or cold symptoms among others. The method comprises administering to a host in need thereof an effective amount of at least one β-D-2'-deoxy-2'-substituted-4'-substituted-2-substituted-$N^6$-methyl-6-aminopurine nucleotide or a β-D-2'-deoxy-2'-substituted-4'-substituted-2-substituted-$N^6$-dimethyl-6-aminopurine nucleotide as described herein, optionally in combination with at least one additional bioactive agent, for example, an additional anti-RSV agent, further in combination with a pharmaceutically acceptable carrier additive and/or excipient.

In yet another aspect, the present invention is a method for prevention or prophylaxis of a RSV infection or a disease state or related or follow-on disease state, condition or complication of an RSV infection, including breathing problems (coughing, sneezing or wheezing) pneumonia, bronchiolitis, middle ear infection, asthma, fever, or cold symptoms among others, said method comprising administering to a patient at risk with an effective amount of at least one compound according to the present invention as described above in combination with a pharmaceutically acceptable carrier, additive, or excipient, optionally in combination with another anti-RSV agent.

The 5'-stabilized β-D-2'-deoxy-2'-substituted-4'-substituted-2-substituted-$N^6$-methyl-6-aminopurine nucleotide or β-D-2'-deoxy-2'-substituted-4'-substituted-2-substituted-$N^6$-dimethyl-6-aminopurine nucleotide can be administered if desired as any salt or prodrug that upon administration to the recipient is capable of providing directly or indirectly the parent compound, or that exhibits activity itself. Non-limiting examples are the pharmaceutically acceptable salts and a compound, which has been modified at a function group, such as a hydroxyl or amine function, to modify the biological activity, pharmacokinetics, half-life, controlled delivery, lipophilicity, absorption kinetics, ease of phosphorylation to the active 5'-triphosphate or efficiency of delivery using a desired route of administration of the compound. Methods to modify the properties of an active compound to achieve target properties are known to those of skill in the art or can easily be assessed by standard methods, for example, acylation, phosphorylation, thiophosphoramidation, phosphoramidation, phosphonation, alkylation, or pegylation.

IV. Pharmaceutical Compositions

In an aspect of the invention, pharmaceutical compositions according to the present invention comprise an anti-Paramyxoviridae or anti-Orthomyxoviridae effective amount of at least one of the β-D-2'-deoxy-2'-substituted-4'-substituted-2-substituted-$N^6$-methyl-6-aminopurine nucleotide or β-D-2'-deoxy-2'-substituted-4'-substituted-2-substituted-$N^6$-dimethyl-6-aminopurine nucleotide compounds described herein, optionally in combination with a pharmaceutically acceptable carrier, additive, or excipient, further optionally in combination or alternation with at least one other active compound.

In an aspect of the invention, pharmaceutical compositions according to the present invention comprise an anti-Paramyxoviridae or anti-Orthomyxoviridae effective amount of at least one of the active β-D-2'-deoxy-2'-substituted-4'-substituted-2-substituted-$N^6$-methyl-6-aminopurine nucleotide or β-D-2'-deoxy-2'-substituted-4'-substituted-2-substituted-$N^6$-dimethyl-6-aminopurine nucleotide compounds described herein, optionally in combination with a pharmaceutically acceptable carrier, additive, or excipient, further optionally in combination with at least one other antiviral, such as an anti-RSV agent.

The invention includes pharmaceutical compositions that include an effective amount to treat a respiratory syncytial virus infection of one of the β-D-2'-deoxy-2'-substituted-4'-substituted-2-substituted-$N^6$-methyl-6-aminopurine nucleotide or β-D-2'-deoxy-2'-substituted-4'-substituted-2-substituted-$N^6$-dimethyl-6-aminopurine nucleotide compounds of the present invention or its salt or prodrug, in a pharmaceutically acceptable carrier or excipient. In an alternative embodiment, the invention includes pharmaceutical compositions that include an effective amount to prevent a respiratory syncytial virus infection, of one of the β-D-2'-deoxy-2'-substituted-4'-substituted-2-substituted-$N^6$-methyl-6-aminopurine nucleotide or β-D-2'-deoxy-2'-substituted-4'-substituted-2-substituted-$N^6$-dimethyl-6-aminopurine nucleotide compounds of the present invention or its salt or prodrug, in a pharmaceutically acceptable carrier or excipient.

One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated, and such therapeutic amount can be determined by the attending physician or specialist.

The 5'-stabilized β-D-2'-deoxy-2'-substituted-4'-substituted-2-substituted-$N^6$-methyl-6-aminopurine nucleotide or β-D-2'-deoxy-2'-substituted-4'-substituted-2-substituted-$N^6$-dimethyl-6-aminopurine nucleotide compounds according to the present invention can be formulated in an admixture with a pharmaceutically acceptable carrier. In general, it is preferable to administer the pharmaceutical composition in orally-administrable form, but certain formulations may be administered via a parenteral, intravenous, intramuscular, topical, transdermal, buccal, subcutaneous, suppository, or other route, including intranasal spray. Intravenous and intramuscular formulations are often administered in sterile saline. One of ordinary skill in the art may modify the formulations to render them more soluble in water or other vehicle, for example, this can be easily accomplished by minor modifications (salt formulation, esterification, etc.) which are well within the ordinary skill in the art. It is also well within the routineers' skill to modify the route of administration and dosage regimen of a particular compound in order to manage the pharmacokinetics of the present compounds for maximum beneficial effect in patients.

In certain pharmaceutical dosage forms, the prodrug form of the compounds, especially including acylated (acetylated or other), and ether (alkyl and related) derivatives, phosphate esters, thiophosphoramidates, phosphoramidates, and various salt forms of the present compounds, are preferred. One of ordinary skill in the art will recognize how to readily modify the present compounds to prodrug forms to facilitate delivery of active compounds to a targeted site within the host organism or patient. The routineer also will take advantage of favorable pharmacokinetic parameters of the prodrug forms, where applicable, in delivering the present compounds to a targeted site within the host organism or patient to maximize the intended effect of the compound.

The amount of compound included within therapeutically active formulations according to the present invention is an effective amount for treating the RSV infection, reducing the likelihood of a RSV infection or the inhibition, reduction, or abolition of RSV or its secondary effects, including disease states, conditions, and/or complications which occur secondary to RSV. In general, a therapeutically effective amount of the present compound in pharmaceutical dosage form usually ranges from about 0.001 mg/kg to about 100 mg/kg per day or more, more often, slightly less than about 0.1 mg/kg to more than about 25 mg/kg per day of the patient or considerably more, depending upon the compound used, the condition or infection treated and the route of administration. The active nucleoside compound according to the present invention is often administered in amounts ranging from about 0.1 mg/kg to about 15 mg/kg per day of the patient, depending upon the pharmacokinetics of the agent in the patient. This dosage range generally produces effective blood level concentrations of active compound which may range from about 0.001 to about 100, about 0.05 to about 100 micrograms/cc of blood in the patient.

Often, to treat, prevent or delay the onset of these infections and/or to reduce the likelihood of an RSV virus infection, or a secondary disease state, condition or complication of RSV, the compositions will be administered in oral dosage form in amounts ranging from about 250 micrograms up to about 500 mg or more at least once a day, for example, at least 25, 50, 100, 150, 250 or 500 milligrams, up to four times a day. The present compounds are often administered orally, but may be administered parenterally, topically, or in suppository form, as well as intranasally, as a nasal spray or as otherwise described herein.

In the case of the co-administration of the present compounds in combination with another anti-RSV compound as otherwise described herein, the amount of the compound according to the present invention to be administered ranges from about 0.01 mg/kg of the patient to about 500 mg/kg. or more of the patient or considerably more, depending upon the second agent to be co-administered and its potency against the virus, the condition of the patient and severity of the disease or infection to be treated and the route of administration. The other anti-RSV agent may for example be administered in amounts ranging from about 0.01 mg/kg to about 500 mg/kg. In certain preferred embodiments, these compounds may be often administered in an amount ranging from about 0.5 mg/kg to about 50 mg/kg or more (usually up to about 100 mg/kg), generally depending upon the pharmacokinetics of the two agents in the patient. These dosage ranges generally produce effective blood level concentrations of active compound in the patient.

For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral or intranasal administrations per day (for example, Q.I.D.) or transdermal administration and may include oral, topical, parenteral, intramuscular, intravenous, sub-cutaneous, transdermal (which may include a penetration enhancement agent), buccal, and suppository administration, among other routes of administration. Enteric coated oral tablets may also be used to enhance bioavailability of the compounds for an oral route of administration. The most effective dosage form will depend upon the bioavailability/pharmacokinetics of the particular agent chosen as well as the severity of disease in the patient. Oral dosage forms are particularly preferred, because of ease of administration and prospective favorable patient compliance.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

To prepare the pharmaceutical compositions according to the present invention, a therapeutically effective amount of one or more of the compounds according to the present invention is often intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, manifold, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intraveneous, intramuscular, inhalation, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

In accordance with the presently disclosed methods, an oral administration can be in any desired form such as a solid, gel or liquid, including a solution, suspension, or emulsion. In some embodiments, the compounds or salts are administered by inhalation, intravenously, or intramuscularly as a liposomal suspension. When administered through inhalation the active compound or salt may be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

The pharmaceutical formulations can comprise an active compound described herein or a pharmaceutically acceptable salt thereof, in any pharmaceutically acceptable carrier. If a solution is desired, water may sometimes be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of a solution suspension, tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the host matter described herein, there are provided injectable, stable, sterile formulations comprising an active compound as described herein, or a salt thereof, in a unit dosage form in a sealed container. The compound or salt is provided in the form of a lyophilizate, which is capable of being reconstituted with a suitable pharmaceutically acceptable carrier to form liquid formulation suitable for injection thereof into a host. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulations can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. In one embodiment, the solid particles provide for controlled release through the use of a degradable polymer. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Pharmaceutical formulations also are provided which provide a controlled release of a compound described herein, including through the use of a degradable polymer, as known in the art.

When the pharmaceutical formulations suitable for administration as an aerosol is in the form of a liquid, the formulations can comprise a water-soluble active compound in a carrier that comprises water. A surfactant can be present, which lowers the surface tension of the formulations sufficiently to result in the formation of droplets within the desired size range when hosted to nebulization.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilic hydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

In typical embodiments according to the present invention, the compounds and compositions are used to treat, prevent or delay a RSV infection or a secondary disease state, condition or complication of RSV.

V. Combination and Alternation Therapy

It is well recognized that drug-resistant variants of viruses can emerge after prolonged treatment with an antiviral agent. Drug resistance most typically occurs by mutation of a gene that encodes for an enzyme used in viral replication. The efficacy of a drug against an RSV infection, can be prolonged, augmented, or restored by administering the compound in combination or alternation with another, and perhaps even two or three other, antiviral compounds that induce a different mutation or act through a different pathway, from that of the principle drug. Alternatively, the pharmacokinetics, bio distribution, half-life, or other parameter of the drug can be altered by such combination therapy (which may include alternation therapy if considered concerted). Since the disclosed β-D-2'-deoxy-2'-substituted-4'-substituted-2-substituted-$N^6$-substituted-6-aminopurine nucleotides are polymerase inhibitors, it may be useful to administer the compound to a host in combination with, for example a:

(1) Nebulized bronchodilator;
(2) Immune globulin;
(3) Antibody, partial antibody or domain antibody to the virus;
(4) RSV polymerase inhibitor;
(5) Nucleosides;
(6) Alpha-adrenergic agonists.

Non limiting examples of anti-RSV agents that can be administered in combination with the β-D-2'-deoxy-2'-substituted-4'-substituted-2-substituted-$N^6$-substituted-6-aminopurine nucleotides of the invention are:

(i) Nebulized bronchodilator such as albuterol;
(ii) Immune globulin such as RespiGam®;
(iii) Antibody to RSV such as Synagis® and
(iv) Another RSV polymerase inhibitor such as a β-D-2'-deoxy-2'-substituted-4'-substituted-$N^6$-substituted-2,6-diaminopurine or a β-D-2'-deoxy-2'-substituted-4'-substituted-$N^2$,$N^6$-substituted-2, 6-diaminopurine nucleotides and,
(v) Nucleoside such as Virzole® (ribavirin by aerosol);
(vi) Alpha agonist such as vaporized epinephrine.

Drugs that are currently approved for influenza are Amantadine, Rimantadine and Oseltamivir. Any of these drugs can be used in combination or alternation with an active compound provided herein to treat a viral infection susceptible to such.

Ribavirin is used to treat measles, Influenza A, influenza B, parainfluenza, severe RSV bronchiolitis and SARS as well as other viral infections, and therefore as illustrated above is particularly useful in combination with the present compound for treatment of the host infected with the RSV virus.

This highlights the importance of the present compounds for viral medical therapy.

V. Process of Preparation of β-D-2'-Deoxy-2'-Substituted-4'-Substituted-2-Substituted-$N^6$-Substituted-6-Aminopurine Nucleotides of the Invention General Methods General methods for providing the compounds of the present invention are known in the art or described herein. $^1$H, $^{19}$F and $^{31}$P NMR spectra were recorded on a 300 MHz Fourier transform Brucker spectrometer. Spectra were obtained from samples prepared in 5 mm diameter tubes in CDCl$_3$, CD$_3$OD or DMSO-d$_6$. The spin multiplicities are indicated by the symbols s (singlet), d (doublet), t (triplet), m (multiplet) and, br (broad). Coupling constants (J) are reported in Hz. MS spectra were obtained using electrospray ionization (ESI) on an Agilent Technologies 6120 quadrupole MS apparatus. The reactions were generally carried out under a dry nitrogen atmosphere using Sigma-Aldrich anhydrous solvents. All common chemicals were purchased from commercial sources.

Compounds of the present invention with stereocenters are drawn racemic for convenience. One skilled in the art will recognize that pure enantiomers can be prepared by methods known in the art. Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including simulated moving bed chromatography, is used in one embodiment. A wide variety of chiral stationary phases are commercially available.

Preparation of Stereospecific Phosphorus Enantiomers

Certain of the active compounds described herein have a chiral phosphorus moiety. Any of the active compounds described herein can be provided as an isolated phosphorus enantiomeric form, for example, at least 80, 90, 95 or 98% of the R or S enantiomer, using methods known to those of skill in the art. For example, there are a number of publications that describe how to obtain such compounds, including but not limited to column chromatography, for example as described in U.S. Pat. Nos. 8,859,756; 8,642,756 and 8,333,309 to Ross, et al.

The following abbreviations are used in the synthetic schemes.

CBr$_4$: Carbon tetrabromide
DBU: 1,8-Diazabicyclo[5.4.0]undec-7-ene
DCM: Dichloromethane
THF: Tetrahydrofuran (THF), anhydrous
EtOAc: Ethyl acetate
EtOH: Ethanol
Li(OtBu)$_3$AlH: Lithium tri-tert-butoxyaluminum hydride
Na$_2$SO$_4$: Sodium sulphate (anhydrous)
MeCN: Acetonitrile
MeNH$_2$: Methylamine
MeOH: Methanol
Na$_2$SO$_4$: Sodium sulfate
NaHCO$_3$: Sodium bicarbonate
NH$_4$Cl: Ammonium chloride
NH$_4$OH: Ammonium hydroxide
PE: Petroleum ether
Ph$_3$P: Triphenylphosphine
Silica gel (230 to 400 mesh, Sorbent)
t-BuMgCl: t-Butyl magnesium chloride
t-BuOK: Sodium tert-butoxide
t-BuOH: Tert-butanol

EXAMPLES

Example 1

Illustrative Synthetic Procedures

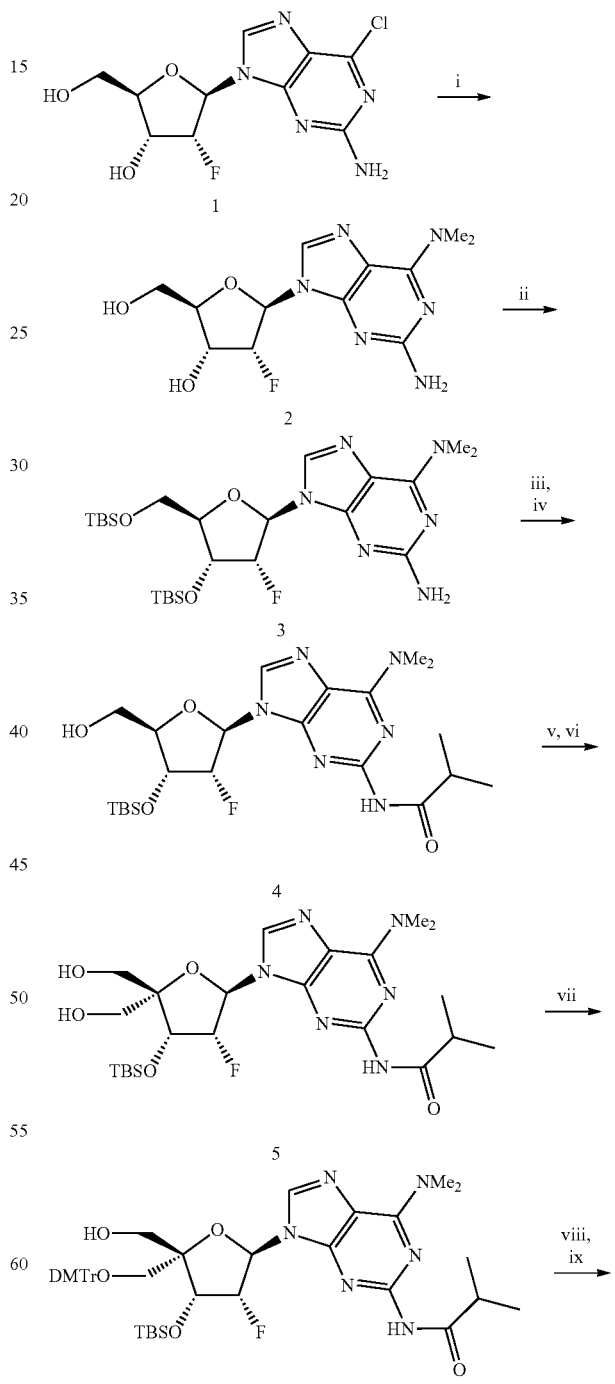

Scheme 1. Preparation of (2S)-Isopropyl 2-(((((2R,3R,4R,5R)-5-(2-amino-6-(dimethylamino)-9H-purin-9-yl)-4-fluoro-3-hydroxy-2-methyltetrahydrofuran-2-yl)methoxy)(phenoxy)phosphoryl)amino)propanoate (Compound B)

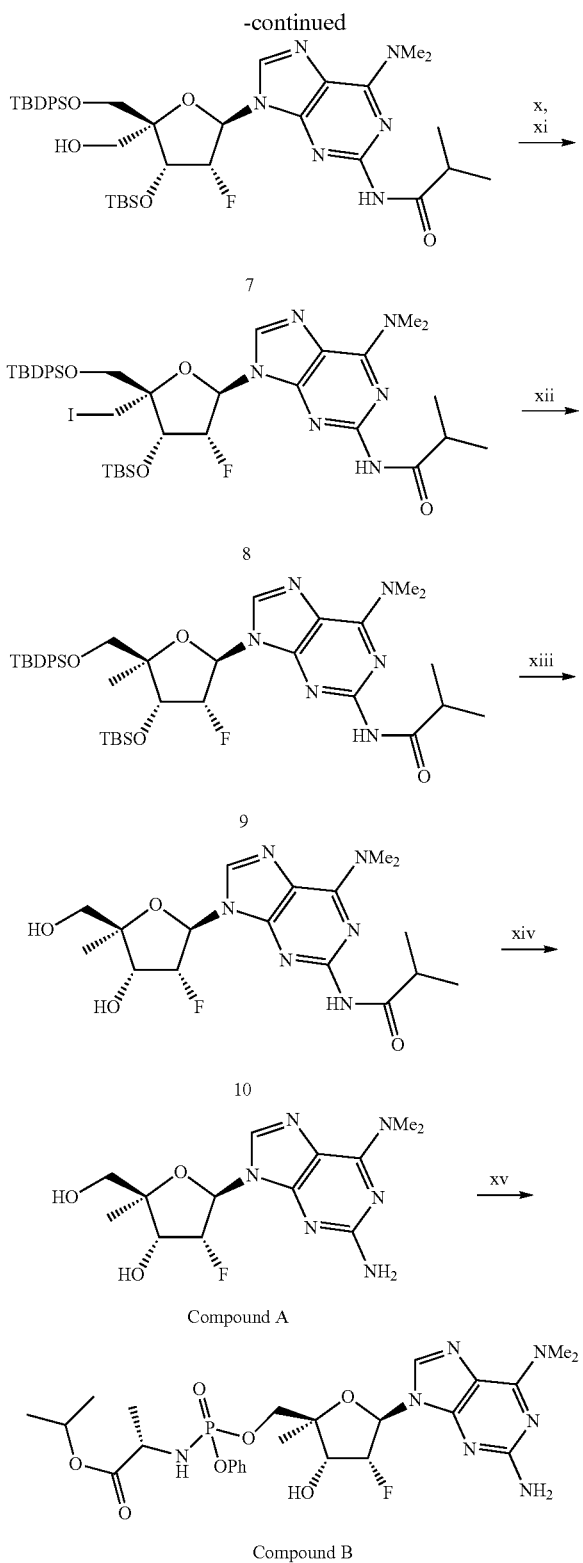

i) Me₂NH·HCl, Et₃N, EtOH, 85° C.; ii) TBSCl, imidazole, DMF; iii) isobutyryl chloride, pyridine; iv) 90% TFA, DCM; v) SO₃·pyridine, DIEA, DMSO, DCM; vi) formaldehyde, 2N NaOH, dioxane then NaBH₄; vii) DMTrCl, Et₃N, DMF; viii) TBDPSCl, AgNO₃, pyridine; ix) 80% AcOH; x) Tf₂O, pyridine, DCM, 0° C.; xi) NaI, DMF, 60° C.; xii) H₂, 10% Pd—C, Et₃N, EtOH; xiii) TBAF, THF; xiv) MeNH₂, EtOH, 75° C.; xv) Isopropyl ((R,S)-(pentafluorophenoxy)-phenoxyphosphoryl)-L-alaninate, t-BuMgCl, DMF, -10° C.

Step 1. Preparation of (2R,3R,4R,5R)-5-(2-Amino-6-(dimethylamino)-9H-purin-9-yl)-4-fluoro-2-(hydroxymethyl)tetrahydrofuran-3-ol (2)

To a solution of compound 1 (10.5 g, 35 mmol) in EtOH (220 mL) was added dimethylamine hydrochloride (14.0 g, 173 mmol) and triethylamine (24.0 mL, 173 mmol). The reaction mixture was heated at 85° C. in a sealed container for 3 h, cooled down to room temperature (RT) and concentrated. The residue was purified by column chromatography (silica gel, DCM/MeOH 0 to 10%). Product 2 (10.8 g, 99%) was obtained as a white solid.

Step 2. Preparation of 9-((2R,3R,4R,5R)-4-((tert-Butyldimethylsilyl)oxy)-5-(((tert-butyldimethylsilyl)oxy)methyl)-3-fluorotetrahydrofuran-2-yl)-$N^6$,$N^6$-dimethyl-9H-purine-2,6-diamine (3)

To a solution of compound 2 (10.7 g, 34.5 mmol) in dry DMF (120 mL) was added imidazole (9.4 g, 138.4 mmol) and TBSCl (20.9 g, 138.4 mmol). The mixture was stirred at RT for 15 h and concentrated. EtOAc (300 mL) was added and the solution was washed with satd. NH₄Cl aq. solution (3×200 mL) and brine (200 mL). The organic phase was dried over anhydrous Na₂SO₄ and concentrated. The residue was purified by column chromatography (silica gel, PE/EtOAc 0 to 40%). Product 3 (16.0 g, 85% yield) was obtained as a yellow oil.

Step 3 and Step 4. Preparation of N-(9-((2R,3R,4R,5R)-4-((tert-Butyldimethylsilyl)oxy)-3-fluoro-5-(hydroxymethyl) tetrahydrofuran-2-yl)-6-(dimethylamino)-9H-purin-2-yl)isobutyramide (4)

To a solution of compound 3 (13.5 g, 25.0 mmol) in dry pyridine (60 mL) was added isobutyryl chloride (3.1 mL, 30.0 mmol) drop-wise at 0° C. The reaction mixture was stirred at RT for 3 h and then concentrated. After co-evaporation with toluene (3×200 mL), the residue was dissolved in DCM (270 mL) and treated TFA/H₂O (9:1, 27 mL) at 0° C. for 15 h. Then, the reaction was quenched by addition of solid NaHCO₃ (50 g) and filtered. The solution was washed with satd. NaHCO₃ aq. solution (2×200 mL) and brine (200 mL). The organic phase was dried over anhydrous Na₂SO₄ and concentrated. The residue was purified by column chromatography (silica gel, PE/EtOAc 0 to 80%). Product 4 (9.3 g, 75% yield over 2 steps) was obtained as a white foam.

Step 5 and Step 6. Preparation of N-(9-((2R,3R,4R)-4-((tert-Butyldimethylsilyl)oxy)-3-fluoro-5,5-bis(hydroxymethyl) tetrahydrofuran-2-yl)-6-(dimethylamino)-9H-purin-2-yl)isobutyramide (5)

To a solution of compound 4 (2.0 g, 4.0 mmol) in dry DCM (35 mL) was added diisopropylethylamine (2.7 mL, 15.6 mmol) and a suspension of SO₃ pyridine complex (1.9 g, 12.0 mmol) in dry DMSO (3.7 mL). The orange solution was stirred for 15 h at RT. Then, H₂O (40 mL) was added, the phases were separated and the aqueous layer was back-extracted with EtOAc (2×30 mL). The combined organics were washed with brine (60 mL), dried over anhydrous Na₂SO₄ and concentrated. The residue was dissolved in dioxane (25 mL). Formaldehyde (37% in H₂O) (1.3 mL, 16.8 mmol) and 2 N NaOH (3.0 mL, 6.0 mmol) were added and the yellow solution was stirred for 3 h at RT. The mixture was cooled down to 0° C. and sodium borohydride (605 mg, 16.0 mmol) was added portion-wise. The cloudy solution was stirred for 1 h at RT and quenched by addition of satd. NH₄Cl aq. solution (100 mL). The product was extracted with EtOAc (3×80 mL). The combined organics were washed with brine (100 mL), dried over anhydrous Na₂SO₄ and concentrated. The residue was purified by column chromatography (silica gel, DCM/MeOH 0 to 10%). Product 5 (1.2 g, 55% yield over 2 steps) was obtained as a white solid.

Step 7. Preparation of N-(9-((2R,3R,4R,5S)-5-((Bis(4-methoxyphenyl)(phenyl)methoxy)methyl)-4-((tert-butyldimethylsilyl)oxy)-3-fluoro-5-(hydroxymethyl)tetrahydrofuran-2-yl)-6-(dimethylamino)-9H-purin-2-yl)isobutyramide (6)

To a solution of compound 5 (1.15 g, 2.21 mmol) in dry DMF (12 mL) was added triethylamine (620 µL, 4.44 mmol) and dimethoxytrityl chloride (1.05 g, 3.11 mmol). The resulting orange solution was stirred for 2 h at RT. The reaction was then diluted with EtOAc (50 mL) and H₂O (40 mL). The phases were separated and the aqueous layer was back-extracted with EtOAc (2×30 mL). The combined organics were washed with brine (50 mL), dried over anhydrous Na₂SO₄ and concentrated. The residue was purified by column chromatography (silica gel, PE/EtOAc 0 to 100%). Product 6 (880 mg, 48% yield) was obtained as a yellow foam.

Step 8 and Step 9. Preparation N-(9-((2R,3R,4R,5R)-4-((tert-Butyldimethylsilyl)oxy)-5-(((tert-butyldiphenylsilyl)oxy)methyl)-3-fluoro-5-(hydroxymethyl)tetrahydrofuran-2-yl)-6-(dimethylamino)-9H-purin-2-yl)isobutyramide (7)

To a solution of compound 6 (875 mg, 1.06 mmol) in dry pyridine (8 mL) was added silver nitrate (538 mg, 3.17 mmol) and TBDPSCl (820 µL, 3.17 mmol). The resulting solution was stirred for 15 h at RT. Then, EtOAc (50 mL) was added and the suspension was filtered. The solution was washed brine (30 mL), dried over anhydrous Na₂SO₄ and concentrated. The residue was dissolved in 80% acetic acid (5 mL) and stirred for 15 h at RT. The solution was poured into satd. NaHCO₃ aq. solution (90 mL) and the mixture was extracted with DCM (3×60 mL). The combined organics were washed with brine (50 mL), dried over anhydrous Na₂SO₄ and concentrated. The residue was purified by column chromatography (silica gel, DCM/MeOH 0 to 10%). Product 7 (662 mg, 82% yield over 2 steps) was obtained as a white solid.

Step 10 and Step 11. Preparation of N-(9-((2R,3R,4R,5R)-4-((tert-Butyldimethylsilyl)oxy)-5-(((tert-butyldiphenylsilyl)oxy)methyl)-3-fluoro-5-(iodomethyl)tetrahydrofuran-2-yl)-6-(dimethylamino)-9H-purin-2-yl)isobutyramide (8)

To a solution of compound 7 (660 mg, 0.86 mmol) in dry DCM (15 mL) was added pyridine (350 µL, 4.30 mmol) and triflic anhydride (220 µL, 1.29 mmol) at 0° C. The resulting orange solution was stirred for 20 mins at 0° C. and H₂O (7 mL) was added. After a further 30 mins, the mixture was diluted with EtOAc (60 mL) and brine (50 mL). The layers were separated and the organics were dried over anhydrous Na₂SO₄ and concentrated. The residue was dissolved in dry DMF (30 mL) and NaI (1.00 g, 6.85 mmol) was added. The suspension was stirred for 15 h at 60° C. and concentrated. Then, EtOAc (90 mL) was added and the solution was washed with satd. NH₄Cl aq. solution (2×50 mL), Na₂S₂O₃ aq. solution (50 mL) and brine (50 mL). The organics were dried over anhydrous Na₂SO₄ and concentrated. The residue was purified by column chromatography (silica gel, PE/EtOAc 0 to 40%). Product 8 (527 mg, 70% yield over 2 steps) was obtained as an orange solid.

Step 12. Preparation of N-(9-((2R,3R,4R,5R)-4-((tert-Butyldimethylsilyl)oxy)-5-(((tert-butyldiphenylsilyl)oxy)methyl)-3-fluoro-5-methyltetrahydrofuran-2-yl)-6-(dimethylamino)-9H-purin-2-yl)isobutyramide (9)

To a solution of compound 8 (525 mg, 0.60 mmol) in EtOH (10 mL) was added triethylamine (435 µL, 3.0 mmol) and palladium (10% on charcoal) (35 mg). The flask was put under an atmosphere of hydrogen and stirred for 24 h at RT. The reaction mixture was filtered over Celite and concentrated. The residue was purified by column chromatography (silica gel, PE/EtOAc 0 to 50%). Product 9 (441 mg, 98% yield) was obtained as a white solid.

Step 13. Preparation of N-(6-(Dimethylamino)-9-((2R,3R,4R,5R)-3-fluoro-4-hydroxy-5-(hydroxymethyl)-5-methyltetrahydrofuran-2-yl)-9H-purin-2-yl)isobutyramide (10)

To a solution of compound 9 (440 mg, 0.59 mmol) in dry THF (6 mL) was added tetrabutylammonium fluoride (1 N in THF) (1.5 mL, 1.5 mmol). The solution was stirred for 1 h at RT and concentrated. The residue was purified by column chromatography (silica gel, DCM/MeOH 0 to 10%). Product 10 (215 mg, 91% yield) was obtained as a white solid.

Step 14. Preparation of (2R,3R,4R,5R)-5-(2-Amino-6-(dimethylamino)-9H-purin-9-yl)-4-fluoro-2-(hydroxymethyl)-2-methyltetrahydrofuran-3-ol (Compound A)

A solution of compound 10 (200 mg, 0.50 mmol) in methylamine (33% in EtOH) (10 mL) in a sealed container was stirred for 15 h at 75° C. and concentrated. The residue was purified by column chromatography (silica gel, DCM/MeOH 0 to 15%). Compound A (160 mg, 98% yield) was obtained as a white solid. ¹H NMR (300 MHz, CD₃OD) δ 7.48 (s, 1H), 6.03-5.81 (m, 2H), 4.68 (br s, 2H), 4.54 (d, J=4.5 Hz, 1H), 3.76 (dd, J=12.5, 0.7 Hz, 1H), 3.54 (d, J=12.5 Hz), 3.44 (br s, 6H), 2.65 (br s, 1H), 1.75 (br s, 1H), 1.30 (d, J=1.0 Hz, 3H). MS (ESI) m/z calcd. for $C_{13}H_{20}FN_6O_3$ [M+H]⁺ 327.2; found 327.2.

Step 15. Preparation of (2S)-Isopropyl 2-(((((2R,3R,4R,5R)-5-(2-amino-6-(dimethylamino)-9H-purin-9-yl)-4-fluoro-3-hydroxy-2-methyltetrahydrofuran-2-yl)methoxy)(phenoxy)phosphoryl)-amino) propanoate (Compound B)

To a solution of Compound A (40 mg, 0.12 mmol) in dry DMF (1.5 mL) was added tert-butylmagnesium chloride (0.7 N in THF) (228 µL, 0.16 mmol) drop-wise at −5° C. The solution was stirred for 15 mins at 0° C. and for 45 mins at RT. Then, the reaction mixture was cooled down to −10° C. and a solution of isopropyl ((R,S)-(pentafluorophenoxy)-phenoxy-phosphoryl)-L-alaninate (61 mg, 0.14 mmol) in dry DMF (1 mL) was added drop-wise. The resulting solution was slowly warmed up to 10° C. and stirred for 15 h at this temperature. The reaction mixture was then diluted with EtOAc (10 mL) and satd. NH₄Cl aq. solution (8 mL). The phases were separated and the aqueous layer was back-extracted with EtOAc (2×5 mL). The combined organics were washed with satd. NH₄Cl aq. solution (10 mL) and brine (10 mL), dried over Na₂SO₄ and concentrated. The residue was purified by column chromatography (silica gel, DCM/MeOH 0 to 10%) and by reverse phase column chromatography (C-18 silica, H₂O/MeOH 0 to 100%). Compound B (24 mg, 34%) was obtained as a white solid. ¹H NMR (300 MHz, CD₃OD) δ 7.54 (s, 1H), 7.34-7.13 (m, 5H), 5.99 (dd, J=18.5, 2.5 Hz, 1H), 5.61 (br d, J=54.4 Hz, 1H), 5.03-4.93 (m, 2H), 4.57 (dd, J=10.7, 8.0 Hz, 1H), 3.99-3.91 (m, 2H), 3.70 (dd, J=11.2, 9.8 Hz, 1H), 3.47 (br s, 6H), 2.98 (s, 1H), 1.72 (br s, 1H), 1.36-1.33 (m, 6H), 1.22-1.20 (m, 6H). ³¹P NMR (121 MHz, CDCl₃) δ 3.24 (s). MS (ESI) m/z calcd. for $C_{25}H_{36}FN_7O_7P$ [M+H]⁺ 596.2; found 596.2.

Scheme 2. Preparation of (2S)-Isopropyl 2-(((((2R,3R,4R,5R)-5-(2-Amino-6-(dimethylamino)-9H-purin-9-yl)-4-fluoro-3-hydroxy-2-methyltetrahydrofuran-2-yl) methoxy)(phenoxy)phosphoryl) amino) propanoate (Compound D).

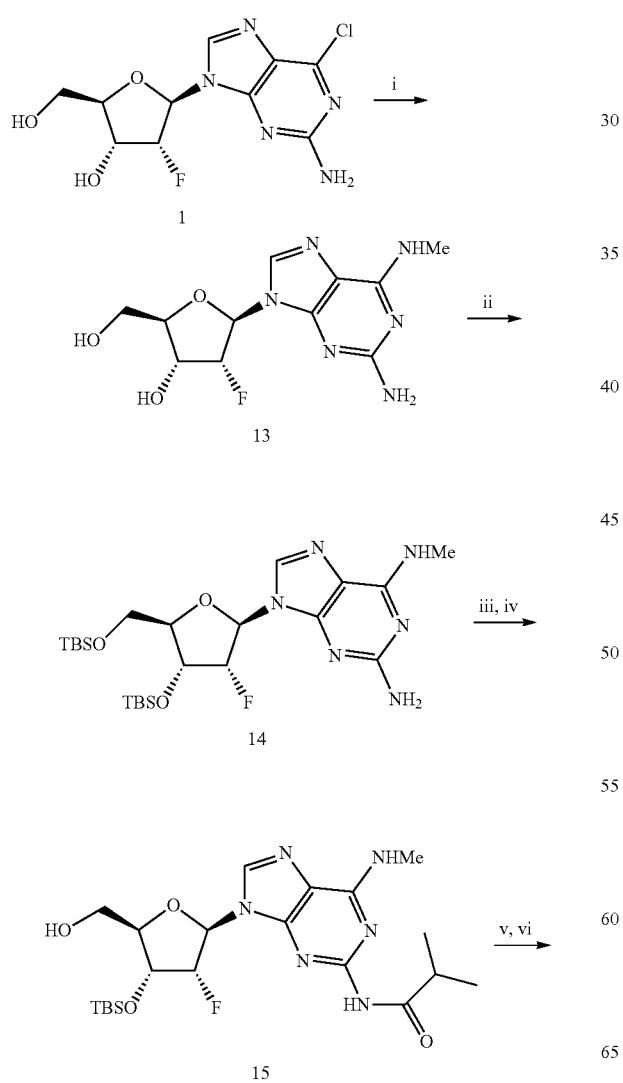

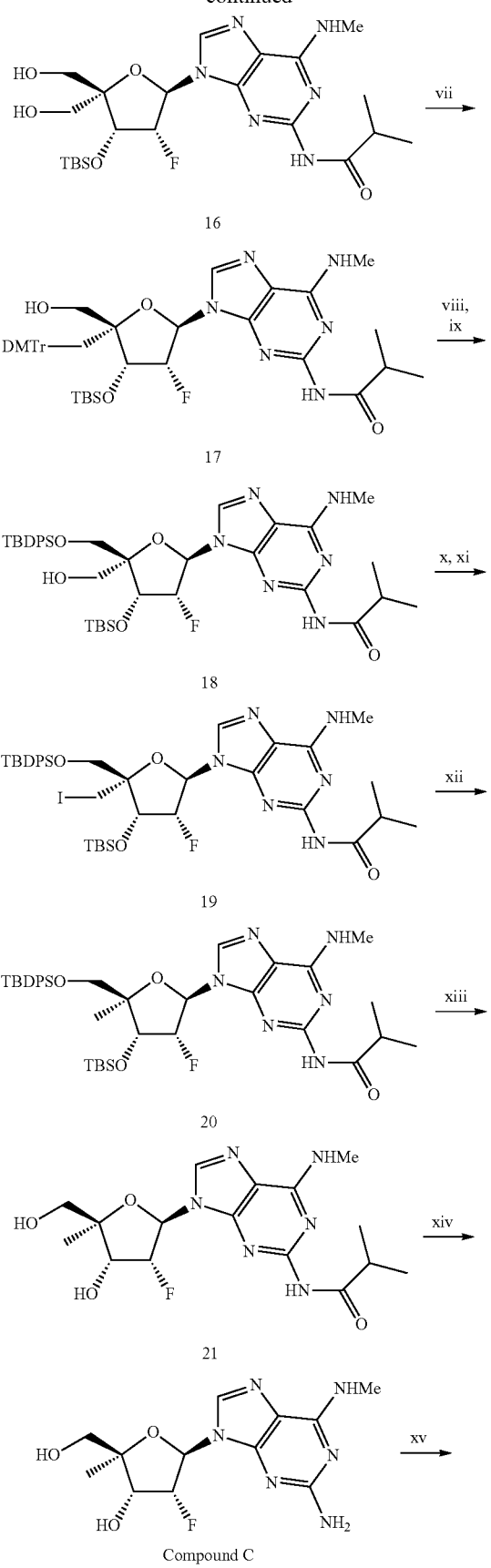

-continued

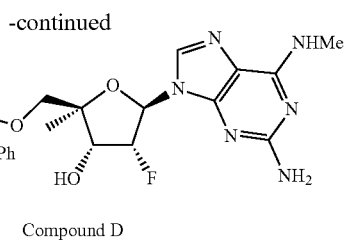

Compound D i) MeNH₂, EtOH, 85° C.; ii) TBSCl, imidazole, DMF; iii) isobutyryl chloride, pyridine; iv) 90% TFA, DCM; v) SO₃, pyridine, DIEA, DMSO, DCM; vi) formaidehyde, 2 N NaOH, dioxane then NaBH₄; vii) DMTrCl, Et₃N, DMF; viii) TBDPSCl, AgNO₃, pyridine; ix) 80% AcOH; x) Tf₂O, pyridine, DCM, 0° C.; xi) NaI, DMF, 60° C.; xii) H₂, 10% Pd-C, Et₃N, EtOH; xiii) TBAF, THF; xiv) MeNH₂, EtOH, 75° C.; xv) Isopropyl ((R,S)-(pentafluorophenoxy)-phenoxy-phosphoryl)-L-alaninate, t-BuMgCl, DMF, -10° C.

Step 1. Preparation of (2R,3R,4R,5R)-5-(2-Amino-6-(methylamino)-9H-purin-9-yl)-4-fluoro-2-(hydroxymethyl) tetrahydrofuran-3-ol (13)

A solution of compound 1 (5.2 g, 17.3 mmol) in methylamine (33% in EtOH) (150 mL) was heated at 85° C. in a sealed container for 3 h, cooled down to RT and concentrated. The residue was purified by column chromatography (silica gel, DCM/MeOH 0 to 15%). Product 13 (4.9 g, 95%) was obtained as a white solid.

Step 2. Preparation of 9-((2R,3R,4R,5R)-4-((tert-Butyldimethylsilyl)oxy)-5-(((tert-butyldimethylsilyl)oxy)methyl)-3-fluorotetrahydrofuran-2-yl)-N6-methyl-9H-purine-2,6-diamine (14)

To a solution of compound 13 (4.7 g, 15.8 mmol) in dry DMF (70 mL) was added imidazole (4.3 g, 63.4 mmol) and TBSCl (9.6 g, 63.4 mmol). The mixture was stirred at RT for 15 h and concentrated. EtOAc (150 mL) was added and the solution was washed with satd. NH₄Cl aq. solution (3×100 mL) and brine (100 mL). The organic phase was dried over anhydrous Na₂SO₄ and concentrated. The residue was purified by column chromatography (silica gel, PE/EtOAc 0 to 60%). Product 14 (7.3 g, 88% yield) was obtained as a yellow oil.

Step 3 and Step 4. Preparation of N-(9-((2R,3R,4R,5R)-4-((tert-Butyldimethylsilyl)oxy)-3-fluoro-5-(hydroxymethyl) tetrahydrofuran-2-yl)-6-(methylamino)-9H-purin-2-yl) isobutyramide (15)

To a solution of compound 14 (7.2 g, 13.7 mmol) in dry pyridine (35 mL) was added isobutyryl chloride (1.7 mL, 16.4 mmol) drop-wise at 0° C. The reaction mixture was stirred at RT for 3 h and then concentrated. After co-evaporation with toluene (3×100 mL), the residue was dissolved in DCM (150 mL) and treated TFA/H₂O (9:1, 15 mL) at 0° C. for 15 h. Then, the reaction was quenched by addition of solid NaHCO₃ (30 g) and filtered. The solution was washed with satd. NaHCO₃ aq. solution (2×100 mL) and brine (100 mL). The organic phase was dried over anhydrous Na₂SO₄ and concentrated. The residue was purified by column chromatography (silica gel, DCM/MeOH 0 to 5%). Product 15 (4.8 g, 73% yield over 2 steps) was obtained as a white foam.

Step 5 and Step 6. Preparation of N-(9-((2R,3R,4R)-4-((tert-Butyldimethylsilyl)oxy)-3-fluoro-5,5-bis(hydroxymethyl) tetrahydrofuran-2-yl)-6-(methylamino)-9H-purin-2-yl)isobutyramide (16)

To a solution of compound 15 (2.5 g, 5.2 mmol) in dry DCM (50 mL) was added diisopropylethylamine (3.5 mL, 20.3 mmol) and a suspension of SO₃ pyridine complex (2.5 g, 15.6 mmol) in dry DMSO (4.8 mL). The orange solution was stirred for 15 h at RT. Then, H₂O (50 mL) was added, the phases were separated and the aqueous layer was back-extracted with EtOAc (2×40 mL). The combined organics were washed with brine (80 mL), dried over anhydrous Na₂SO₄ and concentrated. The residue was dissolved in dioxane (30 mL). Formaldehyde (37% in H₂O) (1.7 mL, 21.8 mmol) and 2 N NaOH (3.9 mL, 7.8 mmol) were added and the yellow solution was stirred for 4 h at RT. The mixture was cooled down to 0° C. and sodium borohydride (787 mg, 20.8 mmol) was added portion-wise. The cloudy solution was stirred for 1 h at RT and quenched by addition of satd. NH₄Cl aq. solution (150 mL). The product was extracted with EtOAc (3×100 mL). The combined organics were washed with brine (150 mL), dried over anhydrous Na₂SO₄ and concentrated. The residue was purified by column chromatography (silica gel, DCM/MeOH 0 to 15%). Product 16 (1.3 g, 50% yield over 2 steps) was obtained as a white solid.

Step 7. Preparation of N-(9-((2R,3R,4R,5S)-5-((Bis (4-methoxyphenyl)(phenyl)methoxy)methyl)-4-((tert-butyldimethylsilyl)oxy)-3-fluoro-5-(hydroxymethyl)tetrahydrofuran-2-yl)-6-(methylamino)-9H-purin-2-yl)isobutyramide (17)

To a solution of compound 16 (1.25 g, 2.44 mmol) in dry DMF (15 mL) was added triethylamine (680 µL, 4.88 mmol) and dimethoxytrityl chloride (1.16 g, 3.42 mmol). The resulting orange solution was stirred for 3 h at RT. The reaction was then diluted with EtOAc (60 mL) and H₂O (50 mL). The phases were separated and the aqueous layer was back-extracted with EtOAc (2×30 mL). The combined organics were washed with brine (60 mL), dried over anhydrous Na₂SO₄ and concentrated. The residue was purified by column chromatography (silica gel, DCM/MeOH 0 to 5%). Product 17 (755 mg, 38% yield) was obtained as a yellow foam.

Step 8 and Step 9. Preparation of N-(9-((2R,3R,4R,5R)-4-((tert-Butyldimethylsilyl)oxy)-5-(((tert-butyldiphenylsilyl)oxy)methyl)-3-fluoro-5-(hydroxymethyl)tetrahydrofuran-2-yl)-6-(methylamino)-9H-purin-2-yl)isobutyramide (18)

To a solution of compound 17 (750 mg, 0.92 mmol) in dry pyridine (7 mL) was added silver nitrate (467 mg, 2.75 mmol) and TBDPSCl (712 2.75 mmol). The resulting solution was stirred for 15 h at RT. Then, EtOAc (50 mL) was added and the suspension was filtered. The solution was washed brine (30 mL), dried over anhydrous Na₂SO₄ and concentrated. The residue was dissolved in 80% acetic acid (5 mL) and stirred for 15 h at RT. The solution was poured into satd. NaHCO₃ aq. solution (90 mL) and the mixture was extracted with DCM (3×60 mL). The combined organics were washed with brine (50 mL), dried over anhydrous Na₂SO₄ and concentrated. The residue was purified by column chromatography (silica gel, DCM/MeOH 0 to 10%). Product 18 (525 mg, 76% yield over 2 steps) was obtained as a white solid.

Step 10 and Step 11. Preparation of N-(9-((2R,3R,4R,5R)-4-((tert-Butyldimethylsilyl)oxy)-5-(((tert-butyldiphenylsilyl)oxy)methyl)-3-fluoro-5-(iodomethyl)tetrahydrofuran-2-yl)-6-(methylamino)-9H-purin-2-yl)isobutyramide (19)

To a solution of compound 18 (520 mg, 0.69 mmol) in dry DCM (12 mL) was added pyridine (280 µL, 3.45 mmol) and triflic anhydride (176 μL, 1.03 mmol) at 0° C. The resulting orange solution was stirred for 15 mins at 0° C. and H₂O (5 mL) was added. After a further 30 mins, the mixture was diluted with EtOAc (50 mL) and brine (40 mL). The layers were separated and the organics were dried over anhydrous Na₂SO₄ and concentrated. The residue was dissolved in dry DMF (25 mL) and NaI (800 mg, 5.49 mmol) was added. The suspension was stirred for 15 h at 60° C. and concentrated. Then, EtOAc (70 mL) was added and the solution was washed with satd. NH₄Cl aq. solution (2×40 mL), Na₂S₂O₃ aq. solution (40 mL) and brine (40 mL). The organics were dried over anhydrous Na₂SO₄ and concentrated. The residue was purified by column chromatography (silica gel, PE/EtOAc 0 to 80%). Product 19 (368 mg, 62% yield over 2 steps) was obtained as an orange solid.

Step 12. Preparation of N-(9-((2R,3R,4R,5R)-4-((tert-Butyldimethylsilyl)oxy)-5-(((tert-butyldiphenylsilyl)oxy)methyl)-3-fluoro-5-methyltetrahydrofuran-2-yl)-6-(methylamino)-9H-purin-2-yl)isobutyramide (20)

To a solution of compound 19 (365 mg, 0.42 mmol) in EtOH (7 mL) was added triethylamine (305 μL, 2.1 mmol) and palladium (10% on charcoal) (25 mg). The flask was put under an atmosphere of hydrogen and stirred for 24 h at RT. The reaction mixture was filtered over Celite and concentrated. The residue was purified by column chromatography (silica gel, PE/EtOAc 0 to 50%). Product 20 (293 mg, 95% yield) was obtained as a white solid.

Step 13. Preparation of N-(6-(Methylamino)-9-((2R, 3R,4R,5R)-3-fluoro-4-hydroxy-5-(hydroxymethyl)-5-methyltetrahydrofuran-2-yl)-9H-purin-2-yl)isobutyramide (21)

To a solution of compound 20 (290 mg, 0.39 mmol) in dry THF (4 mL) was added tetrabutylammonium fluoride (1 N in THF) (1.0 mL, 1.0 mmol). The solution was stirred for 1 h at RT and concentrated. The residue was purified by column chromatography (silica gel, DCM/MeOH 0 to 15%). Product 21 (137 mg, 92% yield) was obtained as a white solid.

Step 14. Preparation of (2R,3R,4R,5R)-5-(2-Amino-6-(methylamino)-9H-purin-9-yl)-4-fluoro-2-(hydroxymethyl)-2-methyltetrahydrofuran-3-ol (Compound C)

A solution of compound 21 (135 mg, 0.35 mmol) in methylamine (33% in EtOH) (7 mL) in a sealed container was stirred for 15 h at 75° C. and concentrated. The residue was purified by column chromatography (silica gel, DCM/MeOH 0 to 20%). Compound C (104 mg, 95% yield) was obtained as a white solid. ¹H NMR (300 MHz, CD₃OD) δ 7.90 (s, 1H), 6.09 (dd, J=13.8, 5.3 Hz, 1H), 5.58 (dt, J=53.2, 5.2 Hz, 1H), 4.51 (dd, J=8.8, 5.1 Hz, 1H), 3.68 (d, J=12.2 Hz, 1H), 3.55 (d, J=12.2 Hz, 1H), 3.04 (s, 3H), 1.26 (d, J=0.8 Hz, 3H). MS (ESI) m/z calcd. for C₁₂H₁₈FN₆O₃ [M+H]⁺ 313.1; found 313.2.

Step 15. Preparation of (2S)-Isopropyl 2-(((((2R, 3R,4R,5R)-5-(2-amino-6-(dimethylamino)-9H-purin-9-yl)-4-fluoro-3-hydroxy-2-methyltetrahydrofuran-2-yl)methoxy)(phenoxy)phosphoryl) amino) propanoate (Compound D)

To a solution of Compound C (38 mg, 0.12 mmol) in dry DMF (1.5 mL) was added tert-butylmagnesium chloride (0.7 N in THF) (228 μL, 0.16 mmol) drop-wise at −5° C. The solution was stirred for 20 mins at 0° C. and for 40 mins at RT. Then, the reaction mixture was cooled down to −10° C. and a solution of isopropyl ((R,S)-(pentafluorophenoxy)-phenoxy-phosphoryl)-L-alaninate (61 mg, 0.14 mmol) in dry DMF (1 mL) was added drop-wise. The resulting solution was slowly warmed up to 10° C. and stirred for 15 h at this temperature. The reaction mixture was then diluted with EtOAc (10 mL) and satd. NH₄Cl aq. solution (8 mL). The phases were separated and the aqueous layer was back-extracted with EtOAc (2×5 mL). The combined organics were washed with satd. NH₄Cl aq. solution (10 mL) and brine (10 mL), dried over Na₂SO₄ and concentrated. The residue was purified by column chromatography (silica gel, DCM/MeOH 0 to 10%) and by reverse phase column chromatography (C-18 silica, H₂O/MeOH 0 to 100%). Compound D (20 mg, 29%) was obtained as a white solid. ¹H NMR (300 MHz, CD₃OD) δ 7.82 (s, 1H), 7.31-7.17 (m, 5H), 6.13 (dd, J=17.2, 3.2 Hz, 1H), 5.55 (ddd, J=53.2, 3.2, 5.2 Hz, 1H), 4.94-4.85 (m, 1H), 4.71 (dd, J=17.2, 5.2 Hz, 1H), 4.29 (dd, J=10.8, 6.0 Hz, 1H), 4.08 (dd, J=10.8, 5.2 Hz, 1H), 3.86 (m, 1H), 3.02 (br s, 3H), 1.33 (br s, 3H), 1.28-1.25 (m, 3H), 1.18-1.16 (m, 6H). ³¹P NMR (121 MHz, CD₃OD) δ 3.24 (s). MS (ESI) m/z calcd. for C₂₄H₃₄FN₇O₇P [M+H]⁺ 582.2; found 582.2.

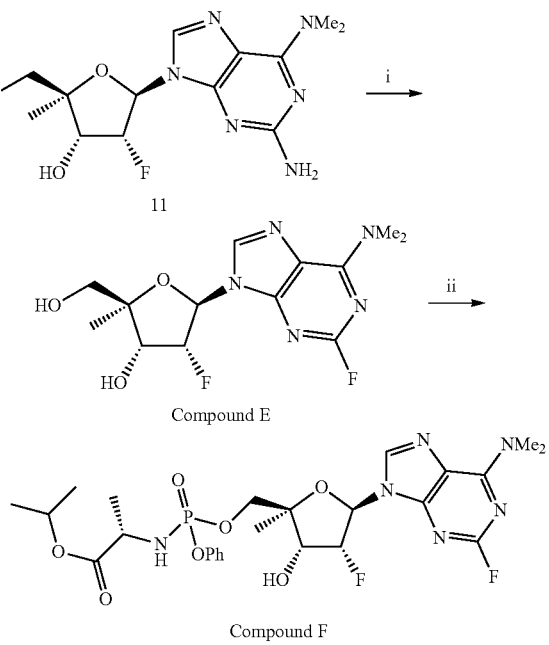

Scheme 3. Preparation of (2S)-Isopropyl 2-(((((2R,3R,4R,5R)-4-fluoro-5-(2-fluoro-6-(methylamino)-9H-purin-9-yl)-3-hydroxy-2-methyltetrahydrofuran-2-yl)methoxy)(phenoxy)phosphoryl)amino) propanoate (Compound F)

i) tBuONO, pyridine, HF, pyridine, -15° C.; ii) Isopropyl ((R,S)-(pentafluorophenoxy)-phenoxy-phosphoryl)-L-alaninate, t-BuMgCl, DMF, -10° C.

Step 1. Preparation of (2R,3R,4R,5R)-5-(6-(Dimethylamino)-2-fluoro-9H-purin-9-yl)-4-fluoro-2-(hydroxymethyl)-2-methyltetrahydrofuran-3-ol (Compound E)

A solution of compound 11 (70 mg, 0.21 mmol) in dry pyridine (400 μL) was cooled down to −15° C. and pyridine hydrofluoride (280 µL) was added. Then, tert-butyl nitrite (51 µL, 0.43 mmol) was added dropwise over 5 mins. The mixture was stirred at 10° C. for 4 h and quenched by addition of a suspension of CaCO$_3$ (700 mg) in H$_2$O (2 mL). The resulting suspension was stirred at RT for 15 mins and extracted with EtOAc (5×5 mL). The combined organics were dried over anhydrous Na$_2$SO$_4$ and concentrated. The residue was purified by column chromatography (silica gel, DCM/MeOH 0 to 7%). Compound E (38 mg, 54% yield) was obtained as an off-white solid. $^1$H NMR (300 MHz, CD$_3$OD) δ 8.22 (s, 1H), 6.20 (dd, J=14.7, 4.2 Hz, 1H), 5.48 (ddd, J=53.4, 5.1, 5.0 Hz, 1H), 4.56 (dd, J=13.5, 5.1 Hz, 1H), 3.67-3.53 (m, 2H), 3.65 (br s, 3H), 3.33 (br s, 3H), 1.28 (s, 3H). MS (ESI) m/z calcd. for C$_{13}$H$_{18}$F$_2$N$_5$O$_3$ [M+H]$^+$ 330.1; found 330.2.

Step 2. Preparation of (2S)-Isopropyl 2-(((((2R,3R, 4R,5R)-4-fluoro-5-(2-fluoro-6-(methylamino)-9H-purin-9-yl)-3-hydroxy-2-methyltetrahydrofuran-2-yl) methoxy)(phenoxy)phosphoryl)amino) propanoate (Compound F)

To a solution of Compound E (35 mg, 0.11 mmol) in dry DMF (1.5 mL) was added tert-butylmagnesium chloride (0.7 N in THF) (209 µL, 0.15 mmol) drop-wise at −5° C. The solution was stirred for 20 mins at 0° C. and for 40 mins at RT. Then, the reaction mixture was cooled down to −10° C. and a solution of isopropyl ((R,S)-(pentafluorophenoxy)-phenoxy-phosphoryl)-L-alaninate (56 mg, 0.13 mmol) in dry DMF (1 mL) was added drop-wise. The resulting solution was slowly warmed up to 10° C. and stirred for 15 h at this temperature. The reaction mixture was then diluted with EtOAc (10 mL) and satd. NH$_4$Cl aq. solution (8 mL). The phases were separated and the aqueous layer was back-extracted with EtOAc (2×5 mL). The combined organics were washed with satd. NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound F (12 mg, 20%) was obtained as a white solid. $^1$H NMR (300 MHz, CD$_3$OD) δ 8.07 (s, 1H), 7.29-7.10 (m, 5H), 6.21 (dd, J=17.7, 2.4 Hz) 5.52 (ddd, J=53.1, 5.1, 2.7 Hz, 1H), 4.91-4.73 (overlapped with H$_2$O, m, 1H), 4.16-4.11 (m, 2H), 3.87-3.81 (m, 1H), 3.65-3.29 (overlapped with MeOH, br m, 6H), 1.34 (s, 3H), 1.27-1.15 (m, 9H). $^{31}$P NMR (121 MHz, CD$_3$OD) δ 3.42 (s). MS (ESI) m/z calcd. for C$_{25}$H$_{34}$F$_2$N$_6$O$_7$P [M+H]$^+$ 599.2; found 599.2.

Scheme 4. Preparation of (2S)-Isopropyl 2-(((((2R,3R,4R,5R)-5-(2-chloro-6-(dimethylamino)-9H-purin-9-yl)-4-fluoro-3-hydroxy-2-methyltetrahydrofuran-2-yl)methoxy) (phenoxy)phosphoryl)amino) propanoate (Compound H).

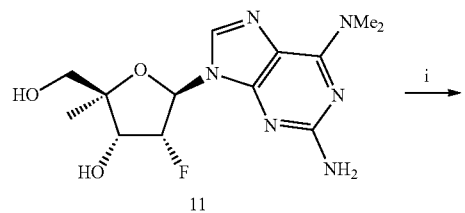

11

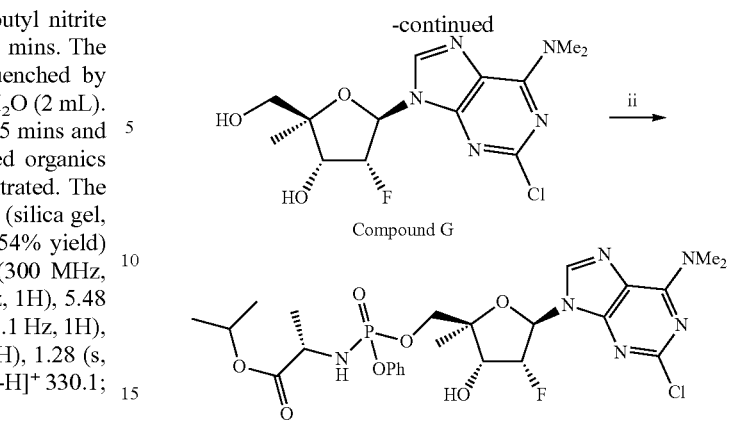

Compound G

Compound H i) tBuONO, SbCl$_3$, DCE, DMSO, 0° C.; ii) Isopropyl ((R,S)-(pentafluorophenoxy)-phenoxy-phosphoryl)-L-alaninate, t-BuMgCl, DMF, −10° C.

Step 1. Preparation of (2R,3R,4R,5R)-5-(2-Chloro-6-(dimethylamino)-9H-purin-9-yl)-4-fluoro-2-(hydroxymethyl)-2-methyltetrahydrofuran-3-ol (Compound G)

A solution of compound 11 (70 mg, 0.21 mmol) in dry DCE/DMSO (4:1) (2.5 mL) was cooled down to 0° C. and antimony trichloride (68 mg, 0.30 mmol) was added. Then, tert-butyl nitrite (54 µL, 0.46 mmol) was added drop-wise over 5 mins. The mixture was stirred at RT for 4 h and quenched by addition of trimethylamine (100 µL). The resulting mixture was diluted with EtOAc (10 mL) and washed with H$_2$O (5 mL). The aqueous layer was back-extracted EtOAc (3×5 mL). The combined organics were washed with brine (10 mL), dried over anhydrous Na$_2$SO$_4$ and concentrated. The residue was purified by column chromatography (silica gel, DCM/MeOH 0 to 7%). Compound G (36 mg, 50% yield) was obtained as a white solid. $^1$H NMR (300 MHz, CD$_3$OD) δ 7.75 (s, 1H), 6.03-5.83 (m, 2H), 4.57 (d, J=3.3 Hz, 1H), 3.79 (d, J=9.6 Hz, 1H), 3.76 (br s, 3H), 3.58 (d, J=9.6 Hz, 1H), 3.30 (br s, 3H), 1.32 (s, 3H). MS (ESI) m/z calcd. for C$_{13}$H$_{18}$ClFN$_5$O$_3$ [M+H]$^+$ 346.1; found 346.2.

Step 2. Preparation of (2S)-Isopropyl 2-(((((2R,3R, 4R,5R)-5-(2-chloro-6-(dimethylamino)-9H-purin-9-yl)-4-fluoro-3-hydroxy-2-methyltetrahydrofuran-2-yl)methoxy)-(phenoxy)phosphoryl)amino) propanoate (Compound H)

To a solution of Compound G (32 mg, 0.09 mmol) in dry DMF (1.3 mL) was added tert-butylmagnesium chloride (0.7 N in THF) (181 µL, 0.13 mmol) drop-wise at −5° C. The solution was stirred for 20 mins at 0° C. and for 40 mins at RT. Then, the reaction mixture was cooled down to −10° C. and a solution of isopropyl ((R,S)-(pentafluorophenoxy)-phenoxy-phosphoryl)-L-alaninate (49 mg, 0.11 mmol) in dry DMF (1 mL) was added drop-wise. The resulting solution was slowly warmed up to 10° C. and stirred for 15 h at this temperature. The reaction mixture was then diluted with EtOAc (10 mL) and satd. NH$_4$Cl aq. solution (8 mL). The phases were separated and the aqueous layer was back-extracted with EtOAc (2×5 mL). The combined organics were washed with satd. NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H₂O/MeOH 0 to 100%). Compound H (10 mg, 18%) was obtained as a white solid. $^1$H NMR (300 MHz, CD$_3$OD) δ 8.10 (s, 1H), 7.30-7.11 (m, 5H), 6.25 (dd, J=17.8, 2.4 Hz, 1H), 5.52 (ddd, J=53.2, 5.2, 2.5 Hz, 1H), 4.95-4.91 (overlapped with H₂O, m, 1H) 4.85-4.77 (overlapped with H₂O, m, 1H), 4.19 (dd, J=10.9, 5.8 Hz, 1H), 4.13 (dd, J=11.0, 5.2 Hz, 1H), 3.92-3.81 (m, 1H), 3.70-3.18 (m, 6H), 1.35 (s, 3H), 1.28 (d, J=7.1 Hz, 3H), 1.19 (d, J=6.3 Hz, 6H). $^{31}$P NMR (121 MHz, CD$_3$OD) δ 1.97 (s). MS (ESI) m/z calcd. for C$_{25}$H$_{34}$ClFN$_6$O$_7$P [M+H]$^+$ 615.2; found 615.2.

Scheme 5. Preparation of (2S)-Isopropyl 2-(((((2R,3R,4R,5R)-5-(6-(dimethylamino)-2-methoxy-9H-purin-9-yl)-4-fluoro-3-hydroxy-2-methyltetrahydrofuran-2-yl)methoxy)(phenoxy)phosphoryl)amino) propanoate (Compound J).

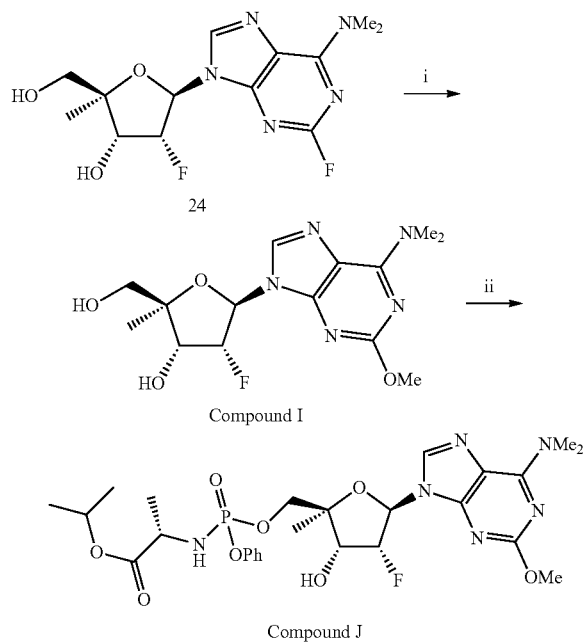

Compound J i) MeONa, MeOH, 60° C.; ii) Isopropyl ((R,S)-(pentafluorophenoxy)-phenoxy-phosphoryl)-L-alaninate, t-BuMgCl, DMF, -10° C.

Step 1. Preparation of (2R,3R,4R,5R)-5-(6-(Dimethylamino)-2-methoxy-9H-purin-9-yl)-4-fluoro-2-(hydroxymethyl)-2-methyltetrahydrofuran-3-ol (Compound I)

To a solution of compound 24 (100 mg, 0.30 mmol) in dry MeOH (5 mL) was added sodium methoxide (25% in MeOH) (140 μL, 0.6 mmol). The resulting solution was stirred at 60° C. for 5 h. The reaction was quenched by addition of acetic acid (40 μL) and the solvent was removed. The residue was purified by column chromatography (silica gel, DCM/MeOH 0 to 8%). Compound I (31 mg, 30% yield) was obtained as a white solid. $^1$H NMR (300 MHz, CD$_3$OD) δ 8.08 (s, 1H), 6.19 (dd, J=15.2, 4.4 Hz, 1H), 5.57 (ddd, J=58.8, 4.8, 5.2 Hz, 1H), 4.60 (dd, J=12.8, 5.2 Hz, 1H), 3.96 (s, 3H), 3.61 (m, 2H), 3.50-3.32 (overlapped with MeOH, m, 6H), 1.28 (s, 3H). MS (ESI) m/z calcd. for C$_{14}$H$_{21}$FN$_5$O$_4$ [M+H]$^+$ 342.2; found 342.2.

Step 2. Preparation of (2S)-Isopropyl 2-(((((2R,3R,4R,5R)-5-(6-(dimethylamino)-2-methoxy-9H-purin-9-yl)-4-fluoro-3-hydroxy-2-methyltetrahydrofuran-2-yl)methoxy)(phenoxy)phosphoryl)-amino) propanoate (Compound J)

To a solution of Compound I (28 mg, 0.08 mmol) in dry DMF (1.2 mL) was added tert-butylmagnesium chloride (0.7 N in THF) (161 μL, 0.12 mmol) drop-wise at -5° C. The solution was stirred for 20 mins at 0° C. and for 40 mins at RT. Then, the reaction mixture was cooled down to -10° C. and a solution of isopropyl ((R,S)-(pentafluorophenoxy)-phenoxy-phosphoryl)-L-alaninate (44 mg, 0.10 mmol) in dry DMF (900 μL) was added drop-wise. The resulting solution was slowly warmed up to 10° C. and stirred for 15 h at this temperature. The reaction mixture was then diluted with EtOAc (10 mL) and satd. NH$_4$Cl aq. solution (8 mL). The phases were separated and the aqueous layer was back-extracted with EtOAc (2×5 mL). The combined organics were washed with satd. NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H₂O/MeOH 0 to 100%). Compound J (12 mg, 23%) was obtained as a white solid. $^1$H NMR (300 MHz, CD$_3$OD) δ 7.97 (m, 1H), 7.31-7.12 (m, 5H), 6.22 (dd, J=18.3, 2.4 Hz) 5.59 (ddd, J=53.7, 5.4, 2.7 Hz, 1H), 4.90 (overlapped with H₂O, m, 1H), 4.22-4.08 (m, 2H), 3.95 (s, 3H), 3.86-3.81 (m, 1H), 3.42-3.30 (overlapped with MeOH, m, 6H), 1.35 (s, 3H), 1.27-1.15 (m, 9H). $^{31}$P NMR (121 MHz, CD$_3$OD) δ 3.57 (s). MS (ESI) m/z calcd. for C$_{26}$H$_{37}$FN$_6$O$_8$P [M+H]$^+$ 611.2; found 611.2.

Scheme 6. Preparation of (2S)-Isopropyl 2-(((((2R,3R,4R,5R)-5-(2-amino-6-(dimethylamino)-9H-purin-9-yl)-2-(chloromethyl)-4-fluoro-3-hydroxytetrahydrofuran-2-yl)methoxy)(phenoxy) phosphoryl)amino)propanoate (Compound L).

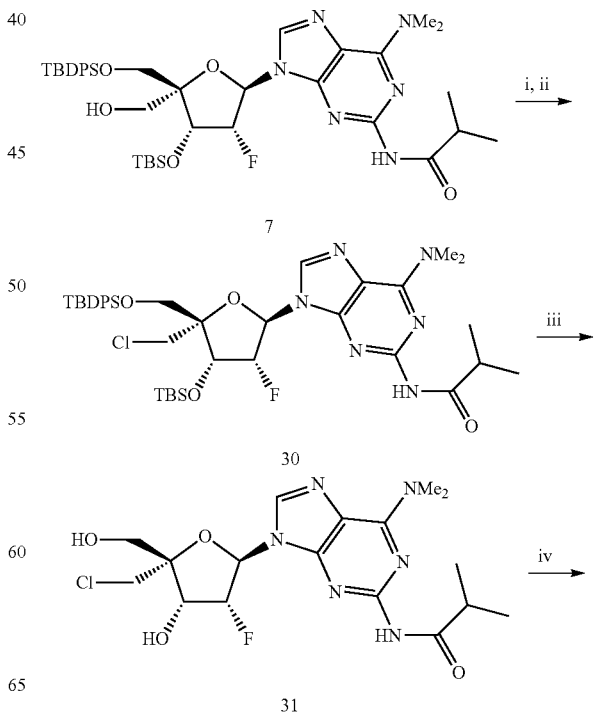

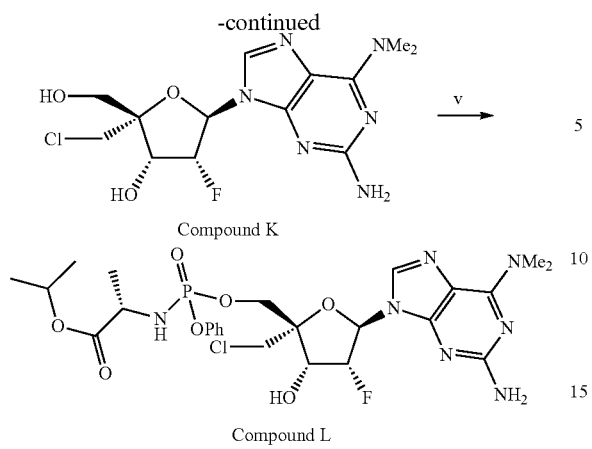

Compound K

Compound L i) Tf₂O, pyridine, DCM, 0° C.; ii) LiCl, DMF, 40° C.; iii) TBAF, THF; iv) MeNH₂, EtOH, 75° C.; v) Isopropyl ((R,S)-(pentafluorophenoxy)-phenoxy-phosphoryl)-L-alaninate, t-BuMgCl, DMF, -10° C.

Step 1 and Step 2. Preparation of N-(9-((2R,3R,4R, 5R)-4-((tert-Butyldimethylsilyl)oxy)-5-(((tert-butyl-diphenylsilyl)oxy)methyl)-5-(chloromethyl)-3-fluorotetrahydrofuran-2-yl)-6-(dimethylamino)-9H-purin-2-yl)isobutyramide (30)

To a solution of compound 7 (600 mg, 0.78 mmol) in dry DCM (15 mL) was added pyridine (315 µL, 3.90 mmol) and triflic anhydride (200 µL, 1.16 mmol) at 0° C. The resulting orange solution was stirred for 20 mins at 0° C. and H₂O (7 mL) was added. After a further 30 mins, the mixture was diluted with EtOAc (60 mL) and brine (50 mL). The layers were separated and the organics were dried over anhydrous Na₂SO₄ and concentrated. The residue was dissolved in dry DMF (30 mL) and LiCl (330 mg, 7.80 mmol) was added. The suspension was stirred for 15 h at 40° C. and concentrated. Then, EtOAc (90 mL) was added and the solution was washed with satd. NH₄Cl aq. solution (2×50 mL), Na₂S₂O₃ aq. solution (50 mL) and brine (50 mL). The organics were dried over anhydrous Na₂SO₄ and concentrated. The residue was purified by column chromatography (silica gel, PE/EtOAc 0 to 50%). Product 30 (522 mg, 85% yield over 2 steps) was obtained as an off-white solid.

Step 3. Preparation of N-(9-((2R,3R,4R,5R)-5-(Chloromethyl)-3-fluoro-4-hydroxy-5-(hydroxymethyl)tetrahydrofuran-2-yl)-6-(dimethyamino)-9H-purin-2-yl)isobutyramide (31)

To a solution of compound 30 (400 mg, 0.51 mmol) in dry THF (6 mL) was added tetrabutylammonium fluoride (1 N in THF) (1.5 mL, 1.5 mmol). The solution was stirred for 1 h at RT and concentrated. The residue was purified by column chromatography (silica gel, DCM/MeOH 0 to 10%). Product 31 (205 mg, 93% yield) was obtained as a white solid.

Step 4. Preparation of (2R,3R,4R,5R)-5-(2-Amino-6-(dimethylamino)-9H-purin-9-yl)-2-(chloromethyl)-4-fluoro-2-(hydroxymethyl)tetrahydrofuran-3-ol (Compound K)

A solution of compound 31 (200 mg, 0.46 mmol) in methylamine (33% in EtOH) (10 mL) in a sealed container was stirred for 15 h at 75° C. and concentrated. The residue was purified by column chromatography (silica gel, DCM/MeOH 0 to 15%). Compound K (159 mg, 95% yield) was obtained as a white solid. ¹H NMR (300 MHz, CD₃OD) δ 7.81 (br, NH), 7.48 (s, 1H), 6.12-5.90 (m, 2H), 4.71 (m, 1H+NH+OH), 4.01-3.88 (m, 2H), 3.59-3.49 (m, 2H), 3.43 (1, 6H), 2.66 (s, 10H). MS (ESI) m/z calcd. for C₁₃H₁₉ClFN₆O₃ [M+H]⁻ 361.1; found 361.2.

Step 5. Preparation of (2S)-Isopropyl 2-(((((2R,3R, 4R,5R)-5-(2-amino-6-(dimethylamino)-9H-purin-9-yl)-2-(chloromethyl)-4-fluoro-3-hydroxytetrahydrofuran-2-yl)methoxy)(phenoxy) phosphoryl)amino) propanoate (Compound L)

To a solution of Compound K (51 mg, 0.14 mmol) in dry DMF (2 mL) was added tert-butylmagnesium chloride (0.7 N in THF) (285 µL, 0.20 mmol) drop-wise at -5° C. The solution was stirred for 15 mins at 0° C. and for 45 mins at RT. Then, the reaction mixture was cooled down to -10° C. and a solution of isopropyl ((R,S)-(pentafluorophenoxy)-phenoxy-phosphoryl)-L-alaninate (76 mg, 0.17 mmol) in dry DMF (1.5 mL) was added drop-wise. The resulting solution was slowly warmed up to 10° C. and stirred for 15 h at this temperature. The reaction mixture was then diluted with EtOAc (12 mL) and satd. NH₄Cl aq. solution (10 mL). The phases were separated and the aqueous layer was back-extracted with EtOAc (2×6 mL). The combined organics were washed with satd. NH₄Cl aq. solution (12 mL) and brine (12 mL), dried over Na₂SO₄ and concentrated. The residue was purified by column chromatography (silica gel, DCM/MeOH 0 to 10%) and by reverse phase column chromatography (C-18 silica, H₂O/MeOH 0 to 100%). Compound L (27 mg, 30%) was obtained as a white solid. ¹H NMR (300 MHz, CD₃OD) δ 7.45,7.46 (s+s, 1H), 7.39-7.13 (m, 5H), 6.08-5.96 (dd+dd overlapped, J=19.2, 3.2 Hz, 1H), 5.80-5.39 (m, 2H), 5.13-4.73 (m, 3H), 4.44-4.25 (m, 1H), 4.11-3.69 (m, 4H), 3.56-3.31 (m, 7H), 1.40-1.36 (m, 3H), 1.25-1.20 (m, 6H). ³¹P NMR (121 MHz, CDCl₃) δ 3.95 (s). MS (ESI) m/z calcd. for C₂₅H₃₅ClFN₇O₇P [M+H]⁺ 630.2; found 630.2.

Scheme 7. (2S)-Isopropyl 2-(((((2R,3R,4R,5R)-5-(2-amino-6-(methylamino)-9H-purin-9-yl)-2-(chloromethyl)-4-fluoro-3-hydroxytetrahydrofuran-2-yl)methoxy)(phenoxy)phosphoryl)amino)propanoate (Compound N).

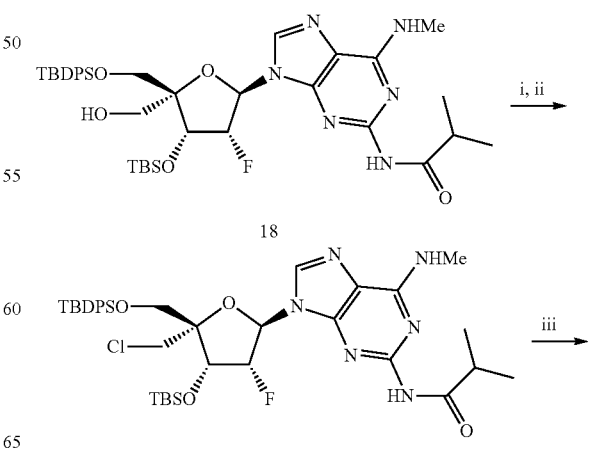

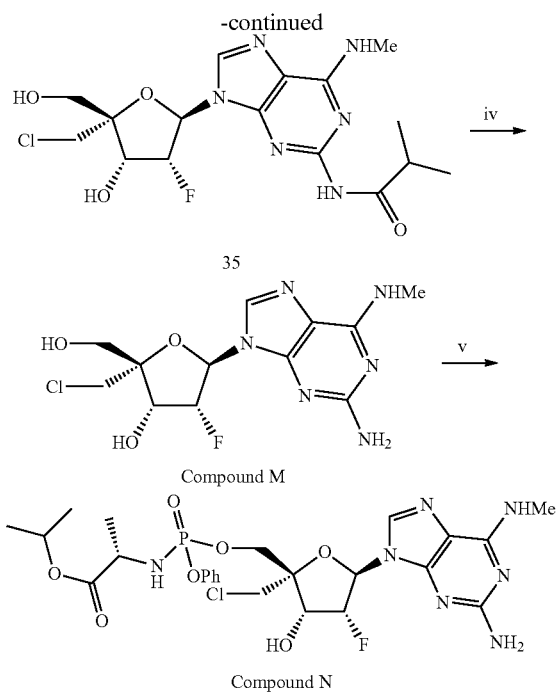

Compound M

Compound N i) Tf₂O, pyridine, DCM, 0° C.; ii) LiCl, DMF, 40° C.; iii) TBAF, THF; iv) MeNH₂, EtOH, 75° C.; v) Isopropyl ((R,S)-(pentafluorophenoxy)-phenoxy-phosphoryl)-L-alaninate, t-BuMgCl, DMF, -10° C.

Step 1 and Step 2. Preparation of N-(9-((2R,3R,4R, 5R)-4-((tert-Butyldimethylsilyl)oxy)-5-(((tert-butyl-diphenylsilyl)oxy)methyl)-5-(chloromethyl)-3-fluorotetrahydrofuran-2-yl)-6-(methylamino)-9H-purin-2-yl)isobutyramide (34)

To a solution of compound 18 (420 mg, 0.56 mmol) in dry DCM (12 mL) was added pyridine (227 μL, 2.81 mmol) and triflic anhydride (145 μL, 0.84 mmol) at 0° C. The resulting orange solution was stirred for 20 mins at 0° C. and H₂O (5 mL) was added. After a further 30 mins, the mixture was diluted with EtOAc (50 mL) and brine (40 mL). The layers were separated and the organics were dried over anhydrous Na₂SO₄ and concentrated. The residue was dissolved in dry DMF (22 mL) and LiCl (238 mg, 5.62 mmol) was added. The suspension was stirred for 15 h at 40° C. and concentrated. Then, EtOAc (80 mL) was added and the solution was washed with satd. NH₄Cl aq. solution (2×40 mL), Na₂S₂O₃ aq. solution (40 mL) and brine (40 mL). The organics were dried over anhydrous Na₂SO₄ and concentrated. The residue was purified by column chromatography (silica gel, PE/EtOAc 0 to 50%). Product 34 (336 mg, 78% yield over 2 steps) was obtained as an off-white solid.

Step 3. Preparation of N-(9-((2R,3R,4R,5R)-5-(Chloromethyl)-3-fluoro-4-hydroxy-5-(hydroxymethyl) tetrahydrofuran-2-yl)-6-(methyamino)-9H-purin-2-yl)isobutyramide (35)

To a solution of compound 34 (290 mg, 0.38 mmol) in dry THF (5 mL) was added tetrabutylammonium fluoride (1 N in THF) (1.1 mL, 1.1 mmol). The solution was stirred for 1 h at RT and concentrated. The residue was purified by column chromatography (silica gel, DCM/MeOH 0 to 10%). Product 35 (145 mg, 92% yield) was obtained as a white solid.

Step 4. Preparation of (2R,3R,4R,5R)-5-(2-Amino-6-(methylamino)-9H-purin-9-yl)-2-(chloromethyl)-4-fluoro-2-(hydroxymethyl)tetrahydrofuran-3-ol (Compound M)

A solution of compound 35 (140 mg, 0.34 mmol) in methylamine (33% in EtOH) (10 mL) in a sealed container was stirred for 15 h at 75° C. and concentrated. The residue was purified by column chromatography (silica gel, DCM/MeOH 0 to 15%). Compound M (107 mg, 92% yield) was obtained as a white solid. ¹H NMR (300 MHz, CD₃OD) δ 7.88 (s, 1H), 6.14 (dd, J=12.5, 6.4 Hz, 1H), 5.73 (dt, J=52.8, 6.2 Hz, 1H), 4.63 (t, J=4.7 Hz, 1H), 3.94-3.84 (m, 3H), 3.73 (d, J=11.5 Hz, 1H), 3.04 (br s, 3H). MS (ESI) m/z calcd. for C₁₂H₁₇ClFN₆O₃ [M+H]⁺ 347.1; found 347.0.

Step 5. Preparation of (2S)-Isopropyl 2-(((((2R,3R, 4R,5R)-5-(2-amino-6-(methylamino)-9H-purin-9-yl)-2-(chloromethyl)-4-fluoro-3-hydroxytetrahydrofuran-2-yl)methoxy)(phenoxy)-phosphoryl) amino) propanoate (Compound N)

To a solution of Compound M (50 mg, 0.14 mmol) in dry DMF (2 mL) was added tert-butylmagnesium chloride (0.7 N in THF) (285 μL, 0.20 mmol) drop-wise at -5° C. The solution was stirred for 15 mins at 0° C. and for 45 mins at RT. Then, the reaction mixture was cooled down to -10° C. and a solution of isopropyl ((R,S)-(pentafluorophenoxy)-phenoxy-phosphoryl)-L-alaninate (76 mg, 0.17 mmol) in dry DMF (1.5 mL) was added drop-wise. The resulting solution was slowly warmed up to 10° C. and stirred for 15 h at this temperature. The reaction mixture was then diluted with EtOAc (12 mL) and satd. NH₄Cl aq. solution (10 mL). The phases were separated and the aqueous layer was back-extracted with EtOAc (2×6 mL). The combined organics were washed with satd. NH₄Cl aq. solution (12 mL) and brine (12 mL), dried over Na₂SO₄ and concentrated. The residue was purified by column chromatography (silica gel, DCM/MeOH 0 to 10%) and by reverse phase column chromatography (C-18 silica, H₂O/MeOH 0 to 100%). Compound N (23 mg, 26%) was obtained as a white solid. ¹H NMR (300 MHz, CD₃OD) δ 7.85, 7.83 (s+s, 1H), 7.32-7.15 (m, 5H), 6.24-6.15 (m, 1H), 5.79, 5.76 (dt, J=52.5, 4.7 Hz overlapped with dt, J=52.5, 4.8 Hz, 1H), 4.99-4.90 (m, 2H), 4.64-4.55 (m, 1H), 4.43, 4.37 (dt, J=10.7, 4.6 Hz overlapped with dt, J=10.8, 5.0 Hz, 1H), 3.91-3.82 (m, 2H), 3.03 (br s, 3H), 1.29-1.18 (m, 9H). ³¹P NMR (121 MHz, CD₃OD) δ 2.61 (s), 2.42 (s). MS (ESI) m/z calcd. for C₂₄H₃₃ClFN₇O₇P [M+H]⁺ 616.2; found 616.2.

Scheme 8. Preparation of (2S)-Isopropyl 2-(((((2R,3R,4R,5R)-5-(2-amino-6-(dimethylamino)-9H-purin-9-yl)-2-ethyl-4-fluoro-3-hydroxytetrahydrofuran-2-yl) methoxy)(phenoxy)phosphoryl)amino) propanoate (Compound P).

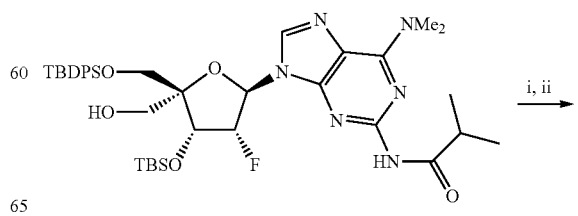

7

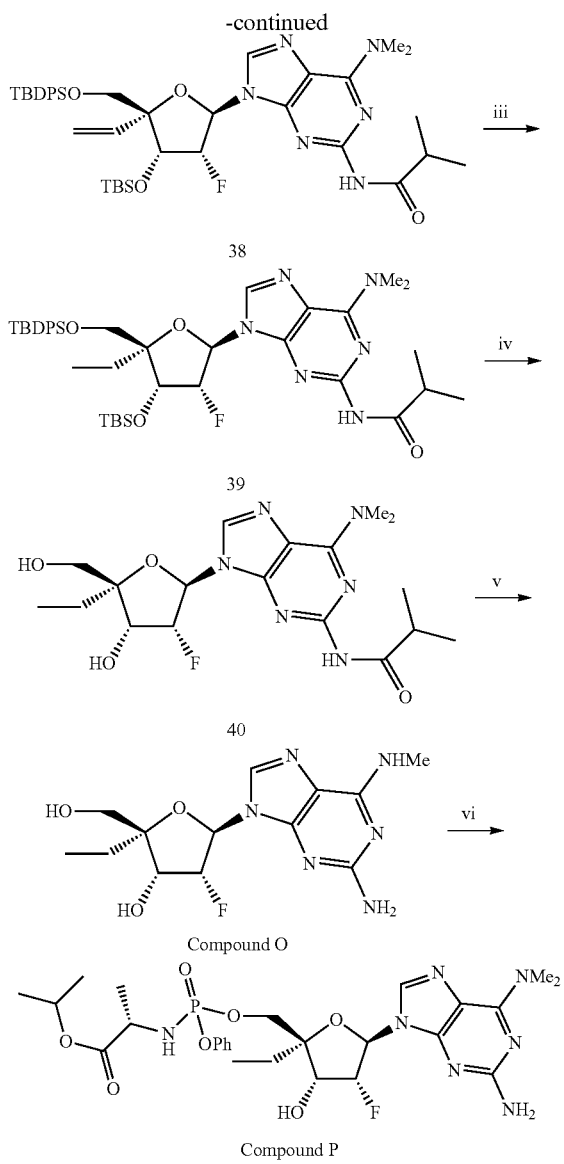

i) SO₃, pyridine, DIEA, DMSO, DCM, -10° C.; ii) PPh₃MeBr, BuLi, THF; iii) H₂, 10% Pd-C, Et₃N, EtOH; iv) TBAF, THF; v) MeNH₂, EtOH, 75° C.; vi) Isopropyl ((R, S)-(pentafluorophenoxy)-phenoxy-phosphoryl)-L-alaninate, t-BuMgCl, DMF, -10° C.

Step 1 and Step 2. Preparation of N-(9-((2R,3R,4R,5R)-4-((tert-Butyldimethylsilyl)oxy)-5-(((tert-butyldiphenylsilyl)oxy)methyl)-3-fluoro-5-vinyltetrahydrofuran-2-yl)-6-(dimethylamino)-9H-purin-2-yl) isobutyramide (38)

To a solution of compound 7 (950 mg, 1.24 mmol) in dry DCM (10 mL) was added diisopropylethylamine (840 μL, 4.84 mmol) and a suspension of SO₃ pyridine complex (594 mg, 3.73 mmol) in dry DMSO (1.1 mL) drop-wise at -10° C. The orange solution was stirred for 30 mins at this temperature and for 5 h at RT. Then, H₂O (6 mL) was added, the phases were separated and the aqueous layer was back-extracted with EtOAc (2×10 mL). The combined organics were washed with brine (20 mL), dried over anhydrous Na₂SO₄ and concentrated. The aldehyde intermediate aldehyde was dissolved in dry THF (4 mL). Methyltriphenylphosphonium bromide (1.33 g, 3.73 mmol) was suspended in dry THF (14 mL) and butyllithium (1.6 N in hexanes) (2.33 mL, 3.73 mmol) was added drop-wise at 0° C. The resulting yellow solution was stirred for 1 h at this temperature. Then, the solution of aldehyde was added drop-wise at 0° C. and the mixture was stirred at RT for 15 h. Then, the solution was diluted with EtOAc (30 mL) and satd. NH₄Cl aq. solution (250 mL). The phases were separated and the aqueous layer was back-extracted with EtOAc (2×20 mL). The combined organics were washed with brine (30 mL), dried over Na₂SO₄ and concentrated. The residue was purified by column chromatography (silica gel, PE/EtOAc 0 to 100%). Product 38 (472 mg, 50%) was obtained as a yellow foam.

Step 3. Preparation of N-(9-((2R,3R,4R,5R)-4-((tert-Butyldimethylsilyl)oxy)-5-(((tert-butyldiphenylsilyl)oxy)methyl)-5-ethyl-3-fluorotetrahydrofuran-2-yl)-6-(dimethylamino)-9H-purin-2-yl) isobutyramide (39)

To a solution of compound 38 (470 mg, 0.62 mmol) in EtOH (10 mL) was added palladium (10% on charcoal) (135 mg). The flask was put under an atmosphere of hydrogen and stirred for 15 h at RT. The reaction mixture was filtered over Celite and concentrated. The residue was purified by column chromatography (silica gel, PE/EtOAc 0 to 100%). Product 39 (426 mg, 90% yield) was obtained as a white solid.

Step 4. Preparation of N-(6-(Dimethylamino)-9-((2R,3R,4R,5R)-5-ethyl-3-fluoro-4-hydroxy-5-(hydroxymethyl) tetrahydrofuran-2-yl)-9H-purin-2-yl) isobutyramide (40)

To a solution of compound 39 (290 mg, 0.38 mmol) in dry THF (10 mL) was added tetrabutylammonium fluoride (1 N in THF) (1.2 mL, 1.2 mmol). The solution was stirred for 1 h at RT and concentrated. The residue was purified by column chromatography (silica gel, DCM/MeOH 0 to 10%). Product 40 (139 mg, 89% yield) was obtained as a white solid.

Step 5. Preparation of (2R,3R,4R,5R)-5-(2-Amino-6-(dimethylamino)-9H-purin-9-yl)-2-ethyl-4-fluoro-2-(hydroxymethyl)tetrahydrofuran-3-ol (Compound O)

A solution of compound 40 (135 mg, 0.33 mmol) in methylamine (33% in EtOH) (8 mL) in a sealed container was stirred for 15 h at 75° C. and concentrated. The residue was purified by column chromatography (silica gel, DCM/MeOH 0 to 15%). Compound 0 (107 mg, 96% yield) was obtained as a white solid. ¹H NMR (300 MHz, CD₃OD) δ 7.86 (s, 1H), 6.06 (dd, J=12.9, 6.3 Hz, 1H), 5.67 (dt, J=53.1, 5.4 Hz, 1H), 4.52 (t, J=9.9 Hz, 1H), 3.75 (d, J=12.3 Hz, 1H), 3.63 (d, J=12.3 Hz, 1H), 3.42 (s, 6H), 1.78 (q, J=7.5 Hz, 2H), 0.88 (t, J=7.5 Hz, 3H). MS (ESI) m/z calcd. for $C_{14}H_{22}FN_6O_3$ [M+H]⁺ 341.2; found 341.2.

Step 6. Preparation of (2S)-Isopropyl 2-(((((2R,3R,4R,5R)-5-(2-amino-6-(dimethylamino)-9H-purin-9-yl)-2-ethyl-4-fluoro-3-hydroxytetrahydrofuran-2-yl) methoxy)(phenoxy)-phosphoryl)amino) propanoate (Compound P)

To a solution of Compound O (40 mg, 0.12 mmol) in dry DMF (2.0 mL) was added tert-butylmagnesium chloride (0.7 N in THF) (225 μL, 0.16 mmol) drop-wise at -5° C. The solution was stirred for 15 mins at 0° C. and for 45 mins at RT. Then, the reaction mixture was cooled down to −10° C. and a solution of isopropyl ((R,S)-(pentafluorophenoxy)-phenoxy-phosphoryl)-L-alaninate (60 mg, 0.14 mmol) in dry DMF (1.0 mL) was added drop-wise. The resulting solution was slowly warmed up to 10° C. and stirred for 15 h at this temperature. The reaction mixture was then diluted with EtOAc (10 mL) and satd. NH$_4$Cl aq. solution (8 mL). The phases were separated and the aqueous layer was back-extracted with EtOAc (2×5 mL). The combined organics were washed with satd. NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound P (16 mg, 22%) was obtained as a white solid. $^1$H NMR (300 MHz, CD$_3$OD) δ 7.50, 7.49 (s+s, 1H), 7.33-7.15 (m, 5H), 5.98 (dd, J=18.3, 2.7 Hz, 0.7H), 5.94 (dd, J=18.6, 3.0 Hz, 0.3H), 5.67 (ddd, J=53.4, 3.0, 5.1 Hz, 0.3H), 5.55 (ddd, J=53.7, 2.7, 5.4 Hz, 0.7H), 5.23-5.14 (m, 1H), 5.04-4.95 (m, 4H), 4.70-4.61 (m, 1H), 4.15-3.92 (m, 2H), 3.68-3.61 (m, 1H), 3.42-3.33 (br s, 6H), 1.91-1.74 (m, 2H), 1.37-1.32 (m, 3H), 1.23-1.19 (m, 6H), 1.02-0.95 (m, 3H). $^{31}$P NMR (121 MHz, CDCl$_3$) δ 3.81,3.49 (s+s). MS (ESI) m/z calcd. for C$_{26}$H$_{38}$FN$_7$O$_7$P [M+H]$^+$ 610.3; found 610.2.

Scheme 9. Preparation of (2S)-Isopropyl 2-(((((2R,3R,4R,5R)-5-(2-amino-6-(methylamino)-9H-purin-9-yl)-2-ethyl-4-fluoro-3-hydroxytetrahydrofuran-2-yl)methoxy)(phenoxy)-phosphoryl)amino)propanoate (Compound R).

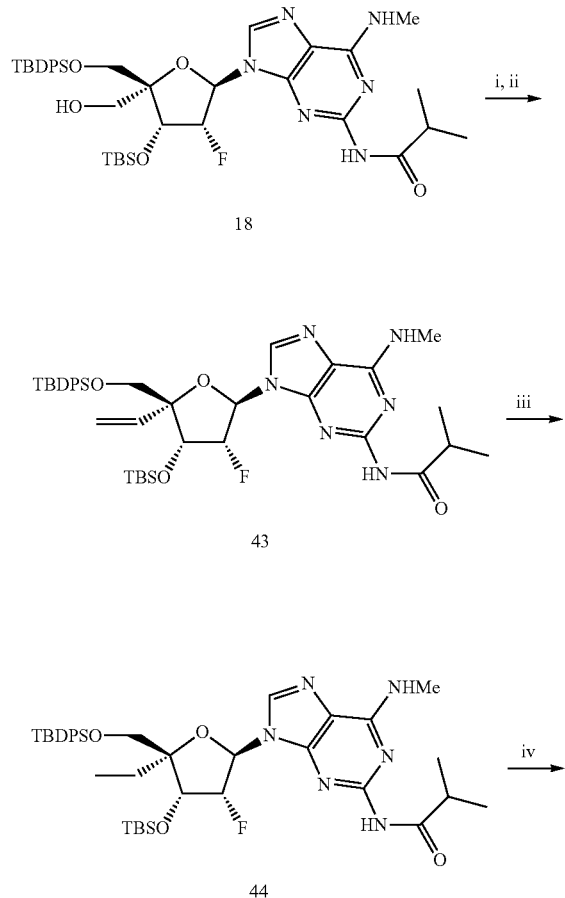

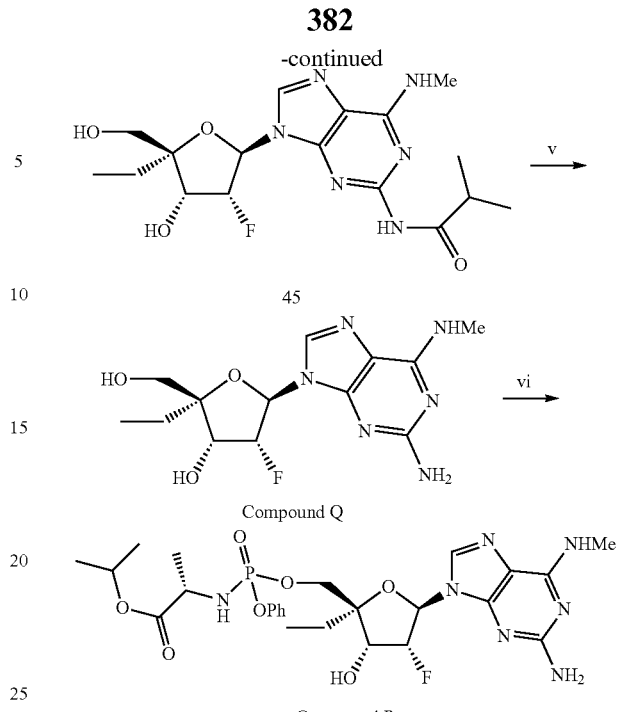

Compound Q

Compound R i) SO$_3$, pyridine, DIEA, DMSO, DCM, -10° C.; ii) PPh$_3$MeBr, BuLi, THF; iii) H$_2$, 10% Pd-C, EtOH; iv) TBAF, THF; v) MeNH$_2$, EtOH, 75° C.; vi) Isopropyl ((R, S)-(pentafluorophenoxy)-phenoxy-phosphoryl)-L-alaninate, t-BuMgCl, DMF, -10° C.

Step 1 and Step 2. Preparation of N-(9-((2R,3R,4R,5R)-4-((tert-Butyldimethylsilyl)oxy)-5-(((tert-butyl-diphenylsilyl)oxy) methyl)-3-fluoro-5-vinyltetrahydrofuran-2-yl)-6-(methylamino)-9H-purin-2-yl) isobutyramide (43)

To a solution of compound 18 (800 mg, 1.07 mmol) in dry DCM (10 mL) was added diisopropylethylamine (725 μL, 4.19 mmol) and a suspension of SO$_3$ pyridine complex (514 mg, 3.23 mmol) in dry DMSO (1.0 mL) drop-wise at -10° C. The orange solution was stirred for 30 mins at this temperature and for 5 h at RT. Then, H$_2$O (6 mL) was added, the phases were separated and the aqueous layer was back-extracted with EtOAc (2×10 mL). The combined organics were washed with brine (20 mL), dried over anhydrous Na$_2$SO$_4$ and concentrated. The aldehyde intermediate aldehyde was dissolved in dry THF (4 mL). Methyltriphenylphosphonium bromide (1.15 g, 3.23 mmol) was suspended in dry THF (12 mL) and butyllithium (1.6 N in hexanes) (2.02 mL, 3.23 mmol) was added drop-wise at 0° C. The resulting yellow solution was stirred for 1 h at this temperature. Then, the solution of aldehyde was added drop-wise at 0° C. and the mixture was stirred at RT for 15 h. Then, the solution was diluted with EtOAc (30 mL) and satd. NH$_4$Cl aq. solution (250 mL). The phases were separated and the aqueous layer was back-extracted with EtOAc (2×20 mL). The combined organics were washed with brine (30 mL), dried over Na$_2$SO$_4$ and concentrated. The residue was purified by column chromatography (silica gel, PE/EtOAc 0 to 100%). Product 43 (382 mg, 48%) was obtained as a yellow foam.

Step 3. Preparation of N-(9-((2R,3R,4R,5R)-4-((tert-Butyldimethylsilyl)oxy)-5-(((tert-butyldiphenylsilyl)oxy)methyl)-5-ethyl-3-fluorotetrahydrofuran-2-yl)-6-(methylamino)-9H-purin-2-yl) isobutyramide (44)

To a solution of compound 43 (370 mg, 0.50 mmol) in EtOH (8 mL) was added palladium (10% on charcoal) (105 mg). The flask was put under an atmosphere of hydrogen and stirred for 15 h at RT. The reaction mixture was filtered over Celite and concentrated. The residue was purified by column chromatography (silica gel, PE/EtOAc 0 to 100%). Product 44 (341 mg, 92% yield) was obtained as a white solid.

Step 4. Preparation of N-(6-(Methylamino)-9-((2R,3R,4R,5R)-5-ethyl-3-fluoro-4-hydroxy-5-(hydroxymethyl) tetrahydrofuran-2-yl)-9H-purin-2-yl) isobutyramide (45)

To a solution of compound 44 (330 mg, 0.44 mmol) in dry THF (12 mL) was added tetrabutylammonium fluoride (1 N in THF) (1.4 mL, 1.4 mmol). The solution was stirred for 1 h at RT and concentrated. The residue was purified by column chromatography (silica gel, DCM/MeOH 0 to 10%). Product 45 (157 mg, 90% yield) was obtained as a white solid.

Step 5. Preparation of (2R,3R,4R,5R)-5-(2-Amino-6-(methylamino)-9H-purin-9-yl)-2-ethyl-4-fluoro-2-(hydroxymethyl)tetrahydrofuran-3-ol (Compound Q)

A solution of compound 45 (155 mg, 0.39 mmol) in methylamine (33% in EtOH) (10 mL) in a sealed container was stirred for 15 h at 75° C. and concentrated. The residue was purified by column chromatography (silica gel, DCM/MeOH 0 to 15%). Compound Q (117 mg, 92% yield) was obtained as a white solid. $^1$H NMR (300 MHz, CD$_3$OD) δ 7.88 (s, 1H), 6.05 (dd, J=12.7, 6.3 Hz, 1H), 5.66 (ddd, J=53.3, 6.2, 5.3 Hz, 1H), 4.51 (t, J=4.9 Hz, 1H), 3.75 (d, J=12.2 Hz, 1H), 3.64 (d, J=12.2 Hz, 1H), 3.04 (br s, 3H), 1.78 (q, J=7.5 Hz, 2H), 0.98 (t, J=7.5 Hz). MS (ESI) m/z calcd. for C$_{13}$H$_{20}$FN$_6$O$_3$ [M+H]$^-$ 327.2; found 327.2.

Step 6. Preparation of (2S)-Isopropyl 2-(((((2R,3R,4R,5R)-5-(2-amino-6-(methylamino)-9H-purin-9-yl)-2-ethyl-4-fluoro-3-hydroxytetrahydrofuran-2-yl)methoxy)(phenoxy)-phosphoryl)amino) propanoate (Compound R)

To a solution of Compound Q (40 mg, 0.12 mmol) in dry DMF (2.0 mL) was added tert-butylmagnesium chloride (0.7 N in THF) (230 µL, 0.16 mmol) drop-wise at −5° C. The solution was stirred for 15 mins at 0° C. and for 45 mins at RT. Then, the reaction mixture was cooled down to −10° C. and a solution of isopropyl ((R,S)-(pentafluorophenoxy)-phenoxy-phosphoryl)-L-alaninate (62 mg, 0.14 mmol) in dry DMF (1.0 mL) was added drop-wise. The resulting solution was slowly warmed up to 10° C. and stirred for 15 h at this temperature. The reaction mixture was then diluted with EtOAc (10 mL) and satd. NH$_4$Cl aq. solution (8 mL). The phases were separated and the aqueous layer was back-extracted with EtOAc (2×5 mL). The combined organics were washed with satd. NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound R (12 mg, 17%) was obtained as a white solid. $^1$H NMR (300 MHz, CD$_3$OD) δ 7.86, 7.84 (s+s, 1H), 7.36-7.15 (m, 5H), 6.16-6.08 (m, 1H), 5.66, 5.61 (dt, J=53.1, 4.8 Hz overlapped with dt, J=53.4, 4.6 Hz, 1H), 5.00-4.90 (m, 1H), 4.68 (dd, J=11.9, 5.1 Hz, 1H), 4.45-4.37 (m, 1H), 4.22-4.12 (m, 1H), 3.94-3.80 (m, 1H), 3.03 (br s, 3H), 1.97-1.71 (m, 2H), 1.30-1.28 (m, 3H), 1.25-1.18 (m, 6H), 1.03-0.95 (m, 3H). $^{31}$P NMR (121 MHz, CD$_3$OD) δ 4.26 (s), 3.97 (s). MS (ESI) m/z calcd. for C$_{25}$H$_{36}$FN$_7$O$_7$P [M+H]$^+$ 596.2; found 596.2.

Scheme 10. Preparation of (2S)-Isopropyl 2-(((((2R,3R,4R,5R)-5-(2-amino-6-(dimethylamino)-9H-purin-9-yl)-4-fluoro-3-hydroxy-2-methyltetrahydrofuran-2-yl) methoxy)(phenoxy)phosphoryl)amino) propanoate (Compound T).

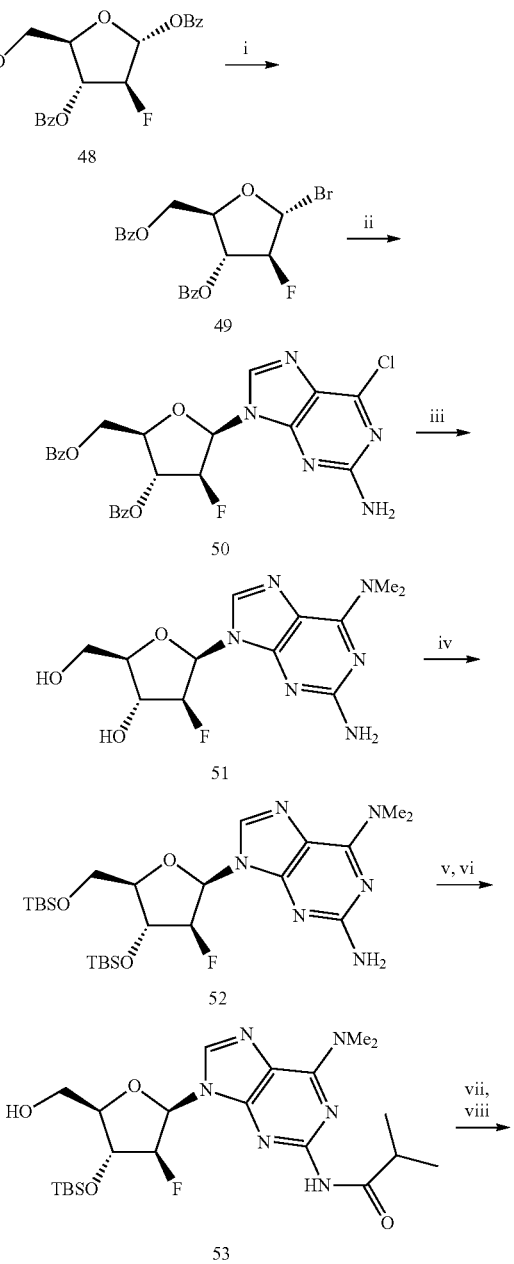

-continued

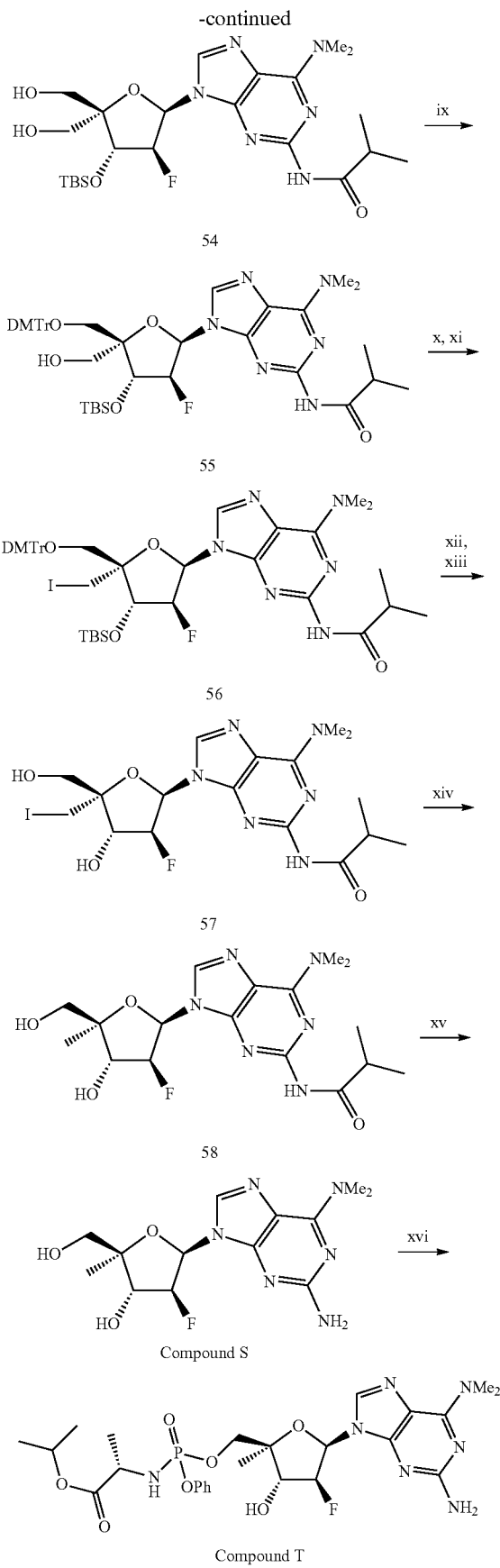

-continued i) HBr, AcOH, DCM, ii) 2-Amino-6-chloropurine, NaH, MeCN; iii) Me₂NH•HCl, Et₃N, EtOH, 85° C.; iv) TBSCl, imidazole, DMF; v) isobutyryl chloride, pyridine; vi) 90% TFA, DCM; vii) SO₃, pyridine, DIEA, DMSO, DCM; viii) formaldehyde, 2 N NaOH, dioxane then NaBH₄; ix) DMTrCl, Et₃N, DMF; x) Tf₂O, pyridine, DCM, 0° C.; xi) NaI, DMF, 60° C.; xii) 80% AcOH; xiii) TBAF, THF; xiv) H₂, 10% Pd-C, Et₃N, EtOH; xv) MeNH₂, EtOH, 75° C.; xvi) Isopropyl ((R,S)-(pentafluorophenoxy)-phenoxy-phosphoryl)-L-alaninate, t-BuMgCl, DMF, -10° C.

Step 1. Preparation of ((2R,3R,4S,5R)-3-(Benzoy-loxy)-5-bromo-4-fluorotetrahydrofuran-2-yl)methyl benzoate (49)

To a solution of compound 48 (5.0 g, 10.8 mmol) in dry DCM (110 mL) was added hydrogen bromide (33% in acetic acid) (10.7 mL, 60.0 mmol) drop-wise. The orange solution was stirred at RT for 15 h and then diluted with DCM (150 mL). The solution was carefully washed with satd. NaHCO₃ aq. solution (3×200 mL) and brine (200 mL). The organic phase was dried over anhydrous Na₂SO₄ and concentrated. The residue was co-evaporated with toluene (3×100 mL). Product 49 (4.5 g) was obtained as an orange oil and used as such in the next step.

Step 2. Preparation of (2R,3R,4S,5R)-5-(2-Amino-6-chloro-9H-purin-9-yl)-2-((benzoyloxy)methyl)-4-fluorotetrahydrofuran-3-yl benzoate (50)

To a suspension of 2-amino-6-chloropurine (2.2 g, 13.0 mmol) in dry acetonitrile (100 mL) was added sodium hydride (60% oil dispersion) (500 mg, 12.5 mmol). The resulting grey suspension was stirred at RT for 1 h. A solution of compound 49 (obtained in the previous step) in dry acetonitrile (100 mL) was added drop-wise over 10 mins. The reaction mixture was stirred at RT for 15 h, filtered over Celite and concentrated. The residue was purified by column chromatography (silica gel, PE/EtOAc 20 to 60%). Product 50 (3.4 g, 61% over 2 steps) was obtained as a white foam.

Step 3. Preparation of (2R,3R,4S,5R)-5-(2-Amino-6-(dimethylamino)-9H-purin-9-yl)-4-fluoro-2-(hydroxymethyl)tetrahydrofuran-3-ol (51)

To a solution of compound 50 (3.3 g, 6.4 mmol) in EtOH (50 mL) was added dimethylamine hydrochloride (2.6 g, 31.6 mmol) and triethylamine (4.4 mL, 31.6 mmol). The reaction mixture was heated at 85° C. in a sealed container for 3 h, cooled down RT and concentrated. The residue was purified by column chromatography (silica gel, DCM/MeOH 0 to 10%). Product 51 (1.9 g, 95%) was obtained as a white solid.

Step 4. Preparation of 9-((2R,3S,4R,5R)-4-((tert-Butyldimethylsilyl)oxy)-5-(((tert-butyldimethylsilyl)oxy)methyl)-3-fluorotetrahydrofuran-2-yl)-N⁶,N⁶-dimethyl-9H-purine-2,6-diamine (52)

To a solution of compound 51 (8.0 g, 25.6 mmol) in dry DMF (90 mL) was added imidazole (7.0 g, 102.7 mmol) and TBSCl (15.5 g, 102.7 mmol). The mixture was stirred at RT for 15 h and concentrated. EtOAc (250 mL) was added and the solution was washed with satd. NH₄Cl aq. solution (3×150 mL) and brine (150 mL). The organic phase was dried over anhydrous Na₂SO₄ and concentrated. The residue was purified by column chromatography (silica gel, PE/EtOAc 0 to 40%). Product 52 (12.1 g, 87% yield) was obtained as a yellow foam.

Step 5 and Step 6. Preparation of N-(9-((2R,3S,4R, 5R)-4-((tert-Butyldimethylsilyl)oxy)-3-fluoro-5-(hydroxymethyl) tetrahydrofuran-2-yl)-6-(dimethylamino)-9H-purin-2-yl)isobutyramide (53)

To a solution of compound 52 (12.0 g, 22.2 mmol) in dry pyridine (55 mL) was added isobutyryl chloride (2.75 mL, 26.6 mmol) drop-wise at 0° C. The reaction mixture was stirred at RT for 3 h and then concentrated. After co-evaporation with toluene (3×150 mL), the residue was dissolved in DCM (240 mL) and treated TFA/H$_2$O (9:1, 24 mL) at 0° C. for 15 h. Then, the reaction was quenched by addition of solid NaHCO$_3$ (45 g) and filtered. The solution was washed with satd. NaHCO$_3$ aq. solution (2×200 mL) and brine (200 mL). The organic phase was dried over anhydrous Na$_2$SO$_4$ and concentrated. The residue was purified by column chromatography (silica gel, PE/EtOAc 0 to 80%). Product 53 (7.9 g, 72% yield over 2 steps) was obtained as a white foam.

Step 7 and Step 8. Preparation of N-(9-((2R,3S, 4R)-4-((tert-Butyldimethylsilyl)oxy)-3-fluoro-5,5-bis(hydroxymethyl) tetrahydrofuran-2-yl)-6-(dimethylamino)-9H-purin-2-yl)isobutyramide (54)

To a solution of compound 53 (7.0 g, 14.1 mmol) in dry DCM (125 mL) was added diisopropylethylamine (9.5 mL, 54.9 mmol) and a suspension of SO$_3$ pyridine complex (6.7 g, 42.2 mmol) in dry DMSO (13.0 mL). The orange solution was stirred for 15 h at RT. Then, H$_2$O (140 mL) was added, the phases were separated and the aqueous layer was back-extracted with EtOAc (2×100 mL). The combined organics were washed with brine (200 mL), dried over anhydrous Na$_2$SO$_4$ and concentrated. The residue was dissolved in dioxane (90 mL). Formaldehyde (37% in H$_2$O) (4.6 mL, 59.1 mmol) and 2 N NaOH (10.6 mL, 21.1 mmol) were added and the yellow solution was stirred for 3 h at RT. The mixture was cooled down to 0° C. and sodium borohydride (2.13 g, 56.3 mmol) was added portion-wise. The cloudy solution was stirred for 1 h at RT and quenched by addition of satd. NH$_4$Cl aq. solution (350 mL). The product was extracted with EtOAc (3×300 mL). The combined organics were washed with brine (350 mL), dried over anhydrous Na$_2$SO$_4$ and concentrated. The residue was purified by column chromatography (silica gel, DCM/MeOH 0 to 10%). Product 54 (3.9 g, 53% yield over 2 steps) was obtained as a white solid.

Step 9. Preparation of N-(9-((2R,3S,4R,5R)-5-((Bis (4-methoxyphenyl)(phenyl)methoxy)methyl)-4-((tert-butyldimethylsilyl)oxy)-3-fluoro-5-(hydroxymethyl)tetrahydrofuran-2-yl)-6-(dimethylamino)-9H-purin-2-yl)isobutyramide (55)

To a solution of compound 54 (3.8 g, 7.2 mmol) in dry DMF (40 mL) was added triethylamine (2.0 mL, 14.5 mmol) and dimethoxytrityl chloride (3.4 g, 10.1 mmol). The resulting orange solution was stirred for 2 h at RT. The reaction was then diluted with EtOAc (150 mL) and H$_2$O (120 mL). The phases were separated and the aqueous layer was back-extracted with EtOAc (2×100 mL). The combined organics were washed with brine (150 mL), dried over anhydrous Na$_2$SO$_4$ and concentrated. The residue was purified by column chromatography (silica gel, PE/EtOAc 0 to 100%). Product 55 (2.1 g, 35% yield) was obtained as a yellow foam.

Step 10 and Step 11. Preparation of N-(9-((2R,3S, 4R,5R)-5-((Bis(4-methoxyphenyl)(phenyl)methoxy) methyl)-4-((tert-butyldimethylsilyl)oxy)-3-fluoro-5-(iodomethyl)tetrahydrofuran-2-yl)-6-(dimethylamino)-9H-purin-2-yl)isobutyramide (56)

To a solution of compound 55 (800 mg, 0.97 mmol) in dry DCM (20 mL) was added pyridine (395 µL, 4.85 mmol) and triflic anhydride (249 µL, 1.46 mmol) at 0° C. The resulting orange solution was stirred for 20 mins at 0° C. and H$_2$O (8 mL) was added. After a further 30 mins, the mixture was diluted with EtOAc (70 mL) and brine (60 mL). The layers were separated and the organics were dried over anhydrous Na$_2$SO$_4$ and concentrated. The residue was dissolved in dry DMF (35 mL) and NaI (1.15 g, 7.80 mmol) was added. The suspension was stirred for 15 h at 60° C. and concentrated. Then, EtOAc (100 mL) was added and the solution was washed with satd. NH$_4$Cl aq. solution (2×60 mL), Na$_2$S$_2$O$_3$ aq. solution (60 mL) and brine (60 mL). The organics were dried over anhydrous Na$_2$SO$_4$ and concentrated. The residue was purified by column chromatography (silica gel, PE/EtOAc 0 to 40%). Product 56 (525 mg, 58% yield over 2 steps) was obtained as an orange solid.

Step 12 and Step 13. Preparation of N-(6-(Dimethylamino)-9-((2R,3S,4R,5R)-3-fluoro-4-hydroxy-5-(hydroxymethyl)-5-(iodomethyl)tetrahydrofuran-2-yl)-9H-purin-2-yl)isobutyramide (57)

Compound 56 (500 mg, 0.53 mmol) was dissolved in 80% acetic acid (5 mL) and stirred for 15 h at RT. The solution was poured into satd. NaHCO$_3$ aq. solution (100 mL) and the mixture was extracted with EtOAc (3×60 mL). The combined organics were washed with brine (50 mL), dried over anhydrous Na$_2$SO$_4$ and concentrated. The residue was dissolved in dry THF (6 mL) and tetrabutylammonium fluoride (1 N in THF) (750 µL, 0.75 mmol) was added. The solution was stirred for 1 h at RT and concentrated. The residue was purified by column chromatography (silica gel, DCM/ MeOH 0 to 10%). Product 57 (228 mg, 82% yield over 2 steps) was obtained as a white solid.

Step 14. Preparation of N-(6-(Dimethylamino)-9-((2R,3S,4R,5R)-3-fluoro-4-hydroxy-5-(hydroxymethyl)-5-methyltetrahydrofuran-2-yl)-9H-purin-2-yl) isobutyramide (58)

To a solution of compound 57 (225 mg, 0.43 mmol) in EtOH (8 mL) was added triethylamine (313 µL, 2.16 mmol) and palladium (10% on charcoal) (25 mg). The flask was put under an atmosphere of hydrogen and stirred for 24 h at RT. The reaction mixture was filtered over Celite and concentrated. The residue was purified by column chromatography (silica gel, DCM/MeOH 0 to 10%). Product 58 (162 mg, 95% yield) was obtained as a white solid.

Step 15. Preparation of (2R,3R,4S,5R)-5-(2-Amino-6-(dimethylamino)-9H-purin-9-yl)-4-fluoro-2-(hydroxymethyl)-2-methyltetrahydrofuran-3-ol (Compound T)

A solution of compound 58 (160 mg, 0.40 mmol) in methylamine (33% in EtOH) (8 mL) in a sealed container was stirred for 15 h at 75° C. and concentrated. The residue was purified by column chromatography (silica gel, DCM/MeOH 0 to 15%). Compound T (126 mg, 96% yield) was obtained as a white solid. $^1$H NMR (300 MHz, CD$_3$OD) δ 7.91 (d, J=1.8 Hz 1H), 6.31 (dd, J=12.8, 5.0 Hz, 1H), 5.17 (ddd, J=53.4, 4.8, 4.7 Hz, 1H), 4.60 (dd, J=20.1, 5.1 Hz, 1H), 3.64-3.60 (m, 2H), 3.40 (br s, 6H), 1.26 (s, 3H). MS (ESI) m/z calcd. for C$_{13}$H$_{20}$FN$_6$O$_3$ [M+H]$^-$ 327.2; found 327.2.

Step 16. Preparation of (2S)-Isopropyl 2-(((((2R,3R,4S,5R)-5-(2-amino-6-(dimethylamino)-9H-purin-9-yl)-4-fluoro-3-hydroxy-2-methyltetrahydrofuran-2-yl)methoxy)(phenoxy)phosphoryl)-amino)propanoate (Compound S)

To a solution of Compound T (40 mg, 0.12 mmol) in dry DMF (1.5 mL) was added tert-butylmagnesium chloride (0.7 N in THF) (230 μL, 0.16 mmol) drop-wise at −5° C. The solution was stirred for 15 mins at 0° C. and for 45 mins at RT. Then, the reaction mixture was cooled down to −10° C. and a solution of isopropyl ((R,S)-(pentafluorophenoxy)-phenoxy-phosphoryl)-L-alaninate (63 mg, 0.14 mmol) in dry DMF (1 mL) was added drop-wise. The resulting solution was slowly warmed up to 10° C. and stirred for 15 h at this temperature. The reaction mixture was then diluted with EtOAc (10 mL) and satd. NH$_4$Cl aq. solution (8 mL). The phases were separated and the aqueous layer was back-extracted with EtOAc (2×5 mL). The combined organics were washed with satd. NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound S (13 mg, 18%) was obtained as a white solid. $^1$H NMR (300 MHz, CD$_3$OD) δ 7.91 (d, J=1.8 Hz 1H), 6.31 (dd, J=12.8, 5.0 Hz, 1H), 5.17 (ddd, J=53.4, 4.8, 4.7 Hz, 1H), 4.60 (dd, J=20.1, 5.1 Hz, 1H), 3.64-3.60 (m, 2H), 3.40 (br s, 6H), 1.26 (s, 3H). $^{31}$P NMR (121 MHz, CDCl$_3$) δ 3.48 (s), 3.06 (s). MS (ESI) m/z calcd. for C$_{25}$H$_{36}$FN$_7$O$_7$P [M+H]$^+$ 596.2; found 596.2.

Scheme 11. Preparation of (2S)-Isopropyl 2-(((((2R,3R,4R,5R)-5-(2-amino-6-(dimethylamino)-9H-purin-9-yl)-2-ethyl-4-fluoro-3-hydroxytetrahydrofuran-2-yl)methoxy)(phenoxy)phosphoryl)amino)propanoate (Compound V).

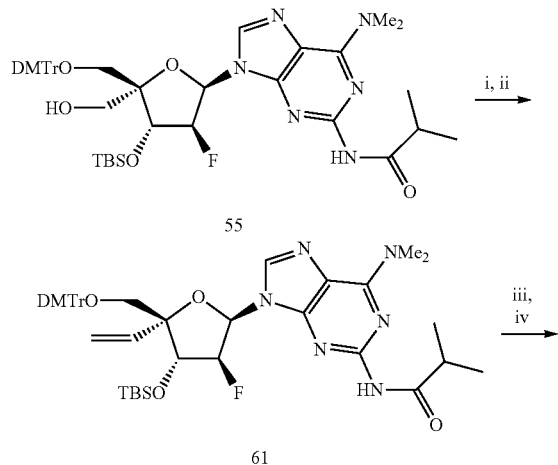

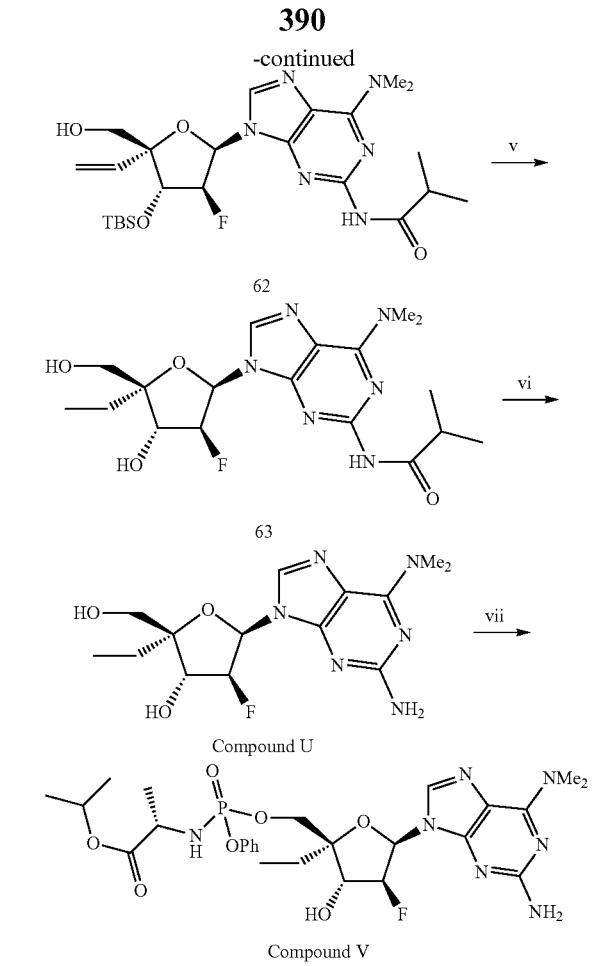

i) SO$_3$, pyridine, DIEA, DMSO, DCM, -10° C.; ii) PPh$_3$MeBr, BuLi, THF; iii) 80% AcOH; iv) TBAF, THF; v) H$_2$, 10% Pd-C, EtOH; vi) MeNH$_2$, 75° C.; vii) Isopropyl ((R,S)-(pentafluorophenoxy)-phenoxy-phosphoryl)-L-alaninate, t-BuMgCl, DMF, -10° C.

Step 1 and Step 2. Preparation of N-(9-((2R,3S,4R,5R)-5-((Bis(4-methoxyphenyl)(phenyl)methoxy)methyl)-4-((tert-butyldimethylsilyl)oxy)-3-fluoro-5-vinyltetrahydrofuran-2-yl)-6-(dimethylamino)-9H-purin-2-yl)isobutyramide (61)

To a solution of compound 55 (900 mg, 1.10 mmol) in dry DCM (10 mL) was added diisopropylethylamine (745 μL, 4.32 mmol) and a suspension of SO$_3$ pyridine complex (529 mg, 3.33 mmol) in dry DMSO (1.0 mL) drop-wise at -10° C. The orange solution was stirred for 30 mins at this temperature and for 5 h at RT. Then, H$_2$O (6 mL) was added, the phases were separated and the aqueous layer was back-extracted with EtOAc (2×10 mL). The combined organics were washed with brine (20 mL), dried over anhydrous Na$_2$SO$_4$ and concentrated. The aldehyde intermediate aldehyde was dissolved in dry THF (4 mL). Methyltriphenylphosphonium bromide (1.18 g, 3.33 mmol) was suspended in dry THF (12 mL) and butyllithium (1.6 N in hexanes) (2.08 mL, 3.33 mmol) was added drop-wise at 0° C. The resulting yellow solution was stirred for 1 h at this temperature. Then, the solution of aldehyde was added drop-wise at 0° C. and the mixture was stirred at RT for 15 h. Then, the solution was diluted with EtOAc (30 mL) and satd. NH$_4$Cl aq. solution (250 mL). The phases were separated and the aqueous layer was back-extracted with EtOAc (2×20 mL).

The combined organics were washed with brine (30 mL), dried over Na$_2$SO$_4$ and concentrated. The residue was purified by column chromatography (silica gel, PE/EtOAc 0 to 100%). Product 61 (394 mg, 44%) was obtained as a yellow foam.

Step 3 and Step 4. Preparation of N-(6-(Dimethylamino)-9-((2R,3S,4R,5R)-3-fluoro-4-hydroxy-5-(hydroxymethyl)-5-vinyltetrahydrofuran-2-yl)-9H-purin-2-yl)isobutyramide (62)

Compound 61 (390 500 mg, 0.47 0.53 mmol) was dissolved in 80% acetic acid (5 mL) and stirred for 15 h at RT. The solution was poured into satd. NaHCO$_3$ aq. solution (100 mL) and the mixture was extracted with EtOAc (3×60 mL). The combined organics were washed with brine (50 mL), dried over anhydrous Na$_2$SO$_4$ and concentrated. The residue was dissolved in dry THF (6 mL) and tetrabutylammonium fluoride (1 N in THF) (700 µL, 0.70 mmol) was added. The solution was stirred for 1 h at RT and concentrated. The residue was purified by column chromatography (silica gel, DCM/MeOH 0 to 10%). Product 62 (151 mg, 78% yield over 2 steps) was obtained as a white solid.

Step 5. Preparation of N-(6-(Dimethylamino)-9-((2R,3S,4R,5R)-5-ethyl-3-fluoro-4-hydroxy-5-(hydroxymethyl) tetrahydrofuran-2-yl)-9H-purin-2-yl)isobutyramide (63)

To a solution of compound 62 (148 mg, 0.36 mmol) in EtOH (6 mL) was added palladium (10% on charcoal) (80 mg). The flask was put under an atmosphere of hydrogen and stirred for 15 h at RT. The reaction mixture was filtered over Celite and concentrated. The residue was purified by column chromatography (silica gel, DCM/MeOH 0 to 10%). Product 63 (141 mg, 95% yield) was obtained as a white solid.

Step 6. Preparation of (2R,3R,4S,5R)-5-(2-Amino-6-(dimethylamino)-9H-purin-9-yl)-2-ethyl-4-fluoro-2-(hydroxymethyl)tetrahydrofuran-3-ol (Compound U)

A solution of compound 63 (138 mg, 0.34 mmol) in methylamine (33% in EtOH) (10 mL) in a sealed container was stirred for 15 h at 75° C. and concentrated. The residue was purified by column chromatography (silica gel, DCM/MeOH 0 to 15%). Compound U (103 mg, 90% yield) was obtained as a white solid. $^1$H NMR (300 MHz, CD$_3$OD) δ 7.92 (d, J=1.8 Hz, 1H), 6.31 (dd, J=12.8, 5.0 Hz, 1H), 5.17 (ddd, J=53.4, 4.8, 4.7 Hz, 1H), 4.68 (dd, J=20.1, 5.1 Hz, 1H), 3.75-3.60 (m, 2H), 3.41 (br s, 6H), 1.82-1.62 (m, 2H), 1.00 (t, J=7.5 Hz, 3H). MS (ESI) m/z calcd. for C$_{14}$H$_{22}$FN$_6$O$_3$ [M+H]$^+$ 341.2; found 341.2.

Step 7. Preparation of (2S)-Isopropyl 2-(((((2R,3R,4S,5R)-5-(2-amino-6-(dimethylamino)-9H-purin-9-yl)-2-ethyl-4-fluoro-3-hydroxytetrahydrofuran-2-yl)methoxy)(phenoxy)phosphoryl)-amino) propanoate (Compound V)

To a solution of Compound U (40 mg, 0.12 mmol) in dry DMF (2.0 mL) was added tert-butylmagnesium chloride (0.7 N in THF) (227 µL, 0.16 mmol) drop-wise at −5° C. The solution was stirred for 15 mins at 0° C. and for 45 mins at RT. Then, the reaction mixture was cooled down to −10° C. and a solution of isopropyl ((R,S)-(pentafluorophenoxy)-phenoxy-phosphoryl)-L-alaninate (60 mg, 0.14 mmol) in dry DMF (1.0 mL) was added drop-wise. The resulting solution was slowly warmed up to 10° C. and stirred for 15 h at this temperature. The reaction mixture was then diluted with EtOAc (10 mL) and satd. NH$_4$Cl aq. solution (8 mL). The phases were separated and the aqueous layer was back-extracted with EtOAc (2×5 mL). The combined organics were washed with satd. NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound V (11 mg, 15%) was obtained as a white solid. $^1$H NMR (300 MHz, CD$_3$OD) δ 7.80 (m, 1H), 7.30-7.11 (m, 5H), 6.40-6.30 (m, 1H), 5.25-4.90 (m, 2H), 4.65-4.52 (m, 1H), 4.33-4.18 (m, 2H), 3.95-3.81 (m, 1H), 3.42 (br s, 6H), 1.82-1.62 (m, 2H), 1.35-1.18 (m, 9H), 1.00 (m, 3H). $^{31}$P NMR (121 MHz, CD$_3$OD) δ 2.32 (s), 2.22 (s). MS (ESI) m/z calcd. for C$_{26}$H$_{38}$FN$_7$O$_7$P [M+H]$^+$ 610.3; found 610.2.

Scheme 12. Preparation of (2R,3R,4R,5R)-5-(2-Amino-6-(methylamino)-9H-purin-9-yl)-4-fluoro-2-(hydroxymethyl)-2-methyltetrahydrofuran-3-ol (Compound C)

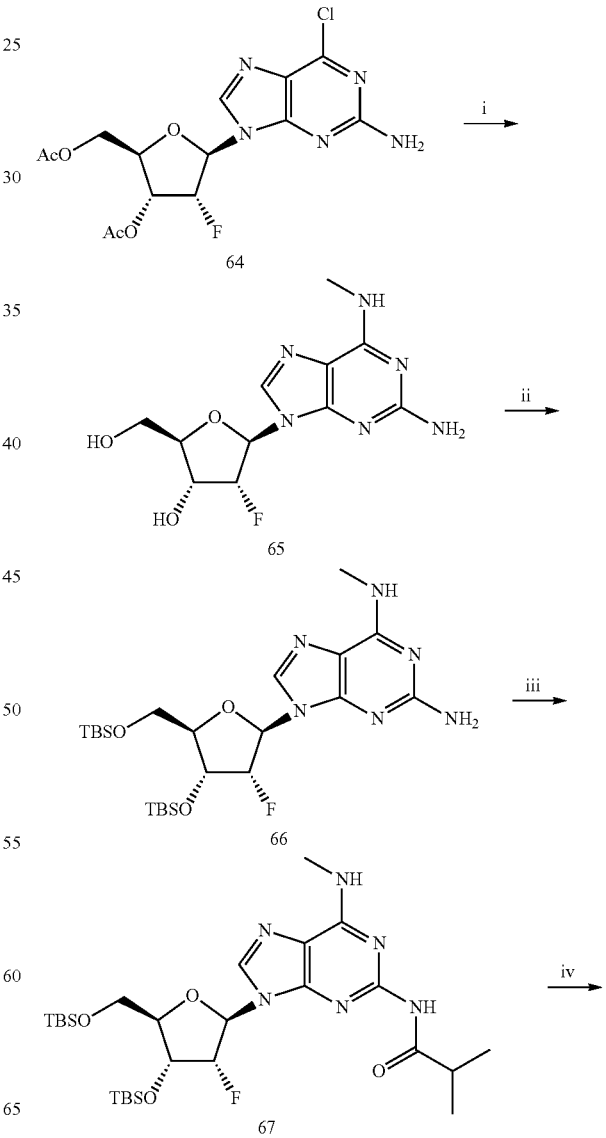

393
-continued
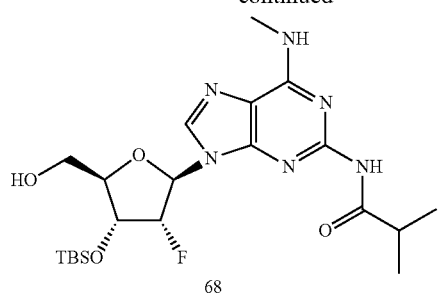
68
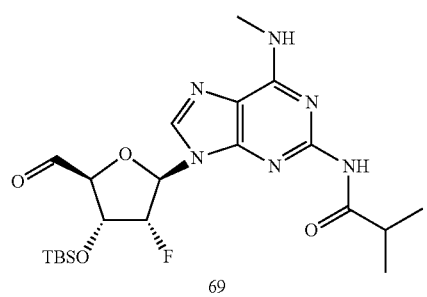
69
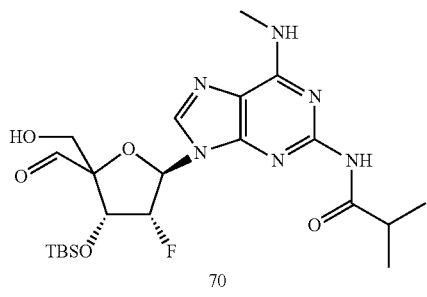
70
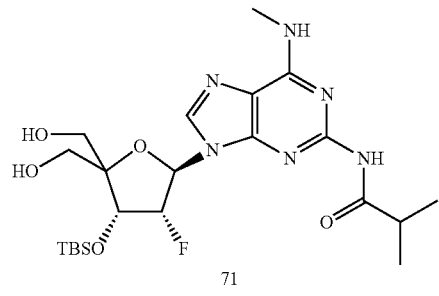
71
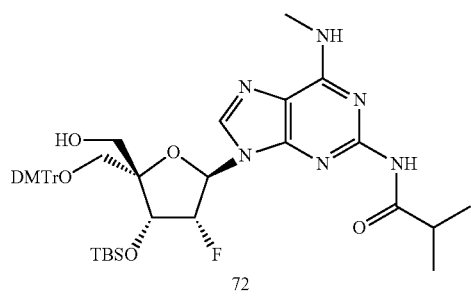
72
394
-continued
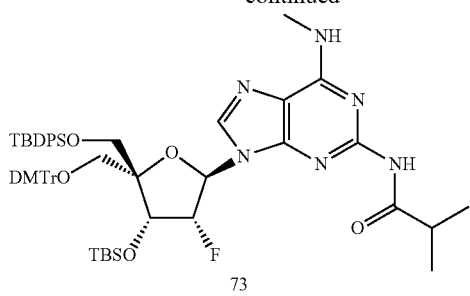
73
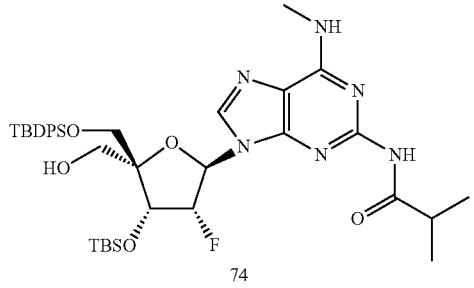
74
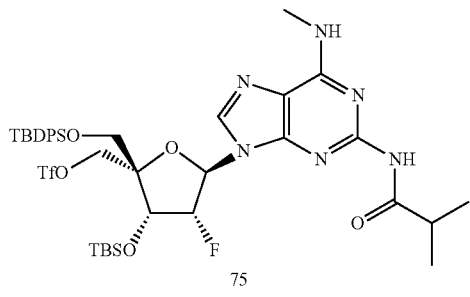
75
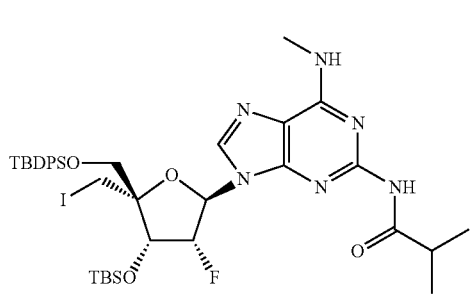
76
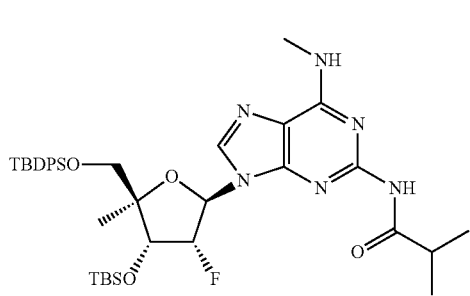
77

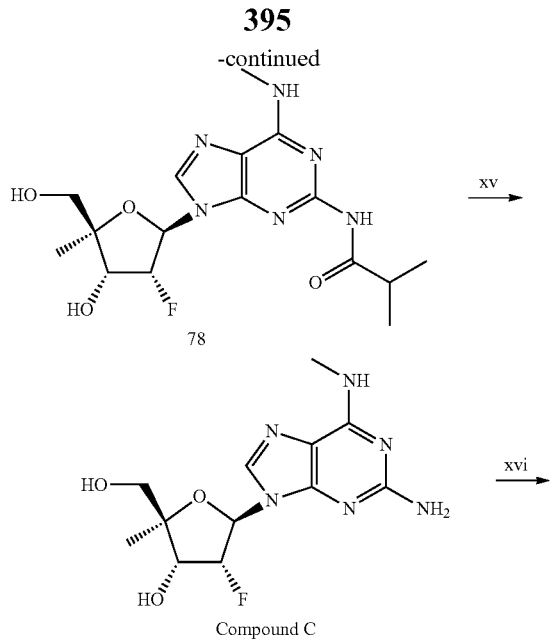

78

Compound C

Step 1. Preparation of (2R,3R,4R,5R)-5-(2-Amino-6-(methylamino)-9H-purin-9-yl)-4-fluoro-2-(hydroxymethyl)tetrahydrofuran-3-ol (65)

A solution of compound 64 (38 g, 98 mmol) in methylamine (25% in MeOH) (380 mL) was heated at 25° C. for 2 h and concentrated to afford crude compound 65 (37 g). $^1$HNMR (400 MHz, DMSO) δ 7.91 (s, 1H), 7.26 (s, 1H), 6.05-6.01 (dd, 1H), 5.65-5.64 (d, 1H), 5.37-5.21 (m, 2H), 4.40-4.36 (m, 1H), 3.92 (s, 1H), 3.72-3.69 (d, 1H), 3.57-3.54 (d, 1H), 2.87 (s, 2H), 2.33 (s,3H). ESIMS m/z 299.5 ([M+H]$^+$)

Step 2. Preparation of 9-((2R,3R,4R,5R)-4-((tert-Butyldimethylsilyl)oxy)-5-(((tert-butyldimethylsilyl)oxy)methyl)-3-fluorotetrahydrofuran-2-yl)-N$^6$-methyl-9H-purine-2,6-diamine (66)

To a solution of compound 65 (98 mmol) in dry DMF (200 mL) was added imidazole (15.6 g, 2.5 eq) and TBSCl (30.6 g, 2.5 eq). The mixture was stirred at RT for 16 h. H$_2$O (800 mL) was added and extracted with EtOAc (200 mL×3). The combined organic layers was washed with brine (100 mL), dried over anhydrous Na$_2$SO$_4$ and concentrated. The residue was purified by column chromatography (silica gel, CH$_2$Cl$_2$/MeOH=50:1) to afford compound 66 (36 g, 69% yield for two steps) as a yellow oil. $^1$HNMR (400 MHz, CDCl$_3$) δ 7.73 (s, 1H), 6.11-6.06 (dd, 1H), 5.55 (s, 1H), 5.34-5.20 (m, 1H), 4.69-4.61 (m, 3 H), 4.08-4.07 (d, 1H), 4.01-3.97 (dd, 1H), 3.79-3.76 (dd,1H), 3.11-3.10 (d, 2H), 0.93-0.89 (d, 13H), 0.14-0.13 (d, 9H), 0.07-0.01 (m, 9H). ESIMS m/z 527.9 ([M+H]$^+$)

Step 3. Preparation of N-(9-((2R,3R,4R,5R)-4-((tert-Butyldimethylsilyl)oxy)-5-(((tert-butyldimethylsilyl)oxy)methyl)-3-fluorotetrahydrofuran-2-yl)-6-(methylamino)-9H-purin-2-yl)isobutyramide (67)

To a solution of compound 66 (36 g, 68 mmol) in pyridine (150 mL) was added isobutyryl chloride (10.8 g, 1.5 eq) dropwise at 0° C. The reaction mixture was stirred at RT for 3 h and then concentrated. The residue was dissolved in EtOAc (400 mL). The reaction was washed with sat. NaHCO$_3$ (400 mL), dried over anhydrous Na$_2$SO$_4$ and concentrated to afford crude compound 67 that was used directly in the next step. ESIMS m/z 597.9([M+H]$^+$)

Step 4. Preparation of N-(9-((2R,3R,4R,5R)-4-((tert-Butyldimethylsilyl)oxy)-3-fluoro-5-(hydroxymethyl)tetrahydrofuran-2-yl)-6-(methylamino)-9H-purin-2-yl)isobutyramide (68)

Crude compound 67 (68 mmol) was dissolved in CH$_2$Cl$_2$ (830 mL) and treated with TFA/H$_2$O (9:1, 68 mL/8 mL) at 0° C. for 15 h. The reaction was quenched by addition of solid NaHCO$_3$ (20 g) and filtered. The solution was washed with sat. NaHCO$_3$ aq. solution (2×200 mL) and brine (100 mL). The organic phase was dried over anhydrous Na$_2$SO$_4$ and concentrated. The residue was purified by column chromatography (silica gel, CH$_2$Cl$_2$/MeOH=50:1). Compound 68 (27 g, 82% yield over 2 steps) was obtained. $^1$H NMR (400 MHz, CDCl$_3$) δ 7.79 (s, 1H), 7.69 (s, 1H), 6.36 (s, 1H), 6.01-5.96 (dd, 1H), 5.67-5.5.64 (t, 1H), 5.54-5.51 (t, 1H), 4.77-4.76 (t, 1H), 4.18 (s, 1H), 3.96-3.93 (d, 1H), 3.76-3.70 (t,1H), 3.11-3.02 (d, 4H), 1.29-1.24 (m, 6H), 0.93-0.87 (m, 6H), 0.14-0.02 (m, 9H). ESIMS m/z 483.6 ([M+H]$^+$), 505.4 ([M+Na]$^-$)

Step 5, Step 6, and Step 7. Preparation of N-(9-((2R,3R,4R)-4-((tert-Butyldimethylsilyl)oxy)-3-fluoro-5,5-bis(hydroxymethyl)tetrahydrofuran-2-yl)-6-(methylamino)-9H-purin-2-yl)isobutyramide (71)

A mixture of compound 68 (27 g, 1 eq), IBX (18.8 g, 1.2 eq) and CH$_3$CN (750 mL) was refluxed for 3 h. The reaction was cooled to RT and filtered. The filtrate was concentrated. Then, 1, 4-dioxane (400 mL) 37% HCHO (17 mL) aqueous solution and 2 M aq. NaOH (43 mL) solution was added, the reaction was stirred for 16 h. NaBH$_4$ (8.5 g, 4 eq) was added and stirred for 30 min. H$_2$O (200 mL) was added and the aqueous layer was extracted with EtOAc (200 mL×2). The combined organics were washed with brine (200 mL), dried over anhydrous Na$_2$SO$_4$ and concentrated. The residue was purified by column chromatography (silica gel, CH$_2$Cl$_2$/MeOH=50:1). Compound 71 (15 g, 46%) was obtained as a white solid. $^1$H NMR (400 MHz, CDCl$_3$) δ 7.70-7.69 (d,2H), 6.07-6.02 (dd, 1H), 5.82 (s, 1H), 5.75-5.59 (tt, 1H), 5.20 (s, 1H), 5.10-5.07 (t, 1H), 3.91-3.80 (m, 2H), 3.70-3.61 (m, 2H), 3.13 (s,3H), 2.56-2.54 (d, 1H), 1.28-1.24 (m, 6H), 0.96-0.94 (d, 9H), 0.21-0.16 (t, 6H). ESIMS m/z 514.0 ([M+H]$^+$), 535.8 ([M+Na]$^+$).

Step 8. Preparation of N-(9-((2R,3R,4R,5S)-5-((Bis(4-methoxyphenyl)(phenyl)methoxy)methyl)-4-((tert-butyldimethylsilyl)oxy)-3-fluoro-5-(hydroxymethyl)tetrahydrofuran-2-yl)-6-(methylamino)-9H-purin-2-yl)isobutyramide (72)

To a solution of compound 71 (16 g, 1 eq) in CH$_2$Cl$_2$ (640 mL) was added triethylamine (6.9 g, 2 eq) and DMTrCl (14.8 g, 1.4 eq) in one portion at 0° C. The mixture was stirred for 2 h at RT. The reaction was then washed with sat. NaHCO$_3$ aq (200 mL) and brine (100 mL), dried over anhydrous Na$_2$SO$_4$ and concentrated. The residue was purified by column chromatography (silica gel, CH$_2$Cl$_2$/MeOH=70:1) to afford compound 72 (15 g, 63% yield). ESIMS m/z 837.9 ([M+Na]$^+$)

Step 9. Preparation of N-(9-((2R,3R,4R,5R)-5-((Bis (4-methoxyphenyl)(phenyl)methoxy)methyl)-4-((tert-butyldimethylsilyl)oxy)-5-(((tert-butyldiphenylsilyl)oxy)methyl)-3-fluorotetrahydrofuran-2-yl)-6-(methylamino)-9H-purin-2-yl)isobutyramide (73)

To a solution of compound 72 (15 g, 1 eq) in DMF (150 mL) was added imidazole (17.6 g, 15 eq) and TBDPSCl (29.4 g, 6 eq). The resulting solution was stirred for 1 h at 0° C. Then, H$_2$O (800 mL) was added and the suspension was extracted with EtOAc (200 mL×2). The organic layers were washed brine (200 mL), dried over anhydrous Na$_2$SO$_4$ and concentrated. The residue was purified by column chromatography (silica gel, CH$_2$Cl$_2$/MeOH=70:1) to compound 73 (15.5 g, 79% yield) as a white solid.

Step 10. Preparation of N-(9-((2R,3R,4R,5R)-4-((tert-Butyldimethylsilyl)oxy)-5-(((tert-butyldiphenylsilyl)oxy)methyl)-3-fluoro-5-(hydroxymethyl) tetrahydrofuran-2-yl)-6-(methylamino)-9H-purin-2-yl)isobutyramide (74)

A solution of compound 73 (15.5 g, 1 eq) in 80% CH$_3$COOH as stirred for 16 h. H$_2$O (60 mL) was added and the mixture was extracted with EtOAc (200 mL×3). The organic layers were washed brine (200 mL), dried over anhydrous Na$_2$SO$_4$ and concentrated. The residue was purified by column chromatography (silica gel, CH$_2$Cl$_2$/MeOH=501) to afford compound 74 (8.4 g, 76%). $^1$HNMR (400 MHz, CDCl$_3$) δ 7.76 (s,1H), 7.60-7.52 (m, 5H), 7.40-7.17 (m, 6H), 6.23-6.18 (dd, 2H), 5.55-5.39 (m, 1H), 5.14-5.11 (dd, 1H), 3.97-3.80 (m, 4H), 3.13 (s, 4H), 1.26-1.10 (m, 6H), 1.04-0.93 (m, 18H), 0.15-0.14 (d, 6H). ESIMS m/z 751.7 ([M+H]$^+$), 773.9 ([M+Na]$^+$)

Step 11 and Step 12. Preparation of N-(9-((2R,3R,4R,5R)-4-((tert-Butyldimethylsilyl)oxy)-5-(((tert-butyldiphenylsilyl)oxy)methyl)-3-fluoro-5-(iodomethyl)tetrahydrofuran-2-yl)-6-(methylamino)-9H-purin-2-yl)isobutyramide (76)

To a solution of compound 74 (8.4 g, 1 eq) in dry CH$_2$Cl$_2$ (170 mL) was added pyridine (4.4 g, 5 eq) and Tf$_2$O (4.8 g, 1.5 eq) at 0° C. The resulting orange solution was stirred for 15 mins at RT and H$_2$O (20 mL) was added. After am additional 10 mins, the layer were separated, dried over anhydrous Na$_2$SO$_4$ and concentrated. The residue was dissolved in dry DMF (170 mL) and NaI (13.4 g, 8 eq) was added. The suspension was stirred for 16 h at RT. Sat. NH$_4$Cl aq. solution (70 mL) was added and extracted with EtOAc (50 mL×3). The organics were dried over anhydrous Na$_2$SO$_4$ and concentrated. Crude compound 76 (10 g) was obtained as an orange solid. ESIMS m/z 861.2 ([M+H]$^+$), 883.2 ([M+Na]$^+$)

Step 13. Preparation of N-(9-((2R,3R,4R,5R)-4-((tert-Butyldimethylsilyl)oxy)-5-(((tert-butyldiphenylsilyl)oxy)methyl)-3-fluoro-5-methyltetrahydrofuran-2-yl)-6-(methylamino)-9H-purin-2-yl) isobutyramide (77)

To a solution of crude compound 76 (10 g) in EtOH (500 mL) was added Et3N (10 mL, 5 eq) and Pd/C (10%, 5 g). The flask was put under an atmosphere of hydrogen and stirred for 16 h at RT. The reaction mixture was filtered over celite and concentrated to afford crude compound 77 (8 g). ESIMS m/z 733.5 ([M–H]$^-$).

Step 14. Preparation of N-(9-((2R,3R,4R,5R)-3-Fluoro-4-hydroxy-5-(hydroxymethyl)-5-methyltetrahydrofuran-2-yl)-6-(methylamino)-9H-purin-2-yl) isobutyramide (78)

To a solution of crude compound 77 (8 g) in THF (120 mL) was added TBFA 3H$_2$O (10 g, 3 eq). The solution was stirred for 2 h at 0° C. H$_2$O (50 mL) was added and extracted with Me-THF (150 mL×3). The organic layers were dried over anhydrous Na$_2$SO$_4$ and concentrated. The residue was purified by column chromatography (silica gel, CH$_2$Cl$_2$/MeOH=80:1) to afford compound 78 (3.9 g). ESIMS m/z 383.2 ([M+H]$^+$), 405.2 ([M+Na]$^+$)

Step 15. Preparation of (2R,3R,4R,5R)-5-(2-Amino-6-(methylamino)-9H-purin-9-yl)-4-fluoro-2-(hydroxymethyl)-2-methyltetrahydrofuran-3-ol (Compound C)

A solution of compound 78 (3.9 g) in methylamine (35% in EtOH) (300 mL) in a sealed container was stirred for 16 h at 85° C. and concentrated. The residue was purified by column chromatography (silica gel, CH$_2$Cl$_2$/MeOH=30:1). Compound C (1.74 g, 55% over five steps) was obtained as a white solid. $^1$H NMR (400 MHz, CDCl$_3$) δ 7.89 (s, 1H), 6.12-6.07 (dd, 1H), 5.64-5.51 (m, 1H), 4.53-4.50 (dd, 1H), 3.69-3.54 (dd, 2H), 3.04 (s, 3H), 1.26 (s, 3H).

Scheme 13. Preparation of Isopropyl ((S)-(((2R,3R,4R,5R)-5-2-amino-6-(methylamino)-9H-purin-9-yl)-4-fluoro-3-hydroxy-2-methyltetrahydrofuran-2-yl)methoxy)(phenoxy)phosphoryl)-L-alaninate (Compound AB)

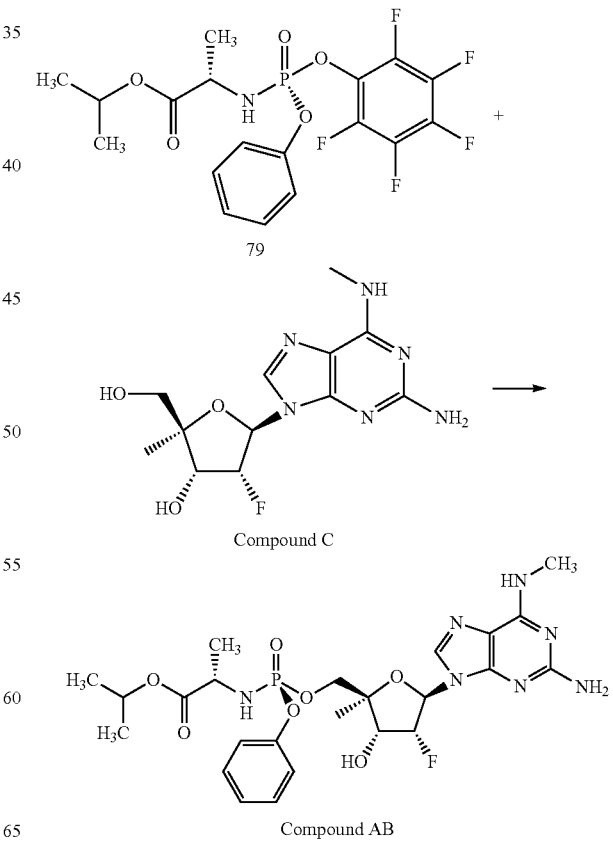

To a mixture of Compound C (1.7 g, 1.0 eq), compound 79 (1.0 eq) and dry THF (17 mL) was added t-BuMgCl (2.1 eq) at 0° C. The reaction was stirred at 0° C. for 1 h. The mixture was then quenched with NH₄Cl aq. solution (20 mL) and extracted with EtOAc (30 mL×3). The organic layers were dried over anhydrous Na₂SO₄ and concentrated. The residue was purified by column chromatography (silica gel, CH₂Cl₂/MeOH=50:1-40:1) to afford Compound AB (1.14 g, 36%) as a white solid. 1H NMR (400 MHz, CD₃OD) δ 7.83 (S, 1H), 7.33-7.15 (m, 5H), 6.16-6.11 (dd, 1H), 5.63-5.48 (m, 1H), 4.94-4.87 (m, 1H), 4.74-4.68 (dd, 1H), 4.31-4.27 (dd, 1H), 4.11-4.07 (dd, 1H), 3.90-3.83 (m, 1H), 3.02 (s, 3H), 1.34 (s, 3H), 1.28-1.26 (d, 3H), 1.18-1.17 (dd, 6H). FNMR (376 MHz, CD₃OD): 202.7-202.9 (m). PNMR (100 MHz, CD₃OD): 3.59 (s). ESIMS m/z 582.7 ([M+H]⁻)

Scheme 14. Preparation of (S)-Isopropyl 2-((S)-(((2R,3R,4R,5R)-5-(2-amino-6-(methylamino)-9H-purin-9-yl)-4-fluoro-3-hydroxy-2-methyltetrahydrofuran-2-yl)methoxy)(phenoxy)phosphorylamino)propanoate sulfate(Compound AC)

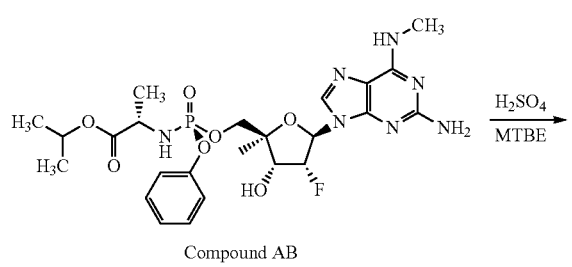

Compound AB

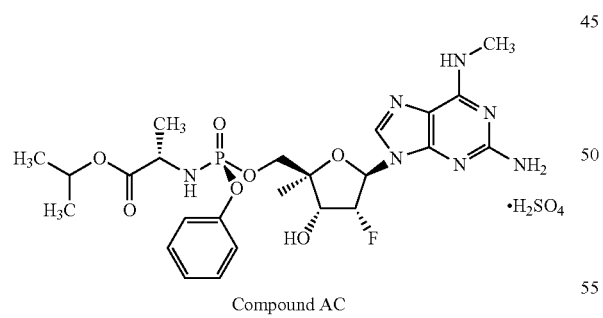

Compound AC

To the solution of Compound AB (53 mg) in MTBE (3.5 mL) was gradually added H₂SO₄ (5.4 mL) solution in MTBE (1.4 mL). After stirring overnight at RT, the mixture was filtrated to afford Compound AC as a white solid (45 mg, 97%). 1H NMR (400 MHz, CD₃OD) δ 8.03 (S, 1H), 7.33-7.16 (m, 5H), 6.20-6.16 (dd, 1H), 5.56-5.42 (m, 1H), 4.93 (m, 1H), 4.71-4.66 (dd, 1H), 4.23-4.09 (m, 2H), 3.86-3.84 (m, 1H), 3.08 (s, 3H), 1.34 (s, 3H), 1.29-1.28 (d, 3H), 1.20-1.18 (dd, 6H). ESIMS m/z 582.7 ([M+H]⁺)

Scheme 15: Preparation of (S)-Isopropyl 2-(((S)-(((2R,3R,4R,5R)-5-(2-amino-6-(methylamino)-9H-purin-9-yl)-4-fluoro-3-hydroxy-2-methyltetrahydrofuran-2-yl)methoxy)(phenoxy)phosphoryl)amino) propanoate (Compound AB)

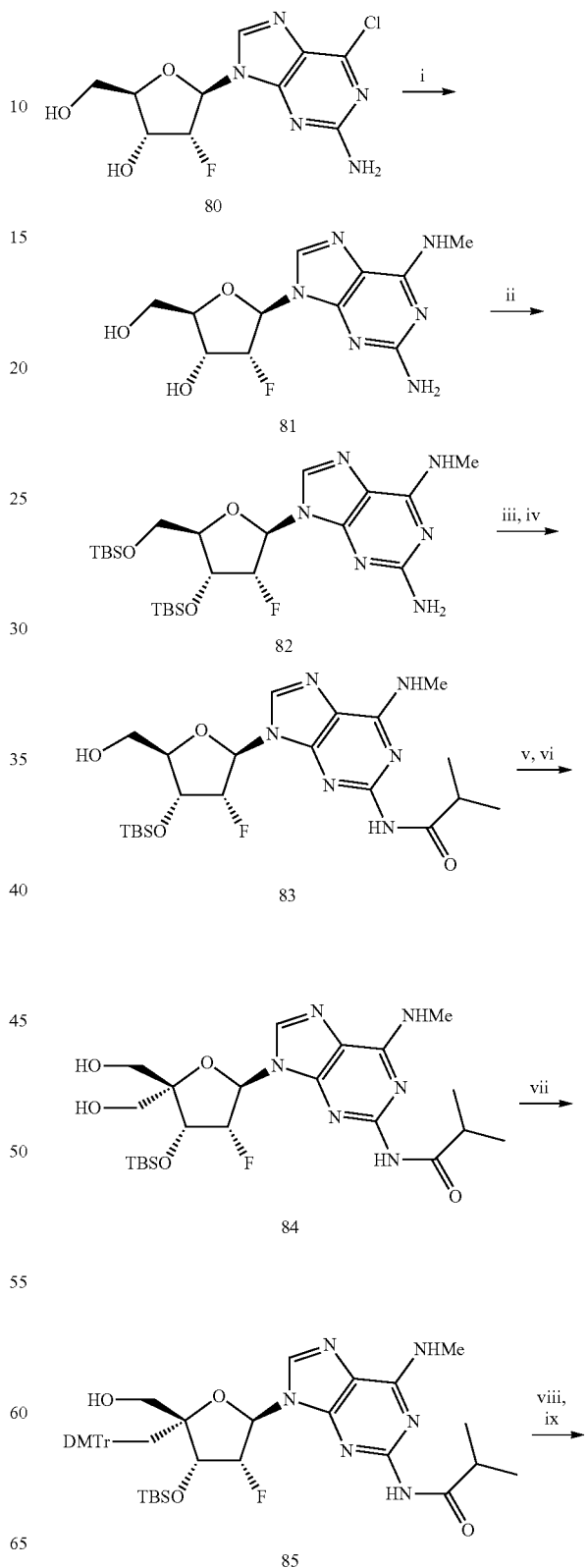

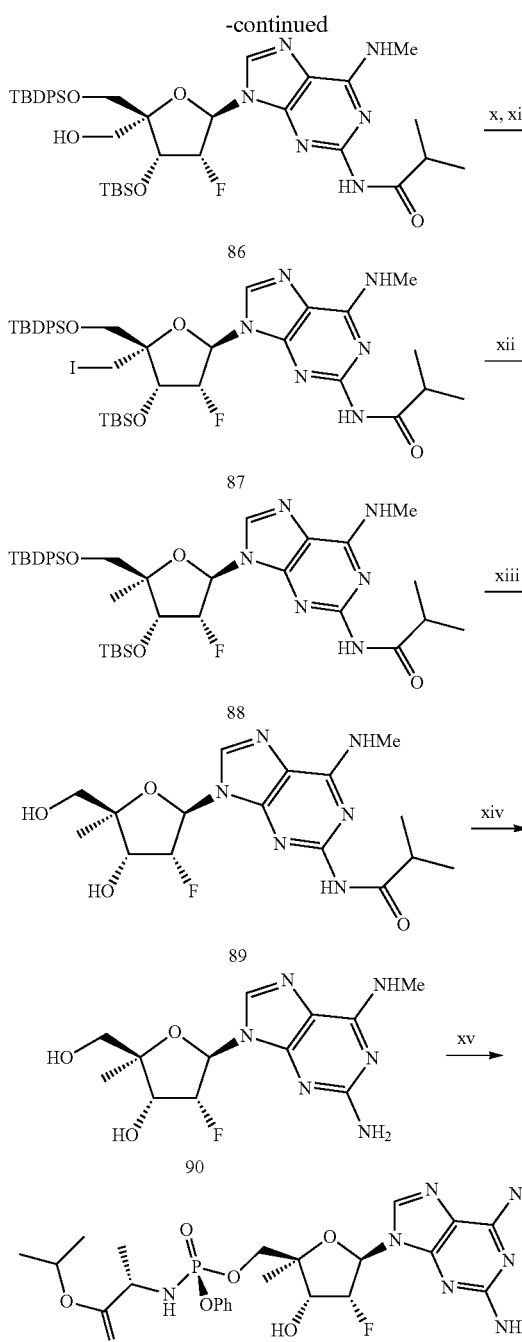

i) MeNH₂, EtOH, 85° C.; ii) TBSCl, imidazole, DMF; iii) isobutyryl chloride, pyridine; iv) 90% TFA, DCM; v) SO₃, pyridine, DIEA, DMSO, DCM; vi) formaldehyde, 2 N NaOH, dioxane then NaBH₄; vii) DMTrCl, Et₃N, DMF; viii) TBDPSCl, AgNO₃, pyridine; ix) 80% AcOH; x) Tf₂O, pyridine, DCM, 0° C.; xi) NaI, DMF, 60° C.; xii) H₂, 10% Pd-C, Et₃N, EtOH; xiii) TBAF, THF; xiv) MeNH₂, EtOH, 75° C.; xv) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(2-Amino-6-(methylamino)-9H-purin-9-yl)-4-fluoro-2-(hydroxymethyl) tetrahydrofuran-3-ol (81)

A solution of compound 80 (5.2 g, 17.3 mmol) in methylamine (33% in EtOH) (150 mL) was heated at 85° C. in a sealed container for 3 h, cooled down to RT and concentrated. The residue was purified by column chromatography (silica gel, DCM/MeOH 0 to 15%). Product 81 (4.9 g, 95% yield) was obtained as a white solid.

Step 2: Preparation of 9-((2R,3R,4R,5R)-4-((tert-Butyldimethylsilyl)oxy)-5-(((tert-butyldimethylsilyl)oxy) methyl)-3-fluorotetrahydrofuran-2-yl)-N6-methyl-9H-purine-2,6-diamine (82)

To a solution of compound 81 (4.7 g, 15.8 mmol) in dry DMF (70 mL) was added imidazole (4.3 g, 63.4 mmol) and TBSCl (9.6 g, 63.4 mmol). The mixture was stirred at RT for 15 h and concentrated. EtOAc (150 mL) was added and the solution was washed with saturated NH₄Cl aq. solution (3×100 mL) and brine (100 mL). The organic phase was dried over anhydrous Na₂SO₄ and concentrated. The residue was purified by column chromatography (silica gel, PE/EtOAc 0 to 60%). Product 82 (7.3 g, 88% yield) was obtained as a yellow oil.

Step 3 and Step 4: Preparation of N-(9-((2R,3R,4R,5R)-4-((tert-Butyldimethylsilyl)oxy)-3-fluoro-5-(hydroxymethyl) tetrahydrofuran-2-yl)-6-(methylamino)-9H-purin-2-yl)isobutyramide (83)

To a solution of compound 82 (7.2 g, 13.7 mmol) in dry pyridine (35 mL) was added isobutyryl chloride (1.7 mL, 16.4 mmol) drop-wise at 0° C. The reaction mixture was stirred at RT for 3 h and then concentrated. After co-evaporation with toluene (3×100 mL), the residue was dissolved in DCM (150 mL) and treated with TFA/H₂O (9:1, 15 mL) at 0° C. for 15 h. Then, the reaction was quenched by addition of solid NaHCO₃ (30 g) and filtered. The solution was washed with saturated NaHCO₃ aq. solution (2×100 mL) and brine (100 mL). The organic phase was dried over anhydrous Na₂SO₄ and concentrated. The residue was purified by column chromatography (silica gel, DCM/MeOH 0 to 5%). Product 83 (4.8 g, 73% yield over 2 steps) was obtained as a white foam.

Step 5 and Step 6: Preparation of N-(9-((2R,3R,4R)-4-((tert-Butyldimethylsilyl)oxy)-3-fluoro-5,5-bis(hydroxymethyl) tetrahydrofuran-2-yl)-6-(methylamino)-9H-purin-2-yl)isobutyramide (84)

To a solution of compound 83 (2.5 g, 5.2 mmol) in dry DCM (50 mL) at 0° C. was added diisopropylethylamine (3.5 mL, 20.3 mmol) and a suspension of SO₃ pyridine complex (2.5 g, 15.6 mmol) in dry DMSO (4.8 mL). The orange solution was stirred for 15 h at RT. Then, H₂O (50 mL) was added, the phases were separated and the aqueous layer was back-extracted with EtOAc (2×40 mL). The combined organics were washed with brine (80 mL), dried over anhydrous Na₂SO₄ and concentrated. The residue was dissolved in dioxane (30 mL). Formaldehyde (37% in H₂O) (1.7 mL, 21.8 mmol) and 2 N NaOH (3.9 mL, 7.8 mmol) were added and the yellow solution was stirred for 4 h at RT. The mixture was cooled down to 0° C. and sodium borohydride (787 mg, 20.8 mmol) was added portion-wise. The cloudy solution was stirred for 1 h at RT and quenched by addition of saturated. NH₄Cl aq. solution (150 mL). The product was extracted with EtOAc (3×100 mL). The combined organics were washed with brine (150 mL), dried over anhydrous Na₂SO₄ and concentrated. The residue was purified by column chromatography (silica gel, DCM/MeOH 0 to 15%). Product 84 (1.3 g, 50% yield over 2 steps) was obtained as a white solid.

Step 7: Preparation of N-(9-((2R,3R,4R,5S)-5-((bis(4-Methoxyphenyl)(phenyl)methoxy)methyl)-4-((tert-butyldimethylsilyl)oxy)-3-fluoro-5-(hydroxymethyl)tetrahydrofuran-2-yl)-6-(methylamino)-9H-purin-2-yl)isobutyramide (85)

To a solution of compound 84 (1.25 g, 2.44 mmol) in dry DMF (15 mL) was added triethylamine (680 μL, 4.88 mmol) and dimethoxytrityl chloride (1.16 g, 3.42 mmol). The resulting orange solution was stirred for 3 h at RT. The reaction was then diluted with EtOAc (60 mL) and H$_2$O (50 mL). The phases were separated and the aqueous layer was back-extracted with EtOAc (2×30 mL). The combined organics were washed with brine (60 mL), dried over anhydrous Na$_2$SO$_4$ and concentrated. The residue was purified by column chromatography (silica gel, DCM/MeOH 0 to 5%). Product 85 (755 mg, 38% yield) was obtained as a yellow foam.

Step 8 and Step 9: Preparation of N-(9-((2R,3R,4R,5R)-4-((tert-Butyldimethylsilyl)oxy)-5-(((tert-butyldiphenylsilyl)oxy) methyl)-3-fluoro-5-(hydroxymethyl)tetrahydrofuran-2-yl)-6-(methylamino)-9H-purin-2-yl)isobutyramide (86)

To a solution of compound 85 (750 mg, 0.92 mmol) in dry pyridine (7 mL) was added silver nitrate (467 mg, 2.75 mmol) and TBDPSCl (712 2.75 mmol). The resulting solution was stirred for 15 h at RT. Then, EtOAc (50 mL) was added and the suspension was filtered. The solution was washed brine (30 mL), dried over anhydrous Na$_2$SO$_4$ and concentrated. The residue was dissolved in 80% acetic acid (5 mL) and stirred for 15 h at RT. The solution was poured into satd. NaHCO$_3$ aq. solution (90 mL) and the mixture was extracted with DCM (3×60 mL). The combined organics were washed with brine (50 mL), dried over anhydrous Na$_2$SO$_4$ and concentrated. The residue was purified by column chromatography (silica gel, DCM/MeOH 0 to 10%). Product 86 (525 mg, 76% yield over 2 steps) was obtained as a white solid.

Step 10 and Step 11: Preparation of N-(9-((2R,3R,4R,5R)-4-((tert-Butyldimethylsilyl)oxy)-5-(((tert-butyldiphenylsilyl)oxy) methyl)-3-fluoro-5-(iodomethyl)tetrahydrofuran-2-yl)-6-(methylamino)-9H-purin-2-yl)isobutyramide (87)

To a solution of compound 86 (520 mg, 0.69 mmol) in dry DCM (12 mL) was added pyridine (280 μL, 3.45 mmol) and triflic anhydride (176 μL, 1.03 mmol) at 0° C. The resulting orange solution was stirred for 15 mins at 0° C. and H$_2$O (5 mL) was added. After a further 30 mins, the mixture was diluted with EtOAc (50 mL) and brine (40 mL). The layers were separated and the organics were dried over anhydrous Na$_2$SO$_4$ and concentrated. The residue was dissolved in dry DMF (25 mL) and NaI (800 mg, 5.49 mmol) was added. The suspension was stirred for 15 h at 60° C. and concentrated. Then, EtOAc (70 mL) was added and the solution was washed with satd. NH$_4$Cl aq. solution (2×40 mL), Na$_2$S$_2$O$_3$ aq. solution (40 mL) and brine (40 mL). The organics were dried over anhydrous Na$_2$SO$_4$ and concentrated. The residue was purified by column chromatography (silica gel, PE/EtOAc 0 to 80%). Product 87 (368 mg, 62% yield over 2 steps) was obtained as an orange solid.

Step 12: Preparation of N-(9-((2R,3R,4R,5R)-4-((tert-Butyldimethylsilyl)oxy)-5-(((tert-butyldiphenylsilyl)oxy) methyl)-3-fluoro-5-methyltetrahydrofuran-2-yl)-6-(methylamino)-9H-purin-2-yl)isobutyramide (88)

To a solution of compound 87 (365 mg, 0.42 mmol) in EtOH (7 mL) was added triethylamine (305 2.1 mmol) and palladium (10% on charcoal) (25 mg). The flask was put under an atmosphere of hydrogen and stirred for 24 h at RT. The reaction mixture was filtered over Celite and concentrated. The residue was purified by column chromatography (silica gel, PE/EtOAc 0 to 50%). Product 88 (293 mg, 95% yield) was obtained as a white solid.

Step 13: Preparation of N-(6-(Methylamino)-9-((2R,3R,4R,5R)-3-fluoro-4-hydroxy-5-(hydroxymethyl)-5-methyltetrahydrofuran-2-yl)-9H-purin-2-yl)isobutyramide (89)

To a solution of compound 88 (290 mg, 0.39 mmol) in dry THF (4 mL) was added tetrabutylammonium fluoride (1 N in THF) (1.0 mL, 1.0 mmol). The solution was stirred for 1 h at RT and concentrated. The residue was purified by column chromatography (silica gel, DCM/MeOH 0 to 15%). Product 89 (137 mg, 92% yield) was obtained as a white solid.

Step 14: Preparation of (2R,3R,4R,5R)-5-(2-amino-6-(methylamino)-9H-purin-9-yl)-4-fluoro-2-(hydroxymethyl)-2-methyltetrahydrofuran-3-ol (90)

A solution of compound 89 (135 mg, 0.35 mmol) in methylamine (33% in EtOH) (7 mL) in a sealed container was stirred for 15 h at 75° C. and concentrated. The residue was purified by column chromatography (silica gel, DCM/MeOH 0 to 20%). Product 90 (104 mg, 95% yield) was obtained as a white solid. $^1$H NMR (300 MHz, CD$_3$OD) δ 7.90 (s, 1H), 6.09 (dd, J=13.8, 5.3 Hz, 1H), 5.58 (dt, J=53.2, 5.2 Hz, 1H), 4.51 (dd, J=8.8, 5.1 Hz, 1H), 3.68 (d, J=12.2 Hz, 1H), 3.55 (d, J=12.2 Hz, 1H), 3.04 (s, 3H), 1.26 (d, J=0.8 Hz, 3H). MS (ESI) m/z calcd. for C$_{12}$H$_{18}$FN$_6$O$_3$ [M+H]$^+$ 313.1; found 313.2.

Step 15: Preparation of (S)-Isopropyl 2-(((S)-(((2R,3R,4R,5R)-5-(2-amino-6-(methylamino)-9H-purin-9-yl)-4-fluoro-3-hydroxy-2-methyltetrahydrofuran-2-yl)methoxy)(phenoxy)phosphoryl)amino)propanoate (Compound AB)

To a solution of compound 90 (75 mg, 0.24 mmol) in dry DMF (3.0 mL) was added tert-butylmagnesium chloride (0.7 N in THF) (560 μL, 0.32 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (122 mg, 0.28 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound AB (30 mg, 22% yield) was obtained as a white solid. $^1$H NMR (300 MHz, CD$_3$OD) δ 7.83 (s, 1H), 7.33-7.14 (m, 5H), 6.14 (dd, J=17.0, 3.2 Hz), 5.63-5.48 (m, 1H), 4.91 (m, 1H), 4.71 (dd, J=17.4, 5.2 MHz), 4.29 (dd, J=10.8, 6.1 MHz) and 4.09 (dd, J=10.8, 4.9 MHz, 2H), 3.86 (m, 1H), 3.02 (br. s, 3H), 1.34 (br. s, 3H), 1.28-1.26 (m, 3H), 1.19-1.17 (m, 6H). $^{31}$P NMR (121 MHz, CD$_3$OD) δ 3.61 (s). MS (ESI) m/z calcd. for C$_{24}$H$_{34}$FN$_7$O$_7$P [M+H]$^+$ 582.2; found 582.2.

Scheme 16: Preparation of (S)-Isopropyl 2-(((S)-(((2R,3R,4R,5R)-5-(6-(dimethylamino)-2-fluoro-9H-purin-9-yl)-4-fluoro-3-hydroxy-2-methyltetrahydrofuran-2-yl)methoxy)(phenoxy)phosphoryl)amino) propanoate (Compound AD).

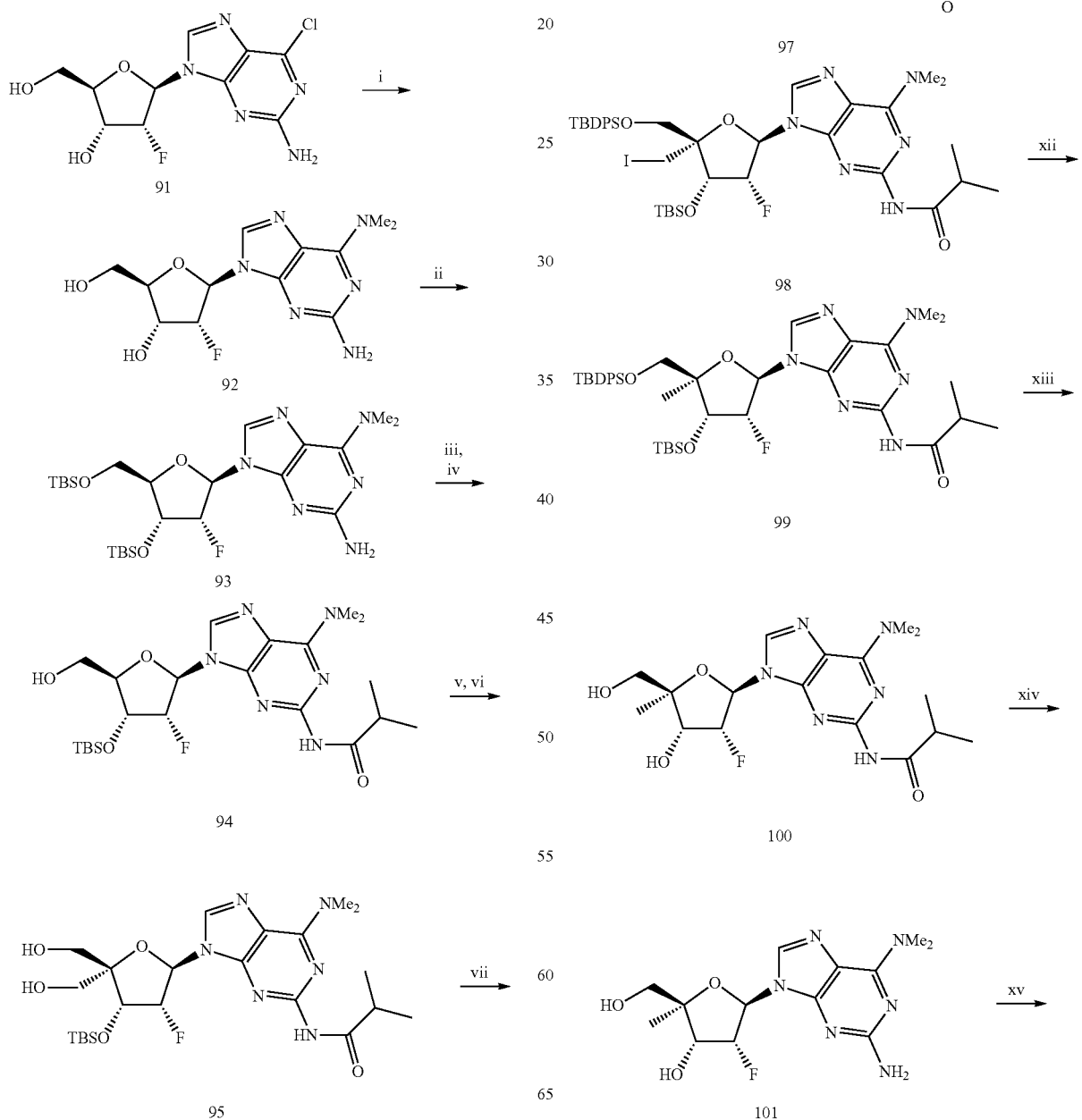

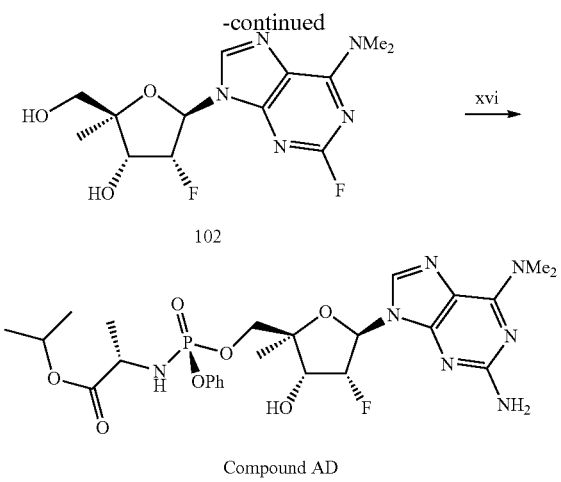

Compound AD i) Me₂NH•HCl, Et₃N, EtOH, 85° C.; ii) TBSCl, imidazole, DMF; iii) isobutyryl chloride, pyridine; iv) 90% TFA, DCM; v) SO₃•pyridine, DIEA, DMSO, DCM; vi) formaldehyde, 2N NaOH, dioxane then NaBH₄; vii) DMTrCl, Et₃N, DMF; viii) TBDPSCl, AgNO₃, pyridine; ix) 80% AcOH; x) Tf₂O, pyridine, DCM, 0° C.; xi) NaI, DMF, 60° C.; xii) H₂, 10% Pd—C, Et₃N, EtOH; xiii) TBAF, THF; xiv) MeNH₂ EtOH, 75° C.; xv) tBuONO, pyridine•HF, pyridine, -15° C.; xvi) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(2-Amino-6-(dimethylamino)-9H-purin-9-yl)-4-fluoro-2-(hydroxymethyl)tetrahydrofuran-3-ol (92)

To a solution of compound 91 (10.5 g, 35 mmol) in EtOH (220 mL) was added dimethylamine hydrochloride (14.0 g, 173 mmol) and triethylamine (24.0 mL, 173 mmol). The reaction mixture was heated at 85° C. in a sealed container for 3 h, cooled down to room temperature (RT) and concentrated. The residue was purified by column chromatography (silica gel, DCM/MeOH 0 to 10%). Product 92 (10.8 g, 99% yield) was obtained as a white solid.

Step 2: Preparation of 9-((2R,3R,4R,5R)-4-((tert-Butyldimethylsilyl)oxy)-5-(((tert-butyldimethylsilyl)oxy) methyl)-3-fluorotetrahydrofuran-2-yl)-N6,N6-dimethyl-9H-purine-2,6-diamine (93)

To a solution of compound 92 (10.7 g, 34.5 mmol) in dry DMF (120 mL) was added imidazole (9.4 g, 138.4 mmol) and TBSCl (20.9 g, 138.4 mmol). The mixture was stirred at RT for 15 h and concentrated. EtOAc (300 mL) was added and the solution was washed with satd. NH₄Cl aq. solution (3×200 mL) and brine (200 mL). The organic phase was dried over anhydrous Na₂SO₄ and concentrated. The residue was purified by column chromatography (silica gel, PE/EtOAc 0 to 40%). Product 93 (16.0 g, 85% yield) was obtained as a yellow oil.

Step 3 and Step 4: Preparation of N-(9-((2R,3R,4R,5R)-4-((tert-Butyldimethylsilyl)oxy)-3-fluoro-5-(hydroxymethyl) tetrahydrofuran-2-yl)-6-(dimethylamino)-9H-purin-2-yl)isobutyramide (94)

To a solution of compound 93 (13.5 g, 25.0 mmol) in dry pyridine (60 mL) was added isobutyryl chloride (3.1 mL, 30.0 mmol) drop-wise at 0° C. The reaction mixture was stirred at RT for 3 h and then concentrated. After co-evaporation with toluene (3×200 mL), the residue was dissolved in DCM (270 mL) and treated with TFA/H₂O (9:1, 27 mL) at 0° C. for 15 h. Then, the reaction was quenched by addition of solid NaHCO₃ (50 g) and filtered. The solution was washed with satd. NaHCO₃ aq. solution (2×200 mL) and brine (200 mL). The organic phase was dried over anhydrous Na₂SO₄ and concentrated. The residue was purified by column chromatography (silica gel, PE/EtOAc 0 to 80%). Product 94 (9.3 g, 75% yield over 2 steps) was obtained as a white foam.

Step 5 and Step 6: Preparation of N-(9-((2R,3R,4R)-4-((tert-Butyldimethylsilyl)oxy)-3-fluoro-5,5-bis(hydroxymethyl) tetrahydrofuran-2-yl)-6-(dimethylamino)-9H-purin-2-yl)isobutyramide (95)

To a solution of compound 94 (2.0 g, 4.0 mmol) in dry DCM (35 mL) at 0° C. was added diisopropylethylamine (2.7 mL, 15.6 mmol) and a suspension of SO₃ pyridine complex (1.9 g, 12.0 mmol) in dry DMSO (3.7 mL). The orange solution was stirred for 15 h at RT. Then, H₂O (40 mL) was added, the phases were separated and the aqueous layer was back-extracted with EtOAc (2×30 mL). The combined organics were washed with brine (60 mL), dried over anhydrous Na₂SO₄ and concentrated. The residue was dissolved in dioxane (25 mL). Formaldehyde (37% in H₂O) (1.3 mL, 16.8 mmol) and 2 N NaOH (3.0 mL, 6.0 mmol) were added and the yellow solution was stirred for 3 h at RT. The mixture was cooled down to 0° C. and sodium borohydride (605 mg, 16.0 mmol) was added portion-wise. The cloudy solution was stirred for 1 h at RT and quenched by addition of satd. NH₄Cl aq. solution (100 mL). The product was extracted with EtOAc (3×80 mL). The combined organics were washed with brine (100 mL), dried over anhydrous Na₂SO₄ and concentrated. The residue was purified by column chromatography (silica gel, DCM/MeOH 0 to 10%). Product 95 (1.2 g, 55% yield over 2 steps) was obtained as a white solid.

Step 7: Preparation of N-(9-((2R,3R,4R,5S)-5-((bis(4-Methoxyphenyl)(phenyl)methoxy)methyl)-4-((tert-butyldimethylsilyl)oxy)-3-fluoro-5-(hydroxymethyl)tetrahydrofuran-2-yl)-6-(dimethylamino)-9H-purin-2-yl)isobutyramide (96)

To a solution of compound 95 (1.15 g, 2.21 mmol) in dry DMF (12 mL) was added triethylamine (620 μL, 4.44 mmol) and dimethoxytrityl chloride (1.05 g, 3.11 mmol). The resulting orange solution was stirred for 2 h at RT. The reaction was then diluted with EtOAc (50 mL) and H₂O (40 mL). The phases were separated and the aqueous layer was back-extracted with EtOAc (2×30 mL). The combined organics were washed with brine (50 mL), dried over anhydrous Na₂SO₄ and concentrated. The residue was purified by column chromatography (silica gel, PE/EtOAc 0 to 100%). Product 96 (880 mg, 48% yield) was obtained as a yellow foam.

Step 8 and Step 9: Preparation of N-(9-((2R,3R,4R,5R)-4-((tert-Butyldimethylsilyl)oxy)-5-(((tert-butyldiphenylsilyl)oxy) methyl)-3-fluoro-5-(hydroxymethyl)tetrahydrofuran-2-yl)-6-(dimethylamino)-9H-purin-2-yl)isobutyramide (97)

To a solution of compound 96 (875 mg, 1.06 mmol) in dry pyridine (8 mL) was added silver nitrate (538 mg, 3.17 mmol) and TBDPSCl (820 μL, 3.17 mmol). The resulting solution was stirred for 15 h at RT. Then, EtOAc (50 mL) was added and the suspension was filtered. The solution was washed brine (30 mL), dried over anhydrous Na$_2$SO$_4$ and concentrated. The residue was dissolved in 80% acetic acid (5 mL) and stirred for 15 h at RT. The solution was poured into satd. NaHCO$_3$ aq. solution (90 mL) and the mixture was extracted with DCM (3×60 mL). The combined organics were washed with brine (50 mL), dried over anhydrous Na$_2$SO$_4$ and concentrated. The residue was purified by column chromatography (silica gel, DCM/MeOH 0 to 10%). Product 97 (662 mg, 82% yield over 2 steps) was obtained as a white solid.

Step 10 and Step 11: Preparation of N-(9-((2R,3R,4R,5R)-4-((tert-Butyldimethylsilyl)oxy)-5-(((tert-butyldiphenylsilyl)oxy) methyl)-3-fluoro-5-(iodomethyl)tetrahydrofuran-2-yl)-6-(dimethylamino)-9H-purin-2-yl)isobutyramide (98)

To a solution of compound 97 (660 mg, 0.86 mmol) in dry DCM (15 mL) was added pyridine (350 μL, 4.30 mmol) and triflic anhydride (220 1.29 mmol) at 0° C. The resulting orange solution was stirred for 20 mins at 0° C. and H$_2$O (7 mL) was added. After a further 30 mins, the mixture was diluted with EtOAc (60 mL) and brine (50 mL). The layers were separated and the organics were dried over anhydrous Na$_2$SO$_4$ and concentrated. The residue was dissolved in dry DMF (30 mL) and NaI (1.00 g, 6.85 mmol) was added. The suspension was stirred for 15 h at 60° C. and concentrated. Then, EtOAc (90 mL) was added and the solution was washed with satd. NH$_4$Cl aq. solution (2×50 mL), Na$_2$S$_2$O$_3$ aq. solution (50 mL) and brine (50 mL). The organics were dried over anhydrous Na$_2$SO$_4$ and concentrated. The residue was purified by column chromatography (silica gel, PE/EtOAc 0 to 40%). Product 98 (527 mg, 70% yield over 2 steps) was obtained as an orange solid.

Step 12: Preparation of N-(9-((2R,3R,4R,5R)-4-((tert-Butyldimethylsilyl)oxy)-5-(((tert-butyldiphenylsilyl)oxy) methyl)-3-fluoro-5-methyltetrahydrofuran-2-yl)-6-(dimethylamino)-9H-purin-2-yl)isobutyramide (99)

To a solution of compound 98 (525 mg, 0.60 mmol) in EtOH (10 mL) was added triethylamine (435 μL, 3.0 mmol) and palladium (10% on charcoal) (35 mg). The flask was put under an atmosphere of hydrogen and stirred for 24 h at RT. The reaction mixture was filtered over Celite and concentrated. The residue was purified by column chromatography (silica gel, PE/EtOAc 0 to 50%). Product 99 (441 mg, 98% yield) was obtained as a white solid.

Step 13: Preparation of N-(6-(Dimethylamino)-9-((2R,3R,4R,5R)-3-fluoro-4-hydroxy-5-(hydroxymethyl)-5-methyltetrahydrofuran-2-yl)-9H-purin-2-yl)isobutyramide (100)

To a solution of compound 99 (440 mg, 0.59 mmol) in dry THF (6 mL) was added tetrabutylammonium fluoride (1 N in THF) (1.5 mL, 1.5 mmol). The solution was stirred for 1 h at RT and concentrated. The residue was purified by column chromatography (silica gel, DCM/MeOH 0 to 10%). Product 100 (215 mg, 91% yield) was obtained as a white solid.

Step 14: Preparation of (2R,3R,4R,5R)-5-(2-amino-6-(dimethylamino)-9H-purin-9-yl)-4-fluoro-2-(hydroxymethyl)-2-methyltetrahydrofuran-3-ol (101)

A solution of compound 100 (200 mg, 0.50 mmol) in methylamine (33% in EtOH) (10 mL) in a sealed container was stirred for 15 h at 75° C. and concentrated. The residue was purified by column chromatography (silica gel, DCM/MeOH 0 to 15%). Product 101 (160 mg, 98% yield) was obtained as a white solid. $^1$H NMR (300 MHz, CD$_3$OD) δ 7.48 (s, 1H), 6.03-5.81 (m, 2H), 4.68 (br s, 2H), 4.54 (d, J=4.5 Hz, 1H), 3.76 (dd, J=12.5, 0.7 Hz, 1H), 3.54 (d, J=12.5 Hz), 3.44 (br s, 6H), 2.65 (br s, 1H), 1.75 (br s, 1H), 1.30 (d, J=1.0 Hz, 3H). MS (ESI) m/z calcd. for C$_{13}$H$_{20}$FN$_6$O$_3$ [M+H]$^+$ 327.2; found 327.2.

Step 15: Preparation of (2R,3R,4R,5R)-5-(6-(Dimethylamino)-2-fluoro-9H-purin-9-yl)-4-fluoro-2-(hydroxymethyl)-2-methyltetrahydrofuran-3-ol (102)

A solution of compound 101 (70 mg, 0.21 mmol) in dry pyridine (400 μL) was cooled down to −15° C. and pyridine hydrofluoride (280 μL) was added. Then, tert-butyl nitrite (51 μL, 0.43 mmol) was added drop-wise over 5 mins. The mixture was stirred at 10° C. for 4 h and quenched by addition of a suspension of CaCO$_3$ (700 mg) in H$_2$O (2 mL). The resulting suspension was stirred at RT for 15 mins and extracted with EtOAc (5×5 mL). The combined organics were dried over anhydrous Na$_2$SO$_4$ and concentrated. The residue was purified by column chromatography (silica gel, DCM/MeOH 0 to 7%). Product 102 (38 mg, 54% yield) was obtained as an off-white solid. $^1$H NMR (300 MHz, CD$_3$OD) δ 8.22 (s, 1H), 6.20 (dd, J=14.7, 4.2 Hz, 1H), 5.48 (ddd, J=53.4, 5.1, 5.0 Hz, 1H), 4.56 (dd, J=13.5, 5.1 Hz, 1H), 3.67-3.53 (m, 2H), 3.65 (br s, 3H), 3.33 (br s, 3H), 1.28 (s, 3H). MS (ESI) m/z calcd. for C$_{13}$H$_{18}$F$_2$N$_5$O$_3$ [M+H]$^+$ 330.1; found 330.2.

Step 16: Preparation of (S)-Isopropyl 2-(((S)-(((2R,3R,4R,5R)-5-(6-(dimethylamino)-2-fluoro-9H-purin-9-yl)-4-fluoro-3-hydroxy-2-methyltetrahydrofuran-2-yl)methoxy)(phenoxy)phosphoryl)amino)propanoate (Compound AD)

To a solution of compound 102 (70 mg, 0.22 mmol) in dry DMF (3.0 mL) was added tert-butylmagnesium chloride (0.7 N in THF) (420 μL, 0.30 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (112 mg, 0.26 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, PE/EtOAc 10 to 100%) and by reverse phase column chromatography (C-18 silica, H$_2$O/MeOH 0 to 100%). Compound AD (25 mg, 20% yield) was obtained as a white solid. $^1$H NMR (300 MHz, CD$_3$OD) δ 8.08 (s, 1H), 7.31-7.11 (m, 5H), 6.22 (dd, J=17.7, 2.6 Hz), 5.53 (ddd, J=53.2, 5.1, 2.5 Hz), 4.96-4.75 (overlapped with H$_2$O, m, 2H), 4.14 (m, 1H), 3.85 (m, 1H), 3.78-3.41 (br. m, 3H), 3.30-3.14 (br. m, 3H), 1.35 (br. s, 3H), 1.29-1.26 (m, 3H), 1.19-1.17 (m, 6H). $^{31}$P NMR (121 MHz, CD$_3$OD) δ 3.42 (s). MS (ESI) m/z calcd. for C$_{25}$H$_{34}$F$_2$N$_6$O$_7$P [M+H]$^+$ 599.2; found 599.2.

Scheme 17: Preparation of (S)-Isopropyl 2-(((S)-(((2R,3R,4R,5R)-5-(6-(dimethylamino)-2-chloro-9H-purin-9-yl)-4-fluoro-3-hydroxy-2-methyltetrahydrofuran-2-yl)methoxy)(phenoxy)phosphoryl)amino) propanoate (Compound AE).

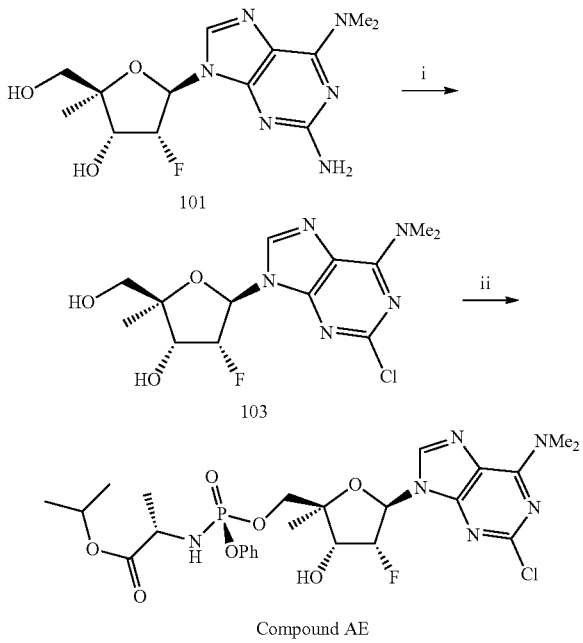

Compound AE i) tBuONO, SbCl₃, DCE, DMSO, 0° C; ii) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(6-(Dimethylamino)-2-chloro-9H-purin-9-yl)-4-fluoro-2-(hydroxymethyl)-2-methyltetrahydrofuran-3-ol (103)

A solution of compound 101 (70 mg, 0.21 mmol) in dry DCE/DMSO (4:1) (2.5 mL) was cooled down to 0° C. and antimony trichloride (68 mg, 0.30 mmol) was added. Then, tert-butyl nitrite (54 µL, 0.46 mmol) was added drop-wise over 5 mins. The mixture was stirred at RT for 4 h and quenched by addition of trimethylamine (100 µL). The resulting mixture was diluted with EtOAc (10 mL) and washed with H₂O (5 mL). The aqueous layer was back-extracted EtOAc (3×5 mL). The combined organics were washed with brine (10 mL), dried over anhydrous Na₂SO₄ and concentrated. The residue was purified by column chromatography (silica gel, DCM/MeOH 0 to 7%). Product 103 (36 mg, 50% yield) was obtained as a white solid. $^1$H NMR (300 MHz, CD₃OD) δ 7.75 (s, 1H), 6.03-5.83 (m, 2H), 4.57 (d, J=3.3 Hz, 1H), 3.79 (d, J=9.6 Hz, 1H), 3.76 (br s, 3H), 3.58 (d, J=9.6 Hz, 1H), 3.30 (br s, 3H), 1.32 (s, 3H). MS (ESI) m/z calcd. for $C_{13}H_{18}ClFN_5O_3$ [M+H]⁺ 346.1; found 346.2.

Step 2: Preparation of (S)-Isopropyl 2-(((S)-(((2R,3R,4R,5R)-5-(6-(dimethylamino)-2-chloro-9H-purin-9-yl)-4-fluoro-3-hydroxy-2-methyltetrahydrofuran-2-yl)methoxy)(phenoxy)phosphoryl)amino) propanoate (Compound AE)

To a solution of compound 103 (63 mg, 0.18 mmol) in dry DMF (2.5 mL) was added tert-butylmagnesium chloride (0.7 N in THF) (360 µL, 0.26 mmol) drop-wise at -5° C. The solution was stirred for 20 mins at 0° C. and for 40 mins at RT. Then, the reaction mixture was cooled down to -10° C. and a solution of isopropyl ((S)-(pentafluorophenoxy)-phenoxy-phosphoryl)-L-alaninate (100 mg, 0.22 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH₄Cl aq. solution (15 mL). The phases were separated and the aqueous layer was back-extracted with EtOAc (2×10 mL). The combined organics were washed with satd. NH₄Cl aq. solution (20 mL) and brine (20 mL), dried over Na₂SO₄ and concentrated. The residue was purified by column chromatography (silica gel, DCM/MeOH 0 to 8%) and by reverse phase column chromatography (C-18 silica, H₂O/MeOH 0 to 100%). Compound AE (20 mg, 18% yield) was obtained as a white solid. $^1$H NMR (300 MHz, CD₃OD) δ 8.10 (s, 1H), 7.30-7.11 (m, 5H), 6.25 (dd, J=17.8, 2.5 Hz, 1H), 5.55 (ddd, J=53.2, 5.2, 2.4 Hz, 1H), 4.95-4.73 (overlapped with H₂O, m, 2H), 4.16 (m, 2H), 3.87 (m, 1H), 3.78-2.99 (overlapped with MeOH, br. m, 6H), 1.35 (br. s, 3H), 1.29-1.28 (m, 3H), 1.20-1.18 (m, 6H). $^{31}$P NMR (121 MHz, CD₃OD) δ 1.97 (s). MS (ESI) m/z calcd. for $C_{25}H_{34}ClFN_6O_7P$ [M+H]⁺ 615.2; found 615.2.

Scheme 18: Preparation of (S)-Isopropyl 2-(((S)-(((2R,3R,4R,5R)-5-(6-(dimethylamino)-2-methoxy-9H-purin-9-yl)-4-fluoro-3-hydroxy-2-methyltetrahydrofuran-2-yl)methoxy)(phenoxy)phosphoryl)amino) propanoate (Compound AF)

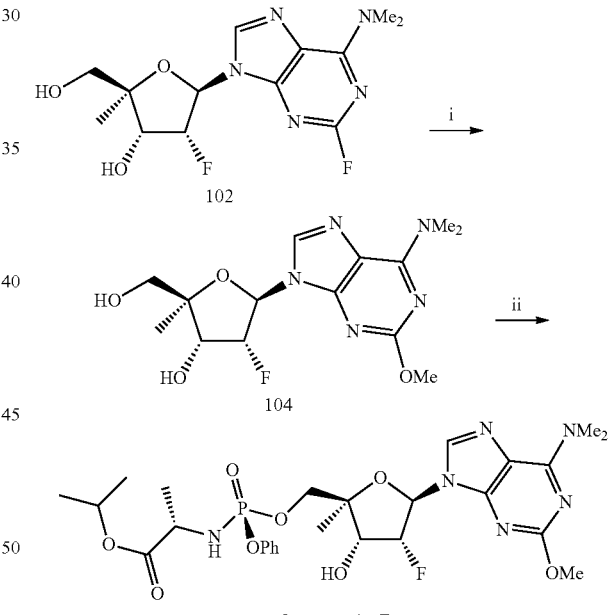

Compound AF i) MeONa, MeOH, 60° C.; ii) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(6-(Dimethylamino)-2-methoxy-9H-purin-9-yl)-4-fluoro-2-(hydroxymethyl)-2-methyltetrahydrofuran-3-ol (104)

To a solution of compound 102 (100 mg, 0.30 mmol) in dry MeOH (5 mL) was added sodium methoxide (25% in MeOH) (140 µL, 0.6 mmol). The resulting solution was stirred at 60° C. for 5 h. The reaction was quenched by addition of acetic acid (40 µL) and the solvent was removed.

The residue was purified by column chromatography (silica gel, DCM/MeOH 0 to 8%). Product 104 (31 mg, 30% yield) was obtained as a white solid. $^1$H NMR (300 MHz, CD$_3$OD) δ 8.08 (s, 1H), 6.19 (dd, J=15.2, 4.4 Hz, 1H), 5.57 (ddd, J=58.8, 4.8, 5.2 Hz, 1H), 4.60 (dd, J=12.8, 5.2 Hz, 1H), 3.96 (s, 3H), 3.61 (m, 2H), 3.50-3.32 (overlapped with MeOH, m, 6H), 1.28 (s, 3H). MS (ESI) m/z calcd. for C$_{14}$H$_{21}$FN$_5$O$_4$ [M+H]$^+$ 342.2; found 342.2.

Step 2: Preparation of (S)-Isopropyl 2-(((S)-(((2R, 3R,4R,5R)-5-(6-(dimethylamino)-2-methoxy-9H-purin-9-yl)-4-fluoro-3-hydroxy-2-methyltetrahydrofuran-2-yl)methoxy)(phenoxy)phosphoryl) amino) propanoate (Compound AF)

To a solution of compound 104 (55 mg, 0.16 mmol) in dry DMF (2.5 mL) was added tert-butylmagnesium chloride (0.7 N in THF) (320 μL, 0.24 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (89 mg, 0.20 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, PE/EtOAc 10 to 100%) and by reverse phase column chromatography (C-18 silica, H$_2$O/MeOH 0 to 100%). Compound AF (25 mg, 23% yield) was obtained as a white solid. $^1$H NMR (300 MHz, CD$_3$OD) δ 7.96 (s, 1H), 7.30-7.11 (m, 5H), 6.22 (dd, J=18.3, 2.6 Hz, 1H), 5.58 (ddd, J=53.6, 5.2, 2.7 Hz, 1H), 4.91-4.80 (overlapped with H$_2$O, m, 2H), 4.19 (dd, J=10.9, 6.0 Hz) and 4.10 (dd, J=10.9, 5.1 Hz, 2H), 3.94 (s, 3H), 3.83 (m, 1H), 3.52-3.33 (br. m, 6H), 1.34 (br. s, 3H), 1.27-1.25 (m, 3H), 1.18-1.15 (m, 6H). $^{31}$P NMR (121 MHz, CD$_3$OD) δ 3.57 (s). MS (ESI) m/z calcd. for C$_{26}$H$_{37}$FN$_6$O$_8$P [M+H]$^+$ 611.2; found 611.2.

Scheme 19: Preparation of (S)-Isopropyl 2-(((S)-(((2R,3R,4R,5R)-5-(2-amino-6-(dimethylamino)-9H-purin-9-yl)-2-(chloromethyl)-4-fluoro-3-hydroxytetrahydrofuran-2-yl)methoxy)(phenoxy)phosphoryl)amino)propanoate (Compound AG).

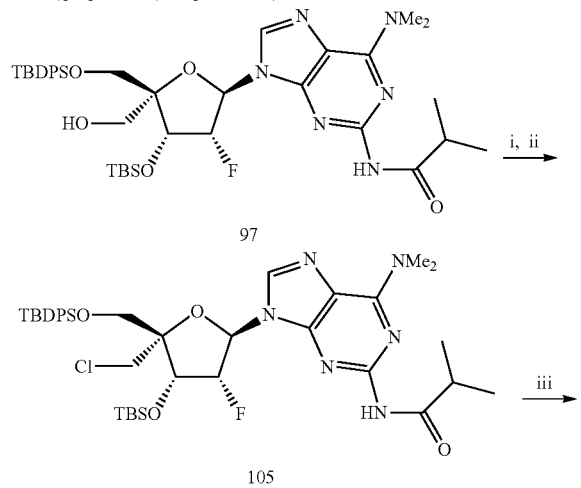

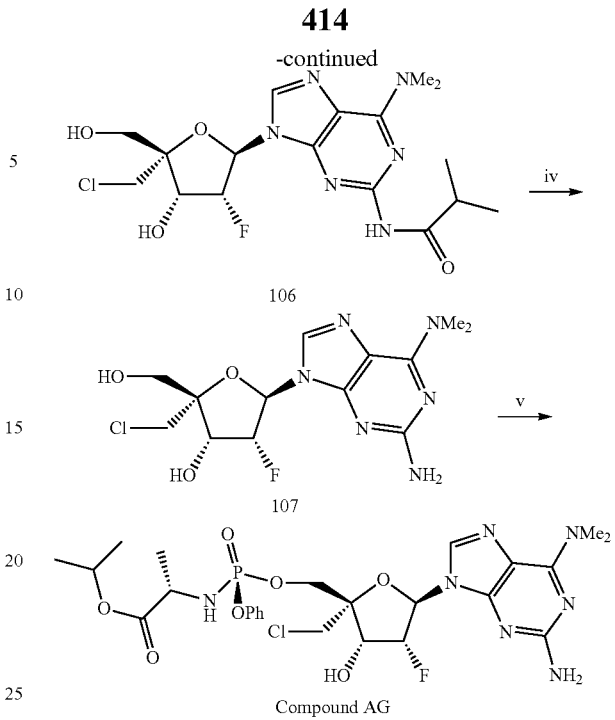

Compound AG i) Tf$_2$O, pyridine, DCM, 0° C.; ii) LiCl, DMF, 40° C.; iii) TBAF, THF; iv) MeNH$_2$, EtOH, 75° C.; v) Isopropyl ((S)-(pentafluorophenoxy)-phenoxy-phosphoryl)-L-alaninate, t-BuMgCl, DMF, -10° C.

Step 1 and Step 2: Preparation of N-(9-((2R,3R,4R,5R)-4-((tert-Butyldimethylsilyl)oxy)-5-(((tert-butyldiphenylsilyl)oxy) methyl)-5-(chloromethyl)-3-fluorotetrahydrofuran-2-yl)-6-(dimethylamino)-9H-purin-2-yl)isobutyramide (105)

To a solution of compound 97 (600 mg, 0.78 mmol) in dry DCM (15 mL) was added pyridine (315 μL, 3.90 mmol) and triflic anhydride (200 μL, 1.16 mmol) at 0° C. The resulting orange solution was stirred for 20 mins at 0° C. and H$_2$O (7 mL) was added. After a further 30 mins, the mixture was diluted with EtOAc (60 mL) and brine (50 mL). The layers were separated and the organics were dried over anhydrous Na$_2$SO$_4$ and concentrated. The residue was dissolved in dry DMF (30 mL) and LiCl (330 mg, 7.80 mmol) was added. The suspension was stirred for 15 h at 40° C. and concentrated. Then, EtOAc (90 mL) was added and the solution was washed with satd. NH$_4$Cl aq. solution (2×50 mL), Na$_2$S$_2$O$_3$ aq. solution (50 mL) and brine (50 mL). The organics were dried over anhydrous Na$_2$SO$_4$ and concentrated. The residue was purified by column chromatography (silica gel, PE/EtOAc 0 to 50%). Product 105 (522 mg, 85% yield over 2 steps) was obtained as an off-white solid.

Step 3: Preparation of N-(9-((2R,3R,4R,5R)-5-(Chloromethyl)-3-fluoro-4-hydroxy-5-(hydroxymethyl) tetrahydrofuran-2-yl)-6-(dimethyamino)-9H-purin-2-yl)isobutyramide (106)

To a solution of compound 105 (400 mg, 0.51 mmol) in dry THF (6 mL) was added tetrabutylammonium fluoride (1 N in THF) (1.5 mL, 1.5 mmol). The solution was stirred for 1 h at RT and concentrated. The residue was purified by column chromatography (silica gel, DCM/MeOH 0 to 10%). Product 106 (205 mg, 93% yield) was obtained as a white solid.

Step 4: Preparation of (2R,3R,4R,5R)-5-(2-Amino-6-(dimethylamino)-9H-purin-9-yl)-2-(chloromethyl)-4-fluoro-2-(hydroxymethyl)tetrahydrofuran-3-ol (107)

A solution of compound 106 (200 mg, 0.46 mmol) in methylamine (33% in EtOH) (10 mL) in a sealed container was stirred for 15 h at 75° C. and concentrated. The residue was purified by column chromatography (silica gel, DCM/MeOH 0 to 15%). Product 107 (159 mg, 95% yield) was obtained as a white solid. $^1$H NMR (300 MHz, CD$_3$OD) δ 7.81 (br, NH), 7.48 (s, 1H), 6.12-5.90 (m, 2H), 4.71 (m, 1H+NH+OH), 4.01-3.88 (m, 2H), 3.59-3.49 (m, 2H), 3.43 (1, 6H), 2.66 (s, 10H). MS (ESI) m/z calcd. for C$_{13}$H$_{19}$ClFN$_6$O$_3$ [M+H]$^-$ 361.1; found 361.2.

Step 5: Preparation of (S)-Isopropyl 2-(((S)-(((2R,3R,4R,5R)-5-(2-amino-6-(dimethylamino)-9H-purin-9-yl)-2-(chloromethyl)-4-fluoro-3-hydroxytetrahydrofuran-2-yl)methoxy)(phenoxy) phosphoryl)amino) propanoate (Compound AG)

To a solution of compound 107 (51 mg, 0.14 mmol) in dry DMF (2.0 mL) was added tert-butylmagnesium chloride (0.7 N in THF) (285 μL, 0.20 mmol) drop-wise at −5° C. The solution was stirred for 15 mins at 0° C. and for 45 mins at RT. Then, the reaction mixture was cooled down to −10° C. and a solution of isopropyl ((S)-(pentafluorophenoxy)-phenoxy-phosphoryl)-L-alaninate (76 mg, 0.17 mmol) in dry DMF (1.5 mL) was added drop-wise. The resulting solution was slowly warmed up to 10° C. and stirred for 15 h at this temperature. The reaction mixture was then diluted with EtOAc (12 mL) and satd. NH$_4$Cl aq. solution (10 mL). The phases were separated and the aqueous layer was back-extracted with EtOAc (2×6 mL). The combined organics were washed with satd. NH$_4$Cl aq. solution (12 mL) and brine (12 mL), dried over Na$_2$SO$_4$ and concentrated. The residue was purified by column chromatography (silica gel, DCM/MeOH 0 to 8%) and by reverse phase column chromatography (C-18 silica, H$_2$O/MeOH 0 to 100%). Compound AG (24 mg, 27% yield) was obtained as a white solid. $^1$H NMR (300 MHz, CDCl$_3$) δ 7.47 (s, 1H), 7.39-7.17 (overlapped with CHCl$_3$, m, 5H), 6.00 (m, 1H), 5.67-5.50 (m, 1H), 5.40-4.85 (m, 2H), 4.75 (m, 1H), 4.28 (m, 1H), 4.02-3.69 (m, 4H), 3.67-3.20 (br. m, 6H), 3.18-3.00 (m, 1H), 1.99-1.52 (m, 2H), 1.42-1.34 (m, 3H), 1.27-1.17 (m, 6H). $^{31}$P NMR (121 MHz, CDCl$_3$) δ 3.89 (s). MS (ESI) m/z calcd. for C$_{25}$H$_{35}$ClFN$_7$O$_7$P [M+H]$^+$ 630.2; found 630.2.

Scheme 20: Preparation of (S)-Isopropyl 2-(((S)-(((2R,3R,4R,5R)-5-(6-(methylamino)-2-fluoro-9H-purin-9-yl)-4-fluoro-3-hydroxy-2-methyltetrahydrofuran-2-yl)methoxy)(phenoxy)phosphoryl)amino) propanoate (Compound AH).

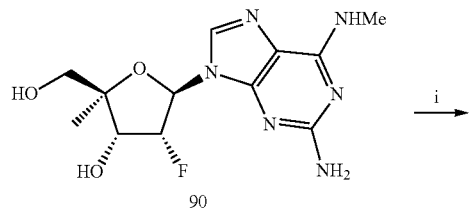

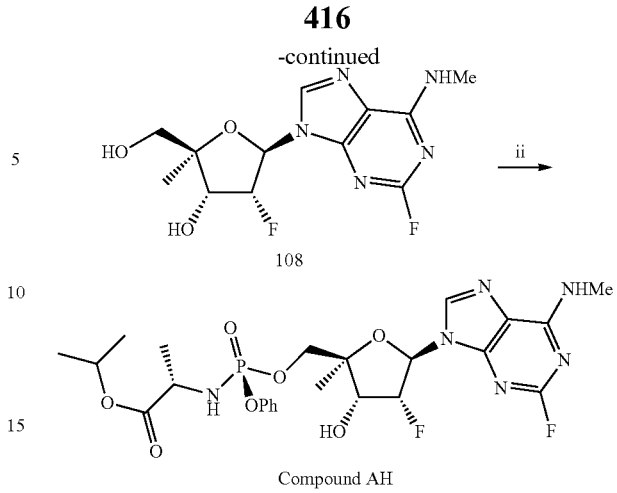

Compound AH i) tBuONO, pyridine, HF, pyridine, −15° C.; ii) Isopropyl ((S)-(pentafluorophenoxy)-phenoxy-phosphoryl)-L-alaninate, t-BuMgCl, DMF, −10° C.

Step 1: Preparation of (2R,3R,4R,5R)-5-(6-(Methylamino)-2-fluoro-9H-purin-9-yl)-4-fluoro-2-(hydroxymethyl)-2-methyltetrahydrofuran-3-ol (108)

A solution of compound 90 (120 mg, 0.38 mmol) in dry pyridine (1.0 mL) was cooled down to −15° C. and pyridine hydrofluoride (495 μL) was added. Then, tert-butyl nitrite (95 μL, 0.76 mmol) was added drop-wise over 5 mins. The mixture was stirred at 10° C. for 4 h and quenched by addition of a suspension of CaCO$_3$ (1.5 g) in H$_2$O (4 mL). The resulting suspension was stirred at RT for 15 mins and extracted with EtOAc (5×10 mL). The combined organics were dried over anhydrous Na$_2$SO$_4$ and concentrated. The residue was purified by column chromatography (silica gel, DCM/MeOH 0 to 10%). Product 108 (72 mg, 60% yield) was obtained as an off-white solid. $^1$H NMR (300 MHz, CD$_3$OD) δ 8.24 (s, 1H), 6.20 (dd, J=14.8, 4.1 Hz, 1H), 5.44 (dt, J=53.3, 4.7 Hz, 1H), 4.58 (dd, J=13.4, 5.0 Hz, 1H), 3.66 (d, J=12.3 Hz) and 3.55 (d, J=12.3 Hz, 2H), 3.06 (br. s, 3H), 1.28 (s, 3H). MS (ESI) m/z calcd. for C$_{12}$H$_{16}$F$_2$N$_5$O$_3$ [M+H]$^+$ 316.1; found 316.2.

Step 2: Preparation of (S)-Isopropyl 2-(((S)-(((2R,3R,4R,5R)-5-(6-(methylamino)-2-fluoro-9H-purin-9-yl)-4-fluoro-3-hydroxy-2-methyltetrahydrofuran-2-yl)methoxy)(phenoxy)phosphoryl)amino) propanoate (Compound AH)

To a solution of compound 108 (60 mg, 0.19 mmol) in dry DMF (3.0 mL) was added tert-butylmagnesium chloride (0.7 N in THF) (365 μL, 0.26 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (96 mg, 0.22 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, PE/EtOAc 10 to 100%) and by reverse phase column chromatography (C-18 silica, H₂O/MeOH 0 to 100%). Compound AH (22 mg, 18% yield) was obtained as a white solid. ¹H NMR (300 MHz, CD₃OD) δ 8.55 (s, 1H), 7.34-7.08 (m, 5H), 6.28 (br. d, J=16.8 Hz, 1H), 5.68-5.43 (m, 1H), 5.01-4.69 (overlapped with H₂O, m, 2H), 4.24-4.05 (m, 2H), 3.85 (m, 1H), 3.05 (s, 3H), 1.36 (br. s, 3H), 1.33-1.13 (m, 9H). ³¹P NMR (121 MHz, CD₃OD) δ 2.06 (s). MS (ESI) m/z calcd. for C₂₄H₃₂F₂N₆O₇P [M+H]⁺ 585.2; found 585.2.

Scheme 21: Preparation of (S)-Isopropyl 2-(((S)-(((2R,3R,4R,5R)-5-(2-amino-6-(methylamino)-9H-purin-9-yl)-2-(chloromethyl)-4-fluoro-3-hydroxytetrahydrofuran-2-yl)methoxy)(phenoxy)phosphoryl)amino) propanoate (Compound AI).

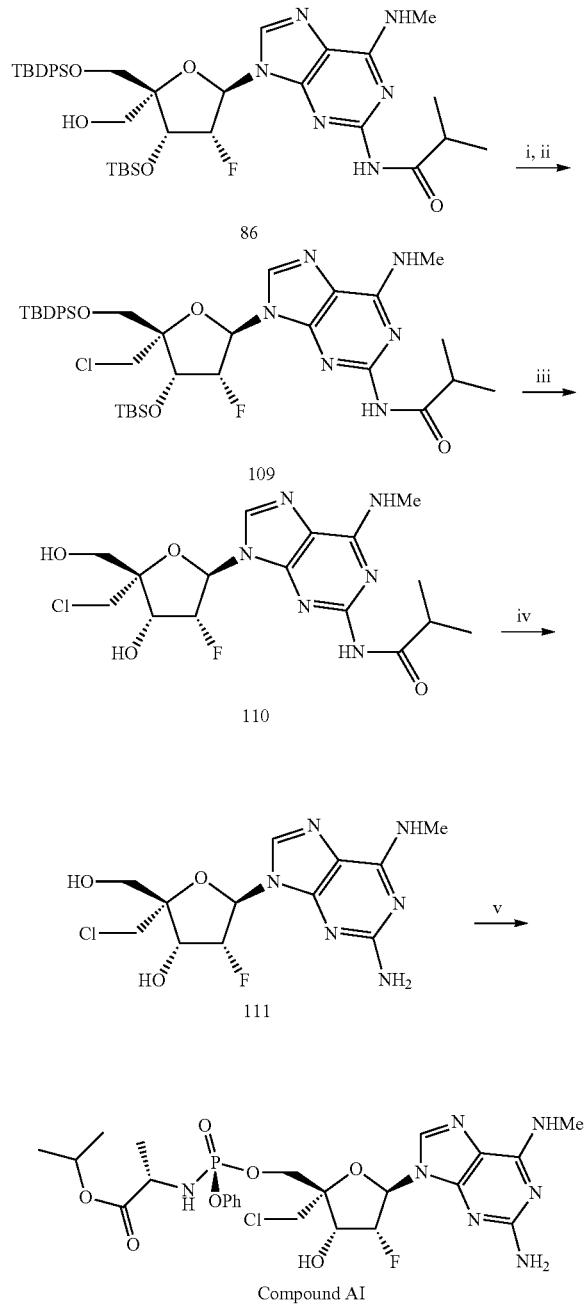

i) Tf₂O, pyridine, DCM, 0° C.; ii) LiCl, DMF, 40° C.; iii) TBAF, THF; iv) MeNH₂, EtOH, 75° C.; v) Isophropyl ((S)-(pentafluorophenoxy)-phenoxy-phosphoryl)-L-alaninate, t-BuMgCl, DMF, -10° C.

Step 1 and Step 2: Preparation of N-(9-((2R,3R,4R, 5R)-4-((tert-Butyldimethylsilyl)oxy)-5-(((tert-butyldiphenylsilyl)oxy) methyl)-5-(chloromethyl)-3-fluorotetrahydrofuran-2-yl)-6-(methylamino)-9H-purin-2-yl)isobutyramide (109)

To a solution of compound 86 (420 mg, 0.56 mmol) in dry DCM (12 mL) was added pyridine (227 μL, 2.81 mmol) and triflic anhydride (145 μL, 0.84 mmol) at 0° C. The resulting orange solution was stirred for 20 mins at 0° C. and H₂O (5 mL) was added. After a further 30 mins, the mixture was diluted with EtOAc (50 mL) and brine (40 mL). The layers were separated and the organics were dried over anhydrous Na₂SO₄ and concentrated. The residue was dissolved in dry DMF (22 mL) and LiCl (238 mg, 5.62 mmol) was added. The suspension was stirred for 15 h at 40° C. and concentrated. Then, EtOAc (80 mL) was added and the solution was washed with satd. NH₄Cl aq. solution (2×40 mL), Na₂S₂O₃ aq. solution (40 mL) and brine (40 mL). The organics were dried over anhydrous Na₂SO₄ and concentrated. The residue was purified by column chromatography (silica gel, PE/EtOAc 0 to 50%). Product 109 (336 mg, 78% yield over 2 steps) was obtained as an off-white solid.

Step 3: Preparation of N-(9-((2R,3R,4R,5R)-5-(Chloromethyl)-3-fluoro-4-hydroxy-5-(hydroxymethyl) tetrahydrofuran-2-yl)-6-(methyamino)-9H-purin-2-yl)isobutyramide (110)

To a solution of compound 109 (290 mg, 0.38 mmol) in dry THF (5 mL) was added tetrabutylammonium fluoride (1 N in THF) (1.1 mL, 1.1 mmol). The solution was stirred for 1 h at RT and concentrated. The residue was purified by column chromatography (silica gel, DCM/MeOH 0 to 10%). Product 110 (145 mg, 92% yield) was obtained as a white solid.

Step 4: Preparation of (2R,3R,4R,5R)-5-(2-Amino-6-(methylamino)-9H-purin-9-yl)-2-(chloromethyl)-4-fluoro-2-(hydroxymethyl)tetrahydrofuran-3-ol (111)

A solution of compound 110 (140 mg, 0.34 mmol) in methylamine (33% in EtOH) (10 mL) in a sealed container was stirred for 15 h at 75° C. and concentrated. The residue was purified by column chromatography (silica gel, DCM/MeOH 0 to 15%). Product 111 (107 mg, 92% yield) was obtained as a white solid. ¹H NMR (300 MHz, CD₃OD) δ 7.88 (s, 1H), 6.14 (dd, J=12.5, 6.4 Hz, 1H), 5.73 (dt, J=52.8, 6.2 Hz, 1H), 4.63 (t, J=4.7 Hz, 1H), 3.94-3.84 (m, 3H), 3.73 (d, J=11.5 Hz, 1H), 3.04 (br s, 3H). MS (ESI) m/z calcd. for C₁₂H₁₇ClFN₆O₃ [M+H]⁺ 347.1; found 347.0.

Step 5: Preparation of (S)-Isopropyl 2-(((S)-(((2R, 3R,4R,5R)-5-(2-amino-6-(methylamino)-9H-purin-9-yl)-2-(chloromethyl)-4-fluoro-3-hydroxytetrahydrofuran-2-yl)methoxy)(phenoxy) phosphoryl) amino) propanoate (Compound AI)

To a solution of compound 111 (74 mg, 0.21 mmol) in dry DMF (3.0 mL) was added tert-butylmagnesium chloride (0.7 N in THF) (428 μL, 0.30 mmol) drop-wise at -5° C. The solution was stirred for 15 mins at 0° C. and for 45 mins at RT. Then, the reaction mixture was cooled down to -10° C. and a solution of isopropyl ((S)-(pentafluorophenoxy)-phenoxy-phosphoryl)-L-alaninate (115 mg, 0.26 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound AI (31 mg, 23% yield) was obtained as a white solid. $^1$H NMR (300 MHz, CD$_3$OD) δ 7.83 (s, 1H), 7.41-7.15 (m, 5H), 6.18 (dd, J=14.7, 4.8 Hz, 1H), 5.79 (dt, J=52.5, 4.8 Hz, 1H), 5.02-4.82 (overlapping with H$_2$O, m, 2H), 4.61 (dd, J=10.8, 6.6 Hz) and 4.37 (dd, J=10.8, 5.0 Hz, 2H), 3.97-3.80 (m, 2H), 3.03 (br. s, 3H), 1.35-1.14 (m, 9H). $^{31}$P NMR (121 MHz, CD$_3$OD) δ 2.42 (s). MS (ESI) m/z calcd. for C$_{24}$H$_{33}$ClFN$_7$O$_7$P [M+H]$^+$ 616.2; found 616.2.

Scheme 22: Preparation of (S)-Isopropyl 2-(((S)-(((2R,3R,4R,5R)-5-(6-methylamino)-2-fluoro-9H-purin-9-yl)-2-(chloromethyl)-4-fluoro-3-hydroxytetrahydrofuran-2-yl)methoxy)(phenoxy)phosphoryl)amino) propanoate (Compound AJ).

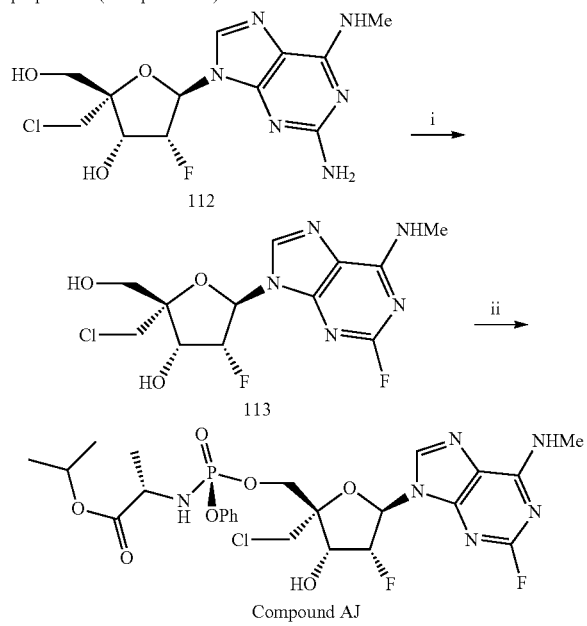

Compound AJ
i) tBuONO, pyridine, HF, pyridine, -15° C.; ii) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(6-(Methylamino)-2-fluoro-9H-purin-9-yl)-2-(chloromethyl)-4-fluoro-2-(hydroxymethyl)tetrahydrofuran-3-ol (113)

A solution of compound 112 (111 mg, 0.32 mmol) in dry pyridine (1.0 mL) was cooled down to -15° C. and pyridine hydrofluoride (420 μL) was added. Then, tert-butyl nitrite (79 μL, 0.64 mmol) was added drop-wise over 5 mins. The mixture was stirred at 10° C. for 4 h and quenched by addition of a suspension of CaCO$_3$ (1.7 g) in H$_2$O (4 mL). The resulting suspension was stirred at RT for 15 mins and extracted with EtOAc (5×10 mL). The combined organics were dried over anhydrous Na$_2$SO$_4$ and concentrated. The residue was purified by column chromatography (silica gel, DCM/MeOH 0 to 9%). Product 113 (70 mg, 62% yield) was obtained as an off-white solid. $^1$H NMR (300 MHz, CD$_3$OD) δ 8.22 (s, 1H), 6.25 (dd, J=13.0, 5.6 Hz, 1H), 5.44 (dt, J=52.9, 5.3 Hz, 1H), 4.70 (dd, J=7.8, 4.9 Hz, 1H), 3.95-3.76 (m, 4H), 3.07 (br. s, 3H). MS (ESI) m/z calcd. for C$_{12}$H$_{15}$ClF$_2$N$_5$O$_3$ [M+H]$^+$ 350.1; found 350.2.

Step 2: Preparation of (S)-Isopropyl 2-(((S)-(((2R, 3R,4R,5R)-5-(6-(methylamino)-2-fluoro-9H-purin-9-yl)-2-(chloromethyl)-4-fluoro-3-hydroxytetrahydrofuran-2-yl)methoxy)(phenoxy) phosphoryl) amino) propanoate (Compound AJ)

To a solution of compound 113 (55 mg, 0.17 mmol) in dry DMF (3.0 mL) was added tert-butylmagnesium chloride (0.7 N in THF) (330 μL, 0.24 mmol) drop-wise at -5° C. The solution was stirred for 20 mins at 0° C. and for 40 mins at RT. Then, the reaction mixture was cooled down to -10° C. and a solution of isopropyl ((S)-(pentafluorophenoxy)-phenoxy-phosphoryl)-L-alaninate (85 mg, 0.20 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, DCM/MeOH 0 to 9%) and by reverse phase column chromatography (C-18 silica, H$_2$O/MeOH 0 to 100%). Compound AJ (20 mg, 17% yield) was obtained as a white solid. $^1$H NMR (300 MHz, CD$_3$OD) δ 8.13 (s, 1H), 7.35-7.13 (m, 5H), 6.28 (dd, J=14.7, 4.5 Hz, 1H), 5.76 (dt, J=52.4, 4.6 Hz, 1H), 5.00-4.86 (overlapped with H$_2$O, m, 2H), 4.44 (dd, J=10.9, 6.0 Hz) and 4.36 (dd, J=10.9, 5.1 Hz, 2H), 3.97-3.83 (m, 2H), 3.02 (br. s, 3H), 1.36-1.12 (m, 9H). $^{31}$P NMR (121 MHz, CD$_3$OD) δ 2.38 (s). MS (ESI) m/z calcd. for C$_{24}$H$_{31}$ClF$_2$N$_6$O$_7$P [M+H]$^+$ 619.2; found 619.2.

Scheme 23: Preparation of (S)-Isopropyl 2-(((S)-(((2R,3R,4S,5R)-5-(2-amino-6-(methylamino)-9H-purin-9-yl)-4-fluoro-3-hydroxy-2-methyltetrahydrofuran-2-yl)methoxy)(phenoxy)phosphoryl)amino) propanoate (Compound AK).

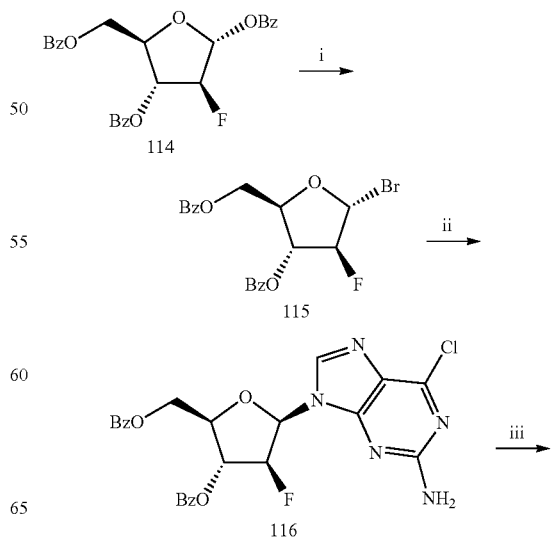

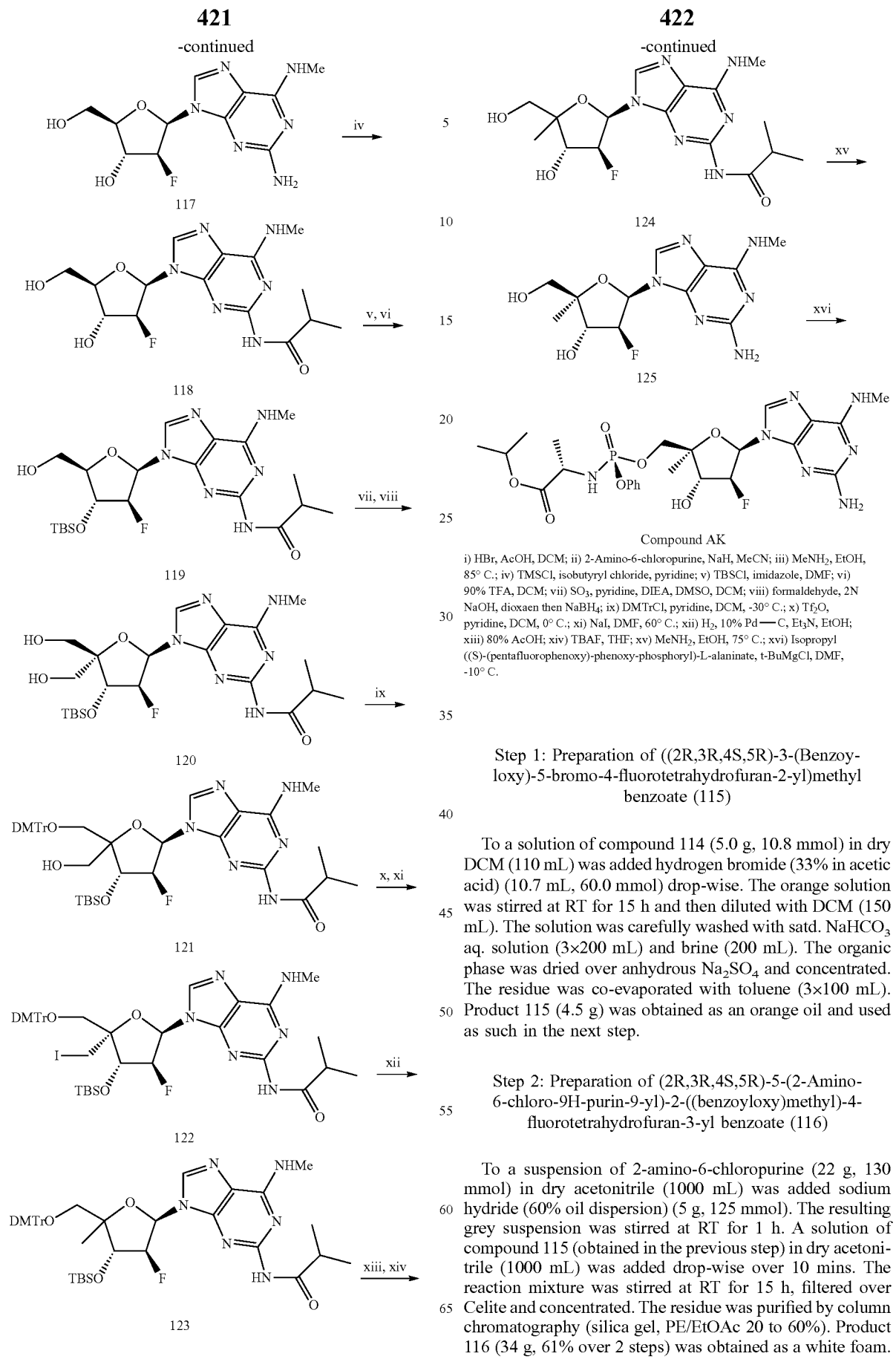

i) HBr, AcOH, DCM; ii) 2-Amino-6-chloropurine, NaH, MeCN; iii) MeNH₂, EtOH, 85° C.; iv) TMSCl, isobutyryl chloride, pyridine; v) TBSCl, imidazole, DMF; vi) 90% TFA, DCM; vii) SO₃, pyridine, DIEA, DMSO, DCM; viii) formaldehyde, 2N NaOH, dioxaen then NaBH₄; ix) DMTrCl, pyridine, DCM, -30° C.; x) Tf₂O, pyridine, DCM, 0° C.; xi) NaI, DMF, 60° C.; xii) H₂, 10% Pd—C, Et₃N, EtOH; xiii) 80% AcOH; xiv) TBAF, THF; xv) MeNH₂, EtOH, 75° C.; xvi) Isopropyl ((S)-(pentafluorophenoxy)-phenoxy-phosphoryl)-L-alaninate, t-BuMgCl, DMF, -10° C.

Step 1: Preparation of ((2R,3R,4S,5R)-3-(Benzoyloxy)-5-bromo-4-fluorotetrahydrofuran-2-yl)methyl benzoate (115)

To a solution of compound 114 (5.0 g, 10.8 mmol) in dry DCM (110 mL) was added hydrogen bromide (33% in acetic acid) (10.7 mL, 60.0 mmol) drop-wise. The orange solution was stirred at RT for 15 h and then diluted with DCM (150 mL). The solution was carefully washed with satd. NaHCO₃ aq. solution (3×200 mL) and brine (200 mL). The organic phase was dried over anhydrous Na₂SO₄ and concentrated. The residue was co-evaporated with toluene (3×100 mL). Product 115 (4.5 g) was obtained as an orange oil and used as such in the next step.

Step 2: Preparation of (2R,3R,4S,5R)-5-(2-Amino-6-chloro-9H-purin-9-yl)-2-((benzoyloxy)methyl)-4-fluorotetrahydrofuran-3-yl benzoate (116)

To a suspension of 2-amino-6-chloropurine (22 g, 130 mmol) in dry acetonitrile (1000 mL) was added sodium hydride (60% oil dispersion) (5 g, 125 mmol). The resulting grey suspension was stirred at RT for 1 h. A solution of compound 115 (obtained in the previous step) in dry acetonitrile (1000 mL) was added drop-wise over 10 mins. The reaction mixture was stirred at RT for 15 h, filtered over Celite and concentrated. The residue was purified by column chromatography (silica gel, PE/EtOAc 20 to 60%). Product 116 (34 g, 61% over 2 steps) was obtained as a white foam.

Step 3: Preparation of (2R,3R,4S,5R)-5-(2-Amino-6-(methylamino)-9H-purin-9-yl)-4-fluoro-2-(hydroxymethyl) tetrahydrofuran-3-ol (117)

A solution of compound 116 (18.9 g, 36.9 mmol) in methylamine (33% in EtOH) (300 mL) was heated at 85° C. in a sealed container for 3 h, cooled down to RT and concentrated. The residue was purified by column chromatography (silica gel, DCM/MeOH 0 to 15%). Product 117 (10.9 g, 95% yield) was obtained as a white solid.

Step 4: Preparation of N-(9-((2R,3S,4R,5R)-3-Fluoro-4-hydroxy-5-(hydroxymethyl)tetrahydrofuran-2-yl)-6-(methylamino)-9H-purin-2-yl)isobutyramide (118)

To a solution of compound 117 (11.0 g, 36.9 mmol) in dry pyridine (180 mL) was added trimethylsilyl chloride (19.0 mL, 147.6 mmol) drop-wise at 0° C. The reaction mixture was stirred for 15 mins at 0° C. and then, isobutyryl chloride (4.3 mL, 40.6 mmol) was added drop-wise over 5 mins. The reaction mixture was stirred at RT for 1 h and cooled down to 0° C. Water (100 mL) and ammonia (33% in $H_2O$) (150 mL) were added. The mixture was stirred at RT for 1 h, concentrated and co-evaporated with toluene (3×150 mL). The residue was purified by column chromatography (silica gel, DCM/MeOH 0 to 5%). Product 118 (8.8 g, 65% yield) was obtained as a white foam.

Step 5 and Step 6: Preparation of N-(9-((2R,3S,4R,5R)-4-((tert-Butyldimethylsilyl)oxy)-3-fluoro-5-(hydroxymethyl) tetrahydrofuran-2-yl)-6-(methylamino)-9H-purin-2-yl)isobutyramide (119)

To a solution of compound 118 (10.8 g, 29.3 mmol) in dry DMF (100 mL) was added imidazole (12.0 g, 176.0 mmol) and TBSCl (26.5 g, 176.0 mmol). The reaction mixture was stirred at RT for 15 h and diluted with EtOAc (400 mL). The resulting suspension was filtered through Celite and concentrated. The white residue was dissolved in DCM (200 mL) and treated with $TFA/H_2O$ (9:1, 20 mL) at 0° C. for 15 h. Then, the reaction was quenched by addition of solid $NaHCO_3$ (40 g) and filtered. The solution was washed with satd. $NaHCO_3$ aq. solution (2×150 mL) and brine (150 mL). The organic phase was dried over anhydrous $Na_2SO_4$ and concentrated. The residue was purified by column chromatography (silica gel, PE/EtOAc 0 to 80%). Product 119 (6.3 g, 45% yield over 2 steps) was obtained as a white foam.

Step 7 and Step 8: Preparation of N-(9-((2R,3S,4R)-4-((tert-Butyldimethylsilyl)oxy)-3-fluoro-5,5-bis(hydroxymethyl) tetrahydrofuran-2-yl)-6-(methylamino)-9H-purin-2-yl)isobutyramide (120)

To a solution of compound 119 (6.3 g, 13.0 mmol) in dry DCM (115 mL) at 0° C. was added diisopropylethylamine (8.8 mL, 50.7 mmol) and a suspension of $SO_3$ pyridine complex (6.2 g, 39.0 mmol) in dry DMSO (12.0 mL). The orange solution was stirred for 15 h at RT. Then, $H_2O$ (150 mL) was added, the phases were separated and the aqueous layer was back-extracted with EtOAc (2×150 mL). The combined organics were washed with brine (200 mL), dried over anhydrous $Na_2SO_4$ and concentrated. The residue was dissolved in dioxane (75 mL). Formaldehyde (37% in $H_2O$) (4.2 mL, 54.6 mmol) and 2 N NaOH (9.7 mL, 19.4 mmol) were added and the yellow solution was stirred for 3 h at RT. The mixture was cooled down to 0° C. and sodium borohydride (2.0 g, 52.0 mmol) was added portion-wise. The cloudy solution was stirred for 1 h at RT and quenched by addition of satd. $NH_4Cl$ aq. solution (300 mL). The product was extracted with EtOAc (3×250 mL). The combined organics were washed with brine (250 mL), dried over anhydrous $Na_2SO_4$ and concentrated. The residue was purified by column chromatography (silica gel, DCM/MeOH 0 to 10%). Product 120 (3.3 g, 50% yield over 2 steps) was obtained as a white solid.

Step 9: Preparation of N-(9-((2R,3S,4R)-5-((bis(4-Methoxyphenyl)(phenyl)methoxy)methyl)-4-((tert-butyldimethylsilyl)oxy)-3-fluoro-5-(hydroxymethyl) tetrahydrofuran-2-yl)-6-(methylamino)-9H-purin-2-yl)isobutyramide (121)

To a solution of compound 120 (1.9 g, 3.6 mmol) in dry DCM (20 mL) was added pyridine (3.0 mL) and a solution of dimethoxytrityl chloride (1.7 g, 5.1 mmol) in dry DCM (5 mL) drop-wise at −30° C. The resulting orange solution was stirred for 2 h at −10° C. MeOH (20 mL) was added and the mixture was concentrated. The residue was purified by column chromatography (silica gel, PE/EtOAc 0 to 100%). Product 121 (1.6 g, 55% yield—mixture of regioisomers) was obtained as a yellow foam.

Step 10 and Step 11: Preparation of N-(9-((2R,3S,4R)-5-((bis(4-Methoxyphenyl)(phenyl)methoxy)methyl)-4-((tert-butyldimethylsilyl)oxy)-3-fluoro-5-(iodomethyl)tetrahydrofuran-2-yl)-6-(methylamino)-9H-purin-2-yl)isobutyramide (122)

To a solution of compound 120 (800 mg, 0.97 mmol) in dry DCM (20 mL) was added pyridine (395 μL, 4.85 mmol) and triflic anhydride (249 μL, 1.46 mmol) at 0° C. The resulting orange solution was stirred for 20 mins at 0° C. and $H_2O$ (8 mL) was added. After a further 30 mins, the mixture was diluted with EtOAc (70 mL) and brine (60 mL). The layers were separated and the organics were dried over anhydrous $Na_2SO_4$ and concentrated. The residue was dissolved in dry DMF (35 mL) and NaI (1.15 g, 7.80 mmol) was added. The suspension was stirred for 15 h at 60° C. and concentrated. Then, EtOAc (100 mL) was added and the solution was washed with satd. $NH_4Cl$ aq. solution (2×60 mL), $Na_2S_2O_3$ aq. solution (60 mL) and brine (60 mL). The organics were dried over anhydrous $Na_2SO_4$ and concentrated. The residue was purified by column chromatography (silica gel, PE/EtOAc 0 to 40%). Product 122 (525 mg, 58% yield over 2 steps—mixture of regioisomers) was obtained as an orange solid.

Step 12: Preparation of N-(9-((2R,3S,4R)-5-((bis(4-Methoxyphenyl)(phenyl)methoxy)methyl)-4-((tert-butyldimethylsilyl)oxy)-3-fluoro-5-methyltetrahydrofuran-2-yl)-6-(methylamino)-9H-purin-2-yl) isobutyramide (123)

To a solution of compound 122 (400 mg, 0.43 mmol) in EtOH (8 mL) was added triethylamine (313 μL, 2.16 mmol) and palladium (10% on charcoal) (50 mg). The flask was put under an atmosphere of hydrogen and stirred for 24 h at RT. The reaction mixture was filtered over Celite and concentrated. Product 123 (345 mg) was obtained as a yellow solid and used as such in the next step.

Step 13 and Step 14: Preparation of N-(9-((2R,3S,4R)-3-Fluoro-4-hydroxy-5-(hydroxymethyl)-5-methyltetrahydrofuran-2-yl)-6-(methylamino)-9H-purin-2-yl)isobutyramide (124)

Compound 123 (345 mg, 0.43 mmol) was dissolved in 80% acetic acid (5 mL) and stirred for 15 h at RT. The solution was poured into satd. NaHCO$_3$ aq. solution (100 mL) and the mixture was extracted with EtOAc (3×60 mL). The combined organics were washed with brine (50 mL), dried over anhydrous Na$_2$SO$_4$ and concentrated. The residue was dissolved in dry THF (6 mL) and tetrabutylammonium fluoride (1 N in THF) (640 µL, 0.64 mmol) was added. The solution was stirred for 1 h at RT and concentrated. The residue was purified by column chromatography (silica gel, DCM/MeOH 0 to 9%). Product 124 (135 mg, 82% yield over 3 steps—mixture of regioisomers) was obtained as a white solid.

Step 15: Preparation of (2R,3R,4S,5R)-5-(2-Amino-6-(methylamino)-9H-purin-9-yl)-4-fluoro-2-(hydroxymethyl)-2-methyltetrahydrofuran-3-ol (125)

A solution of compound 124 (134 mg, 0.35 mmol) in methylamine (33% in EtOH) (8 mL) in a sealed container was stirred for 15 h at 75° C. and concentrated. The residue was purified by column chromatography (silica gel, DCM/MeOH 0 to 15%). Product 125 (55 mg, 48% yield) was obtained as a white solid. $^1$H NMR (300 MHz, CD$_3$OD) δ 7.93 (m, 1H), 6.30 (dd, J=12.5, 5.0 Hz, 1H), 5.19 (dt, J=53.3, 4.8 Hz, 1H), 4.62 (m, 1H), 3.68-3.57 (m, 2H), 3.05 (br. s, 3H), 1.25 (s, 3H). MS (ESI) m/z calcd. for C$_{12}$H$_{18}$FN$_6$O$_3$ [M+H]$^+$ 313.1; found 313.2.

Step 16: Preparation of (S)-Isopropyl 2-(((S)-(((2R,3R,4S,5R)-5-(2-amino-6-(methylamino)-9H-purin-9-yl)-4-fluoro-3-hydroxy-2-methyltetrahydrofuran-2-yl)methoxy)(phenoxy)phosphoryl)amino)propanoate (Compound AK)

To a solution of compound 125 (50 mg, 0.15 mmol) in dry DMF (2.0 mL) was added tert-butylmagnesium chloride (0.7 N in THF) (275 µL, 0.20 mmol) drop-wise at −5° C. The solution was stirred for 15 mins at 0° C. and for 45 mins at RT. Then, the reaction mixture was cooled down to −10° C. and a solution of isopropyl ((S)-(pentafluorophenoxy)-phenoxy-phosphoryl)-L-alaninate (76 mg, 0.17 mmol) in dry DMF (1.5 mL) was added drop-wise. The resulting solution was slowly warmed up to 10° C. and stirred for 15 h at this temperature. The reaction mixture was then diluted with EtOAc (10 mL) and satd. NH$_4$Cl aq. solution (8 mL). The phases were separated and the aqueous layer was back-extracted with EtOAc (2×5 mL). The combined organics were washed with satd. NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound AK (15 mg, 16%) was obtained as a white solid. $^1$H NMR (300 MHz, CD$_3$OD) δ 7.82 (s, 1H), 7.41-7.14 (m, 5H), 6.33 (dd, J=16.7, 3.9 Hz, 1H), 5.26-5.01 (m, 1H), 5.00-4.77 (overlapped with H$_2$O, m, 1H), 4.52 (m, 1H), 4.25-4.13 (m, 2H), 3.90 (m, 1H), 3.04 (br. s, 3H), 1.37-1.16 (m, 12H). $^{31}$P NMR (121 MHz, CD$_3$OD) δ 2.17 (s). MS (ESI) m/z calcd. for C$_{24}$H$_{34}$FN$_7$O$_7$P [M+H]$^+$ 582.2; found 582.2.

Scheme 24: Step 6: Preparation of (S)-Isopropyl 2-(((S)-(((2R,3R,4S,5R)-5-(2-amino-6-(methylamino)-9H-purin-9-yl)-2-(chloromethyl)-4-fluoro-3-hydroxytetrahydrofuran-2-yl)methoxy)(phenoxy)phosphoryl)amino)propanoate (Compound AL).

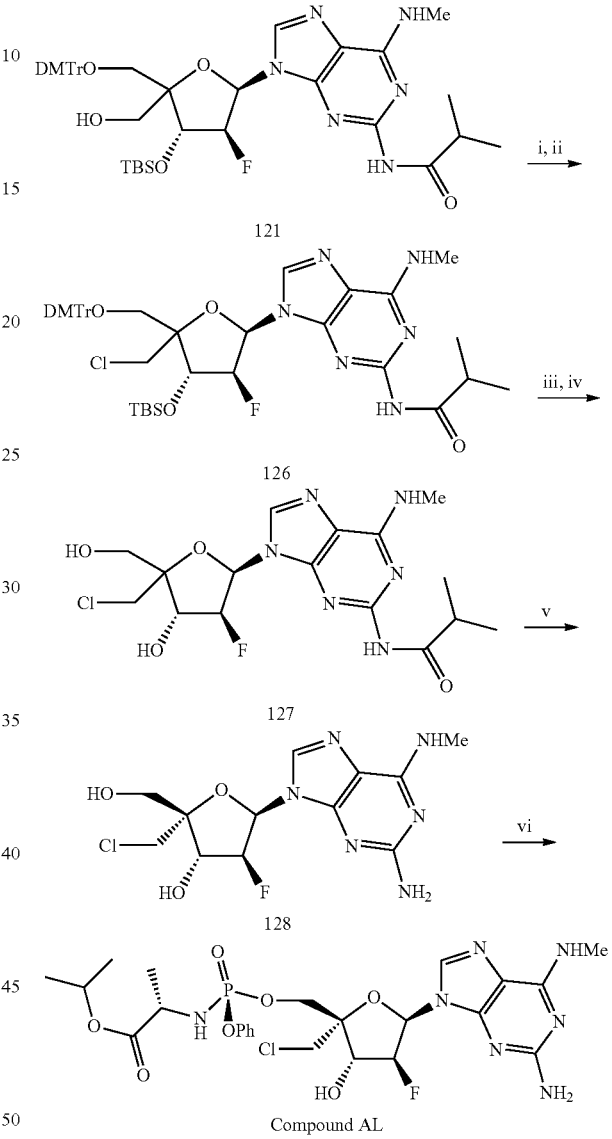

i) Tf$_2$O, pyridine, DCM, 0° C.; ii) LiCl, DMF, 40° C.; iii) 80% AcOH; iv) TBAF, THF; v) MeNH$_2$, EtOH, 75° C.; vi) Isopropyl ((S)-(pentafluorophenoxy)-phenoxy-phosphoryl)-L-alaninate, t-BuMgCl, DMF, -10° C.

Step 1 and Step 2: Preparation of N-(9-((2R,3S,4R)-5-((bis(4-Methoxyphenyl)(phenyl)methoxy)methyl)-4-((tert-butyldimethylsilyl)oxy)-5-(chloromethyl)-3-fluorotetrahydrofuran-2-yl)-6-(methylamino)-9H-purin-2-yl)isobutyramide (126)

To a solution of compound 121 (900 mg, 1.10 mmol) in dry DCM (25 mL) was added pyridine (450 µL, 5.58 mmol) and triflic anhydride (285 µL, 1.66 mmol) at 0° C. The resulting orange solution was stirred for 20 mins at 0° C. and H$_2$O (10 mL) was added. After a further 30 mins, the mixture was diluted with EtOAc (100 mL) and brine (80 mL). The layers were separated and the organics were dried over anhydrous $Na_2SO_4$ and concentrated. The residue was dissolved in dry DMF (50 mL) and LiCl (465 mg, 11.0 mmol) was added. The suspension was stirred for 15 h at 40° C. and concentrated. Then, EtOAc (150 mL) was added and the solution was washed with satd. $NH_4Cl$ aq. solution (2×80 mL), $Na_2S_2O_3$ aq. solution (80 mL) and brine (80 mL). The organics were dried over anhydrous $Na_2SO_4$ and concentrated. The residue was purified by column chromatography (silica gel, PE/EtOAc 0 to 50%). Product 126 (685 mg, 75% yield over 2 steps—mixture of regioisomers) was obtained as a yellow solid.

Step 3 and Step 4: Preparation of N-(9-((2R,3S,4R)-5-(Chloromethyl)-3-fluoro-4-hydroxy-5-(hydroxymethyl) tetrahydrofuran-2-yl)-6-(methylamino)-9H-purin-2-yl)isobutyramide (127)

Compound 126 (500 mg, 0.60 mmol) was dissolved in 80% acetic acid (10 mL) and stirred for 15 h at RT. The solution was poured into satd. $NaHCO_3$ aq. solution (180 mL) and the mixture was extracted with EtOAc (3×100 mL). The combined organics were washed with brine (100 mL), dried over anhydrous $Na_2SO_4$ and concentrated. The residue was dissolved in dry THF (10 mL) and tetrabutylammonium fluoride (1 N in THF) (900 μL, 0.90 mmol) was added. The solution was stirred for 1 h at RT and concentrated. The residue was purified by column chromatography (silica gel, DCM/MeOH 0 to 8%). Product 127 (200 mg, 80% yield over 2 steps—mixture of regioisomers) was obtained as a white solid.

Step 5: Preparation of (2R,3R,4S,5R)-5-(2-Amino-6-(methylamino)-9H-purin-9-yl)-2-(chloromethyl)-4-fluoro-2-(hydroxymethyl)tetrahydrofuran-3-ol (128)

A solution of compound 127 (180 mg, 0.43 mmol) in methylamine (33% in EtOH) (20 mL) in a sealed container was stirred for 15 h at 75° C. and concentrated. The residue was purified by column chromatography (silica gel, DCM/MeOH 0 to 15%). Product 128 (66 mg, 44% yield) was obtained as a white solid. $^1H$ NMR (300 MHz, $CD_3OD$) δ 7.88 (m, 1H), 6.45 (dd, J=15.2, 4.5 Hz, 1H), 5.27 (dt, J=53.3, 4.1 Hz, 1H), 4.73 (dd, J=18.6, 3.7 Hz, 1H), 3.94-3.74 (m, 4H), 3.05 (br. s, 3H). MS (ESI) m/z calcd. for $C_{12}H_{17}ClFN_6O_3$ $[M+H]^+$ 347.1; found 347.2.

Step 6: Preparation of (S)-Isopropyl 2-(((S)-(((2R,3R,4S,5R)-5-(2-amino-6-(methylamino)-9H-purin-9-yl)-2-(chloromethyl)-4-fluoro-3-hydroxytetrahydrofuran-2-yl)methoxy)(phenoxy)phosphoryl) amino) propanoate (Compound AL)

To a solution of compound 128 (63 mg, 0.18 mmol) in dry DMF (2.5 mL) was added tert-butylmagnesium chloride (0.7 N in THF) (370 μL, 0.26 mmol) drop-wise at −5° C. The solution was stirred for 15 mins at 0° C. and for 45 mins at RT. Then, the reaction mixture was cooled down to −10° C. and a solution of isopropyl ((S)-(pentafluorophenoxy)-phenoxy-phosphoryl)-L-alaninate (99 mg, 0.22 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. $NH_4Cl$ aq. solution (15 mL). The phases were separated and the aqueous layer was back-extracted with EtOAc (2×10 mL). The combined organics were washed with satd. $NH_4Cl$ aq. solution (20 mL) and brine (20 mL), dried over $Na_2SO_4$ and concentrated. The residue was purified by column chromatography (silica gel, DCM/MeOH 0 to 10%) and by reverse phase column chromatography (C-18 silica, $H_2O$/MeOH 0 to 100%). Compound AL (22 mg, 20% yield) was obtained as a white solid. $^1H$ NMR (300 MHz, $CD_3OD$) δ 7.85 (m, 1H), 7.41-7.16 (m, 5H), 6.43 (dd, J=19.1, 3.5 Hz, 1H), 5.18 (m, 1H), 4.99-4.85 (overlapped with $H_2O$, m, 1H), 4.71 (m, 1H), 4.43 (m, 1H), 3.97-3.76 (m, 2H), 3.04 (br. s, 3H), 1.35-1.16 (m, 9H). $^{31}P$ NMR (121 MHz, $CD_3OD$) δ 2.12 (s). MS (ESI) m/z calcd. for $C_{24}H_{33}ClFN_7O_7P$ $[M+H]^+$ 616.2; found 616.2.

Scheme 25: Preparation of (S)-Isopropyl 2-(((S)-(((2R,3R,4R,5R)-5-(6-methylamino)-2-methoxy-9H-purin-9-yl)-4-fluoro-3-hydroxy-2-methyltetrahydrofuran-2-yl)methoxy)(phenoxy)phosphoryl)amino) propanoate (Compound AM).

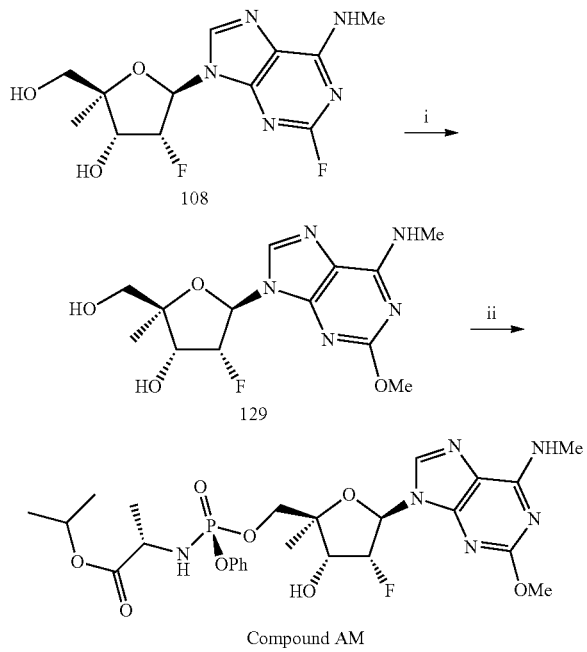

i) MeONa, MeOH, 60° C.; ii) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(6-(Methylamino)-2-methoxy-9H-purin-9-yl)-4-fluoro-2-(hydroxymethyl)-2-methyltetrahydrofuran-3-ol (129)

To a solution of compound 108 (130 mg, 0.41 mmol) in dry MeOH (10 mL) was added sodium methoxide (25% in MeOH) (180 μL, 0.78 mmol). The resulting solution was stirred at 60° C. for 5 h. The reaction was quenched by addition of acetic acid (60 μL) and the solvent was removed. The residue was purified by column chromatography (silica gel, DCM/MeOH 0 to 8%). Product 129 (38 mg, 28% yield) was obtained as a white solid. $^1H$ NMR (300 MHz, $CD_3OD$) δ 8.10 (s, 1H), 6.19 (dd, J=15.5, 4.2 Hz, 1H), 5.58 (dt, J=53.5, 4.6 Hz, 1H), 4.64 (dd, J=13.6, 5.0 Hz, 1H), 3.97 (s, 3H), 3.65 (d, J=12.2 Hz) and 3.55 (d, J=12.2 Hz, 2H), 3.07 (br. s, 3H), 1.28 (s, 3H). MS (ESI) m/z calcd. for $C_{13}H_{19}FN_5O_4$ $[M+H]^+$ 328.1; found 328.2.

Step 2: Preparation of (S)-Isopropyl 2-(((S)-(((2R,3R,4R,5R)-5-(6-(methylamino)-2-methoxy-9H-purin-9-yl)-4-fluoro-3-hydroxy-2-methyltetrahydrofuran-2-yl)methoxy)(phenoxy)phosphoryl) amino) propanoate (Compound AM)

To a solution of compound 129 (54 mg, 0.16 mmol) in dry DMF (2.5 mL) was added tert-butylmagnesium chloride (0.7 N in THF) (320 µL, 0.24 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (89 mg, 0.20 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, PE/EtOAc 10 to 100%) and by reverse phase column chromatography (C-18 silica, H$_2$O/MeOH 0 to 100%). Compound AM (19 mg, 19% yield) was obtained as a white solid. $^1$H NMR (300 MHz, CD$_3$OD) δ 7.99 (s, 1H), 7.32-7.10 (m, 5H), 6.21 (dd, J=18.3, 2.4 Hz, 1H), 5.61 (m, 1H), 4.93-4.82 (overlapped with H$_2$O, m, 2H), 4.20 (dd, J=11.0, 6.1 Hz) and 4.11 (dd, J=11.0, 5.0 Hz, 2H), 3.96 (s, 3H), 3.81 (m, 1H), 3.01 (br. s, 3H), 1.37-1.12 (m, 12H). $^{31}$P NMR (121 MHz, CD$_3$OD) δ 2.03 (s). MS (ESI) m/z calcd. for C$_{25}$H$_{35}$FN$_6$O$_8$P [M+H]$^+$ 597.2; found 597.2.

Scheme 26: Preparation of (S)-Isopropyl 2-(((S)-(((2R,3R,4R,5R)-5-(6-methylamino)-2-methoxy-9H-purin-9-yl)-2-(chloromethyl)-4-fluoro-3-hydroxytetrahydrofuran-2-yl)methoxy)(phenoxy)phosphoryl)amino) propanoate (Compound AN).

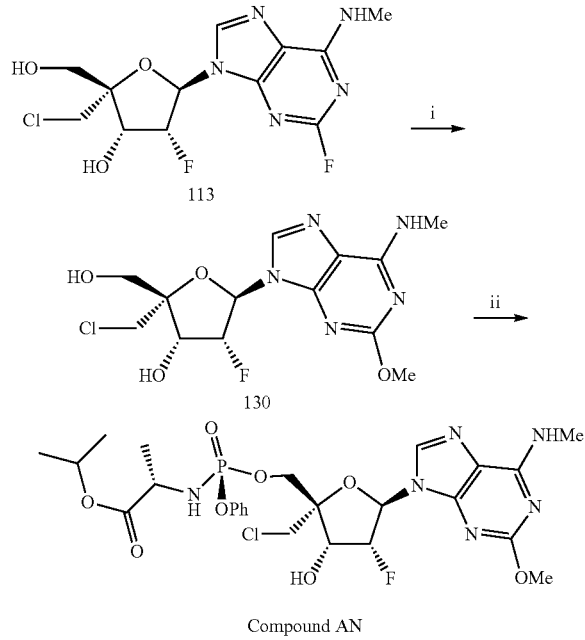

Compound AN i) MeONa, MeOH, 60° C.; ii) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(6-(Methylamino)-2-methoxy-9H-purin-9-yl)-2-(chloromethyl)-4-fluoro-2-(hydroxymethyl)tetrahydrofuran-3-ol (130)

To a solution of compound 113 (110 mg, 0.35 mmol) in dry MeOH (10 mL) was added sodium methoxide (25% in MeOH) (152 µL, 0.66 mmol). The resulting solution was stirred at 60° C. for 5 h. The reaction was quenched by addition of acetic acid (50 µL) and the solvent was removed. The residue was purified by column chromatography (silica gel, DCM/MeOH 0 to 8%). Product 130 (35 mg, 31% yield) was obtained as a white solid. $^1$H NMR (300 MHz, CD$_3$OD) δ 8.07 (s, 1H), 6.24 (dd, J=13.6, 5.6 Hz, 1H), 5.78 (dt, J=53.0, 5.1 Hz, 1H), 4.75 (dd, J=8.1, 4.9 Hz, 1H), 3.98 (s, 3H), 3.94-3.77 (m, 4H), 3.08 (br. s, 3H). MS (ESI) m/z calcd. for C$_{13}$H$_{18}$ClFN$_5$O$_4$ [M+H]$^+$ 362.1; found 362.2.

Step 2: Preparation of (S)-Isopropyl 2-(((S)-(((2R,3R,4R,5R)-5-(6-(methylamino)-2-methoxy-9H-purin-9-yl)-2-(chloromethyl)-4-fluoro-3-hydroxytetrahydrofuran-2-yl)methoxy)(phenoxy)phosphoryl) amino) propanoate (Compound AN)

To a solution of compound 130 (60 mg, 0.17 mmol) in dry DMF (3.0 mL) was added tert-butylmagnesium chloride (0.7 N in THF) (325 µL, 0.25 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (92 mg, 0.21 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, DCM/MeOH 0 to 9%) and by reverse phase column chromatography (C-18 silica, H$_2$O/MeOH 0 to 100%). Compound AN (21 mg, 21% yield) was obtained as a white solid. $^1$H NMR (300 MHz, CD$_3$OD) δ 8.00 (s, 1H), 7.36-7.13 (m, 5H), 6.27 (dd, J=15.3, 4.5 Hz, 1H), 5.89 (dt, J=52.6, 4.7 Hz, 1H), 5.01-4.82 (overlapped with H$_2$O, m, 1H), 4.45 (dd, J=10.7, 6.0 Hz) and 4.35 (dd, J=10.7, 5.0 Hz, 2H), 3.96 (s, 3H), 3.94-3.79 (m, 3H), 3.02 (br. s, 3H), 1.33-1.15 (m, 9H). $^{31}$P NMR (121 MHz, CD$_3$OD) δ 2.01 (s). MS (ESI) m/z calcd. for C$_{25}$H$_{34}$ClFN$_6$O$_8$P [M+H]$^+$ 531.2; found 531.2.

Scheme 27: Preparation of (S)-Isopropyl 2-(((S)-(((2R,3R,4R,5R)-5-(6-(dimethylamino)-2-isobutyramido-9H-purin-9-yl)-4-fluoro-3-hydroxy-2-methyltetrahydrofuran-2-yl)methoxy)(phenoxy)phosphoryl)amino) propanoate (Compound AO).

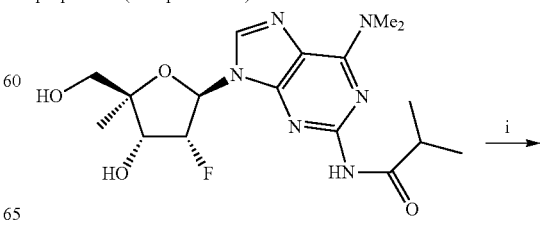

100

431
-continued

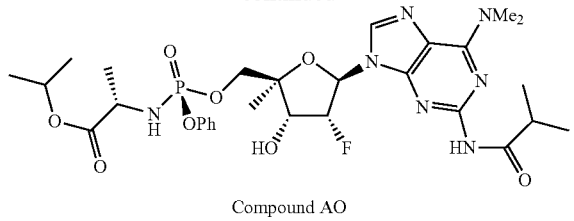

Compound AO i) Isopropyl ((S)-(pentafluorophenoxy)-phenoxy-phosphoryl)-L-alaninate, t-BuMgCl, DMF, -10° C.

Step 1: Preparation of (S)-Isopropyl 2-(((S)-(((2R,3R,4R,5R)-5-(6-(dimethylamino)-2-isobutyramido-9H-purin-9-yl)-4-fluoro-3-hydroxy-2-methyltetrahydrofuran-2-yl)methoxy)(phenoxy)phosphoryl)amino) propanoate (Compound AO)

To a solution of compound 100 (100 mg, 0.25 mmol) in dry DMF (3.0 mL) was added tert-butylmagnesium chloride (0.7 N in THF) (480 µL, 0.34 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (127 mg, 0.30 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, PE/EtOAc 10 to 100%) and by reverse phase column chromatography (C-18 silica, H$_2$O/MeOH 0 to 100%). Compound AO (35 mg, 21% yield) was obtained as a white solid. $^1$H NMR (300 MHz, CD$_3$OD) δ 8.02 (s, 1H), 7.31-7.08 (m, 5H), 6.26 (dd, J=18.9, 2.1 Hz, 1H), 5.60 (ddd, J=53.6, 5.2, 2.2 Hz, 1H), 5.14 (dd, J=21.3, 5.2 Hz, 1H), 4.92-4.80 (overlapped with H$_2$O, m, 1H), 4.19 (d, J=5.8 Hz, 2H), 3.83 (m, 1H), 3.44 (br. s, 6H), 2.88 (br. m, 1H), 1.38-1.12 (m, 18H). $^{31}$P NMR (121 MHz, CD$_3$OD) δ 3.60 (s). MS (ESI) m/z calcd. for C$_{29}$H$_{42}$FN$_7$O$_8$P [M+H]$^+$ 666.3; found 666.2.

Scheme 28: Preparation of (S)-Isopropyl 2-(((S)-(((2R,3R,4S,5R)-5-(6-(methylamino)-2-fluoro-9H-purin-9-yl)-4-fluoro-3-hydroxy-2-methyltetrahydrofuran-2-yl)methoxy)(phenoxy)phosphoryl)amino) propanoate (Compound AP).

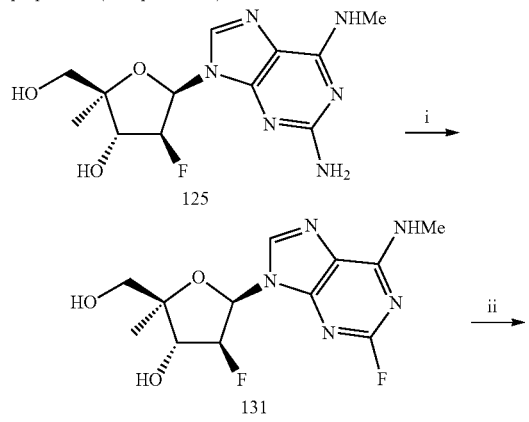

432
-continued

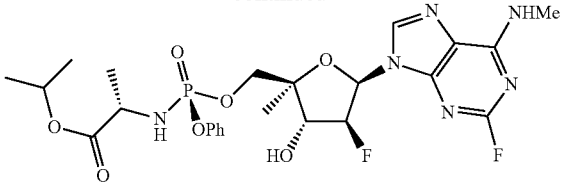

Compound AP i) tBuONO, pyridine, HF, pyridine, -15° C.; ii) Isopropyl ((S)-(pentafluorophenoxy)-phenoxy-phosphoryl)-L-alaninate, t-BuMgCl, DMF, -10° C.

Step 1: Preparation of (2R,3R,4S,5R)-5-(6-(Methylamino)-2-fluoro-9H-purin-9-yl)-4-fluoro-2-(hydroxymethyl)-2-methyltetrahydrofuran-3-ol (131)

A solution of compound 125 (150 mg, 0.48 mmol) in dry pyridine (1.5 mL) was cooled down to −15° C. and pyridine hydrofluoride (630 µL) was added. Then, tert-butyl nitrite (120 µL, 0.97 mmol) was added drop-wise over 5 mins. The mixture was stirred at 10° C. for 4 h and quenched by addition of a suspension of CaCO$_3$ (2.5 g) in H$_2$O (6 mL). The resulting suspension was stirred at RT for 15 mins and extracted with EtOAc (5×15 mL). The combined organics were dried over anhydrous Na$_2$SO$_4$ and concentrated. The residue was purified by column chromatography (silica gel, DCM/MeOH 0 to 9%). Product 131 (91 mg, 60% yield) was obtained as a white solid. $^1$H NMR (300 MHz, CD$_3$OD) δ 8.26 (s, 1H), 6.36 (dd, J=11.2, 5.1 Hz, 1H), 5.25 (dt, J=53.4, 5.0 Hz, 1H), 4.62 (dd, J=20.2, 4.9 Hz, 1H), 3.64 (s, 2H), 3.06 (br. s, 3H), 1.26 (s, 3H). MS (ESI) m/z calcd. for C$_{12}$H$_{16}$F$_2$N$_5$O$_3$ [M+H]$^+$ 316.1; found 316.2.

Step 2: Preparation of (S)-Isopropyl 2-(((S)-(((2R,3R,4S,5R)-5-(6-(methylamino)-2-fluoro-9H-purin-9-yl)-4-fluoro-3-hydroxy-2-methyltetrahydrofuran-2-yl)methoxy)(phenoxy) phosphoryl) amino) propanoate (Compound AP)

To a solution of compound 131 (60 mg, 0.19 mmol) in dry DMF (3.0 mL) was added tert-butylmagnesium chloride (0.7 N in THF) (370 µL, 0.27 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (95 mg, 0.22 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, PE/EtOAc 10 to 100%) and by reverse phase column chromatography (C-18 silica, H$_2$O/MeOH 0 to 100%). Compound AP (23 mg, 21% yield) was obtained as a white solid. $^1$H NMR (300 MHz, CD$_3$OD) δ 8.19 (m, 1H), 7.40-7.14 (m, 5H), 6.39 (dd, J=15.0, 4.5 Hz, 1H), 5.22 (dt, J=52.6, 4.0 Hz, 1H), 4.99-4.83 (overlapped with H$_2$O, m, 1H), 4.57 (dd, J=18.1, 3.7 Hz, 1H), 4.20 (m, 2H), 3.90 (m, 1H), 3.07 (br. s, 3H), 1.38-1.15 (m, 12H). $^{31}$P NMR (121 MHz, CD$_3$OD) δ 2.16 (s). MS (ESI) m/z calcd. for C$_{24}$H$_{32}$F$_2$N$_6$O$_7$P [M+H]$^+$ 585.2; found 585.2.

Scheme 29: Preparation of (S)-Isopropyl 2-(((S)-(((2R,3R,4S,5R)-5-(6-(methylamino)-2-fluoro-9H-purin-9-yl)-2-(chloromethyl)-4-fluoro-3-hydroxytetrahydrofuran-2-yl)methoxy)(phenoxy)phosphoryl)amino)propanoate (Compound AQ).

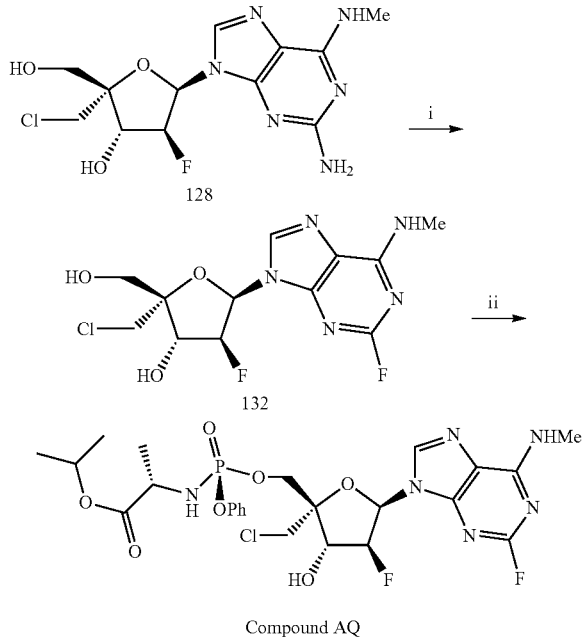

Compound AQ i) tBuONO, pyridine, HF, pyridine, -15° C.; ii) Isopropyl ((S)-(pentafluorophenoxy)-phenoxy-phosphoryl)-L-alaninate, t-BuMgCl, DMF, -10° C.

Step 1: Preparation of (2R,3R,4S,5R)-5-(6-(Methylamino)-2-fluoro-9H-purin-9-yl)-2-(chloromethyl)-4-fluoro-2-(hydroxymethyl)tetrahydrofuran-3-ol (132)

A solution of compound 128 (110 mg, 0.32 mmol) in dry pyridine (1.0 mL) was cooled down to -15° C. and pyridine hydrofluoride (420 µL) was added. Then, tert-butyl nitrite (79 µL, 0.64 mmol) was added drop-wise over 5 mins. The mixture was stirred at 10° C. for 4 h and quenched by addition of a suspension of $CaCO_3$ (1.7 g) in $H_2O$ (4 mL). The resulting suspension was stirred at RT for 15 mins and extracted with EtOAc (5×10 mL). The combined organics were dried over anhydrous $Na_2SO_4$ and concentrated. The residue was purified by column chromatography (silica gel, DCM/MeOH 0 to 9%). Product 132 (66 mg, 60% yield) was obtained as an off-white solid. $^1$H NMR (300 MHz, $CD_3OD$) δ 8.19 (m, 1H), 6.50 (dd, J=13.9, 4.7 Hz, 1H), 5.35 (dt, J=53.3, 4.3 Hz, 1H), 4.75 (dd, J=18.9, 4.0 Hz, 1H), 3.95-3.76 (m, 4H), 3.07 (br. s, 3H). MS (ESI) m/z calcd. for $C_{12}H_{15}ClF_2N_5O_3$ [M+H]$^+$ 350.1; found 350.2.

Step 2: Preparation of (S)-Isopropyl 2-(((S)-(((2R,3R,4S,5R)-5-(6-(methylamino)-2-fluoro-9H-purin-9-yl)-2-(chloromethyl)-4-fluoro-3-hydroxytetrahydrofuran-2-yl)methoxy)(phenoxy) phosphoryl) amino) propanoate (Compound AQ)

To a solution of compound 132 (58 mg, 0.17 mmol) in dry DMF (3.0 mL) was added tert-butylmagnesium chloride (0.7 N in THF) (330 µL, 0.24 mmol) drop-wise at -5° C. The solution was stirred for 20 mins at 0° C. and for 40 mins at RT. Then, the reaction mixture was cooled down to -10° C. and a solution of isopropyl ((S)-(pentafluorophenoxy)-phenoxy-phosphoryl)-L-alaninate (85 mg, 0.20 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. $NH_4Cl$ aq. solution (15 mL). The phases were separated and the aqueous layer was back-extracted with EtOAc (2×10 mL). The combined organics were washed with satd. $NH_4Cl$ aq. solution (20 mL) and brine (20 mL), dried over $Na_2SO_4$ and concentrated. The residue was purified by column chromatography (silica gel, PE/EtOAc 10 to 100%) and by reverse phase column chromatography (C-18 silica, $H_2O$/MeOH 0 to 100%). Compound AQ (19 mg, 19% yield) was obtained as a white solid. $^1$H NMR (300 MHz, $CD_3OD$) δ 8.14 (m, 1H), 7.40-7.16 (m, 5H), 6.50 (dd, J=17.5, 3.9 Hz, 1H), 5.27 (dt, J=52.4, 3.6 Hz, 1H), 4.97-4.84 (overlapped with $H_2O$, m, 1H), 4.72 (m, 1H), 4.51 (dd, J=10.7, 5.5 Hz) and 4.38 (dd, J=10.7, 6.4 Hz, 2H), 3.96-3.78 (m, 3H), 3.06 (br. s, 3H), 1.34-1.16 (m, 9H). $^{31}$P NMR (121 MHz, $CD_3OD$) δ 2.01 (s). MS (ESI) m/z calcd. for $C_{24}H_{31}ClF_2N_6O_7P$ [M+H]$^+$ 619.2; found 619.2.

Scheme 30: Preparation of (S)-Isopropyl 2-(((S)-(((2R,3R,4R,5R)-5-(6-(methylamino)-2-chloro-9H-purin-9-yl)-4-fluoro-3-hydroxy-2-methyltetrahydrofuran-2-yl)methoxy)(phenoxy)phosphoryl)amino)propanoate (Compound AR).

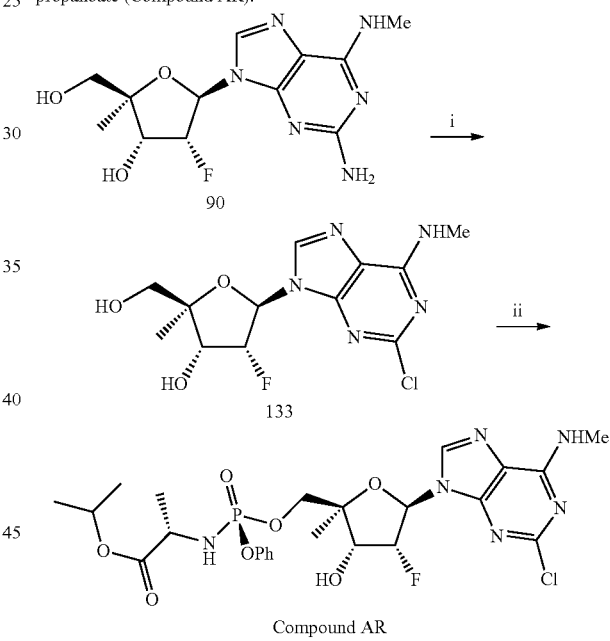

Compound AR i) tBuONO, $SbCl_3$, DCE, DMSO, 0° C.; ii) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(6-(Methylamino)-2-chloro-9H-purin-9-yl)-4-fluoro-2-(hydroxymethyl)-2-methyltetrahydrofuran-3-ol (133)

A solution of compound 90 (130 mg, 0.40 mmol) in dry DCE/DMSO (4:1) (4.0 mL) was cooled down to 0° C. and antimony trichloride (130 mg, 0.56 mmol) was added. Then, tert-butyl nitrite (100 µL, 0.84 mmol) was added drop-wise over 5 mins. The mixture was stirred at RT for 4 h and quenched by addition of trimethylamine (240 The resulting mixture was diluted with EtOAc (20 mL) and washed with $H_2O$ (10 mL). The aqueous layer was back-extracted EtOAc (3×10 mL). The combined organics were washed with brine (20 mL), dried over anhydrous $Na_2SO_4$ and concentrated.

The residue was purified by column chromatography (silica gel, DCM/MeOH 0 to 9%). Product 133 (40 mg, 30% yield) was obtained as a white solid. ¹H NMR (300 MHz, CD₃OD) δ 8.26 (s, 1H), 6.22 (dd, J=14.4, 4.5 Hz, 1H), 5.53 (dt, J=53.3, 4.8 Hz, 1H), 4.56 (dd, J=12.4, 5.0 Hz, 1H), 3.71-3.53 (m, 2H), 3.07 (br. s, 3H), 1.28 (s, 3H). MS (ESI) m/z calcd. for $C_{12}H_{16}ClFN_5O_3$ [M+H]⁺ 332.1; found 332.0.

Step 2: Preparation of (S)-Isopropyl 2-(((S)-(((2R, 3R,4R,5R)-5-(6-(methylamino)-2-chloro-9H-purin-9-yl)-4-fluoro-3-hydroxy-2-methyltetrahydrofuran-2-yl)methoxy)(phenoxy)phosphoryl)amino) propanoate (Compound AR)

To a solution of compound 133 (66 mg, 0.20 mmol) in dry DMF (3.0 mL) was added tert-butylmagnesium chloride (0.7 N in THF) (400 μL, 0.29 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (111 mg, 0.24 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH₄Cl aq. solution (15 mL). The phases were separated and the aqueous layer was back-extracted with EtOAc (2×10 mL). The combined organics were washed with satd. NH₄Cl aq. solution (20 mL) and brine (20 mL), dried over Na₂SO₄ and concentrated. The residue was purified by column chromatography (silica gel, DCM/MeOH 0 to 9%) and by reverse phase column chromatography (C-18 silica, H₂O/MeOH 0 to 100%). Compound AR (21 mg, 18% yield) was obtained as a white solid. ¹H NMR (300 MHz, CD₃OD) δ 8.14 (s, 1H), 7.32-7.09 (m, 5H), 6.25 (dd, J=17.5, 2.4 Hz, 1H), 5.63-5.41 (m, 1H), 4.96-4.73 (overlapped with H₂O, m, 2H), 4.23-4.08 (m, 2H), 3.86 (m, 1H), 3.03 (br. s, 3H), 1.37-1.15 (m, 12H). ³¹P NMR (121 MHz, CD₃OD) δ 1.99 (s). MS (ESI) m/z calcd. for $C_{24}H_{32}ClFN_6O_7P$ [M+H]⁺ 601.2; found 601.2.

Scheme 31: Preparation of (S)-Isopropyl 2-(((S)-(((2R,3R,4R,5R)-5-(2-amino-6-(cyclopropyl(methyl)amino)-9H-purin-9-yl)-4-fluoro-3-hydroxy-2-methyltetrahydrofuran-2-yl)methoxy)(phenoxy)phosphoryl)amino) propanoate (Compound AS).

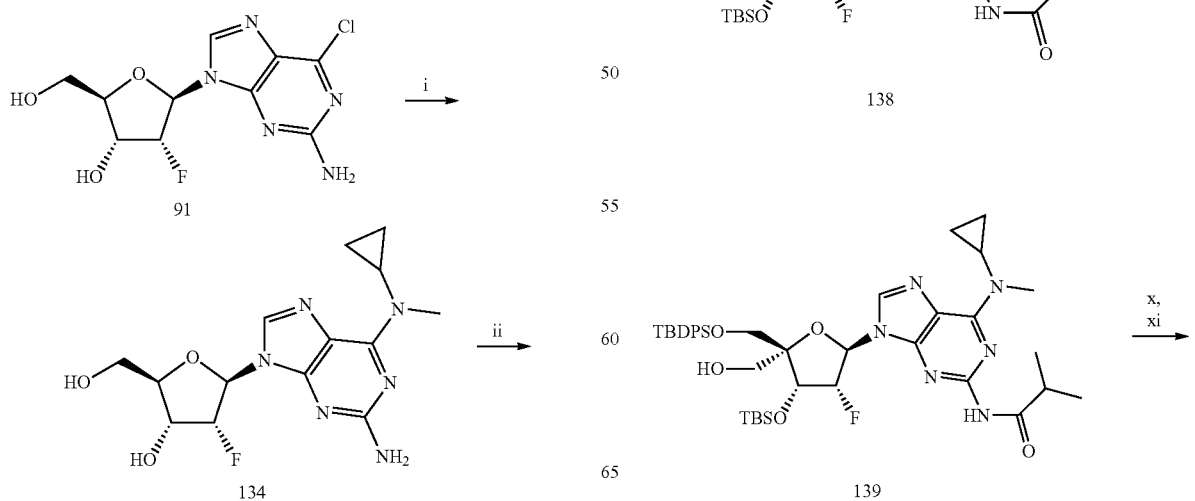

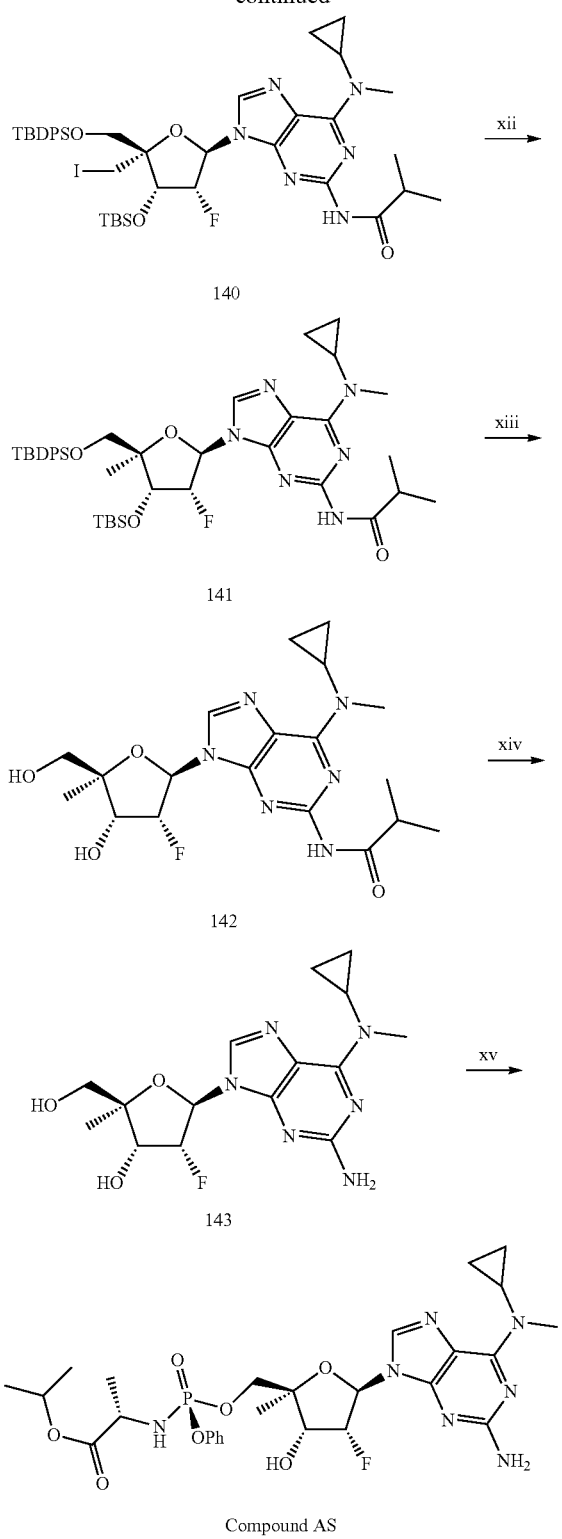

i) N-Methyl-cyclopropylamine•HCl, Et₃N, EtOH, 85° C.; ii) TBSCl, imidazole, DMF; iii) isobutyryl chloride, pyridine; iv) 90% TFA, DCM; v) SO₃•pyridine, DIEA, DMSO, DCM; vi) formaldehyde, 2N NaOH, dioxane then NaBH₄; vii) DMTrCl, Et₃N, DMF; viii) TBDPSCl, AgNO₃, pyridine; ix) 80% AcOH; x) Tf₂O, pyridine, DCM, 0° C.; xi) NaI, DMF, 60° C.; xii) H₂, 10% Pd—C, Et₃N, EtOH; xiii) TBAF, THF; xiv) MeNH₂, EtOH, 75° C.; xv) Isopropyl ((S)-(pentafluorophenoxy)-phenoxyphosphoryl)-L-alaninate, t-BuMgCl, DMF, -10° C.

Step 1: Preparation of (2R,3R,4R,5R)-5-(2-Amino-6-(cyclopropyl(methyl)amino)-9H-purin-9-yl)-4-fluoro-2-(hydroxymethyl) tetrahydrofuran-3-ol (134)

To a solution of compound 91 (6.0 g, 19.8 mmol) and N-methyl-cyclopropylamine hydrochloride (6.4 g, 59.4 mmol) in EtOH (300 mL) was added triethylamine (14.3 mL, 99 mmol). The mixture was heated at 85° C. in a sealed container for 3 h, cooled down to RT and concentrated. The residue was purified by column chromatography (silica gel, DCM/MeOH 0 to 10%). Product 134 (6.0 g, 90% yield) was obtained as a white solid.

Step 2: Preparation of 9-((2R,3R,4R,5R)-4-((tert-Butyldimethylsilyl)oxy)-5-(((tert-butyldimethylsilyl)oxy) methyl)-3-fluorotetrahydrofuran-2-yl)-N6-cyclopropyl-N6-methyl-9H-purine-2,6-diamine (135)

To a solution of compound 134 (6.0 g, 17.8 mmol) in dry DMF (80 mL) was added imidazole (6.0 g, 88.5 mmol) and TBSCl (10.7 g, 71.2 mmol). The mixture was stirred at RT for 15 h and concentrated. EtOAc (300 mL) was added and the solution was washed with satd. NH₄Cl aq. solution (3×200 mL) and brine (200 mL). The organic phase was dried over anhydrous Na₂SO₄ and concentrated. The residue was purified by column chromatography (silica gel, PE/EtOAc 0 to 70%). Product 135 (9.2 g, 92% yield) was obtained as a yellow oil.

Step 3 and Step 4: Preparation of N-(9-((2R,3R,4R,5R)-4-((tert-Butyldimethylsilyl)oxy)-3-fluoro-5-(hydroxymethyl) tetrahydrofuran-2-yl)-6-(cyclopropyl(methyl)amino)-9H-purin-2-yl)isobutyramide (136)

To a solution of compound 135 (9.1 g, 16.0 mmol) in dry pyridine (40 mL) was added isobutyryl chloride (2.0 mL, 19.3 mmol) drop-wise at 0° C. The reaction mixture was stirred at RT for 3 h and then concentrated. After co-evaporation with toluene (3×100 mL), the residue was dissolved in DCM (200 mL) and treated with TFA/H₂O (9:1, 20 mL) at 0° C. for 15 h. Then, the reaction was quenched by addition of solid NaHCO₃ (40 g) and filtered. The solution was washed with satd. NaHCO₃ aq. solution (2×100 mL) and brine (100 mL). The organic phase was dried over anhydrous Na₂SO₄ and concentrated. The residue was purified by column chromatography (silica gel, PE/EtOAc 10 to 100%). Product 136 (5.9 g, 70% yield over 2 steps) was obtained as a white foam.

Step 5 and Step 6: Preparation of N-(9-((2R,3R,4R)-4-((tert-Butyldimethylsilyl)oxy)-3-fluoro-5,5-bis(hydroxymethyl) tetrahydrofuran-2-yl)-6-(cyclopropyl(methyl)amino)-9H-purin-2-yl)isobutyramide (137)

To a solution of compound 136 (4.3 g, 8.2 mmol) in dry DCM (80 mL) at 0° C. was added diisopropylethylamine (5.5 mL, 32.1 mmol) and a suspension of SO₃ pyridine complex (3.9 g, 24.8 mmol) in dry DMSO (8.5 mL). The orange solution was stirred for 15 h at RT. Then, H₂O (100 mL) was added, the phases were separated and the aqueous layer was back-extracted with EtOAc (2×80 mL). The combined organics were washed with brine (150 mL), dried over anhydrous Na₂SO₄ and concentrated. The residue was dissolved in dioxane (50 mL). Formaldehyde (37% in H₂O) (2.8 mL, 34.6 mmol) and 2 N NaOH (6.0 mL, 12.0 mmol)

were added and the yellow solution was stirred for 4 h at RT. The mixture was cooled down to 0° C. and sodium borohydride (1.25 g, 33.0 mmol) was added portion-wise. The cloudy solution was stirred for 1 h at RT and quenched by addition of satd. $NH_4Cl$ aq. solution (150 mL). The product was extracted with EtOAc (3×100 mL). The combined organics were washed with brine (150 mL), dried over anhydrous $Na_2SO_4$ and concentrated. The residue was purified by column chromatography (silica gel, DCM/MeOH 0 to 10%). Product 137 (2.4 g, 52% yield over 2 steps) was obtained as a white solid.

Step 7: Preparation of N-(9-((2R,3R,4R,5S)-5-((bis(4-Methoxyphenyl)(phenyl)methoxy)methyl)-4-((tert-butyldimethylsilyl)oxy)-3-fluoro-5-(hydroxymethyl)tetrahydrofuran-2-yl)-6-(cyclopropyl(methyl)amino)-9H-purin-2-yl)isobutyramide (138)

To a solution of compound 137 (2.34 g, 4.23 mmol) in dry DMF (30 mL) was added triethylamine (1.23 mL, 8.46 mmol) and dimethoxytrityl chloride (2.01 g, 5.94 mmol). The resulting orange solution was stirred for 3 h at RT. The reaction was then diluted with EtOAc (120 mL) and $H_2O$ (100 mL). The phases were separated and the aqueous layer was back-extracted with EtOAc (2×60 mL). The combined organics were washed with brine (120 mL), dried over anhydrous $Na_2SO_4$ and concentrated. The residue was purified by column chromatography (silica gel, PE/EtOAc 10 to 100%). Product 138 (2.69 g, 74% yield) was obtained as an orange foam.

Step 8 and Step 9: Preparation of N-(9-((2R,3R,4R,5R)-4-((tert-Butyldimethylsilyl)oxy)-5-(((tert-butyldiphenylsilyl)oxy) methyl)-3-fluoro-5-(hydroxymethyl)tetrahydrofuran-2-yl)-6-(cyclopropyl(methyl)amino)-9H-purin-2-yl)isobutyramide (139)

To a solution of compound 138 (1.79 g, 2.10 mmol) in dry pyridine (30 mL) was added silver nitrate (1.07 g, 6.32 mmol) and TBDPSCl (1.56 mL, 6.32 mmol). The resulting solution was stirred for 15 h at RT. Then, EtOAc (120 mL) was added and the suspension was filtered. The solution was washed brine (60 mL), dried over anhydrous $Na_2SO_4$ and concentrated. The residue was dissolved in 80% acetic acid (20 mL) and stirred for 15 h at RT. The solution was poured into satd. $NaHCO_3$ aq. solution (200 mL) and the mixture was extracted with DCM (3×100 mL). The combined organics were washed with brine (100 mL), dried over anhydrous $Na_2SO_4$ and concentrated. The residue was purified by column chromatography (silica gel, PE/EtOAc 10 to 100%). Product 139 (1.19 g, 71% yield over 2 steps) was obtained as a white solid.

Step 10 and Step 11: Preparation of N-(9-((2R,3R,4R,5R)-4-((tert-Butyldimethylsilyl)oxy)-5-(((tert-butyldiphenylsilyl)oxy) methyl)-3-fluoro-5-(iodomethyl)tetrahydrofuran-2-yl)-6-(cyclopropyl(methyl)amino)-9H-purin-2-yl)isobutyramide (140)

To a solution of compound 139 (1.18 g, 1.50 mmol) in dry DCM (40 mL) was added dry pyridine (600 μL, 7.46 mmol) and triflic anhydride (302 μL, 1.80 mmol) at 0° C. The resulting orange solution was stirred for 15 mins at 0° C. and $H_2O$ (10 mL) was added. After a further 30 mins, the mixture was diluted with EtOAc (150 mL) and brine (80 mL). The layers were separated and the organics were dried over anhydrous $Na_2SO_4$ and concentrated. The residue was dissolved in dry DMF (60 mL) and NaI (1.79 g, 11.94 mmol) was added. The suspension was stirred for 15 h at 60° C. and concentrated. Then, EtOAc (200 mL) was added and the solution was washed with satd. $NH_4Cl$ aq. solution (2×100 mL), $Na_2S_2O_3$ aq. solution (100 mL) and brine (100 mL). The organics were dried over anhydrous $Na_2SO_4$ and concentrated. The residue was purified by column chromatography (silica gel, PE/EtOAc 0 to 80%). Product 140 (1.39 g, 95% yield over 2 steps) was obtained as an orange solid.

Step 12: Preparation of N-(9-((2R,3R,4R,5R)-4-((tert-Butyldimethylsilyl)oxy)-5-(((tert-butyldiphenylsilyl)oxy) methyl)-3-fluoro-5-methyltetrahydrofuran-2-yl)-6-(cyclopropyl(methyl)amino)-9H-purin-2-yl) isobutyramide (141)

To a solution of compound 140 (1.28 g, 1.42 mmol) in EtOH (25 mL) was added triethylamine (1.05 mL, 7.10 mmol) and palladium (10% on charcoal) (150 mg). The flask was put under an atmosphere of hydrogen and stirred for 24 h at RT. The reaction mixture was filtered over Celite and concentrated. The residue was purified by column chromatography (silica gel, PE/EtOAc 10 to 60%). Product 141 (900 mg, 82% yield) was obtained as a white solid.

Step 13: Preparation of N-(6-(Cyclopropyl(methyl)amino)-9-((2R,3R,4R,5R)-3-fluoro-4-hydroxy-5-(hydroxymethyl)-5-methyltetrahydrofuran-2-yl)-9H-purin-2-yl)isobutyramide (142)

To a solution of compound 141 (750 mg, 0.97 mmol) in dry THF (15 mL) was added tetrabutylammonium fluoride (1 N in THF) (2.90 mL, 2.90 mmol). The solution was stirred for 1 h at RT and concentrated. The residue was purified by column chromatography (silica gel, DCM/MeOH 0 to 9%). Product 142 (337 mg, 82% yield) was obtained as a white solid.

Step 14: Preparation of (2R,3R,4R,5R)-5-(2-amino-6-(cyclopropyhmethyl)amino)-9H-purin-9-yl)-4-fluoro-2-(hydroxymethyl)-2-methyltetrahydrofuran-3-ol (143)

A solution of compound 142 (167 mg, 0.43 mmol) in methylamine (33% in EtOH) (10 mL) in a sealed container was stirred for 15 h at 75° C. and concentrated. The residue was purified by column chromatography (silica gel, DCM/MeOH 0 to 15%). Product 143 (129 mg, 95% yield) was obtained as a white solid. $^1$H NMR (300 MHz, $CD_3OD$) δ 7.94 (s, 1H), 6.12 (dd, J=14.1, 5.2 Hz, 1H), 5.58 (dt, J=53.3, 5.2 Hz, 1H), 4.53 (dd, J=9.7, 5.1 Hz, 1H), 3.67 (d, J=12.0 Hz) and 3.56 (d, J=12.0 Hz, 2H), 3.32 (overlapping with MeOH, m, 3H), 3.16 (m, 1H), 1.27 (s, 3H), 0.97-0.89 (m, 2H), 0.76-0.68 (m, 2H). MS (ESI) m/z calcd. for $C_{15}H_{22}FN_6O_3$ $[M+H]^+$ 353.2; found 353.2.

Step 15: Preparation of (S)-Isopropyl 2-(((S)-(((2R,3R,4R,5R)-5-(2-amino-6-(cyclopropyl(methyl)amino)-9H-purin-9-yl)-4-fluoro-3-hydroxy-2-methyltetrahydrofuran-2-yl)methoxy)(phenoxy)phosphoryl)amino) propanoate (Compound AS)

To a solution of compound 143 (80 mg, 0.23 mmol) in dry DMF (3.0 mL) was added tert-butylmagnesium chloride (0.7 N in THF) (560 μL, 0.32 mmol) drop-wise at −5° C. The solution was stirred for 20 mins at 0° C. and for 40 mins at RT. Then, the reaction mixture was cooled down to −10° C.

and a solution of isopropyl ((S)-(pentafluorophenoxy)-phenoxy-phosphoryl)-L-alaninate (122 mg, 0.28 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Compound AS (25 mg, 18% yield) was obtained as a white solid. $^1$H NMR (300 MHz, CD$_3$OD) δ 7.86 (s, 1H), 7.35-7.12 (m, 5H), 6.16 (dd, J=17.3, 2.9 Hz, 1H), 5.69-5.47 (m, 1H), 4.97-4.84 (overlapped with H$_2$O, m, 1H), 4.74 (dd, J=17.5, 5.1 Hz, 1H), 4.30 (dd, J=10.9, 6.1 Hz) and 4.08 (dd, J=10.9, 4.9 Hz, 2H), 3.87 (m, 1H), 3.30 (overlapped with MeOH, m, 3H), 3.12 (m, 1H), 1.37-1.15 (m, 12H), 0.95-0.87 (m, 2H), 0.72-0.65 (m, 2H). $^{31}$P NMR (121 MHz, CD$_3$OD) δ 3.77 (s). MS (ESI) m/z calcd. for C$_{27}$H$_{38}$FN$_7$O$_7$P [M+H]$^+$ 622.3; found 622.2.

Scheme 32: Preparation of (S)-Isopropyl 2-(((S)-(((2R,3R,4S,5R)-5-(2-amino-6-(methylamino)-9H-purin-9-yl)-4-fluoro-2-(fluoromethyl)-3-hydroxytetrahydrofuran-2-yl)methoxy)(phenoxy)phosphoryl)amino)propanoate (Compound AT).

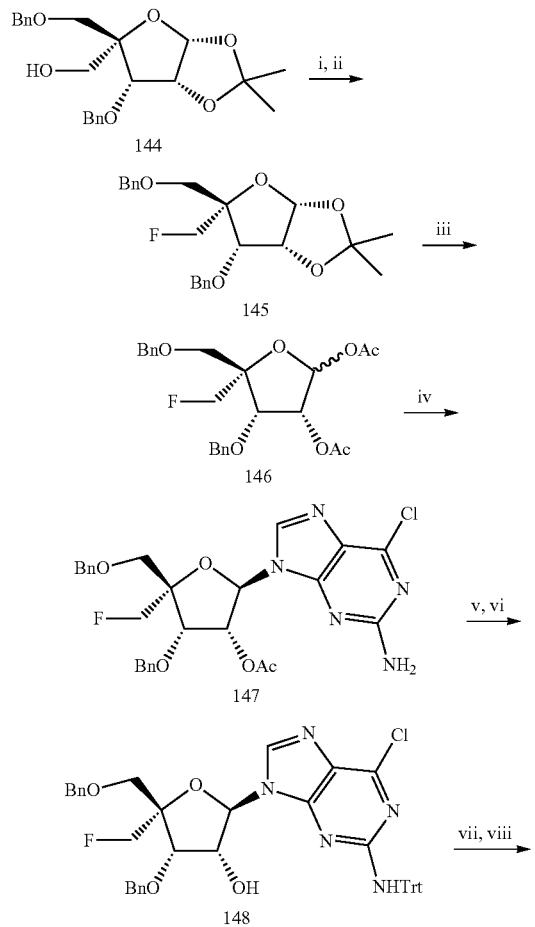

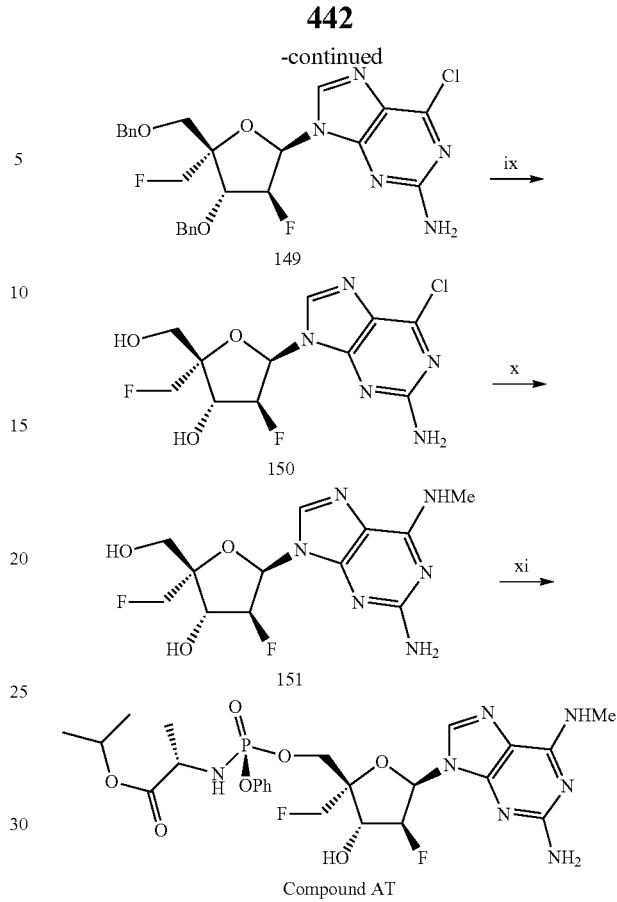

i) Tf$_2$O, pyridine, DCM, 0° C.; ii) TBAF, THF, 50° C.; iii) Ac$_2$O, H$_2$SO$_4$, AcOH; iv) 2-Amino-6-chloropurine, BSA, TMSOTf, MeCN, 80° C.; v) 1N NaOH, THF, vi) Trityl chloride, DMAP, Et$_3$N, DMF, 50° C.; vii) DAST, DCM, -78° C.; viii) TFA, MeOH, DCM; ix) BCl$_3$, DCM, -78° C.; x) MeNH$_2$, EtOH, 75° C.; xi) Isopropyl ((S)-(pentafluorophenoxy)-phenoxy-phosphoryl)-L-alaninate, t-BuMgCl, DMF, -10° C.

Step 1 and Step 2: Preparation of (3aR,5R,6S,6aR)-6-(Benzyloxy)-5-((benzyloxy)methyl)-5-(fluoromethyl)-2,2-dimethyltetrahydrofuro[2,3-d][1,3]dioxole (145)

To a solution of compound 144 (12.2 g, 30.4 mmol) and dry pyridine (9.4 mL, 115.5 mmol) in dry DCM (300 mL) at 0° C. was added triflic anhydride (6.1 mL, 36.5 mmol) drop-wise. The orange solution was stirred at 0° C. for 1 h and then, satd. NH$_4$Cl aq. solution (300 mL) was added. The layers were separated and the organic phase was dried over anhydrous Na$_2$SO$_4$ and concentrated. The residue was dissolved in dry THF (250 mL) and treated with tetrabutylammonium fluoride (1 N in THF) (100 mL, 100 mmol). The solution was stirred at 50° C. for 15 h and the solvent was removed. The residue was purified by column chromatography (silica gel, PE/EtOAc 0 to 20%). Product 145 (9.8 g, 80% yield over 2 steps) was obtained as a colorless oil.

Step 3: Preparation of (3R,4S,5R)-4-(Benzyloxy)-5-((benzyloxy)methyl)-5-(fluoromethyl)tetrahydrofuran-2,3-diyl diacetate (146)

To a solution of 145 (9.6 g, 23.9 mmol) in acetic acid (140 mL) at 10° C. were added acetic anhydride (22.6 mL, 239 mmol) and conc. H$_2$SO$_4$ (127 µL, 2.4 mmol). The solution was stirred at RT for 1.5 h and then, diluted with H$_2$O (250 mL). The mixture was extracted with EtOAc (2×500 mL) and the combined organics were washed with satd. NaHCO₃ aq. solution (2×200 mL) and brine (200 mL). The organic phase was dried over anhydrous Na₂SO₄ and concentrated. The residue was purified by column chromatography (silica gel, PE/EtOAc 0 to 35%). Product 146 (10.6 g, 99% yield) was obtained as a colorless oil.

Step 4: Preparation of (2R,3R,4S,5R)-2-(2-Amino-6-chloro-9H-purin-9-yl)-4-(benzyloxy)-5-((benzyloxy)methyl)-5-(fluoromethyl)tetrahydrofuran-3-yl acetate (147)

To a suspension of 2-amino-6-chloropurine (7.3 g, 43.0 mmol) in dry acetonitrile (300 mL) was added N,O-bis(trimethylsilyl)acetamide (17.6 mL, 71.7 mmol). The mixture was stirred at 80° C. for 3 h and cooled down to 0° C. A solution of 146 (10.6 g, 23.9 mmol) in dry acetonitrile (90 mL) was added, followed by TMSOTf (13.0 mL, 71.7 mmol). The solution was stirred at 80° C. for 2 h and concentrated. EtOAc (500 mL) and satd. NaHCO₃ aq. solution (250 mL) were added and the layers were separated. The organic phase was filtered through Celite and washed with brine (200 mL). The organic phase was dried over anhydrous Na₂SO₄ and concentrated. The residue was purified by column chromatography (silica gel, PE/EtOAc 10 to 60%). Product 147 (10.0 g, 75% yield) was obtained as a white foam.

Step 5 and Step 6: Preparation of (2R,3R,4S,5R)-2-(6-Chloro-2-(tritylamino)-9H-purin-9-yl)-4-(benzyloxy)-5-((benzyloxy) methyl)-5-(fluoromethyl)tetrahydrofuran-3-ol (148)

To a solution of compound 147 (10.0 g, 18.0 mmol) in THF (340 mL) was added 1 N NaOH (140.0 mL, 140.0 mmol) drop-wise. The reaction mixture was stirred for 45 mins at RT and then, the layers were separated. The aqueous phase was extracted with EtOAc (2×150 mL). The combined organics were washed with satd. NH₄Cl aq. solution (250 mL), dried over anhydrous Na₂SO₄ and concentrated. The residue was dissolved in dry DMF (150 mL) and treated with triethylamine (6.2 mL, 44.8 mmol), DMAP (440 mg, 3.6 mmol) and trityl chloride (12.5 g, 44.8 mmol). The mixture was stirred at 50° C. for 22 h and then, diluted with EtOAc (500 mL). The solution was washed with satd. NH₄Cl aq. solution (3×250 mL) and brine (250 mL). The organic phase was dried over anhydrous Na₂SO₄ and concentrated. The residue was purified by column chromatography (silica gel, PE/EtOAc 10 to 90%). Product 148 (11.3 g, 82% yield over 2 steps) was obtained as an off-white foam.

Step 7 and Step 8: Preparation of 9-((2R,3S,4R,5R)-4-(Benzyloxy)-5-((benzyloxy) methyl)-3-fluoro-5-(fluoromethyl) tetrahydrofuran -2-yl)-6-chloro-9H-purin-2-amine (149)

To a solution of compound 148 (11.3 g, 14.9 mmol) in dry DCM (350 mL) at −78° C. was added (diethylamino)sulfur trifluoride (16.0 mL, 120.0 mmol) dropwise over 10 mins. The reaction mixture was stirred at −78° C. for 20 mins and then, slowly allowed to warm-up to RT. After stirring for 24 h, the solution was poured into ice-cold satd. NaHCO₃ aq. solution (500 mL). DCM (400 mL) was added and the layers were separated. The organic phase was washed with H₂O (450 mL), satd. NaHCO₃ aq. solution (450 mL) and brine (450 mL), dried over anhydrous Na₂SO₄ and concentrated. The residue was dissolved in DCM (250 mL) and treated with MeOH (1.5 mL) and TFA (2.5 mL). The reaction mixture was stirred at RT for 15 h. Then, triethylamine (4.5 mL) was added and the solvent was removed. The residue was purified by column chromatography (silica gel, PE/EtOAc 0 to 90%). Product 149 (1.9 g, 25% yield over 2 steps) was obtained as a white foam.

Step 9: Preparation of (2R,3R,4S,5R)-5-(2-Amino-6-chloro-9H-purin-9-yl)-4-fluoro-2-(fluoromethyl)-2-(hydroxymethyl)tetrahydrofuran-3-ol (150)

To a solution of compound 149 (988 mg, 1.92 mmol) in dry DCM (20 mL) at −78° C. was added boron trichloride (1 M in DCM) (9.60 mL, 9.60 mmol) dropwise over 10 mins. The reaction mixture was stirred at −78° C. for 30 mins and then, slowly allowed to warm-up to 0° C. The solution was cooled down to −78° C. and ammonia (2 M in EtOH) (10.55 mL, 21.10 mmol) was added dropwise. Then, the mixture was allowed to warm-up to RT and concentrated. The residue was directly purified by column chromatography (silica gel, DCM/MeOH 0 to 9%). Product 150 (256 mg, 40% yield) was obtained as an amorphous solid.

Step 10: Preparation of (2R,3R,4S,5R)-5-(2-Amino-6-(methylamino)-9H-purin-9-yl)-4-fluoro-2-(fluoromethyl)-2-(hydroxymethyl)tetrahydrofuran-3-ol (151)

A solution of compound 150 (255 mg, 0.76 mmol) in methylamine (33% in EtOH) (10 mL) in a sealed container was stirred for 15 h at 75° C. and concentrated. The residue was purified by column chromatography (silica gel, DCM/MeOH 0 to 15%). Product 151 (246 mg, 98% yield) was obtained as a white solid. ¹H NMR (300 MHz, CD₃OD) δ 7.88 (m, 1H), 6.41 (dd, J=11.5, 5.2 Hz, 1H), 5.36-5.12 (m, 1H), 4.90-4.76 (overlapping with H₂O, m, 1H), 4.78-4.41 (m, 2H), 3.80-3.65 (m, 2H), 3.05 (br. s, 3H). MS (ESI) m/z calcd. for $C_{12}H_{17}F_2N_6O_3$ [M+H]⁺ 331.1; found 331.2.

Step 11: Preparation of (S)-Isopropyl 2-(((S)-(((2R,3R,4S,5R)-5-(2-amino-6-(methylamino)-9H-purin-9-yl)-4-fluoro-2-(fluoromethyl)-3-hydroxytetrahydrofuran-2-yl)methoxy)(phenoxy)phosphoryl) amino) propanoate (Compound AT)

To a solution of compound 151 (80 mg, 0.24 mmol) in dry DMF (3.0 mL) was added tert-butylmagnesium chloride (0.7 N in THF) (440 μL, 0.32 mmol) drop-wise at −5° C. The solution was stirred for 15 mins at 0° C. and for 45 mins at RT. Then, the reaction mixture was cooled down to −10° C. and a solution of isopropyl ((S)-(pentafluorophenoxy)-phenoxy-phosphoryl)-L-alaninate (122 mg, 0.27 mmol) in dry DMF (2.0 mL) was added drop-wise. The resulting solution was slowly warmed up to 10° C. and stirred for 15 h at this temperature. The reaction mixture was then diluted with EtOAc (15 mL) and satd. NH₄Cl aq. solution (12 mL). The phases were separated and the aqueous layer was back-extracted with EtOAc (2×10 mL). The combined organics were washed with satd. NH₄Cl aq. solution (15 mL) and brine (15 mL), dried over Na₂SO₄ and concentrated. The residue was purified by column chromatography (silica gel, DCM/MeOH 0 to 9%) and by reverse phase column chromatography (C-18 silica, H₂O/MeOH 0 to 100%). Compound AT (25 mg, 17%) was obtained as a white solid. ¹H NMR (300 MHz, CD₃OD) δ 7.82 (m, 1H), 7.40-7.16 (m, 5H), 6.41 (dd, J=14.9, 4.5 Hz, 1H), 5.31-5.06 (m, 1H), 4.97-4.79 (overlapped with H$_2$O, m, 1H), 4.82-4.46 (m, 2H), 4.44-4.26 (m, 2H), 3.90 (m, 1H), 3.05 (br. s, 3H), 1.36-1.14 (m, 9H). $^{31}$P NMR (121 MHz, CD$_3$OD) δ 2.13 (s). MS (ESI) m/z calcd. for C$_{24}$H$_{33}$F$_2$N$_7$O$_7$P [M+H]$^+$ 600.2; found 600.2.

Scheme 33: Preparation of (S)-Isopropyl 2-(((S)-(((2R,3R,4R,5R)-5-(2,6-bis(methylamino)-9H-purin-9-yl)-4-fluoro-3-hydroxy-2-methyltetrahydrofuran-2-yl)methoxy)(phenoxy)phosphoryl)amino)propanoate (Compound AU).

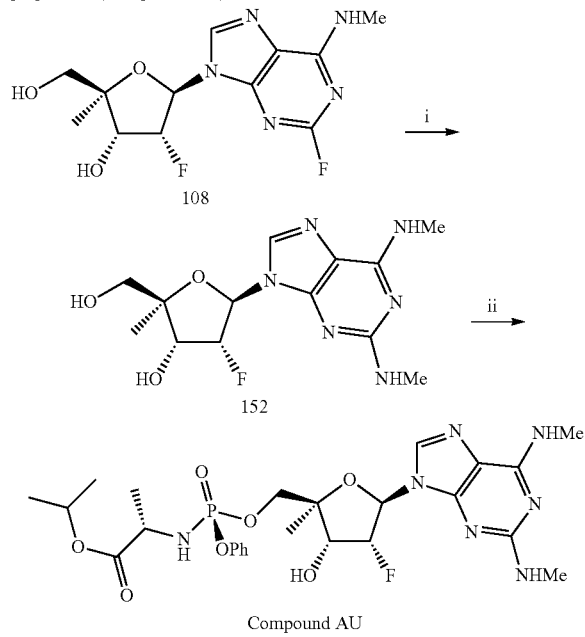

Compound AU i) MeNH$_2$, EtOH, μW, 100° C.; ii) Isopropyl( ((S)-(pentafluorophenoxy)-phenoxy-phosphoryl)-L-alaninate, t-BuMgCl, DMF, -10° C.

Step 1: Preparation of (2R,3R,4R,5R)-5-(2,6-Bis(methylamino)-9H-purin-9-yl)-4-fluoro-2-(hydroxymethyl)-2-methyltetrahydrofuran-3-ol (152)

A solution of compound 108 (90 mg, 0.29 mmol) in methylamine (33% in EtOH) (5 mL) was stirred at 100° C. under microwave irradiation for 10 mins. The reaction was cooled down to RT and the solvent was removed. The residue was purified by reverse phase column chromatography (C-18 silica, H$_2$O/MeOH 0 to 100%). Product 152 (87 mg, 94% yield) was obtained as a white solid. $^1$H NMR (300 MHz, CD$_3$OD) δ 7.86 (s, 1H), 6.11 (dd, J=15.2, 4.6 Hz, 1H), 5.63 (dt, J=53.6, 4.9 Hz, 1H), 4.61 (dd, J=11.6, 5.1 Hz, 1H), 3.66 (d, J=12.0 Hz) and 3.55 (d, J=12.0 Hz, 2H), 3.05 (br. s, 3H), 2.93 (br. s, 3H), 1.27 (s, 3H). MS (ESI) m/z calcd. for C$_{13}$H$_{20}$FN$_6$O$_3$ [M+H]$^+$ 327.2; found 327.2.

Step 2: Preparation of (S)-Isopropyl 2-(((S)-(((2R,3R,4R,5R)-5-(2,6-bis(methylamino)-9H-purin-9-yl)-4-fluoro-3-hydroxy-2-methyltetrahydrofuran-2-yl)methoxy)(phenoxy)phosphoryl) amino) propanoate (Compound AU)

To a solution of compound 152 (65 mg, 0.20 mmol) in dry DMF (3.0 mL) was added tert-butylmagnesium chloride (0.7 N in THF) (400 μL, 0.30 mmol) drop-wise at -5° C. The solution was stirred for 20 mins at 0° C. and for 40 mins at RT. Then, the reaction mixture was cooled down to -10° C. and a solution of isopropyl ((S)-(pentafluorophenoxy)-phe-noxy-phosphoryl)-L-alaninate (111 mg, 0.25 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, PE/EtOAc 10 to 100%) and by reverse phase column chromatography (C-18 silica, H$_2$O/MeOH 0 to 100%). Compound AU (24 mg, 20% yield) was obtained as a white solid. $^1$H NMR (300 MHz, CD$_3$OD) δ 7.78 (s, 1H), 7.33-7.12 (m, 5H), 6.14 (dd, J=18.6, 2.5 Hz, 1H), 5.71-5.55 (m, 1H), 4.97-4.82 (overlapped with H$_2$O, m, 1H), 4.23 (dd, J=10.8, 6.1 Hz) and 4.12 (dd, J=10.8, 5.1 Hz, 2H), 3.83 (m, 1H), 3.02 (br. s, 3H), 2.92 (br. s, 3H), 1.35-1.13 (m, 12H). $^{31}$P NMR (121 MHz, CD$_3$OD) δ 3.61 (s). MS (ESI) m/z calcd. for C$_{25}$H$_{36}$FN$_7$O$_7$P [M+H]$^+$ 596.2; found 596.2.

Scheme 34: Preparation of (S)-Isopropyl 2-(((S)-(((2R,3R,4R,5R)-5-(2-amino-6-(cyclopropylamino)-9H-purin-9-yl)-4-fluoro-3-hydroxy-2-methyltetrahydrofuran-2-yl)methoxy)(phenoxy)phosphoryl)amino)propanoate (Compound AV).

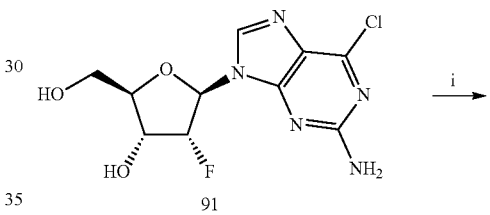

91

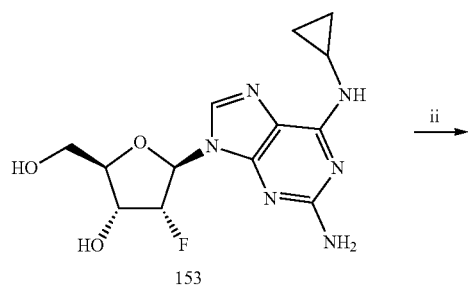

153

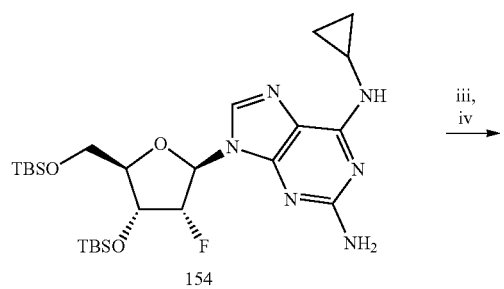

154

447
-continued

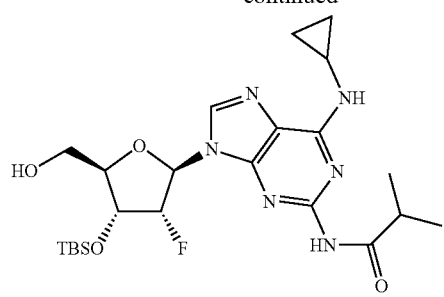
155

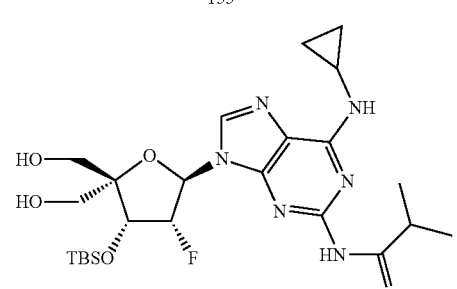
156

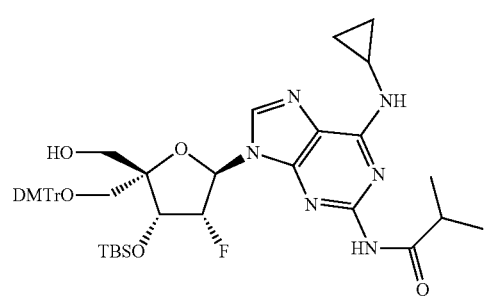
157

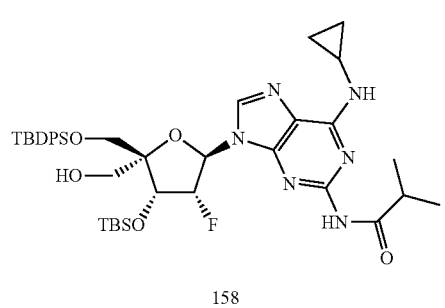
158

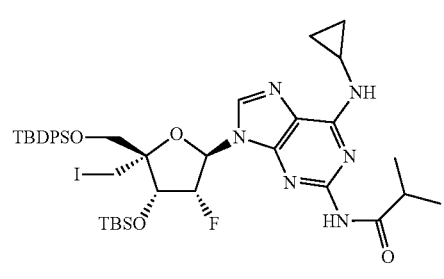
159

448
-continued

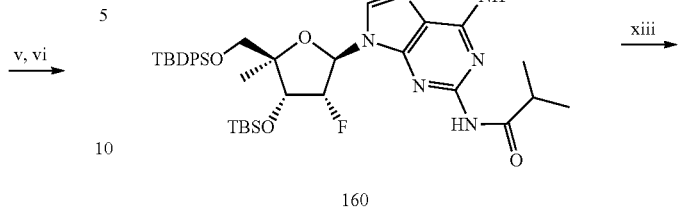
160

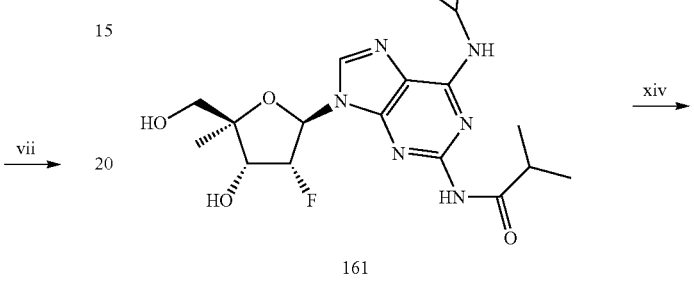
161

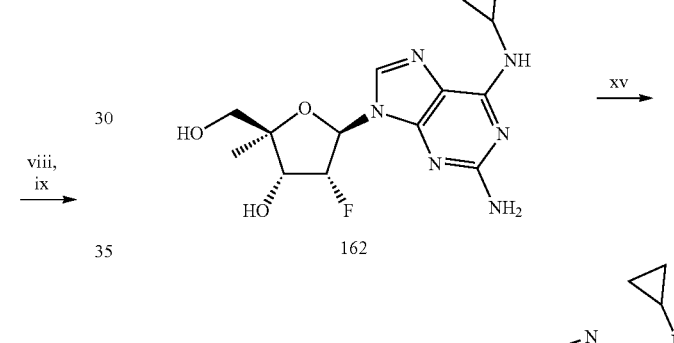
162

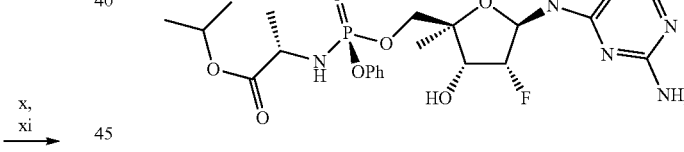
Compound AV i) Cyclopropylamine, EtOH, 85° C.; ii) TBSCl, imidazole, DMF;
iii) isobutyryl chloride, pyridine; iv) 90% TFA, DCM; v) SO₃•pyridine, DIEA, DMSO, DCM; vi) formaldehyde, 2N NaOH, dioxane then NaBH₄; vii) DMTrCl, Et₃N, DMF;
viii) TBDPSCl, AgNO₃, pyridine; ix) 80% AcOH; x) Tf₂O, pyridine, DCM, 0° C.;
xi) NaI, DMF, 60° C.; xii) H₂, 10% Pd—C, Et₃N, EtOH; xiii) TBAF, THF;
xiv) MeNH₂, EtOH, 75° C.; xv) Isopropyl ((S)-(pentafluorophenoxy)-phenoxy-phosphoryl)-L-alaninate, t-BuMgCl, DMF, -10° C.

Step 1: Preparation of (2R,3R,4R,5R)-5-(2-Amino-6-(cyclopropylamino)-9H-purin-9-yl)-4-fluoro-2-(hydroxymethyl)tetrahydrofuran-3-ol (153)

To a solution of compound 91 (5.2 g, 17.1 mmol) in EtOH (150 mL) was added cyclopropylamine (3.8 mL, 54.8 mmol). The mixture was heated at 85° C. in a sealed container for 3 h, cooled down to RT and concentrated. The residue was purified by column chromatography (silica gel, DCM/MeOH 0 to 10%). Product 153 (5.1 g, 92% yield) was obtained as a white solid.

Step 2: Preparation of 9-((2R,3R,4R,5R)-4-((tert-Butyldimethylsilyl)oxy)-5-(((tert-butyldimethylsilyl)oxy) methyl)-3-fluorotetrahydrofuran-2-yl)-N6-cyclopropyl-9H-purine-2,6-diamine (154)

To a solution of compound 153 (5.1 g, 15.7 mmol) in dry DMF (75 mL) was added imidazole (5.3 g, 78.1 mmol) and TBSCl (9.4 g, 62.8 mmol). The mixture was stirred at RT for 15 h and concentrated. EtOAc (250 mL) was added and the solution was washed with satd. $NH_4Cl$ aq. solution (3×180 mL) and brine (150 mL). The organic phase was dried over anhydrous $Na_2SO_4$ and concentrated. The residue was purified by column chromatography (silica gel, PE/EtOAc 0 to 80%). Product 154 (7.8 g, 90% yield) was obtained as a yellow oil.

Step 3 and Step 4: Preparation of N-(9-((2R,3R,4R,5R)-4-((tert-Butyldimethylsilyl)oxy)-3-fluoro-5-(hydroxymethyl) tetrahydrofuran-2-yl)-6-(cyclopropylamino)-9H-purin-2-yl)isobutyramide (155)

To a solution of compound 154 (7.7 g, 13.9 mmol) in dry pyridine (35 mL) was added isobutyryl chloride (1.75 mL, 16.8 mmol) drop-wise at 0° C. The reaction mixture was stirred at RT for 3 h and then concentrated. After co-evaporation with toluene (3×100 mL), the residue was dissolved in DCM (180 mL) and treated with $TFA/H_2O$ (9:1, 18 mL) at 0° C. for 15 h. Then, the reaction was quenched by addition of solid $NaHCO_3$ (35 g) and filtered. The solution was washed with satd. $NaHCO_3$ aq. solution (2×100 mL) and brine (100 mL). The organic phase was dried over anhydrous $Na_2SO_4$ and concentrated. The residue was purified by column chromatography (silica gel, PE/EtOAc 10 to 100%). Product 155 (5.1 g, 72% yield over 2 steps) was obtained as a white foam.

Step 5 and Step 6: Preparation of N-(9-((2R,3R,4R)-4-((tert-Butyldimethylsilyl)oxy)-3-fluoro-5,5-bis(hydroxymethyl) tetrahydrofuran-2-yl)-6-(cyclopropylamino)-9H-purin-2-yl)isobutyramide (156)

To a solution of compound 155 (4.6 g, 9.0 mmol) in dry DCM (90 mL) at 0° C. was added diisopropylethylamine (6.1 mL, 35.3 mmol) and a suspension of $SO_3$ pyridine complex (4.3 g, 27.1 mmol) in dry DMSO (9 mL). The orange solution was stirred for 15 h at RT. Then, $H_2O$ (100 mL) was added, the phases were separated and the aqueous layer was back-extracted with EtOAc (2×100 mL). The combined organics were washed with brine (150 mL), dried over anhydrous $Na_2SO_4$ and concentrated. The residue was dissolved in dioxane (100 mL). Formaldehyde (37% in $H_2O$) (3.1 mL, 38.0 mmol) and 2 N NaOH (6.8 mL, 13.6 mmol) were added and the yellow solution was stirred for 4 h at RT. The mixture was cooled down to 0° C. and sodium borohydride (1.37 g, 36.2 mmol) was added portion-wise. The cloudy solution was stirred for 1 h at RT and quenched by addition of satd. $NH_4Cl$ aq. solution (150 mL). The product was extracted with EtOAc (3×100 mL). The combined organics were washed with brine (150 mL), dried over anhydrous $Na_2SO_4$ and concentrated. The residue was purified by column chromatography (silica gel, DCM/MeOH 0 to 9%). Product 156 (3.2 g, 66% yield over 2 steps) was obtained as a white solid.

Step 7: Preparation of N-(9-((2R,3R, 4R, 5S)-5-((bis(4-Methoxyphenyl)(phenyl)methoxy)methyl)-4-((tert-butyldimethylsilyl)oxy)-3-fluoro-5-(hydroxymethyl)tetrahydrofuran-2-yl)-6-(cyclopropylamino)-9H-purin-2-yl)isobutyramide (157)

To a solution of compound 156 (3.2 g, 5.94 mmol) in dry DMF (40 mL) was added triethylamine (1.7 mL, 11.90 mmol) and dimethoxytrityl chloride (2.6 g, 7.72 mmol). The resulting orange solution was stirred for 3 h at RT. The reaction was then diluted with EtOAc (150 mL) and $H_2O$ (100 mL). The phases were separated and the aqueous layer was back-extracted with EtOAc (2×80 mL). The combined organics were washed with brine (150 mL), dried over anhydrous $Na_2SO_4$ and concentrated. The residue was purified by column chromatography (silica gel, PE/EtOAc 10 to 100%). Product 157 (2.5 g, 50% yield) was obtained as an orange foam.

Step 8 and Step 9: Preparation of N-(9-((2R,3R,4R,5R)-4-((tert-Butyldimethylsilyl)oxy)-5-(((tert-butyldiphenylsilyl)oxy) methyl)-3-fluoro-5-(hydroxymethyl)tetrahydrofuran-2-yl)-6-(cyclopropylamino)-9H-purin-2-yl)isobutyramide (158)

To a solution of compound 157 (2.50 g, 2.97 mmol) in dry pyridine (30 mL) was added silver nitrate (1.51 g, 8.92 mmol) and TBDPSCl (2.30 mL, 8.92 mmol). The resulting solution was stirred for 15 h at RT. Then, EtOAc (150 mL) was added and the suspension was filtered. The solution was washed brine (80 mL), dried over anhydrous $Na_2SO_4$ and concentrated. The residue was dissolved in 80% acetic acid (20 mL) and stirred for 15 h at RT. The solution was poured into satd. $NaHCO_3$ aq. solution (200 mL) and the mixture was extracted with DCM (3×100 mL). The combined organics were washed with brine (100 mL), dried over anhydrous $Na_2SO_4$ and concentrated. The residue was purified by column chromatography (silica gel, DCM/MeOH 0 to 4%). Product 158 (2.00 g, 87% yield over 2 steps) was obtained as a white solid.

Step 10 and Step 11: Preparation of N-(9-((2R,3R,4R,5R)-4-((tert-Butyldimethylsilyl)oxy)-5-(((tert-butyldiphenylsilyl)oxy) methyl)-3-fluoro-5-(iodomethyl)tetrahydrofuran-2-yl)-6-(cyclopropylamino)-9H-purin-2-yl)isobutyramide (159)

To a solution of compound 158 (1.53 g, 2.00 mmol) in dry DCM (50 mL) was added dry pyridine (810 μL, 9.84 mmol) and triflic anhydride (510 μL, 2.94 mmol) at 0° C. The resulting orange solution was stirred for 15 mins at 0° C. and $H_2O$ (15 mL) was added. After a further 30 mins, the mixture was diluted with EtOAc (200 mL) and brine (100 mL). The layers were separated and the organics were dried over anhydrous $Na_2SO_4$ and concentrated. The residue was dissolved in dry DMF (50 mL) and NaI (2.36 g, 15.75 mmol) was added. The suspension was stirred for 15 h at 60° C. and concentrated. Then, EtOAc (250 mL) was added and the solution was washed with satd. $NH_4Cl$ aq. solution (2×120 mL), $Na_2S_2O_3$ aq. solution (120 mL) and brine (120 mL). The organics were dried over anhydrous $Na_2SO_4$ and concentrated. The residue was purified by column chromatography (silica gel, PE/EtOAc 10 to 60%). Product 159 (1.28 g, 73% yield over 2 steps) was obtained as an orange solid.

Step 12: Preparation of N-(9-((2R,3R,4R,5R)-4-((tert-Butyldimethylsilyl)oxy)-5-(((tert-butyldiphenylsilyl)oxy) methyl)-3-fluoro-5-methyltetrahydrofuran-2-yl)-6-(cyclopropylamino)-9H-purin-2-yl) isobutyramide (160)

To a solution of compound 159 (1.26 g, 1.41 mmol) in EtOH (25 mL) was added triethylamine (1.05 mL, 7.10 mmol) and palladium (10% on charcoal) (150 mg). The flask was put under an atmosphere of hydrogen and stirred for 24 h at RT. The reaction mixture was filtered over Celite and concentrated. The residue was purified by column chromatography (silica gel, PE/EtOAc 10 to 70%). Product 160 (920 mg, 85% yield) was obtained as a white solid.

Step 13: Preparation of N-(6-(Cyclopropylamino)-9-((2R,3R,4R,5R)-3-fluoro-4-hydroxy-5-(hydroxymethyl)-5-methyltetrahydrofuran-2-yl)-9H-purin-2-yl) isobutyramide (161)

To a solution of compound 160 (500 mg, 0.66 mmol) in dry THF (15 mL) was added tetrabutylammonium fluoride (1 N in THF) (2.00 mL, 2.00 mmol). The solution was stirred for 1 h at RT and concentrated. The residue was purified by column chromatography (silica gel, DCM/MeOH 0 to 10%). Product 161 (228 mg, 85% yield) was obtained as a white solid.

Step 14: Preparation of (2R,3R,4R,5R)-5-(2-amino-6-(cyclopropylamino)-9H-purin-9-yl)-4-fluoro-2-(hydroxymethyl)-2-methyltetrahydrofuran-3-ol (162)

A solution of compound 161 (227 mg, 0.56 mmol) in methylamine (33% in EtOH) (20 mL) in a sealed container was stirred for 15 h at 75° C. and concentrated. The residue was purified by column chromatography (silica gel, DCM/MeOH 0 to 15%). Product 162 (173 mg, 92% yield) was obtained as a white solid. $^1$H NMR (300 MHz, CD$_3$OD) δ 7.91 (s, 1H), 6.10 (dd, J=14.1, 5.2 Hz, 1H), 5.63 (dt, J=53.3, 5.2 Hz, 1H), 4.53 (dd, J=9.5, 5.0 Hz, 1H), 3.67 (d, J=12.2 Hz) and 3.56 (d, J=12.2 Hz, 2H), 2.92 (m, 1H), 1.26 (m, 3H), 0.86-081 (m, 2H), 0.63-0.58 (m, 2H). MS (ESI) m/z calcd. for C$_{14}$H$_{20}$FN$_6$O$_3$ [M+H]$^+$ 339.2; found 339.2.

Step 15: Preparation of (S)-Isopropyl 2-(((S)-(((2R,3R,4R,5R)-5-(2-amino-6-(cyclopropylamino)-9H-purin-9-yl)-4-fluoro-3-hydroxy-2-methyltetrahydrofuran-2-yl)methoxy)(phenoxy) phosphoryl) amino) propanoate (Compound AV)

To a solution of compound 162 (78 mg, 0.23 mmol) in dry DMF (3.0 mL) was added tert-butylmagnesium chloride (0.7 N in THF) (560 μL, 0.32 mmol) drop-wise at −5° C. The solution was stirred for 20 mins at 0° C. and for 40 mins at RT. Then, the reaction mixture was cooled down to −10° C. and a solution of isopropyl ((S)-(pentafluorophenoxy)-phenoxy-phosphoryl)-L-alaninate (122 mg, 0.28 mmol) in dry DMF (2.0 mL) was added drop-wise. The resulting solution was slowly warmed up to 10° C. and stirred for 15 h at this temperature. The reaction mixture was then diluted with EtOAc (20 mL) and satd. NH$_4$Cl aq. solution (15 mL). The phases were separated and the aqueous layer was back-extracted with EtOAc (2×10 mL). The combined organics were washed with satd. NH$_4$Cl aq. solution (20 mL) and brine (20 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Product Compound AV (24 mg, 17% yield) was obtained as a white solid. $^1$H NMR (300 MHz, CD$_3$OD) δ 7.83(s, 1H), 7.34-7.13 (m, 5H), 6.14 (dd, J=17.2, 3.0 Hz, 1H), 5.64-5.49 (m, 1H), 4.96-4.86 (m, 1H), 4.72 (dd, J=17.6, 5.2 Hz, 1H), 4.29 (dd, J=10.9, 6.2 Hz) and 4.09 (dd, J=10.9, 4.9 Hz, 2H), 3.87 (m, 1H), 2.89 (m, 1H), 1.35-1.15 (m, 12H), 0.55-0.80 (m, 2H), 0.60-0.56 (m, 2H). $^{31}$P NMR (121 MHz, CD$_3$OD) δ 3.64 (s). MS (ESI) m/z calcd. for C$_{26}$H$_{36}$FN$_7$O$_7$P [M+H]$^+$ 608.2; found 608.2.

Example 2

Non-Limiting Compounds of the Present Invention

Table 1 and Table 2 show illustrative compounds of the present invention.

TABLE 1

Non-limiting Compounds of Formula I, Formula II, Formula III, and Formula IV

| Cmpd | Structure |
|---|---|
| A | *(structure of nucleoside with HO, F, NMe$_2$, NH$_2$ substituents on purine-tetrahydrofuran scaffold)* |
| B | *(structure of phosphoramidate prodrug with isopropyl ester, alanine, phenoxy phosphoryl, and nucleoside bearing NMe$_2$, NH$_2$, F, HO groups)* |

TABLE 1-continued

Non-limiting Compounds of Formula I, Formula II, Formula III, and Formula IV

| Cmpd | Structure |
|---|---|
| C | 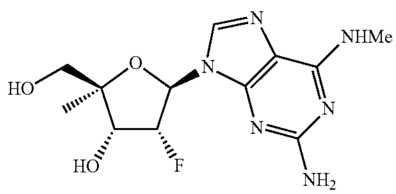 [SMILES: CNc1nc(N)nc2c1ncn2[C@@H]1O[C@](C)(CO)[C@@H](O)[C@H]1F] |
| D | 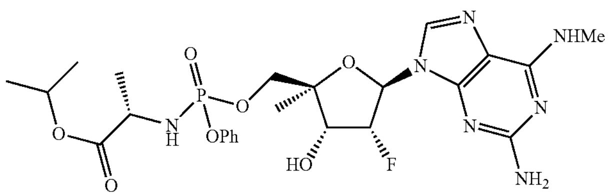 [SMILES: CNc1nc(N)nc2c1ncn2[C@@H]1O[C@](C)(COP(=O)(N[C@@H](C)C(=O)OC(C)C)Oc2ccccc2)[C@@H](O)[C@H]1F] |
| E | 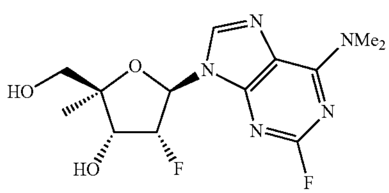 [SMILES: CN(C)c1nc(F)nc2c1ncn2[C@@H]1O[C@](C)(CO)[C@@H](O)[C@H]1F] |
| F | 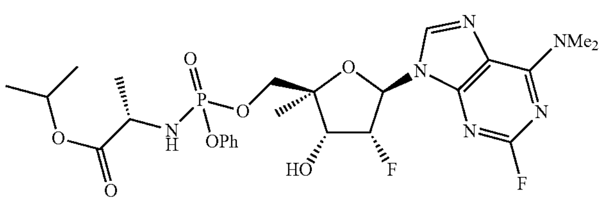 [SMILES: CC(C)OC(=O)[C@H](C)NP(=O)(OC[C@@]1(C)O[C@@H](n2cnc3c(N(C)C)nc(F)nc32)[C@H](F)[C@@H]1O)Oc1ccccc1] |
| G | 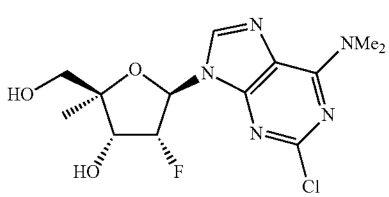 [SMILES: CN(C)c1nc(Cl)nc2c1ncn2[C@@H]1O[C@](C)(CO)[C@@H](O)[C@H]1F] |
| H | 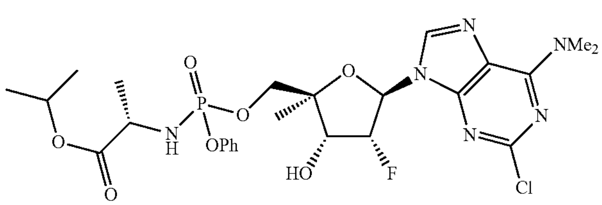 [SMILES: CC(C)OC(=O)[C@H](C)NP(=O)(OC[C@@]1(C)O[C@@H](n2cnc3c(N(C)C)nc(Cl)nc32)[C@H](F)[C@@H]1O)Oc1ccccc1] |
| I | 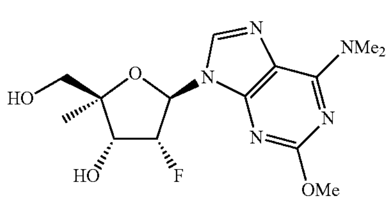 [SMILES: COc1nc(N(C)C)c2ncn([C@@H]3O[C@](C)(CO)[C@@H](O)[C@H]3F)c2n1] |

TABLE 1-continued

Non-limiting Compounds of Formula I, Formula II, Formula III, and Formula IV

| Cmpd | Structure |
|---|---|
| J | 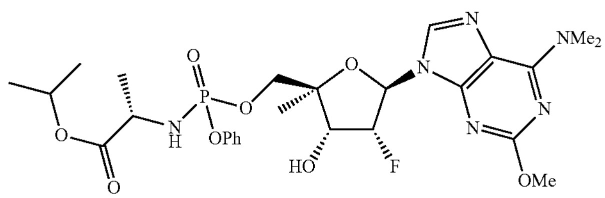 [SMILES: COc1nc(N(C)C)c2ncn([C@@H]3O[C@](C)(COP(=O)(N[C@@H](C)C(=O)OC(C)C)Oc4ccccc4)[C@@H](O)[C@H]3F)c2n1] |
| K | 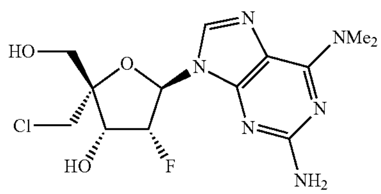 [SMILES: CN(C)c1nc(N)nc2c1ncn2[C@@H]1O[C@@](CO)(CCl)[C@@H](O)[C@H]1F] |
| L | 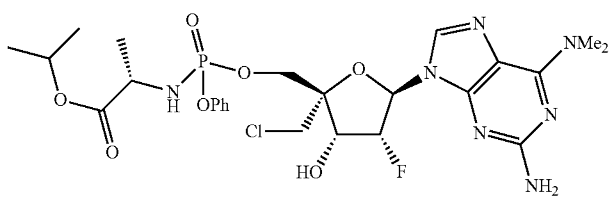 [SMILES: CC(C)OC(=O)[C@H](C)NP(=O)(OC[C@@]1(CCl)O[C@@H](n2cnc3c(N(C)C)nc(N)nc32)[C@H](F)[C@@H]1O)Oc1ccccc1] |
| M | 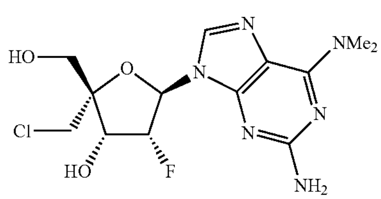 [SMILES: CN(C)c1nc(N)nc2c1ncn2[C@@H]1O[C@@](CO)(CCl)[C@@H](O)[C@H]1F] |
| N | 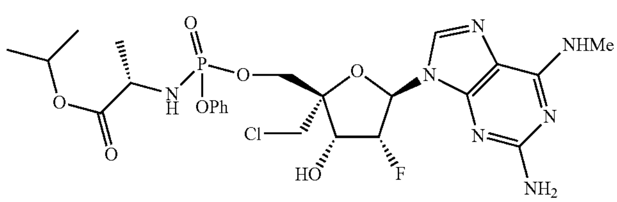 [SMILES: CNc1nc(N)nc2c1ncn2[C@@H]1O[C@](CCl)(COP(=O)(N[C@@H](C)C(=O)OC(C)C)Oc2ccccc2)[C@@H](O)[C@H]1F] |
| O | 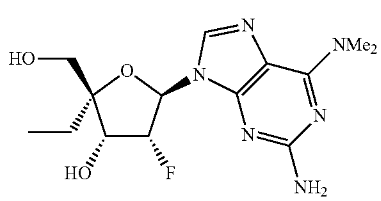 [SMILES: CC[C@]1(CO)O[C@@H](n2cnc3c(N(C)C)nc(N)nc32)[C@H](F)[C@@H]1O] |
| P | 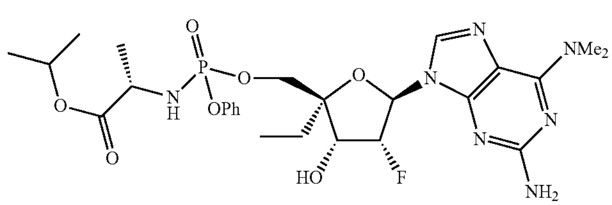 [SMILES: CC[C@]1(COP(=O)(N[C@@H](C)C(=O)OC(C)C)Oc2ccccc2)O[C@@H](n2cnc3c(N(C)C)nc(N)nc32)[C@H](F)[C@@H]1O] |

TABLE 1-continued

Non-limiting Compounds of Formula I, Formula II, Formula III, and Formula IV

| Cmpd | Structure |
|------|-----------|
| Q | 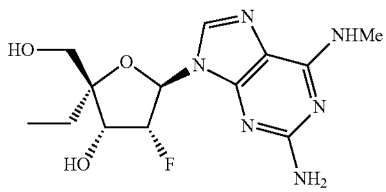 [SMILES: CC[C@]1(CO)O[C@@H](n2cnc3c(NC)nc(N)nc32)[C@H](F)[C@@H]1O] |
| R | 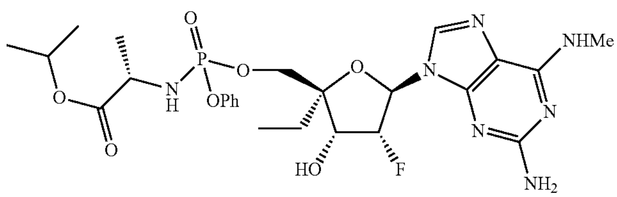 |
| S | 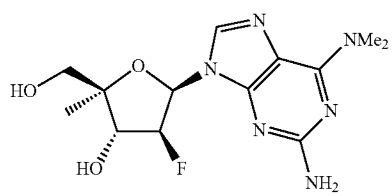 [SMILES: CN(C)c1nc(N)nc2c1ncn2[C@@H]1O[C@](C)(CO)[C@@H](O)[C@@H]1F] |
| T | 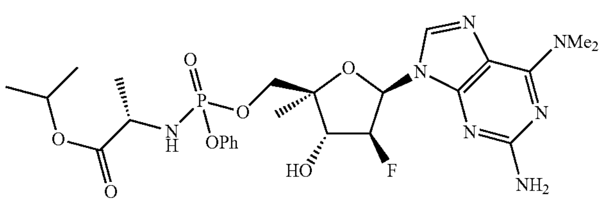 [SMILES: CC(C)OC(=O)[C@H](C)NP(=O)(OC[C@@]1(C)O[C@@H](n2cnc3c(N(C)C)nc(N)nc32)[C@@H](F)[C@@H]1O)Oc1ccccc1] |
| U | 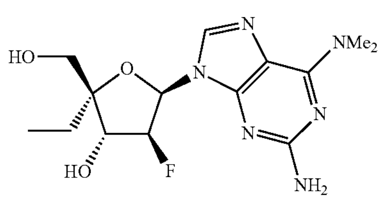 [SMILES: CC[C@]1(CO)O[C@@H](n2cnc3c(N(C)C)nc(N)nc32)[C@@H](F)[C@@H]1O] |
| V | 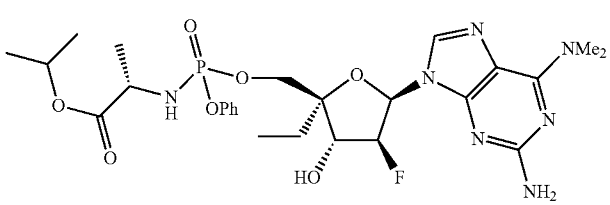 [SMILES: CC[C@]1(COP(=O)(N[C@@H](C)C(=O)OC(C)C)Oc2ccccc2)O[C@@H](n2cnc3c(N(C)C)nc(N)nc32)[C@@H](F)[C@@H]1O] |
| W | 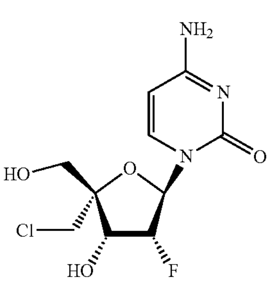 |

TABLE 1-continued

Non-limiting Compounds of Formula I, Formula II, Formula III, and Formula IV

| Cmpd | Structure |
|------|-----------|
| X | 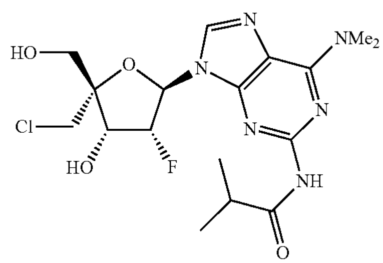 [SMILES: CC(C)C(=O)Nc1nc(N(C)C)c2ncn([C@@H]3O[C@@](CO)(CCl)[C@@H](O)[C@H]3F)c2n1] |
| Y | 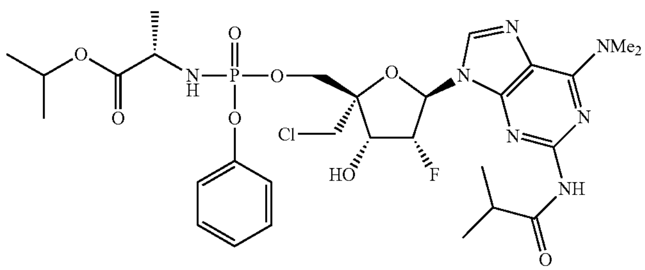 [SMILES: CC(C)OC(=O)[C@H](C)NP(=O)(OC[C@@]1(CCl)O[C@@H](n2cnc3c(N(C)C)nc(NC(=O)C(C)C)nc32)[C@H](F)[C@@H]1O)Oc1ccccc1] |
| Z | 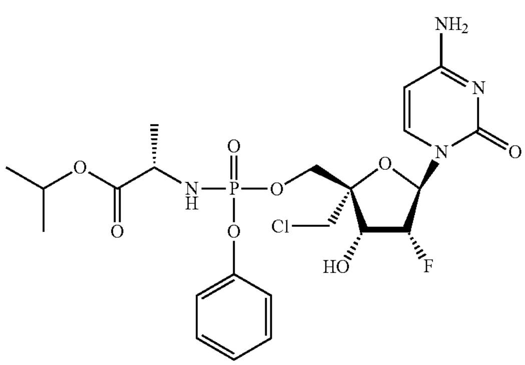 |
| AA | 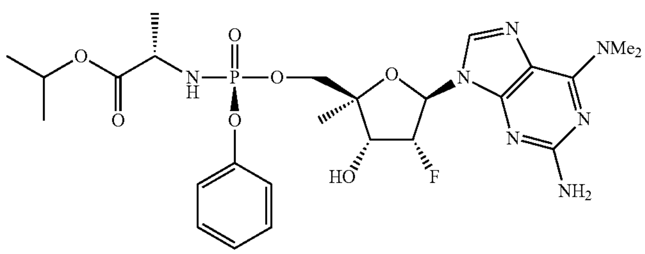 [SMILES: CC(C)OC(=O)[C@H](C)N[P@](=O)(OC[C@@]1(C)O[C@@H](n2cnc3c(N(C)C)nc(N)nc32)[C@H](F)[C@@H]1O)Oc1ccccc1] |

TABLE 2
Additional Non-limiting Compounds of Formula I, Formula II, Formula III, and Formula IV
AB
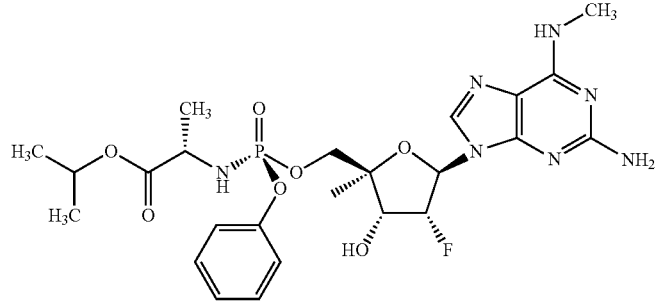 [SMILES: CNc1nc(N)nc2c1ncn2[C@@H]1O[C@](C)(CO[P@@](=O)(N[C@@H](C)C(=O)OC(C)C)Oc2ccccc2)[C@@H](O)[C@H]1F]
AC
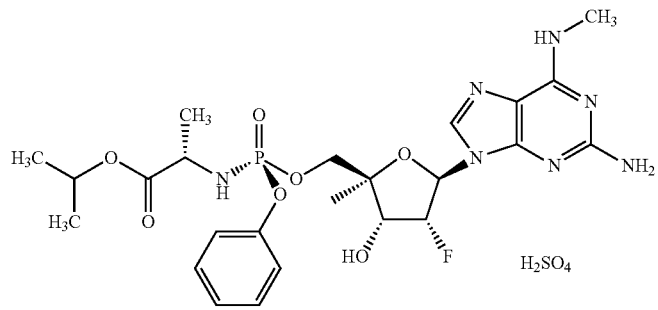
AD
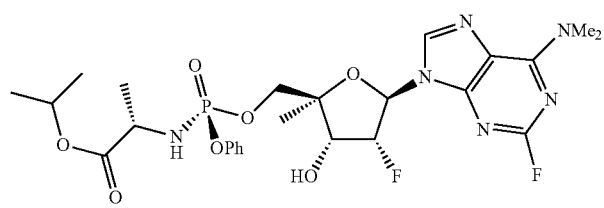
AE
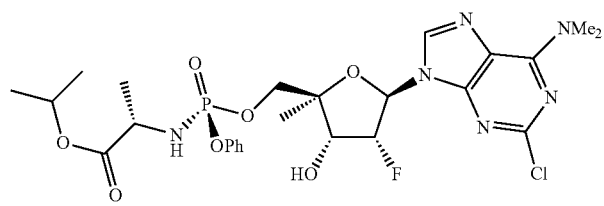 [SMILES: CC(C)OC(=O)[C@H](C)N[P@](=O)(OC[C@@]1(C)O[C@@H](n2cnc3c(N(C)C)nc(F)nc32)[C@H](F)[C@@H]1O)Oc1ccccc1]
AF
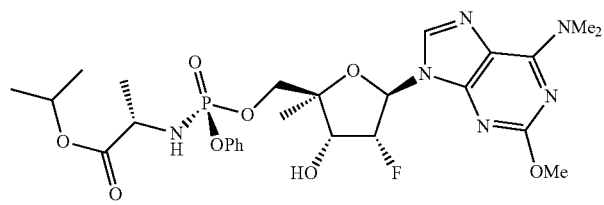 [SMILES: COc1nc(N(C)C)c2ncn([C@@H]3O[C@](C)(CO[P@@](=O)(N[C@@H](C)C(=O)OC(C)C)Oc4ccccc4)[C@@H](O)[C@H]3F)c2n1]
AG
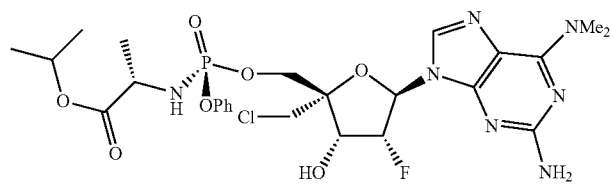 [SMILES: CC(C)OC(=O)[C@H](C)N[P@](=O)(OC[C@@]1(CCl)O[C@@H](n2cnc3c(N(C)C)nc(N)nc32)[C@H](F)[C@@H]1O)Oc1ccccc1]

TABLE 2-continued
Additional Non-limiting Compounds of Formula I, Formula II, Formula III, and Formula IV
AH
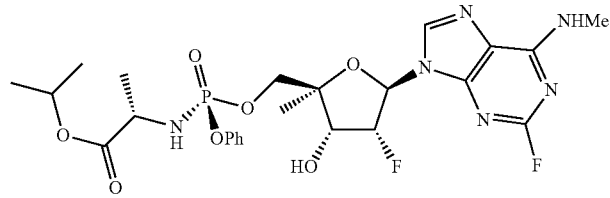 [SMILES: CNc1nc(F)nc2c1ncn2[C@@H]1O[C@](C)(CO[P@@](=O)(N[C@@H](C)C(=O)OC(C)C)Oc2ccccc2)[C@@H](O)[C@H]1F]
AI
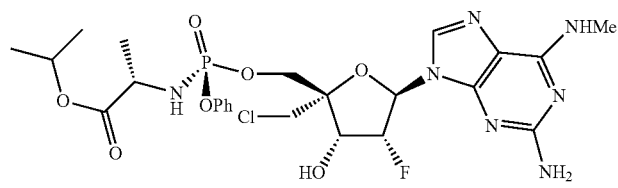
AJ
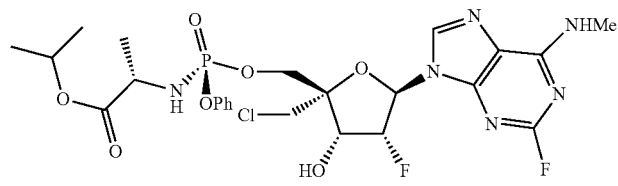 [SMILES: CNc1nc(F)nc2c1ncn2[C@@H]1O[C@](CCl)(CO[P@@](=O)(N[C@@H](C)C(=O)OC(C)C)Oc2ccccc2)[C@@H](O)[C@H]1F]
AK
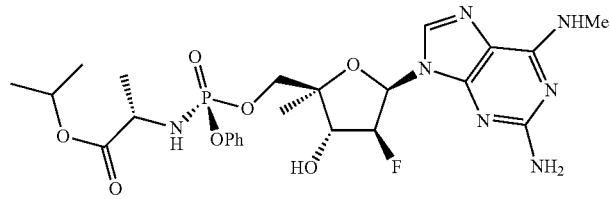 [SMILES: CNc1nc(N)nc2c1ncn2[C@@H]1O[C@](C)(CO[P@@](=O)(N[C@@H](C)C(=O)OC(C)C)Oc2ccccc2)[C@@H](O)[C@@H]1F]
AL
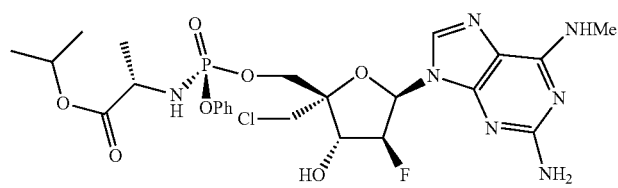
AM
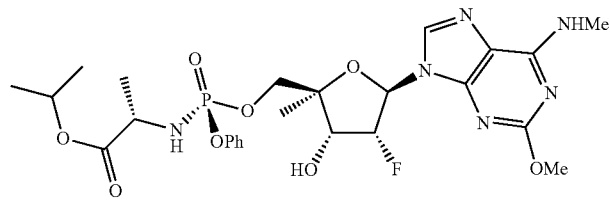 [SMILES: CNc1nc(OC)nc2c1ncn2[C@@H]1O[C@](C)(CO[P@@](=O)(N[C@@H](C)C(=O)OC(C)C)Oc2ccccc2)[C@@H](O)[C@H]1F]
AN
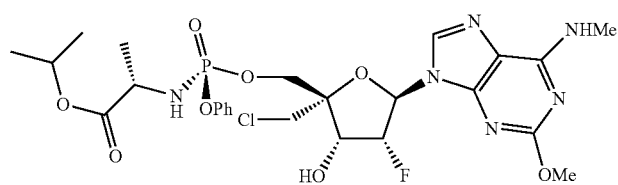 [SMILES: CNc1nc(OC)nc2c1ncn2[C@@H]1O[C@](CCl)(CO[P@@](=O)(N[C@@H](C)C(=O)OC(C)C)Oc2ccccc2)[C@@H](O)[C@H]1F]

TABLE 2-continued
Additional Non-limiting Compounds of Formula I, Formula II, Formula III, and Formula IV
AO
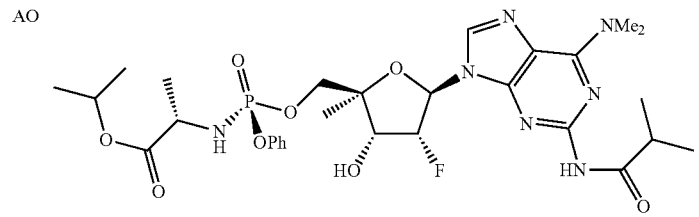
AP
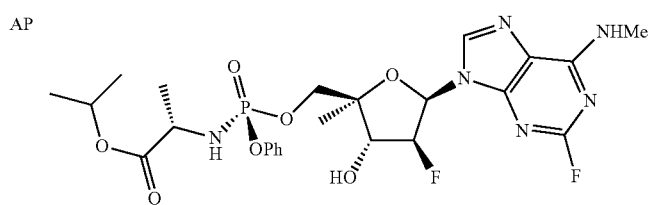
AQ
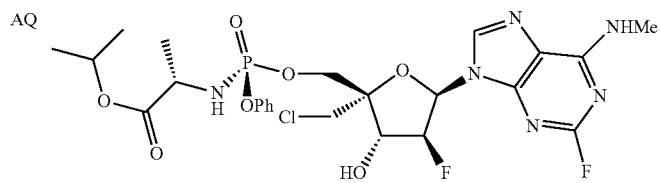
AR
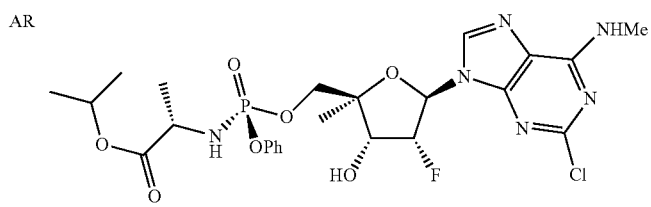
AS
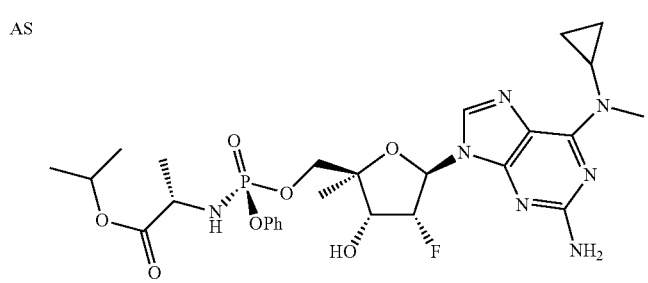
AT
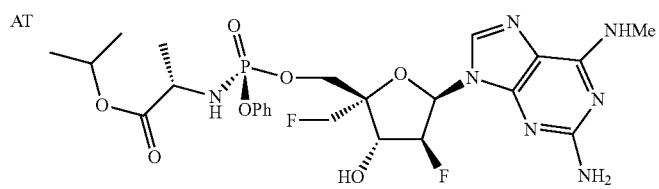
AU
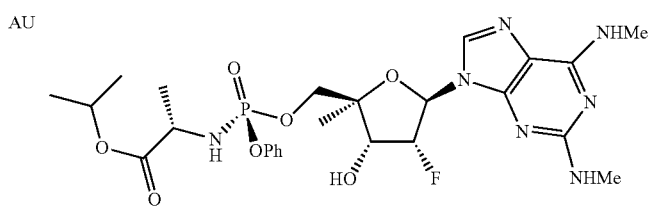

TABLE 2-continued

Additional Non-limiting Compounds of Formula I, Formula II, Formula III, and Formula IV

AV

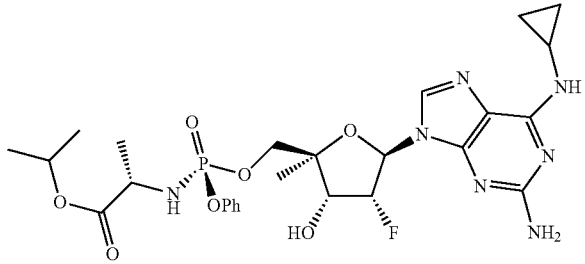 [SMILES: CC(C)OC(=O)[C@H](C)N[P@](=O)(OC[C@@]1(C)O[C@@H](n2cnc3c(NC4CC4)nc(N)nc32)[C@H](F)[C@@H]1O)Oc1ccccc1]

Biological Data

Example 3 dNHBE Assay Method and Results

Differentiated normal human bronchial epithelial (dNHBE) cells were grown on 6 mm mesh disks in transwell inserts to approximately $1.2 \times 10^6$ cells/disk and disks were transferred to individual wells of a 6-well plate. 1 mL of proprietary culture medium was added to the basolateral side of the cells and the apical side was exposed to a humidified 95% air/5% $CO_2$ environment. Cells were cultured at 37° C. for one day and then the mucin layer was removed from the apical side of the cells by repeated (3×) washing with 500 μL 30 mM HEPES buffered saline solution and culture medium on the basal side was replenished.

Respiratory syncytial virus (RSV) type A, strain A2 (ATCC VR-1540), previously passaged in MA-104 cells to make working stock cultures, was diluted 1/10 in medium before infection, using a multiplicity of infection (MOI) of ≤0.03 $CCID_{50}$ per cell.

Various concentrations of test compounds in medium were applied in duplicate to the apical (140 μL) and basal sides (1 mL) for a 1 hour pre-treatment, followed by addition of 140 μL of virus inoculum to each cell insert on the apical side. The viral inoculum and treatments were removed after 2 hours. Control cells were treated with placebo (culture medium only). Following infection, the apical medium was removed and the basal side was replaced with fresh compound in medium. The cells were maintained at the air-liquid interface, and cell culture medium on the basal side was replaced daily with fresh medium containing test compound. After 4 days, the liquid was removed from the basal side and discarded and virus released into the apical compartment was harvested by the addition of 500 μL of culture medium. The medium was thoroughly mixed, then removed, diluted 1:1 with 40% sucrose and stored at ≤−80° C.

To determine the virus titer from each treated cell culture, MA-104 cells were seeded in 96-well plates and grown overnight (37° C.) to confluence. Samples containing virus were diluted in 10-fold increments in infection medium and 200 μL of each dilution transferred into respective wells of a 96-well microtiter plate. Four microwells were used for each dilution to determine 50% viral endpoints. After 7 days of incubation, each well was scored positive for virus if any cytopathic effect was observed as compared with the uninfected control. The virus dose that was able to infect 50% of the cell cultures ($CCID_{50}$ per 0.1 mL) was calculated by the Reed-Muench method. This was repeated in duplicate for each test sample, so that values reported are an average of 2 independent CCID5o determinations. Untreated, uninfected cell controls were tested as negative controls. Statistical differences in the titers were evaluated with a one-way analysis of variance (ANOVA) followed by Dunnett's multiple comparisons test compared with the untreated virus controls.

Concentrations of test compounds that reduced virus yield by 1 $log_{10}$ (90% effective concentration; $EC_{90}$) were calculated by regression analysis. The reported $EC_{90}$ value is the mean of at least two experiments. Potential toxicity of the test compounds was evaluated microscopically. See Table 3 and Table 4 below.

TABLE 3

Activity of Nucleos(t)ide Against RSV (A2) in dNHBE Cells

| Cmpd | Structure | RSV $EC_{90}$ (μM) | Visual toxicity |
|---|---|---|---|
| A | 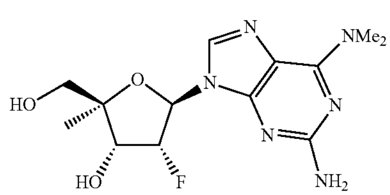 [SMILES: CN(C)c1nc(N)nc2c1ncn2[C@@H]1O[C@](C)(CO)[C@@H](O)[C@H]1F] | 142 | >306 |

TABLE 3-continued

Activity of Nucleos(t)ide Against RSV (A2) in dNHBE Cells

| Cmpd | Structure | RSV EC$_{90}$ (μM) | Visual toxicity |
|---|---|---|---|
| B | 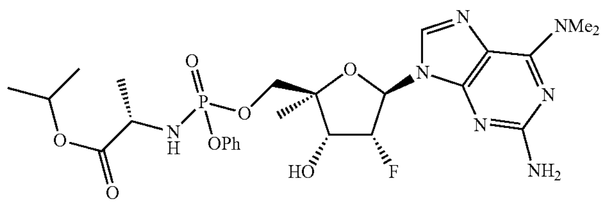 [SMILES: CC(C)OC(=O)[C@H](C)NP(=O)(OC[C@@]1(C)O[C@@H](n2cnc3c(N(C)C)nc(N)nc32)[C@H](F)[C@@H]1O)Oc1ccccc1] | 5.9 | >167 |
| C | 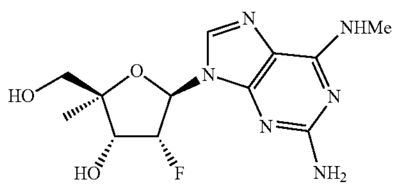 [SMILES: CNc1nc(N)nc2c1ncn2[C@@H]1O[C@](C)(CO)[C@@H](O)[C@H]1F] | 3.2 | >320 |
| D | 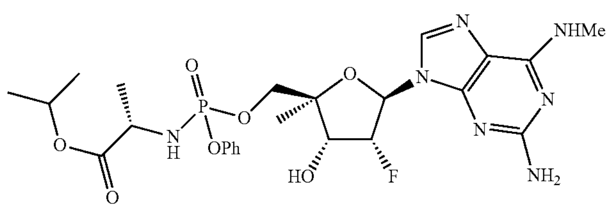 [SMILES: CNc1nc(N)nc2c1ncn2[C@@H]1O[C@](C)(COP(=O)(N[C@@H](C)C(=O)OC(C)C)Oc2ccccc2)[C@@H](O)[C@H]1F] | 1.7 | >172 |
| K | 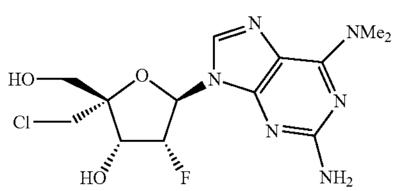 | 74.8 | >277 |
| L | 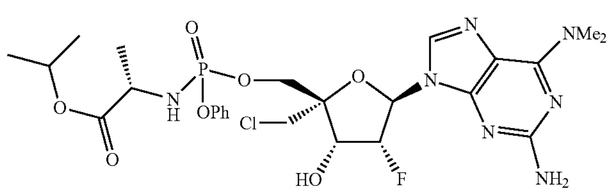 [SMILES: CC(C)OC(=O)[C@H](C)NP(=O)(OC[C@@]1(CCl)O[C@@H](n2cnc3c(N(C)C)nc(N)nc32)[C@H](F)[C@@H]1O)Oc1ccccc1] | 13.5 | 158 |
| M | 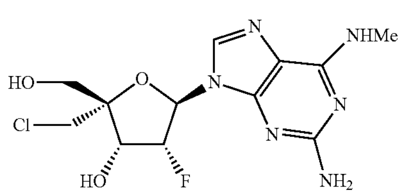 | 2.9 | >288 |
| N | 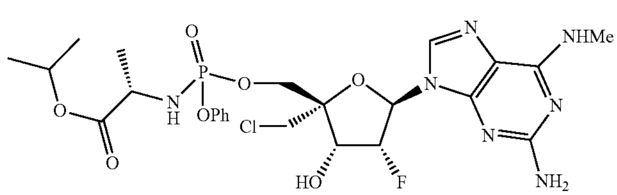 [SMILES: CNc1nc(N)nc2c1ncn2[C@@H]1O[C@](CCl)(COP(=O)(N[C@@H](C)C(=O)OC(C)C)Oc2ccccc2)[C@@H](O)[C@H]1F] | 0.83 | >162 |

TABLE 3-continued

Activity of Nucleos(t)ide Against RSV (A2) in dNHBE Cells

| Cmpd | Structure | RSV EC$_{90}$ (µM) | Visual toxicity |
|---|---|---|---|
| O | 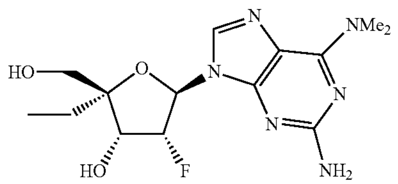 [SMILES: CC[C@]1(CO)O[C@@H](n2cnc3c(N(C)C)nc(N)nc32)[C@H](F)[C@@H]1O] | >293 | >293 |
| P | 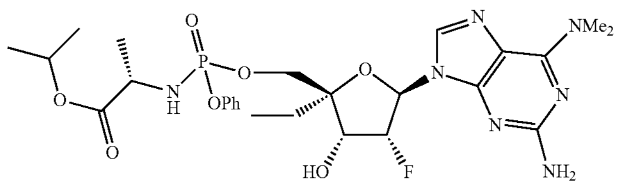 [SMILES: CC[C@]1(COP(=O)(N[C@@H](C)C(=O)OC(C)C)Oc2ccccc2)O[C@@H](n2cnc3c(N(C)C)nc(N)nc32)[C@H](F)[C@@H]1O] | 88.6 | >143 |
| Q | 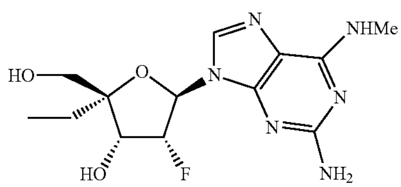 [SMILES: CC[C@]1(CO)O[C@@H](n2cnc3c(NC)nc(N)nc32)[C@H](F)[C@@H]1O] | 7.3 | >306 |
| R | 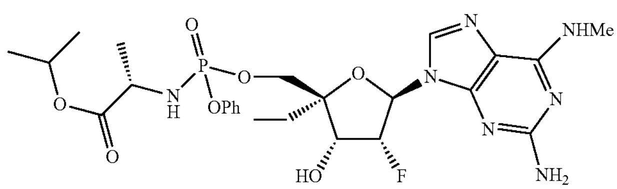 | 2.3 | >167 |
| S | 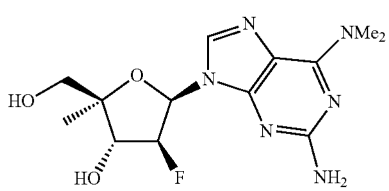 [SMILES: CN(C)c1nc(N)nc2c1ncn2[C@@H]1O[C@](C)(CO)[C@@H](O)[C@@H]1F] | >300 | >307 |
| T | 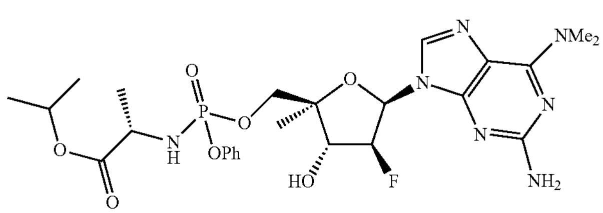 [SMILES: CC(C)OC(=O)[C@H](C)NP(=O)(OC[C@@]1(C)O[C@@H](n2cnc3c(N(C)C)nc(N)nc32)[C@@H](F)[C@@H]1O)Oc1ccccc1] | 1.1 | >167 |
| U | 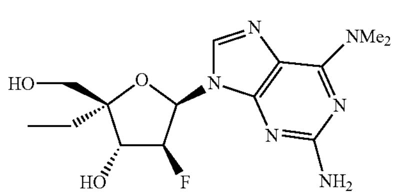 [SMILES: CC[C@]1(CO)O[C@@H](n2cnc3c(N(C)C)nc(N)nc32)[C@@H](F)[C@@H]1O] | >294 | >294 |

TABLE 3-continued

Activity of Nucleos(t)ide Against RSV (A2) in dNHBE Cells

| Cmpd | Structure | RSV EC$_{90}$ (μM) | Visual toxicity |
|---|---|---|---|
| V | [structure] | 44.8 | 164 |
| W | [structure] | 0.58 | >338 |
| Z | [structure] | 2.0 | >177 |
| AA | [structure] | 3.5 | >167 |

TABLE 4

Activity of Nucleos(t)ide Against RSV (A2) in dNHBE Cells in Additional Compounds

| Cmpd | Structure | RSV EC$_{90}$ (μM) | Visual toxicity |
|---|---|---|---|
| AB | 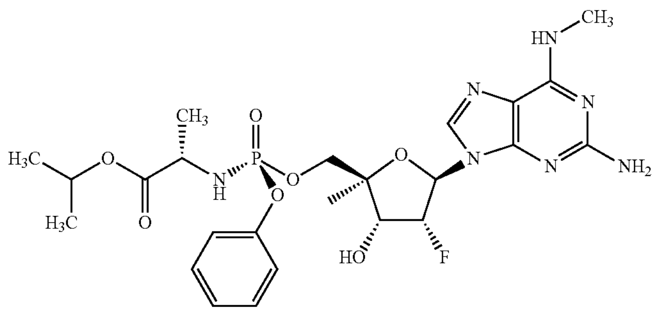 [SMILES: CNc1nc(N)nc2c1ncn2[C@@H]1O[C@](C)(CO[P@@](=O)(N[C@@H](C)C(=O)OC(C)C)Oc2ccccc2)[C@@H](O)[C@H]1F] | 0.052 | >17 |
| AC | 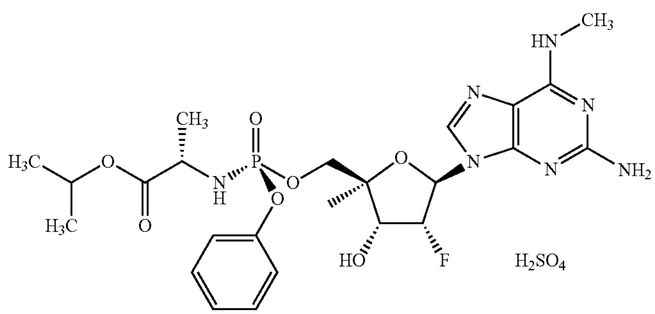 | 0.074 | >1.4 |
| AD | 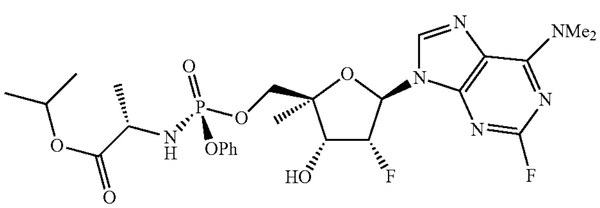 [SMILES: CC(C)OC(=O)[C@H](C)N[P@](=O)(OC[C@@]1(C)O[C@@H](n2cnc3c(N(C)C)nc(F)nc32)[C@H](F)[C@@H]1O)Oc1ccccc1] | 8.4 | >16 |
| AE | 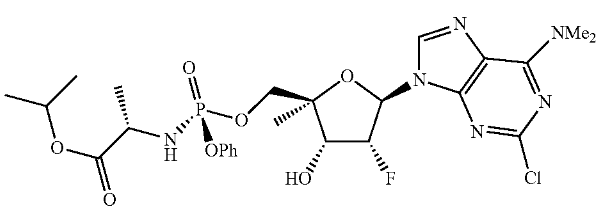 | 9.3 | >16 |
| AF | 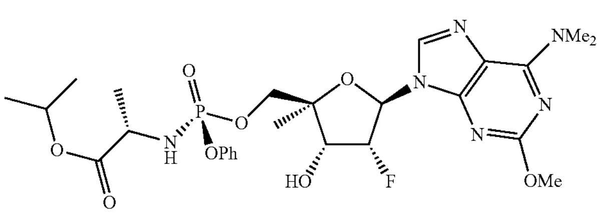 [SMILES: COc1nc(N(C)C)c2ncn([C@@H]3O[C@](C)(CO[P@@](=O)(N[C@@H](C)C(=O)OC(C)C)Oc4ccccc4)[C@@H](O)[C@H]3F)c2n1] | 0.18 | >16 |
| AG | 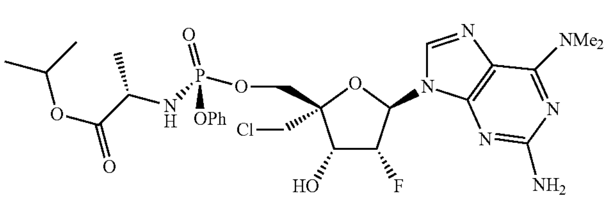 [SMILES: CC(C)OC(=O)[C@H](C)N[P@](=O)(OC[C@@]1(CCl)O[C@@H](n2cnc3c(N(C)C)nc(N)nc32)[C@H](F)[C@@H]1O)Oc1ccccc1] | <0.16 | >15 |

TABLE 4-continued

Activity of Nucleos(t)ide Against RSV (A2) in dNHBE Cells in Additional Compounds

| Cmpd | Structure | RSV EC$_{90}$ (μM) | Visual toxicity |
|------|-----------|---------------------|-----------------|
| AH   | 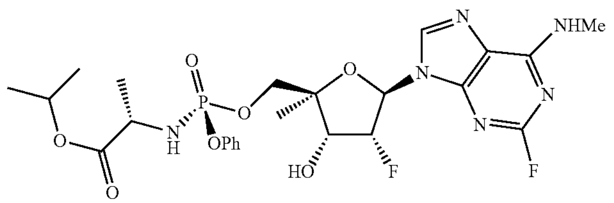          | 0.12                | >1.7            |
| AI   | 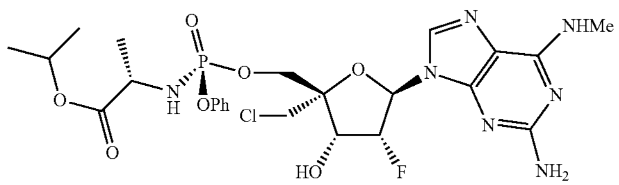 [SMILES: CNc1nc(N)nc2c1ncn2[C@@H]1O[C@](CCl)(CO[P@@](=O)(N[C@@H](C)C(=O)OC(C)C)Oc2ccccc2)[C@@H](O)[C@H]1F]          | 0.13                | >1.6            |
| AJ   | 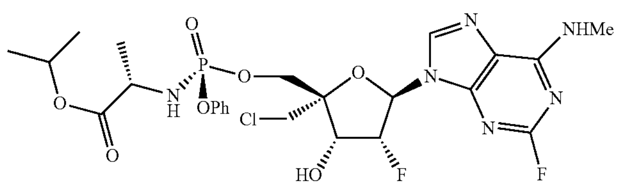 [SMILES: CNc1nc(F)nc2c1ncn2[C@@H]1O[C@](CCl)(CO[P@@](=O)(N[C@@H](C)C(=O)OC(C)C)Oc2ccccc2)[C@@H](O)[C@H]1F]          | >1.6                | >1.6            |
| AK   | 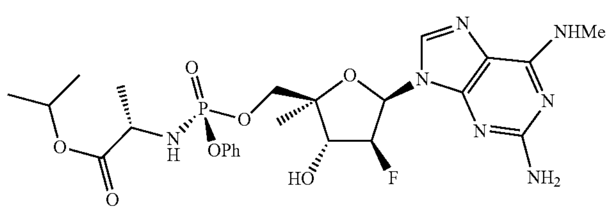 [SMILES: CNc1nc(N)nc2c1ncn2[C@@H]1O[C@](C)(CO[P@@](=O)(N[C@@H](C)C(=O)OC(C)C)Oc2ccccc2)[C@@H](O)[C@@H]1F]          | 1.1                 | >1.7            |
| AL   | 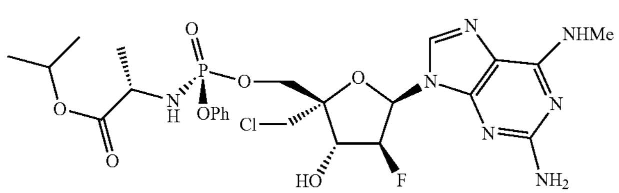          | >1.6                | >1.6            |
| AM   | 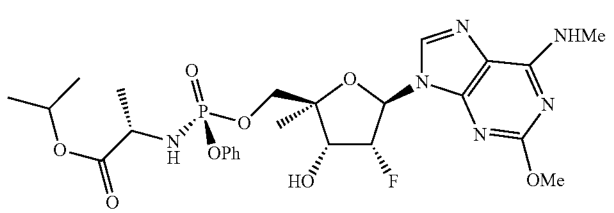 [SMILES: CNc1nc(OC)nc2c1ncn2[C@@H]1O[C@](C)(CO[P@@](=O)(N[C@@H](C)C(=O)OC(C)C)Oc2ccccc2)[C@@H](O)[C@H]1F]          | 1.1                 | >1.7            |
| AN   | 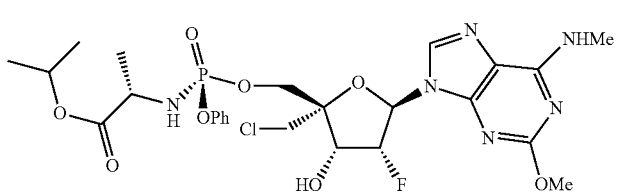 [SMILES: CNc1nc(OC)nc2c1ncn2[C@@H]1O[C@](CCl)(CO[P@@](=O)(N[C@@H](C)C(=O)OC(C)C)Oc2ccccc2)[C@@H](O)[C@H]1F]          | >1.6                | >1.6            |

TABLE 4-continued

Activity of Nucleos(t)ide Against RSV (A2) in dNHBE Cells in Additional Compounds

| Cmpd | Structure | RSV EC$_{90}$ (µM) | Visual toxicity |
|---|---|---|---|
| AO | 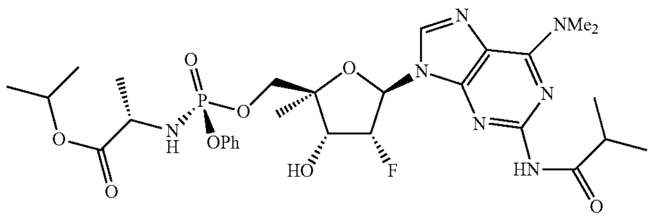 [SMILES: CC(C)OC(=O)[C@H](C)N[P@](=O)(OC[C@@]1(C)O[C@@H](n2cnc3c(N(C)C)nc(NC(=O)C(C)C)nc32)[C@H](F)[C@@H]1O)Oc1ccccc1] | 0.096 | >1.5 |
| AP | 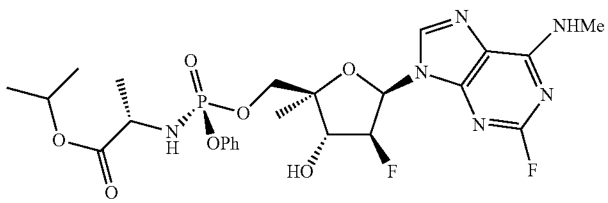 [SMILES: CNc1nc(F)nc2c1ncn2[C@@H]1O[C@](C)(CO[P@@](=O)(N[C@@H](C)C(=O)OC(C)C)Oc2ccccc2)[C@@H](O)[C@@H]1F] | 0.034 | >1.7 |
| AQ | 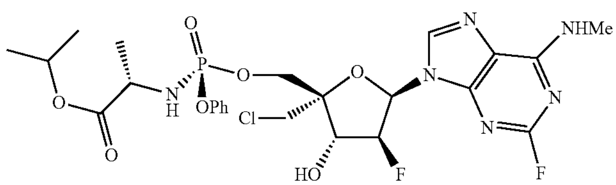 [SMILES: CNc1nc(F)nc2c1ncn2[C@@H]1O[C@](CCl)(CO[P@@](=O)(N[C@@H](C)C(=O)OC(C)C)Oc2ccccc2)[C@@H](O)[C@@H]1F] | 0.18 | >1.6 |
| AR | 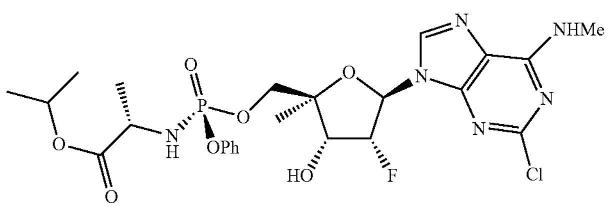 | 1.0 | >1.6 |
| AS | 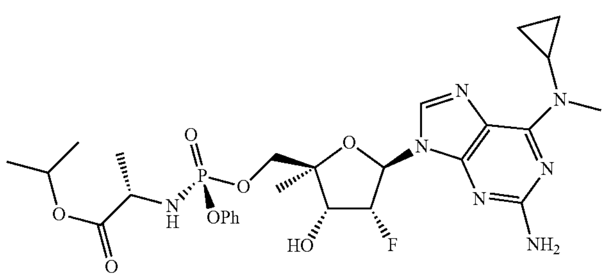 [SMILES: CC(C)OC(=O)[C@H](C)N[P@](=O)(OC[C@@]1(C)O[C@@H](n2cnc3c(N(C)C4CC4)nc(N)nc32)[C@H](F)[C@@H]1O)Oc1ccccc1] | 1.5 | >1.6 |
| AT | 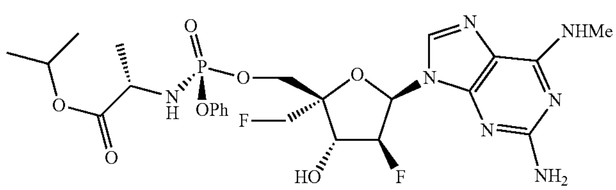 | 0.18 | >1.6 |
| AU | 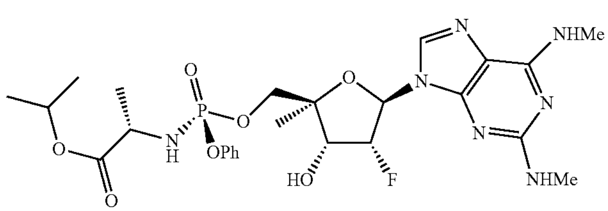 [SMILES: CNc1nc(NC)c2ncn([C@@H]3O[C@](C)(CO[P@@](=O)(N[C@@H](C)C(=O)OC(C)C)Oc4ccccc4)[C@@H](O)[C@H]3F)c2n1] | >1.7 | >1.7 |

TABLE 4-continued

Activity of Nucleos(t)ide Against RSV (A2) in dNHBE Cells in Additional Compounds

| Cmpd | Structure | RSV EC$_{90}$ (µM) | Visual toxicity |
|---|---|---|---|
| AV | 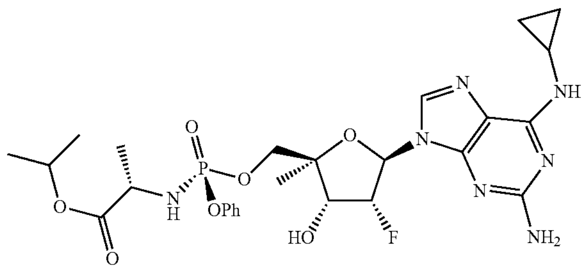 [SMILES: CC(C)OC(=O)[C@H](C)N[P@](=O)(OC[C@@]1(C)O[C@@H](n2cnc3c(NC4CC4)nc(N)nc32)[C@H](F)[C@@H]1O)Oc1ccccc1] | 0.099 | >1.6 |

Example 4

Cytopathic Effect Assay with RSV A2 in MA-104 and HEp-2 Cells

Test compounds were dissolved in DMSO and then prepared in eight half-log dilutions in MEM medium with 50 µg/mL gentamicin and 2% FBS (MA-104 cells only). Each dilution was added to 5 wells of a 96-well plate with 80-100% confluent cells (either MA-104 cells or HEp-2 cells). Three wells of each dilution were infected with respiratory syncytial virus A2 (ATCC VR-1540) and two wells remained uninfected as toxicity controls. After maximum cytopathic effect (CPE) was observed microscopically in untreated virus control wells, plates were stained with neutral red dye for approximately 2 hours, then supernatant dye was removed and the incorporated dye was extracted in 50:50 Sorensen citrate buffer/ethanol and read on a spectrophotometer. Optical density values were normalized based on cell and virus controls, then the concentration of test compound required to inhibit CPE by 50% (EC$_{50}$) was calculated by regression analysis. The reported EC$_{50}$ value is the mean of at least two experiments. The concentration of compound that caused 50% CPE in the absence of virus was similarly calculated to determine cytotoxicity (CC$_{50}$). See Tables 5 and 6 below.

TABLE 5

Activity of Nucleos(t)ide Against RSV A2 in MA-104 Cells

| Cmpd | Structure | RSV EC$_{50}$ (µM) | CC$_{50}$ |
|---|---|---|---|
| A | 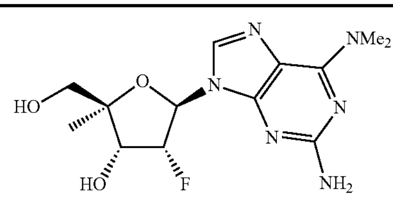 | >306 | >306 |
| B | 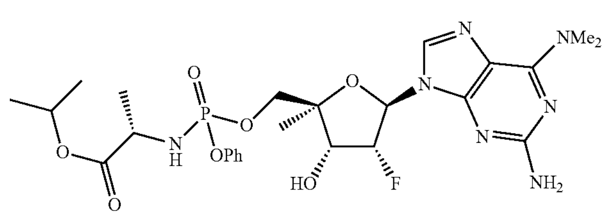 [SMILES: CC(C)OC(=O)[C@H](C)NP(=O)(OC[C@@]1(C)O[C@@H](n2cnc3c(N(C)C)nc(N)nc32)[C@H](F)[C@@H]1O)Oc1ccccc1] | <168 | <168 |
| K | 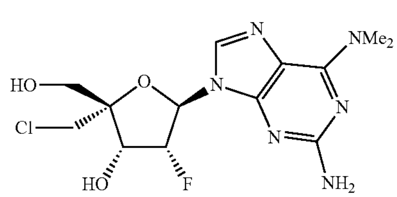 [SMILES: CN(C)c1nc(N)nc2c1ncn2[C@@H]1O[C@@](CO)(CCl)[C@@H](O)[C@H]1F] | >225 | 225 |

TABLE 5-continued

Activity of Nucleos(t)ide Against RSV A2 in MA-104 Cells

| Cmpd | Structure | RSV EC$_{50}$ (µM) | CC$_{50}$ |
|---|---|---|---|
| L | [structure] | >159 | >159 |
| O | [structure] | >293 | 285 |
| P | [structure] | >164 | >164 |
| S | [structure] | >306 | >306 |
| T | [structure] | >167 | >167 |
| U | [structure] | >294 | >294 |
| V | [structure] | >164 | >164 |

TABLE 5-continued

Activity of Nucleos(t)ide Against RSV A2 in MA-104 Cells

| Cmpd | Structure | RSV EC$_{50}$ (μM) | CC$_{50}$ |
|---|---|---|---|
| W | 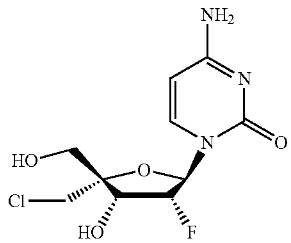 | 9.6 | >338 |
| X | 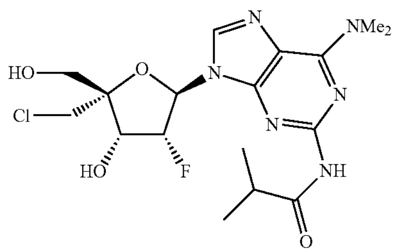 [SMILES: CC(C)C(=O)Nc1nc(N(C)C)c2ncn([C@@H]3O[C@@](CO)(CCl)[C@@H](O)[C@H]3F)c2n1] | >232 | 204 |
| Y | 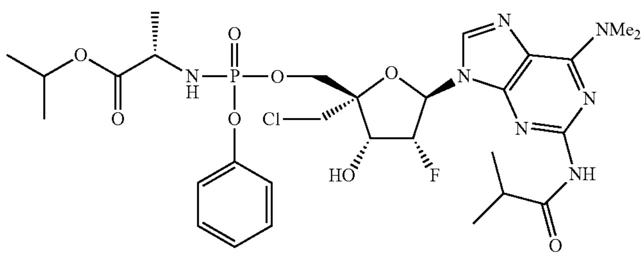 [SMILES: CC(C)OC(=O)[C@H](C)NP(=O)(OC[C@@]1(CCl)O[C@@H](n2cnc3c(N(C)C)nc(NC(=O)C(C)C)nc32)[C@H](F)[C@@H]1O)Oc1ccccc1] | >142 | >142 |
| Z | 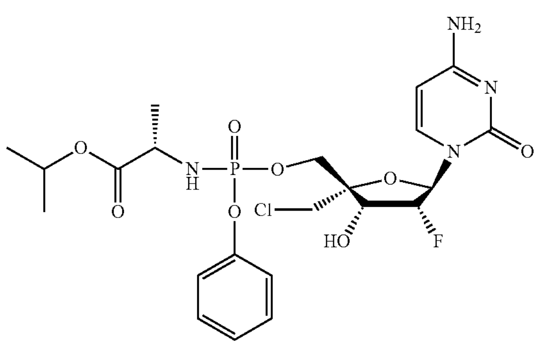 | >177 | >177 |

TABLE 6

Activity of Nucleos(t)ide Against RSV HEp-2 cells

| Cmpd | Structure | RSV EC$_{50}$ (μM) | TC$_{50}$ |
|---|---|---|---|
| C | 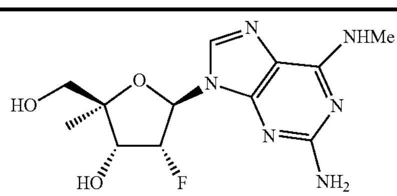 | >100 | >100 |

TABLE 6-continued

Activity of Nucleos(t)ide Against RSV HEp-2 cells

| Cmpd | Structure | RSV EC$_{50}$ (μM) | TC$_{50}$ |
|---|---|---|---|
| D | (structure: isopropyl alaninate phenyl phosphoramidate of 2'-fluoro-4'-methyl nucleoside with 6-NHMe, 2-NH$_2$ purine) | >100 | >100 |
| O | (structure: nucleoside with 4'-ethyl, 2'-fluoro, 3'-OH, 5'-OH sugar and 6-NMe$_2$, 2-NH$_2$ purine base) | >100 | >100 |
| P | (structure: isopropyl alaninate phenyl phosphoramidate of 2'-fluoro nucleoside with 6-NMe$_2$, 2-NH$_2$ purine) | >100 | >100 |
| W | (structure: 4'-chloromethyl, 2'-fluoro cytidine analog) | 0.6 | >100 |

Example 4

Hamster Lung Triphosphate Assay Method and Results

Male Golden Syrian hamsters (n=3 per test compound) were fasted overnight and then administered test compounds in PEG400 at a target dose of 50 mg/kg by oral gavage. Food was returned 4 h after dosing. At 72 h post dose, animals were anesthetized and a sample of lung tissue was removed and flash-frozen in liquid nitrogen. Approximately 0.5 g of frozen tissue was homogenized using a Polytron homogenizer in 5 volumes homogenization solution (MeOH:50% aqueous KOH:268 mM EDTA, pH 8, 1750:5:750, v/v) in a dry ice/ethanol bath. Supernatants were prepared by centrifugation and analyzed by LC-MS/MS for concentrations of the corresponding analog triphosphates. See Table 7 below for the 72 hour lung triphosphate concentration. After 72 hours, the lung triphosphate concentration following administration of Compound AB and Compound AC was greater than 800 ng/g.

TABLE 7

Analog Triphosphate (TP) Concentration in Hamster Lung Tissue 72 Hours after Oral Administration of a Target Dose of 50 mg/kg

| Cmpd | Structure | 72 h Lung TP Concentration (ng/g) |
|---|---|---|
| AB | 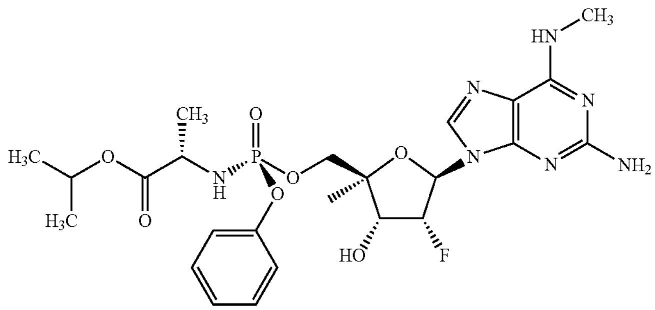 [SMILES: CNc1nc(N)nc2c1ncn2[C@@H]1O[C@](C)(CO[P@@](=O)(N[C@@H](C)C(=O)OC(C)C)Oc2ccccc2)[C@@H](O)[C@H]1F] | 864 |
| AC | 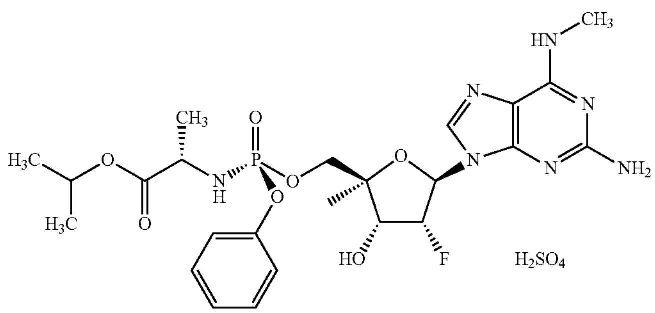 | 817 |
| AH | 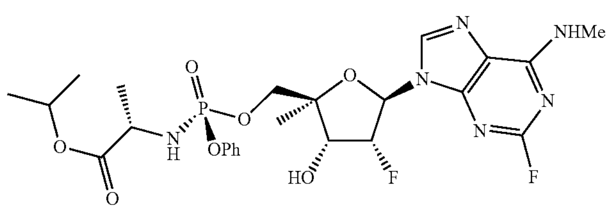 | <18 |
| AI | 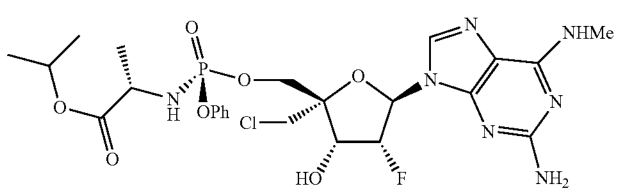 | 220 |
| AL | 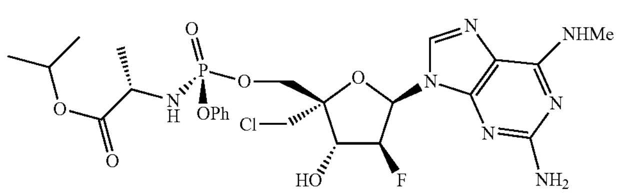 [SMILES: CNc1nc(N)nc2c1ncn2[C@@H]1O[C@](CCl)(CO[P@@](=O)(N[C@@H](C)C(=O)OC(C)C)Oc2ccccc2)[C@@H](O)[C@@H]1F] | <18 |
| AO | 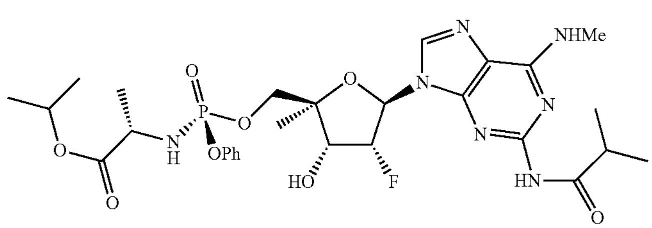 [SMILES: CNc1nc(NC(=O)C(C)C)nc2c1ncn2[C@@H]1O[C@](C)(CO[P@@](=O)(N[C@@H](C)C(=O)OC(C)C)Oc2ccccc2)[C@@H](O)[C@H]1F] | 108 |

TABLE 7-continued

Analog Triphosphate (TP) Concentration in Hamster Lung Tissue 72 Hours after Oral Administration of a Target Dose of 50 mg/kg

| Cmpd | Structure | 72 h Lung TP Concentration (ng/g) |
|---|---|---|
| AP | [structure: isopropyl alaninate phenoxy phosphoramidate of 2'-deoxy-2',2-difluoro-4'-methyl-N6-methyladenosine] | <30 |
| AQ | [structure: isopropyl alaninate phenoxy phosphoramidate of 5'-chloromethyl-2'-fluoro-2-fluoro-N6-methyladenosine analog] | <30 |
| AU | [structure: isopropyl alaninate phenoxy phosphoramidate of 2'-fluoro-4'-methyl-N6-methyl-2-methylamino-adenosine] | 174 |

Example 6

Human Bone Marrow Progenitor Cell Assay Method and Results

Select compounds were tested in an in vitro selectivity study with human bone marrow progenitor cells. Fresh human bone marrow progenitor cells (Invitrogen) suspended in either BFU-E or GM-CSF-specific culture medium were added, at 105 cells/well, to triplicate serial dilutions of TA in 6-well plates. After 14-day incubations, colony counts were used to determine $CC_{60}$ values. BFU-E colonies were confirmed using the benzidene technique. No cytotoxicity was observed from any of the tested compounds. For comparison, AZT has an $EC_{50}$ value of 2.59 μM in BFU-E-specific culture and an $IC_{50}$ value of 4.56 μM in GM-CSF-specific culture. Results are presented in Table 8.

TABLE 8

Activity of Selected Compounds in Bone Marrow Stem Cells

| Cmpd | Structure | Bone Marrow Stem Cell $IC_{50}$ (μM) | |
|---|---|---|---|
| | | BFU-E | CFU-GM |
| AB | [structure: isopropyl alaninate phenoxy phosphoramidate of 2'-fluoro-4'-methyl-N6-methyl-2-amino-adenosine] | >100 | >100 |

TABLE 8-continued

Activity of Selected Compounds in Bone Marrow Stem Cells

| Cmpd | Structure | Bone Marrow Stem Cell IC$_{50}$ (μM) | |
|---|---|---|---|
| | | BFU-E | CFU-GM |
| AH | [structure] | >100 | >100 |
| AI | [structure] | >100 | >100 |
| AQ | [structure] | >100 | >100 |
| AZT | | 2.59 | 4.56 |

Example 7 iPS Cardiomyocyte Assay Methods and Results

Select compounds were tested in an in vitro selectivity study with iPS cardiomyocytes. iPS cardiomyocytes (Cellular Dynamics) were seeded in microliter plates at 1.5×104 cells per well. After 48-hr incubation, cells were washed and maintenance medium containing 30 serially diluted TA was added in triplicate. After incubating for an additional 3 days, cellviability was measured by staining with XTT and CC$_{50}$ values were calculated. No cytotoxicity was observed from any of the tested compounds. For comparison, Doxazosin has an IC$_{50}$ value of 12.5 μM in the iPS cardiomyocyte assay. Results are shown in Table 9.

TABLE 9

Activity of Selected Compounds on iPS Cardiomyocytes

| Cmpd | Structure | iPS Cardiomyocyte IC$_{50}$ (μM) |
|---|---|---|
| AB | [structure] | >100 |

TABLE 9-continued

Activity of Selected Compounds on iPS Cardiomyocytes

| Cmpd | Structure | iPS Cardiomyocyte IC$_{50}$ (μM) |
|---|---|---|
| AH | 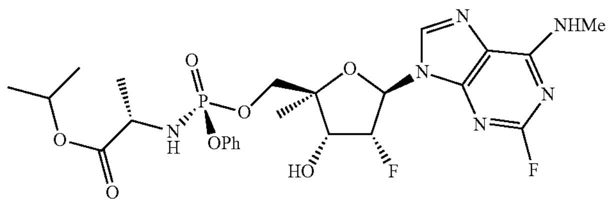 | >100 |
| AI | 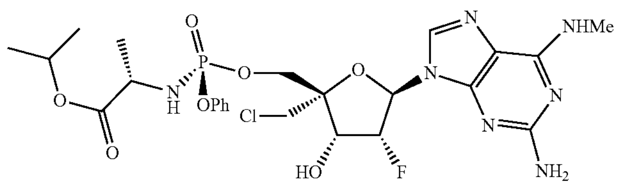 [SMILES: CNc1nc(N)nc2c1ncn2[C@@H]1O[C@](CCl)(CO[P@@](=O)(N[C@@H](C)C(=O)OC(C)C)Oc2ccccc2)[C@@H](O)[C@H]1F] | >100 |
| AQ | 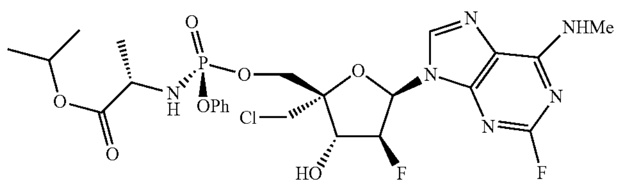 [SMILES: CNc1nc(F)nc2c1ncn2[C@@H]1O[C@](CCl)(CO[P@@](=O)(N[C@@H](C)C(=O)OC(C)C)Oc2ccccc2)[C@@H](O)[C@@H]1F] | >100 |
| Doxazosin | | 12.5 |

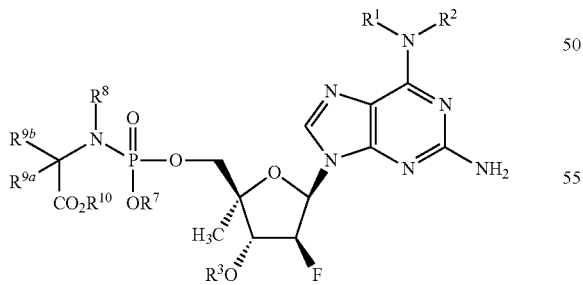

All publications and patent applications cited in this specification are herein incorporated by reference as if each individual publication or patent application were specifically and individually indicated to be incorporated by reference.

The descriptions herein are described by way of illustration and example for purposes of clarity of understanding for embodiments only. It will be readily apparent to one of ordinary skill in the art in light of the teachings of this invention that certain changes and modifications may be made thereto without departing from the spirit or scope of the invention as defined in the appended claims.

We claim:

1. A compound of Formula or a pharmaceutically acceptable salt thereof,
wherein:
$R^1$ is methyl;
$R^2$ is hydrogen;
$R^3$ is hydrogen
$R^7$ is hydrogen, $C_{1-6}$akyl, $C_{3-7}$cycloalkyl, heteroaryl, heterocyclic, or aryl;

$R^8$ is hydrogen, $C_{1-6}$akyl, or $R^{9a}$ or $R^{9b}$ and $R^8$ together are $(CH_2)n$ so as to form a cyclic ring that includes the adjoining N and C atoms $R^9a$ and $R^{9b}$ are
(i) independently selected from hydrogen, $C_{1-6}$akyl, cycloalkyl, —$(CH_2)_c(NR^{9'})_2$, $C_{1-6}$hydroxyalkyl, —$CH_2$ SH, —$(CH_2)_2$ S(O)(Me), —$(CH_2)_3$NHC (=NH)NH$_2$, (1H-indol-3-yl)methyl, (1H-imidazol-4-yl)methyl, —$(CH_2)_c$COR$^{9''}$, aryl, and aryl($C_{1-3}$ akyl);
(ii) $R^{9a}$ and $R^{9b}$ both are $C_{1-6}$akyl;
(iii) $R^{9a}$ and $R^{9b}$ together are $(CH_2)_r$ so as to form a spiro ring;
(iv) $R^{9a}$ is hydrogen and $R^{9b}$ and $R^8$ together are $(CH_2)_n$, so as to form a cyclic ring that includes the adjoining N and C atoms;
(v) $R^{9b}$ is hydrogen and $R^{9a}$ and $R^8$ together are $(CH_2)_n$ so as to form a cyclic ring that includes the adjoining N and C atoms
(vi) $R^{9a}$ is hydrogen and $R^{9b}$ is hydrogen, $CH_3$, $CH_2CH_3$, $CH(CH_3)_2$, $CH_2CH(CH_3)_2$, $CH(CH_3)$ $CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$,$CH2CH2CH2CH2NH2$,— $CH_2CH_2CH_2NHC(NH)NH2$, $CH_2$-imidazol-4-yl, $CH_2OH$, $CH(OH)CH_3$, $CH_2((4'-OH)-Ph)$, $CH_2SH$, or lower cycloalkyl; or,
(vii) $R^{9a}$ is $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)$ NH$_2$, $CH_2$-imidazol-4-yl, $CH_2OH$, $CH(OH)CH_3$, $CH_2((4'-OH)-Ph)$, $CH_2SH$, or lower cycloalkyl and $R^{9b}$ is hydrogen;

$R^{9'}$ is independently hydrogen or $C_{1-6}$alkyl;
$R^{9''}$ is —$OR^{11}$,
$R^{10}$ is hydrogen, $C_{1-6}$alkyl, $C_{1-6}$haloalkyl, $(C_0-C_2)(C_{3-7}$cycloalkyl), $(C_0-C_2)$(heterocycloalkyl), aminoacyl, $(C_0-C2)$(aryl), or substituted $(C_0-C2)$(heteroaryl);
$R_{11}$ is $C_{1-6}$alkyl, cycloalkyl, $C_{2-6}$alkynyl, $C_{2-6}$alkenyl, or acyl;
n is 2 to 4;
c is 1 to 6;and
r is 2 to 5.

2. The compound of claim 1,
wherein
$R^7$ is phenyl;
$R^8$ is hydrogen;
$R^{9a}$ and $R^{9b}$ are independently selected from hydrogen and methyl; and
$R^{10}$ is $C_1$-$C6$alkyl.

3. The compound of claim 1, wherein $R^7$ is phenyl.

4. The compound of claim 3, wherein $R^8$ is hydrogen.

5. The compound of claim 4, wherein $R^{9a}$ is methyl and $R^{9b}$ is hydrogen.

6. The compound of claim 5, wherein $R^{10}$ is methyl, ethyl, or isopropyl.

7. The compound of claim 6, wherein $R^{10}$ is isopropyl.

8. The compound of claim 1, wherein $R^7$ is napthyl.

9. The compound of claim 1, wherein $R^8$ is hydrogen.

10. The compound of claim 1, wherein $R^{9a}$ and $R^{9b}$ are both $C_{1-6}$akyl.

11. The compound of claim 1, wherein $R^{9a}$ is methyl and $R^{9b}$ is hydrogen.

12. The compound of claim 1, wherein $R^{10}$ is methyl, ethyl, or isopropyl.

13. The compound of claim 12, wherein $R^{10}$ is isopropyl.

14. The compound of formula

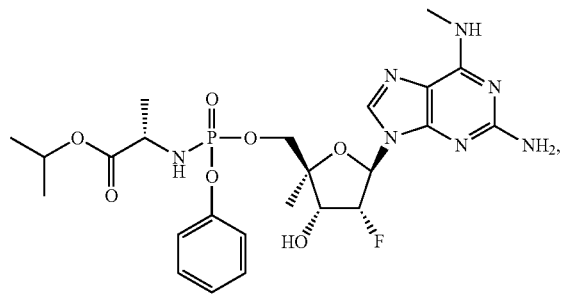

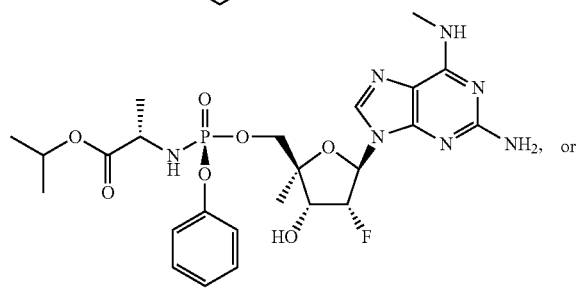

or a pharmaceutically acceptable salt thereof.

15. The compound of claim 14 of formula

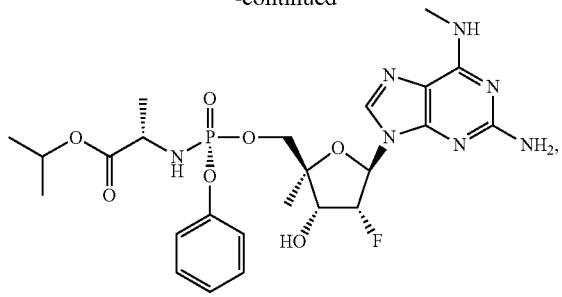

or a pharmaceutically acceptable salt thereof.

16. The compound of claim 14 of formula

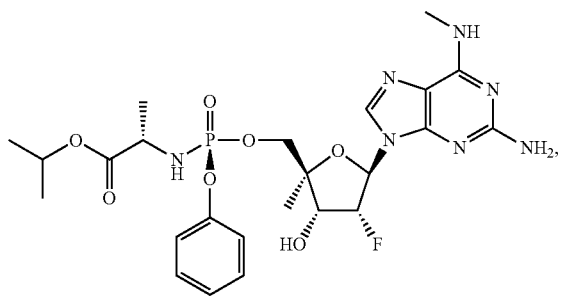 [SMILES: CNc1nc(N)nc2c1ncn2[C@@H]1O[C@](C)(CO[P@@](=O)(N[C@@H](C)C(=O)OC(C)C)Oc2ccccc2)[C@@H](O)[C@H]1F]

or a pharmaceutically acceptable salt thereof.

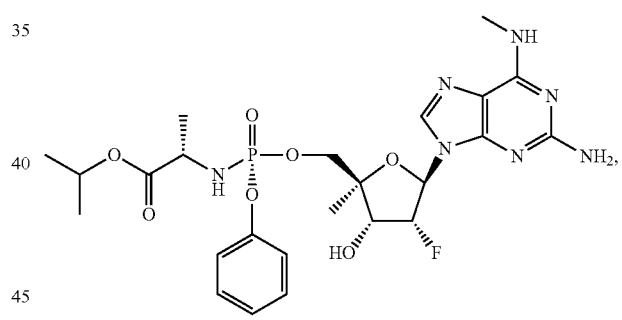

or a pharmaceutically acceptable salt thereof.

17. A method of treating a host infected with a virus of the Paramyxoviridae or Orthomyxoviridae family comprising providing an effective amount of a compound or pharmaceutically salt thereof of claim 1, optionally in a pharmaceutically acceptable carrier.

18. The method of claim 17, wherein the host is a human.

19. The method of claim 17, wherein the virus is respiratory syncytial virus.

20. The method of claim 19, wherein the host is a human.

* * * * *